US006420427B1

(12) United States Patent
Takahashi et al.

(10) Patent No.: US 6,420,427 B1
(45) Date of Patent: Jul. 16, 2002

(54) AMINOBUTYRIC ACID DERIVATIVES

(75) Inventors: Kanji Takahashi; Tsuneyuki Sugiura, both of Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/529,056

(22) PCT Filed: Sep. 7, 1998

(86) PCT No.: PCT/JP98/04529

§ 371 (c)(1), (2), (4) Date: Apr. 7, 2000

(87) PCT Pub. No.: WO99/19296

PCT Pub. Date: Apr. 22, 1999

(30) Foreign Application Priority Data

Oct. 9, 1997 (JP) ............................................. 9-291834
Feb. 10, 1998 (JP) ............................................. 10-28533

(51) Int. Cl.[7] ...................... A01N 37/18; A61K 31/165; A61K 31/195; A61K 31/34; A61K 31/415; A61K 31/535

(52) U.S. Cl. .................... 514/617; 544/153; 548/338.1; 548/504; 548/561; 546/192; 546/216; 514/233.5; 514/327; 514/331; 514/399; 514/427; 514/466; 514/469; 514/470; 514/471; 514/562; 514/563; 514/616; 514/618; 549/214; 549/467; 549/487; 564/154; 564/155; 564/158; 562/430; 562/444; 562/450

(58) Field of Search .......................... 564/188; 514/617, 514/623, 233.5, 399, 466, 469, 471, 470, 427, 562, 563; 549/214, 467, 487; 544/153; 562/444, 450, 430; 548/338.1, 504, 561; 546/192, 216

(56) References Cited

U.S. PATENT DOCUMENTS 2,745,875 A 5/1956 Ehrhart et al. .............. 260/558
4,826,878 A 5/1989 Makovec et al. ........... 514/312

FOREIGN PATENT DOCUMENTS

| | | |
|---|---|---|
| EP | 0757037 | 2/1997 |
| EP | 0757984 | 2/1997 |
| JP | 6210052 | 1/1987 |
| WO | 8902431 | 3/1989 |
| WO | 9512603 | 5/1995 |
| WO | 9718188 | 5/1997 |
| WO | 9723459 | 7/1997 |
| WO | 9846563 | 10/1998 |
| WO | 9906340 | 2/1999 |

OTHER PUBLICATIONS

Osapay, G. et al., "Conversion of Amino Acids and Dipeptides into their Phosphonic Analogs", Tetrahedron, 1987, vol. 43, No. 13, p. 2977–2983.
"Current Pharmaceutical Design", 1996, 2, 624–661.
"Clin Chim Acta", Feb. 15, 2000; 291 (2):223–34.
"J Am Soc Nephrol", Mar. 1998; 9(3):397–407.
"Current Pharamaceutical Design", 1997, 3, 45–58.
"Am J Respir Crit Care Med", Mar. 2001; 163 (3 Pt 1): 786–91.
"Am J. Physiol Gastrointest Liver Physiol", Aug. 2000; 279 (2):G254–9.
Clin Exp Immunol:, May 2000; 120(2):241–6.
"Matrix Biol"; Oct. 1998; 17(5): 335–47.
"Stem Cells", 197; 15(3): 180–9.
"Ann NY Acad Sci", Jun. 30, 1999; 878:159–78.
"Ann NY Acad Sci"Jun. 30, 1999; 878:191–200.
"J Am Soc Nephrol", Mar. 1998; 9(3):397–407.
"Clinical Obstetrics and Gynecology", 1999 43(3):566–585.

*Primary Examiner*—Amelia Owens
(74) *Attorney, Agent, or Firm*—Stevens, Davis, Miller & Mosher, L.L.P.

(57) ABSTRACT

An aminobutyric acid derivative of the formula (I):

(I)

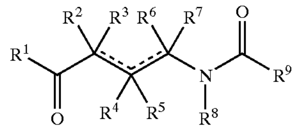

(wherein all symbols are as defined in the specification) and salt thereof. salt thereof.

The compounds of the formula (I) possess an inhibitory activity on matrix metalloproteinase and are useful for prevention and/or treatment of diseases, for example, rheumatoid diseases, arthrosteitis, unusual bone resorption, osteoporosis, periodontitis, interstitial nephritis, arteriosclerosis, pulmonary emphysema, cirrhosis, cornea injury, metastasis of, invasion of or growth of tumor cells, autoimmune disease (e.g. Crohn's disease, Sjogren's syndrome), disease caused by vascular emigration or infiltration of leukocytes, arterialization, multiple sclerosis, aorta aneurysm, endometriosis.

20 Claims, No Drawings

AMINOBUTYRIC ACID DERIVATIVES

SUMMARY

This invention relates to aminobutyric acid derivatives, processes for the preparation thereof and pharmaceutical agents containing them as active ingredient. More particularly, this invention relates to:

aminobutyric acid derivatives of the formula (I):

(I)

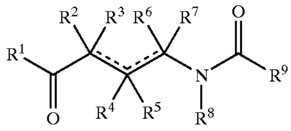

wherein all the symbols are as hereinafter defined, and non-toxic salts thereof, processes for the preparation thereof and pharmaceutical agents containing them as active ingredient.

BACKGROUND

The matrix metalloproteinases (MMPS) are neutral metalloproteinases and zinc ($Zn^{2+}$) is essential in the active site for their activation. They degrade collagen, laminin, proteoglycans, fibronectin, elastin, gelatin etc. under physiological conditions and therefore, are effective on growth and tissue remodeling of articulation tissue, bone tissue and connective tissue. At least 10 classes of MMPs which differ in primary structure are identified. Concretely, there are Interstitial Coliagenase (MMP-1), Neutrophil Collagenase (MMP-8), Gelatinase A (MMP-2), Gelatinase B (MMP-9), Stromelysin-1 (MMP-3), Stromelysin-2 (MMP-10), Matrilysin (MMP-7), metalloerastase (MMP-12) etc.

As common characteristics of these enzymes, MMPs (1) have $Zn^{2+}$ in the active site and the activity depends on calcium ion ($Ca^{2+}$), (2) are secreted as an inactive proenzyme and activated outside of cells, (3) have high homology on amino acid sequence, (4) have an ability to degrade on various extracellular matrix components in vivo, (5) are regulated by tissue inhibitors of metalloproteinases (TIMP) which are specific to MMPs.

MMP inhibitors are useful for prevention and/or treatment of various diseases induced by overexpression and excess activation of MMP. Such diseases are, for example, rheumatoid disease, arthrosteitis, unusual bone resorption, osteoporosis, periodontitis, interstitial nephritis, arteriosclerosis, pulmonary emphysema, cirrhosis, cornea injury, metastasis of, invasion of or growth of tumor cells, autoimmune diseases (e.g. Crohn's disease, Sjogren's syndrome), diseases caused by vascular emigration or infiltration of leukocytes, arterialization, multiple sclerosis, aorta aneurysm, endometriosis.

Some compounds possessing inhibitory activity against MMP are known. A sequence in the vicinity of cleavage site of collagen (Gly-Ile-Ala-Gly or Gly-Leu-Ala-Gly) has high affinity for collagenase.

Much research and development on substrate analogous MMP inhibitors, which are chemically modified so as to have zinc affinity groups on a cleaving site of the substrate, has energetically been carried out [Inhibitors of matrix metalloproteinases (MMP's), Nigel R A Beeley, Phillip R J Ansell, Andrew J P Docherty et al., Curr. Opin. Ther. Patents., 4, 7–16 (1994), Current Drugs Ltd ISSN 0962-2594]. However, these substrate-analogues inhibitors might have various problems. Therefore, it is desired to obtain a non-peptide inhibitor and some compounds are reported.

For example, in the specification of EP 757037 as the Example, sulfonylamino acid derivatives of the formula (W):

(W)

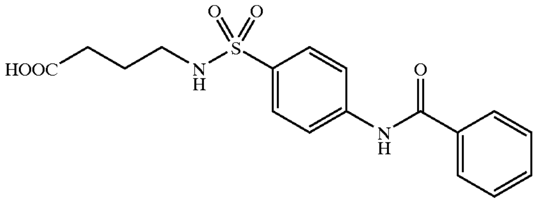

are disclosed to have an activity of inhibiting matrix metalloproteinase.

In the specification of EP 757984 as the Example, hydroxamic acid derivatives of the formula (X):

(X)

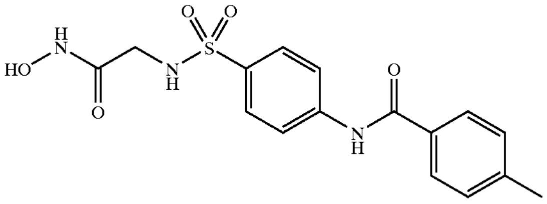

are disclosed to have an activity of inhibiting matrix metalloproteinase.

In the specification of WO 9723459 as the Example, aromatic keto-acid derivatives of the formula (Y):

(Y)

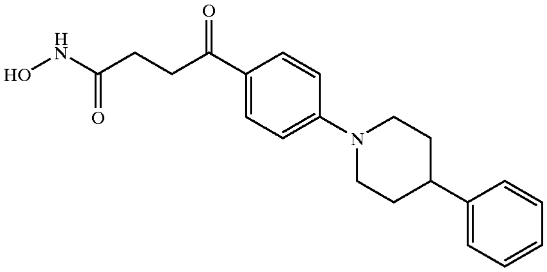

are disclosed to have an activity of inhibiting matrix metalloproteinase.

In the specification of WO 9718188 as the Example, hydroxamic acid derivatives of the formula (Z):

(Z)

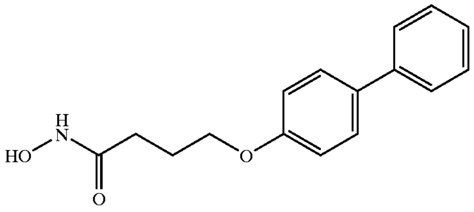

are disclosed to have an activity of inhibiting matrix metalloproteinase and TNFα secretion.

DISCLOSURE OF THE INVENTION

Energetic investigations have been carried out in order to make a matrix metalloproteinase, e.g. gelatinase, stromelysin or collagenase, inhibitor. The present inventors have found that novel compounds of aminobutyric acid derivatives of the formula (I) which are carboxylic amino derivatives of γ-amino acid, accomplished the present purpose.

The present invention relates to:

1) an aminobutyric acid derivative of the formula (I):

(I)

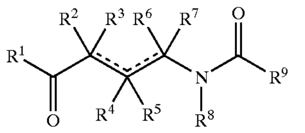

wherein $R^1$ is —$COOR^{10}$, —$CONHOR^{10}$, —$CONHNHR^{10}$, —$(CH_2)_nSR^{50}$ or —Y—$P(OR^{51})_2$;

$R^{10}$ is (i) hydrogen, (ii) C1–8 alkyl, (iii) phenyl, (iv) C1–8 alkyl substituted by phenyl or C1–8 alkoxy, or (v) oxycarbonyl substituted by phenyl, benzyl or C1–8 alkyl;

n is 0–3;

$R^{50}$ is (i) hydrogen, (ii) C1–8 alkyl, (iii) —$COR^{52}$, in which $R^{52}$ C1–8 alkyl or phenyl; or (iv) —$SR^{53}$, in which $R^{53}$ is hydrogen, C1–8 alkyl or phenyl;

$R^{51}$ is hydrogen, C1–8 alkyl or phenyl;

Y is a single bond, —$CH_2$— or —O—;

$R^2$, $R^3$, $R^4$, $R^5$, $R^6$ and $R^7$ each, independently, is (1) hydrogen, (2) C1–8 alkyl, (3) C2–8 alkenyl, (4) —$OR^{11}$, (5) —$SR^{11}$, (6) —$NR^{12}R^{13}$, (7) —$COR^{14}$, (8) Cyc1, (9) C1–8 alkyl substituted by —$OR^{11}$, —$SR^{11}$, —$NR^{12}R^{13}$, —$COR^{14}$, guanidino or Cyc1, or

(10) C2–8 alkenyl substituted by —$OR^{11}$, —$SR^{11}$, —$NR^{12}R^{13}$, —$COR^{14}$, guanidino or Cyc1, or $R^2$ and $R^4$, taken together is C1–8 alkylene, $R^5$ and $R^6$, taken together is C1–8 alkylene, $R^3$ and $R^6$, taken together is C1–8 alkylene, $R^2$ and $R^3$, taken together is C2–8 alkylene, $R^4$ and $R^5$, taken together is C2–8 alkylene, or $R^6$ and $R^7$, taken together is C2–8 alkylene;

in which Cyc1 is carbocyclic ring or heterocyclic ring and these carbocyclic ring and heterocyclic ring may be substituted by one or more of (i) C1–8 alkyl, (ii) C1–8 alkoxy, (iii) nitro, (iv) guanidino, (v) amidino, (vi) halogen atom, (vii) nitrile (viii) hydroxy, (ix) benzyloxy, (x) —$NR^{101}R^{102}$, in which $R^{101}$ and $R^{102}$ each, independently, is hydrogen or C1–8 alkyl, (xi) —$COOR^{103}$, in which $R^{103}$ is hydrogen or C1–8 alkyl, (xii) trifluoromethyl, (xiii) trifluoromethyloxy, (xiv) phenyl, (xv) phenyl substituted by C1–8 alkyl or C1–8 alkoxy, (xvi) phenyloxy, (xvii) phenylsulfonyl, (xviii) C1–8 alkyl substituted by phenyl or nitrile, (xix) heterocyclic ring, (xx) keto, and (xxi) C1–8 alkoxy substituted by —$CONR^{104}R^{105}$, in which $R^{104}$ and $R^{105}$ each, independently, is hydrogen, C1–8 alkyl or phenyl;

$R^{11}$ is (i) hydrogen, (ii) C1–8 alkyl, (iii) Cyc1, or (iv) —$COR^{18}$, or C1–8 alkyl substituted by —$OR^{15}$, —$SR^{15}$, —$NR^{16}R^{17}$, —$COR^{18}$, guanidino or Cyc1;

$R^{15}$ is hydrogen, C1–8 alkyl, Cyc1 or C1–8 alkyl substituted by Cyc1 or C1–8 alkoxy;

$R^{16}$ is hydrogen or C1–8 alkyl;

$R^{17}$ is hydrogen, C1–8 alkyl or —$COR^{19}$, in which $R^{19}$ is C1–8 alkyl, Cyc1 or C1–8 alkyl substituted by Cyc1;

$R^{18}$ is hydroxy, C1–8 alkyl, C1–8 alkoxy or —$NR^{20}R^{21}$, in which $R^{20}$ and $R^{21}$, each independently, is hydrogen, C1–8 alkyl, Cyc1 or C1–8 alkyl substituted by Cyc1;

$R^{12}$ is hydrogen, C1–8 alkyl, Cyc1 or C1–8 alkyl substituted by Cyc1;

$R^{13}$ is hydrogen, C1–8 alkyl, Cyc1, C1–8 alkyl substituted by Cyc1, or —$COR^{22}$, in which $R^{22}$ is C1–8 alkyl, Cyc1 or C1–8 alkyl substituted by Cyc1;

$R^{14}$ is hydroxy, C1–8 alkyl, C1–8 alkoxy, Cyc1, C1–8 alkyl substituted by Cyc1, or —$NR^{23}R^{24}$, in which $R^{23}$ and $R^{24}$, each independently, is (i) hydrogen, (ii) C1–8 alkyl, (iii) Cyc1 or (iv) C1–8 alkyl substituted by Cyc1 or hydroxy;

(1) $R^8$ is 1) hydrogen,

2) C1–8 alkyl,

3) C1–8 alkoxycarbonyl,

4) C1–8 alkyl substituted by —$OR^{26}$, —$SR^{26}$, —$NR^{27}R^{28}$ or —$COR^{29}$, or 5) C1–8 alkoxycarbonyl substituted by Cyc2, and $R^9$ is

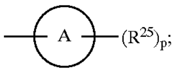 or (2) $R^8$ is

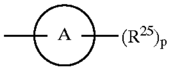 or

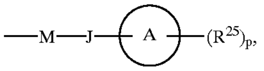 and $R^9$ is

1) C1–8 alkyl,

2) C1–8 alkoxy,

3) C1–8 alkoxy substituted by Cyc2,

4) C1–8 alkyl substituted by —$OR^{26}$, —$SR^{26}$, —$NR^{27}R^{28}$, —$COR^{29}$ or Cyc2 or

5)

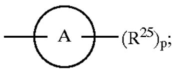

in which Cyc2 is carbocyclic ring or heterocyclic ring and these carbocyclic ring and heterocyclic ring may be substituted by one or more of (i) C1–8 alkyl, (ii) C1–8 alkoxy, (iii) nitro, (iv) guanidino, (v) amidino, (vi) halogen atom, (vii) nitrile (viii) hydroxy, (ix) benzyloxy, (x) —$NR^{201}R^{202}$, in which $R^{201}$ and $R^{202}$ each, independently, is hydrogen or C1–8 alkyl, (xi) —$COOR^{203}$, in which $R^{203}$ is hydrogen or C1–8 alkyl, (xii) trifluoromethyl, (xiii) trifluoromethyloxy, (xiv) phenyl, (xv) phenyl substituted by C1–8 alkyl or C1–8 alkoxy, (xvi) phenyloxy, (xvii) phenylsulfonyl, (xviii) C1–8 alkyl substituted by phenyl or nitrite, (xix) heterocyclic ring, (xx) keto, and (xxi) C1–8 alkoxy substituted by —CONR$^{204}$R$^{205}$, in which R$^{204}$ and R$^{205}$ each, independently, is hydrogen, C1–8 alkyl or phenyl;

R$^{26}$ is hydrogen, C1–8 alkyl, Cyc2 or C1–8 alkyl substituted by Cyc2;

R$^{27}$ is hydrogen, C1–8 alkyl, Cyc2 or C1–8 alkyl substituted by Cyc2;

R$^{28}$ is hydrogen, C1–8 alkyl, Cyc2, C1–8 alkyl substituted by Cyc2, or —COR$^{30}$, in which R$^{30}$ is C1–8 alkyl, Cyc2 or C1–8 alkyl substituted by Cyc2;

R$^{29}$ is hydroxy, C1–8 alkyl, Cyc2, C1–8 alkyl substituted by Cyc2, or —NR$^{31}$R$^{32}$, in which R$^{31}$ and R$^{32}$, each independently, is hydrogen, C1–8 alkyl, Cyc2 or C1–8 alkyl substituted by Cyc2;

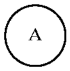

is carbocyclic ring or heterocyclic ring;

R$^{25}$ is —E—G;

E is 1) a single bond,
2) —CONR$^{33}$—,
3) —NR$^{33}$CO—,
4) —CO—O—,
5) —O—CO—,
6) —NR$^{33}$—CO—NR$^{34}$—,
7) —CO—CH$_2$—,
8) —CO—,
9) —O—CO—NR$^{33}$—,
10) —NR$^{33}$—CO—O—,
11) —O—CO—O—,
12) —CS—NR$^{33}$—,
13) —NR$^{33}$—CS—,
14) —CS—O—,
15) —O—CS—,
16) —NR$^{33}$—CS—R$^{34}$—,
17) —CS—CH$_2$—,
18) —CS—,
19) —O—CS—NR$^{33}$—,
20) NR$^{33}$—CS—O—,
21) —O—CS—O—,
22) —CH$_2$—CH$_2$—,
23) —HC═CH—,
24) —C≡C—,
25) —SO$_2$—NR$^{33}$—,
26) —NR$^{33}$—SO$_2$—,
27) —SO$_2$—CH$_2$— or
28) —CH$_2$—SO$_2$—;

R$^{33}$ and R$^{34}$, each independently, is hydrogen, C1–8 alkyl, Cyc3 or C1–8 alkyl substituted by Cyc3;

Cyc 3 is carbocyclic ring or heterocyclic ring and these carbocyclic ring and heterocyclic ring may be substituted by one or more of (i) C1–8 alkyl, (ii) C1–8 alkoxy, (iii) nitro, (iv) guanidino, (v) amidino, (vi) halogen atom, (vii) nitrile, (viii) hydroxy, (ix) benzyloxy, (x) —NR$^{301}$R$^{302}$, in which R$^{301}$ and R$^{302}$ each, independently, is hydrogen or C1–8 alkyl, (xi) —COOR$^{303}$, in which R$^{303}$ is hydrogen or C1–8 alkyl, (xii) trifluoromethyl, (xiii) trifluoromethyloxy, (xiv) phenyl, (xv) phenyl substituted by C1–8 alkyl or C1–8 alkoxy, (xvi) phenyloxy, (xvii) phenylsulfonyl, (xviii) C1–8 alkyl substituted by phenyl or nitrite, (xix) heterocyclic ring, (xx) keto, and (xxi) C1–8 alkoxy substituted by —CONR$^{304}$R$^{305}$, in which R$^{304}$ and R$^{305}$ each, independently, is hydrogen, C1–8 alkyl or phenyl;

G is 1) hydrogen,
2) C1–8 alkyl,
3) Cyc4,
4) —OR$^{35}$,
5) —SR$^{35}$,
6) halogen atom,
7) nitro,
8) nitrite,
9) —NR$^{36}$R$^{37}$,
10) —COR$^{38}$,
11) C1–8 alkyl substituted by Cyc4, —OR$^{35}$, —SR$^{35}$, halogen atom, —NR$^{36}$R$^{37}$ or —COR$^{38}$;

in which Cyc4 is carbocyclic ring or heterocyclic ring and these carbocyclic ring and heterocyclic ring may be substituted by one or more of (i) C1–8 alkyl, (ii) C1–8 alkoxy, (iii) nitro, (iv) guanidino, (v) amidino, (vi) halogen atom, (vii) nitrile (viii) hydroxy, (ix) benzyloxy, (x) —NR$^{401}$R$^{402}$, in which R$^{401}$ and R$^{402}$ each, independently, is hydrogen or C1–8 alkyl, (xi) —COOR$^{403}$, in which R$^{403}$ is hydrogen or C1–8 alkyl, (xii) trifluoromethyl, (xiii) trifluoromethyloxy, (xiv) phenyl, (xv) phenyl substituted by C1–8 alkyl or C1–8 alkoxy, (xvi) phenyloxy, (xvii) phenylsulfonyl, (xviii) C1–8 alkyl substituted by phenyl or nitrile, (xix) heterocyclic ring, (xx) keto, and (xxi) C1–8 alkoxy substituted by —CONR$^{404}$R$^{405}$, in which R$^{404}$ and R$^{405}$ each, independently, is hydrogen, C1–8 alkyl or phenyl;

R$^{35}$ is hydrogen, C1–8 alkyl, C1–8 alkoxy, Cyc4 or C1–8 alkyl substituted by Cyc4;, R$^{36}$ is hydrogen, C1–8 alkyl, Cyc4 or C1–8 alkyl substituted by Cyc4;

R$^{37}$ is hydrogen, C1–8 alkyl, Cyc4, C1–8 alkyl substituted by Cyc4, or —COR$^{39}$, in which R$^{39}$ is C1–8 alkyl, Cyc4 or C1–8 alkyl substituted by Cyc4;

R$^{38}$ is hydroxy, C1–8 alkyl, Cyc4, C1–8 alkyl substituted by Cyc4, or —NR$^{40}$R$^{41}$, in which R$^{40}$ and R$^{41}$, each independently, is hydrogen, C1–8 alkyl, Cyc4 or C1–8 alkyl substituted by Cyc4; or —E—G taken together, is C1–4 alkylidene;

p is 1–5;

M is C1–8 alkylene;

J is a single bond, an oxygen atom, a sulfur atom or —NR$^{42}$—, in which R$^{42}$ is hydrogen or C1–8 alkyl;

═══ may be double bond, by releasing the hydrogens, when two of R$^2$, R$^3$, R$^4$, R$^5$, R$^6$ and R$^7$ that do not bond to the same carbon atom and bond to neighboring carbon atoms, are hydrogens, with the proviso that ═══ is not double bond, when R$^3$ and R$^4$, taken together is C1–8 alkylene, R$^5$ and R$^6$, taken together is C1–8 alkylene, or R$^3$ and R$^6$, taken together is C1–8 alkylene;

or a non-toxic salt thereof, 2) a process for the preparation of an aminobutyric acid derivative of the formula (I) or a non-toxic salt thereof, and 3) a pharmaceutical agent containing an aminobutyric acid derivative of the formula (I) or a non-toxic salt thereof as active ingredient.

Unless otherwise specified, all isomers are included in the present invention. For example, alkyl, alkoxy and alkylene include straight and branched isomers. Double bond in alkenylene includes structure of configurations E, Z and EZ mixture. Isomers resulting from the presence of asymmetric carbon(s) e.g. branched alkyl, alkoxy and alkylene are also included within the present invention.

In the present invention, C1–8 alkyl is methyl, ethyl, propyl, butyl, pentyl, hexyl, heptyl, octyl and isomeric groups thereof.

C1–8 alkoxy is methoxy, ethoxy, propoxy, butoxy, pentyloxy, hexyloxy, heptyloxy, octyloxy and isomeric groups thereof.

C1–8 alkyl substituted by phenyl is methyl, ethyl, propyl, butyl, pentyl, hexyl, heptyl, octyl and isomeric groups thereof substituted by one of phenyl.

C1–8 alkyl substituted by C1–8 alkoxy is methyl, ethyl, propyl, butyl, pentyl, hexyl, heptyl, octyl and isomeric groups thereof substituted by one of methoxy, ethoxy, propoxy, butoxy, pentyloxy, hexyloxy, heptyloxy, octyloxy and isomeric groups thereof.

C1–8 alkyl substituted by nitrile is methyl, ethyl, propyl, butyl, pentyl, hexyl, heptyl, octyl and isomeric groups thereof substituted by one of nitrile.

Oxycarbonyl substituted by phenyl is phenyloxycarbonyl.

Oxycarbonyl substituted by benzyl is benzyloxycarbonyl.

Oxycarbonyl substituted by C1–8 alkyl is methyloxycarbonyl, ethyloxycarbonyl, propyloxycarbonyl, butyloxycarbonyl, pentyloxycarbonyl, hexyloxycarbonyl, heptyloxycarbonyl, octyloxycarbonyl and isomeric groups thereof.

C2–8 alkenyl is vinyl, propenyl, butenyl, pentenyl, hexenyl, heptenyl, octenyl, butadienyl, pentadienyl, hexadienyl, heptadienyl, octadienyl, hexatrienyl, heptatrienyl, octatrienyl and isomeric groups thereof.

C1–8 alkylene is methylene, ethylene, trimethylene, tetramethylene, pentamethylene, hexamethylene, heptamethylene, octamethylene, and isomeric groups thereof.

C2–8 alkylene is ethylene, trimethylene, tetramethylene, pentamethylene, hexamethylene, heptamethylene, octamethylene, and isomeric groups thereof.

Halogen atom is chlorine, bromine, fluorine, or iodine.

C1–8 alkoxycarbonyl is methyloxycarbonyl, ethyloxycarbonyl, propyloxycarbonyl, butyloxycarbonyl, pentyloxycarbonyl, hexyloxycarbonyl, heptyloxycarbonyl, octyloxycarbonyl and isomeric groups thereof.

C1–4 alkylidene is methylidene, ethylidene, propylidene, butylidene and isomeric groups thereof.

Carbocyclic ring is C3–15 mono-, bi- or tri-carbocyclic ring, for example, cyclopropane, cyclobutane, cyclopentane, cyclohexane, cycloheptane, cyclopentene, cyclohexene, cyclopentadiene, cyclohexadiene, benzene, pentalene, indene, naphthalene, azulene, fluorene, phenanthrene, anthracene, acenaphthylene, biphenylene, perhydropentalene, perhydroindene, perhydronaphthalene, perhydroazulene, perhydrofluorene, perhydrophenanthrene, perhydroanthracene, perhydroacenaphthylene, perhydrobiphenylene, adamantane.

Heterocyclic ring is 5–18 membered mono-, bi- or tri-heterocyclic ring containing 1–4 of nitrogen(s), 1–2 of oxygen(s) and/or 1–2 of sulfur(s). 5–18 membered mono-, bi- or tri-heterocyclic ring containing 1–4 of nitrogen(s), 1–2 of oxygen(s) and/or 1–2 of sulfur(s) includes 5–18 membered mono-, bi- or tri-heterocyclic aryl containing 1–4 of nitrogen(s), 1–2 of oxygen(s) and/or 1–2 of sulfur(s), and partially or fully saturated thereof.

5–18 membered mono-, bi- or tri-heterocyclic aryl containing 1–4 of nitrogen(s), 1–2 of oxygen(s) and/or 1–2 of sulfur(s), is, for example, pyrrole, imidazole, triazole, tetrazole, pyrazole, pyridine, pyrazine, pyrimidine, pyridazine, azepine, diazepine, furan, pyran, oxepin, oxazepine, thiophene, thiain (thiopyran), thiepin, oxazole, isoxazole, thiazole, isothiazole, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzoimidazole, carbazole or acridine.

Partially or fully saturated 5–18 membered mono- or bi-heterocyclic ring containing 1–4 of nitrogen(s), 1–2 of oxygen(s) and/or 1–2 of sulfur(s), for example, pyrroline, pyrrolidine, imidazoline, imidazolidine, triazoline, triazolidine, tetrazoline, tetrazolidine, pyrazoline, pyrazolidine, piperidine, piperazine, tetrahydropyridine, tetrahydropyrimidine, tetrahydropyridazine, dihydrofuran, tetrahydrofuran, dihydropyran, tetrahydropyran, dihydrothiophene, tetrahydrothiophene, dihydrothiain (dihydrothiopyran), tetrahydrothiain (tetrahydrothiopyran), dihydrooxazole, tetrahydrooxazole, dihydroisoxazole, tetrahydroisoxazole, dihydrothiazole, tetrahydrothiazole, dihydroisothiazole, tetrahydroisothiazole, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzimidazole, perhydrobenzimidazole, benzoxazepine, benzoxadiazepine, benzothiazepine, benzothiadiazepine, benzoazepine, benzodiazepine, indolooxazepine, indolotetrahydrooxazepine, indolooxadiazepine, indolotetrahydrooxadiazepine, indolothiazepine, indolotetrahydrothiazepine, indolothiadiazepine, indolotetrahydrothiadiazepine, indoloazepine, indolotetrahydroazepine, indolodiazepine, indolotetrahydrodiazepine, benzofurazan, benzothiadiazole, benzotriazole, camphor, imidazothiazole, dihydrocarbazole, tetrahydrocarbazole, perhydrocarbazole, dihydroacridine, tetrahydroacridine, perhydroacridine, dioxolane, dioxane, dithiolane, dithiane, dioxazine, dithiazine.

Salts

Non-toxic salts of the present invention include all pharmaceutically acceptable salts, for example, general salts, acid addition salts, hydrate salts.

The compounds of formula (I) of the present invention may be converted into the corresponding salts. Non-toxic salts and water-soluble salts are preferred. Suitable salts, for example, include: salts of alkali metals (e.g. potassium, sodium), salts of alkaline earth metals (e.g. calcium, magnesium), ammonium salts, salts of pharmaceutically acceptable organic amines (e.g. tetramethylammonium, triethylamine, methylamine, dimethylamine, cyclopentylamine benzylamine, phenethylamine, piperidine, monoethanolamine, diethanolamine, tris(hydroxymethyl) amine, lysine, arginine, N-methyl-D-glucamine).

The compounds of formula (I) may be converted into the corresponding acid addition salts. Non-toxic acid addition salts and water-soluble acid addition salts are preferred.

Suitable salts, for example, include: salts of inorganic acids e.g. hydrochloride, hydrobromide, sulfate, phosphate, nitrate; salts of organic acids e.g. acetate, trifluoroacetate, lactate, tartarate, oxalate, fumarate, maleate, citrate, benzoate, methanesulphonate, ethanesulphonate, benzenesulphonate, toluenesulphonate, isethionate, glucuronate, gluconate.

The compounds of formula (I) and salts thereof may be converted into the corresponding hydrates by conventional means.

In the compounds of the present invention of formula (I), the compounds of the following formula are preferred:

(I-A)

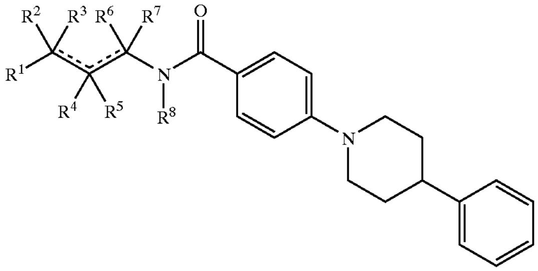

wherein all the symbols are as hereinbefore defined;

(I-B)

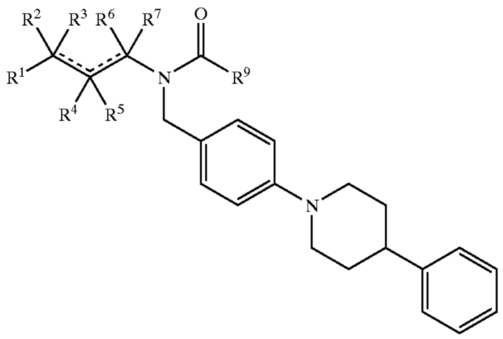

wherein the symbols are as hereinbefore defined;

(I-C)

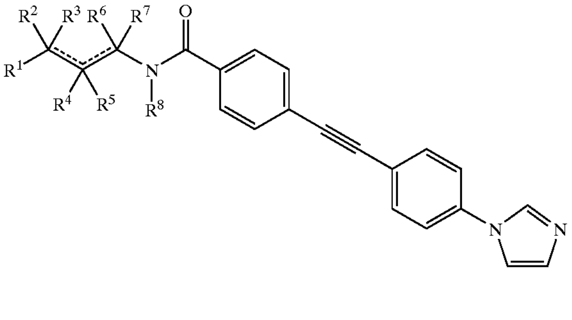

wherein all the symbols are as hereinbefore defined;

(I-D)

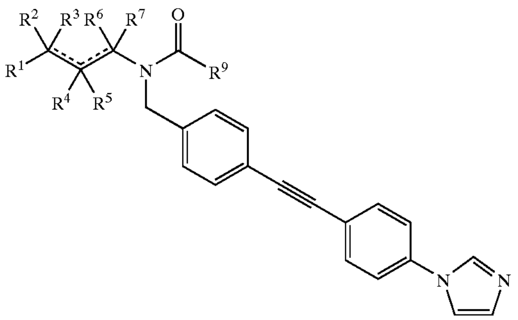

wherein all the symbols are as hereinbefore defined;

(I-E)

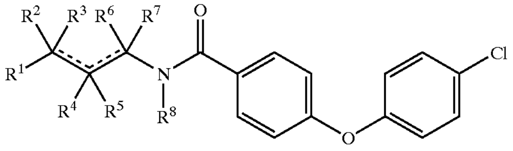

wherein all the symbols are as hereinbefore defined;

(I-F)

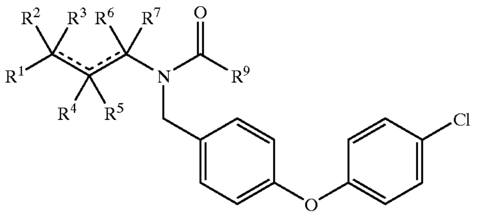

wherein all the symbols are as hereinbefore defined;

(I-G)

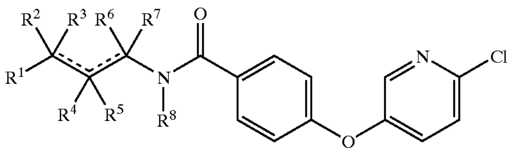

wherein all the symbols are as hereinbefore defined;

(I-H)

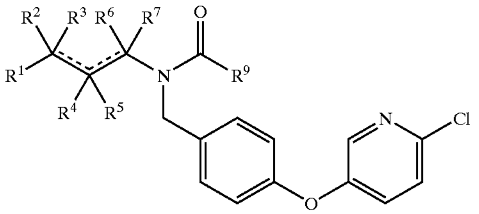

wherein all the symbols are as hereinbefore defined;

(I-J)

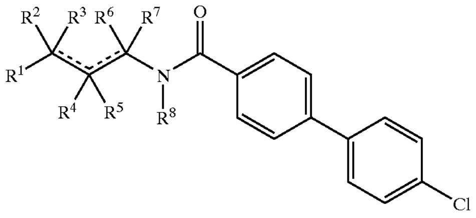

wherein all the symbols are as hereinbefore defined;

(I-K)

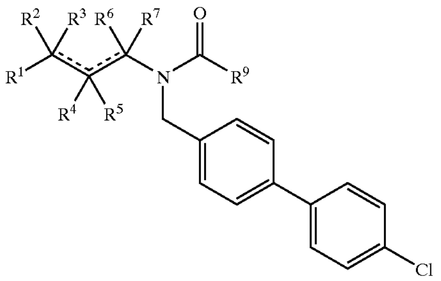

wherein all the symbols are as hereinbefore defined;

(I-L)

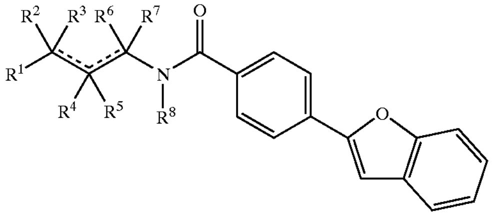

wherein all the symbols are as hereinbefore defined;

(I-M)

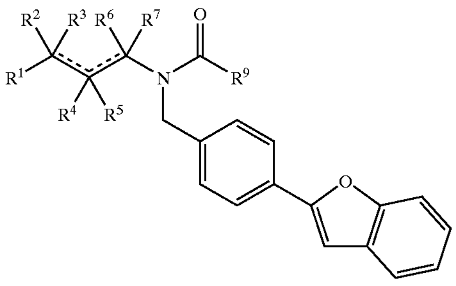

wherein all the symbols are as hereinbefore defined;

(I-N)

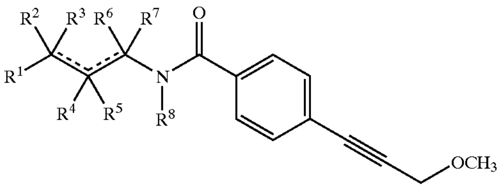

wherein all the symbols are as hereinbefore defined;

(I-O)

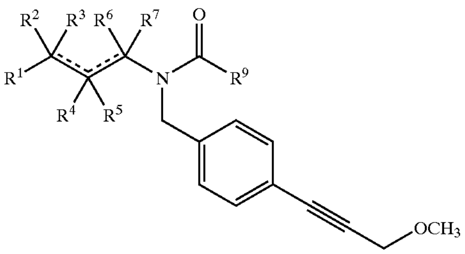

wherein all the symbols are as hereinbefore defined;

(I-P)

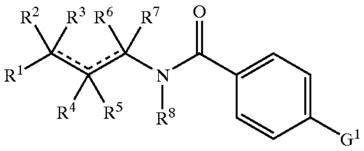

wherein $G^1$ is methyl, halogen atom, nitro or nitrite and the other symbols are as hereinbefore defined;

(I-Q)

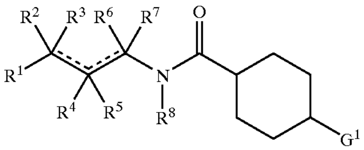

wherein all the symbols are as hereinbefore defined.

The compounds in Table1–Table105 and non-toxic salts thereof, and the compounds described in the Examples are more preferred. In the following Tables, Phth is phthalimide, Ph is phenyl, MOM is methoxymethyl, EOM is ethoxymethyl, MEM is (2-methoxyethoxy)methyl, BOM is benzyloxymethyl.

TABLE 1

(I-A-1)

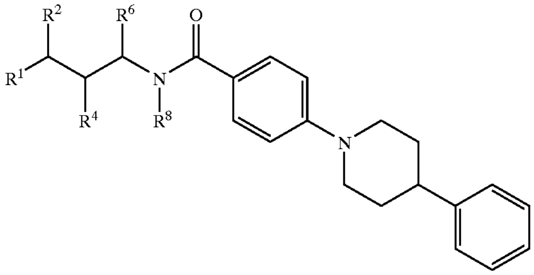

$R^1$=COOH

| No. | $R^2$ | $R^4$ | $R^6$ | $R^8$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-COCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 2

(I-A-2)

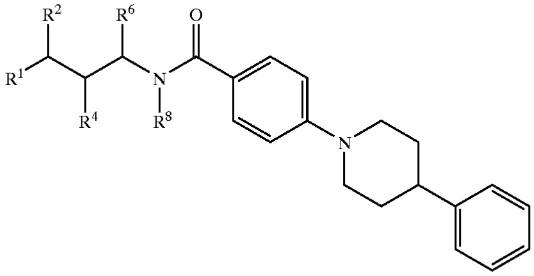

$R^1$=CONHOH

| No. | $R^2$ | $R^4$ | $R^6$ | $R^8$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-COCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 3

(I-A-3)

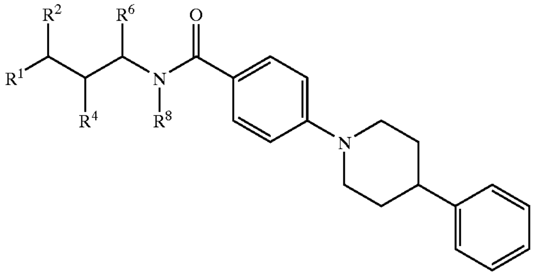

$R^1$=$CONHNH_2$

| No. | $R^2$ | $R^4$ | $R^6$ | $R^8$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-COCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 4

(I-A-4)

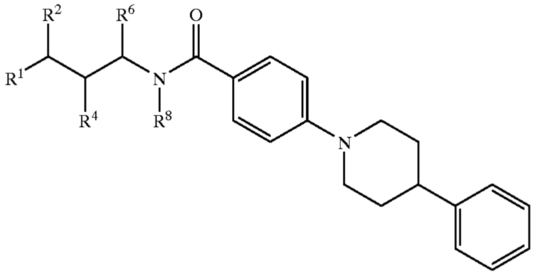

$R^1$=$CH_2SH$

| No. | $R^2$ | $R^4$ | $R^6$ | $R^8$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-COCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 5

(I-A-5)

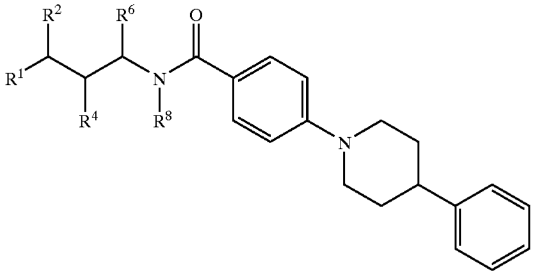

$R^1$=$PO(OH)_2$

| No. | $R^2$ | $R^4$ | $R^6$ | $R^8$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-COCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 6

(I-B-1)

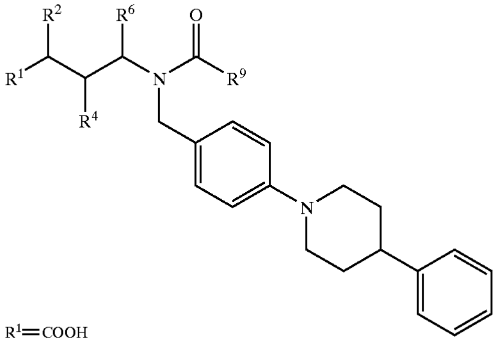

$R^1$=COOH

| No. | $R^2$ | $R^4$ | $R^6$ | $R^9$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-OCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 7

(I-B-2)

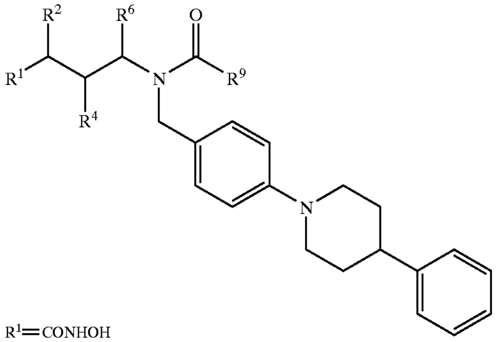

$R^1$=CONHOH

| No. | $R^2$ | $R^4$ | $R^6$ | $R^9$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-OCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 8

(I-B-3)

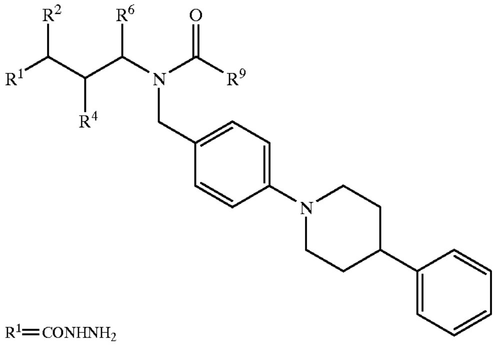

$R^1$=CONHNH$_2$

| No. | $R^2$ | $R^4$ | $R^6$ | $R^9$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-OCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 9

(I-B-4)

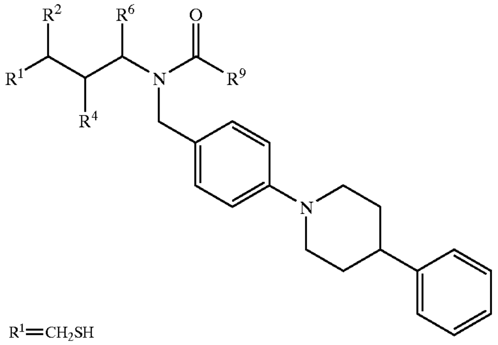

$R^1$=$CH_2SH$

| No. | $R^2$ | $R^4$ | $R^6$ | $R^9$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-OCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 10

(I-B-5)

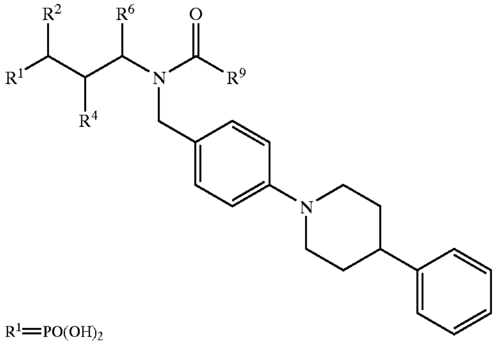

$R^1$=$PO(OH)_2$

| No. | $R^2$ | $R^4$ | $R^6$ | $R^9$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-OCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 11

(I-C-1)

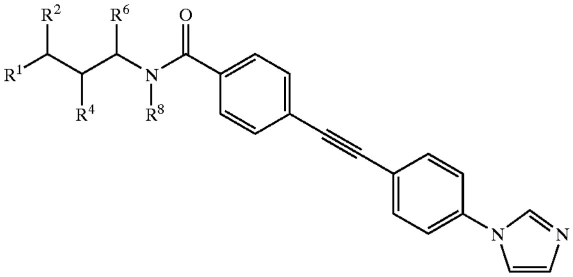

$R^1$ = COOH

| No | $R^2$ | $R^4$ | $R^6$ | $R^8$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-COCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4-$Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 12

(I-C-2)

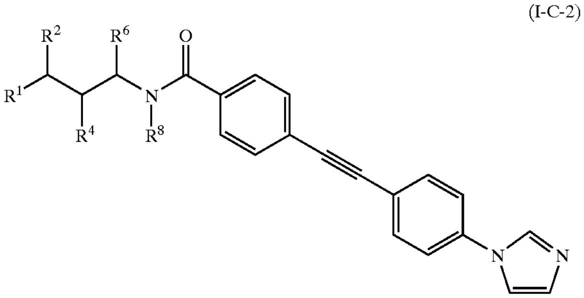

$R^1$ = CONHOH

| No | $R^2$ | $R^4$ | $R^6$ | $R^8$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-COCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4-$Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 13

(I-C-3)

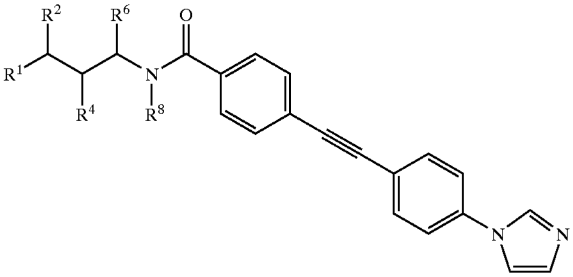

$R^1$ = $CONHNH_2$

| No | $R^2$ | $R^4$ | $R^6$ | $R^8$ |
|---|---|---|---|---|
| 1 | H | H | H | H |
| 2 | $-(CH_2)_2$-Phth | H | H | H |
| 3 | H | $-(CH_2)_2-$Phth | H | H |
| 4 | H | H | $-(CH_2)_2$-Phth | H |
| 5 | H | H | H | $-CH_3$ |
| 6 | H | H | H | $-COCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4-$Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 14

(I-C-4)

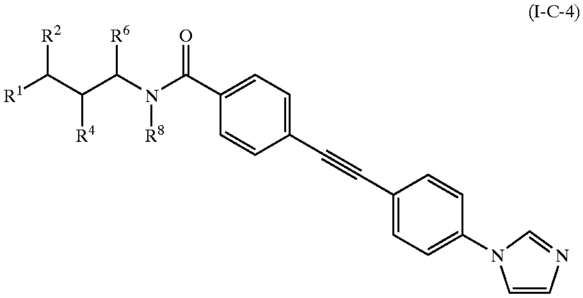

$R^1$ = $CH_2SH$

| No | $R^2$ | $R^4$ | $R^6$ | $R^8$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-COCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4-$Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 15

(I-C-5)

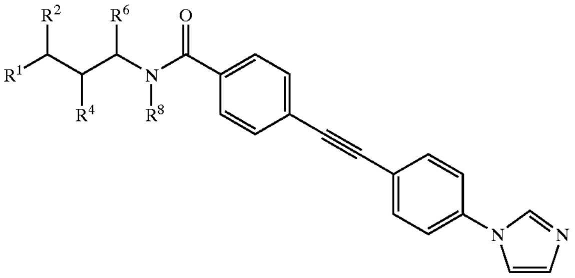

$R^1 = PO(OH)_2$

| No | $R^2$ | $R^4$ | $R^6$ | $R^8$ |
|---|---|---|---|---|
| 1 | H | H | H | H |
| 2 | $—(CH_2)_2$-Phth | H | H | H |
| 3 | H | $—(CH_2)_2$-Phth | H | H |
| 4 | H | H | $—(CH_2)_2$-Phth | H |
| 5 | H | H | H | $—CH_3$ |
| 6 | H | H | H | $—COCH_3$ |
| 7 | $—(CH_2)_2$-Phth | $—(CH_2)_5—CH_3$ | H | H |
| 8 | H | $—(CH_2)_2$-Phth | $—(CH_2)_5—CH_3$ | H |
| 9 | $—(CH_2)_4—Ph$ | $—(CH_2)_5—CH_3$ | H | H |
| 10 | $—(CH_2)_4—OH$ | $—(CH_2)_5—CH_3$ | H | H |
| 11 | H | $—(CH_2)_4—OH$ | H | H |
| 12 | H | H | $—(CH_2)_4—OH$ | H |
| 13 | $—(CH_2)_4—NH_2$ | H | H | H |
| 14 | H | $—(CH_2)_4—NH_2$ | H | H |

TABLE 16

(I-D-1)

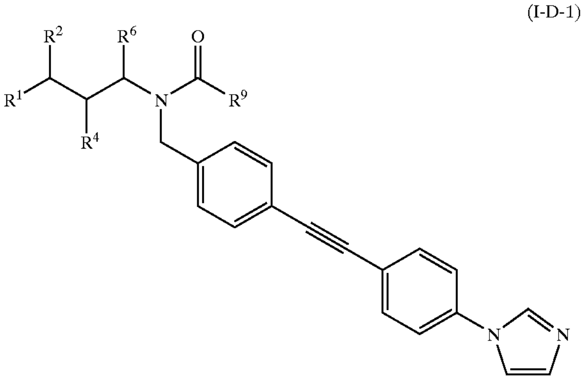

$R^1 = COOH$

| No | $R^2$ | $R^4$ | $R^6$ | $R^8$ |
|---|---|---|---|---|
| 1 | H | H | H | H |
| 2 | $—(CH_2)_2$-Phth | H | H | H |
| 3 | H | $—(CH_2)_2$-Phth | H | H |
| 4 | H | H | $—(CH_2)_2$-Phth | H |
| 5 | H | H | H | $—CH_3$ |
| 6 | H | H | H | $—OCH_3$ |
| 7 | $—(CH_2)_2$-Phth | $—(CH_2)_5—CH_3$ | H | H |
| 8 | H | $—(CH_2)_2$-Phth | $—(CH_2)_5—CH_3$ | H |
| 9 | $—(CH_2)_4—Ph$ | $—(CH_2)_5—CH_3$ | H | H |
| 10 | $—(CH_2)_4—OH$ | $—(CH_2)_5—CH_3$ | H | H |
| 11 | H | $—(CH_2)_4—OH$ | H | H |
| 12 | H | H | $—(CH_2)_4—OH$ | H |
| 13 | $—(CH_2)_4—NH_2$ | H | H | H |
| 14 | H | $—(CH_2)_4—NH_2$ | H | H |

TABLE 17

(I-D-2)

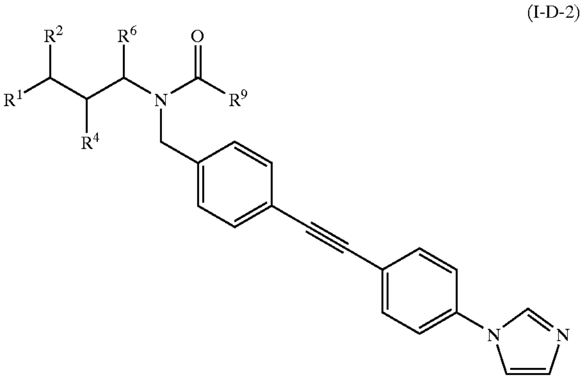

$R^1 = CONHOH$

| No | $R^2$ | $R^4$ | $R^6$ | $R^8$ |
|---|---|---|---|---|
| 1 | H | H | H | H |
| 2 | $—(CH_2)_2$-Phth | H | H | H |
| 3 | H | $—(CH_2)_2$-Phth | H | H |
| 4 | H | H | $—(CH_2)_2$-Phth | H |
| 5 | H | H | H | $—CH_3$ |
| 6 | H | H | H | $—OCH_3$ |
| 7 | $—(CH_2)_2$-Phth | $—(CH_2)_5—CH_3$ | H | H |
| 8 | H | $—(CH_2)_2$-Phth | $—(CH_2)_5—CH_3$ | H |
| 9 | $—(CH_2)_4—Ph$ | $—(CH_2)_5—CH_3$ | H | H |
| 10 | $—(CH_2)_4—OH$ | $—(CH_2)_5—CH_3$ | H | H |
| 11 | H | $—(CH_2)_4—OH$ | H | H |
| 12 | H | H | $—(CH_2)_4—OH$ | H |
| 13 | $—(CH_2)_4—NH_2$ | H | H | H |
| 14 | H | $—(CH_2)_4—NH_2$ | H | H |

TABLE 18

(I-D-3)

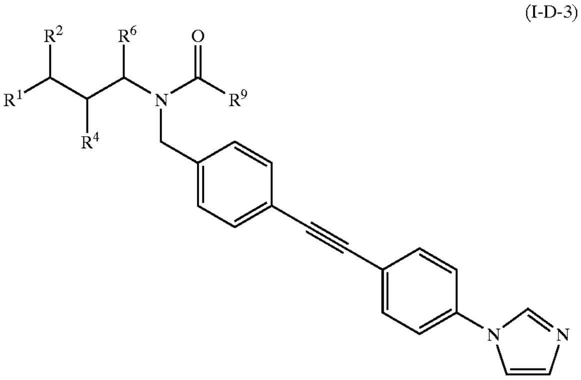

$R^1 = CONHNH_2$

| No | $R^2$ | $R^4$ | $R^6$ | $R^8$ |
|---|---|---|---|---|
| 1 | H | H | H | H |
| 2 | $—(CH_2)_2$-Phth | H | H | H |
| 3 | H | $—(CH_2)_2$-Phth | H | H |
| 4 | H | H | $—(CH_2)_2$-Phth | H |
| 5 | H | H | H | $—CH_3$ |
| 6 | H | H | H | $—OCH_3$ |
| 7 | $—(CH_2)_2$-Phth | $—(CH_2)_5—CH_3$ | H | H |
| 8 | H | $—(CH_2)_2$-Phth | $—(CH_2)_5—CH_3$ | H |
| 9 | $—(CH_2)_4—Ph$ | $—(CH_2)_5—CH_3$ | H | H |
| 10 | $—(CH_2)_4—OH$ | $—(CH_2)_5—CH_3$ | H | H |
| 11 | H | $—(CH_2)_4—OH$ | H | H |
| 12 | H | H | $—(CH_2)_4—OH$ | H |
| 13 | $—(CH_2)_4—NH_2$ | H | H | H |
| 14 | H | $—(CH_2)_4—NH_2$ | H | H |

TABLE 19

(I-D-4)

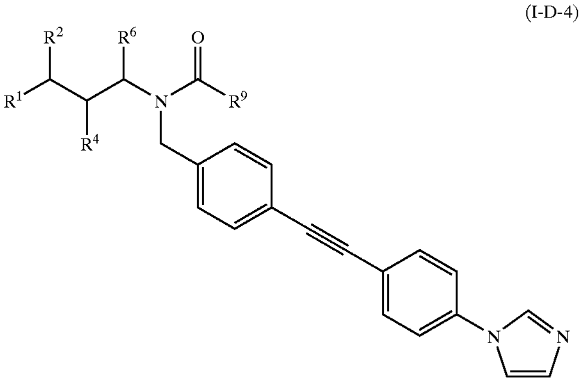

$R^1 = CH_2SH$

| No | $R^2$ | $R^4$ | $R^6$ | $R^8$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-OCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4-Ph$ | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 20

(I-D-5)

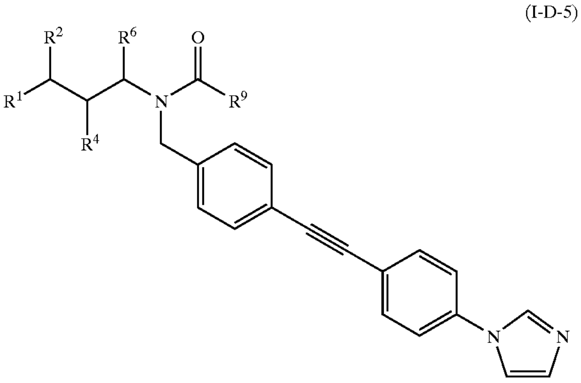

$R^1 = PO(OH)_2$

| No | $R^2$ | $R^4$ | $R^6$ | $R^8$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-OCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4-Ph$ | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 21

(I-E-1)

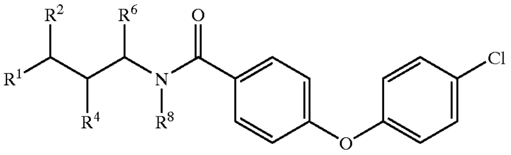

$R^1 = COOH$

| No. | $R^2$ | $R^4$ | $R^6$ | $R^8$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-COCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 22

(I-E-2)

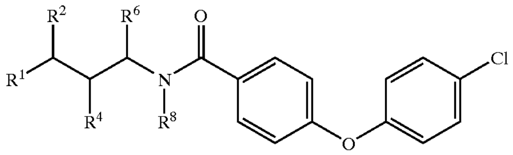

$R^1$ = CONHOH

| No. | $R^2$ | $R^4$ | $R^6$ | $R^8$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-COCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 23

(I-E-3)

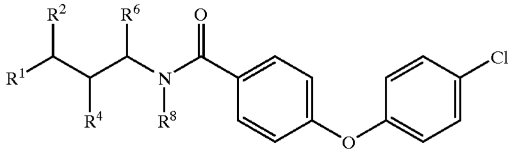

$R^1$ = $CONHNH_2$

| No. | $R^2$ | $R^4$ | $R^6$ | $R^8$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-COCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 24

(I-E-4)

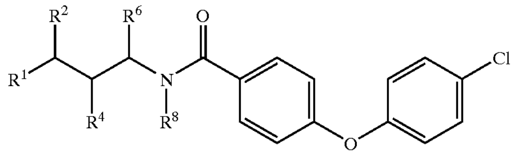

$R^1 = CH_2SH$

| No. | $R^2$ | $R^4$ | $R^6$ | $R^8$ |
|---|---|---|---|---|
| 1 | H | H | H | H |
| 2 | $—(CH_2)_2$-Phth | H | H | H |
| 3 | H | $—(CH_2)_2$-Phth | H | H |
| 4 | H | H | $—(CH_2)_2$-Phth | H |
| 5 | H | H | H | $—CH_3$ |
| 6 | H | H | H | $—COCH_3$ |
| 7 | $—(CH_2)_2$-Phth | $—(CH_2)_5—CH_3$ | H | H |
| 8 | H | $—(CH_2)_2$-Phth | $—(CH_2)_5—CH_3$ | H |
| 9 | $—(CH_2)_4$-Ph | $—(CH_2)_5—CH_3$ | H | H |
| 10 | $—(CH_2)_4—OH$ | $—(CH_2)_5—CH_3$ | H | H |
| 11 | H | $—(CH_2)_4—OH$ | H | H |
| 12 | H | H | $—(CH_2)_4—OH$ | H |
| 13 | $—(CH_2)_4—NH_2$ | H | H | H |
| 14 | H | $—(CH_2)_4—NH_2$ | H | H |

TABLE 25

(I-E-5)

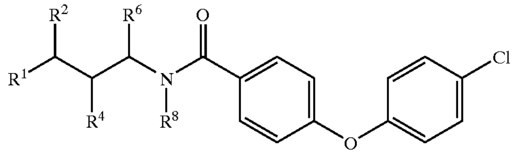

$R^1 = PO(OH)_2$

| No. | $R^2$ | $R^4$ | $R^6$ | $R^8$ |
|---|---|---|---|---|
| 1 | H | H | H | H |
| 2 | $—(CH_2)_2$-Phth | H | H | H |
| 3 | H | $—(CH_2)_2$-Phth | H | H |
| 4 | H | H | $—(CH_2)_2$-Phth | H |
| 5 | H | H | H | $—CH_3$ |
| 6 | H | H | H | $—COCH_3$ |
| 7 | $—(CH_2)_2$-Phth | $—(CH_2)_5—CH_3$ | H | H |
| 8 | H | $—(CH_2)_2$-Phth | $—(CH_2)_5—CH_3$ | H |
| 9 | $—(CH_2)_4$-Ph | $—(CH_2)_5—CH_3$ | H | H |
| 10 | $—(CH_2)_4—OH$ | $—(CH_2)_5—CH_3$ | H | H |
| 11 | H | $—(CH_2)_4—OH$ | H | H |
| 12 | H | H | $—(CH_2)_4—OH$ | H |
| 13 | $—(CH_2)_4—NH_2$ | H | H | H |
| 14 | H | $—(CH_2)_4—NH_2$ | H | H |

TABLE 26

(I-F-1)

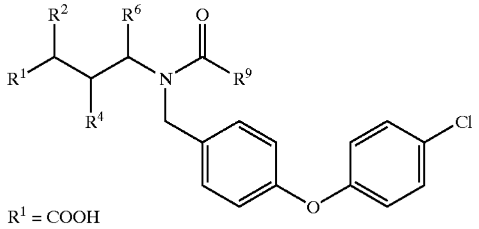

| No. | $R^2$ | $R^4$ | $R^6$ | $R^9$ |
|---|---|---|---|---|
| 1 | H | H | H | H |
| 2 | $—(CH_2)_2$-Phth | H | H | H |
| 3 | H | $—(CH_2)_2$-Phth | H | H |
| 4 | H | H | $—(CH_2)_2$-Phth | H |
| 5 | H | H | H | $—CH_3$ |
| 6 | H | H | H | $—OCH_3$ |
| 7 | $—(CH_2)_2$-Phth | $—(CH_2)_5—CH_3$ | H | H |
| 8 | H | $—(CH_2)_2$-Phth | $—(CH_2)_5—CH_3$ | H |
| 9 | $—(CH_2)_4$-Ph | $—(CH_2)_5—CH_3$ | H | H |
| 10 | $—(CH_2)_4—OH$ | $—(CH_2)_5—CH_3$ | H | H |
| 11 | H | $—(CH_2)_4—OH$ | H | H |
| 12 | H | H | $—(CH_2)_4—OH$ | H |
| 13 | $—(CH_2)_4—NH_2$ | H | H | H |
| 14 | H | $—(CH_2)_4—NH_2$ | H | H |

TABLE 27

(I-F-2)

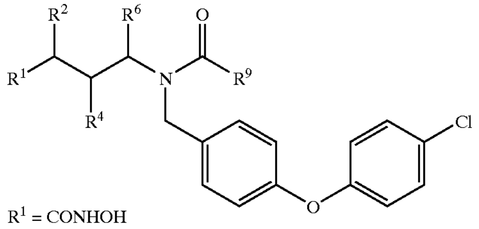

| No. | $R^2$ | $R^4$ | $R^6$ | $R^9$ |
|---|---|---|---|---|
| 1 | H | H | H | H |
| 2 | $—(CH_2)_2$-Phth | H | H | H |
| 3 | H | $—(CH_2)_2$-Phth | H | H |
| 4 | H | H | $—(CH_2)_2$-Phth | H |
| 5 | H | H | H | $—CH_3$ |
| 6 | H | H | H | $—OCH_3$ |
| 7 | $—(CH_2)_2$-Phth | $—(CH_2)_5—CH_3$ | H | H |
| 8 | H | $—(CH_2)_2$-Phth | $—(CH_2)_5—CH_3$ | H |
| 9 | $—(CH_2)_4$-Ph | $—(CH_2)_5—CH_3$ | H | H |
| 10 | $—(CH_2)_4—OH$ | $—(CH_2)_5—CH_3$ | H | H |
| 11 | H | $—(CH_2)_4—OH$ | H | H |
| 12 | H | H | $—(CH_2)_4—OH$ | H |
| 13 | $—(CH_2)_4—NH_2$ | H | H | H |
| 14 | H | $—(CH_2)_4—NH_2$ | H | H |

TABLE 28

(I-F-3)

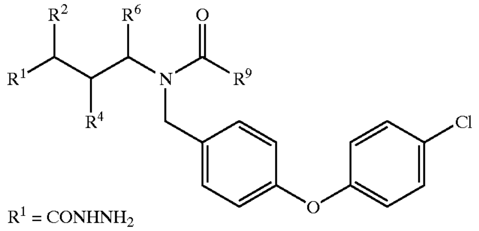

$R^1 = CONHNH_2$

| No. | $R^2$ | $R^4$ | $R^6$ | $R^9$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-OCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 29

(I-F-4)

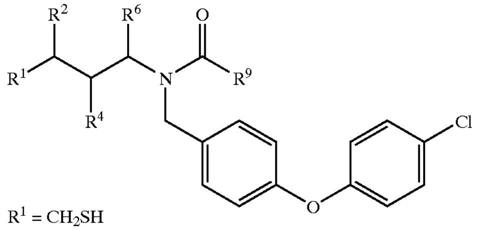

$R^1 = CH_2SH$

| No. | $R^2$ | $R^4$ | $R^6$ | $R^9$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-OCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 30

(I-F-5)

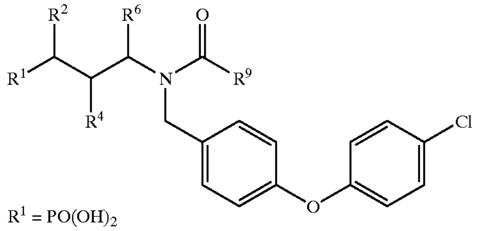

$R^1 = PO(OH)_2$

| No. | $R^2$ | $R^4$ | $R^6$ | $R^9$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-OCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 31

(I-G-1)

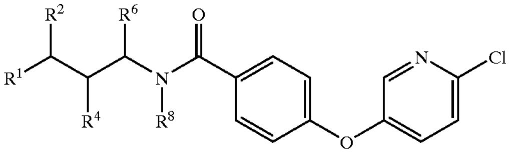

$R^1 = COOH$

| No. | $R^2$ | $R^4$ | $R^6$ | $R^8$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-COCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 32

(I-G-2)

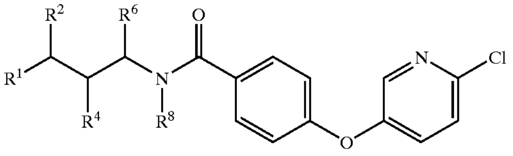

$R^1$ = CONHOH

| No. | $R^2$ | $R^4$ | $R^6$ | $R^8$ |
|---|---|---|---|---|
| 1 | H | H | H | H |
| 2 | $—(CH_2)_2$-Phth | H | H | H |
| 3 | H | $—(CH_2)_2$-Phth | H | H |
| 4 | H | H | $—(CH_2)_2$-Phth | H |
| 5 | H | H | H | $—CH_3$ |
| 6 | H | H | H | $—COCH_3$ |
| 7 | $—(CH_2)_2$-Phth | $—(CH_2)_5—CH_3$ | H | H |
| 8 | H | $—(CH_2)_2$-Phth | $—(CH_2)_5—CH_3$ | H |
| 9 | $—(CH_2)_4$-Ph | $—(CH_2)_5—CH_3$ | H | H |
| 10 | $—(CH_2)_4—OH$ | $—(CH_2)5—CH_3$ | H | H |
| 11 | H | $—(CH_2)_4—OH$ | H | H |
| 12 | H | H | $—(CH_2)_4—OH$ | H |
| 13 | $—(CH_2)_4—NH_2$ | H | H | H |
| 14 | H | $—(CH_2)_4—NH_2$ | H | H |

TABLE 33

(I-G-3)

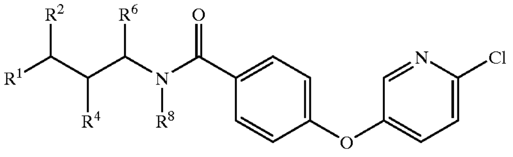

$R^1$ = $CONHNH_2$

| No. | $R^2$ | $R^4$ | $R^6$ | $R^8$ |
|---|---|---|---|---|
| 1 | H | H | H | H |
| 2 | $—(CH_2)_2$-Phth | H | H | H |
| 3 | H | $—(CH_2)_2$-Phth | H | H |
| 4 | H | H | $—(CH_2)_2$-Phth | H |
| 5 | H | H | H | $—CH_3$ |
| 6 | H | H | H | $—COCH_3$ |
| 7 | $—(CH_2)_2$-Phth | $—(CH_2)_5—CH_3$ | H | H |
| 8 | H | $—(CH_2)_2$-Phth | $—(CH_2)_5—CH_3$ | H |
| 9 | $—(CH_2)_4$-Ph | $—(CH_2)_5—CH_3$ | H | H |
| 10 | $—(CH_2)_4—OH$ | $—(CH_2)_5—CH_3$ | H | H |
| 11 | H | $—(CH_2)_4—OH$ | H | H |
| 12 | H | H | $—(CH_2)_4—OH$ | H |
| 13 | $—(CH_2)_4—NH_2$ | H | H | H |
| 14 | H | $—(CH_2)_4—NH_2$ | H | H |

TABLE 34

(I-G-4)

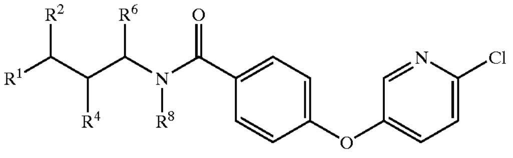

$R^1 = CH_2SH$

| No. | $R^2$ | $R^4$ | $R^6$ | $R^8$ |
|---|---|---|---|---|
| 1 | H | H | H | H |
| 2 | $—(CH_2)_2$-Phth | H | H | H |
| 3 | H | $—(CH_2)_2$-Phth | H | H |
| 4 | H | H | $—(CH_2)_2$-Phth | H |
| 5 | H | H | H | $—CH_3$ |
| 6 | H | H | H | $—COCH_3$ |
| 7 | $—(CH_2)_2$-Phth | $—(CH_2)_5—CH_3$ | H | H |
| 8 | H | $—(CH_2)_2$-Phth | $—(CH_2)_5—CH_3$ | H |
| 9 | $—(CH_2)_4$-Ph | $—(CH_2)_5—CH_3$ | H | H |
| 10 | $—(CH_2)_4—OH$ | $—(CH_2)_5—CH_3$ | H | H |
| 11 | H | $—(CH_2)_4—OH$ | H | H |
| 12 | H | H | $—(CH_2)_4—OH$ | H |
| 13 | $—(CH_2)_4—NH_2$ | H | H | H |
| 14 | H | $—(CH_2)_4—NH_2$ | H | H |

TABLE 35

(I-G-5)

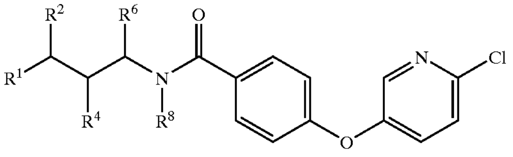

$R^1 = PO(OH)_2$

| No. | $R^2$ | $R^4$ | $R^6$ | $R^8$ |
|---|---|---|---|---|
| 1 | H | H | H | H |
| 2 | $—(CH_2)_2$-Phth | H | H | H |
| 3 | H | $—(CH_2)_2$-Phth | H | H |
| 4 | H | H | $—(CH_2)_2$-Phth | H |
| 5 | H | H | H | $—CH_3$ |
| 6 | H | H | H | $—COCH_3$ |
| 7 | $—(CH_2)_2$-Phth | $—(CH_2)_5—CH_3$ | H | |
| 8 | H | $—(CH_2)_2$-Phth | $—(CH_2)_5—CH_3$ | H |
| 9 | $—(CH_2)_4$-Ph | $—(CH_2)_5—CH_3$ | H | H |
| 10 | $—(CH_2)_4—OH$ | $—(CH_2)_5—CH_3$ | H | H |
| 11 | H | $—(CH_2)_4—OH$ | H | H |
| 12 | H | H | $—(CH_2)_4—OH$ | H |
| 13 | $—(CH_2)_4—NH_2$ | H | H | H |
| 14 | H | $—(CH_2)_4—NH_2$ | H | H |

TABLE 36

(I-H-1)

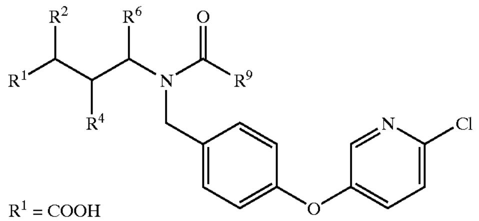

$R^1$ = COOH

| No. | $R^2$ | $R^4$ | $R^6$ | $R^9$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-OCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 37

(I-H-2)

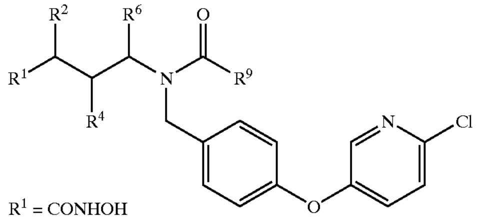

$R^1$ = CONHOH

| No. | $R^2$ | $R^4$ | $R^6$ | $R^9$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-OCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 38

(I-H-3)

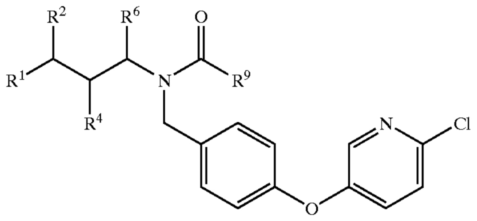

$R^1$ = $CONHNH_2$

| No. | $R^2$ | $R^4$ | $R^6$ | $R^9$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-OCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 39

(I-H-4)

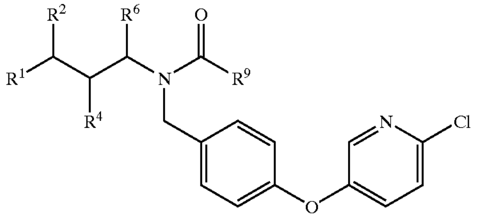

$R^1$ = $CH_2SH$

| No. | $R^2$ | $R^4$ | $R^6$ | $R^9$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-OCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 40

(I-H-5)

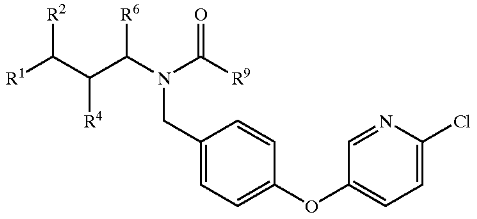

$R^1 = PO(OH)_2$

| No. | $R^2$ | $R^4$ | $R^6$ | $R^9$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-OCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 41

(I-J-1)

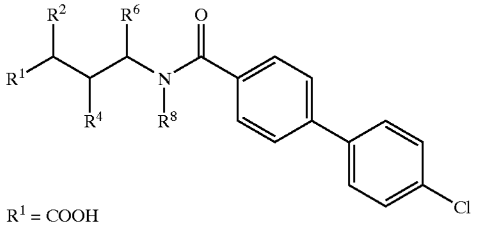

$R^1 = COOH$

| No. | $R^2$ | $R^4$ | $R^6$ | $R^8$ |
|---|---|---|---|---|
| 1 | H | H | H | H |
| 2 | $-(CH_2)_2$-Phth | H | H | H |
| 3 | H | $-(CH_2)_{2\text{-Phth}}$ | H | H |
| 4 | H | H | $-(CH_2)_2$-Phth | H |
| 5 | H | H | H | $-CH_3$ |
| 6 | H | H | H | $-COCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 42

(I-J-2)

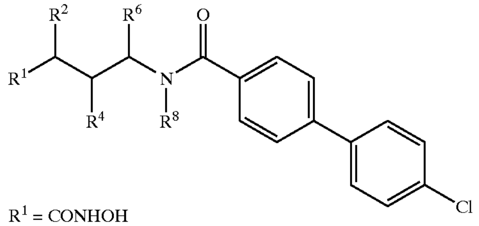

$R^1$ = CONHOH

| No. | $R^2$ | $R^4$ | $R^6$ | $R^8$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-COCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 43

(I-J-3)

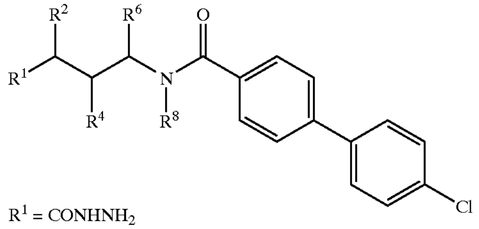

$R^1$ = $CONHNH_2$

| No. | $R^2$ | $R^4$ | $R^6$ | $R^8$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-COCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 44

(I-J-4)

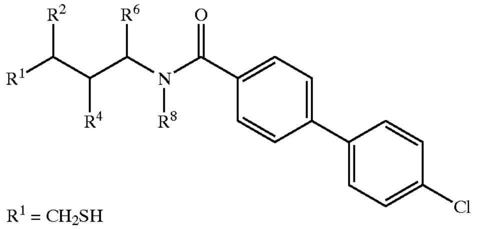

$R^1 = CH_2SH$

| No. | $R^2$ | $R^4$ | $R^6$ | $R^8$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-COCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 45

(I-J-5)

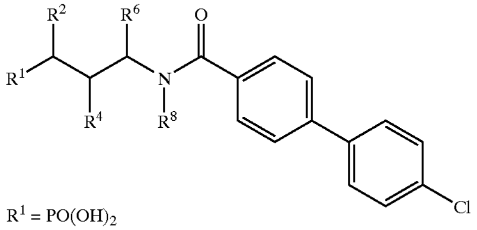

$R^1 = PO(OH)_2$

| No. | $R^2$ | $R^4$ | $R^6$ | $R^8$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-COCH_3$ |
| 7 | $-(CH_2)_2$-Phth | $-(CH_2)_5-CH_3$ | H | H |
| 8 | H | $-(CH_2)_4$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 46

(I-K-1)

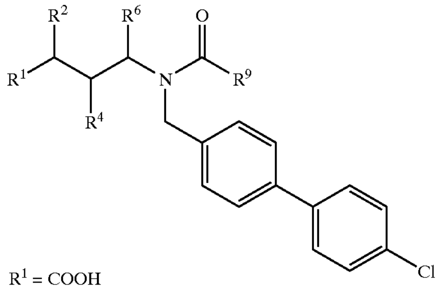

$R^1$ = COOH

| No. | $R^2$ | $R^4$ | $R^6$ | $R^9$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-OCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 47

(I-K-2)

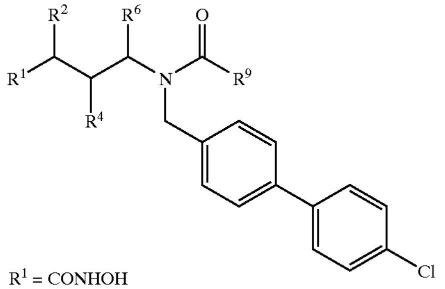

$R^1$ = CONHOH

| No. | $R^2$ | $R^4$ | $R^6$ | $R^9$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-OCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 48

(I-K-3)

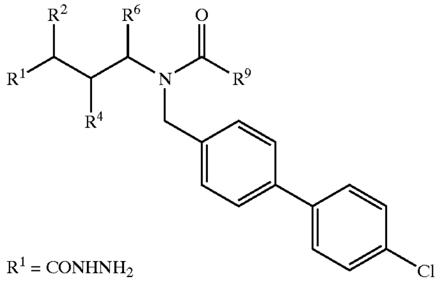

$R^1 = CONHNH_2$

| No. | $R^2$ | $R^4$ | $R^6$ | $R^9$ |
|---|---|---|---|---|
| 1 | H | H | H | H |
| 2 | $-(CH_2)_2-$Phth | H | H | H |
| 3 | H | $-(CH_2)_2-$Phth | H | H |
| 4 | H | H | $-(CH_2)_2-$Phth | H |
| 5 | H | H | H | $-CH_3$ |
| 6 | H | H | H | $-OCH_3$ |
| 7 | $-(CH_2)_2-$Phth | $-(CH_2)_5-CH_3$ | H | H |
| 8 | H | $-(CH_2)_2-$Phth | $-(CH_2)_5-CH_3$ | H |
| 9 | $-(CH_2)_4-$Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 49

(I-K-4)

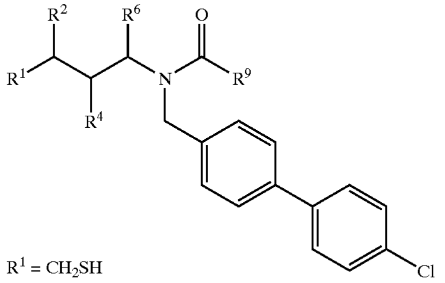

$R^1 = CH_2SH$

| No. | $R^2$ | $R^4$ | $R^6$ | $R^9$ |
|---|---|---|---|---|
| 1 | H | H | H | H |
| 2 | $-(CH_2)_2-$Phth | H | H | H |
| 3 | H | $-(CH_2)_2-$Phth | H | H |
| 4 | H | H | $-(CH_2)_2-$Phth | H |
| 5 | H | H | H | $-CH_3$ |
| 6 | H | H | H | $-OCH_3$ |
| 7 | $-(CH_2)_2-$Phth | $-(CH_2)_5-CH_3$ | H | H |
| 8 | H | $-(CH_2)_2-$Phth | $-(CH_2)_5-CH_3$ | H |
| 9 | $-(CH_2)_4-$Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 50

(I-K-5)

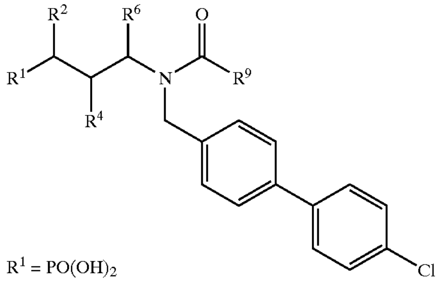

$R^1 = PO(OH)_2$

| No. | $R^2$ | $R^4$ | $R^6$ | $R^9$ |
|---|---|---|---|---|
| 1 | H | H | H | H |
| 2 | $-(CH_2)_2-$Phth | H | H | H |
| 3 | H | $-(CH_2)_2-$Phth | H | H |
| 4 | H | H | $-(CH_2)_2-$Phth | H |
| 5 | H | H | H | $-CH_3$ |
| 6 | H | H | H | $-OCH_3$ |
| 7 | $-(CH_2)_2-$Phth | $-(CH_2)_5-CH_3$ | H | H |
| 8 | H | $-(CH_2)_2-$Phth | $-(CH_2)_5-CH_3$ | H |
| 9 | $-(CH_2)_4-$Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 51

(I-L-1)

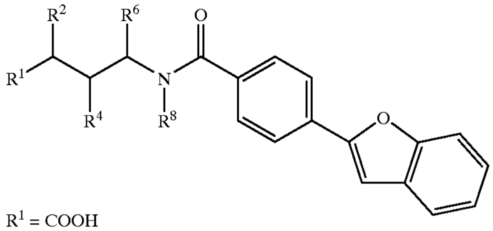

$R^1 = COOH$

| No. | $R^2$ | $R^4$ | $R^6$ | $R^8$ |
|---|---|---|---|---|
| 1 | H | H | H | H |
| 2 | $-(CH_2)_2-$Phth | H | H | H |
| 3 | H | $-(CH_2)_2-$Phth | H | H |
| 4 | H | H | $-(CH_2)_2-$Phth | H |
| 5 | H | H | H | $-CH_3$ |
| 6 | H | H | H | $-COCH_3$ |
| 7 | $-(CH_2)_2-$Phth | $-(CH_2)_5-CH_3$ | H | H |
| 8 | H | $-(CH_2)_2-$Phth | $-(CH_2)_5-CH_3$ | H |
| 9 | $-(CH_2)_4-$Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 52

(I-L-2)

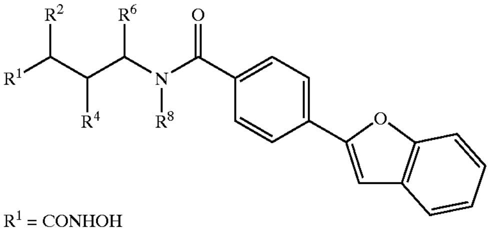

$R^1$ = CONHOH

| No. | $R^2$ | $R^4$ | $R^6$ | $R^8$ |
|---|---|---|---|---|
| 1 | H | H | H | H |
| 2 | $-(CH_2)_2-$Phth | H | H | H |
| 3 | H | $-(CH_2)_2-$Phth | H | H |
| 4 | H | H | $-(CH_2)_2-$Phth | H |
| 5 | H | H | H | $-CH_3$ |
| 6 | H | H | H | $-COCH_3$ |
| 7 | $-(CH_2)_2-$Phth | $-(CH_2)_5-CH_3$ | H | H |
| 8 | H | $-(CH_2)_2-$Phth | $-(CH_2)_5-CH_3$ | H |
| 9 | $-(CH_2)_4-$Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 53

(I-L-3)

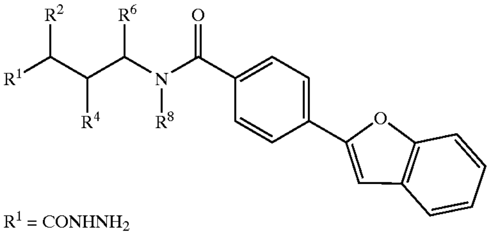

$R^1$ = $CONHNH_2$

| No. | $R^2$ | $R^4$ | $R^6$ | $R^8$ |
|---|---|---|---|---|
| 1 | H | H | H | H |
| 2 | $-(CH_2)_2-$Phth | H | H | H |
| 3 | H | $-(CH_2)_2-$Phth | H | H |
| 4 | H | H | $-(CH_2)_2-$Phth | H |
| 5 | H | H | H | $-CH_3$ |
| 6 | H | H | H | $-COCH_3$ |
| 7 | $-(CH_2)_2-$Phth | $-(CH_2)_5-CH_3$ | H | H |
| 8 | H | $-(CH_2)_2-$Phth | $-(CH_2)_5-CH_3$ | H |
| 9 | $-(CH_2)_4-$Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 54

(I-L-4)

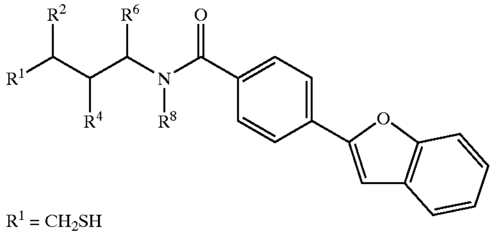

$R^1 = CH_2SH$

| No. | $R^2$ | $R^4$ | $R^6$ | $R^8$ |
|---|---|---|---|---|
| 1 | H | H | H | H |
| 2 | $-(CH_2)_2-$Phth | H | H | H |
| 3 | H | $-(CH_2)_2-$Phth | H | H |
| 4 | H | H | $-(CH_2)_2-$Phth | H |
| 5 | H | H | H | $-CH_3$ |
| 6 | H | H | H | $-COCH_3$ |
| 7 | $-(CH_2)_2-$Phth | $-(CH_2)_5-CH_3$ | H | H |
| 8 | H | $-(CH_2)_2-$Phth | $-(CH_2)_5-CH_3$ | H |
| 9 | $-(CH_2)_4-$Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 55

(I-L-5)

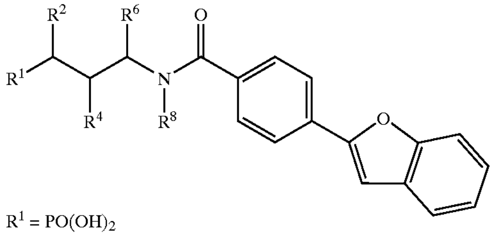

$R^1 = PO(OH)_2$

| No. | $R^2$ | $R^4$ | $R^6$ | $R^8$ |
|---|---|---|---|---|
| 1 | H | H | H | H |
| 2 | $-(CH_2)_2-$Phth | H | H | H |
| 3 | H | $-(CH_2)_2-$Phth | H | H |
| 4 | H | H | $-(CH_2)_2-$Phth | H |
| 5 | H | H | H | $-CH_3$ |
| 6 | H | H | H | $-COCH_3$ |
| 7 | $-(CH_2)_2-$Phth | $-(CH_2)_5-CH_3$ | H | H |
| 8 | H | $-(CH_2)_2-$Phth | $-(CH_2)_5-CH_3$ | H |
| 9 | $-(CH_2)_4-$Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 56

(I-M-1)

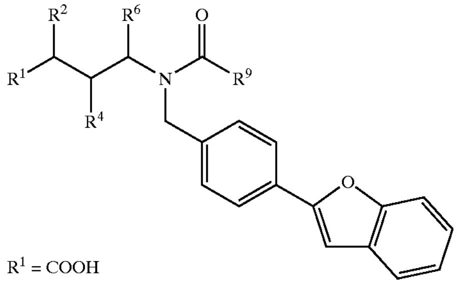

$R^1$ = COOH

| No. | $R^2$ | $R^4$ | $R^6$ | $R^9$ |
|---|---|---|---|---|
| 1 | H | H | H | H |
| 2 | $-(CH_2)_2$—Phth | H | H | H |
| 3 | H | $-(CH_2)_2$—Phth | H | H |
| 4 | H | H | $-(CH_2)_2$—Phth | H |
| 5 | H | H | H | $-CH_3$ |
| 6 | H | H | H | $-OCH_3$ |
| 7 | $-(CH_2)_2$—Phth | $-(CH_2)_5-CH_3$ | H | H |
| 8 | H | $-(CH_2)_2$—Phth | $-(CH_2)_5-CH_3$ | H |
| 9 | $-(CH_2)_4$—Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 57

(I-M-2)

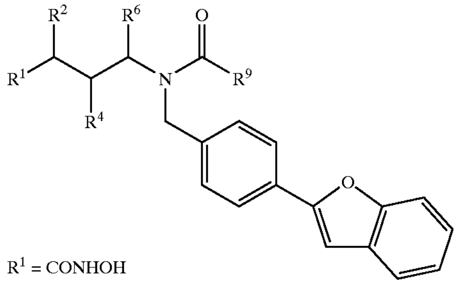

$R^1$ = CONHOH

| No. | $R^2$ | $R^4$ | $R^6$ | $R^9$ |
|---|---|---|---|---|
| 1 | H | H | H | H |
| 2 | $-(CH_2)_2$—Phth | H | H | H |
| 3 | H | $-(CH_2)_2$—Phth | H | H |
| 4 | H | H | $-(CH_2)_2$—Phth | H |
| 5 | H | H | H | $-CH_3$ |
| 6 | H | H | H | $-OCH_3$ |
| 7 | $-(CH_2)_2$—Phth | $-(CH_2)_5-CH_3$ | H | H |
| 8 | H | $-(CH_2)_2$—Phth | $-(CH_2)_5-CH_3$ | H |
| 9 | $-(CH_2)_4$—Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 58

(I-M-3)

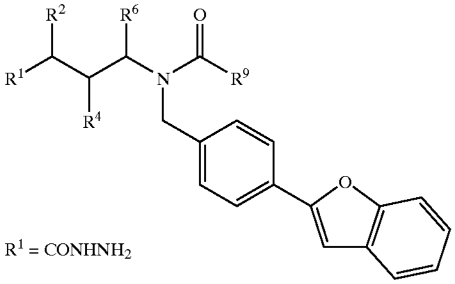

$R^1$ = $CONHNH_2$

| No. | $R^2$ | $R^4$ | $R^6$ | $R^9$ |
|---|---|---|---|---|
| 1 | H | H | H | H |
| 2 | $-(CH_2)_2-Phth$ | H | H | H |
| 3 | H | $-(CH_2)_2-Phth$ | H | H |
| 4 | H | H | $-(CH_2)_2-Phth$ | H |
| 5 | H | H | H | $-CH_3$ |
| 6 | H | H | H | $-OCH_3$ |
| 7 | $-(CH_2)_2-Phth$ | $-(CH_2)_5-CH_3$ | H | H |
| 8 | H | $-(CH_2)_2-Phth$ | $-(CH_2)_5-CH_3$ | H |
| 9 | $-(CH_2)_4-Ph$ | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-OH$ | H | H |

TABLE 59

(I-M-4)

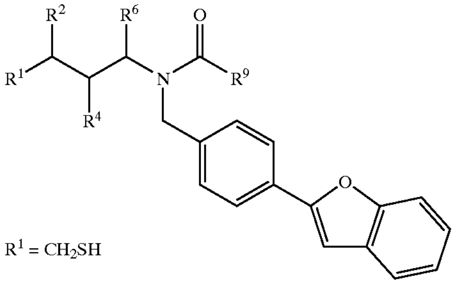

$R^1$ = $CH_2SH$

| No. | $R^2$ | $R^4$ | $R^6$ | $R^9$ |
|---|---|---|---|---|
| 1 | H | H | H | H |
| 2 | $-(CH_2)_2-Phth$ | H | H | H |
| 3 | H | $-(CH_2)_2-Phth$ | H | H |
| 4 | H | H | $-(CH_2)_2-Phth$ | H |
| 5 | H | H | H | $-CH_3$ |
| 6 | H | H | H | $-OCH_3$ |
| 7 | $-(CH_2)_2-Phth$ | $-(CH_2)_5-CH_3$ | H | H |
| 8 | H | $-(CH_2)_2-Phth$ | $-(CH_2)_5-CH_3$ | H |
| 9 | $-(CH_2)_4-Ph$ | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |

TABLE 59-continued (I-M-4)

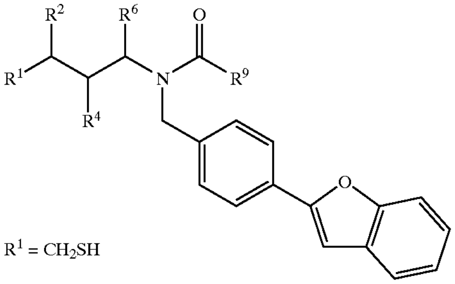

$R^1$ = $CH_2SH$

| No. | $R^2$ | $R^4$ | $R^6$ | $R^9$ |
|---|---|---|---|---|
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 60

(I-M-5)

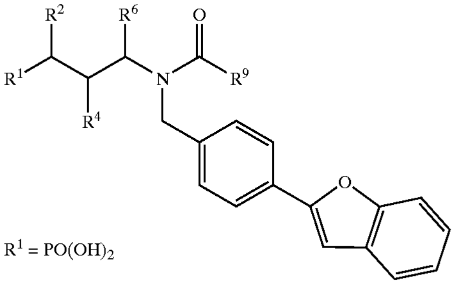

$R^1$ = $PO(OH)_2$

| No. | $R^2$ | $R^4$ | $R^6$ | $R^9$ |
|---|---|---|---|---|
| 1 | H | H | H | H |
| 2 | $-(CH_2)_2-Phth$ | H | H | H |
| 3 | H | $-(CH_2)_2-Phth$ | H | H |
| 4 | H | H | $-(CH_2)_2-Phth$ | H |
| 5 | H | H | H | $-CH_3$ |
| 6 | H | H | H | $-OCH_3$ |
| 7 | $-(CH_2)_2-Phth$ | $-(CH_2)_5-CH_3$ | H | H |
| 8 | H | $-(CH_2)_2-Phth$ | $-(CH_2)_5-CH_3$ | H |
| 9 | $-(CH_2)_4-Ph$ | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 61

(I-N-1)

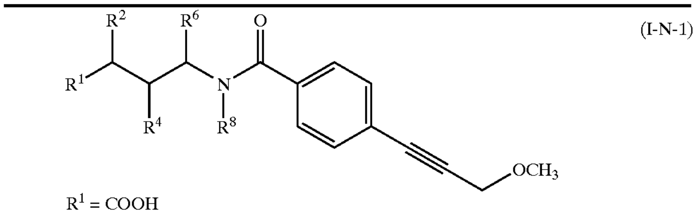

$R^1$ = COOH

| No. | $R^2$ | $R^4$ | $R^6$ | $R^8$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-COCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 62

(I-N-2)

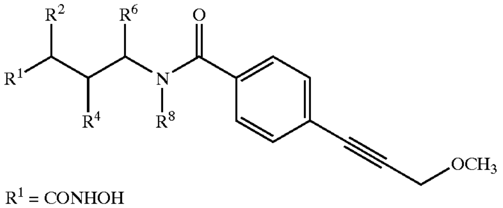

$R^1$ = CONHOH

| No. | $R^2$ | $R^4$ | $R^6$ | $R^8$ |
|---|---|---|---|---|
| 1 | H | H | H | H |
| 2 | $-(CH_2)_2$-Phth | H | H | H |
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-COCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 63

(I-N-3)

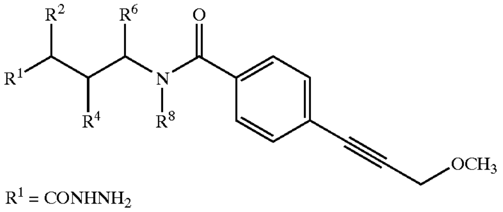

$R^1$ = $CONHNH_2$

| No. | $R^2$ | $R^4$ | $R^6$ | $R^8$ |
|---|---|---|---|---|
| 1 | H | H | H | H |
| 2 | $-(CH_2)_2$-Phth | H | H | H |

TABLE 63-continued (I-N-3)

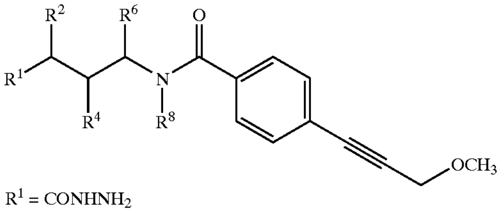

$R^1$ = CONHNH$_2$

| No. | $R^2$ | $R^4$ | $R^6$ | $R^8$ |
|---|---|---|---|---|
| 3 | H | $-(CH_2)_2$-Phth | H | H |
| 4 | H | H | $-(CH_2)_2$-Phth | H |
| 5 | H | H | H | $-CH_3$ |
| 6 | H | H | H | $-COCH_3$ |
| 7 | $-(CH_2)_2$-Phth | $-(CH_2)_5-CH_3$ | H | H |
| 8 | H | $-(CH_2)_2$-Phth | $-(CH_2)_5-CH_3$ | H |
| 9 | $-(CH_2)_4$-Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 64

(I-N-4)

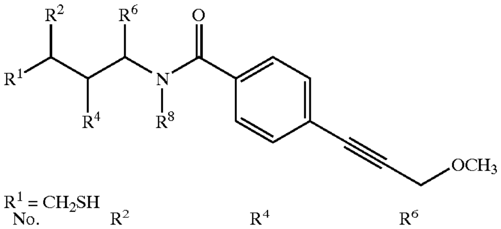

$R^1$ = CH$_2$SH

| No. | $R^2$ | $R^4$ | $R^6$ | $R^8$ |
|---|---|---|---|---|
| 1 | H | H | H | H |
| 2 | $-(CH_2)_2-$Phth | H | H | H |
| 3 | H | $-(CH_2)_2-$Phth | H | H |
| 4 | H | H | $-(CH_2)_2-$Phth | H |
| 5 | H | H | H | $-CH_3$ |
| 6 | H | H | H | $-COCH_3$ |
| 7 | $-(CH_2)_2-$Phth | $-(CH_2)_5-CH_3$ | H | H |
| 8 | H | $-(CH_2)_2-$Phth | $-(CH_2)_5-CH_3$ | H |
| 9 | $-(CH_2)_4-$Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 65

(I-N-5)

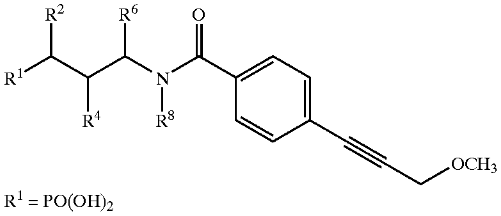

$R^1$ = PO(OH)$_2$

| No. | $R^2$ | $R^4$ | $R^6$ | $R^8$ |
|---|---|---|---|---|
| 1 | H | H | H | H |
| 2 | $-(CH_2)_2-$Phth | H | H | H |
| 3 | H | $-(CH_2)_2-$Phth | H | H |
| 4 | H | H | $-(CH_2)_2-$Phth | H |

TABLE 65-continued (I-N-5)

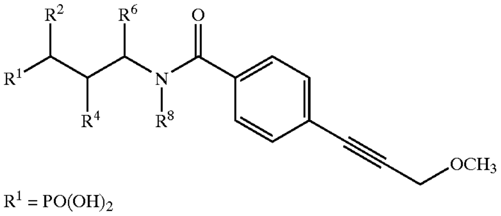

$R^1$ = PO(OH)$_2$

| No. | $R^2$ | $R^4$ | $R^6$ | $R^8$ |
|---|---|---|---|---|
| 5 | H | H | H | $-CH_3$ |
| 6 | H | H | H | $-COCH_3$ |
| 7 | $-(CH_2)_2-$Phth | $-(CH_2)_5-CH_3$ | H | H |
| 8 | H | $-(CH_2)_2-$Phth | $-(CH_2)_5-CH_3$ | H |
| 9 | $-(CH_2)_4-$Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 66

(I-O-1)

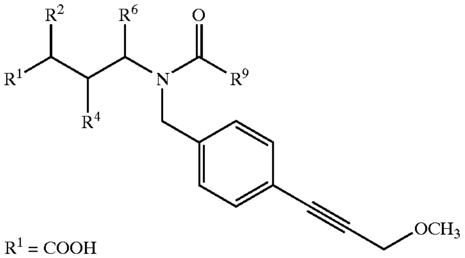

$R^1$ = COOH

| No. | $R^2$ | $R^4$ | $R^6$ | $R^9$ |
|---|---|---|---|---|
| 1 | H | H | H | H |
| 2 | $-(CH_2)_2-$Phth | H | H | H |
| 3 | H | $-(CH_2)_2-$Phth | H | H |

TABLE 66-continued (I-O-1)

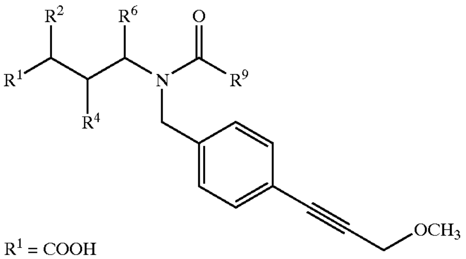

$R^1$ = COOH

| No. | $R^2$ | $R^4$ | $R^6$ | $R^9$ |
|---|---|---|---|---|
| 4 | H | H | $—(CH_2)_2—Phth$ | H |
| 5 | H | H | H | $—CH_3$ |
| 6 | H | H | H | $—OCH_3$ |
| 7 | $—(CH_2)_2—Phth$ | $—(CH_2)_5—CH_3$ | H | H |
| 8 | H | $—(CH_2)_2—Phth$ | $—(CH_2)_5—CH_3$ | H |
| 9 | $—(CH_2)_4—Ph$ | $—(CH_2)_5—CH_3$ | H | H |
| 10 | $—(CH_2)_4—OH$ | $—(CH_2)_5—CH_3$ | H | H |
| 11 | H | $—(CH_2)_4—OH$ | H | H |
| 12 | H | H | $—(CH_2)_4—OH$ | H |
| 13 | $—(CH_2)_4—NH_2$ | H | H | H |
| 14 | H | $—(CH_2)_4—NH_2$ | H | H |

TABLE 67

(I-O-2)

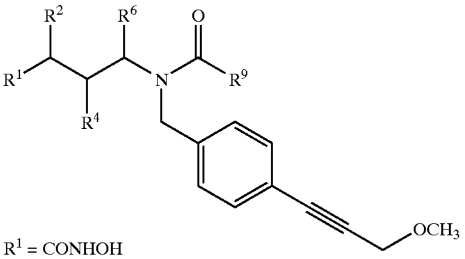

$R^1$ = CONHOH

| No. | $R^2$ | $R^4$ | $R^6$ | $R^9$ |
|---|---|---|---|---|
| 1 | H | H | H | H |
| 2 | $—(CH_2)_2—Phth$ | H | H | H |
| 3 | H | $—(CH_2)_2—Phth$ | H | H |
| 4 | H | H | $—(CH_2)_2—Phth$ | H |
| 5 | H | H | H | $—CH_3$ |
| 6 | H | H | H | $—OCH_3$ |
| 7 | $—(CH_2)_2—Phth$ | $—(CH_2)_5—CH_3$ | H | H |
| 8 | H | $—(CH_2)_2—Phth$ | $—(CH_2)_5—CH_3$ | H |
| 9 | $—(CH_2)_4—Ph$ | $—(CH_2)_5—CH_3$ | H | H |
| 10 | $—(CH_2)_4—OH$ | $—(CH_2)_5—CH_3$ | H | H |
| 11 | H | $—(CH_2)_4—OH$ | H | H |
| 12 | H | H | $—(CH_2)_4—OH$ | H |
| 13 | $—(CH_2)_4—NH_2$ | H | H | H |
| 14 | H | $—(CH_2)_4—NH_2$ | H | H |

TABLE 68

(I-O-3)

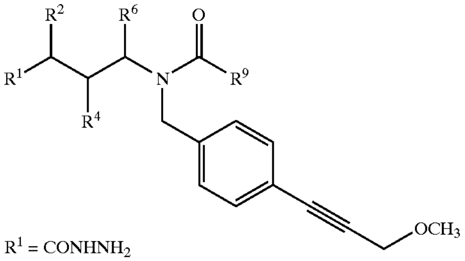

$R^1$ = $CONHNH_2$

| No. | $R^2$ | $R^4$ | $R^6$ | $R^9$ |
|---|---|---|---|---|
| 1 | H | H | H | H |
| 2 | $—(CH_2)_2—Phth$ | H | H | H |
| 3 | H | $—(CH_2)_2—Phth$ | H | H |
| 4 | H | H | $—(CH_2)_2—Phth$ | H |
| 5 | H | H | H | $—CH_3$ |
| 6 | H | H | H | $—OCH_3$ |
| 7 | $—(CH_2)_2—Phth$ | $—(CH_2)_5—CH_3$ | H | H |
| 8 | H | $—(CH_2)_2—Phth$ | $—(CH_2)_5—CH_3$ | H |
| 9 | $—(CH_2)_4—Ph$ | $—(CH_2)_5—CH_3$ | H | H |
| 10 | $—(CH_2)_4—OH$ | $—(CH_2)_5—CH_3$ | H | H |
| 11 | H | $—(CH_2)_4—OH$ | H | H |
| 12 | H | H | $—(CH_2)_4—OH$ | H |
| 13 | $—(CH_2)_4—NH_2$ | H | H | H |
| 14 | H | $—(CH_2)_4—NH_2$ | H | H |

TABLE 69

(I-O-4)

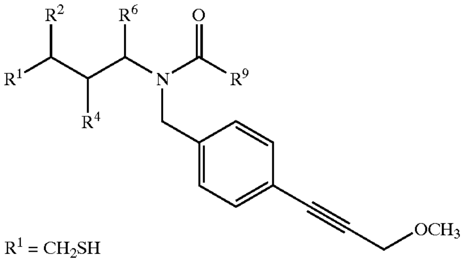

$R^1$ = $CH_2SH$

| No. | $R^2$ | $R^4$ | $R^6$ | $R^9$ |
|---|---|---|---|---|
| 1 | H | H | H | H |
| 2 | $—(CH_2)_2—Phth$ | H | H | H |
| 3 | H | $—(CH_2)_2—Phth$ | H | H |
| 4 | H | H | $—(CH_2)_2—Phth$ | H |
| 5 | H | H | H | $—CH_3$ |
| 6 | H | H | H | $—OCH_3$ |
| 7 | $—(CH_2)_2—Phth$ | $—(CH_2)_5—CH_3$ | H | H |
| 8 | H | $—(CH_2)_2—Phth$ | $—(CH_2)_5—CH_3$ | H |
| 9 | $—(CH_2)_4—Ph$ | $—(CH_2)_5—CH_3$ | H | H |
| 10 | $—(CH_2)_4—OH$ | $—(CH_2)_5—CH_3$ | H | H |
| 11 | H | $—(CH_2)_4—OH$ | H | H |
| 12 | H | H | $—(CH_2)_4—OH$ | H |
| 13 | $—(CH_2)_4—NH_2$ | H | H | H |
| 14 | H | $—(CH_2)_4—NH_2$ | H | H |

TABLE 70

(I-O-5)

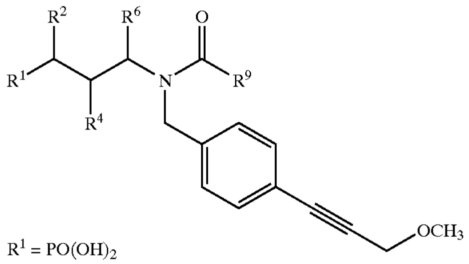

$R^1 = PO(OH)_2$

| No. | $R^2$ | $R^4$ | $R^6$ | $R^9$ |
|---|---|---|---|---|
| 1 | H | H | H | H |
| 2 | $-(CH_2)_2-$Phth | H | H | H |
| 3 | H | $-(CH_2)_2-$Phth | H | H |
| 4 | H | H | $-(CH_2)_2-$Phth | H |
| 5 | H | H | H | $-CH_3$ |
| 6 | H | H | H | $-OCH_3$ |
| 7 | $-(CH_2)_2-$Phth | $-(CH_2)_5-CH_3$ | H | H |
| 8 | H | $-(CH_2)_2-$Phth | $-(CH_2)_5-CH_3$ | H |
| 9 | $-(CH_2)_4-$Ph | $-(CH_2)_5-CH_3$ | H | H |
| 10 | $-(CH_2)_4-OH$ | $-(CH_2)_5-CH_3$ | H | H |
| 11 | H | $-(CH_2)_4-OH$ | H | H |
| 12 | H | H | $-(CH_2)_4-OH$ | H |
| 13 | $-(CH_2)_4-NH_2$ | H | H | H |
| 14 | H | $-(CH_2)_4-NH_2$ | H | H |

TABLE 71

(I-P1-1)

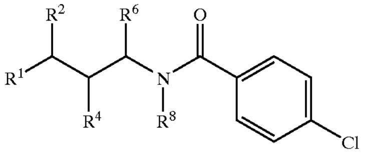

$R^1$ = COOH

| No. | $R^2$ | $R^4$ | $R^6$ | $R^8$ |
|---|---|---|---|---|
| 1 | $-CH_3$ | H | $-CH_2-$O-EOM | H |
| 2 | 2-propenyl | H | $-CH_2-$O-EOM | H |
| 3 | 2-propynyl | H | $-CH_2-$O-EOM | H |
| 4 | MOM | H | $-CH_2-$O-EOM | H |
| 5 | EOM | H | $-CH_2-$O-EOM | H |
| 6 | MEM | H | $-CH_2-$O-EOM | H |
| 7 | BOM | H | $-CH_2-$O-EOM | H |
| 8 | $-CH_3$ | H | $-CH_2-$O-EOM | $-CH_3$ |
| 9 | 2-propenyl | H | $-CH_2-$O-EOM | $-CH_3$ |
| 10 | 2-propynyl | H | $-CH_2-$O-EOM | $-CH_3$ |
| 11 | MOM | H | $-CH_2-$O-EOM | $-CH_3$ |
| 12 | EOM | H | $-CH_2-$O-EOM | $-CH_3$ |
| 13 | MEM | H | $-CH_2-$O-EOM | $-CH_3$ |
| 14 | BOM | H | $-CH_2-$O-EOM | $-CH_3$ |

TABLE 72

(I-P1-2)

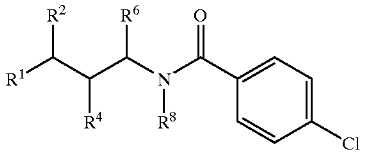

$R^1$ = CONHOH

| No. | $R^2$ | $R^4$ | $R^6$ | $R^8$ |
|---|---|---|---|---|
| 1 | $-CH_3$ | H | $-CH_2-$O-EOM | H |
| 2 | 2-propenyl | H | $-CH_2-$O-EOM | H |
| 3 | 2-propynyl | H | $-CH_2-$O-EOM | H |
| 4 | MOM | H | $-CH_2-$O-EOM | H |
| 5 | EOM | H | $-CH_2-$O-EOM | H |
| 6 | MEM | H | $-CH_2-$O-EOM | H |
| 7 | BOM | H | $-CH_2-$O-EOM | H |
| 8 | $-CH_3$ | H | $-CH_2-$O-EOM | $-CH_3$ |
| 9 | 2-propenyl | H | $-CH_2-$O-EOM | $-CH_3$ |
| 10 | 2-propynyl | H | $-CH_2-$O-EOM | $-CH_3$ |
| 11 | MOM | H | $-CH_2-$O-EOM | $-CH_3$ |
| 12 | EOM | H | $-CH_2-$O-EOM | $-CH_3$ |
| 13 | MEM | H | $-CH_2-$O-EOM | $-CH_3$ |
| 14 | BOM | H | $-CH_2-$O-EOM | $-CH_3$ |

TABLE 73

(I-P1-3)

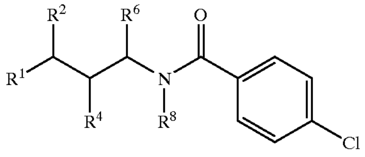

$R^1 = CONHNH_2$

| No. | $R^2$ | $R^4$ | $R^6$ | $R^8$ |
|---|---|---|---|---|
| 1 | $-CH_3$ | H | $-CH_2-$O-EOM | H |
| 2 | 2-propenyl | H | $-CH_2-$O-EOM | H |
| 3 | 2-propynyl | H | $-CH_2-$O-EOM | H |
| 4 | MOM | H | $-CH_2-$O-EOM | H |
| 5 | EOM | H | $-CH_2-$O-EOM | H |
| 6 | MEM | H | $-CH_2-$O-EOM | H |
| 7 | BOM | H | $-CH_2-$O-EOM | H |
| 8 | $-CH_3$ | H | $-CH_2-$O-EOM | $-CH_3$ |
| 9 | 2-propenyl | H | $-CH_2-$O-EOM | $-CH_3$ |
| 10 | 2-propynyl | H | $-CH_2-$O-EOM | $-CH_3$ |
| 11 | MOM | H | $-CH_2-$O-EOM | $-CH_3$ |
| 12 | EOM | H | $-CH_2-$O-EOM | $-CH_3$ |
| 13 | MEM | H | $-CH_2-$O-EOM | $-CH_3$ |
| 14 | BOM | H | $-CH_2-$O-EOM | $-CH_3$ |

TABLE 74

(I-P1-4)

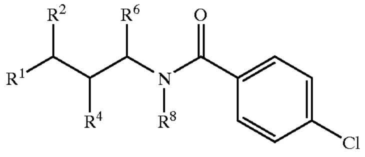

$R^1 = CH_2SH$

| No. | $R^2$ | $R^4$ | $R^6$ | $R^8$ |
|---|---|---|---|---|
| 1 | $-CH_3$ | H | $-CH_2-$O-EOM | H |
| 2 | 2-propenyl | H | $-CH_2-$O-EOM | H |

TABLE 74-continued (I-P1-4)

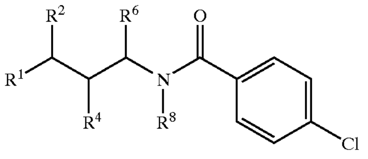

$R^1 = CH_2SH$

| No. | $R^2$ | $R^4$ | $R^6$ | $R^8$ |
|---|---|---|---|---|
| 3 | 2-propynyl | H | $—CH_2—O-EOM$ | H |
| 4 | MOM | H | $—CH_2—O-EOM$ | H |
| 5 | EOM | H | $—CH_2—O-EOM$ | H |
| 6 | MEM | H | $—CH_2—O-EOM$ | H |
| 7 | BOM | H | $—CH_2—O-EOM$ | H |
| 8 | $—CH_3$ | H | $—CH_2—O-EOM$ | $—CH_3$ |
| 9 | 2-propenyl | H | $—CH_2—O-EOM$ | $—CH_3$ |
| 10 | 2-propynyl | H | $—CH_2—O-EOM$ | $—CH_3$ |
| 11 | MOM | H | $—CH_2—O-EOM$ | $—CH_3$ |
| 12 | EOM | H | $—CH_2—O-EOM$ | $—CH_3$ |
| 13 | MEM | H | $—CH_2—O-EOM$ | $—CH_3$ |
| 14 | BOM | H | $—CH_2—O-EOM$ | $—CH_3$ |

TABLE 75

(I-P1-5)

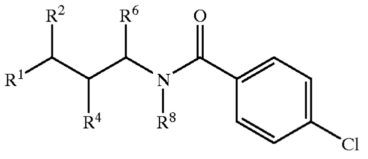

$R^1 = PO(OH)_2$

| No. | $R^2$ | $R^4$ | $R^6$ | $R^8$ |
|---|---|---|---|---|
| 1 | $—CH_3$ | H | $—CH_2—O-EOM$ | H |
| 2 | 2-propenyl | H | $—CH_2—O-EOM$ | H |
| 3 | 2-propynyl | H | $—CH_2—O-EOM$ | H |
| 4 | MOM | H | $—CH_2—O-EOM$ | H |
| 5 | EOM | H | $—CH_2—O-EOM$ | H |
| 6 | MEM | H | $—CH_2—O-EOM$ | H |
| 7 | BOM | H | $—CH_2—O-EOM$ | H |
| 8 | $—CH_3$ | H | $—CH_2—O-EOM$ | $—CH_3$ |
| 9 | 2-propenyl | H | $—CH_2—O-EOM$ | $—CH_3$ |
| 10 | 2-propynyl | H | $—CH_2—O-EOM$ | $—CH_3$ |
| 11 | MOM | H | $—CH_2—O-EOM$ | $—CH_3$ |
| 12 | EOM | H | $—CH_2—O-EOM$ | $—CH_3$ |
| 13 | MEM | H | $—CH_2—O-EOM$ | $—CH_3$ |
| 14 | BOM | H | $—CH_2—O-EOM$ | $—CH_3$ |

TABLE 76

(I-P2-1)

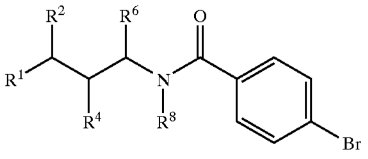

$R^1 = COOH$

| No. | $R^2$ | $R^4$ | $R^6$ | $R^8$ |
|---|---|---|---|---|
| 1 | $—CH_3$ | H | $—CH_2—O-EOM$ | H |
| 2 | 2-propenyl | H | $—CH_2—O-EOM$ | H |
| 3 | 2-propynyl | H | $—CH_2—O-EOM$ | H |
| 4 | MOM | H | $—CH_2—O-EOM$ | H |

TABLE 76-continued (I-P2-1)

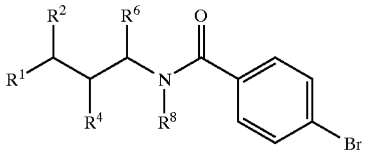

$R^1 = COOH$

| No. | $R^2$ | $R^4$ | $R^6$ | $R^8$ |
|---|---|---|---|---|
| 5 | EOM | H | $—CH_2—O-EOM$ | H |
| 6 | MEM | H | $—CH_2—O-EOM$ | H |
| 7 | BOM | H | $—CH_2—O-EOM$ | H |
| 8 | $—CH_3$ | H | $—CH_2—O-EOM$ | $—CH_3$ |
| 9 | 2-propenyl | H | $—CH_2—O-EOM$ | $—CH_3$ |
| 10 | 2-propynyl | H | $—CH_2—O-EOM$ | $—CH_3$ |
| 11 | MOM | H | $—CH_2—O-EOM$ | $—CH_3$ |
| 12 | EOM | H | $—CH_2—O-EOM$ | $—CH_3$ |
| 13 | MEM | H | $—CH_2—O-EOM$ | $—CH_3$ |
| 14 | BOM | H | $—CH_2—O-EOM$ | $—CH_3$ |

TABLE 77

(I-P2-2)

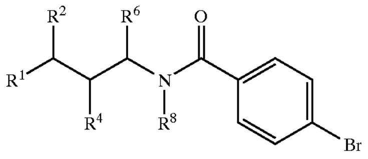

$R^1 = CONHOH$

| No. | $R^2$ | $R^4$ | $R^6$ | $R^8$ |
|---|---|---|---|---|
| 1 | $—CH_3$ | H | $—CH_2—O-EOM$ | H |
| 2 | 2-propenyl | H | $—CH_2—O-EOM$ | H |
| 3 | 2-propynyl | H | $—CH_2—O-EOM$ | H |
| 4 | MOM | H | $—CH_2—O-EOM$ | H |
| 5 | EOM | H | $—CH_2—O-EOM$ | H |
| 6 | MEM | H | $—CH_2—O-EOM$ | H |
| 7 | BOM | H | $—CH_2—O-EOM$ | H |
| 8 | $—CH_3$ | H | $—CH_2—O-EOM$ | $—CH_3$ |
| 9 | 2-propenyl | H | $—CH_2—O-EOM$ | $—CH_3$ |
| 10 | 2-propynyl | H | $—CH_2—O-EOM$ | $—CH_3$ |
| 11 | MOM | H | $—CH_2—O-EOM$ | $—CH_3$ |
| 12 | EOM | H | $—CH_2—O-EOM$ | $—CH_3$ |
| 13 | MEM | H | $—CH_2—O-EOM$ | $—CH_3$ |
| 14 | BOM | H | $—CH_2—O-EOM$ | $—CH_3$ |

TABLE 78

(I-P2-3)

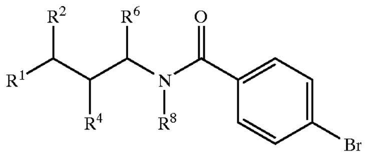

$R^1 = CONHNH_2$

| No. | $R^2$ | $R^4$ | $R^6$ | $R^8$ |
|---|---|---|---|---|
| 1 | $—CH_3$ | H | $—CH_2—O-EOM$ | H |
| 2 | 2-propenyl | H | $—CH_2—O-EOM$ | H |
| 3 | 2-propynyl | H | $—CH_2—O-EOM$ | H |
| 4 | MOM | H | $—CH_2—O-EOM$ | H |
| 5 | EOM | H | $—CH_2—O-EOM$ | H |
| 6 | MEM | H | $—CH_2—O-EOM$ | H |

TABLE 78-continued (I-P2-3)

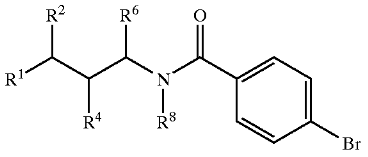

$R^1 = CONHNH_2$

| No. | $R^2$ | $R^4$ | $R^6$ | $R^8$ |
|---|---|---|---|---|
| 7 | BOM | H | —$CH_2$—O-EOM | H |
| 8 | —$CH_3$ | H | —$CH_2$—O-EOM | —$CH_3$ |
| 9 | 2-propenyl | H | —$CH_2$—O-EOM | —$CH_3$ |
| 10 | 2-propynyl | H | —$CH_2$—O-EOM | —$CH_3$ |
| 11 | MOM | H | —$CH_2$—O-EOM | —$CH_3$ |
| 12 | EOM | H | —$CH_2$—O-EOM | —$CH_3$ |
| 13 | MEM | H | —$CH_2$—O-EOM | —$CH_3$ |
| 14 | BOM | H | —$CH_2$—O-EOM | —$CH_3$ |

TABLE 79

(I-P2-4)

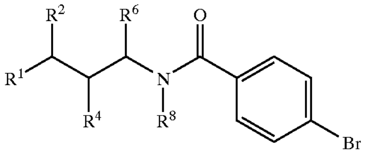

$R^1 = CH_2SH$

| No. | $R^2$ | $R^4$ | $R^6$ | $R^8$ |
|---|---|---|---|---|
| 1 | —$CH_3$ | H | —$CH_2$—O-EOM | H |
| 2 | 2-propenyl | H | —$CH_2$—O-EOM | H |
| 3 | 2-propynyl | H | —$CH_2$—O-EOM | H |
| 4 | MOM | H | —$CH_2$—O-EOM | H |
| 5 | EOM | H | —$CH_2$—O-EOM | H |
| 6 | MEM | H | —$CH_2$—O-EOM | H |
| 7 | BOM | H | —$CH_2$—O-EOM | H |
| 8 | —$CH_3$ | H | —$CH_2$—O-EOM | —$CH_3$ |
| 9 | 2-propenyl | H | —$CH_2$—O-EOM | —$CH_3$ |
| 10 | 2-propynyl | H | —$CH_2$—O-EOM | —$CH_3$ |
| 11 | MOM | H | —$CH_2$—O-EOM | —$CH_3$ |
| 12 | EOM | H | —$CH_2$—O-EOM | —$CH_3$ |
| 13 | MEM | H | —$CH_2$—O-EOM | —$CH_3$ |
| 14 | BOM | H | —$CH_2$—O-EOM | —$CH_3$ |

TABLE 80

(I-P2-5)

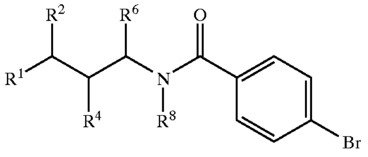

$R^1 = PO(OH)_2$

| No. | $R^2$ | $R^4$ | $R^6$ | $R^8$ |
|---|---|---|---|---|
| 1 | —$CH_3$ | H | —$CH_2$—O-EOM | H |
| 2 | 2-propenyl | H | —$CH_2$—O-EOM | H |
| 3 | 2-propynyl | H | —$CH_2$—O-EOM | H |
| 4 | MOM | H | —$CH_2$—O-EOM | H |
| 5 | EOM | H | —$CH_2$—O-EOM | H |
| 6 | MEM | H | —$CH_2$—O-EOM | H |
| 7 | BOM | H | —$CH_2$—O-EOM | H |
| 8 | —$CH_3$ | H | —$CH_2$—O-EOM | —$CH_3$ |

TABLE 80-continued (I-P2-5)

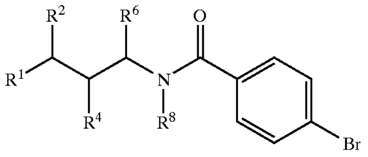

$R^1 = PO(OH)_2$

| No. | $R^2$ | $R^4$ | $R^6$ | $R^8$ |
|---|---|---|---|---|
| 9 | 2-propenyl | H | —$CH_2$—O-EOM | —$CH_3$ |
| 10 | 2-propynyl | H | —$CH_2$—O-EOM | —$CH_3$ |
| 11 | MOM | H | —$CH_2$—O-EOM | —$CH_3$ |
| 12 | EOM | H | —$CH_2$—O-EOM | —$CH_3$ |
| 13 | MEM | H | —$CH_2$—O-EOM | —$CH_3$ |
| 14 | BOM | H | —$CH_2$—O-EOM | —$CH_3$ |

TABLE 81

(I-P3-1)

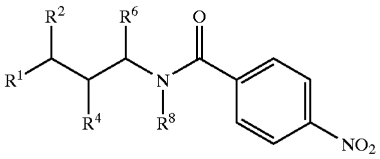

$R^1 = COOH$

| No. | $R^2$ | $R^4$ | $R^6$ | $R^8$ |
|---|---|---|---|---|
| 1 | —$CH_3$ | H | —$CH_2$—O-EOM | H |
| 2 | 2-propenyl | H | —$CH_2$—O-EOM | H |
| 3 | 2-propynyl | H | —$CH_2$—O-EOM | H |
| 4 | MOM | H | —$CH_2$—O-EOM | H |
| 5 | EOM | H | —$CH_2$—O-EOM | H |
| 6 | MEM | H | —$CH_2$—O-EOM | H |
| 7 | BOM | H | —$CH_2$—O-EOM | H |
| 8 | —$CH_3$ | H | —$CH_2$—O-EOM | —$CH_3$ |
| 9 | 2-propenyl | H | —$CH_2$—O-EOM | —$CH_3$ |
| 10 | 2-propynyl | H | —$CH_2$—O-EOM | —$CH_3$ |
| 11 | MOM | H | —$CH_2$—O-EOM | —$CH_3$ |
| 12 | EOM | H | —$CH_2$—O-EOM | —$CH_3$ |
| 13 | MEM | H | —$CH_2$—O-EOM | —$CH_3$ |
| 14 | BOM | H | —$CH_2$—O-EOM | —$CH_3$ |

TABLE 82

(I-P3-2)

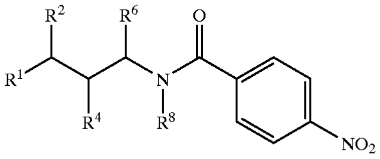

$R^1 = CONHOH$

| No. | $R^2$ | $R^4$ | $R^6$ | $R^8$ |
|---|---|---|---|---|
| 1 | —$CH_3$ | H | —$CH_2$—O-EOM | H |
| 2 | 2-propenyl | H | —$CH_2$—O-EOM | H |
| 3 | 2-propynyl | H | —$CH_2$—O-EOM | H |
| 4 | MOM | H | —$CH_2$—O-EOM | H |
| 5 | EOM | H | —$CH_2$—O-EOM | H |
| 6 | MEM | H | —$CH_2$—O-EOM | H |
| 7 | BOM | H | —$CH_2$—O-EOM | H |
| 8 | —$CH_3$ | H | —$CH_2$—O-EOM | —$CH_3$ |
| 9 | 2-propenyl | H | —$CH_2$—O-EOM | —$CH_3$ |
| 10 | 2-propynyl | H | —$CH_2$—O-EOM | —$CH_3$ |

TABLE 82-continued (I-P3-2)

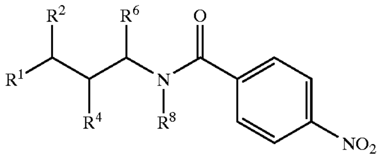

$R^1$ = CONHOH

| No. | $R^2$ | $R^4$ | $R^6$ | $R^8$ |
|---|---|---|---|---|
| 11 | MOM | H | $—CH_2—$O-EOM | $—CH_3$ |
| 12 | EOM | H | $—CH_2—$O-EOM | $—CH_3$ |
| 13 | MEM | H | $—CH_2—$O-EOM | $—CH_3$ |
| 14 | BOM | H | $—CH_2—$O-EOM | $—CH_3$ |

TABLE 83

(I-P3-3)

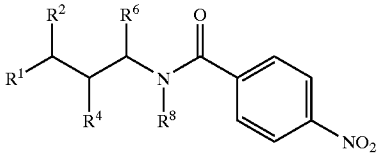

$R^1$ = $CONHNH_2$

| No. | $R^2$ | $R^4$ | $R^6$ | $R^8$ |
|---|---|---|---|---|
| 1 | $—CH_3$ | H | $—CH_2—$O-EOM | H |
| 2 | 2-propenyl | H | $—CH_2—$O-EOM | H |
| 3 | 2-propynyl | H | $—CH_2—$O-EOM | H |
| 4 | MOM | H | $—CH_2—$O-EOM | H |
| 5 | EOM | H | $—CH_2—$O-EOM | H |
| 6 | MEM | H | $—CH_2—$O-EOM | H |
| 7 | BOM | H | $—CH_2—$O-EOM | H |
| 8 | $—CH_3$ | H | $—CH_2—$O-EOM | $—CH_3$ |
| 9 | 2-propenyl | H | $—CH_2—$O-EOM | $—CH_3$ |
| 10 | 2-propynyl | H | $—CH_2—$O-EOM | $—CH_3$ |
| 11 | MOM | H | $—CH_2—$O-EOM | $—CH_3$ |
| 12 | EOM | H | $—CH_2—$O-EOM | $—CH_3$ |
| 13 | MEM | H | $—CH_2—$O-EOM | $—CH_3$ |
| 14 | BOM | H | $—CH_2—$O-EOM | $—CH_3$ |

TABLE 84

(I-P3-4)

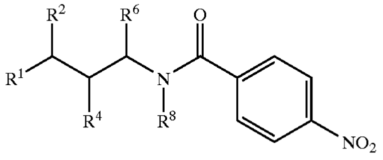

$R^1$ = $CH_2SH$

| No. | $R^2$ | $R^4$ | $R^6$ | $R^8$ |
|---|---|---|---|---|
| 1 | $—CH_3$ | H | $—CH_2—$O-EOM | H |
| 2 | 2-propenyl | H | $—CH_2—$O-EOM | H |
| 3 | 2-propynyl | H | $—CH_2—$O-EOM | H |
| 4 | MOM | H | $—CH_2—$O-EOM | H |
| 5 | EOM | H | $—CH_2—$O-EOM | H |
| 6 | MEM | H | $—CH_2—$O-EOM | H |
| 7 | BOM | H | $—CH_2—$O-EOM | H |
| 8 | $—CH_3$ | H | $—CH_2—$O-EOM | $—CH_3$ |
| 9 | 2-propenyl | H | $—CH_2—$O-EOM | $—CH_3$ |
| 10 | 2-propynyl | H | $—CH_2—$O-EOM | $—CH_3$ |
| 11 | MOM | H | $—CH_2—$O-EOM | $—CH_3$ |
| 12 | EOM | H | $—CH_2—$O-EOM | $—CH_3$ |

TABLE 84-continued (I-P3-4)

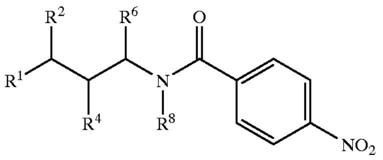

$R^1$ = $CH_2SH$

| No. | $R^2$ | $R^4$ | $R^6$ | $R^8$ |
|---|---|---|---|---|
| 13 | MEM | H | $—CH_2—$O-EOM | $—CH_3$ |
| 14 | BOM | H | $—CH_2—$O-EOM | $—CH_3$ |

TABLE 85

(I-P3-5)

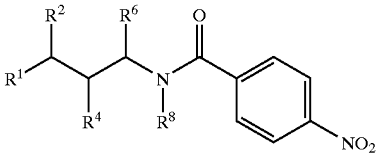

$R^1$ = $PO(OH)_2$

| No. | $R^2$ | $R^4$ | $R^6$ | $R^8$ |
|---|---|---|---|---|
| 1 | $—CH_3$ | H | $—CH_2—$O-EOM | H |
| 2 | 2-propenyl | H | $—CH_2—$O-EOM | H |
| 3 | 2-propynyl | H | $—CH_2—$O-EOM | H |
| 4 | MOM | H | $—CH_2—$O-EOM | H |
| 5 | EOM | H | $—CH_2—$O-EOM | H |
| 6 | MEM | H | $—CH_2—$O-EOM | H |
| 7 | BOM | H | $—CH_2—$O-EOM | H |
| 8 | $—CH_3$ | H | $—CH_2—$O-EOM | $—CH_3$ |
| 9 | 2-propenyl | H | $—CH_2—$O-EOM | $—CH_3$ |
| 10 | 2-propynyl | H | $—CH_2—$O-EOM | $—CH_3$ |
| 11 | MOM | H | $—CH_2—$O-EOM | $—CH_3$ |
| 12 | EOM | H | $—CH_2—$O-EOM | $—CH_3$ |
| 13 | MEM | H | $—CH_2—$O-EOM | $—CH_3$ |
| 14 | BOM | H | $—CH_2—$O-EOM | $—CH_3$ |

TABLE 86

(I-P4-1)

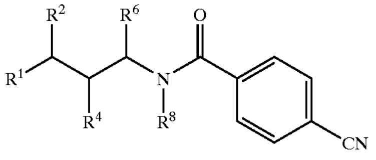

$R^1$ = COOH

| No. | $R^2$ | $R^4$ | $R^6$ | $R^8$ |
|---|---|---|---|---|
| 1 | $—CH_3$ | H | $—CH_2—$O-EOM | H |
| 2 | 2-propenyl | H | $—CH_2—$O-EOM | H |
| 3 | 2-propynyl | H | $—CH_2—$O-EOM | H |
| 4 | MOM | H | $—CH_2—$O-EOM | H |
| 5 | EOM | H | $—CH_2—$O-EOM | H |
| 6 | MEM | H | $—CH_2—$O-EOM | H |
| 7 | BOM | H | $—CH_2—$O-EOM | H |
| 8 | $—CH_3$ | H | $—CH_2—$O-EOM | $—CH_3$ |
| 9 | 2-propenyl | H | $—CH_2—$O-EOM | $—CH_3$ |
| 10 | 2-propynyl | H | $—CH_2—$O-EOM | $—CH_3$ |
| 11 | MOM | H | $—CH_2—$O-EOM | $—CH_3$ |
| 12 | EOM | H | $—CH_2—$O-EOM | $—CH_3$ |
| 13 | MEM | H | $—CH_2—$O-EOM | $—CH_3$ |
| 14 | BOM | H | $—CH_2—$O-EOM | $—CH_3$ |

TABLE 87

(I-P4-2)

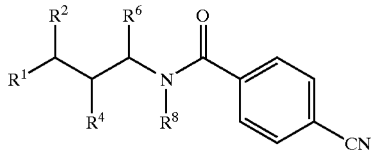

$R^1$ = CONHOH

| No. | $R^2$ | $R^4$ | $R^6$ | $R^8$ |
|---|---|---|---|---|
| 1 | —$CH_3$ | H | —$CH_2$—O-EOM | H |
| 2 | 2-propenyl | H | —$CH_2$—O-EOM | H |
| 3 | 2-propynyl | H | —$CH_2$—O-EOM | H |
| 4 | MOM | H | —$CH_2$—O-EOM | H |
| 5 | EOM | H | —$CH_2$—O-EOM | H |
| 6 | MEM | H | —$CH_2$—O-EOM | H |
| 7 | BOM | H | —$CH_2$—O-EOM | H |
| 8 | —$CH_3$ | H | —$CH_2$—O-EOM | —$CH_3$ |
| 9 | 2-propenyl | H | —$CH_2$—O-EOM | —$CH_3$ |
| 10 | 2-propynyl | H | —$CH_2$—O-EOM | —$CH_3$ |
| 11 | MOM | H | —$CH_2$—O-EOM | —$CH_3$ |
| 12 | EOM | H | —$CH_2$—O-EOM | —$CH_3$ |
| 13 | MEM | H | —$CH_2$—O-EOM | —$CH_3$ |
| 14 | BOM | H | —$CH_2$—O-EOM | —$CH_3$ |

TABLE 88

(I-P4-3)

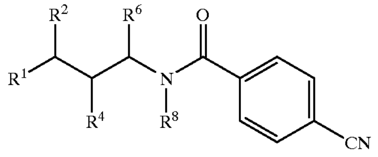

$R^1$ = $CONHNH_2$

| No. | $R^2$ | $R^4$ | $R^6$ | $R^8$ |
|---|---|---|---|---|
| 1 | —$CH_3$ | H | —$CH_2$—O-EOM | H |
| 2 | 2-propenyl | H | —$CH_2$—O-EOM | H |
| 3 | 2-propynyl | H | —$CH_2$—O-EOM | H |
| 4 | MOM | H | —$CH_2$—O-EOM | H |
| 5 | EOM | H | —$CH_2$—O-EOM | H |
| 6 | MEM | H | —$CH_2$—O-EOM | H |
| 7 | BOM | H | —$CH_2$—O-EOM | H |
| 8 | —$CH_3$ | H | —$CH_2$—O-EOM | —$CH_3$ |
| 9 | 2-propenyl | H | —$CH_2$—O-EOM | —$CH_3$ |
| 10 | 2-propynyl | H | —$CH_2$—O-EOM | —$CH_3$ |
| 11 | MOM | H | —$CH_2$—O-EOM | —$CH_3$ |
| 12 | EOM | H | —$CH_2$—O-EOM | —$CH_3$ |
| 13 | MEM | H | —$CH_2$—O-EOM | —$CH_3$ |
| 14 | BOM | H | —$CH_2$—O-EOM | —$CH_3$ |

TABLE 89

(I-P4-4)

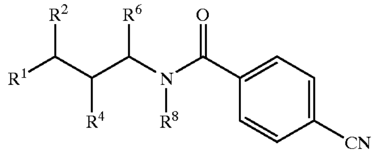

$R^1$ = $CH_2SH$

| No. | $R^2$ | $R^4$ | $R^6$ | $R^8$ |
|---|---|---|---|---|
| 1 | —$CH_3$ | H | —$CH_2$—O-EOM | H |
| 2 | 2-propenyl | H | —$CH_2$—O-EOM | H |

TABLE 89-continued (I-P4-4)

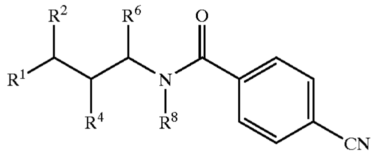

$R^1$ = $CH_2SH$

| No. | $R^2$ | $R^4$ | $R^6$ | $R^8$ |
|---|---|---|---|---|
| 3 | 2-propynyl | H | —$CH_2$—O-EOM | H |
| 4 | MOM | H | —$CH_2$—O-EOM | H |
| 5 | EOM | H | —$CH_2$—O-EOM | H |
| 6 | MEM | H | —$CH_2$—O-EOM | H |
| 7 | BOM | H | —$CH_2$—O-EOM | H |
| 8 | —$CH_3$ | H | —$CH_2$—O-EOM | —$CH_3$ |
| 9 | 2-propenyl | H | —$CH_2$—O-EOM | —$CH_3$ |
| 10 | 2-propynyl | H | —$CH_2$—O-EOM | —$CH_3$ |
| 11 | MOM | H | —$CH_2$—O-EOM | —$CH_3$ |
| 12 | EOM | H | —$CH_2$—O-EOM | —$CH_3$ |
| 13 | MEM | H | —$CH_2$—O-EOM | —$CH_3$ |
| 14 | BOM | H | —$CH_2$—O-EOM | —$CH_3$ |

TABLE 90

(I-P4-5)

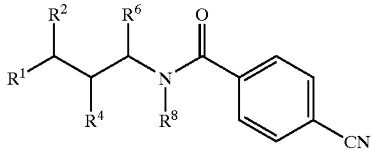

$R^1$ = $PO(OH)_2$

| No. | $R^2$ | $R^4$ | $R^6$ | $R^8$ |
|---|---|---|---|---|
| 1 | —$CH_3$ | H | —$CH_2$—O-EOM | H |
| 2 | 2-propenyl | H | —$CH_2$—O-EOM | H |
| 3 | 2-propynyl | H | —$CH_2$—O-EOM | H |
| 4 | MOM | H | —$CH_2$—O-EOM | H |
| 5 | EOM | H | —$CH_2$—O-EOM | H |
| 6 | MEM | H | —$CH_2$—O-EOM | H |
| 7 | BOM | H | —$CH_2$—O-EOM | H |
| 8 | —$CH_3$ | H | —$CH_2$—O-EOM | —$CH_3$ |
| 9 | 2-propenyl | H | —$CH_2$—O-EOM | —$CH_3$ |
| 10 | 2-propynyl | H | —$CH_2$—O-EOM | —$CH_3$ |
| 11 | MOM | H | —$CH_2$—O-EOM | —$CH_3$ |
| 12 | EOM | H | —$CH_2$—O-EOM | —$CH_3$ |
| 13 | MEM | H | —$CH_2$—O-EOM | —$CH_3$ |
| 14 | BOM | H | —$CH_2$—O-EOM | —$CH_3$ |

TABLE 91

(I-Q-1)

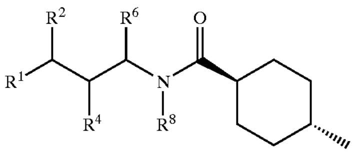

$R^1$ = COOH

| No. | $R^2$ | $R^4$ | $R^6$ | $R^8$ |
|---|---|---|---|---|
| 1 | —$CH_3$ | H | —$CH_2$—O-EOM | H |
| 2 | 2-propenyl | H | —$CH_2$—O-EOM | H |
| 3 | 2-propynyl | H | —$CH_2$—O-EOM | H |
| 4 | MOM | H | —$CH_2$—O-EOM | H |

TABLE 91-continued (I-Q-1)

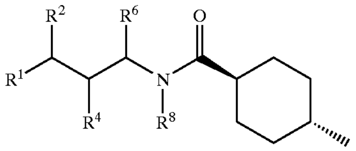

$R^1$ = COOH

| No. | $R^2$ | $R^4$ | $R^6$ | $R^8$ |
|---|---|---|---|---|
| 5 | EOM | H | —$CH_2$—O-EOM | H |
| 6 | MEM | H | —$CH_2$—O-EOM | H |
| 7 | BOM | H | —$CH_2$—O-EOM | H |
| 8 | —$CH_3$ | H | —$CH_2$—O-EOM | —$CH_3$ |
| 9 | 2-propenyl | H | —$CH_2$—O-EOM | —$CH_3$ |
| 10 | 2-propynyl | H | —$CH_2$—O-EOM | —$CH_3$ |
| 11 | MOM | H | —$CH_2$—O-EOM | —$CH_3$ |
| 12 | EOM | H | —$CH_2$—O-EOM | —$CH_3$ |
| 13 | MEM | H | —$CH_2$—O-EOM | —$CH_3$ |
| 14 | BOM | H | —$CH_2$—O-EOM | —$CH_3$ |

TABLE 92

(I-Q-2)

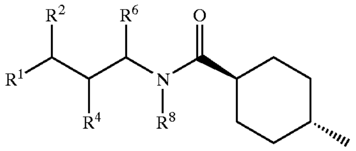

$R^1$ = CONHOH

| No. | $R^2$ | $R^4$ | $R^6$ | $R^8$ |
|---|---|---|---|---|
| 1 | —$CH_3$ | H | —$CH_2$—O-EOM | H |
| 2 | 2-propenyl | H | —$CH_2$—O-EOM | H |
| 3 | 2-propynyl | H | —$CH_2$—O-EOM | H |
| 4 | MOM | H | —$CH_2$—O-EOM | H |
| 5 | EOM | H | —$CH_2$—O-EOM | H |
| 6 | MEM | H | —$CH_2$—O-EOM | H |
| 7 | BOM | H | —$CH_2$—O-EOM | H |
| 8 | —$CH_3$ | H | —$CH_2$—O-EOM | —$CH_3$ |
| 9 | 2-propenyl | H | —$CH_2$—O-EOM | —$CH_3$ |
| 10 | 2-propynyl | H | —$CH_2$—O-EOM | —$CH_3$ |
| 11 | MOM | H | —$CH_2$—O-EOM | —$CH_3$ |
| 12 | EOM | H | —$CH_2$—O-EOM | —$CH_3$ |
| 13 | MEM | H | —$CH_2$—O-EOM | —$CH_3$ |
| 14 | BOM | H | —$CH_2$—O-EOM | —$CH_3$ |

TABLE 93

(I-Q-3)

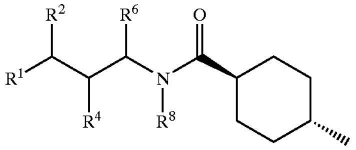

$R^1$ = $CONHNH_2$

| No. | $R^2$ | $R^4$ | $R^6$ | $R^8$ |
|---|---|---|---|---|
| 1 | —$CH_3$ | H | —$CH_2$—O-EOM | H |
| 2 | 2-propenyl | H | —$CH_2$—O-EOM | H |
| 3 | 2-propynyl | H | —$CH_2$—O-EOM | H |
| 4 | MOM | H | —$CH_2$—O-EOM | H |
| 5 | EOM | H | —$CH_2$—O-EOM | H |

TABLE 93-continued (I-Q-3)

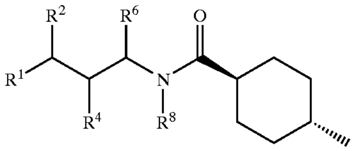

$R^1$ = $CONHNH_2$

| No. | $R^2$ | $R^4$ | $R^6$ | $R^8$ |
|---|---|---|---|---|
| 6 | MEM | H | —$CH_2$—O-EOM | H |
| 7 | BOM | H | —$CH_2$—O-EOM | H |
| 8 | —$CH_3$ | H | —$CH_2$—O-EOM | —$CH_3$ |
| 9 | 2-propenyl | H | —$CH_2$—O-EOM | —$CH_3$ |
| 10 | 2-propynyl | H | —$CH_2$—O-EOM | —$CH_3$ |
| 11 | MOM | H | —$CH_2$—O-EOM | —$CH_3$ |
| 12 | EOM | H | —$CH_2$—O-EOM | —$CH_3$ |
| 13 | MEM | H | —$CH_2$—O-EOM | —$CH_3$ |
| 14 | BOM | H | —$CH_2$—O-EOM | —$CH_3$ |

TABLE 94

(I-Q-4)

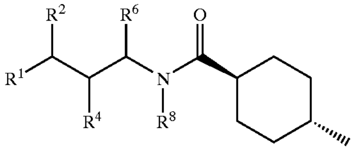

$R^1$ = $CH_2SH$

| No. | $R^2$ | $R^4$ | $R^6$ | $R^8$ |
|---|---|---|---|---|
| 1 | —$CH_3$ | H | —$CH_2$—O-EOM | H |
| 2 | 2-propenyl | H | —$CH_2$—O-EOM | H |
| 3 | 2-propynyl | H | —$CH_2$—O-EOM | H |
| 4 | MOM | H | —$CH_2$—O-EOM | H |
| 5 | EOM | H | —$CH_2$—O-EOM | H |
| 6 | MEM | H | —$CH_2$—O-EOM | H |
| 7 | BOM | H | —$CH_2$—O-EOM | H |
| 8 | —$CH_3$ | H | —$CH_2$—O-EOM | —$CH_3$ |
| 9 | 2-propenyl | H | —$CH_2$—O-EOM | —$CH_3$ |
| 10 | 2-propynyl | H | —$CH_2$—O-EOM | —$CH_3$ |
| 11 | MOM | H | —$CH_2$—O-EOM | —$CH_3$ |
| 12 | EOM | H | —$CH_2$—O-EOM | —$CH_3$ |
| 13 | MEM | H | —$CH_2$—O-EOM | —$CH_3$ |
| 14 | BOM | H | —$CH_2$—O-EOM | —$CH_3$ |

TABLE 95

(I-Q-5)

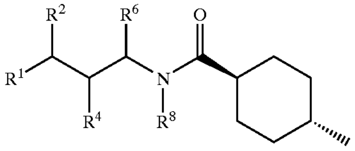

$R^1$ = $PO(OH)_2$

| No. | $R^2$ | $R^4$ | $R^6$ | $R^8$ |
|---|---|---|---|---|
| 1 | —$CH_3$ | H | —$CH_2$—O-EOM | H |
| 2 | 2-propenyl | H | —$CH_2$—O-EOM | H |
| 3 | 2-propynyl | H | —$CH_2$—O-EOM | H |
| 4 | MOM | H | —$CH_2$—O-EOM | H |
| 5 | EOM | H | —$CH_2$—O-EOM | H |
| 6 | MEM | H | —$CH_2$—O-EOM | H |

TABLE 95-continued (I-Q-5)

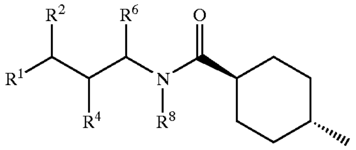

$R^1 = PO(OH)_2$

| No. | $R^2$ | $R^4$ | $R^6$ | $R^8$ |
|---|---|---|---|---|
| 7 | BOM | H | —$CH_2$—O-EOM | H |
| 8 | —$CH_3$ | H | —$CH_2$—O-EOM | —$CH_3$ |
| 9 | 2-propenyl | H | —$CH_2$—O-EOM | —$CH_3$ |
| 10 | 2-propynyl | H | —$CH_2$—O-EOM | —$CH_3$ |
| 11 | MOM | H | —$CH_2$—O-EOM | —$CH_3$ |
| 12 | EOM | H | —$CH_2$—O-EOM | —$CH_3$ |
| 13 | MEM | H | —$CH_2$—O-EOM | —$CH_3$ |
| 14 | BOM | H | —$CH_2$—O-EOM | —$CH_3$ |

TABLE 96

(I-R-1)

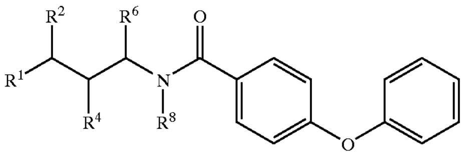

$R^1$ = COOH

| No. | $R^2$ | $R^4$ | $R^6$ | $R^8$ |
|---|---|---|---|---|
| 1 | —$CH_3$ | H | —$CH_2$—O-EOM | H |
| 2 | 2-propenyl | H | —$CH_2$—O-EOM | H |
| 3 | 2-propynyl | H | —$CH_2$—O-EOM | H |
| 4 | MOM | H | —$CH_2$—O-EOM | H |
| 5 | EOM | H | —$CH_2$—O-EOM | H |
| 6 | MEM | H | —$CH_2$—O-EOM | H |
| 7 | BOM | H | —$CH_2$—O-EOM | H |
| 8 | —$CH_3$ | H | —$CH_2$—O-EOM | —$CH_3$ |
| 9 | 2-propenyl | H | —$CH_2$—O-EOM | —$CH_3$ |
| 10 | 2-propynyl | H | —$CH_2$—O-EOM | —$CH_3$ |
| 11 | MOM | H | —$CH_2$—O-EOM | —$CH_3$ |
| 12 | EOM | H | —$CH_2$—O-EOM | —$CH_3$ |
| 13 | MEM | H | —$CH_2$—O-EOM | —$CH_3$ |
| 14 | BOM | H | —$CH_2$—O-EOM | —$CH_3$ |

TABLE 97

(I-R-2)

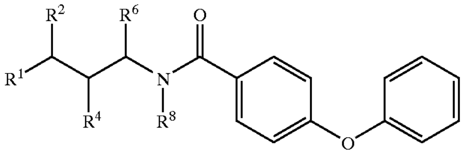

$R^1$ = CONHOH

| No. | $R^2$ | $R^4$ | $R^6$ | $R^8$ |
|---|---|---|---|---|
| 1 | —$CH_3$ | H | —$CH_2$—O-EOM | H |
| 2 | 2-propenyl | H | —$CH_2$—O-EOM | H |
| 3 | 2-propynyl | H | —$CH_2$—O-EOM | H |
| 4 | MOM | H | —$CH_2$—O-EOM | H |
| 5 | EOM | H | —$CH_2$—O-EOM | H |
| 6 | MEM | H | —$CH_2$—O-EOM | H |
| 7 | BOM | H | —$CH_2$—O-EOM | H |

TABLE 97-continued (I-R-2)

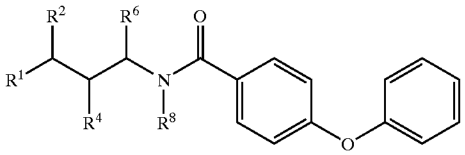

$R^1$ = CONHOH

| No. | $R^2$ | $R^4$ | $R^6$ | $R^8$ |
|---|---|---|---|---|
| 8 | —$CH_3$ | H | —$CH_2$—O-EOM | —$CH_3$ |
| 9 | 2-propenyl | H | —$CH_2$—O-EOM | —$CH_3$ |
| 10 | 2-propynyl | H | —$CH_2$—O-EOM | —$CH_3$ |
| 11 | MOM | H | —$CH_2$—O-EOM | —$CH_3$ |
| 12 | EOM | H | —$CH_2$—O-EOM | —$CH_3$ |
| 13 | MEM | H | —$CH_2$—O-EOM | —$CH_3$ |
| 14 | BOM | H | —$CH_2$—O-EOM | —$CH_3$ |

TABLE 98

(I-R-3)

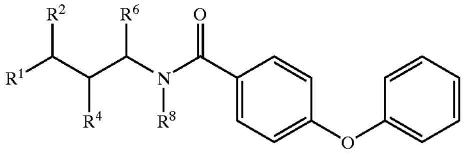

$R^1 = CONHNH_2$

| No. | $R^2$ | $R^4$ | $R^6$ | $R^8$ |
|---|---|---|---|---|
| 1 | —$CH_3$ | H | —$CH_2$—O-EOM | H |
| 2 | 2-propenyl | H | —$CH_2$—O-EOM | H |
| 3 | 2-propynyl | H | —$CH_2$—O-EOM | H |
| 4 | MOM | H | —$CH_2$—O-EOM | H |
| 5 | EOM | H | —$CH_2$—O-EOM | H |
| 6 | MEM | H | —$CH_2$—O-EOM | H |
| 7 | BOM | H | —$CH_2$—O-EOM | H |
| 8 | —$CH_3$ | H | —$CH_2$—O-EOM | —$CH_3$ |
| 9 | 2-propenyl | H | —$CH_2$—O-EOM | —$CH_3$ |
| 10 | 2-propynyl | H | —$CH_2$—O-EOM | —$CH_3$ |
| 11 | MOM | H | —$CH_2$—O-EOM | —$CH_3$ |
| 12 | EOM | H | —$CH_2$—O-EOM | —$CH_3$ |
| 13 | MEM | H | —$CH_2$—O-EOM | —$CH_3$ |
| 14 | BOM | H | —$CH_2$—O-EOM | —$CH_3$ |

TABLE 99

(I-R-4)

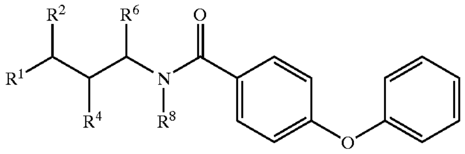

$R^1 = CH_2SH$

| No. | $R^2$ | $R^4$ | $R^6$ | $R^8$ |
|---|---|---|---|---|
| 1 | —$CH_3$ | H | —$CH_2$—O-EOM | H |
| 2 | 2-propenyl | H | —$CH_2$—O-EOM | H |
| 3 | 2-propynyl | H | —$CH_2$—O-EOM | H |
| 4 | MOM | H | —$CH_2$—O-EOM | H |
| 5 | EOM | H | —$CH_2$—O-EOM | H |
| 6 | MEM | H | —$CH_2$—O-EOM | H |
| 7 | BOM | H | —$CH_2$—O-EOM | H |
| 8 | —$CH_3$ | H | —$CH_2$—O-EOM | —$CH_3$ |

TABLE 99-continued (I-R-4)

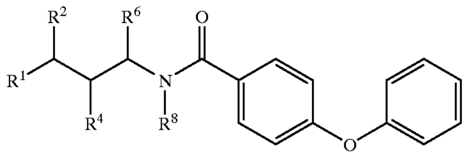

$R^1 = CH_2SH$

| No. | $R^2$ | $R^4$ | $R^6$ | $R^8$ |
|---|---|---|---|---|
| 9 | 2-propenyl | H | $—CH_2—O-EOM$ | $—CH_3$ |
| 10 | 2-propynyl | H | $—CH_2—O-EOM$ | $—CH_3$ |
| 11 | MOM | H | $—CH_2—O-EOM$ | $—CH_3$ |
| 12 | EOM | H | $—CH_2—O-EOM$ | $—CH_3$ |
| 13 | MEM | H | $—CH_2—O-EOM$ | $—CH_3$ |
| 14 | BOM | H | $—CH_2—O-EOM$ | $—CH_3$ |

TABLE 100

(I-R-5)

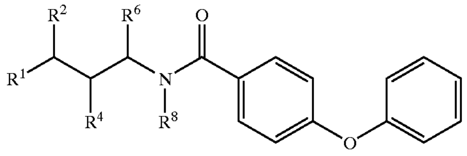

$R^1 = PO(OH)_2$

| No. | $R^2$ | $R^4$ | $R^6$ | $R^8$ |
|---|---|---|---|---|
| 1 | $—CH_3$ | H | $—CH_2—O-EOM$ | H |
| 2 | 2-propenyl | H | $—CH_2—O-EOM$ | H |
| 3 | 2-propynyl | H | $—CH_2—O-EOM$ | H |
| 4 | MOM | H | $—CH_2—O-EOM$ | H |
| 5 | EOM | H | $—CH_2—O-EOM$ | H |
| 6 | MEM | H | $—CH_2—O-EOM$ | H |
| 7 | BOM | H | $—CH_2—O-EOM$ | H |
| 8 | $—CH_3$ | H | $—CH_2—O-EOM$ | $—CH_3$ |
| 9 | 2-propenyl | H | $—CH_2—O-EOM$ | $—CH_3$ |
| 10 | 2-propynyl | H | $—CH_2—O-EOM$ | $—CH_3$ |
| 11 | MOM | H | $—CH_2—O-EOM$ | $—CH_3$ |
| 12 | EOM | H | $—CH_2—O-EOM$ | $—CH_3$ |
| 13 | MEM | H | $—CH_2—O-EOM$ | $—CH_3$ |
| 14 | BOM | H | $—CH_2—O-EOM$ | $—CH_3$ |

TABLE 101

(I-S-1)

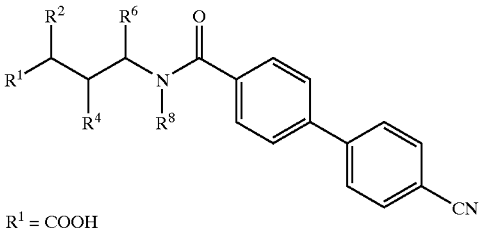

$R^1 = COOH$

| No. | $R^2$ | $R^4$ | $R^6$ | $R^8$ |
|---|---|---|---|---|
| 1 | $—CH_3$ | H | $—CH_2—O—EOM$ | H |
| 2 | 2-propenyl | H | $—CH_2—O—EOM$ | H |
| 3 | 2-propynyl | H | $—CH_2—O—EOM$ | H |
| 4 | MOM | H | $—CH_2—O—EOM$ | H |
| 5 | EOM | H | $—CH_2—O—EOM$ | H |
| 6 | MEM | H | $—CH_2—O—EOM$ | H |
| 7 | BOM | H | $—CH_2—O—EOM$ | H |
| 8 | $—CH_3$ | H | $—CH_2—O—EOM$ | $—CH_3$ |

TABLE 101-continued (I-S-1)

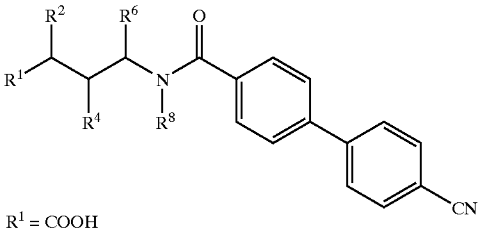

$R^1 = COOH$

| No. | $R^2$ | $R^4$ | $R^6$ | $R^8$ |
|---|---|---|---|---|
| 9 | 2-propenyl | H | $—CH_2—O—EOM$ | $—CH_3$ |
| 10 | 2-propynyl | H | $—CH_2—O—EOM$ | $—CH_3$ |
| 11 | MOM | H | $—CH_2—O—EOM$ | $—CH_3$ |
| 12 | EOM | H | $—CH_2—O—EOM$ | $—CH_3$ |
| 13 | MEM | H | $—CH_2—O—EOM$ | $—CH_3$ |
| 14 | BOM | H | $—CH_2—O—EOM$ | $—CH_3$ |

TABLE 102

(I-S-2)

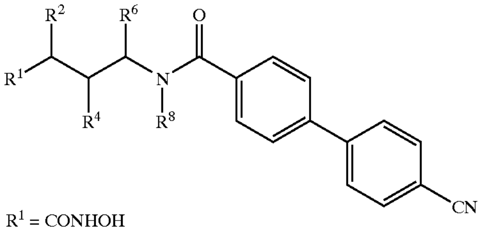

$R^1 = CONHOH$

| No. | $R^2$ | $R^4$ | $R^6$ | $R^8$ |
|---|---|---|---|---|
| 1 | $—CH_3$ | H | $—CH_2—O—EOM$ | H |
| 2 | 2-propenyl | H | $—CH_2—O—EOM$ | H |
| 3 | 2-propynyl | H | $—CH_2—O—EOM$ | H |
| 4 | MOM | H | $—CH_2—O—EOM$ | H |
| 5 | EOM | H | $—CH_2—O—EOM$ | H |
| 6 | MEM | H | $—CH_2—O—EOM$ | H |
| 7 | BOM | H | $—CH_2—O—EOM$ | H |
| 8 | $—CH_3$ | H | $—CH_2—O—EOM$ | $—CH_3$ |
| 9 | 2-propenyl | H | $—CH_2—O—EOM$ | $—CH_3$ |
| 10 | 2-propynyl | H | $—CH_2—O—EOM$ | $—CH_3$ |
| 11 | MOM | H | $—CH_2—O—EOM$ | $—CH_3$ |
| 12 | EOM | H | $—CH_2—O—EOM$ | $—CH_3$ |
| 13 | MEM | H | $—CH_2—O—EOM$ | $—CH_3$ |
| 14 | BOM | H | $—CH_2—O—EOM$ | $—CH_3$ |

TABLE 103

(I-S-3)

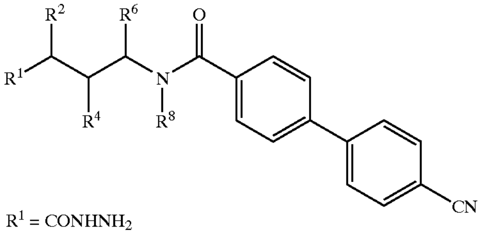

$R^1 = CONHNH_2$

| No. | $R^2$ | $R^4$ | $R^6$ | $R^8$ |
|---|---|---|---|---|
| 1 | $—CH_3$ | H | $—CH_2—O—EOM$ | H |
| 2 | 2-propenyl | H | $—CH_2—O—EOM$ | H |
| 3 | 2-propynyl | H | $—CH_2—O—EOM$ | H |
| 4 | MOM | H | $—CH_2—O—EOM$ | H |

TABLE 103-continued (I-S-3)

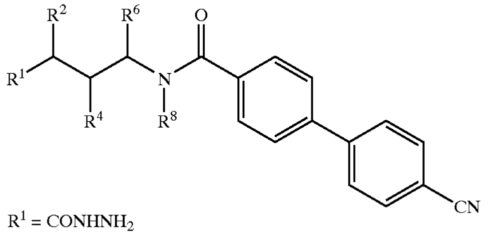

$R^1 = CONHNH_2$

| No. | $R^2$ | $R^4$ | $R^6$ | $R^8$ |
|---|---|---|---|---|
| 5 | EOM | H | $—CH_2—O—EOM$ | H |
| 6 | MEM | H | $—CH_2—O—EOM$ | H |
| 7 | BOM | H | $—CH_2—O—EOM$ | H |
| 8 | $—CH_3$ | H | $—CH_2—O—EOM$ | $—CH_3$ |
| 9 | 2-propenyl | H | $—CH_2—O—EOM$ | $—CH_3$ |
| 10 | 2-propynyl | H | $—CH_2—O—EOM$ | $—CH_3$ |
| 11 | MOM | H | $—CH_2—O—EOM$ | $—CH_3$ |
| 12 | EOM | H | $—CH_2—O—EOM$ | $—CH_3$ |
| 13 | MEM | H | $—CH_2—O—EOM$ | $—CH_3$ |
| 14 | BOM | H | $—CH_2—O—EOM$ | $—CH_3$ |

TABLE 104

(I-S-4)

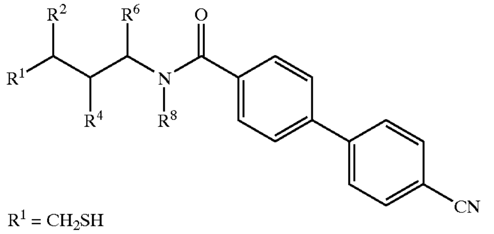

$R^1 = CH_2SH$

| No. | $R^2$ | $R^4$ | $R^6$ | $R^8$ |
|---|---|---|---|---|
| 1 | $—CH_3$ | H | $—CH_2—O—EOM$ | H |
| 2 | 2-propenyl | H | $—CH_2—O—EOM$ | H |
| 3 | 2-propynyl | H | $—CH_2—O—EOM$ | H |
| 4 | MOM | H | $—CH_2—O—EOM$ | H |
| 5 | EOM | H | $—CH_2—O—EOM$ | H |
| 6 | MEM | H | $—CH_2—O—EOM$ | H |
| 7 | BOM | H | $—CH_2—O—EOM$ | H |
| 8 | $—CH_3$ | H | $—CH_2—O—EOM$ | $—CH_3$ |
| 9 | 2-propenyl | H | $—CH_2—O—EOM$ | $—CH_3$ |
| 10 | 2-propynyl | H | $—CH_2—O—EOM$ | $—CH_3$ |
| 11 | MOM | H | $—CH_2—O—EOM$ | $—CH_3$ |
| 12 | EOM | H | $—CH_2—O—EOM$ | $—CH_3$ |
| 13 | MEM | H | $—CH_2—O—EOM$ | $—CH_3$ |
| 14 | BOM | H | $—CH_2—O—EOM$ | $—CH_3$ |

TABLE 105

(I-S-5)

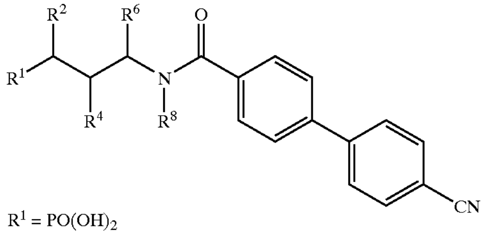

$R^1 = PO(OH)_2$

| No. | $R^2$ | $R^4$ | $R^6$ | $R^8$ |
|---|---|---|---|---|
| 1 | $—CH_3$ | H | $—CH_2—O—EOM$ | H |
| 2 | 2-propenyl | H | $—CH_2—O—EOM$ | H |
| 3 | 2-propynyl | H | $—CH_2—O—EOM$ | H |

TABLE 105-continued (I-S-5)

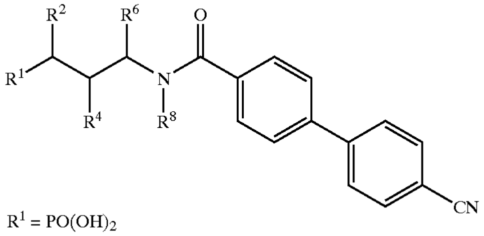

$R^1 = PO(OH)_2$

| No. | $R^2$ | $R^4$ | $R^6$ | $R^8$ |
|---|---|---|---|---|
| 4 | MOM | H | $—CH_2—O—EOM$ | H |
| 5 | EOM | H | $—CH_2—O—EOM$ | H |
| 6 | MEM | H | $—CH_2—O—EOM$ | H |
| 7 | BOM | H | $—CH_2—O—EOM$ | H |
| 8 | $—CH_3$ | H | $—CH_2—O—EOM$ | $—CH_3$ |
| 9 | 2-propenyl | H | $—CH_2—O—EOM$ | $—CH_3$ |
| 10 | 2-propynyl | H | $—CH_2—O—EOM$ | $—CH_3$ |
| 11 | MOM | H | $—CH_2—O—EOM$ | $—CH_3$ |
| 12 | EOM | H | $—CH_2—O—EOM$ | $—CH_3$ |
| 13 | MEM | H | $—CH_2—O—EOM$ | $—CH_3$ |
| 14 | BOM | H | $—CH_2—O—EOM$ | $—CH_3$ |

Process for the Preparation

The compounds of the present invention of the formula (I), may be prepared by following methods or the methods described in the Examples.

[1] In the compounds of the present invention of the formula (I), the compound in which $R^1$ is $—COOR^{10}$, that is the compound of the formula (I-1):

(I-1)

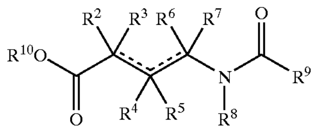

wherein all the symbols are as hereinbefore defined; may be prepared by following methods (a)–(c).

(a) The compound in which $—COOR^{10}$ in $R^1$ is not —COOH, and all of $R^2$, $R^3$, $R^4$, $R^5$, $R^6$, $R^7$, $R^8$ and $R^9$ are not —COOH or a group including it, hydroxy or a group including it, amino or a group including it, that is the compound of the formula (I-1a):

(I-1a)

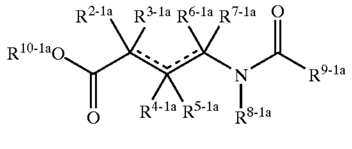

wherein $R^{10\text{-}1a}$ is C1–8 alkyl, phenyl, C1–8 alkyl substituted by phenyl or C1–8 alkoxy, oxycarbonyl substituted by phenyl, benzyl or C1–8 alkyl, each of $R^{2\text{-}1a}$ $R^{3\text{-}1a}$, $R^{4\text{-}1a}$, $R^{5\text{-}1a}$, $R^{6\text{-}1a}$, $R^{7\text{-}1a}$, $R^{8\text{-}1a}$, $R^{9\text{-}1a}$ has the same meaning as $R^2$, $R^3$, $R^4$, $R^5$, $R^6$, $R^7$, $R^8$, $R^9$, with the proviso that, all of $R^{2\text{-}1a}$, $R^{3\text{-}1a}$, $R^{4\text{-}1a}$, $R^{5\text{-}1a}$, $R^{6\text{-}1a}$, $R^{7\text{-}1a}$, $R^{8\text{-}1a}$, $R^{9\text{-}1a}$ are not —COOH, hydroxy or amino or groups including them, and the other symbols are as hereinbefore defined;

may be prepared by amidation of the compound of the formula (II):

(II)

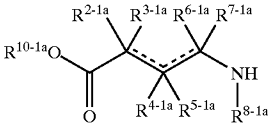

wherein all the symbols are as hereinbefore defined; with the compound of the formula (III):

(III)

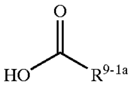

wherein all the symbols are as hereinbefore defined.

The method of amidation of the compound of the formula (II) with the compound of the formula (III) is known. It includes the method (1) via an acyl halide, (2) via a mixed acid anhydride, (3) using a condensing agent.

These methods are explained as follows.

(1) The method via an acyl halide, for example, may be carried out in an organic solvent (e.g. chloroform, methylene chloride, diethyl ether or tetrahydrofuran) or without a solvent, using an acyl halide (e.g. oxalyl chloride or thionyl chloride etc.) at −20° C. to reflux temperature, and the obtained acyl halide derivative may be reacted with an amine in an organic solvent (e.g. chloroform, methylene chloride, diethyl ether or tetrahydrofuran) in the presence of a tertiary amine (e.g. pyridine, triethyl amine, dimethyl aniline or dimethylaminopyridine) at 0–40° C.

(2) The method via a mixed acid anhydride may be carried out, for example, by reacting a carboxylic acid with an acyl halide (e.g. pivaloyl chloride, tosyl chloride or mesyl chloride) or an acid derivative (e.g. ethyl chloroformate or isobutyl chloroformate) in an organic solvent (e.g. chloroform, methylene chloride, diethyl ether or tetrahydrofuran) or without a solvent, in the presence of a tertiary amine (e.g. pyridine, triethylamine, dimethylaniline or dimethylaminopyridine) at 0–40° C., and the obtained mixed acid anhydride derivative may be reacted with a corresponding amine in an organic solvent (e.g. chloroform, methylene chloride, diethyl ether or tetrahydrofuran) at 0–40° C.

(3) The method using a condensing agent (e.g. 1,3-dicyclohexyl carbodiimide (DCC), 1-ethyl-3-[3-(dimethylamino)propyl]carbodiimide (EDC), 1,1'-carbonyldiimidazole (CDI) or 2-chloro-1-methylpyridinium iodide) may be carried out, for example, by reacting a carboxylic acid with an amine in an organic solvent (e.g. chloroform, methylene chloride, dimethylformamide, diethyl ether or tetrahydrofuran) or without a solvent, optionally in the presence of a tertiary amine (e.g. pyridine, triethylamine, dimethylaniline or dimethylaminopyridine) using a condensing agent, and optionally in the presence of 1-hydroxybenzotriazole (HOBt) at 0–40° C.

The reaction described in (1), (2) and (3) may be carried out under an inert gas (e.g. argon, nitrogen) to avoid water in order to obtain a preferable result.

(b) The compound in which —$COOR^{10}$ in $R^1$ is not —COOH, and at least one of $R^2$, $R^3$, $R^4$, $R^5$, $R^6$, $R^7$, $R^8$ and $R^9$ is —COOH or a group including it, hydroxy or a group including it, amino or a group including it, that is the compound of the formula (I-1b):

(I-1b)

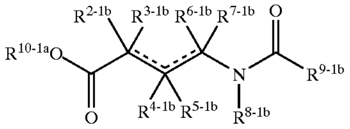

wherein each of $R^{2-1b}$, $R^{3-1b}$, $R^{4-1b}$, $R^{5-1b}$, $R^{6-1b}$, $R^{7-1b}$, $R^{8-1b}$, $R^{9-1b}$ has the same meaning as $R^2$, $R^3$, $R^4$, $R^5$, $R^6$, $R^7$, $R^8$, $R^9$, with the proviso that, at least one of $R^{2-1b}$, $R^{3-1b}$, $R^{4-1b}$, $R^{5-1b}$, $R^{6-1b}$, $R^{7-1b}$, $R^{8-1b}$, $R^{9-1b}$ is —COOH, hydroxy or amino or groups including them, and the other symbols are as hereinbefore defined;

may be prepared by deprotection under alkaline conditions, deprotection under acidic conditions, deprotection of a silyl group or hydrogenolysis of the compound having protected —COOH, hydroxy or amino or groups including protected —COOH, hydroxy or amino in the compound of the formula (I-1a), that is the compound of the formula (I-1a1):

(I-1a1)

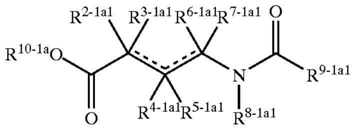

wherein each of $R^{2-1a1}$, $R^{3-1a1}$, $R^{4-1a1}$, $R^{5-1a1}$, $R^{6-1a1}$, $R^{7-1a1}$, $R^{8-1a1}$, $R^{9-1a1}$ has the same meaning as $R^2$, $R^3$, $R^4$, $R^5$, $R^6$, $R^7$, $R^8$, $R^9$, with the proviso that, at least one of $R^{2-1a1}$, $R^{3-1a1}$, $R^{4-1a1}$, $R^{5-1a1}$, $R^{6-1a1}$, $R^{7-1a1}$, $R^{8-1a1}$, $R^{9-1a1}$ is protected —COOH (e.g. protected by methyl, ethyl, t-butyl and benzyl), protected hydroxy (e.g. protected by methoxymethyl, tetrahydropyranyl, t-butyldimethylsilyl, acetyl, benzyl) or protected amino (e.g. protected by benzyloxycarboyl, t-butoxycarbonyl, trifluoroacetyl) or a group including protected —COOH, hydroxy or amino, and the other symbols are as hereinbefore defined.

Deprotection under alkaline conditions was known, for example, it may be carried out in an organic solvent (e.g. methanol, tetrahydrofuran or dioxane), using an alkali metal hydroxide (e.g. sodium hydroxide, potassium hydroxide or lithium hydroxide), an alkaline earth metal hydroxide (e.g. barium hydroxide or calcium hydroxide) or a carbonate (e.g. sodium carbonate or potassium carbonate), an aqueous solution thereof or mixture thereof at 0–40° C.

Deprotection under acidic conditions was known, for example, it may be carried out in an organic solvent (e.g. methylene chloride, chloroform, dioxane, ethyl acetate, anisole), using an organic acid (e.g. acetic acid, trifluoroacetic acid, methansulfonic acid or trimethylsilyl iodide), or an inorganic acid (e.g. hydrochloric acid or sulfuric acid) or a mixture thereof (e.g. hydrogen bromide in acetic acid) at 0–100° C.

Deprotection of a silyl group was known, for example, it may be carried out in a water miscible organic solvent (e.g. tetrahydrofuran or acetonitrile), using tetrabutylammonium fluoride at 0–40° C.

Hydrogenolysis was known, for example, it may be carried out in a solvent [e.g. ether (such as tetrahydrofuran, dioxane, dimethoxyethane or diethyl ether), alcohol (such as methanol or ethanol), benzene (such as benzene or toluene), ketone (such as acetone or methyl ethyl ketone), nitrile (such as acetonitrile), amide (such as dimethylformamide), water, ethyl acetate, acetic acid or two more mixture thereof], in the presence of a catalyst (e.g. palladium on carbon, palladium black, palladium, palladium hydroxide, platinum dioxide, nickel or Raney-nickel), optionally in the presence of an inorganic acid (e.g. hydrochloric acid, sulfuric acid, hypochlorous acid, boric acid or tetrafluoroboric acid) or an organic acid (e.g. acetic acid, p-toluenesulfonic acid, oxalic acid, trifluoroacetic acid or formic acid), at ordinary or elevated pressure of hydrogen gas or ammonium formate at 0–200° C. There is no difficulty in using a salt of acid, when it is carried out using an acid.

(c) The compound in which —COOR$^{10}$ in R$^1$ is —COOH, that is the compound of the formula (I-1c):

(I-1c)

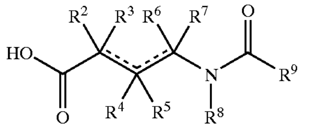

wherein all the symbols are the same meaning as hereinbefore defined;

may be prepared by deprotection under alkaline conditions, deprotection under acidic conditions or hydrogenolysis of the above compounds of the formula (I-1a) and the formula (I-1b), that is the compound of the formula (I-1ab):

(I-1ab)

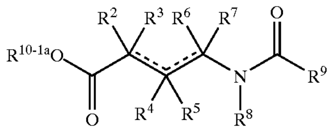

wherein all the symbols are the same meaning as hereinbefore defined.

The reactions of deprotection under alkaline conditions, deprotection under acidic conditions and hydrogenolysis are known and they may be carried out by the same method as hereinbefore described.

[2] In the compounds of the present invention of the formula (I), the compound in which R$^1$ is —CONHOR$^{10}$ or —CONHNHR$^{10}$, that is the compound of the formula (I-2):

(I-2)

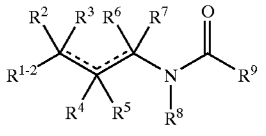

wherein R$^{1\text{-}2}$ is —CONHOR$^{10}$ or —CONHNHR$^{10}$, and the other symbols are the same meaning as hereinbefore defined; may be prepared by following methods (a) and (b).

(a) The compound in which R$^1$ is —CONHOR$^{10}$ or —CONHNHR$^{10}$, and all of R$^2$, R$^3$, R$^4$, R$^5$, R$^6$, R$^7$, R$^8$ and R$^9$ are not —COOH or a group including it, that is the compound of the formula (I-2a):

(I-2a)

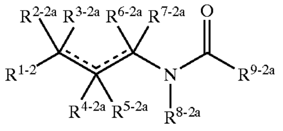

wherein each of R$^{2\text{-}2a}$, R$^{3\text{-}2a}$, R$^{4\text{-}2a}$, R$^{5\text{-}2a}$, R$^{6\text{-}2a}$, R$^{7\text{-}2a}$, R$^{8\text{-}2a}$, R$^{9\text{-}2a}$ is the a same meaning as R$^2$, R$^3$, R$^4$, R$^5$, R$^6$, R$^7$, R$^8$ , R$^9$, with the proviso that, all of R$^{2\text{-}2a}$, R$^{3\text{-}2a}$, R$^{4\text{-}2a}$, R$^{5\text{-}2a}$, R$^{6\text{-}2a}$, R$^{7\text{-}2a}$, R$^{8\text{-}2a}$, R$^{9\text{-}2a}$ are not —COOH or a group including it, and the other symbols are as hereinbefore defined;

may be prepared by amidation of the compound in which R$^1$ is COOH, and all of R$^2$, R$^3$, R$^4$, R$^5$, R$^6$, R$^7$, R$^8$, R$^9$, are not —COOH or a group including it in the compound of the above formula (I-1), that is the compound of the formula (I-1d):

(I-1d)

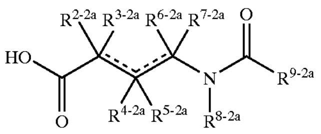

wherein all the symbols are the same meaning as hereinbefore defined;

with the compound of the formula (IV):

$H_2N—OR^{10}$ (IV)

wherein R$^{10}$ is the same meaning as hereinbefore defined; or the compound of the formula (V):

$H_2N—NHR^{10}$ (V)

wherein R$^{10}$ is the same meaning as hereinbefore defined; if necessary, followed by deprotection under alkaline conditions and/or deprotection under acidic conditions and/or hydrogenolysis.

This reaction of amidation, the reactions of deprotection under alkaline conditions, deprotection under acidic conditions and hydrogenolysis are known, and may be carried out by the same method as hereinbefore described.

(b) The compound in which R$^1$ is —CONHOR$^{10}$ or —CONHNHR$^{10}$, and at least one of R$^2$, R$^3$, R$^4$, R$^5$, R$^6$, R$^7$, R$^8$ and R$^9$ is —COOH or a group including it, that is the compound of the formula (I-2b):

(I-2b)

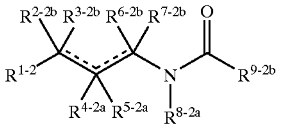

wherein each of R$^{2\text{-}2b}$, R$^{3\text{-}2b}$, R$^{4\text{-}2b}$, R$^{5\text{-}2b}$, R$^{6\text{-}2b}$, R$^{7\text{-}2b}$, R$^{8\text{-}2b}$, R$^{9\text{-}2b}$ is the a same meaning as R$^2$, R$^3$, R$^4$, R$^5$, R$^6$, R$^7$, R$^8$, R$^9$, with the proviso that, at least one of R$^{2\text{-}2b}$, R$^{3\text{-}2b}$, R$^{4\text{-}2b}$, R$^{5\text{-}2b}$, R$^{6\text{-}2b}$, R$^{7\text{-}2b}$, R$^{8\text{-}2b}$, R$^{9\text{-}2b}$ is —COOH or a group including it, and the other symbols are as hereinbefore defined;

may be prepared by deprotection under alkaline conditions, deprotection under acidic conditions or hydrogenolysis of the compound having protected —COOH or a group including protected —COOH in the compound of the above formula (I-2a), that is the compound of the formula (I-2a1):

(I-2a1)

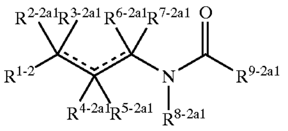

wherein each of $R^{2-2a1}$, $R^{3-2a1}$, $R^{4-2a1}$, $R^{5-2a1}$, $R^{6-2a1}$, $R^{7-2a1}$, $R^{8-2a1}$, $R^{9-2a1}$ has the same meaning as $R^2$, $R^3$, $R^4$, $R^5$, $R^6$, $R^7$, $R^8$, $R^9$, with the proviso that, at least one of $R^{2-2a1}$, $R^{3-2a1}$, $R^{4-2a1}$, $R^{5-2a1}$, $R^{6-2a1}$, $R^{7-2a1}$, $R^{8-2a1}$, $R^{9-2a1}$, is protected —COOH (e.g. protected by methyl, ethyl, t-butyl and benzyl) or a group including protected —COOH, and the other symbols are as hereinbefore defined.

The reactions of deprotection under alkaline conditions, deprotection under acidic conditions and hydrogenolysis are known, and may be carried out by the same method as hereinbefore described.

[3] In the compounds of the present invention of the formula (I), the compound in which $R^1$ is $—(CH_2)_nSR^{50}$, that is the compound of the formula (I-3):

(I-3)

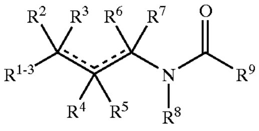

wherein $R^{1-3}$ is $—(CH_2)_nSR^{50}$, and the other symbols are as hereinbefore defined; may be prepared by following methods (a) and (b).

(a) The compound in which $R^1$ is $—(CH_2)_nSR^{50}$, and all of $R^2$, $R^3$, $R^4$, $R^5$, $R^6$, $R^7$, $R^8$ and $R^9$ are not —COOH or a group including it, that is the compound of the formula (I-3a):

(I-3a)

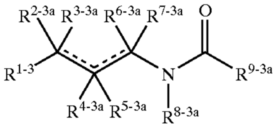

wherein each of $R^{2-3a}$, $R^{3-3a}$, $R^{4-3a}$, $R^{5-3a}$, $R^{6-3a}$, $R^{7-3a}$, $R^{8-3a}$, $R^{9-3a}$ has the same meaning as $R^2$, $R^3$, $R^4$, $R^5$, $R^6$, $R^7$, $R^8$, $R^9$, with the proviso that, all of $R^{2-3a}$, $R^{3-3a}$, $R^{4-3a}$, $R^{5-3a}$, $R^{6-3a}$, $R^{7-3a}$, $R^{8-3a}$, $R^{9-3a}$ are not —COOH or a group including it, and the other symbols are as hereinbefore defined;

may be prepared by reaction of the compound of the formula (VI):

(VI)

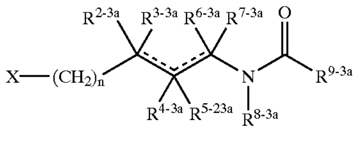

wherein X is halogen atom and the other symbols are as hereinbefore defined; and the compound of the formula (VII):

$R^{501}SK$ (VII)

wherein $R^{501}$ is C1–8 alkyl, $—COR^{52}$ or $—SR^{531}$, in which $R^{531}$ is C1–8 alkyl or phenyl.

The compound in which $R^{50}$ is hydrogen or —SH may be prepared by a reaction of deprotection of the compound obtained by the above method.

The above method was known, for example, it may be carried out by refluxing in an organic solvent (e.g. acetone, tetrahydrofuran).

The continuous reaction of deprotection was known, for example, it may be carried out in an organic solvent (e.g. methanol, tetrahydrofuran or dioxane), using an alkali metal hydroxide (e.g. sodium hydroxide, potassium hydroxide or lithium hydroxide), an alkaline earth metal hydroxide (e.g. barium hydroxide or calcium hydroxide) or a carbonate (e.g. sodium carbonate or potassium carbonate), an aqueous solution thereof or mixture thereof at 0–40° C.

(b) The compound in which $R^1$ is $—(CH_2)_nSR^{50}$, and at least one of $R^2$, $R^3$, $R^4$, $R^5$, $R^6$, $R^7$, $R^8$ and $R^9$ is —COOH or a group including it, that is the compound of the formula (I-3b):

(I-3b)

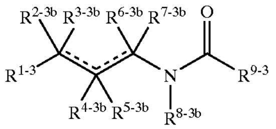

wherein each of $R^{2-3b}$, $R^{3-3b}$, $R^{4-3b}$, $R^{5-3b}$, $R^{6-3b}$, $R^{7-3b}$, $R^{8-3b}$, $R^{9-3b}$ has the same meaning as $R^2$, $R^3$, $R^4$, $R^5$, $R^6$, $R^7$, $R^8$, $R^9$, with the proviso that, at least one of $R^{2-3b}$, $R^{3-3b}$, $R^{4-3b}$, $R^{5-3b}$, $R^{6-3b}$, $R^{7-3b}$, $R^{8-3b}$, $R^{9-3b}$ is —COOH or a group including it, and the other symbols are as hereinbefore defined;

may be prepared by deprotection under alkaline conditions, deprotection under acidic conditions or hydrogenolysis of the compound having protected —COOH or a group including protected —COOH in the compound of the above formula (I-3a), that is the compound of the formula (I-3a1):

(I-3a1)

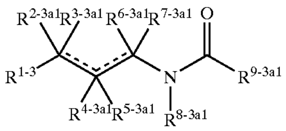

wherein each of $R^{2-3a1}$, $R^{3-3a1}$, $R^{4-3a1}$, $R^{5-3a1}$, $R^{6-3a1}$, $R^{7-3a1}$, $R^{8-3a1}$, $R^{9-3a1}$ has the same meaning as $R^2$, $R^3$, $R^4$, $R^5$, $R^6$, $R^7$, $R^8$, $R^9$, with the proviso that, at least one of $R^{2-3a1}$, $R^{3-3a1}$, $R^{4-3a1}$, $R^{5-3a1}$, $R^{6-3a1}$, $R^{7-3a1}$, $R^{8-3a1}$, $R^{9-3a1}$ is protected —COOH (e.g. protected by methyl, ethyl, t-butyl and benzyl) or a group including protected —COOH, and the other symbols are as hereinbefore defined.

The reactions of deprotection under alkaline conditions, deprotection under acidic conditions and hydrogenolysis are known, and may be carried out by the same method as hereinbefore described.

[4] In the compounds of the present invention of the formula (I), the compound in which $R^1$ is —Y—PO($OR^{51}$)$_2$, that is the compound of the formula (I-4):

(I-4)

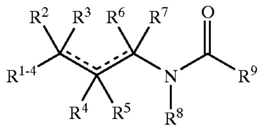

wherein $R^{1-4}$ is —Y—PO($OR^{51}$)$_2$, and the other symbols are as hereinbefore defined; may be prepared by following methods (a)–(d).

(a) The compound in which $R^1$ is —Y—PO($OR^{51}$)$_2$, in which $Y^1$ is —O— and the other symbols are as hereinbefore defined; and all of $R^2$, $R^3$, $R^4$, $R^5$, $R^6$, $R^7$, $R^8$ and $R^9$ are not —COOH or a group including it, that is the compound of the formula (I-4a):

(I-4a)

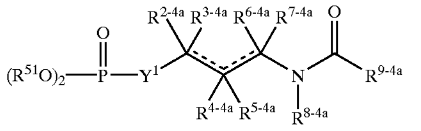

wherein each of $R^{2-4a}$, $R^{3-4a}$, $R^{4-4a}$, $R^{5-4a}$, $R^{6-4a}$, $R^{7-4a}$, $R^{8-4a}$, $R^{9-4a}$ has the same meaning as $R^2$, $R^3$, $R^4$, $R^5$, $R^6$, $R^7$, $R^8$, $R^9$, with the proviso that, all of $R^{2-4a}$, $R^{3-4a}$, $R^{4-34a}$, $R^{5-4a}$, $R^{6-4a}$, $R^{7-4a}$, $R^{8-4a}$, $R^{9-4a}$ are not —COOH or a group including it, and the other symbols are as hereinbefore defined;

may be prepared by reaction of the compound of the formula (VIII):

(VIII)

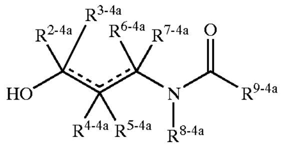

wherein all the symbols are as hereinbefore defined; and the compound of the formula (IX):

(IX)

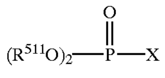

wherein $R^{511}$ is C1–8 alkyl, phenyl or a known protecting group of phosphoric acid and the other symbols are as hereinbefore defined. Furthermore, the compound of the formula (I-4a) may be prepared, followed by deprotection of the compound having a protecting phosphoric acid.

The above reaction was known, for example, it may be carried out in an organic solvent (e.g. pyridine) at 0–40° C.

The reaction of deprotection of phosphoric acid was known, for example, it may be carried out in an organic solvent (e.g. pyridine), using zinc acetate at 0–40° C.

(b) The compound in which $R^1$ is —$Y^1$—PO($OR^{51}$)$_2$, and at least one of $R^2$, $R^3$, $R^4$, $R^5$, $R^6$, $R^7$, $R^8$ and $R^9$ is —COOH or a group including it, that is the compound of the formula (I-4b):

(I-4b)

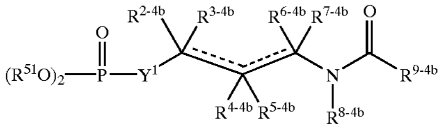

wherein each of $R^{2-4b}$, $R^{3-4b}$, $R^{4-4b}$, $R^{5-4b}$, $R^{6-4b}$, $R^{7-4b}$, $R^{8-4b}$, $R^{9-4b}$ has the same meaning as $R^2$, $R^3$, $R^4$, $R^5$, $R^6$, $R^7$, $R^8$, $R^9$, with the proviso that, at least one of $R^{2-4b}$, $R^{3-4b}$, $R^{4-4b}$, $R^{5-4b}$, $R^{6-4b}$, $R^{7-4b}$, $R^{8-4b}$, $R^{9-4b}$ is —COOH or a group including it, and the other symbols are as hereinbefore defined;

may be prepared by deprotection under alkaline conditions, deprotection under acidic conditions or hydrogenolysis of the compound having protected —COOH or a group including protected —COOH in the compound of the above formula (I-4a), that is the compound of the formula (I-4a1);

(I-4a1)

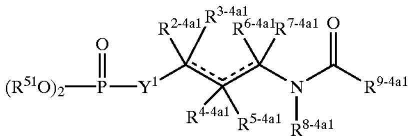

wherein each of $R^{2-4a1}$, $R^{3-4a1}$, $R^{4-4a1}$, $R^{5-4a1}$, $R^{6-4a1}$, $R^{7-4a1}$, $R^{8-4al}$, $R^{9-4a1}$ has the same meaning as $R^2$, $R^3$, $R^4$, $R^5$, $R^6$, $R^7$, $R^8$, $R^9$, with the proviso that, at least one of $R^{2-4a1}$, $R^{3-4a1}$, $R^{4-4a1}$, $R^{5-4a1}$, $R^{6-4a1}$, $R^{7-4a1}$, $R^{8-4a1}$, $R^{9-4a1}$ is protected —COOH (e.g. protected by methyl, ethyl, t-butyl and benzyl) or a group including protected —COOH, and the other symbols are as hereinbefore defined.

The reactions of deprotection under alkaline conditions, deprotection under acidic conditions and hydrogenolysis are known, and may be carried out by the same method as hereinbefore described.

(c) The compound in which $R^1$ is —$Y^2$—PO($OR^{51}$)$_2$, in which $Y^2$ is a single bond or —$CH_2$— and the other symbols are as hereinbefore defined; and all of $R^2$, $R^3$, $R^4$, $R^5$, $R^6$, $R^7$, $R^8$ and $R^9$ are not —COOH or a group including it, that is the compound of the formula (I-4c):

(I-4c)

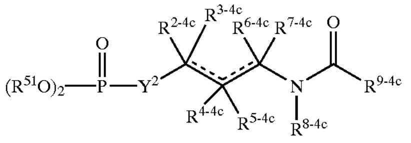

wherein each of $R^{2-4c}$, $R^{3-4c}$, $R^{4-4c}$, $R^{5-4c}$, $R^{6-4c}$, $R^{7-4c}$, $R^{8-4c}$, $R^{9-4c}$ has the same meaning as $R^2$, $R^3$, $R^4$, $R^5$, $R^6$, $R^7$, $R^8$, $R^9$, with the proviso that, all of $R^{2-4c}$, $R^{3-4c}$, $R^{4-4c}$, $R^{5-4c}$, $R^{6-4c}$, $R^{7-4c}$, $R^{8-4c}$, $R^{9-4c}$ are not —COOH or a group including it, and the other symbols are as hereinbefore defined;

may be prepared by reaction of the compound of the formula (X):

(X)

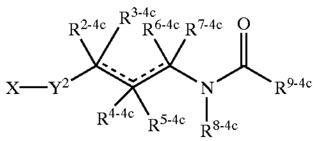

wherein all the symbols are as hereinbefore defined; and the compound of the formula (XI) or (XII):

$(R^{511}O)_3P$ (XI)

or $(R^{511}O)_2POK$ (XII)

wherein all the symbols are as hereinbefore defined. Furthermore, the compound of the formula (I-4c) may be prepared, followed by deprotection of the compound having a protecting phosphoric acid.

The above reaction was known, for example, it may be carried out in an organic solvent (e.g. tetrahydrofuran, dimethylformamide) at 0–120° C.

The reaction of deprotection of phosphoric acid was known, and it may be carried out by the same method as hereinbefore described.

(d) The compound in which $R^1$ is —$Y^2$—$PO(OR^{51})_2$, and at least one of $R^2$, $R^3$, $R^4$, $R^5$, $R^6$, $R^7$, $R^8$ and $R^9$ is —COOH or a group including it, that is the compound of the formula (I-4d):

(I-4d)

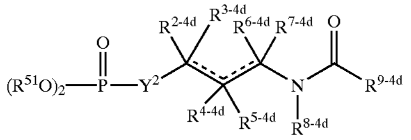

wherein each of $R^{2\text{-}4d}$, $R^{3\text{-}4d}$, $R^{4\text{-}4d}$, $R^{5\text{-}4d}$, $R^{6\text{-}4d}$, $R^{7\text{-}4d}$, $R^{8\text{-}4d}$, $R^{9\text{-}4d}$ has the same meaning as $R^2$, $R^3$, $R^4$, $R^5$, $R^6$, $R^7$, $R^8$, $R^9$, with the proviso that, at least one of $R^{2\text{-}4d}$, $R^{3\text{-}4d}$, $R^{4\text{-}4d}$, $R^{5\text{-}4d}$, $R^{6\text{-}4d}$, $R^{7\text{-}4d}$, $R^{8\text{-}4d}$, $R^{9\text{-}4d}$ is —COOH or a group including it, and the other symbols are as hereinbefore defined;

may be prepared by deprotection under alkaline conditions, deprotection under acidic conditions or hydrogenolysis of the compound having protected —COOH or a group including protected —COOH in the compound of the above formula (I-4c), that is the compound of the formula (I-4c1):

(I-4c1)

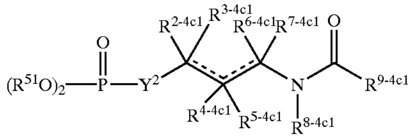

wherein each of $R^{2\text{-}4c1}$, $R^{3\text{-}4c1}$, $R^{4\text{-}4c1}$, $R^{5\text{-}4c1}$, $R^{6\text{-}4c1}$, $R^{7\text{-}4c1}$, $R^{8\text{-}4c1}$, $R^{9\text{-}4c1}$ has the same meaning as $R^2$, $R^3$, $R^4$, $R^5$, $R^6$, $R^7$, $R^8$, $R^9$, with the proviso that, at least one of $R^{2\text{-}4c1}$, $R^{3\text{-}4c1}$, $R^{4\text{-}4c1}$, $R^{5\text{-}4c1}$, $R^{6\text{-}4c1}$, $R^{7\text{-}4c1}$, $R^{8\text{-}4c1}$, $R^{9\text{-}4c1}$ is protected —COOH (e.g. protected by methyl, ethyl, t-butyl and benzyl) or a group including protected —COOH, and the other symbols are as hereinbefore defined.

The reactions of deprotection under alkaline conditions, deprotection under acidic conditions and hydrogenolysis are known, and may be carried out by the same method as hereinbefore described.

The reactions of deprotection in the present invention are common reactions of deprotection as will be apparent to those skilled in the art, for example, deprotection under alkaline conditions, deprotection under acidic conditions or hydrogenolysis. The desired compound of the present invention may be easily prepared using these protecting groups.

As will be apparent to those skilled in the art, methyl, ethyl, t-butyl or benzyl may be used as protecting groups for carboxyl, but other groups which may be removed easily and selectively are also preferred. For example, the groups described in T. W. Greene, Protective Groups in Organic Synthesis, Wiley, New York, 1991, may be used.

Methoxymethyl, tetrahydropyranyl, t-butyldimethylsilyl, acetyl or benzyl may be used as protecting groups for hydroxy, but other groups which may be removed easily and selectively are also preferred. For example, the groups described in T. W. Greene, Protective Groups in Organic Synthesis, Wiley, New York, 1991, may be used.

Benzyloxycarbonyl, t-butoxycarbonyl or trifluoroacetyl maybe used as protecting groups for amino, but other groups which may be removed easily and selectively are also preferred. For example, the groups described in T. W. Greene, Protective Groups in Organic Synthesis, Wiley, New York, 1991, may be used.

The compounds of the formulae (II), (III), (IV), (V), (VI), (VII), (VIII), (IX), (X), (XI), and (XII) are known per se or may be prepared by known methods.

In each reaction in the present specification, products may be purified by conventional techniques. For example, purification may be carried out by distillation at atmospheric or reduced pressure, by high performance liquid chromatography, by thin layer chromatography or by column chromatography using silica gel or magnesium silicate, by washing or by recrystallization. Purification may be carried out after each reaction, or after a series of reactions.

Pharmacological Activities

The potency of inhibitory activity against each matrix metalloproteinase of the compound of the formula (I) was confirmed as below.

(1) Inhibitory Activity Against Gelatinase A

[Method]

The progelatinase A (5 μl; in assay buffer (40 μl)) was purified from human normal skin dermal fibroblasts (HNDF). It was activated by the addition of 10 mM of p-aminophenylmercuric acetate (APMA) (5 μg) for 1 hour at 37° C.

A mixture of the synthetic substrate (MOCAc-Pro-Leu-Gly-A2pr(Dnp)-Ala-Arg-$NH_2$) (130 μl; a final concentration 13.5 μM) and a solution (20 μl) with or without various concentrations of the test compound was preincubated for 5 minutes at 37° C.

The solution of activated gelatinase A (50 μl/well) was mixed with the mixture and the mixture was incubated for 15 minutes at 37° C. The enzyme reaction was started. The enzyme activity was represented by increasing value of fluorescent intensity [Ex=325 nm (Ex)/393 nm (Em)] per 1 minute. Inhibitory activity was represented by inhibitory percentage (%) per enzyme activity without the test compound. For example, $IC_{50}$ of the compound as Example 71 is 0.50 nM.

(2) Inhibitory Activity Against Collagenase

[Method]

The procollagenase (5 μl; in assay buffer (105 μl)) was purified from human normal skin dermal fibroblasts (HNDF). It was activated by the addition of 1 mg/ml Trypsin (45 μl) for 1 minute at 37° C. Trypsin was inactivated by addition of 5 mg/ml soybean trypsin inhibitor (SBTI; 50 μl).

A mixture of the synthetic substrate (Ac-Pro-Leu-Gly-[2-mercapto-4-methyl-pentanoyl]-Leu-Gly-OEt) (105 μl; a final concentration 1.33 mM) and a solution (20 μl) with or without various concentrations of the test compound was preincubated for 5 minutes at 26° C.

The solution of activated enzyme (75 μl/tube, 50 μl) was mixed with the mixture and the mixture was incubated for 10 minutes at 26° C.

Absorption at 324 nm was measured at 40 points over 10 minutes. Vmax value was determined as measured value in 30 points therein. For example, $IC_{50}$ of the compound as Example 71 is 2.5 μM.

(3) Inhibitory Activity Against Stromelysin ps [Method]

The mixture of human stromelysin (Yagai; 9 volume) and 10 mM p-aminophenylmercury acetate (1 volume) was activated for 20 hours at 37° C. A solution of the test compound in dimethylsulfoxide (10 μl) and 0.5 mM solution (10 μl) of 10 mM solution of the synthetic substrate NFF-3 (Mca-Arg-Pro-Lys-Pro-Val-Glu-Nva-Trp-Arg-Lys(DNP)-$NH_2$., Nva: norvaline, Peptide Laboratory) in dimethylsulfoxide diluted by water were added to assay buffer (50 mM tris-HCl, 10 mM $CaCl_2$, 0.05% Brij35, 0.02% NaN3 (pH 7.5)) (150 μl). Furthermore, assay buffer (30 μl) was added to the mixture. The mixture was incubated for 10 minutes at 37° C. The reaction was started by addition of a solution of the above activated stromelysin solution (50 μl). The enzyme activity was represented by increasing value of fluorescent intensity [Ex=325 nm (Ex)/393 nm (Em)] per 1 minute. Inhibitory activity was represented by inhibitory percentage (%) per enzyme activity without the test compound. For example, $IC_{50}$ of the compound as Example 71 is 26 nM.

Toxicity

The toxicity of the compounds of the present invention is very low and therefore, the compounds may be considered safe for pharmaceutical use.

Application for Pharmaceuticals

Inhibition of matrix metalloproteinase, for example, gelatinase, stromelysin or collagenase, is useful for prevention and/or treatment of diseases, for example, rheumatoid diseases, arthrosteitis, unusual bone resorption, osteoporosis, periodontitis, interstitial nephritis, arteriosclerosis, pulmonary emphysema, cirrhosis, cornea injury, metastasis of, invasion of or growth of tumor cells, autoimmune disease (e.g. Crohn's disease, Sjogren's syndrome), disease caused by vascular emigration or infiltration of leukocytes, arterialization, multiple sclerosis, aorta aneurysm, endometriosis in animals including human beings, especially human beings.

For the purpose above described, the compounds of formulae (I) of the present invention and non-toxic salts, acid addition salts or hydrates may be normally administered systemically or locally, usually by oral or parenteral administration.

The doses to be administered are determined depending upon, for example, age, body weight, symptom, the desired therapeutic effect, the route of administration, and the duration of the treatment. In the human adult, the doses per person are generally from 1 mg to 1000 mg, by oral administration, up to several times per day, and from 1 mg to 100 mg, by parenteral administration (preferably intravenous administration), up to several times per day, or continuous administration from 1 to 24 hours per day from vein.

As mentioned above, the doses to be used depend upon various conditions. Therefore, there are cases in which doses lower than or greater than the ranges specified above may be used.

The compounds of the present invention may be administered in the form of, for example, solid compositions, liquid compositions or other compositions for oral administration, injections, liniments or suppositories for parenteral administration.

Solid compositions for oral administration include compressed tablets, pills, capsules, dispersible powders, and granules.

Capsules include hard capsules and soft capsules.

In such compositions, one or more of the active compound(s) may be admixed with at least one inert diluent (such as lactose, mannitol, glucose, hydroxypropyl cellulose, microcrystalline cellulose, starch, polyvinylpyrrolidone or magnesium metasilicate aluminate). The compositions may also comprise, as is normal practice, additional substances other than inert diluents: e.g. lubricating agents (such as magnesium stearate), disintegrating agents (such as cellulose calcium glycolate), stabilizing agents, and agents to assist dissolution (such as glutamic acid or aspartic acid).

The tablets or pills may, if desired, be coated with a film of gastric or enteric material (such as sugar, gelatin, hydroxypropyl cellulose or hydroxypropylmethyl cellulose phthalate), or be coated with two or more films. And further, coating may include containment within capsules of absorbable materials such as gelatin.

Liquid compositions for oral administration include pharmaceutically acceptable emulsions, solutions, syrups and elixirs. In such compositions, one or more of the active compound(s) may be contained in an inert diluent(s) commonly used in the art (e.g. purified water or ethanol). Besides inert diluents, such compositions may also comprise adjuvants (such as wetting agents or suspending agents), sweetening agents, flavouring agents, perfuming agents, and preserving agents.

Other compositions for oral administration include spray compositions which may be prepared by known methods and which comprise one or more of the active compound(s). Spray compositions may comprise additional substances other than inert diluents: e.g. stabilizing agents (such as sodium sulfate), isotonic buffer (such as sodium chloride, sodium citrate or citric acid). For preparation of such spray compositions, for example, the method described in the U.S. Pat. No. 2,868,691 or U.S. Pat. No. 3,095,355 may be used.

Injections for parenteral administration include sterile aqueous or non-aqueous solutions, suspensions and emulsions. Aqueous solutions and suspensions may include distilled water for injection or physiological salt solution. Non-aqueous solutions and suspensions may include propylene glycol, polyethylene glycol, vegetable oil such as olive oil, alcohol such as ethanol or POLYSORBATE80 (registered trade mark).

Injections may comprise additional ingredients other than inert diluents: e.g. preserving agents, wetting agents, emulsifying agents, dispersing agents, stabilizing agents, assisting agents such as agents to assist dissolution (e.g. glutamic acid or aspartic acid).

They may be sterilized for example, by filtration through a bacteria-retaining filter, by incorporation of sterilizing agents in the compositions or by irradiation. They may also be manufactured in the form of sterile solid compositions which may be dissolved in sterile water or some other sterile diluent(s) for injection immediately before use.

Other compositions for parenteral administration include liquids for external use, and endermic liniments, ointment, suppositories for rectal administration and pessaries for vaginal administration which comprise one or more of the active compound(s) and may be prepared by methods known per se.

Reference Example and Example

The following reference examples and examples illustrate the present invention, but do not limit the present invention.

The solvents in the parentheses show the developing or eluting solvents and the ratios of the solvents used are by volume in chromatographic separations or TLC.

The solvents in the parentheses in NMR show the solvents used in measurement.

Reference Example 1

2-(Dihydroxyboronyl)benzofuran

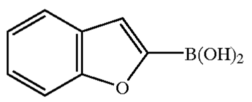

To a solution of benzofuran (128 g) in tetrahydrofuran (540 ml), 1.6N solution of n-butyl lithium in hexane (750 ml) was dropped in the dry ice-methanol bath. The reaction mixture was stirred at 0° C. for 30 minutes. Triisopropyl borate (275 ml) was dropped to the mixture in dry ice-methanol bath, and the mixture was stirred at 0° C. for 1 hour. The reaction mixture was concentrated. To the residue, 1N hydrochloric acid was added. The solution was extracted with ethyl acetate. The extract was washed with water and a saturated aqueous solution of sodium chloride, dried over anhydrous magnesium sulfate and concentrated. The precipitated crystals was washed with hexane and dried to give the title compound (157 g) having the following physical data.

TLC: Rf 0.28 (n-Hexane:Ethyl acetate=1:1).

Reference Example 2

4-(Benzofuran-2-yl)benzoic acid ethyl ester

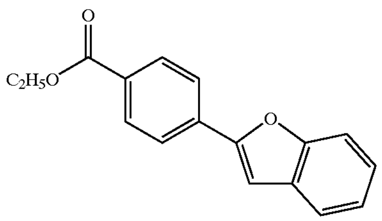

The compound prepared in Reference Example 1 (2.64 g), dichlorobis(triphenylphosphine)palladium (II) [$PdCl_2(PPh_3)_2$] (0.635 g) and triethylamine (10 ml) were added to a solution of 4-iodobenzoic acid ethyl ester (5 g) in dimethylformamide (10 ml). The mixture was stirred at 80° C. for 6 hours. To the reaction mixture, 1N hydrochloric acid was added. The mixture was extracted with ethyl acetate. The extract was washed with a saturated aqueous solution of sodium chloride, dried over anhydrous sodium sulfate and concentrated. The precipitated crystals was washed with hexane/diethyl ether and dried to give the title compound (3.6 g) having the following physical data.

TLC Rf 0.61 (n-Hexane:Ethyl acetate=9:1).

Reference Example 3

4-(Benzofuran-2-yl)benzoic acid

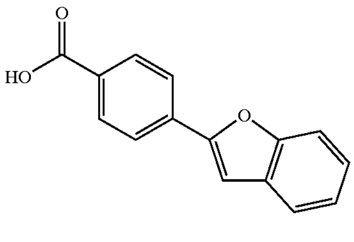

To a solution of the compound prepared in Reference Example 2 (3.4 g) in dioxane (15 ml), 1N aqueous solution of sodium hydroxide (15.3 ml) was added. The mixture was stirred at room temperature for 9 hours. The reaction mixture was acidified by adding 1N hydrochloric acid. The solution was extracted with a mixture of ethyl acetate and tetrahydrofuran (2:1). The extract was washed with a saturated aqueous solution of sodium chloride, dried over anhydrous sodium sulfate and concentrated. The precipitated crystals was washed with ethyl acetate/diethyl ether and dried to give the title compound (2.1 g) having the following physical data.

TLC: Rf 0.43 (Chloroform:Methanol:Acetic acid=100:10:1).

Reference Example 4

4-(Benzofuran-2-yl)benzoyl chloride

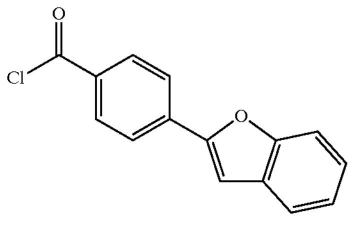

The mixture of the compound prepared in Reference Example 3 (13.4 g) and thionyl chloride (80 ml) was stirred at 80° C. for 6 hours. The reaction mixture was cooled to room temperature and concentrated. The residue was washed with hexane/diethyl ether to give the title compound (12.7 g) having the following physical data.

NMR ($CDCl_3$): δ8.19 (2H, d, J=8.8 Hz), 7.98 (2H, d, J=8.8 Hz), 7.68–7.61 (1H, m), 7.59–7.53 (1H, m), 7.42–7.23 (3H, m).

Example 1

4-(N-(4-(Benzofuran-2-yl)phenylcarbonyl)amino) butyric acid ethyl ester

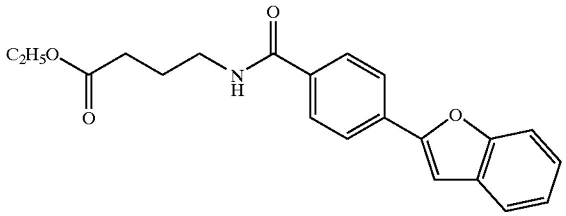

Triethylamine (1 ml) was added to a solution of 4-aminobutyric acid ethyl ester (0.5 g) in dichloromethane (20 ml). A solution of the compound prepared in Reference Example 4 (0.72 g) in dichloromethane (10 ml) was added to the mixture at 0° C. The mixture was stirred at room temperature for 30 minutes. To the reaction mixture, 1N hydrochloric acid was added. The mixture was extracted with ethyl acetate. The extract was washed with a saturated aqueous solution of sodium chloride, dried over anhydrous sodium sulfate and concentrated. The residue was washed with ethyl acetate/diethyl ether and dried to give the title compound (0.732 g) having the following physical data.

TLC: Rf 0.38 (n-Hexane:Ethyl acetate=1:1).

Example 2

4-(N-(4-(Benzofuran-2-yl)phenylcarbonyl)amino) butyric acid

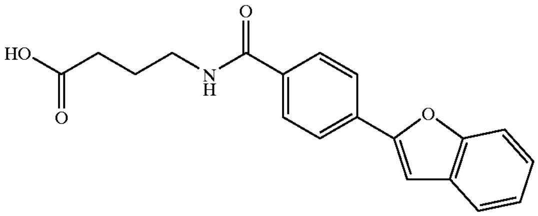

To a solution of the compound prepared in Example 1 (670 mg) in tetrahydrofuran (5 ml), 1N aqueous solution of sodium hydroxide (4.4 ml) was added. The mixture was stirred at room temperature for 3 hours. The reaction mixture was acidified by adding 1N hydrochloric acid, and extracted with ethyl acetate/tetrahydrofuran. The extract was washed with a saturated aqueous solution of sodium chloride, dried over anhydrous sodium sulfate and concentrated to give the title compound (0.617 g) having the following physical data.

TLC: Rf 0.40 (Chloroform:Methanol:Acetic acid=100:10:1);

NMR ($CD_3OD$): δ8.58 (1H, t, J=5.6 Hz), 8.01 (2H, d, J=8.8 Hz), 7.96 (2H, d, J=8.8 Hz), 7.71–7.63 (2H, m), 7.57 (1H, d, J=0.8 Hz), 7.39–7.23 (2H, m), 3.32–3.25 (2H, m), 2.29 (2H, t, J=7.6 Hz), 1.84–1.70 (2H, m).

Example 2(1)~2(24)

The following compounds were obtained by the same procedure as a series of reaction of Example 1→Example 2, using a corresponding acyl halide instead of the compound prepared in Reference Example 4.

Example 2(1)

4-(N-(4-Methylphenylcarbonyl)amino)butyric acid

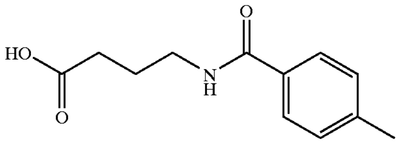

TLC: Rf 0.50 (Chloroform:Methanol:Acetic acid=18:2:1);

NMR ($CD_3OD$): δ12.10 (1H, brs), 8.30 (1H, t, J=5.5 Hz), 7.76 (2H, d, J=8.0 Hz), 7.28 (2H, d, J=8.0 Hz), 3.30 (2H, m), 2.30 (2H, t, J=7.2 Hz), 1.75 (2H, m).

Example 2(2)

4-(N-(4-Butyloxyphenylcarbonyl)amino)butyric acid

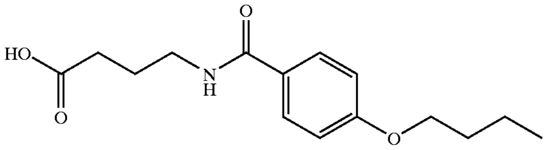

TLC: Rf 0.48 (Chloroform:Methanol:Acetic acid=18:2:1);

NMR ($d_6$-DMSO): δ12.03 (1H, brs), 8.29 (1H, t, J=5.5 Hz), 7.78 (2H, d, J=8.8 Hz), 6.95 (2H, d, J=8.8 Hz), 3.99 (2H, t, J=6.4 Hz), 3.30–3.14 (2H, m), 2.24 (2H, t, J=7.6 Hz), 1.79–1.62 (4H, m), 1.51–1.32 (2H, m), 0.91 (3H, t, J=7.4 Hz).

Example 2(3)

4-(N-(3-Butyloxyphenylcarbonyl)amino)butyric acid

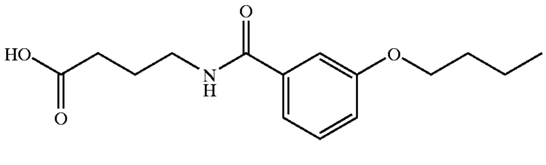

TLC: Rf 0.58 (Chloroform:Methanol:Acetic acid=18:2:1);

NMR ($d_6$-DMSO): δ12.04 (1 H, brs), 8.42 (1H, t, J=5.4 Hz), 7.41–7.28 (3H, m), 7.07–7.00 (1H, m), 3.99 (2H, t, J=6.4 Hz), 3.24 (2H, m), 2.25 (2H, t, J=7.3 Hz), 1.80–1.64 (4H, m), 1.42 (2H, m), 0.92 (3H, t, J=7.3 Hz).

Example 2(4)

4-[N-[4-(2-(4-Methylphenyl)ethynyl)furan-2-ylcarbonyl]amino]butyric acid

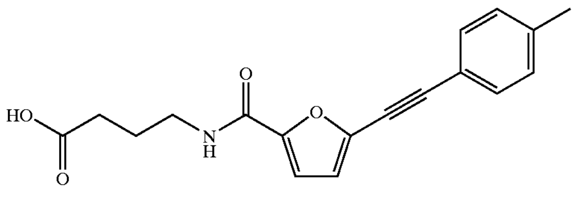

TLC: Rf 0.54 (Chloroform:Methanol:Acetic acid=18:2:1);

NMR ($d_6$-DMSO): δ12.07 (1H, brs), 8.51 (1H, t, J=6.0 Hz), 7.44 (2H, d, J=8.1 Hz), 7.25 (2H, d, J=8.1 Hz), 7.12 (1H, d, J=3.7 Hz), 6.94 (1H, d, J=3.7 Hz), 3.26–3.23 (2H, m), 2.33 (3H, s), 2.23 (2H, d, J=7.5 Hz), 1.79–1.63 (2H, m).

Example 2(5)

4-(N-(4-(Pyrrol-1-yl)phenylcarbonyl)amino)butyric acid

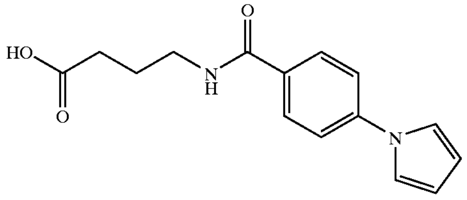

TLC: Rf 0.59 (Chloroform:Methanol:Acetic acid=18:2:1);

NMR ($d_6$-DMSO): δ12.04 (1H, brs), 7.94 (2H, d, J=8.8 Hz), 7.66 (2H, d, J=8.8 Hz), 7.47–7.44 (2H, m), 6.31–6.28 (2H, m), 3.32–3.25 (2H, m), 2.29 (2H, t, J=7.3 Hz), 1.77 (2H, m).

Example 2(6)

4-(N-(trans-4-Methylcyclohexylcarbonyl)amino) butyric acid

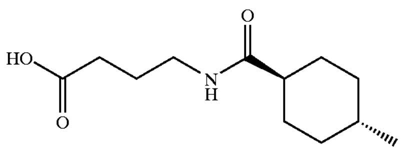

TLC: Rf 0.55 (Chloroform:Methanol:Acetic acid=18:2:1);

NMR ($d_6$-DMSO): δ12.01 (1H, brs), 7.67 (1H, t, J=6.0 Hz), 3.02 (2H, m), 2.19 (2H, t, J=7.5 Hz), 2.06–1.91 (1H, m), 1.74–1.52 (6H, m), 1.46–1.18 (4H, m), 0.98–0.76 (4H, m).

Example 2(7)

4-(N-(4-(3-Methoxy-1-propynyl)phenylcarbonyl) amino)butyric acid

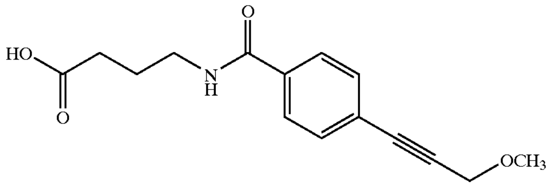

TLC: Rf 0.45 (Chloroform:Methanol:Acetic acid=18:2:1);

NMR ($d_6$-DMSO): δ12.03 (1H, brs), 8.54 (1H, t, J=5.3 Hz), 7.85 (2H, d, J=8.2 Hz), 7.52 (2H, d, J=8.2 Hz), 4.34 (2H, s), 3.35 (3H, s), 3.34–3.22 (2H, m), 2.28 (2H, t, J=7.0 Hz), 1.76 (2H, m).

Example 2(8)

4-(N-(4-Butylphenylcarbonyl)amino)butyric acid

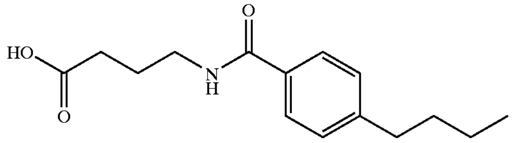

TLC: Rf 0.54 (Chloroform:Methanol:Acetic acid=18:2:1);

NMR ($CD_3OD$): δ12.03 (1H, brs), 8.37 (1H, t, J=5.5 Hz), 7.75 (2H, d, J=8.2 Hz), 7.25 (2H, d, J=8.2 Hz), 3.33–3.22 (2H, m), 2.62 (2H, t, J=7.5 Hz), 227 (2H, t, J=7.4 Hz), 1.83–1.67 (2H, m), 1.65–1.48 (2H, m), 1.40–1.22 (2H, m), 0.90 (3H, t, J=7.1 Hz).

Example 2(9)

4-(N-(Benzofuran-2-ylcarbonyl)amino)butyric acid

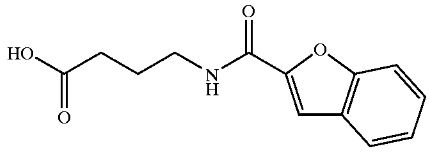

TLC: Rf 0.32 (Chloroform:Methanol:Acetic acid=100:10:1);

NMR ($d_6$-DMSO): δ8.73 (1H, t, J=5.4 Hz), 7.78–7.73 (1H, m), 7.66–7.61 (1H, m), 7.51 (1H, d, J=0.8 Hz), 7.49–7.41 (1H, m), 7.36–7.28 (1H, m), 3.28 (2H, m), 2.27 (2H, t, J=7.4 Hz), 1.83–1.68 (2H, m).

Example 2(10)

4-[N-[4-(2-(4-Chlorophenyl)ethenyl) phenylcarbonyl]amino]butyric acid

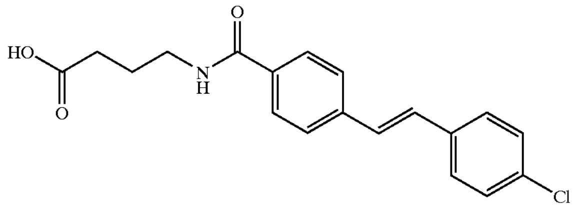

TLC: Rf 0.28 (Chloroform:Methanol=10:1);

NMR ($d_6$-DMSO): δ8.48 (1H, t, J=5.6 Hz), 7.85 (2H, d, J=8.4 Hz), 7.67 (2H, d, J=8.4 Hz), 7.65 (2H, d, J=8.8 Hz), 7.44 (2H, d, J=8.8 Hz), 7.40 (1H, d, J=16.4 Hz), 7.30 (1H, d, J=16.4 Hz), 3.27 (2H, m), 2.27 (2H, t, J=7.4 Hz), 1.82–1.68 (2H, m).

Example 2(11)

4-[N-[4-(2-(4-(Imidazol-1-yl)phenyl)ethynyl) phenylcarbonyl]amino]butyric acid

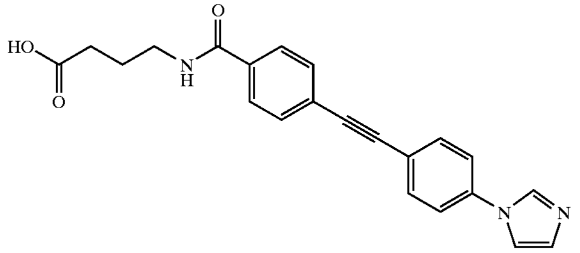

TLC: Rf 0.29 (Chloroform:Methanol:Acetic acid=100:10:1);

NMR ($d_6$-DMSO): δ8.65 (1H, t, J=5.4 Hz), 8.36 (1H, brs), 7.90 (2H, d, J=8.4 Hz), 7.84 (1H, brs), 7.77 (2H, d, J=9.2 Hz), 7.71 (2H, d, J=9.2 Hz), 7.65 (2H, d, J=8.4 Hz), 7.13 (1H, brs), 3.28 (2H, m), 2.31 (2H, t, J=7.2 Hz), 1.82–1.68 (2H, m).

Example 2(12)

4-(N-(trans-4-Propylcyclohexylcarbonyl)amino) butyric acid

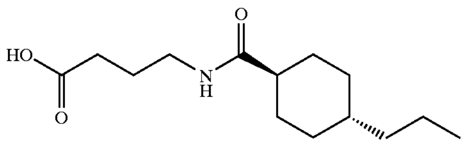

TLC: Rf 0.65 (Chloroform:Methanol:Acetic acid=18:2:1);

NMR ($d_6$-DMSO): δ12.00 (1H, s), 7.74–7.61 (1H, t, J=6.0 Hz), 3.02 (2H, m), 2.19 (2H, t, J=7.2 Hz), 2.11–1.92 (1H, m), 1.78–1.53 (6H, m), 1.43–1.08 (7H, m), 0.95–0.89 (5H, m).

Example 2(13)

4-[N-[4-(2-(4-Methylphenyl)ethynyl) phenylcarbonyl]amino]butyric acid

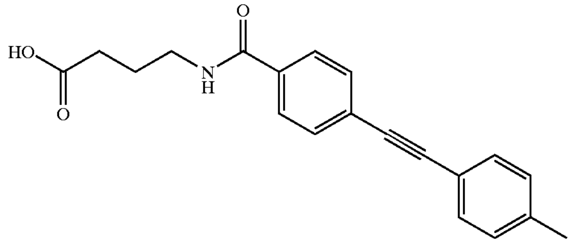

TLC: Rf 0.57 (Chloroform:Methanol:Acetic acid=18:2:1);

NMR ($CD_3OD$): δ12.05 (1H, s), 8.57 (1H, t, J=5.5 Hz), 7.88 (2H, d, J=8.3 Hz), 7.61 (2H, d, J=8.3 Hz), 7.47 (2H, d, J=8.3 Hz), 7.25 (2H, d, J=8.3 Hz), 3.34–3.24 (2H, m), 2.35 (3H, s), 2.29 (2H, t, J=7.2 Hz), 1.77 (2H, m).

Example 2(14)

4-[N-[4-((4-Bromophenyl)aminosulfonyl) phenylcarbonyl]amino]butyric acid

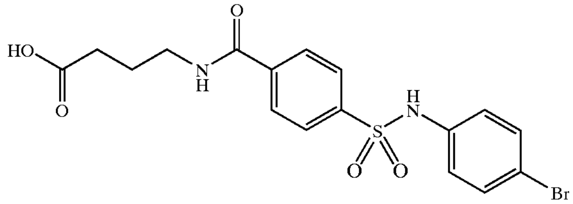

TLC: Rf 0.45 (Chloroform:Methanol:Acetic acid=18:2:1);

NMR ($d_6$-DMSO): δ12.03 (1H, brs), 10.53 (1H, brs), 8.68–8.62 (1H, m), 7.95 (2H, d, J=8.6 Hz), 7.81 (2H, d, J=8.6 Hz), 7.42 (2H, d, J=9.0 Hz), 7.05 (2H, d, J=9.0 Hz), 3.33–3.21 (2H, m), 2.27 (2H, t, J=7.3 Hz), 1.74 (2H, m).

Example 2(15)

4-[N-(4-Cyclohexylphenylcarbonyl)amino]butyric acid

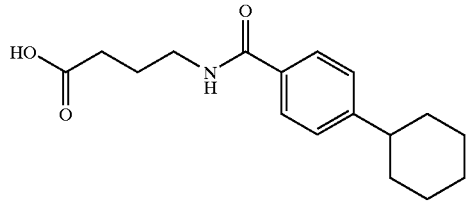

TLC: Rf 0.33 (Chloroform:Methanol=9:1);

NMR ($d_6$-DMSO): δ12.04 (1H, s), 8.45–8.27 (1H, m), 7.75 (2H, d, J=8.4 Hz), 7.28 (2H, d, J=8.4 Hz), 3.34–3.21 (2H, m), 2.64–2.44 (1H, m), 2.26 (2H, t, J=7.3 Hz), 1.85–1.61 (7H, m), 1.56–1.19 (5H, m).

Example 2(16)

4-[N-[4-(4-Propylphenyl)phenylcarbonyl]amino] butyric acid

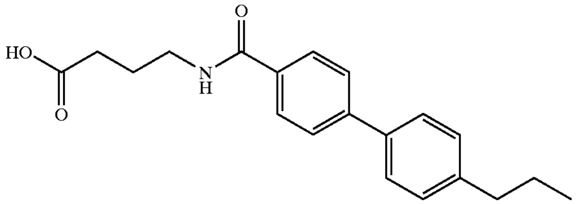

TLC: Rf 0.32 (Chloroform:Methanol=9:1);

NMR ($d_6$-DMSO): δ12.05 (1H, s), 8.56–8.44 (1H, m), 7.93 (2H, d, J=8.4 Hz), 7.73 (2H, d, J=8.4 Hz), 7.64 (2H, d, J=8.4 Hz), 7.30 (2H, d, J=8.4 Hz), 3.40–3.25 (2H, m), 2.61 (2H, t, J=7.4 Hz), 2.29 (2H, t, J=7.3 Hz), 1.86–1.54 (4H, m), 0.92 (3H, t, J=7.4 Hz).

Example 2(17)

4-[N-[4-(4-Hydroxyphenyl)phenylcarbonyl]amino] butyric acid

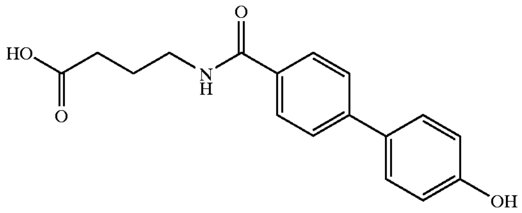

TLC: Rf 0.17 (Chloroform:Methanol=9:1);

NMR ($d_6$-DMSO): δ12.05 (1H, s), 9.62 (1H, s), 8.53–8.42 (1H, m), 7.89 (2H, d, J=8.5 Hz), 7.66 (2H, d, J=8.2 Hz), 7.56 (2H, d, J=8.5 Hz), 6.87 (2H, d, J=8.2 Hz), 3.36–3.26 (2H, m), 2.29 (2H, t, J=7.2 Hz), 1.77 (2H, m).

Example 2(18)

4-[N-[4-(4-Chlorophenyl)furan-2-ylcarbonyl]amino] butyric acid

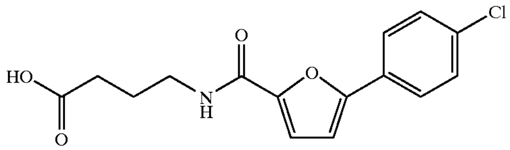

TLC: Rf 0.24 (Chloroform:Methanol=9:1);

NMR ($d_6$-DMSO): δ12.07 (1H, s), 8.62–8.51 (1H, m), 7.94 (2H, d, J=8.4 Hz), 7.54 (2H, d, J=8.4 Hz), 7.17–7.11 (2H, m), 3.33–3.22 (2H, m), 2.29 (2H, t, J=7.2 Hz), 1.77 (2H, m).

Example 2(19)

4-[N-[4-(4-Heptynylphenyl)phenylcarbonyl]amino] butyric acid

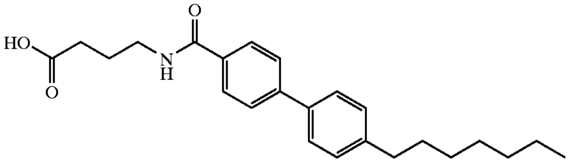

TLC: Rf 0.65 (Chloroform:Methanol:Acetic acid= 18:2:1);

NMR ($d_6$-DMSO): δ12.04 (1H, s), 8.55–8.45 (1H, m), 7.93 (2H, d, J=8.4 Hz), 7.73 (2H, d, J=8.4 Hz), 7.63 (2H, d, J=8.4 Hz), 7.29 (2H, d, J=8.4 Hz), 3.37–3.23 (2H, m), 2.62 (2H, t, J=7.5 Hz), 2.29 (2H, t, J=7.1 Hz), 1.78 (2H, m), 1.68–1.48 (2H, m), 1.39–1.15 (8H, m), 0.86 (3H, t, J=6.6 Hz).

Example 2(20)

4-[N-[4-(4-Methoxyphenyl)phenylcarbonyl]amino] butyric acid

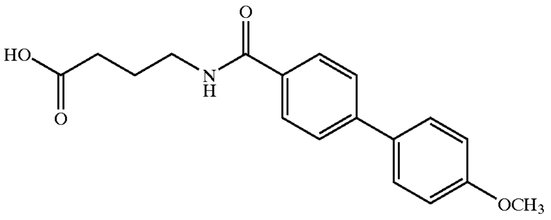

TLC: Rf 0.11 (Chloroform:Methanol=9:1);

NMR ($d_6$-DMSO): δ12.05 (1H, s), 8.55–8.45 (1H, m), 7.91 (2H, d, J=8.4 Hz), 7.71 (2H, d, J=8.4 Hz), 7.68 (2H, d, J=8.9 Hz), 7.05 (2H, d, J=8.9 Hz), 3.81 (3H, s), 3.35–3.22 (2H, m), 2.29 (2H, t, J=7.3 Hz), 1.76 (2H, m).

Example 2(21)

4-[N-[4-(4-Chlorophenyl)phenylcarbonyl]amino] butyric acid

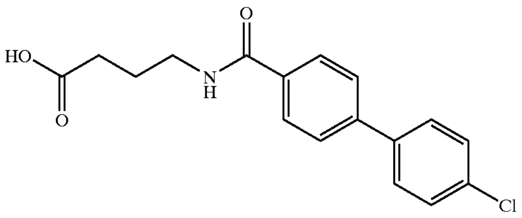

NMR ($d_6$-DMSO): δ12.07 (1H, s), 8.59–8.50 (1H, m), 7.95 (2H, d, J=8.4 Hz), 7.81–7.71 (4H, m), 7.54 (2H, d, J=8.8 Hz), 3.33–3.24 (2H, m), 2.29 (2H, t, J=7.3 Hz), 1.82–1.71 (2H, m).

Example 2(22)

4-[N-(5-Benzyloxyindol-2-ylcarbonyl)amino]butyric acid

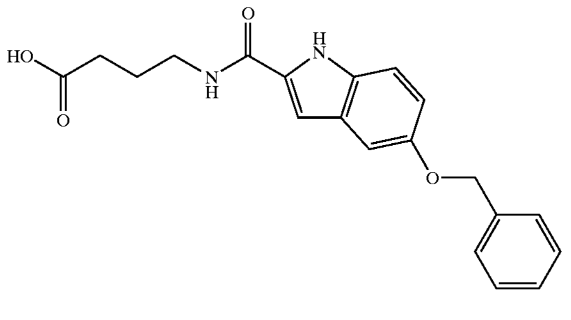

TLC: Rf 0.13 (Chloroform:Methanol=9:1);

NMR ($d_6$-DMSO): δ11.39 (1H, s), 8.42 (1H, t, J=5.6 Hz), 7.50–7.20 (6H, m), 7.15 (1H, d, J=2.2 Hz), 6.99 (1H, d, J=1.8 Hz), 6.89 (1H, dd, J=8.6, 2.2 Hz), 5.07 (2H, s), 3.27 (2H, m), 2.27 (2H, t, J=7.4 Hz), 1.73 (2H, m).

Example 2(23)

4-[N-[5-(2-(4-Chlorophenyl)ethenyl)furan-2-ylcarbonyl]amino]butyric acid

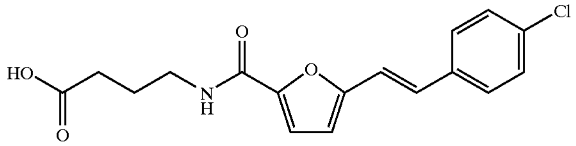

TLC: Rf 0.52 (Chloroform:Methanol:Acetic acid:Water=100:10:1:1);

NMR ($d_6$-DMSO): δ12.06 (1H, brs), 8.43 (1H, t, J=5.8 Hz), 7.59 (2H, d, J=8.8 Hz), 7.42 (2H, d, J=8.8 Hz), 7.26 (1H, d, J=16.6 Hz), 7.14 (1H, d, J=16.6 Hz), 7.09 (1H, d, J=3.2 Hz), 6.63 (1H, d, J=3.2 Hz), 3.25 (2H, m), 2.26 (2H, t, J=7.2 Hz), 1.73 (2H, m).

Example 2(24)

(4-Phenoxyphenylcarbonyl)amino]butyric acid

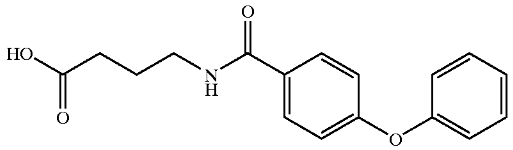

TLC: Rf 0.47 (Chloroform:Methanol:Acetic acid:Water=100:10:1:1);

NMR ($d_6$-DMSO): δ8.41 (1H, t, J=5.4 Hz), 7.85 (2H, d, J=8.4 Hz), 7.42 (2H, t, J=8.0 Hz), 7.18 (1H, t, J=7.2 Hz), 6.97–7.08 (4H, m), 3.24 (2H, m), 2.25 (2H, t, J=7.4 Hz), 1.72 (2H, m).

Example 3

N-(1-Methoxy-1,1-dimethylmethyl)oxy-4-(N-(4-(benzofuran-2-yl)phenylcarbonyl)amino)butyramide

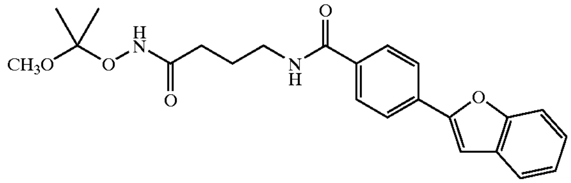

N-(1-Methoxy-1,1-dimethyloxy)amine (0.455 g), 1-hydroxy-benzotriazole.hydrate (0.391 g), and 1-ethyl-3-(3-dimethylaminopropyl)carbodiimide.hydrochloride (0.489 g) were added to a solution of the compound prepared in Example 2 (0.55 g) in dimethylformamide (10 ml) under cooling with ice. The mixture was stirred at room temperature for 3 hours. Water was added to the reaction mixture. The mixture was extracted with ethyl acetate. The extract was washed with a saturated aqueous solution of sodium hydrogen carbonate and a saturated aqueous solution of sodium chloride, dried over anhydrous sodium sulfate and concentrated to give the title compound (0.230 g) having the following physical data.

TLC: Rf 0.13 (Chloroform:Methanol=10:1).

Example 4

N-Hydroxy-4-(N-(4-(benzofuran-2-yl)phenylcarbonyl)amino)butyramide

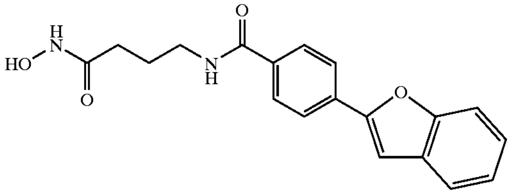

To a solution of the compound prepared in Example 3 (0.230 g) in methanol (10 ml), 1N hydrochloric acid (100 ml) was added. The mixture was stirred at room temperature for 10 minutes. The reaction mixture was concentrated. The residue was washed with diethyl ether to give the title compound (0.218 g) having the following physical data.

TLC: Rf 0.22 (Chloroform:Methanol:Acetic acid=100:10:1);

NMR ($d_6$-DMSO): δ10.39 (1H, brs), 8.59 (1H, t, J=5.8 Hz), 8.01 (2H, d, J=9.0 Hz), 7.96 (2H, d, J=9.0 Hz), 7.67 (2H, m), 7.57 (1H, d, J=0.5 Hz), 7.39–7.23 (2H, m), 3.27 (2H, q, J=5.8 Hz), 2.03 (2H, t, J=7.6 Hz), 1.76 (2H, m).

Example 4(1)~4(36)

The following compounds were obtained by the same procedure as a series of reaction of Example 3→Example 4, using the compounds prepared in Example 2(1)~2(24) or the compounds which were obtained by the same procedure as a series of reaction of Example 1→Example 2 by using a corresponding compound, instead of the compound prepared in Example 2.

Example 4(1)

N-Hydroxy-4-(N-(4-methylphenylcarbonyl)amino)butyramide

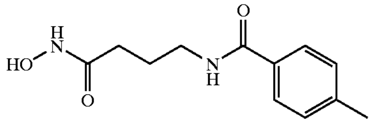

TLC: Rf 0.23 (Chloroform:Methanol=10:1);

NMR ($d_6$-DMSO): δ10.39 (1H, s), 8.70 (1H, s), 8.40 (1H, t, J=5.2 Hz), 7.74 (2H, d, J=8.1 Hz), 7.25 (2H, d, J=8.1 Hz), 3.24 (2H, td, J=6.6, 5.2 Hz), 2.35 (3H, s), 2.02 (2H, t, J=7.7 Hz), 1.74 (2H, m).

Example 4(2)

N-Hydroxy-4-(N-(4-butyloxyphenylcarbonyl)amino)butyramide

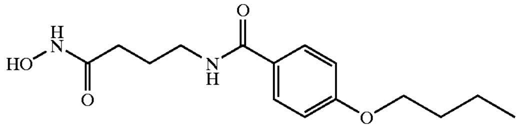

TLC: Rf 0.29 (Chloroform:Methanol:Acetic acid=18:2:1);

NMR ($d_6$-DMSO): δ10.39 (1H, s), 8.70 (1H, brs), 8.32 (1H, t, J=5.8 Hz), 7.80 (2H, d, J=9.0 Hz), 6.96 (2H, d, J=9.0 Hz), 4.01 (2H, t, J=6.4 Hz), 3.35–3.15 (2H, m), 2.01 (2H, t, J=7.3 Hz), 1.81–1.64 (4 H, m), 1.44 (2H, m), 0.94 (3H, t, J=7.4 Hz).

Example 4(3)

N-Hydroxy-4-(N-(3-butyloxyphenylcarbonyl)amino)butyramide

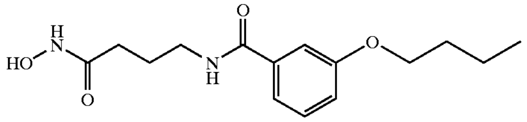

TLC: Rf 0.31 (Chloroform:Methanol:Acetic acid=18:2:1);

NMR (d6-DMSO): δ10.39 (1H, s), 8.45 (1H, t, J=5.2 Hz), 7.43–7.29 (3H, m), 7.19–7.01 (1H, m), 4.01 (2H, t, J=6.3 Hz), 3.30–3.18 (2H, m), 2.02 (2H, t, J=7.5 Hz), 1.83–1.64 (4H, m), 1.49 (2H, m), 0.95 (3H, t, J=7.3 Hz).

Example 4(4)

N-Hydroxy-4-[N-[4-((4-methylphenyl)ethynyl)furan-2-ylcarbonyl]amino]butyramide

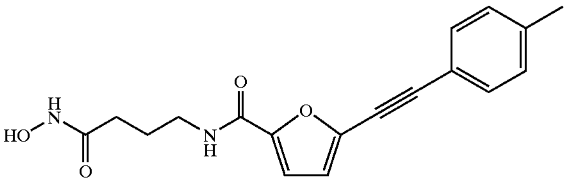

TLC: Rf 0.32 (Chloroform:Methanol:Acetic acid=18:2:1);

NMR ($d_6$-DMSO): δ10.40 (1H, brs), 10.22 (1H, s), 8.56 (1H, t, J=5.7 Hz), 7.47 (2H, d, J=8.3 Hz), 7.28 (2H, d, J=8.3 Hz), 7.16 (1H, d, J=3.6 Hz), 6.96 (1H, d, J=3.6 Hz), 3.28–3.14 (2H, m), 2.36 (3H, s), 2.00 (2H, t, J=7.5 Hz), 1.83–1.64 (2H, m).

Example 4(5)

N-Hydroxy-4-(N-(4-(pyrrol-1-yl)phenylcarbonyl)amino)butyramide

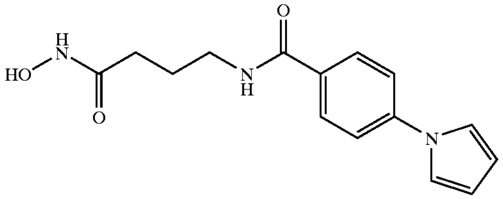

TLC: Rf 0.31 (Chloroform:Methanol:Acetic acid=18:2:1);

NMR ($d_6$-DMSO): δ10.40 (1H, s), 9.00–8.24 (1H, brs), 8.52 (1H, t, J=5.6 Hz), 7.94 (2H, d, J=8.5 Hz), 7.68 (2H, d, J=8.5 Hz), 7.50–7.44 (2H, m), 6.34–6.29 (2H, m), 3.38–3.31 (2H, m), 2.04 (2H, t, J=7.5 Hz), 1.76 (2H, m).

Example 4(6)

N-Hydroxy-4-(N-(trans-4-methylcyclohexylcarbonyl)amino)butyramide

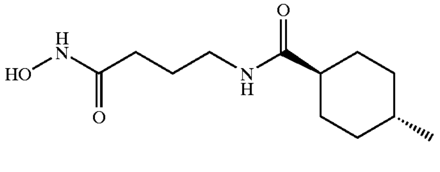

TLC: Rf 0.29 (Chloroform:Methanol:Acetic acid=18:2:1);

NMR ($d_6$-DMSO): δ10.37 (1H, s), 10.20 (1H, s), 7.69 (1H, t, J=5.3 Hz), 3.07–2.92 (2H, m), 2.31–1.88 (3H, m), 1.74–1.52 (6H, m), 1.46–1.18 (3H, m), 0.98–0.76 (2H, m), 0.85 (3H, d, J=6.6 Hz).

Example 4(7)

N-Hydroxy-4-(N-(4-(3-methoxy-1-propynyl)phenylcarbonyl)amino)butyramide

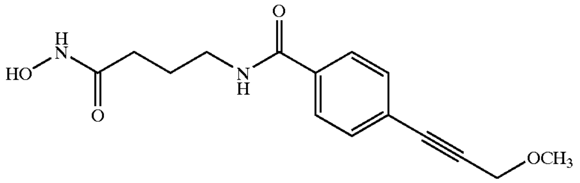

TLC: Rf 0.32 (Chloroform:Methanol:Acetic acid=18:2:1);

NMR ($d_6$-DMSO): δ10.39 (1H, s), 8.57 (1H, t, J=5.5 Hz), 7.85 (2H, d, J=8.6 Hz), 7.53 (2H, d, J=8.6 Hz), 4.35 (2H, s), 3.35 (3H, s), 3.25 (2H, dt, J=5.5, 7.2 Hz), 2.02 (2H, t, J=7.2 Hz), 1.74 (2H, quint, J=7.2 Hz).

Example 4(8)

N-Hydroxy-4-(N-(4-butylphenylcarbonyl)amino)butyramide

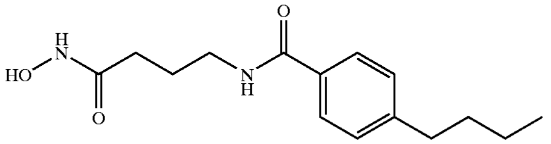

TLC: Rf 0.37 (Chloroform:Methanol:Acetic acid=18:2:1);

NMR ($d_6$-DMSO): δ10.40 (1H, brs), 10.20 (1H, s), 8.41 (1H, t, J=5.4 Hz),7.76 (2H, d, J=8.0 Hz), 7.25 (2H, d, J=8.0 Hz), 3.23 (2H, dt, J=5.4 Hz, J=7.0 Hz), 2.62 (2H, t, J=8.2 Hz), 2.02 (2H, t, J=7.0 Hz), 1.83–1.66 (2H, m), 1.64–1.48 (2H, m), 1.30 (2H, m), 0.90 (3H, t, J=7.2 Hz).

Example 4(9)

N-Hydroxy-4-(N-(benzofuran-2-ylcarbonyl)amino)butyramide

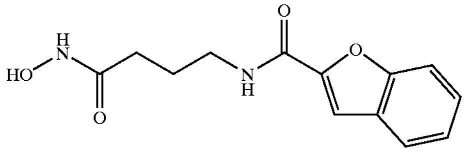

TLC: Rf 0.16 (Chloroform:Methanol:Acetic acid=100:10:1);

NMR ($d_6$-DMSO): δ10.38 (1H, brs), 9.30–8.10 (1H, br), 8.75 (1H, t, J=6.2 Hz), 7.76 (1H, m), 7.64 (1H, m), 7.51 (1H, d, J=0.6 Hz), 7.45 (1H, dt, J=1.6, 7.0 Hz), 7.32 (1H, dt, J=1.0, 7.6 Hz), 3.25 (2H, q, J=6.2 Hz), 2.01 (2H, t, J=7.0 Hz), 1.74 (2H, m).

Example 4(10)

N-Hydroxy-4-[N-[4-(2-(4-chlorophenyl)ethenyl)phenylcarbonyl]amino]butyramide

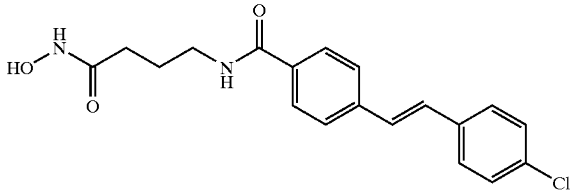

TLC: Rf 0.17 (Chloroform:Methanol:Acetic acid=100:10:1);

NMR ($d_6$-DMSO): δ10.39 (1H, brs), 8.50 (1H, t, J=5.8 Hz), 7.86 (2H, d, J=8.4 Hz), 7.67 (2H, d, J=8.4 Hz), 7.65 (2H, d, J=8.4 Hz), 7.44 (2H, d, J=8.4 Hz), 7.39 (1H, d, J=16.2 Hz), 7.30 (1H, d, J=16.2 Hz), 3.25 (2H, m), 2.02 (2H, t, J=7.6 Hz), 1.74 (2H, m).

Example 4(11)

N-Hydroxy-4-[N-[4-((4-(imidazol-1-yl)phenyl)ethynyl)phenylcarbonyl]amino]butyramide

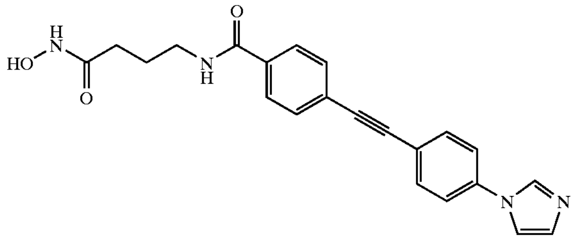

TLC: Rf 0.14 (Chloroform:Methanol:Acetic acid=100:10:1);

NMR ($d_6$-DMSO): δ10.43 (1H, brs), 9.71 (1H, s), 8.67 (1H, t, J=5.6 Hz), 8.33 (1H, brs), 7.95–7.82 (8H, m), 7.67 (2H, d, J=8.4 Hz), 3.25 (2H, m), 2.02 (2H, t, J=7.4 Hz),1.74 (2H, m).

Example 4(12)

N-Hydroxy-4-(N-(trans-4-propylcyclohexylcarbonyl)amino)butyramide

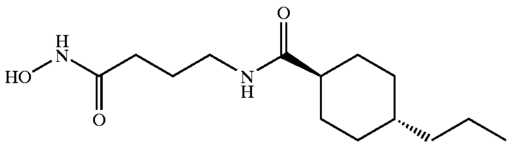

TLC: Rf 0.34 (Chloroform:Methanol:Acetic acid=18:2:1);

NMR ($d_6$-DMSO): δ10.35 (1H, s), 7.67 (1H, t, J=5.3 Hz), 2.99 (2H, m), 2.39–1.88 (3H, m), 1.78–1.61 (6H, m), 1.45–1.07 (7H, m), 0.95–0.76 (5H, m).

Example 4(13)

N-Hydroxy-4-[N-[4-((4-methylphenyl)ethyny) phenylcarbonyl]amino]butyramide

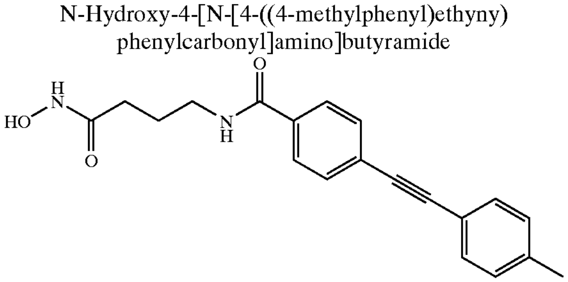

TLC: Rf 0.38 (Chloroform:Methanol:Acetic acid=18:2:1);

NMR ($d_6$-DMSO): δ10.39 (1H, s), 8.62–8.53 (1H, t, J=5.3 Hz), 7.89 (2H, d, J=8.6 Hz), 7.61 (2H, d, J=8.6 Hz), 7.47 (2H, d, J=8.0 Hz), 7.25 (2H, d, J=8.0 Hz), 3.27 (2H, m), 2.35 (3H, s), 2.03 (2H, t, J=6.8 Hz), 1.76 (2H, m).

Example 4(14)

N-Hydroxy-4-[N-[4-((4-bromophenyl) aminosulfonyl)phenylcarbonyl]amino]butyramide

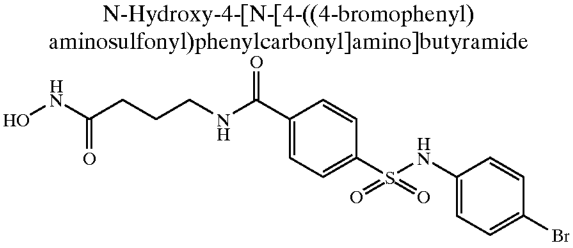

TLC: Rf 0.16 (Chloroform:Methanol:Acetic acid=18:2:1);

NMR ($d_6$-DMSO): δ10.55 (1H, s), 10.38 (1H, brs), 8.67 (1H, m), 7.96 (2H, d, J=8.4 Hz), 7.82 (2H, d, J=8.4 Hz), 7.43 (2H, d, J=9.0 Hz), 7.06 (2H, d, J=9.0 Hz), 3.32–3.16 (2H, m), 2.01 (2H, t, J=7.4 Hz), 1.82–1.66 (2H, m).

Example 4(15)

N-Hydroxy-4-[N-(4-cyclohexylphenylcarbonyl) amino]butyramide

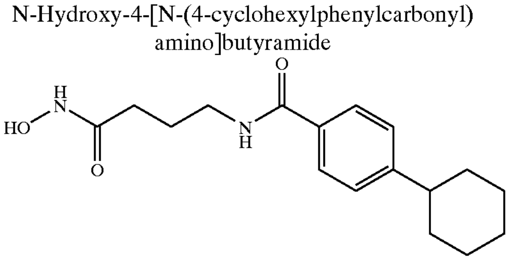

TLC: Rf 0.40 (Chloroform:Methanol:Acetic acid=18:2:1);

NMR ($d_6$-DMSO): δ10.39 (1H, s), 8.43–8.36 (1H, m), 7.76 (2H, d, J=8.4 Hz), 7.34 (2H, d, J=8.4 Hz), 3.30–3.13 (2H, m), 2.63–2.54 (1H, m), 2.01 (2H, t, J=7.6 Hz), 1.86–1.65 (6H, m), 1.48–1.24 (6H, m).

Example 4(16)

N-Hydroxy-4-[N-[4-(4-propylphenyl) phenylcarbonyl]amino]butyramide

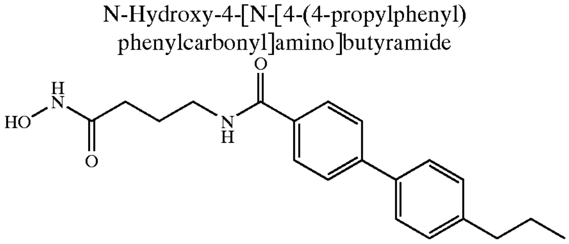

TLC: Rf 0.40 (Chloroform:Methanol:Acetic acid 18:2:1);

NMR ($d_6$-DMSO): δ10.40 (1H, s), 8.70 (1H, brs), 8.57–8.49 (1H, m), 7.93 (2H, d, J=8.5 Hz), 7.74 (2H, d, J=8.5 Hz), 7.64 (2H, d, J=8.5 Hz), 7.31 (2H, d, J=8.5 Hz), 3.31–3.20 (2H, m), 2.61 (2H, t, J=7.4 Hz), 2.04 (2H, t, J=7.2 Hz), 1.76 (2H, m), 1.62 (2H, m), 0.92 (3H, t, J=7.4 Hz).

Example 4(17)

N-Hydroxy-4-[N-[4-(4-hydroxyphenyl) phenylcarbonyl]amino]butyramide

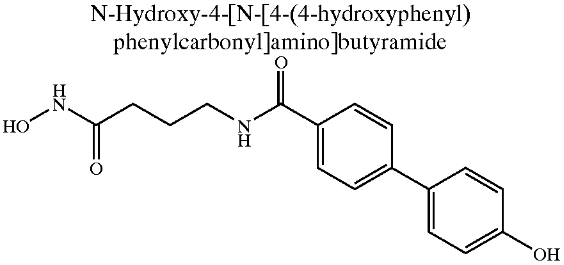

TLC: Rf 0.23 (Chloroform:Methanol:Acetic acid=18:2:1);

NMR ($d_6$-DMSO): δ10.40 (1H, s), 9.80–9.45 (1H, brs), 8.53–8.44 (1H, m), 7.89 (2H, d, J=8.5 Hz), 7.67 (2H, d, J=8.5 Hz), 7.56 (2H, d, J=8.8 Hz), 6.87 (2H, d, J=8.8 Hz), 3.31–3.20 (2H, m), 2.03 (2H, t, J=7.4 Hz), 1.83–1.68 (2H, m).

Example 4(18)

N-Hydroxy-4-[N-[4-(4-chlorophenyl)furan-2-ylcarbonyl]amino]butyramide

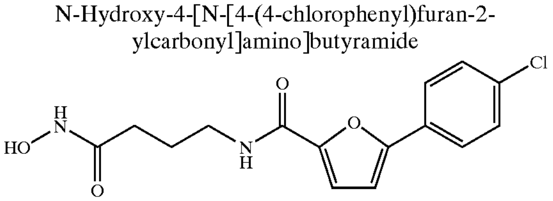

TLC: Rf 0.38 (Chloroform:Methanol:Acetic acid=18:2:1);

NMR ($d_6$-DMSO): δ10.40 (1H, s), 8.64–8.51 (1H, m), 7.95 (2H, d, J=8.4 Hz), 7.54 (2H, d, J=8.4 Hz), 7.16–7.11 (2H, m), 3.31–3.18 (2H, m), 2.08–1.95 (2H, m), 1.76 (2H, m).

Example 4(19)

N-Hydroxy-4-[N-[4-(4-heptynylphenyl) phenylcarbonyl]amino]butyramide

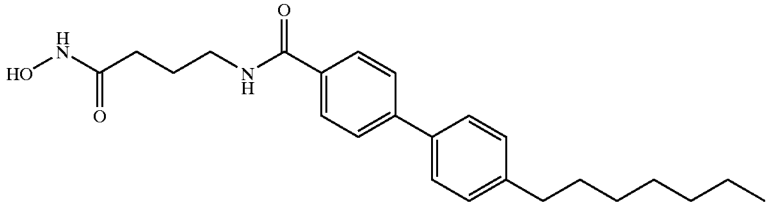

TLC: Rf 0.34 (Chloroform:Methanol:Acetic acid=18:2:1);

NMR ($d_6$-DMSO): δ10.40 (1H, brs), 8.57–8.50 (1H, m), 7.93 (2H, d, J=8.4 Hz), 7.74 (2H, d, J=8.4 Hz), 7.64 (2H, d, J=8.4 Hz), 7.30 (2H, d, J=8.4 Hz), 3.32–3.22 (2H, m), 2.62 (2H, t, J=7.7 Hz), 2.04 (2H, t, J=7.3 Hz), 1.76 (2H, m), 1.69–1.52 (2H, m), 1.38–1.17 (8H, m), 0.86 (3H, t, J=6.6 Hz).

Example 4(20)

N-Hydroxy-4-[N-[4-(4-methoxyphenyl)phenylcarbonyl]amino]butyramide

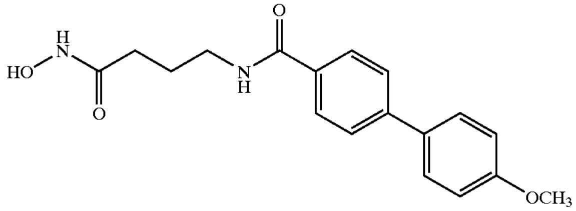

TLC: Rf 0.26 (Chloroform:Methanol=9:1);

NMR ($d_6$-DMSO): δ10.40 (1H, s), 8.57–8.47 (1H, m), 7.91 (2H, d, J=8.5 Hz), 7.71 (2H, d, J=8.5 Hz), 7.68 (2H, d, J=8.8 Hz), 7.05 (2H, d, J=8.8 Hz), 3.81 (3H, s), 3.26 (2H, m), 2.03 (2H, t, J=7.5 Hz), 1.83–1.69 (2H, m).

Example 4(21)

N-Hydroxy-4-[N-[4-(4-chlorophenyl)phenylcarbonyl]amino]butyramide

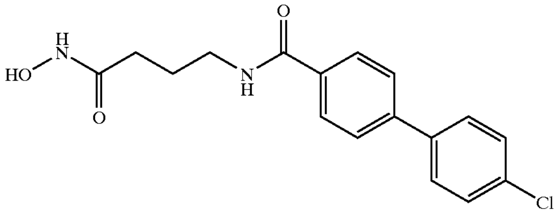

TLC: Rf 0.34 (Chloroform:Methanol:Acetic acid=18:2:1);

NMR ($d_6$-DMSO): δ10.41 (1H, s), 8.62–8.52 (1H, m), 7.95 (2H, d, J=8.4 Hz), 7.82–7.72 (4H, m), 7.55 (2H, d, J=8.4 Hz), 3.35–3.20 (2H, m), 2.04 (2H, t, J=7.5 Hz), 1.83–1.69 (2H, m).

Example 4(22)

N-Hydroxy-4-[N-(5-benzyloxyindol-2-ylcarbonyl)amino]butyramide

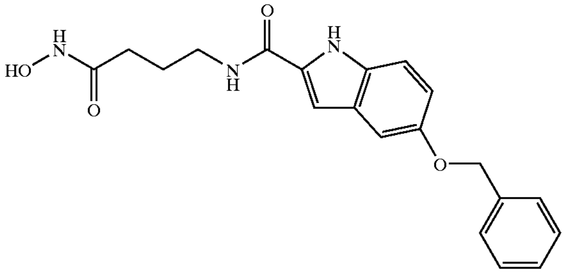

TLC: Rf 0.26 (Chloroform:Methanol:Acetic acid:Water=100:10:1:1);

NMR ($d_6$-DMSO): δ11.38 (1H, brs), 10.38 (1H, brs), 8.70 (1H, brs), 8.43 (1H, t, J=5.8 Hz), 7.28–7.48 (6H, m), 7.16 (1H, d, J=2.2 Hz), 6.99 (1H, d, J=1.4 Hz), 6.89 (1H, dd, J=8.7 Hz, 2.4 Hz), 5.07 (2H, s), 3.25 (2H, m), 2.02 (2H, t, J=6.8 Hz), 1.70–1.81 (2H, m).

Example 4(23)

N-Hydroxy-4-[N-[5-(2-(4-chlorophenyl)ethenyl)furan-2-ylcarbonyl]amino]butyramide

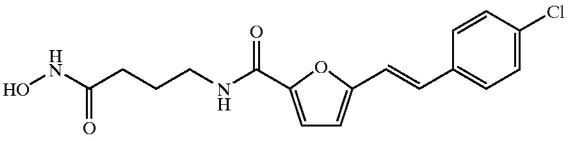

TLC: Rf 0.27 (Chloroform:Methanol:Acetic acid:Water=100:10:1:1);

NMR ($d_6$-DMSO): δ10.38 (1H, brs), 8.71 (1H, brs), 8.46 (1H, t, J=5.8 Hz), 7.60 (2H, d, J=8.8 Hz), 7.43 (2H, d, J=8.8 Hz), 7.23 (1H, d, J=16.6 Hz), 7.15 (1H, d, J=16.6 Hz), 7.09 (1H, d, J=3.4 Hz), 6.63 (1H, d, J=3.4 Hz), 3.22 (2H, m), 2.00 (2H, t, J=7.4 Hz), 1.73 (2H, m).

Example 4(24)

N-Hydroxy-4-[N-(4phenoxyphenylcarbonyl)amino] butyramide

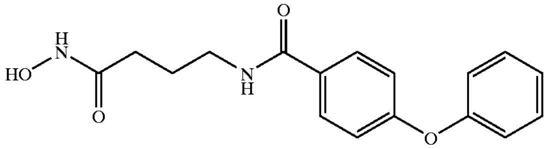

TLC: Rf 0.25 (Chloroform:Methanol:Acetic acid:Water=100:10:1:1);

NMR ($d_6$-DMSO): δ10.36 (1H, brs), 8.69 (1H, brs), 8.41 (1H, t, J=5.6 Hz), 7.85 (2H, d, J=8.8 Hz), 7.41 (2H, t, J=7.4 Hz), 7.19 (1H, t, J=7.4 Hz), 6.97–7.09 (4H, m), 3.22 (2H, m), 1.99 (2H, t, J=7.6 Hz), 1.71 (2H, m).

Example 4(25)

N-Hydroxy-5-[N-[4-(benzofuran-2-yl) phenylcarbonyl]amino]pentanamide

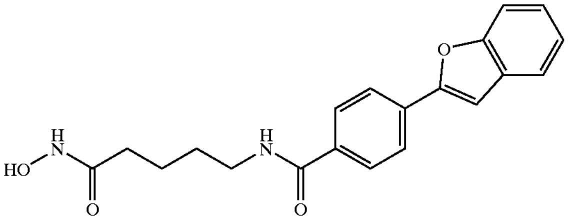

TLC: Rf 0.26 (Chloroform:Methanol=10:1);

NMR ($d_6$-DMSO): δ10.36 (1H, s), 8.67 (1H, br.s), 8.57 (1H, t, J=5.6 Hz), 8.01 (2H, d, J=8.8 Hz), 7.96 (2H, d, J=8.8 Hz), 7.71–7.63 (2H, m), 7.57 (1H, br.s), 7.39–7.23 (2H, m), 3.30–3.23 (2H, m), 2.02–1.94 (2H, m), 1.60–1.44 (4H, m).

Example 4(26)

N-Hydroxy-6-[N-[4-(benzofuran-2-yl) phenylcarbonyl]amino]hexanamide

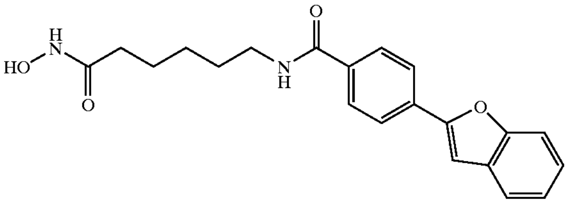

TLC: Rf 0.28 (Chloroform:Methanol=10:1);

NMR ($d_6$-DMSO): δ10.33 (1H, s), 8.80–8.50 (1H, br.s), 8.54 (1H, t, J=5.6 Hz), 8.01 (2H, d, J=8.8 Hz), 7.95 (2H, d, J=8.8 Hz), 7.71–7.62 (2H, m), 7.56 (1H, s), 7.39–7.23 (2H, m), 3.30–3.21 (2H, m), 1.95 (2H, t, J=7.2 Hz), 1.59–1.46 (4H, m), 1.36–1.20 (2H, m).

Example 4(27)

N-Hydroxy-4-[N-[[(4'-carbamoylmethoxy)biphenyl-4-yl]carbonyl]amino]butyramide

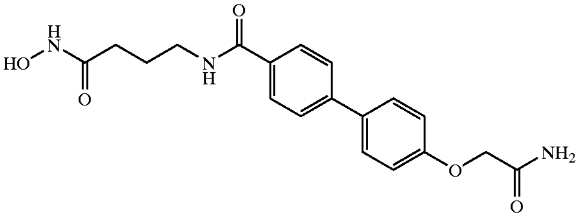

TLC: Rf 0.22 (Chloroform:Methanol:Acetic acid:Water=50:10:1:1);

NMR ($d_6$-DMSO): δ10.37(1H, brs), 8.70(1H, brs), 8.49 (1H, t, J=5.4 Hz), 7.89(2H, d, J=8.8 Hz), 7.70(2H, d, J=8.2 Hz), 7.67(2H, d, J=8.2 Hz), 7.54(1H, brs), 7.39(1H, brs), 7.04(2H, d, J=8.8 Hz), 4.46(2H, s), 3.20–3.31(2H, m), 2.01(2H, t, J=7.2 Hz), 1.66–1.80(2H, m).

Example 4(28)

N-Hydroxy-4-[N-[4-(4-phenylpiperidin-1-yl) phenylcarbonyl]amino]butyramide

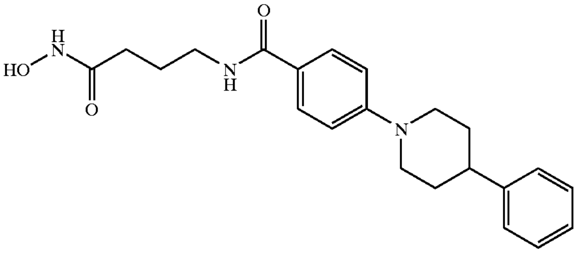

TLC: Rf 0.32 (Chloroform:Methanol=9:1);

NMR ($d_6$-DMSO): δ10.39 (1H, s), 8.69 (1H, s), 8.20 (1H, t, J=5.8 Hz), 7.73 (2H, d, J=8.6 Hz), 7.40–7.12 (5H, m), 6.98 (2H, d, J=8.6 Hz), 4.06–3.90 (2H, m), 3.30–3.16 (2H, m), 2.96–2.60 (3H, m), 2.00 (2H, t, J=7.6 Hz), 1.95–1.59 (6H, m).

Example 4(29)

N-Hydroxy-4-[N-[4-[3-(4-chlorophenoxy)-1-propinyl]phenylcarbonyl]amino]butyramide

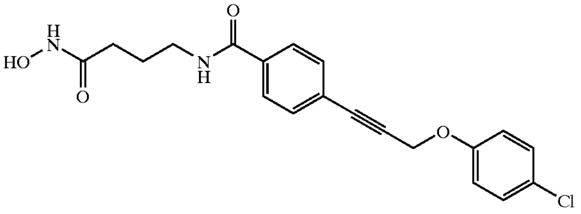

TLC: Rf 0.26 (Chloroform:Methanol=8:1);

NMR ($d_6$-DMSO): δ10.38 (1H, s), 8.71 (1H, s), 8.57 (1H, t, J=5.4 Hz), 7.85 (2H, d, J=8.4 Hz), 7.53 (2H, d, J=8.4 Hz), 7.38 (2H, d, J=9.2 Hz), 7.08 (2H, d, J=9.2 Hz), 5.08 (2H, s), 3.40–3.15 (2H, m, overlap with H2O in dmso), 2.02 (2H, t, J=7.2 Hz), 1.74 (2H, m).

Example 4(30)

N-Hydroxy-4-[N-[4-(3-phenoxy-1-propynyl)phenylcarbonyl]amino]butyramide

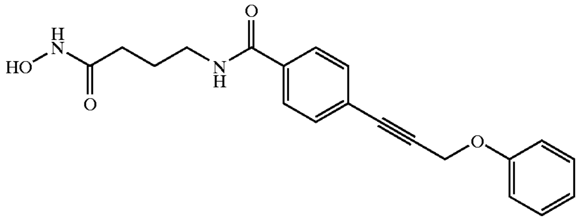

TLC: Rf 0.38 (Chloroform:Methanol=9:1);

NMR (d6-DMSO): δ10.38 (1H, s), 8.70 (1H, s), 8.57 (1H, t, J=5.4 Hz), 7.85 (2H, d, J=8.3 Hz), 7.52 (2H, d, J=8.3 Hz), 7.34 (2H, dd, J=7.0 and 8.6 Hz), 7.10–6.90 (3H, m), 5.06 (2H, s), 3.25 (2H, dt, J=5.4 and 7.2 Hz), 2.02 (2H, t, J=7.2 Hz), 1.74 (2H, m).

Example 4(31)

N-Hydroxy-4-[N-[4-(4-methoxyphenoxy)phenylcarbonyl]amino]butyramide

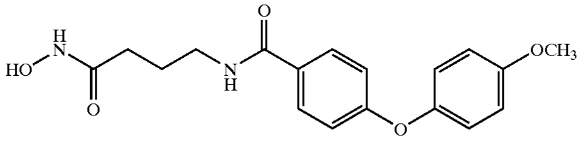

TLC: Rf 0.40 (Chloroform:Methanol:Acetic acid:Water=50:10:1:1);

NMR ($d_6$-DMSO): δ10.37 (1H, brs), 8.70 (1H, brs), 8.40 (1H, t, J=5.5 Hz), 7.82 (2H, d, J=9.1 Hz), 7.06–6.91 (6H, m), 3.79 (3H, s), 3.21 (2H, m), 1.96 (2H, m), 1.72 (2H, m).

Example 4(32)

N-Hydroxy-4-[N-[4-(4-hydroxyphenoxy)phenylcarbonyl]amino]butyramide

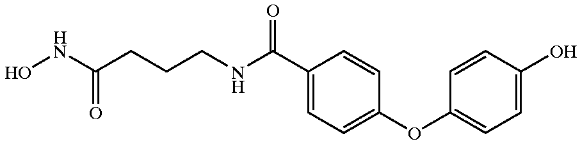

TLC: Rf 0.25 (Chloroform:Methanol:Acetic acid:Water=50:10:1:1);

NMR ($d_6$-DMSO): δ8.37 (1H, t, J=5.5 Hz), 7.81 (2H, d, J=8.8 Hz), 6.92 (2H, d, J=9.1 Hz), 6.90 (2H, d, J=8.8 Hz), 6.80 (2H, d, J=9.1 Hz), 3.21 (2H, m), 1.99 (2H, m), 1.71 (2H, m).

Example 4(33)

N-Hydroxy-4-[N-[4-(4-phenoxypiperadin-1-yl)phenylcarbonyl]amino]butyramide

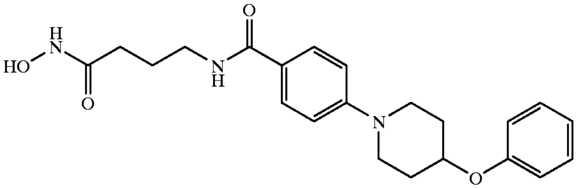

TLC: Rf 0.31 (Chloroform:Methanol=9:1);

NMR ($d_6$-DMSO): δ10.38 (1H, s), 8.69 (1H, s), 8.19 (1H, t, J=5.2 Hz), 7.73 (2H, d, J=8.8 Hz), 7.28 (2H, dd, J=8.8, 7.4 Hz), 7.02–6.87 (5H, m), 4.68–4.52 (1H, m), 3.73–3.56 (2H, m), 3.32–3.10 (4H, m), 2.11–1.92 (4H, m), 1.82–1.59 (4H, m).

Example 4(34)

N-Hydroxy-4-[N-[4-(4-phenyl-1,2,5,6-tetrahydropyridin-1-yl)phenylcarbonyl]amino]butyramide

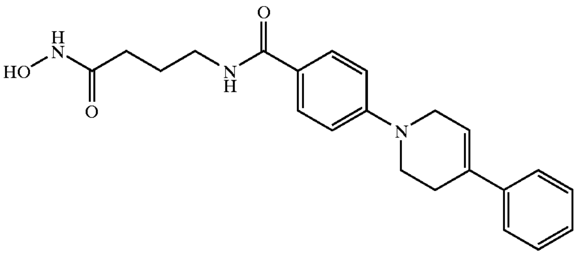

TLC: Rf 0.42 (Chloroform:Methanol:Acetic acid:Water=50:10:1:1);

NMR ($d_6$-DMSO): δ10.38 and 9.78 (total 1H, both brs), 9.02 and 8.69 (total 1H, both brs), 8.20 (1H, t, J=5.5 Hz), 7.75 (2H, d, J=9.1 Hz), 7.48 (2H, m), 7.36 (2H, m), 7.26 (1H, m), 6.98 (2H, d, J=9.1 Hz), 6.29 (1H, brs), 3.94 (2H, m), 3.58 (2H, m), 3.20 (2H, m), 2.62 (2H, m), 1.99 (2H, m), 1.71 (2H, m).

Example 4(35)

N-Hydroxy-4-[N-[4-(1-heptynyl)phenylcarbonyl]amino]butyramide

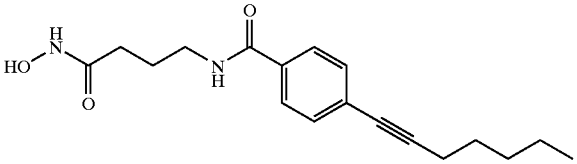

TLC: Rf 0.24 (Chloroform:Methanol=10:1);

NMR ($d_6$-DMSO): δ10.37 (1H, s), 8.52 (1H, t, J=5.6 Hz), 7.80 (2H, d, J=8.4 Hz), 7.44 (2H, d, J=8.4 Hz), 3.23 (2H, br.q, J=5.8 Hz), 2.43 (2H, t, J=6.6 Hz), 2.00 (2H, t, J=7.4 Hz), 1.79–1.65 (2H, m), 1.62–1.48 (2H, m), 1.44–1.22 (4H, m), 0.88 (3H, t, J=6.6 Hz).

Example 4(36)

N-Hydroxy-4-[N-(4-benzyloxyphenylcarbonyl)amino]butyramide

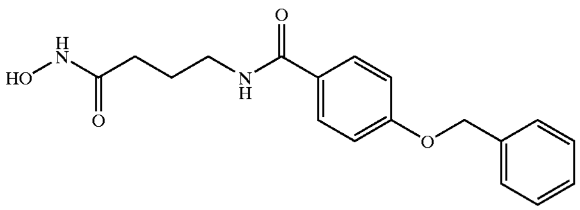

TLC: Rf 0.11 (Chloroform:Methanol:Acetic acid:Water=100:10:1:1);

NMR ($d_6$-DMSO): δ10.36 and 9.78 (total 1H, each br), 8.99 and 8.68 (total 1H, each br), 8.31 (1H, m), 7.80 (2H, d, J=8.8 Hz), 7.45–7.3 (5H, m), 7.05 (2H, d, J=8.8 Hz), 5.15 (2H, s), 3.21 (2H, m), 1.99 (2H, t, J=7.4 Hz), 1.72 (2H, m).

Example 5

4-(N-Methyl-N-(4-(benzofuran-2-yl)phenylcarbonyl)amino)butyric acid ethyl ester

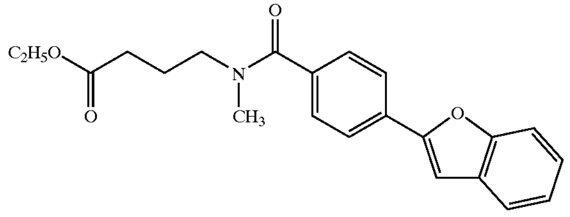

Methyl iodide (0.35 ml) was added to a solution of the compound prepared in Example 1 (0.1 g) in dimethylformamide (3 ml). To the mixture, 60% sodium hydride (13 mg) was added at 0° C. The mixture was stirred at room temperature for 1 hour. To the reaction mixture, 1N hydrochloric acid was added. The mixture was extracted with ethyl acetate. The extract was washed with a saturated aqueous solution of sodium chloride, dried over anhydrous sodium sulfate and concentrated to give the title compound (113 mg) having the following physical data.

TLC: Rf 0.33 (n-Hexane:Ethyl acetate=1:1).

Example 6

4-(N-Methyl-N-(4-(benzofuran-2-yl)phenylcarbonyl)amino)butyric acid

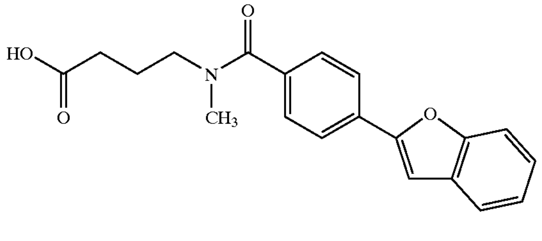

The title compound having the following physical data was obtained by the same procedure as a series of reaction of Example 2, using the compounds prepared in Example 5 instead of the, compound prepared in Example 1.

TLC: Rf 0.51 (Chloroform:Methanol=9:1);

NMR ($CD_3OD$): δ7.98 (2H, d, J=8.4 Hz), 7.66–7.59 (1H, m), 7.57–7.46 (3H, m), 7.37–7.19 (3H, m), 3.62 and 3.40 (2H, t, J=7.5 Hz), 3.10 and 3.03 (3H, s), 2.45 and 2.20 (2H, t, J=7.5 Hz), 2.10–1.75 (2H, m).

Example 7

N-Hydroxy-4-(N-methyl-N-(4-(benzofuran-2-yl)phenylcarbonyl)amino)butyramide

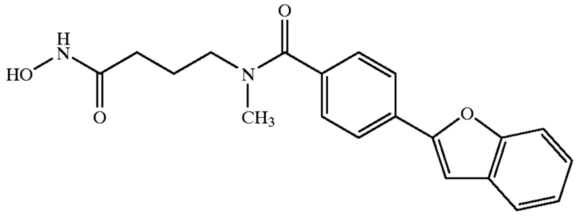

The title compound having the following physical data was obtained by the same procedure as a series of reaction of Example 3→Example 4, using the compounds prepared in Example 6 instead of the compound prepared in Example 2.

TLC: Rf 0.31 (Chloroform:Methanol=9:1);

NMR ($CD_3OD$): δ7.99 (2H, d, J=8.4 Hz), 7.66–7.59 (1H, m), 7.58–7.45 (3H, m), 7.37–7.20 (3H, m), 3.70–3.54 and 3.42–3.30 (2H, m), 3.16–2.95 (3H, m), 2.30–1.80 (4H, m).

Example 8

4-(N-(4-(Benzofuran-2-yl)phenylcarbonyl)amino)-2(S)-hydroxybutyric acid methyl ester

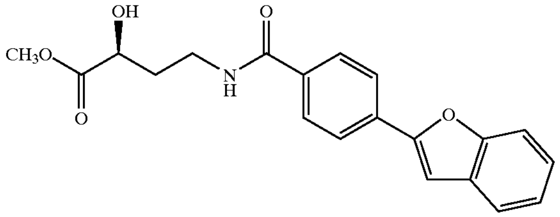

The title compound having the following physical data was obtained by the same procedure as a series of reaction of Example 1, using 4-amino-2(S)-hydroxybutyric acid methyl ester (It was prepared by the same procedure as a series of reaction described in EP 393441.) instead of 4-aminobutyric acid ethyl ester.

TLC: Rf 0.11 (n-Hexane:Ethyl acetate=1:1);

NMR ($d_6$-DMSO): δ8.58 (1H, t, J=6.0 Hz), 8.01 (2H, d, J=8.8 Hz), 7.96 (2H, d, J=8.8 Hz), 7.71–7.63 (2H, m), 7.57 (1H, brs), 7.39–7.24 (2H, m), 4.19–4.10 (1H, m), 3.62 (3H, s), 3.38 (2H, q, J=6.0 Hz), 2.06–1.68 (2H, m).

Example 9

4-(N-(4-(Benzofuran-2-yl)phenylcarbonyl)amino)-2 (S)-hydroxybutyric acid

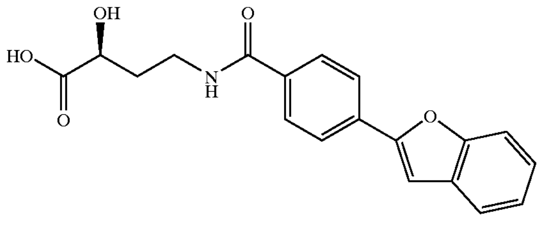

The title compound having the following physical data was obtained by the same procedure as a series of reaction of Example 2, using the compounds prepared in Example 8 instead of the compound prepared in Example 1.

TLC: Rf 0.10 (Chloroform:Methanol:Acetic acid=100:10:1);

NMR ($d_6$-DMSO): δ8.49 (1H, t, J=5.6 Hz), 7.92 (2H, d, J=8.8 Hz), 7.87 (2H, d, J=8.8 Hz), 7.62–7.53 (2H, m), 7.48 (1H, d, J=0.6 Hz), 7.30–7.14 (2H, m), 3.95 (1H, dd, J=4.4, 8.4 Hz), 3.29 (2H, m), 1.98–1.58 (2H, m).

Example 9(1)

4-(N-(4-(Benzofuran-2-yl)phenylcarbonyl)amino)-2 (R)-hydroxybutyric acid

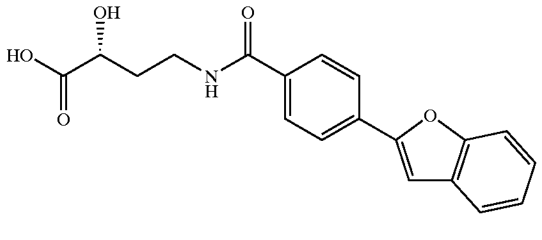

The title compound having the following physical data was obtained by the same procedure as a series of reaction of Example 8→Example 9, using 4-amino-2(R)-hydroxybutyric acid methyl ester instead of 4-amino-2(S)-hydroxybutyric acid methyl ester.

TLC: Rf 0.10 (Chloroform:Methanol:Acetic acid=100:10:1);

NMR ($d_6$-DMSO): δ8.49 (1H, t, J=5.6 Hz), 7.92 (2H, d, J=8.8 Hz), 7.87 (2H, d, J=8.8 Hz), 7.62–7.53 (2H, m), 7.48 (1H, d, J=0.6 Hz), 7.30–7.14 (2H, m), 3.95 (1H, dd, J=4.4, 8.4 Hz), 3.29 (2H, m), 1.98–1.58 (2H, m).

Example 10

4-(N-(4-(Benzofuran-2-yl)phenylcarbonyl)amino)-2 (S)-benzyloxymethoxybutyric acid methyl ester

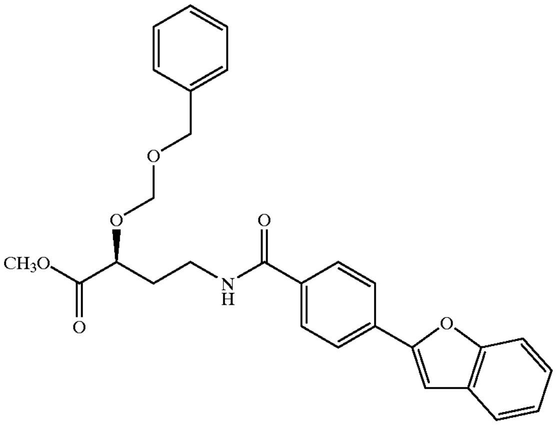

Disopropylethylamine (2 ml) was added to a solution of the compound prepared in Example 8 (0.2 g) in methylene chloride (1 ml). Benzyloxymethyl chloride (0.79 ml) was added to the mixture. The mixture was stirred at 50° C. for 30 minutes. To the reaction mixture, 1N hydrochloric acid was added and the mixture was extracted with ethyl acetate. The extract was washed with water and a saturated aqueous solution of sodium chloride, dried over anhydrous sodium sulfate and concentrated. The residue was purified by column chromatography on silica gel (n-hexane:ethyl acetate=3:2) to give the title compound (0.176 g) having the following physical data.

TLC: Rf 0.47 (n-Hexane:Ethyl acetate=1:1).

Example 11

4-(N-(4-(Benzofuran-2-yl)phenylcarbonyl)amino)-2 (S)-benzyloxymethoxybutyric acid

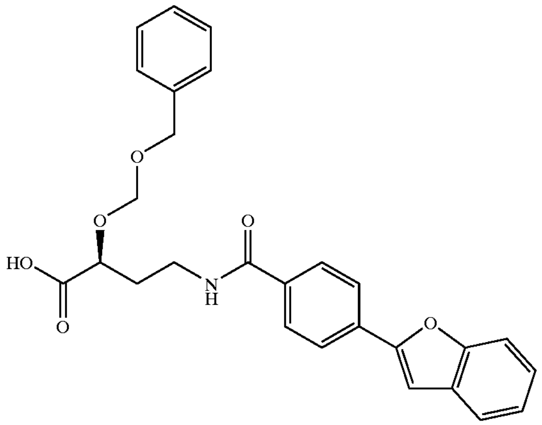

The title compound having the following physical data was obtained by the same procedure as a series of reaction of Example 2, using the compound prepared in Example 10 instead of the compound prepared in Example 1.

TLC: Rf 0.45 (Chloroform:Methanol:Acetic acid=100:20:1);

NMR ($d_6$-DMSO): δ8.61 (1H, t, J=5.4 Hz), 8.01 (2H, d, J=8.8 Hz), 7.95 (2H, d, J=8.8 Hz), 7.709–7.63 (2H, m), 7.57

(1H, brs), 4.80 (1H, d, J=8.8 Hz), 4.79 (1H, d, J=8.8 Hz), 4.64 (1H, d, J=11.8 Hz), 4.54 (1H, d, J=11.8 Hz), 4.13 (1H, dd, J=4.2, 8.2 Hz), 3.52–3.28 (2H, m), 2.12–1.82 (2H, m).

Example 11(1)~11(3)

The following compounds were obtained by the same procedure as a series of reaction of Example 8→Example 10→Example 11, using corresponding an amine and an acyl halide.

Example 11(1)

4-(N-(4-(Benzofuran-2-yl)phenylcarbonyl)amino)-2 (R)-benzyloxymethoxybutyric acid

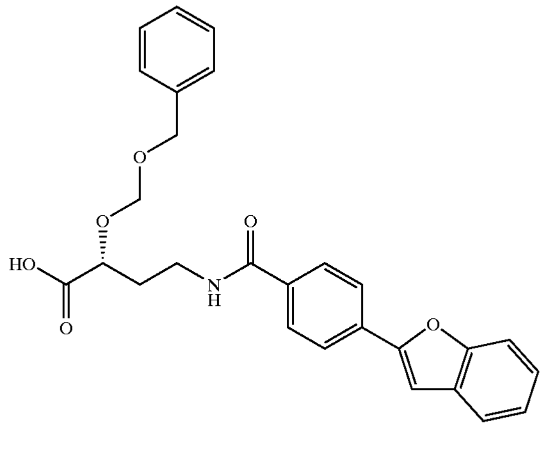

TLC: Rf 0.45 (Chloroform:Methanol:Acetic acid=100:20:1);

NMR ($d_6$-DMSO): δ8.61 (1H, t, J=5.4 Hz), 8.01 (2H, d, J=8.8 Hz), 7.95 (2H, d, J=8.8 Hz), 7.709–7.63 (2H, m), 7.57 (1H, brs), 4.80 (1H, d, J=8.8 Hz), 4.79 (1H, d, J=8.8 Hz), 4.64 (1H, d, J=11.8 Hz), 4.54 (1H, d, J=11.8 Hz), 4.13 (1H, dd, J=4.2, 8.2 Hz), 3.52–3.28 (2H, m), 2.12–1.82 (2H, m).

Example 11(2)

4-(N(4-(2-(4-Chlorophenyl)ethenyl)phenylcarbonyl) amino)-2(S)-benzyloxymethoxybutyric acid

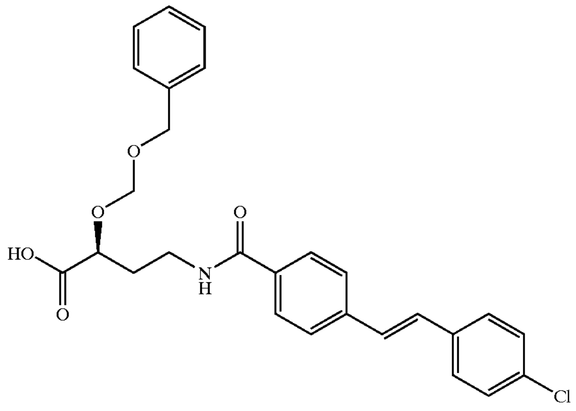

TLC: Rf 0.18 (Chloroform:Methanol=10:1);

NMR ($d_6$-DMSO): δ8.52 (1H, t, J=5.4 Hz), 7.84 (2H, d, J=8.4 Hz), 7.67 (2H, d, J=8.4 Hz), 7.65 (2H, d, J=8.8 Hz), 7.44 (2H, d, J=8.8 Hz), 7.35–7.28 (7H, m), 4.80 (1H, d, J=8.8 Hz), 4.77 (1H, d, J=8.8 Hz), 4.63 (1H, d, J=11.8 Hz), 4.54 (1H, d, J=11.8 Hz), 4.12 (1H, dd, J=4.4, 8.0 Hz), 3.50–3.26 (2H, m), 2.10–1.78 (2H, m).

Example 11(3)

4-(N-(4-Chlorophenylcarbonyl)amino)-2-benzyloxymethoxybutyric acid

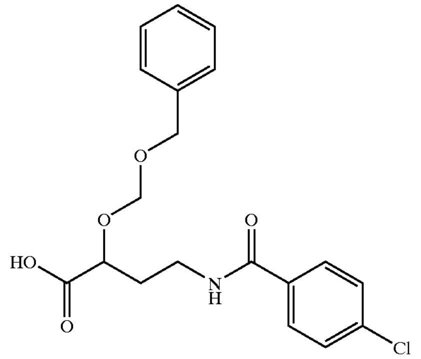

TLC: Rf 0.32 (Chloroform:Methanol:Acetic acid=100:10:1);

NMR ($d_6$-DMSO): δ8.57 (1H, t, J=5.6 Hz), 7.84 (2H, d, J=8.8 Hz), 7.52 (2H, d, J=8.8 Hz), 7.30 (5H, s), 4.80 (1H, d, J=8.8 Hz), 4.76 (1H, d, J=8.8 Hz), 4.63 (1H, d, J=11.8 Hz), 4.53 (1H, d, J=11.8 Hz), 4.11 (1H, dd, J=4.4, 8.2 Hz), 3.49–3.24 (2H, m), 2.08–1.77 (2H, m).

Example 12

N-Hydroxy-4-(N-(4-(benzofuran-2-yl) phenylcarbonyl)amino)-2(S)-hydroxybutyramide

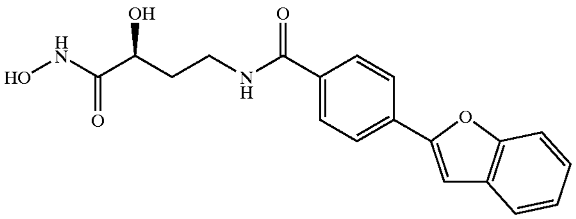

The title compound having the following physical data was obtained by the same procedure as a series of reaction of Example 3→Example 4, using the compound prepared in Example 9 instead of the compound prepared in Example 2.

TLC: Rf 0.42 (Chloroform:Methanol:Water=100:20:1);

NMR ($d_6$-DMSO): δ10.49 (1H, brs), 8.55 (1H, t, J=5.4 Hz), 8.01 (2H, d, J=9.0 Hz), 7.96 (2H, d, J=9.0 Hz), 7.71–7.62 (2H, m), 7.57 (1H, brs), 7.39–7.23 (2H, m), 3.94 (1H, dd, J=4.2, 8.2 Hz), 3.41–3.31 (2H, m), 2.02–1.64 (2H, m).

Example 12(1)~12(5)

The following compounds were obtained by the same procedure as a series of reaction of Example 12, using the compound prepared in Example 9(1), Example 11 and Example 11(1)~11(3) instead of the compound prepared in Example 9.

Example 12(1)

N-Hydroxy-4-(N-(4-(benzofuran-2-yl) phenylcarbonyl)amino)-2(R)-hydroxybutyramide

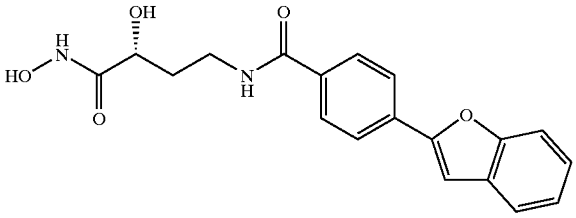

TLC: Rf 0.42 (Chloroform:Methanol:Water=100:20:1);

NMR ($d_6$-DMSO): δ10.49 (1H, brs), 8.55 (1H, t, J=5.4 Hz), 8.01 (2H, d, J=9.0 Hz), 7.96 (2H, d, J=9.0 Hz), 7.71–7.63 (2H, m), 7.57 (1H, brs), 7.39–7.23 (2H, m), 3.94 (1H, dd, J=4.2, 8.2 Hz), 3.41–3.31 (2H, m), 2.02–1.62 (2H, m).

Example 12(2)

N-Hydroxy-4-(N-(4-(benzofuran-2-yl) phenylcarbonyl)amino)-2(S)-benzyloxymethoxybutyramide

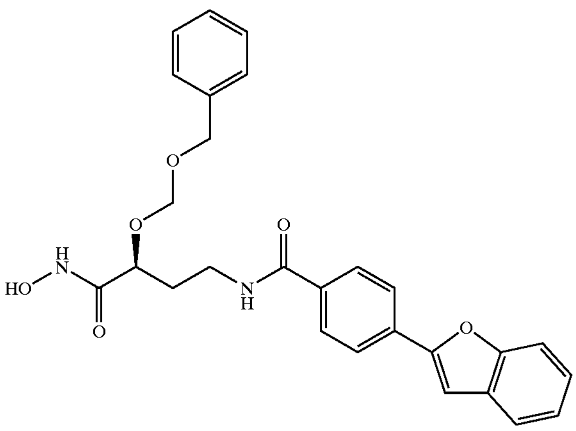

TLC: Rf 0.24 (Chloroform:Methanol=10:1);

NMR ($d_6$-DMSO): δ10.75 (1H, brs), 8.90 (1H, brs), 8.55 (1H, t, J=5.6 Hz), 8.01 (2H, d, J=8.8 Hz), 7.96 (2H, d, J=8.8 Hz), 7.71–7.63 (2H, m), 7.58 (1H, brs), 7.39–7.24 (7H, m), 4.77 (1H, d, J=8.8 Hz), 4.68 (1H, d, J=8.8 Hz), 4.58 (2H, s), 4.04 (1H, t, J=5.8 Hz), 3.49–3.25 (2H, m), 1.93 (2H, m).

Example 12(3)

N-Hydroxy-4-(N-(4-(benzofuran-2-yl) phenylcarbonyl)amino)-2(R)-benzyloxymethoxybutyramide

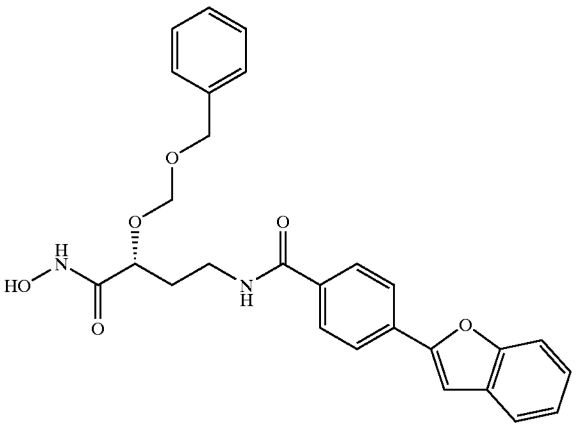

TLC: Rf 0.24 (Chloroform:Methanol=10:1);

NMR ($d_6$-DMSO): δ10.75 (1H, brs), 8.90 (1H, brs), 8.55 (1H, t, J=5.6 Hz), 8.01 (2H, d, J=8.8 Hz), 7.96 (2H, d, J=8.8 Hz), 7.71–7.63 (2H, m), 7.58 (1H, brs), 7.39–7.24 (7H, m), 4.77 (1H, d, J=8.8 Hz), 4.68 (1H, d, J=8.8 Hz), 4.58 (2H, s), 4.04 (1H, t, J=5.8 Hz), 3.49–3.25 (2H, m), 1.93 (2H, m).

Example 12(4)

N-Hydroxy-4-(N-(4-(2-(4-chlorophenyl)ethenyl) phenylcarbonyl)amino)-2(S)-benzyloxymethoxybutyramide

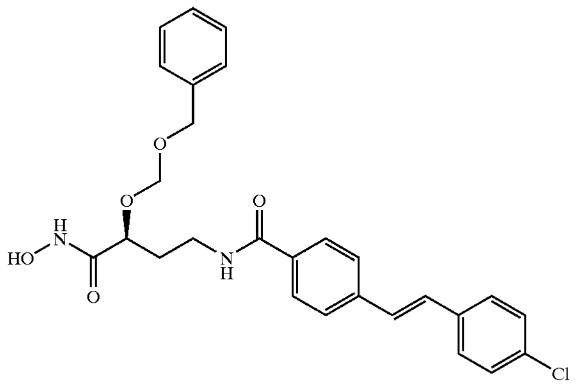

TLC: Rf 0.22 (Chloroform:Methanol=10:1);

NMR ($d_6$-DMSO): δ10.74 (1H, brs), 8.89 (1H, brs), 8.45 (1H, t, J=5.6 Hz), 7.85 (2H, d, J=8.4 Hz), 7.67 (2H, d, J=8.4 Hz), 7.65 (2H, d, J=8.6 Hz), 7.45 (2H, d, J=8.6 Hz), 7.35–7.26 (7H, m), 4.76 (1H, d, J=8.8 Hz), 4.67 (1H, d, J=8.8 Hz), 4.57 (2H, s), 4.02 (1H, t, J=5.8 Hz), 3.48–3.28 (2H, m), 1.91 (2H, m).

Example 12(5)

N-Hydroxy-4-(N-(4-chlorophenylcarbonyl)amino)-2-benzyloxymethoxybutyramide

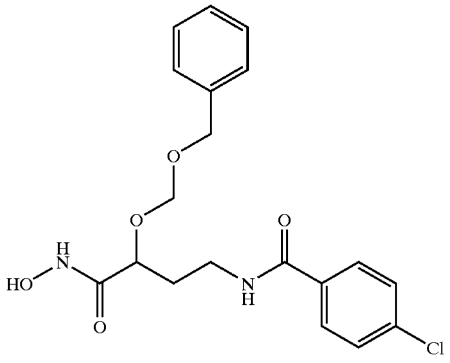

TLC: Rf 0.34 (Chloroform:Methanol=10:1);

NMR ($d_6$-DMSO): δ10.73 (1H, brs), 8.89 (1H, brs), 8.52 (1H, m), 7.84 (2H, d, J=8.4 Hz), 7.52 (2H, d, J=8.4 Hz), 7.30 (5H, brs), 4.75 (1H, d, J=8.8 Hz), 4.66 (1H, d, J=8.8 Hz), 4.56 (2H, s), 4.01 (1H, t, J=6.6 Hz), 3.45–3.25 (2H, m), 1.89 (2H, m).

Example 13

4-(N-(4-Chlorophenylcarbonyl)amino)-2-(t-butyloxycarbonylmethoxy)butyric acid methyl ester

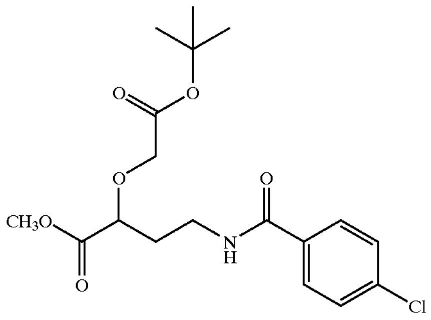

A solution of 4-(N-(4-chlorophenylcarbonyl)amino)-2-hydroxybutyric acid methyl ester (3 g) in tetrahydrofuran (15 ml) was dropped to a mixture of 60% sodium hydride (2.38 g) in tetrahydrofuran (10 ml) at −78° C. The mixture was stirred at 0° C. for 30 minutes. t-Butyl bromoacetate (0.975 g) was dropped to the mixture at −78° C. The mixture was stirred at 0° C. for 1.5 hours. To the reaction mixture, 1N hydrochloric acid was added and the mixture was extracted with ethyl acetate. The extract was washed with a saturated aqueous solution of sodium hydrogen carbonate and a saturated aqueous solution of sodium chloride, dried over anhydrous sodium sulfate and concentrated. The residue was purified by column chromatography on silica gel (n-Hexane:Ethyl acetate=1:1) to give the title compound (3.194 g) having the following physical data.

TLC: Rf 0.63 (n-Hexane:Ethyl acetate=1:1).

Example 14

4-(N-(4-Chlorophenylcarbonyl)amino)-2-(carboxymethoxy)butyric acid methyl ester

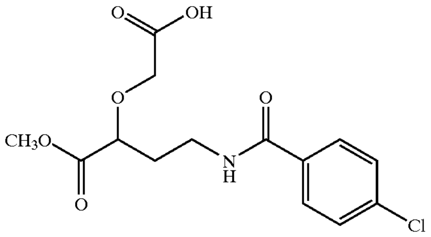

A solution of the compound prepared in Example 13 (3.194 g) in trifluoroacetic acid (50 ml) was stirred at room temperature for 1 hour. The reaction mixture was concentrated. Diethyl ether was added to the residue. The precipitated crystals was washed with diethyl ether, and dried to give the title compound (2.275 g) having the following physical data.

TLC: Rf 0.28 (Chloroform:Methanol:Acetic acid=100:10:1).

Example 15

4-(N-(4-Chlorophenylcarbonyl)amino)-2-((N-benzyl-N-methylamino)carbonylmethoxy)butyric acid methyl ester

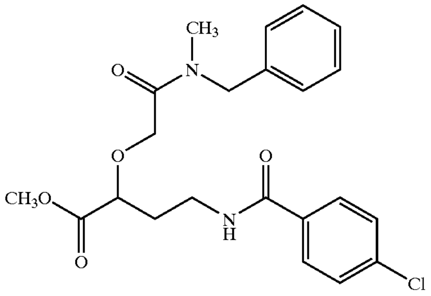

N-Benzyl-N-methylamine (0.213 g), 1-hydroxybenzotriazole.hydrate (0.27 g), 1-Ethyl-3-(3-dimethylaminopropyl)carbodiimide.hydrochloride (0.337 g) were added to a solution of the compound prepared in Example 14 (0.5 g) in dimethylformamide (5 ml) under cooling with ice. The mixture was stirred at room temperature for 1 hour. To the reaction mixture, 1 N Hydrochloric acid was added and the mixture was extracted with ethyl acetate. The extract was washed with a saturated aqueous solution of sodium hydlrogen carbonate and a saturated aqueous solution of sodium chloride, dried over anhydrous sodium sulfate and concentrated to give the title compound (0.664 g) having the following physical data.

TLC: Rf 0.60 (n-Hexane:Ethyl acetate=1:1).

Example 16

4-(N-(4-Chlorophenylcarbonyl)amino)-2-((N-benzyl-N-methylamino)carbonylmethoxy)butyric acid

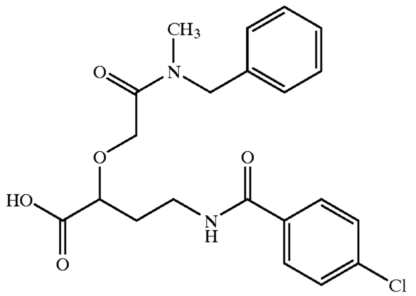

The title compound having the following physical data was obtained by the same procedure as a series of reaction of Example 2, using the compound prepared in Example 15 instead of the compound prepared in Example 1.

TLC: Rf 0.21 (Chloroform:Methanol:Acetic acid=100:10:1);

NMR ($d_6$-DMSO): δ8.83 and 8.72 (total 1H, m), 7.87 and 7.86 (total 2H, d, J=8.8 Hz), 7.53–7.23 (7H, m), 4.53 and 4.49 (total 2H, s), 4.38 (1H, d, J=15.0 Hz), 4.24 (1H, d, J=15.0 Hz), 3.52–3.37 (1H, m), 2.86 and 2.80 (total 3H, s), 2.08–1.72 (2H, m).

Example 16(1) and 16(2)

The following compounds were obtained by the same procedure as a series of reaction of Example 15→Example 16, using a corresponding amine instead of N-benzyl-N-methylamine.

Example 16(1)

4-(N-(4-Chlorophenylcarbonyl)amino)-2-((N-phenyl-N-methylamino)carbonylmethoxy)butyric acid

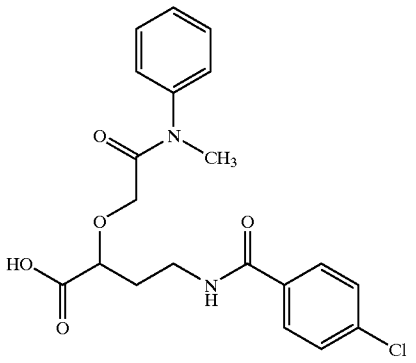

TLC: Rf 0.29 (Chloroform:Methanol:Acetic acid=100:10:1);

NMR ($d_6$-DMSO): δ8.72 (1H, t, J=5.8 Hz), 7.88 (2H, d, J=8.4 Hz), 7.53 (2H, d, J=8.4 Hz), 7.49–7.34 (5H, m), 4.05–3.82 (3H, m), 3.44–3.33 (2H, m),:3.19 (3H, s), 2.04–1.64 (2H, m).

Example 16(2)

4-(N-(4-Chlorophenylcarbonyl)amino)-2-((N-phenylethyl-N-methylamino)carbonylmethoxy) butyric acid

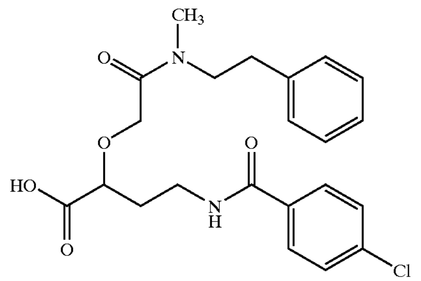

TLC: Rf 0.32 (Chloroform:Methanol:Acetic acid=100:10:1);

NMR ($d_6$-DMSO): δ8.83 (0.5H, t, J=5.5 Hz), 8.75 (0.5H, t, J=5.5 Hz), 7.89 (1H, d, J=8.4 Hz), 7.86 (1H, d, J=8.4 Hz), 7.53 (1 H, d, J=8.4 Hz), 7.49 (1H, d, J=8.4 Hz), 7.30 (5H, s), 4.39 (0.5H, d, J=15.4 Hz), 4.17 (0.5H, d, J=15.4 Hz), 4.13 (0.5H, d, J=14.6 Hz), 3.95 (0.5H, dd, J=8.8, 3.0 Hz), 3.90 (0.5H, d, J=14.6 Hz), 3.79 (0.5H, dd, J=9.0, 3.6 Hz), 3.60–3.30 (4H, m), 2.90–2.70 (2H, m), 2.10–1.60 (2H, m).

Example 17

N-Hydroxy-4-(N-(4-chlorophenylcarbonyl)amino)-2-((N-benzyl-N-methylamino)carbonylmethoxy) butyramide

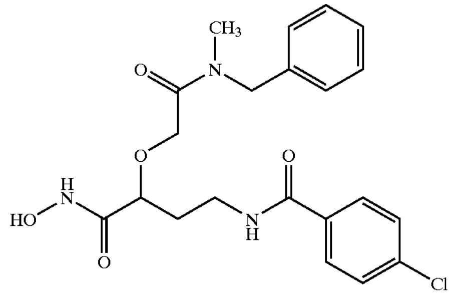

The title compound having the following physical data was obtained by the same procedure as a series of reaction of Example 3→Example 4, using the compound prepared in Example 16 instead of the compound prepared in Example 2.

TLC: Rf 0.39 (Chloroform:Methanol=10:1);

NMR($d_6$-DMSO): δ10.93 and 10.90 (total 1H, brs, and brs), 9.05–8.65 (2H, m), 7.87 and 7.86 (total 2H, d and d, J=8.8 Hz and J=8.8 Hz), 7.52 and 7.45 (total 2H, d and d, J=8.8 Hz and J=8.8 Hz), 7.37–7.19 (5H, m), 4.54 and 4.50 (total 2H, s and s), 4.44 and 4.36 (total 1H, d and d, J=14.2 Hz and J=15.0 Hz), 4.24 and 4.20 (total 1H, d and d, J=14.2 Hz and J=15.0 Hz), 3.94–3.88 (1H, m), 2.84 and 2.80 (total 3H, s and s), 2.00–1.68 (2H, m).

Example 17(1) and 17(2)

The following compounds were obtained by the same procedure as a series of reaction of Example 17, using the compound prepared in Example 16(1) and 16(2) instead of the compound prepared in Example 16.

Example 17(1)

N-Hydroxy-4-(N-(4-chlorophenylcarbonyl)amino)-2-((N-phenyl-N-methylamino)carbonylmethoxy) butyramide

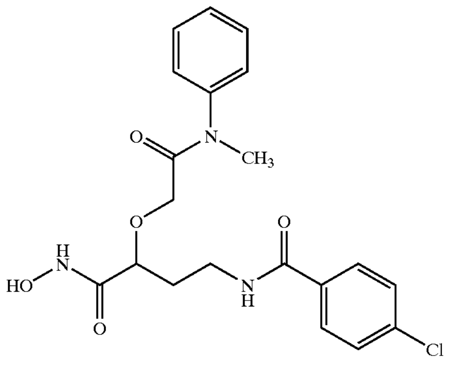

TLC: Rf 0.48 (Chloroform:Methanol=10:1);

NMR($d_6$-DMSO): δ10.79 (1H, brs), 9.20–8.40 (1H, br), 8.68 (1H, m), 7.87 (2H, d, J=8.8 Hz), 7.53 (2H, d, J=8.8 Hz), 7.46–7.34 (5H, m), 4.14–3.67 (3H, m), 3.55–3.25 (2H, m), 3.19 (3H, s), 1.95–1.60 (2H, m).

Example 17(2)

N-Hydroxy-4-(N-(4-chlorophenylcarbonyl)amino)-2-((N-phenylethyl-N-methylamino) carbonylmethoxy)butyramide

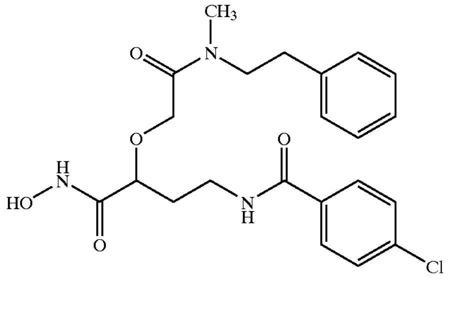

TLC: Rf 0.40 (Chloroform:Methanol=10:1);

NMR ($d_6$-DMSO): δ10.90 (1H, brs), 8.87 (1H, brs), 8.83–8.67 (1H, m), 7.89 and 7.87 (total 2H, d and d, J=8.4 Hz and J=8.4 Hz), 7.53 and 7.49 (total 2H, d and d, J=8.4 Hz and J=8.4 Hz), 7.33–7.17 (5H, m), 4.31 and 4.10 and 3.99 (total 2H, d and d and s, J=15.4 Hz and J=15.4 Hz), 3.85 and 3.69 (total 1H, dd and dd, J=4.4, 8.8 Hz and J=4.0, 8.4 Hz), 3.56–3.32 (2H, m), 2.84–2.72 (2H, m), 1.97–1.68 (2H, m).

Example 18

3(S)-Hydroxy-4-(N-(4-(benzofuran-2-yl) phenylcarbonyl)amino)butyric acid methyl ester

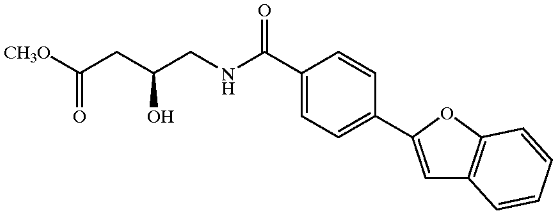

The title compound having the following physical data was obtained by the same procedure as a series of reaction of Example 1, using 3(S)-hydroxy-4-aminobutyric acid ethyl ester (it is described in Acta Chem. Scand., Ser. B, 37, 341 (1983).) instead of 4-aminobutyric acid ethyl ester.

TLC: Rf 0.31 (n-Hexane:methyl acetate=1:1);

NMR ($d_6$-DMSO): δ8.57 (1H, t, J=6.0 Hz), 8.00 (4H, s), 7.71–7.63 (2H, m), 7.57 (1H, brs), 7.40–7.24 (2H, m), 5.13 (1H, d, J=5.6 Hz), 4.18–4.00 (1H, m), 3.57 (3H, s), 3.30 (2H, t, J=6.0 Hz), 2.55 (1H, dd, J=4.0, 15.0 Hz), 2.31 (1H, dd, J=4.0, 15.0 Hz).

Example 19

3(S)-Hydroxy-4-(N-(4-(benzofuran-2-yl) phenylcarbonyl)amino)butyric acid

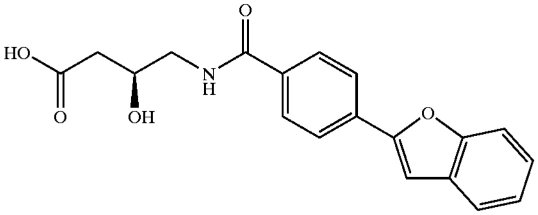

The title compound having the following physical data was obtained by the same procedure as a series of reaction of Example 2, using the compound prepared in Example 18 instead of the compound prepared in Example 1.

TLC: Rf 0.24 (Chloroform:Methanol:Acetic acid=100:10:1);

NMR ($d_6$-DMSO): δ8.55 (1H, t, J=5.8 Hz), 8.00 (4H, s), 7.71–7.63 (2H, m), 7.58 (1H, brs), 7.39–7.23 (2H, m), 5.16–4.92 (1H, brs), 4.14–4.00 (1H, m), 3.30 (2H, t, J=5.8 Hz), 2.46 (1H, dd, J=4.2, 15.0 Hz), 2.23 (1H, dd, J=8.4, 15.0 Hz).

Example 19(1)

3(R)-Hydroxy-4-(N-(4-(benzofuran-2-yl) phenylcarbonyl)amino)butyric acid

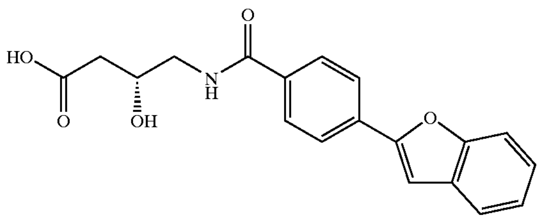

The title compound having the following physical data was obtained by the same procedure as a series of reaction of Example 18→Example 19, using 3(R)-hydroxy-4-aminobutyric acid methyl ester instead of 3(S)-hydroxy-4-aminobutyric acid ethyl ester.

TLC: Rf 0.24 (Chloroform:Methanol:Acetic acid=100:10:1);

NMR ($d_6$-DMSO): δ8.55 (1H, t, J=5.8 Hz), 8.00 (4H, s), 7.71–7.63 (2H, m), 7.58 (1H, brs), 7.39–7.23 (2H, m), 5.16–4.92 (1H, brs), 4.14–4.00 (1H, m), 3.30 (2H, t, J=5.8 Hz), 2.46 (1H, dd, J=4.2, 15.0 Hz), 2.23 (1H, dd, J=8.4, 15.0 Hz).

Example 20

3(S)-Methoxymethyloxy-4-(N-(4-(benzofuran-2-yl) phenylcarbonyl)amino)butyric acid and 4-(N-(4-(Benzofuran-2-yl)phenylcarbonyl)amino)-2-butenoic acid

20(1)

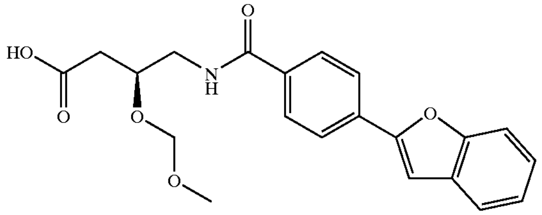

20(2)

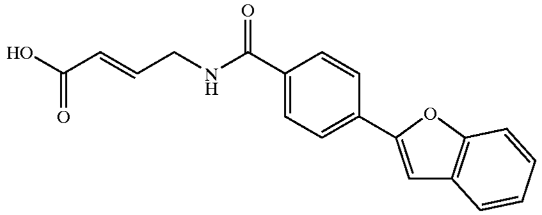

The title compounds having the following physical data were obtained by the same procedure as a series of reaction of Example. 10 (using methoxymethyl chloride instead of benzyloxymethyl chloride)→Example 11, using the compound prepared in Example 18.

Example 20(1)

TLC: Rf 0.21 (Chloroform:Methanol=10:1);

NMR ($d_6$-DMSO): δ8.72 (1H, t, J=5.6 Hz), 8.00 (4H, s), 7.72–7.64 (2H, m), 7.60 (1 H, brs), 7.40–7.20 (2H, m), 4.63 (2H, s), 4.08 (1H, m), 3.40 (2H, m), 2.40–2.20 (2H, m).

Example 20(2)

TLC: Rf 0.12 (Chloroform:Methanol=10:1);

NMR (d6-DMSO):δ8.88 (1H, t, J=5.6 Hz), 8.02 (4H, s), 7.71–7.62 (2H, m), 7.59 (1H, brs), 7.40–7.20 (2H, m), 6.80 (1H, dt, J=15.0, 5.0 Hz), 5.85 (1H, d, J=15.0 Hz), 4.09–4.01 (2H, m).

Example 20(3)

3(R)-Methoxymethyloxy-4-(N-(4-(benzofuran-2-yl) phenylcarbonyl)amino)butyric acid

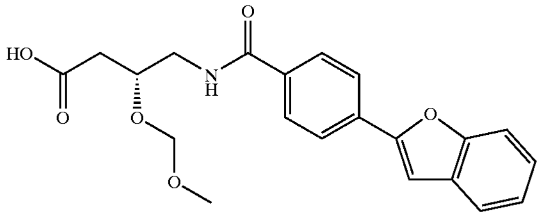

The title compound having the following physical data was obtained by the same procedure as a series of reaction of Example 18→Example 20, using 3(R)-hydroxy-4-aminobutyric acid ethyl ester instead of 3(S)-hydroxy-4-aminobutyric acid methyl ester.

TLC: Rf 0.21 (Chloroform:Methanol=10:1);

NMR ($d_6$-DMSO): δ8.72 (1H, t, J=5.6 Hz), 8.01 (4H, s), 7.70–7.65 (2H, m), 7.61 (1H, brs), 7.40–7.20 (2H, m), 4.62 (2H, s), 4.08 (1H, m), 3.42 (2H, m), 2.40–2.20 (2H, m).

Example 21

3(S)-Acetyloxy-4-(N-(4-(benzofuran-2-yl) phenylcarbonyl)amino)butyric acid methyl ester

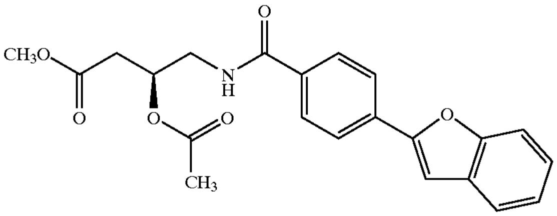

Anhydride acetic acid (0.6 ml) was added to a solution of the compound prepared in Example 18 (0.3 g) in pyridine (5 ml) at 0° C. The mixture was stirred at room temperature for 1 hour. To the reaction mixture, 1N hydrochloric acid was added. The mixture was extracted with ethyl acetate. The extract was washed with water and a saturated aqueous solution of sodium chloride, dried over anhydrous sodium sulfate and concentrated to give the title compound (0.325 g) having the following physical data.

TLC: Rf 0.52 (n-Hexane:Ethyl acetate=1:2).

Example 22

4-(N-(4-(Benzofuran-2-yl)phenylcarbonyl)amino)-3-butenoic acid methyl ester

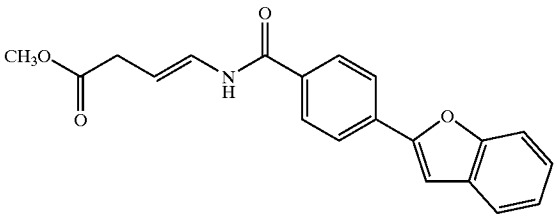

1,8-Diazabicyclo[5.4.0]undec-7-ene [DBU] (0.13 ml) was added to a solution of the compound prepared in Example 21 (0.15 g) in tetrahydrofuran (1 ml). The mixture was stirred at 50° C. for 3 hours. To the reaction mixture, 1N hydrochloric acid was added. The mixture was extracted with ethyl acetate. The extract was washed with water and a saturated aqueous solution of sodium chloride, dried over anhydrous sodium sulfate and concentrated to give the title compound (0.096 g) having the following physical data.

TLC: Rf 0.70 (n-Hexane:Ethyl acetate=1:2).

Example 23

4-(N-(4-(Benzofuran-2-yl)phenylcarbonyl)amino)-3-butenoic acid

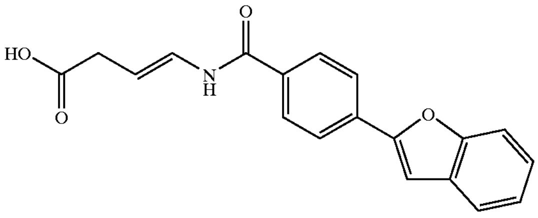

The title compound having the following physical data was obtained by the same procedure as a series of reaction of Example 2, using the compound prepared in Example 22 instead of the compound prepared in Example 1.

TLC: Rf 0.22 (Chloroform:Methanol:Acetic acid=100:10:1);

NMR ($d_6$-DMSO): δ10.39 (1H, d, J=9.8 Hz), 8.05 (4H, s), 7.72–7.64 (2H, m), 7.61 (1H, d, J=0.6 Hz), 7.41–7.24 (2H, m), 6.95 (1H, dd, J=9.8, 14.4 Hz), 5.54 (1H, dt, J=14.4, 7.2 Hz), 3.05 (2H, d, J=7.2 Hz).

Example 24

N-Hydroxy-3(S)-hydroxy-4-(N-(4-(benzofuran-2-yl)phenylcarbonyl)amino)butyramide

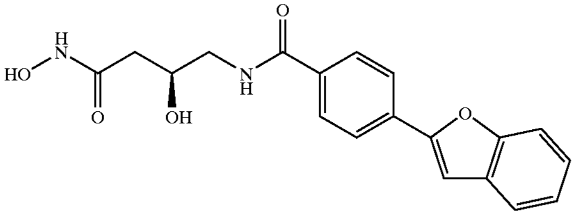

The title compound having the following physical data was obtained by the same procedure as a series of reaction of Example 3→Example 4, using the compound prepared in Example 19 instead of the compound prepared in Example 2.

TLC: Rf 0.41 (Chloroform:Methanol:Water=100:20:1);

NMR ($d_6$-DMSO): δ10.39 (1H, brs), 8.55 (1H, m), 8.00 (4H, s), 7.71–7.63 (2H, m), 7.57 (1H, brs), 7.39–7.23 (2H, m), 5.50–4.30 (1H, br), 4.12–3.98 (1H, m), 3.40–3.18 (2H, m), 2.16 (1H, dd, J=4.8, 14.0 Hz), 2.03 (1H, dd, J=8.2, 14.0 Hz).

Example 24(1)~24(6)

The title compounds having the following physical data were obtained by the same procedure as a series of reaction of Example 24, using the compound prepared in Example 19(1), Example 20(1)~20(3) and Example 23 instead of the compound prepared in Example 19 or by the same procedure as a series of reaction of Example 10→Example 11→Example 24, using the compound prepared in Example 18.

Example 24(1)

N-Hydroxy-3(R)-hydroxy-4-(N-(4-(benzofuran-2-yl)phenylcarbonyl)amino)butyramide

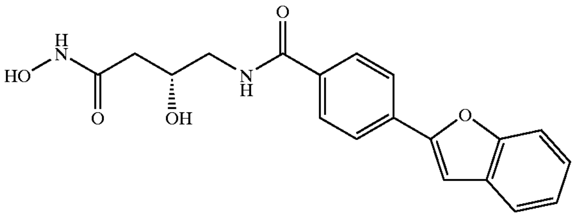

TLC: Rf 0.41 (Chloroform:Methanol Water=100:20:1);

NMR ($d_6$-DMSO): δ10.39 (1H, brs), 8.55 (1H, m), 8.00 (4H, s), 7.71–7.63 (2H, m), 7.58 (1H, brs), 7.39–7.24 (2H, m), 5.20–3.80 (1H, br), 4.12–3.98 (1H, m), 3.40–3.18 (2H, m), 2.16 (1H, dd, J=4.8, 14.0 Hz), 2.03 (1H, dd, J=8.2, 14.0 Hz).

Example 24(2)

N-Hydroxy-3(S)-methoxymethyloxy-4-(N-(4-(benzofuran-2-yl)phenylcarbonyl)amino)butyramide

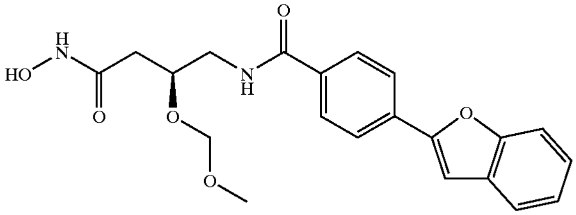

TLC: Rf 0.19 (Chloroform:Methanol=10:1);

NMR ($d_6$-DMSO): δ10.47 (1H, brs), 8.80 (1H, brs), 8.64 (1H, t, J=5.8 Hz), 8.02 (2H, d, J=9.2 Hz), 7.97 (2H, d, J=9.2 Hz), 7.71–7.63 (2H, m), 7.57 (1H, brs), 7.40–7.24 (2H, m), 4.60 (2H, s), 4.16–4.04 (1H, m), 3.41 (2H, t, J=5.8 Hz), 3.21 (3H, s), 2.22–2.18 (2H, m).

Example 24(3)

N-Hydroxy-4-(N-(4-(benzofuran-2-yl)phenylcarbonyl)amino)-2-butenamide

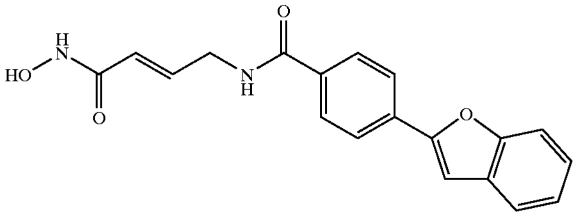

TLC: Rf 0.20 (Chloroform:Methanol:Acetic acid=100:10:1);

NMR ($d_6$-DMSO): δ10.60 (1H, brs), 8.89 (1H, t, J=5.8 Hz), 8.02 (4H, s), 7.71–7.63 (2H, m), 7.59 (1H, brs), 7.40 (2H, m), 6.69 (1H, dt, J=15.4, 4.8 Hz), 5.86 (1H, d, J=15.4 Hz), 4.08–4.02 (2H, m).

Example 24(4)

N-Hydroxy-3(R)-methoxymethyloxy-4-(N-(4-(benzofuran-2-yl)phenylcarbonyl)amino)butyramide

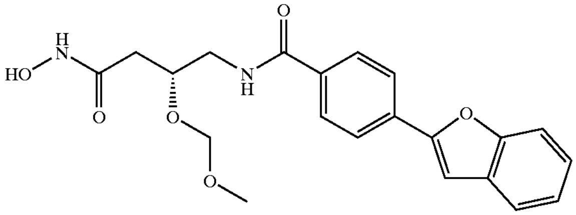

TLC: Rf 0.19 (Chloroform:Methanol=10:1);

NMR ($d_6$-DMSQ): δ10.46 (1H, brs), 8.77 (1H, brs), 8.64 (1H, t, J=5.8 Hz), 8.02 (2H, d, J=9.2 Hz), 7.97 (2H, d, J=9.2 Hz), 7.71–7.63 (2H, m), 7.58 (1H, brs), 7.40–7.24 (2H, m), 4.60 (2H, s), 4.16–4.05 (1H, m), 3.42 (2H, t, J=5.8 Hz), 3.22 (3H, s), 2.22–2.19 (2H, m).

Example 24(5)

N-Hydroxy-4-(N-(4-(benzofuran-2-yl)phenylcarbonyl)amino)-3-butenamide

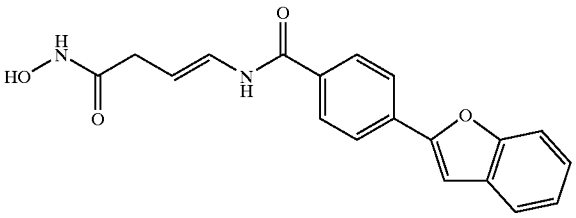

TLC: Rf 0.21 (Chloroform:Methanol:Acetic acid=100:10:1);

NMR ($d_6$-DMSO): δ10.45 (1H, brs), 10.37 (1H, d, J=9.6 Hz), 8.98–8.52 (1H, brs), 8.04 (4H, s), 7.72–7.63 (2H, m), 7.61 (1H, brs), 7.41–7.24 (2H, m),6.94 (1H, dd, J=9.6, 14.2 Hz), 5.53 (1H, dt, J=14.2, 7.8 Hz), 2.76 (2H, d, J=7.8 Hz).

Example 24(6)

N-Hydroxy-4-[N-[4-(benzofuran-2-yl)phenylcarbonyl]anmino]-3(S)-benzyloxymethoxybutyramide

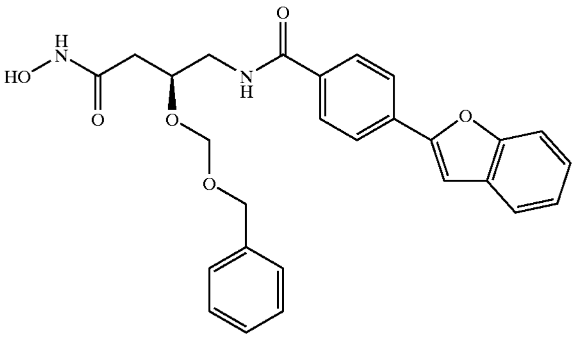

TLC: Rf 0.31 (Chloroform:Methanol=10:1);

NMR ($d_6$-DMSO): δ10.51 (1H, s), 8.67 (1H, t, J=5.6 Hz), 7.98 (4H, m), 7.71–7.60 (2H, m), 7.57 (1H, br.s), 7.39–7.20 (7H, m), 4.77 (1H, d, J=6.8 Hz), 4.73 (1H, d, J=6.8 Hz), 4.51 (2H, s), 4.20 (1H, m), 3.49–3.43 (2H, m), 2.25 (2H, d, J=6.2 Hz).

Example 25

2-Benzyloxymethyl-4-(N-(4-methylphenylcarbonyl)amino)butyric acid

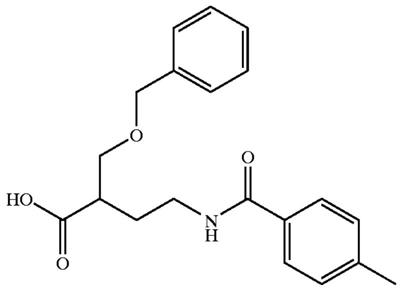

Under an atmosphere of argon, 1.63M n-butyl lithium in hexane (4.05 ml) was added to a solution of diisopropylamine (0.925 ml) in tetrahydrofuran (5 ml) and hexamethyl phosphoramide (HMPA) (3 ml) at −78° C. The mixture was stirred at −78° C. for 15 minutes. A solution of the compound prepared in Example 2(1) (0.442 g) in tetrahydrofuran (3 ml) was added to this solution at −78° C. The mixture was stirred at room temperature for 30 minutes. Benzyloxymethyl chloride (0.313 g) was added to the reaction mixture at −78° C. The mixture was stirred at −78° C. for 2 hours. To the reaction mixture, 1N hydrochloric acid was added. The mixture was extracted with ethyl acetate. The extract was washed with a saturated aqueous solution of sodium chloride, dried over anhydrous magnesium sulfate and concentrated to give the title compound (0.22 g) having the following physical data.

TLC: Rf 0.67 (Chloroform:Methanol:Acetic acid=18:2:1).

Example 26

N-Hydroxy-2-benzyloxymethyl-4-(N-(4-methylphenylcarbonyl)amino)butyramide

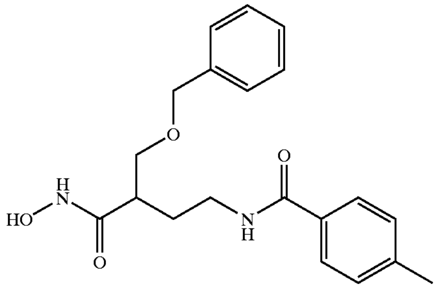

The title compound having the following physical data was obtained by the same procedure as a series of reaction of Example 3→Example 4, using the compound prepared in Example 25 instead of the compound prepared in Example 2.

TLC: Rf 0.36 (Chloroform:Methanol=10:1);

NMR ($d_6$-DMSO): δ10.52 (1H, s), 8.86 (1H, s), 8.32 (1H, t, J=8.4 Hz), 7.74 (2H, d, J=8.4 Hz), 7.31 (5H, m), 7.24 (2H, d, J=8.4 Hz), 4.46 (1H, d, J=12.5 Hz), 4.44 (1H, d, J=12.5 Hz), 3.59 (1H, dd, J=8.8, 8.8 Hz), 3.41 (1H, dd, J=8.8, 5.5 Hz), 3.21 (2H, m), 2.44 (1H, m), 2.35 (3H, s), 1.66 (2H, m).

Example 27

N-Hydroxy-2-hydroxymethyl-4-(N-(4-methylphenylcarbonyl)amino)butyramide

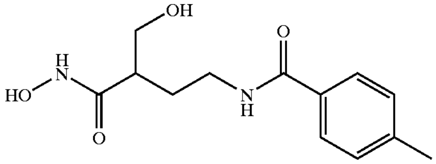

Under an atmosphere of argon, 10% Palladium-Carbon (0.024 g) was added to a solution of the compound prepared in Example 26 (0.24 g) in methanol (10 ml). The mixture was stirred at room temperature for 2 hours under an atmosphere of hydrogen gas. The reaction mixture was filtered through celite (registered trade mark). The filtrate was concentrated. The residue was purified by column chromatography on silica gel (Chloroform:Methanol=10:1) to give the title compound (0.158 g) having the following physical data.

TLC: Rf 0.39 (Ethyl acetate:Acetic acid:Water=16:3:2);

NMR ($d_6$-DMSO): δ8.41 (1H, m), 7.76 (2H, d, J=8.0 Hz), 7.24 (2H, d, J=8.0 Hz), 3.52 (1H, m), 3.37 (1H, m), 3.20 (2H, m), 2.35 (3H, s), 2.23 (1H, m), 1.64 (2H, m).

Example 27(1) and 27(2)

The following compounds were obtained by the same procedure as a series of reaction of Example 3→Example 4→Example 27, using the compound obtained by liquid chromatography separation of the compound prepared in Example 25.

Example 27(1)

N-Hydroxy-2-hydroxymethyl-4-(N-(4-methylphenylcarbonyl)amino)butyramide

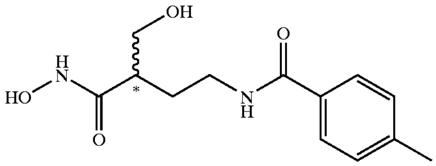

(Wherein * represents R or S configuration. The steric structure of this compound has not been determined. This compound possesses a reverse steric structure with the compound described in Example 27(2).)

TLC: Rf 0.17 (Chloroform:Methanol=4:1);

NMR ($CD_3OD$): δ7.70 (2H, d, J=8.2 Hz), 7.26 (2H, d, J=8.2 Hz), 3.79–3.52 (2H, m), 3.50–3.25 (2H, m), 2.38 (3H, s), 2.38–2.25 (1H, m), 1.80 (2H, q-like).

Example 27(2)

N-Hydroxy-2-hydroxymethyl-4-(N-(4-methylphenylcarbonyl)amino)butyramide

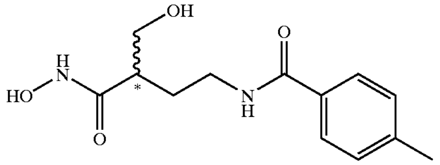

(Wherein * represents R or S configuration. The steric structure of this compound has not been determined. This compound possesses a reverse steric structure with the compound described in Example 27(1).)

TLC: Rf 0.17 (Chloroform:Methanol=4:1);

NMR ($CD_3OD$): δ7.70 (2H, d, J=8.2 Hz), 7.26 (2H, d, J=8.2 Hz), 3.79–3.52 (2H, m), 3.50–3.25 (2H, m), 2.38 (3H, s), 2.38–2.25 (1H, m), 1.80 (2H, q-like).

Reference Example 5

4(S)-Methylaminocarbonyl-4-(N-benzyloxycarbonylamino)butyric acid t-butyl ester

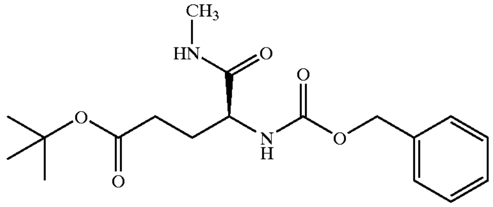

The title compound having the following physical data was obtained by the same procedure as a series of reaction of Example 15, using 4(S)-carboxy-4-(N-benzyloxycarbonylamino)butyric acid t-butyl ester and methylamine.

TLC: Rf 0.73 (Chloroform:Methanol=9:1);

NMR ($CDCl_3$): δ7.38–7.31 (5H, m), 6.24 (1H, m), 5.65 (1H, m), 5.10 (2H, s), 4.20–4.12 (1H, m), 2.81 (3H, d, J=5.0 Hz), 2.49–2.24 (2H, m), 2.17–1.85 (2H, m),

Reference Example 6

4(S)-Methylaminocarbonyl-4-aminobutyric acid t-butyl ester

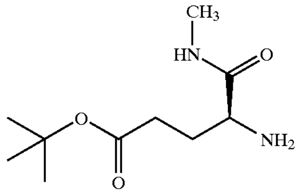

The title compound having the following physical data was obtained by the same procedure as a series of reaction of Example 27, using the compound prepared in Reference Example 5 instead of the compound prepared in Example 26.

TLC: Rf 0.28 (Chloroform:Methanol=9:1).

Example 28

4(S)-Methylaminocarbonyl-4-(N-(4-methylphenylcarbonyl)amino)butyric acid t-butyl ester

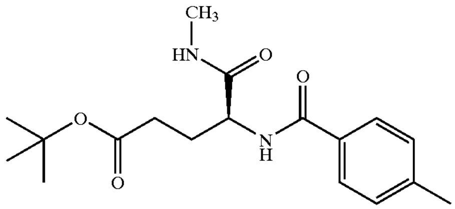

The title compound having the following physical data was obtained by the same procedure as a series of reaction of Example 1, using the compound prepared in Reference Example 6 instead of the compound prepared in Reference Example 4.

TLC: Rf 0.46 (Chloroform:Methanol=9:1).

Example 29

4(S)-Methylaminocarbonyl-4-(N-(4-methylphenylcarbonyl)amino)butyric acid

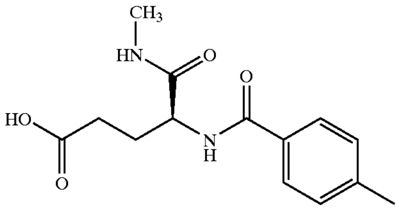

The title compound having the following physical data was obtained by the same procedure as a series of reaction of Example 14, using the compound prepared in Example 28 instead of the compound prepared in Example 13.

TLC: Rf 0.40 (Chloroform:Methanol=9:1);

NMR ($d_6$-DMSO): δ12.13 (1H, brs), 8.33 (1H, d, J=7.8 Hz), 7.86–7.78 (3H, m), 7.26 (2H, d, J=8.1 Hz), 4.40–4.25 (1H, m), 2.59 (3H, d, J=4.8 Hz), 2.36 (3H, s), 2.30–2.23 (2H, m), 2.05–1.82 (2H, m).

Example 29(1)~29(3)

The following compound were obtained by the same procedure as a series of reaction of Reference Example 5→Reference Example 6→Example 28→Example 29, using a corresponding amine instead of methylamine.

Example 29(1)

4(R)-Methylaminocarbonyl-4-(N-(4-methylphenylcarbonyl)amino)butyric acid

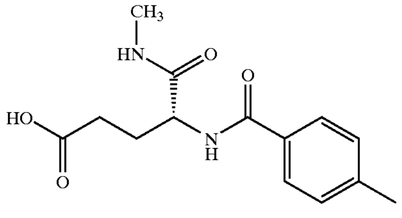

TLC: Rf 0.20 (Chloroform:Methanol=5:1);

NMR ($CDCl_3$+$CD_3OD$): δ7.60–7.33 (2H, m), 7.14–7.22 (2H, m), 4.52–4.66 (1H, m), 2.76 (3H, s), 2.30–2.56 (2H, m), 2.34 (3H, s), 1.84–2.22(2H, m).

Example 29(2)

4(S)-Benzylaminocarbonyl-4-(N-(4-methylphenylcarbonyl)amino)butyric acid

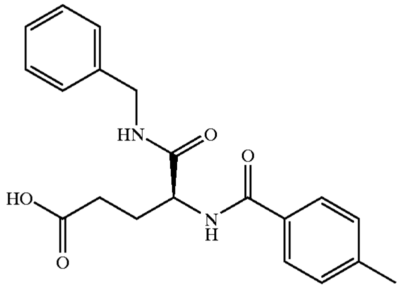

TLC: Rf 0.51 (Chloroform:Methanol=4:1);

NMR ($d_6$-DMSO): δ12.10 (1H, brs), 8.44 (2H, d, J=8.0 Hz), 7.82 (2H, d, J=8.0 Hz), 7.27–7.21 (5H, m), 4.49–4.40 (1H, m), 3.60 (1H, brs), 3.17 (2H, s), 2.36 (3H, s), 2.40–2.25 (2H, m), 2.20–1.95 (2H, m).

Example 29(3)

4(S)-(4-Hydroxybutyl)aminocarbonyl-4-(N-(4-methylphenylcarbonyl)amino)butyric acid

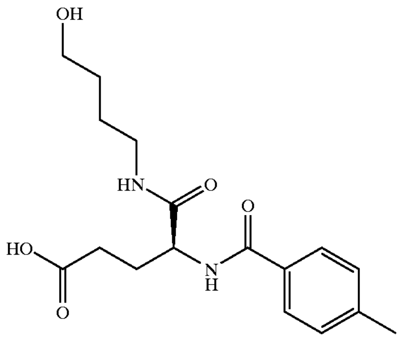

TLC: Rf 0.33 (Chloroform:Methanol=4:1).

Example 30

N-Hydroxy-4(S)-methylaminocarbonyl-4-(N-(4-methylphenylcarbonyl)amino)butyramide

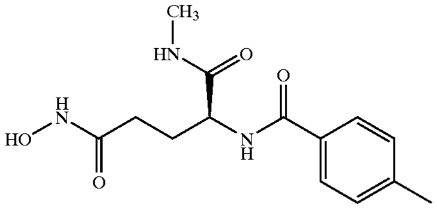

The title compound having the following physical data was obtained by the same procedure as a series of reaction of Example 3→Example 4, using the compound prepared in Example 29 instead of the compound prepared in Example 2.

TLC: Rf 0.69 (Chloroform:Methanol=4:1);

NMR ($d_6$-DMSO): δ10.37 (1H, brs), 8.69 (1H, m), 8.43 (1H, d, J=7.6 Hz), 7.85–7.79 (3H, m), 7.25 (2H, d, J=8.0 Hz), 4.40–4.25 (1H, m), 2.59 (3H, d, J=4.6 Hz), 2.06 (3H, s), 2.10–1.85 (4H, m).

Example 30(1)~30(3)

The following compounds were obtained by the same procedure as a series of reaction of Example 30, using the compound prepared in Example 29(1)~29(3) instead of the compound prepared in Example 29.

Example 30(1)

N-Hydroxy-4(R)-methylaminocarbonyl-4-(N-(4-methylphenylcarbonyl)amino)butyramide

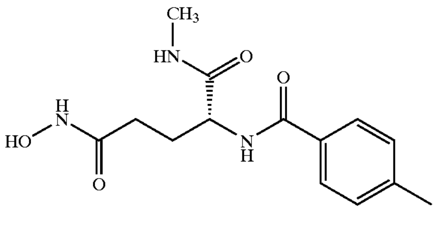

TLC: Rf 0.30 (Chloroform:Methanol=10:1);

NMR ($CD_3OD$): δ7.72 (2H, d, J=8 Hz), 7.20 (2H, d, J=8 Hz), 4.44–4.50 (1H, m), 2.67 (3H, s), 2.31 (3H, s), 2.22–1.85 (4H, m).

Example 30(2)

N-Hydroxy-4(S)-benzylaminocarbonyl-4-(N-(4-methylphenylcarbonyl)amino)butyramide

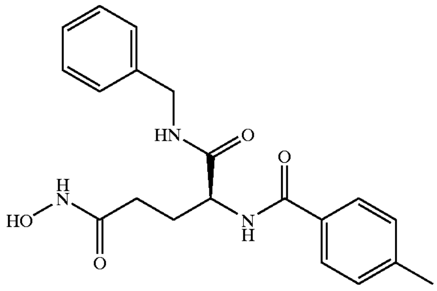

TLC: Rf 0.42 (Chloroform:Methanol=4:1).

Example 30(3)

N-Hydroxy-4(S)-(4-hydroxybutyl)aminocarbonyl-4-(N-(4-methylphenylcarbonyl)amino)butyramide

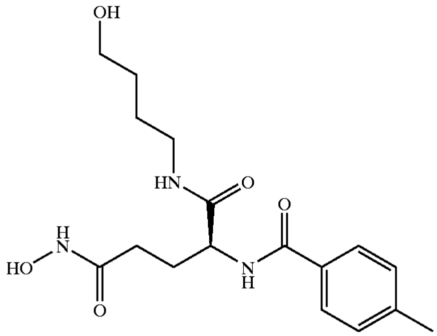

TLC: Rf 0.23 (Chloroform:Methanol:Acetic acid=18:2:1);

NMR ($CDCl_3$): δ7.74 (2H, d, J=7.5 Hz), 7.39 (1H, s), 7.25 (2H, d, J=7.5 Hz), 4.60–4.43 (1H, m), 3.61–3.56 (2H, m), 3.31–3.15 (2H, m), 2.40 (3H, s), 2.30–2.04 (4H, m), 1.62–1.48 (4H, m).

Example 31

4(S)-Methoxycarbonyl-4-[N-[4-(4-(tetrahydropyran-2-yloxy)-1-butynyl)phenylcarbonyl]amino]butyric acid t-butyl ester

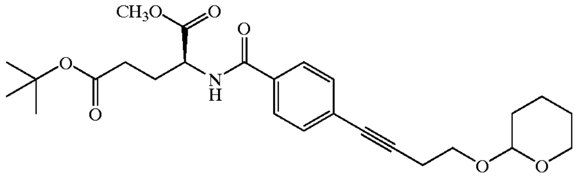

The title compound having the following physical data was obtained by the same procedure as a series of reaction of Example 1, using 4(S)-methoxycarbonyl-4-aminobutyric acid t-butyl ester and a corresponding acyl halide.

TLC: Rf 0.35 (n-Hexane:Ethyl acetate=1:2);

NMR ($CDCl_3$): δ7.78 (2H, d, J=8.4 Hz), 7.44 (2H, d, J=8.4 Hz), 7.21 (3H, s), 3.70–3.50 (2H, m), 2.75 (2H, t, J=6.9 Hz), 2.42 (2H, m), 2.30–2.00 (2H, m), 2.00–1.50 (6H, m), 1.42 (9H, 5).

Example 32

4(S)-Methoxycarbonyl-4-[N-[4-(4-hydroxy-1-butynyl)phenylcarbonyl]amino]butyric acid

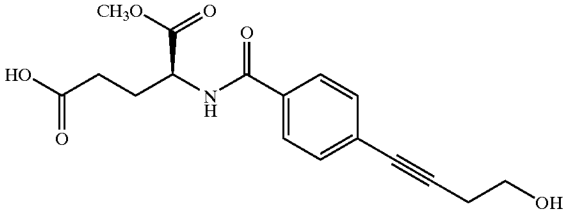

The title compound having the following physical data was obtained by the same procedure as a series of reaction of Example 14, using the compound prepared in Example 31 instead of the compound prepared in Example 13.

TLC: Rf 0.11 (n-Hexane:Ethyl acetate=1:1);

NMR ($CDCl_3$+$CD_3OD$): δ8.02 (1H, d, J=7.6 Hz), 7.77 (2H, d, J=8.6 Hz), 7.44 (2H, d, J=8.6 Hz), 4.82–4.70 (1H, m), 3.83–3.69 (5H, m), 2.68 (2H, t, J=6.6 Hz), 2.41 (2H, t, J=6.6 Hz), 2.26–1.99 (2H, m).

Example 33

N-Hydroxy-4(S)-methoxycarbonyl-4-[N-[4-(4-hydroxy-1-butynyl)phenylcarbonyl]amino]butyramide

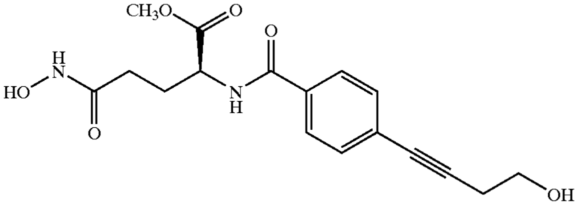

The title compound having the following physical data was obtained by the same procedure as a series of reaction of Example 3→Example 4, using the compound prepared in Example 32 instead of the compound prepared in Example 2.

TLC: Rf 0.30 (Chloroform:Methanol:Acetic acid=18:2:1);

NMR ($d_6$-DMSO): δ10.44 (1H, s), 10.20 (1H, s), 8.89 (1H, d, J=6.6 Hz), 7.87(2H, d, J=7.8 Hz), 7.47 (2H, d, J=7.8 Hz), 4.41 (1H, m), 3.66 (3H, s), 3.65–3.59 (2H, m), 2.58 (2H, t, J=6.6 Hz), 2.18–1.95 (2H, m), 1.28–1.21 (2H, m).

Example 33(1)

N-Hydroxy-4(R)-carbonyl-4-[N-[4-(3-methoxy-1-propynyl)phenylcarbonyl]amino]butyramide

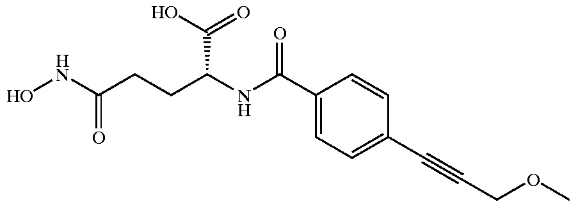

The title compound having the following physical data was obtained by the same procedure as a series of reaction of Example 31→Example 2→Example 33→Example 14, using 4(R)-t-butoxycarbonyl-4-aminobutyric acid methyl ester and a corresponding acyl halide.

TLC: Rf 0.18 (Chloroform:Methanol:Acetic acid:Water=85:15:1:1);

NMR ($d_6$-DMSO): δ7.86(2H, d, J=8.8 Hz), 7.53(2H, d, J=8.8 Hz), 4.54–4.59(1H, m), 4.34(2H, s), 3.43(3H, s), 2.05–2.36(4H, m).

Example 34

4(S)-t-Butoxycarbonyl-4-(N-(4-methylphenylcarbonyl)amino)butyric acid benzyl ester

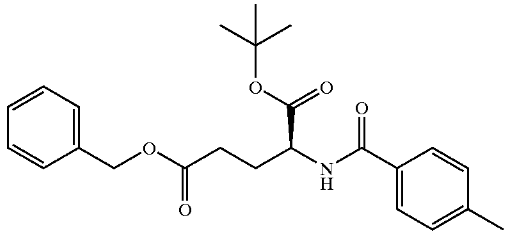

The title compound having the following physical data was obtained by the same procedure as a series of reaction of Example 1, using 4(S)-t-butoxycarbonyl-4-aminobutyric acid benzyl ester and a corresponding acyl halide.

TLC: Rf 0.19 (n-Hexane:Ethyl acetate=4:1).

Example 35

4(S)-t-Butoxycarbonyl-4-(N-(4-methylphenylcarbonyl)amino)butyric acid

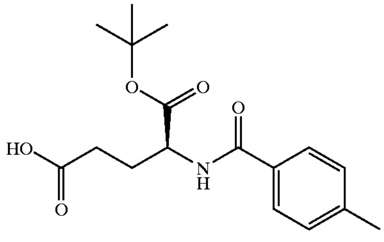

The title compound having the following physical data was obtained by the same procedure as a series of reaction of Example 27, using the compound prepared in Example 34 instead of the compound prepared in Example 26.

TLC: Rf 0.38 (Chloroform:Methanol=5:1);

NMR ($CDCl_3$): δ7.70 (2H, d, J=8.2 Hz), 7.22 (2H, d, J=8.2 Hz), 6.97 (1H, d, J=7.5 Hz), 4.71 (1H, m), 2.47 (2H, m), 2.38 (3H, s), 2.28 (1H, m), 2.05 (1H, m), 1.49 (9H, s).

Example 36

N-Hydroxy-4(S)-carboxy-4-(N-(4-methylphenylcarbonyl)amino)butyramide

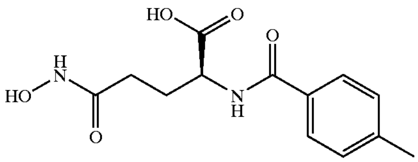

The title compound having the following physical data was obtained by the same procedure as a series of reaction of Example 3→Example 14, using the compound prepared in Example 35 instead of the compound prepared in Example 2.

TLC: Rf 0.43 (Ethyl acetate:Acetic acid:Water=8:1:1);

NMR ($CD_3OD$) δ7.78 (2H, d, J=8.0 Hz), 7.28 (2H, d, J=8.0 Hz), 4.56 (1 H, m), 2.40 (3H, s), 2.00–2.38 (4H, m).

Example 37

4(S)-Carboxy-4-(N-(4-(benzofuran-2-yl)phenylcarbonyl)amino)butyric acid methyl ester

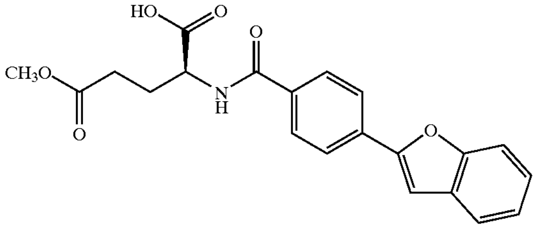

The title compound having the following physical data was obtained by the same procedure as a series of reaction of Example 1, using 4(S)-carboxy-4-aminobutyric acid methyl ester and the compound prepared in Reference Example 4.

TLC: Rf 0.64 (Chloroform:Methanol:Acetic acid=18:2:1);

NMR ($CD_3OD$): δ12.74 (1H, brs), 8.74 (1H, d, J=7.8 Hz), 8.04 (4H, s), 7.71–7.58 (3H, m), 7.42–7.26 (2H, m), 4.45 (1H, m), 3.60 (3H, s), 2.51–2.44 (2H, m), 2.26–1.96 (2H, m).

Example 38

4(S)-(Morpholin-1-yl)carbonyl-4-(N-(4-(benzofuran-2-yl)phenylcarbonyl)amino)butyric acid

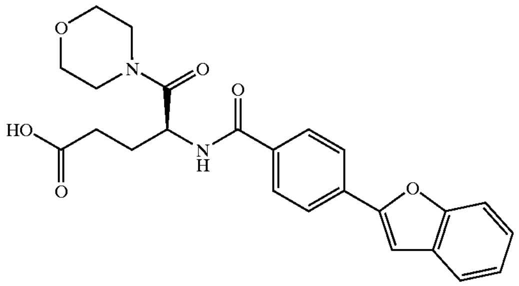

The title compound having the following physical data was obtained by the same procedure as a series of reaction of Example 15→Example 16, using the compound prepared in Example 37 instead of the compound prepared in Example 14.

TLC: Rf 0.48 (Chloroform:Methanol=4:1);

NMR ($d_6$-DMSO): δ12.23 (1H, brs), 8.72 (1H, d, J=8.0 Hz), 8.05–8.01 (4H, m), 7.74–7.58 (3H, m), 7.42–7.24 (2H, m), 5.03–4.86 (1H, m), 3.63–3.45 (8H, m), 2.37 (2H, t, J=7.0 Hz), 2.04–1.84 (2H, m).

Example 39

4(S)-Hydroxymethyl-4-(N-(4-(benzofuran-2-yl)phenylcarbonyl)amino)butyric acid methyl ester

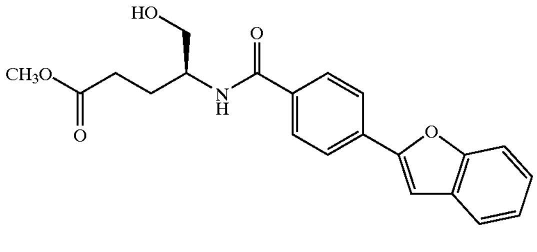

N-Hydroxysuccinimide (2.2 g) and dichlorohexylcarbodiimide (4.01 g) were added to a solution of the compound prepared in Example 37 (5.7 g) in tetrahydrofuran (30 ml) at 0° C. The mixture was stirred at 0° C. for 5 hours. The reaction mixture was filtered. Sodium borohydride (1.19 g) and water (5 ml) were added to the filtrate. The mixture was stirred at room temperature for 30 minutes. A saturated aqueous solution of ammonium chloride was added to the reaction mixture. The mixture was extracted with ethyl acetate. The extract was washed with a saturated aqueous solution of sodium chloride, dried over anhydrous magnesium sulfate and concentrated to give the title compound (4.89 g) having the following physical data.

TLC: Rf 0.21 (n-Hexane:Ethyl acetate=3:7);

NMR ($d_6$-DMSO): δ8.14 (1H, d, J=8.4 Hz), 7.99 (4H, s), 7.72–7.60 (2H, m), 7.55 (1H, d, J=0.8 Hz), 7.40–7.24 (2H, m), 4.75 (1H, t, J=5.8 Hz), 4.10–3.90 (1H, m), 3.56 (3H, s), 3.55–3.39 (2H, m), 2.36 (2H, t, J=7.4 Hz), 2.06–1.62 (2H, m).

Example 40

4(S)-Hydroxymethyl-4-(N-(4-(benzofuran-2-yl)phenylcarbonyl)amino)butyric acid

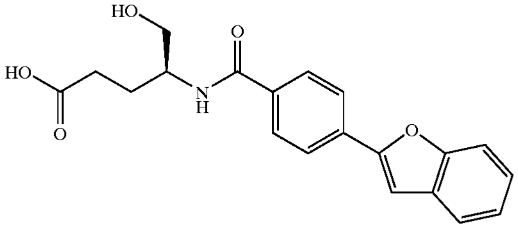

The title compound having the following physical data was obtained by the same procedure as a series of reaction of Example 2, using the compound prepared in Example 39 instead of the compound prepared in Example 1.

TLC: Rf 0.33 (Chloroform:Methanol:Acetic acid=190:10:1);

NMR ($d_6$-DMSO): δ12.10–11.90 (1H, br), 8.14 (1H, d, J=8.8 Hz), 8.00 (4H, s), 7.73–7.60 (2H, m), 7.55 (1H, s), 7.41–7.22 (2H, m), 4.80–4.64 (1H, m), 4.10–3.90 (1H, m), 3.54–3.35 (2H, m), 2.28 (2H, t, J=6.8 Hz), 2.02–1.60 (2H, m).

Example 41

4(S)-Methoxymethyloxymethyl-4-(N-(4-(benzofuran-2-yl)phenylcarbonyl)amino)butyric acid methyl ester

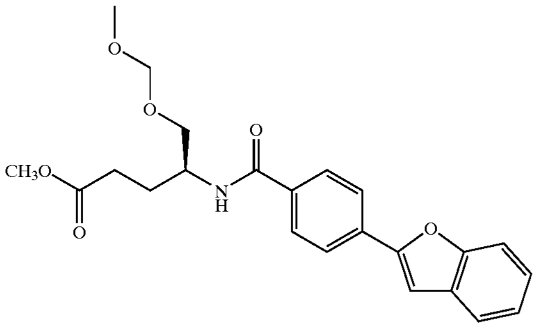

The title compound having the following physical data was obtained by the same procedure as a series of reaction of Example 10 (using methoxymethyl chloride instead of benzyloxymethyl chloride), using the compound prepared in Example 39 instead of the compound prepared in Example 8.

TLC: Rf 0.65 (n-Hexane:Ethyl acetate=3:7);

NMR ($CDCl_3$): δ7.94 (2H, d, J=8.8 Hz), 7.87 (2H, d, J=8.8 Hz) 7.64–7.50 (2H, m), 7.38–7.21 (2H, m), 7.13 (1H, d, J=0.8 Hz), 6.78 (1H, d, J=7.8 Hz), 4.67 (2H, s), 4.46–4.28 (1H, m), 3.78 (1H, dd, J=10.2, 3.4 Hz), 3.65 (1H, dd, J=10.2, 4.4 Hz), 3.64 (3H, s), 3.39 (3H, s), 2.62–2.38 (2H, m), 2.16–2.00 (2H, m).

Example 42

4(S)-Methoxymethyloxymethyl-4-(N-(4-(benzofuran-2-yl)phenylcarbonyl)amino)butyric acid

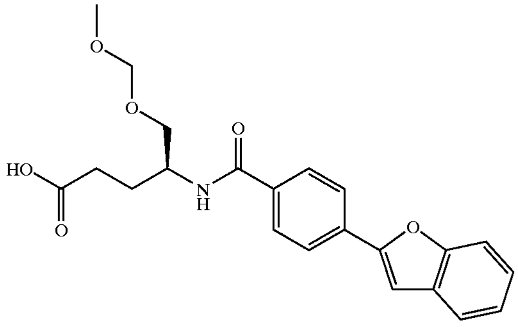

The title compound having the following physical data was obtained by the same procedure as a series of reaction of Example 2, using the compound prepared in Example 41 instead of the compound prepared in Example 1.

TLC: Rf 0.19 (Chloroform:Methanol=19:1);

NMR ($d_6$-DMSO): δ12.02 (1H, s), 8.30 (1H, d, J=8.2 Hz), 8.00 (4H, s), 7.73–7.60 (2H, m), 7.56 (1H, s), 7.41–7.22 (2H, m), 4.58 (2H, s), 4.26–4.08 (1H, m), 3.62–3.42 (2H, m), 3.32 (3H, s), 3.26 (3H, s), 2.29 (2H, t, J=6.8 Hz), 2.02–1.62 (2H, m).

Example 43

2(S)-Benzyl-4(S)-methoxymethyloxymethyl-4-(N-(4-(benzofuran-2-yl)phenylcarbonyl)amino)butyric acid methyl ester

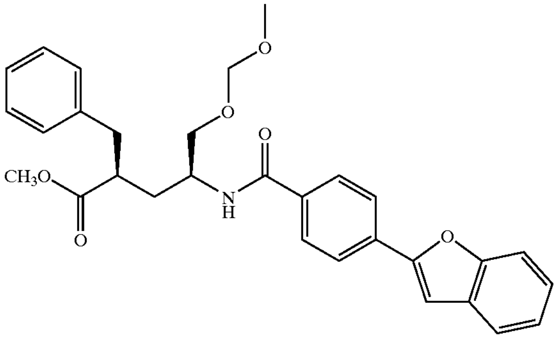

A solution of the compound prepared in Example 41 (0.474 g) in tetrahydrofuran (5 ml) was added to a solution of 1.0M lithium bis(trimethylsilyl)amide in tetrahydrofuran (0.695 ml) in tetrahydrofuran (5 ml) at −78° C. The mixture was stirred at −78° C. for 1 hour. Benzyl bromide (0.113 ml) was added to the reaction mixture. The mixture was stirred at −78° C. for 3 hours. A saturated aqueous solution of ammonium chloride was added to the reaction mixture. The mixture was extracted with ethyl acetate. The extract was washed with a saturated aqueous solution of sodium chloride, dried over anhydrous magnesium sulfate and concentrated. The residue was purified by column chromatography on silica gel (n-Hexane:Ethyl acetate=3:2) to give the title compound (0.429 g) having the following physical data.

TLC: Rf 0.51 (n-Hexane:Ethyl acetate=1:1);

NMR ($CDCl_3$): δ7.96 (2H, d, J=8.8 Hz), 7.84 (2H, d, J=8.8 Hz), 7.63–7.50 (2H, m), 7.38–7.10 (8H, m), 6.57 (1H, d, J=8.8 Hz), 4.64 (1H, d, J=8.8 Hz), 4.60 (1H, d, J=8.8 Hz), 4.50–4.30 (1H, m), 3.70 (1H, dd, J=10.2, 3.2 Hz), 3.59 (1H, dd, J=10.2, 3.8 Hz), 3.40 (3H, s), 3.35 (3H, s), 3.04–2.72 (3H, m), 2.19 (1H, ddd, J=14.2, 10.4, 8.4 Hz), 1.82 (1H, dt, J=14.2, 4.4 Hz).

Example 44

2(S)-Benzyl-4(S)-methoxymethyloxymethyl-4-(N-(4-(benzofuran-2-yl)phenylcarbonyl)amino)butyric acid

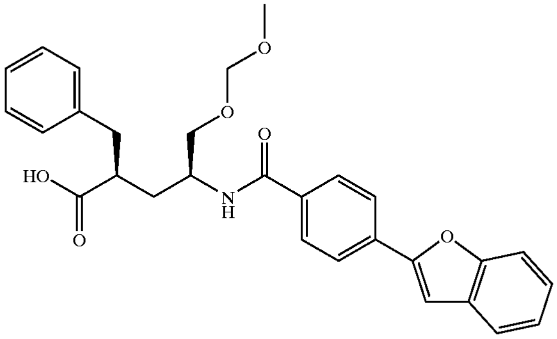

The title compound having the following physical data was obtained by the same procedure as a series of reaction of Example 2, using the compound prepared in Example 43 instead of the compound prepared in Example 1.

TLC: Rf 0.31 (Chloroform:Methanol=19:1);

NMR ($CDCl_3$): δ7.85 (2H, d, J=8.8 Hz), 7.79 (2H, d, J=8.8 Hz), 7.58–7.45 (2H, m), 7.36–7.10 (7H, m), 7.04 (1H, d, J=0.8 Hz), 6.73 (1H, d, J=8.8 Hz), 4.60 (1H, d, J=8.8 Hz), 4.56 (1H, d, J=8.8 Hz), 4.50–4.30 (1H, m), 3.70 (1H, dd, J=10.6, 3.2 Hz), 3.57 (1H, dd, J=10.6, 3.8 Hz), 3.29 (3H, s), 3.11–2.95 (1H, m), 2.90–2.75 (2H, m), 2.24–2.01 (1H, m), 1.90–1.72 (1H, m).

Example 44(1)–4(27)

The following compounds were obtained by the same procedure as a series of reaction of Example 37→Example 39→Example 41 (using a corresponding compound instead of methoxymethyl chloride, if necessary.)→Example, 43 (using a corresponding compound instead of benzyl bromide.)→Example 44, using a corresponding compound instead of the compound prepared in Reference Example 4.

Example 44(1)

2(S)-Methyl-4(S)-methoxymethyloxymethyl-4-(N-(4-(benzofuran-2-yl)phenylcarbonyl)amino)butyric acid

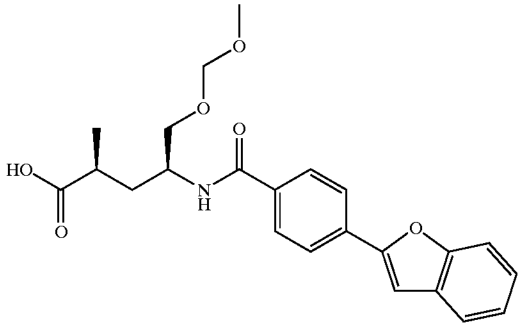

TLC: Rf 0.25 (Chloroform:Methanol=19:1);

NMR ($CDCl_3$): δ7.89 (2H, d, J=8.8 Hz), 7.83 (2H, d, J=8.8 Hz), 7.62–7.50 (2H, m), 7.37–7.20 (2H, m), 7.09 (1H, d, J=1.0 Hz), 6.63 (1H, d, J=8.8 Hz), 4.65 (2H, s), 4.55–4.36 (1H, m), 3.75 (1H, dd, J=10.2, 3.2 Hz), 3.62 (1H, dd, J=10.2, 4.0 Hz), 3.38 (3H, s), 2.70–2.50 (1H, m), 2.23 (1H, ddd, J=14.0, 11.0, 8.2 Hz), 1.72 (1H, ddd, J=14.0, 6.0, 4.4 Hz), 1.30 (3H, d, J=6.8 Hz).

Example 44(2)

2(S)-(3-Phenyl-2-propenyl)-4(S)-methoxymethyloxymethyl-4-(N-(4-(benzofuran-2-yl)phenylcarbonyl)amino)butyric acid

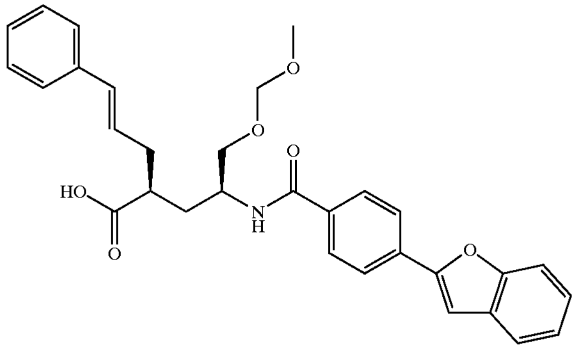

TLC: Rf 0.44 (n-Hexane:Ethyl acetate=3:7);

NMR ($d_6$-DMSO): δ12.23 (1H, s), 8.34 (1H, d, J=8.4 Hz), 8.00 (4H, s), 7.74–7.61 (2H, m), 7.57 (1H, s), 7.41–7.18 (7H, m), 6.43 (1H, d, J=15.6 Hz), 6.20 (1H, dt, J=15.6, 6.4 Hz), 4.57 (2H, s), 4.40–4.20 (1H, m), 3.62–3.48 (2H, m), 3.23 (3H, s), 2.60–2.40 (3H, m), 1.92–1.80 (2H, m).

Example 44(3)

2(S)-(3-Phenylpropyl)-4(S)-methoxymethyloxymethyl-4-(N-(4-(benzofuran-2-yl)phenylcarbonyl)amino)butyric acid

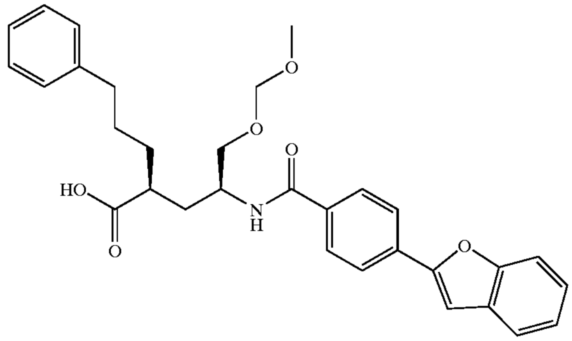

TLC: Rf 0.44 (n-Hexane:Ethyl acetate=3:7);

NMR ($CDCl_3$): δ7.85 (2H, d, J=8.8 Hz), 7.79 (2H, d, J=8.8 Hz), 7.60–7.44 (2H, m), 7.34–7.06 (7H, m), 7.03 (1H, d, J=0.8 Hz), 6.69 (1H, d, J=8.8 Hz), 4.62 (1H, d, J=8.8 Hz), 4.60 (1H, d, J=8.8 Hz), 4.48–4.28 (1H, m), 3.73 (1H, dd, J=10.2, 3.4 Hz), 3.59 (1H, dd, J=1 0.2, 4.0 Hz), 3.34 (3H, s), 2.68–2.42 (3H, m), 2.21–2.00 (1H, m), 1.86–1.52 (5H, m).

Example 44(4)

2(S)-Methyl-5-ethoxymethoxy-4(S)-[N-(4-chlorophenylcarbonyl)amino]pentanoic acid

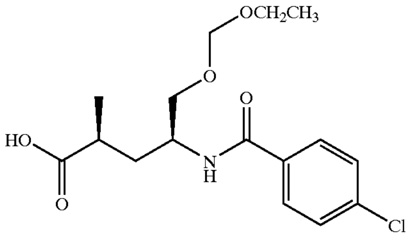

TLC: Rf 0.46 (Chloroform:Methanol=9:1);

NMR ($d_6$-DMSO): δ12.06 (1H, s), 8.24 (1H, d, J=8.7 Hz), 7.83 (2H, d, J=8.4 Hz), 7.51 (2H, d, J=8.4 Hz), 4.57 (2H, s), 4.24–4.13 (1H, m), 3.52–3.42 (4H, m), 2.37–2.25 (1H, m), 1.92–1.80 (1H, m), 1.63–1.52 (1H, m), 1.06 (3H, t, J=6.9 Hz), 1.05 (3H, d, J=6.9 Hz).

Example 44(5)

2(S)-Methyl-5-ethoxymethoxy-4(S)-[N-(4-nitrophenylcarbonyl)amino]pentanoic acid

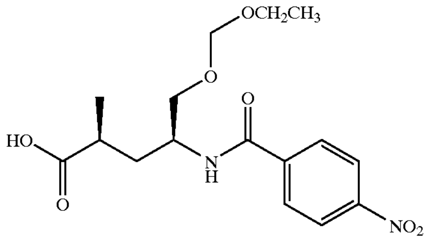

TLC: Rf 0.45 (Methylene chloride:Methanol=9:1);

NMR ($CDCl_3$): δ8.27 (d, J=9.0 Hz, 2H), 7.96 (d, J=9.0 Hz, 2H), 6.89 (brd, J=9.0 Hz, 1H), 4.73 (d, J=7.0 Hz, 1H), 4.68 (d, J=7.0 Hz, 1H), 4.40 (m, 1H), 3.78 (dd, J=10.6, 3.2 Hz, 1H), 3.68–3.55 (m, 3H), 2.55 (m, 1H), 2.16 (ddd, J=14.4, 10.2, 7.6 Hz, 1H), 1.70 (ddd, J=14.4, 5.8, 5.0 Hz, 1H), 1.28 (d, J=7.0 Hz, 3H), 1.20 (t, J=7.0 Hz, 3H).

Example 44(6)

2(S)-Methyl-5-ethoxymethoxy-4(S)-[N-(4-bromophenylcarbonyl)amino]pentanoic acid

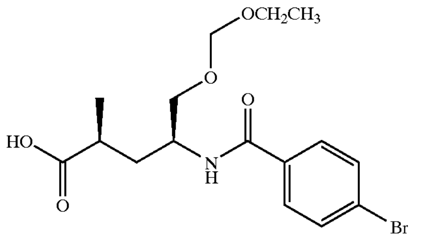

TLC: Rf 0.47 (Methylene chloride:Methanol=9:1);

NMR ($CDCl_3$): δ7.65 (d, J=8.8 Hz, 2H), 7.54 (d, J=8.8 Hz, 2H), 6.67 (brd, J=9.2 Hz, 1H), 4.72 (d, J=7.0 Hz, 1H), 4.67 (d, J=7.0 Hz, 1H), 4.40 (m, 1H), 3.75 (dd, J=10.4, 3.2 Hz, 1H), 3.66–3.55 (m, 3H), 2.55 (m, 1H), 2.16 (ddd, J=14.4, 10.2, 7.6 Hz, 1H), 1.70 (ddd, J=14.4, 6.6, 4.8 Hz, 1H), 1.27 (d, J=7.0 Hz, 3H), 1.20 (t, J=7.0 Hz, 3H).

Example 44(7)

2(S)-Allyl-5-ethoxymethoxy-4(S)-[N-(4-nitrophenylcarbonyl)amino]pentanoic acid

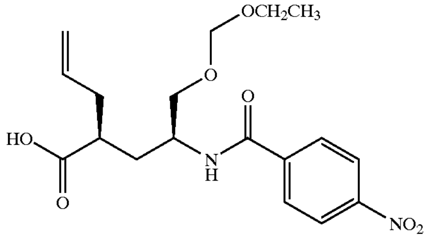

TLC: Rf 0.31 (Chloroform:Methanol=9:1);

NMR ($CDCl_3$): δ8.25 (d, J=8.7 Hz, 2H),7.94 (d, J=8.7 Hz, 2H),6.92 (d, J=8.7 Hz, 1H), 5.82–5.68 (m, 1H), 5.14–5.06 (m, 2H), 4.73 (d, J=6.9 Hz, 1H), 4.68 (d, J=6.9 Hz, 1H), 4.45–4.32 (m, 1H), 3.79 (dd, J=10.2, 3.3 Hz, 1H), 3.66–3.56 (m, 3H), 2.63–2.31 (m, 3H), 2.14–2.03 (m, 1H), 1.82 (dt, J=14.1, 5.4 Hz, 1H), 1.20 (t, J=7.2 Hz, 3H).

Example 44(8)

2(R)-Methoxymethyl-5-ethoxymethoxy-4(S)-[N-(4-nitrophenylcarbonyl)amino]pentanoic acid

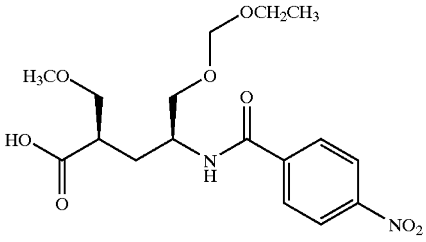

TLC: Rf 0.24 (Chloroform:Methanol=19: 1);

NMR ($CDCl_3$): δ8.25 (d, J=8.7 Hz, 2H), 7.95 (d, J=8.7 Hz, 2H), 7.11 (d, J=8.4 Hz, 1H), 4.73 (d, J=5.7 Hz, 1H), 4.67 (d, J=5.7 Hz, 1H), 4.42–4.31 (m, 1H), 3.80 (dd, J=10.2, 3.3 Hz, 1H), 3.69–3.57 (m, 5H), 3.39 (s, 3H), 2.82–2.70 (m, 1H), 2.17 (ddd, J=14.4, 10.2, 8.1 Hz, 1H), 1.88 (dt, J=14.4, 5.1 Hz, 1H), 1.20 (t, J=7.2 Hz, 3H).

Example 44(9)

2(R)-Benzyloxymethyl-5-ethoxymethoxy-4(S)-[N-(4-nitrophenylcarbonyl)amino]pentanoic acid

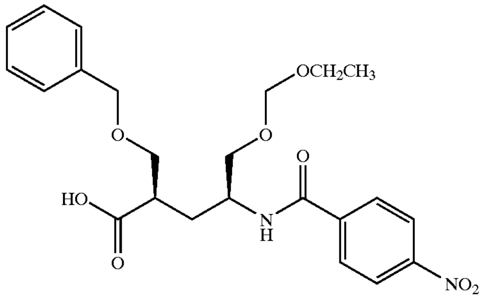

TLC: Rf 0.41 (Chloroform:Methanol=19:1);

NMR ($CDCl_3$): δ8.24 (d, J=8.8 Hz, 2H), 7.93 (d, J=8.8 Hz, 2H), 7.41–7.20 (m, 5H), 7.01 (d, J=8.8 Hz, 1H), 4.72 (d, J=7.4 Hz, 1H), 4.67 (d, J=7.4 Hz, 1H), 4.57 (s, 2H), 4.43–4.25 (m, 1H), 3.82–3.52 (m, 6H), 2.89–2.70 (m, 1H), 2.19 (ddd, J=14.8, 10.2, 8.0 Hz, 1H), 1.70 (dt, J=14.8, 5.0 Hz, 1H), 1.19 (t, J=7.0 Hz, 3H).

Example 44(10)

2(S)-Methyl-5-(2-methoxyethoxy)methoxy-4(S)-[N-(4-cyanophenylcarbonyl)amino]pentanoic acid

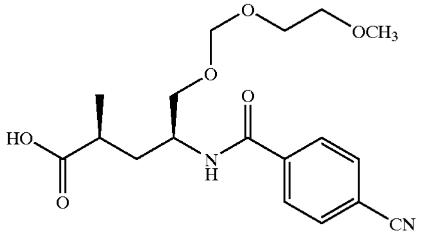

TLC: Rf 0.40 (Chloroform:Methanol=19:1);

NMR ($CDCl_3$): δ7.91 (d, J=8.4 Hz, 2H), 7.70 (d, J=8.4 Hz, 2H), 7.07 (d, J=9.0 Hz, 1H), 4.75 (d, J=6.9 Hz, 1H), 4.70 (d, J=6.9 Hz, 1H), 4.45–4.34 (m, 1H), 3.84 (dd, J=10.5, 3.3 Hz, 1H), 3.78–3.60 (m, 3H), 3.54–3.51 (m, 2H), 3.29 (s, 3H), 2.61–2.49 (m, 1H), 2.15 (ddd, J=14.1, 10.2, 7.5 Hz, 1H), 1.70 (ddd, J=14.1, 6.6, 5.1 Hz, 1H), 1.20 (d, J=6.9 Hz, 3H).

Example 44(11)

2(R)-(2-Methoxyethoxy)methyl-5-ethoxymethoxy-4(S)-[N-(4-nitrophenylcarbonyl)amino]pentanoic acid

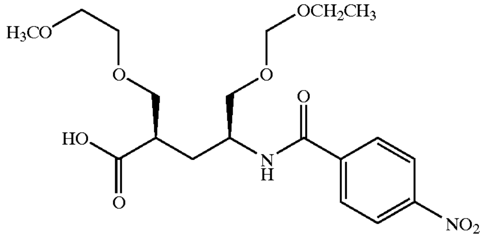

TLC: Rf 0.17 (Chloroform:Methanol=19:1);

NMR($CDCl_3$): δ8.26 (d, J=8.8 Hz, 2H), 7.97 (d, J=8.8 Hz, 2H), 7.08 (d, J=8.8 Hz, 1H), 4.75–4.62 (m, 2H), 4.44–4.28 (m, 1H), 3.82–3.48 (m, 10H), 3.37 (s, 3H), 2.90–2.66 (m, 1H), 2.21 (ddd, J=14.4, 10.0, 8.6 Hz, 1H), 1.92 (dt, J=14.4, 4.8 Hz, 1H), 1.20 (t, J=7.0 Hz, 3H).

Example 44(12)

2(S)-(2-Propynyl)-5-ethoxymethoxy-4(S)-[N-(4-nitrophenylcarbonyl)amino]pentanoic acid

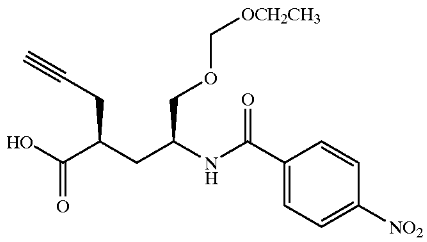

TLC: Rf 0.30 (Chloroform:Methanol=9:1);

NMR($CDCl_3$): δ8.28 (d, J=9.0 Hz, 2H), 7.96 (d, J=9.0 Hz, 2H), 6.98 (d, J=8.7 Hz, 1H), 4.75 (d, J=6.9 Hz, 1H), 4.70 (d, J=6.9 Hz, 1H), 4.50–4.38 (m, 1H), 3.84 (dd, J=10.5, 3.0 Hz, 1H), 3.70–3.55 (m, 3H), 2.80–2.40 (m, 3H), 2.28–2.10 (m, 1H), 2.10–1.95 (m, 2H), 1.21 (t, J=7.2 Hz, 3H).

Example 44(13)

2(S)-Allyl-5-(2-methoxyethoxy)methoxy-4(S)-[N-(4-cyanophenylcarbonyl)amino]pentanoic acid

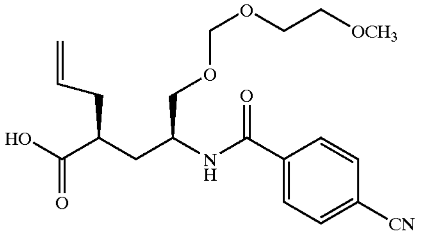

TLC: Rf 0.26 (Chloroform:Methanol=19:1);

NMR($CDCl_3$): δ7.90 (d, J=8.4 Hz, 2H), 7.71 (d, J=8.4 Hz, 2H), 7.10 (d, J=9.0 Hz, 1H), 5.82–5.66 (m, 1H), 5.16–5.03 (m, 2H), 4.75 (d, J=6.9 Hz, 1H), 4.70 (d, J=6.9 Hz, 1H), 4.38 (m, 1H), 3.85 (dd, J=10.5, 3.6 Hz, 1H), 3.80–3.58 (m, 3H), 3.54 (t, J=4.5 Hz, 2H), 3.31 (s, 3H), 2.62–2.50 (m, 1H), 2.49–2.30 (m, 2H), 2.07 (dt, J=14.4, 9.0 Hz, 1H), 1.83 (dt, J=14.4, 5.4 Hz, 1H).

Example 44(14)

2(S)-Methoxymethyl-5-(2-methoxyethoxy)methoxy-4(S)-[N-(4-cyanophenylcarbonyl)amino]pentanoic acid

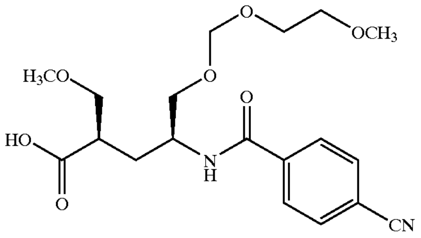

TLC: Rf 0.35 (Chloroform:Methanol=9:1);

NMR($CD_3OD$): δ7.94 (d, J=8.7 Hz, 2H), 7.82 (d, J=8.7 Hz, 2H), 4.71 (d, J=6.6 Hz, 1H), 4.68 (d, J=6.6 Hz, 1H), 4.39–4.31 (m, 1H), 3.68–3.49 (m, 8H), 3.32 (s, 3H), 3.31 (s, 3H), 2.76–2.66 (m, 1H), 2.08–1.86 (m, 2H).

Example 44(15)

2(S)-(2-Propynyl)-5-ethoxymethoxy-4(S)-[N-(4-bromophenylcarbonyl)amino]pentanoic acid

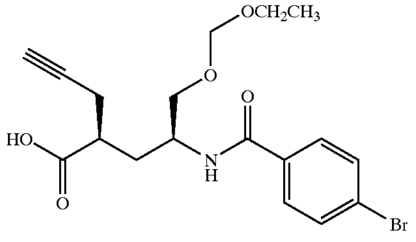

TLC: Rf 0.36 (Chloroform:Methanol=9:1);

NMR($CDCl_3$): δ7.64 (d, J=8.6 Hz, 2H), 7.54 (d, J=8.6 Hz, 2H), 6.82 (d, J=9.0 Hz, 1H), 4.72 (d, J=6.9 Hz, 1H), 4.69 (d, J=6.9 Hz, 1H), 4.50–4.35 (m, 1H), 3.80 (dd, J=10.4, 3.2 Hz, 1H), 3.70–3.55 (m, 3H), 2.78–2.45 (m, 3H), 2.25–2.10 (m, 1H), 2.10–1.95 (m, 2H),1.20 (t, J=7.2 Hz, 3H).

Example 44(16)

2(S)-(2-Propynyl)-5-ethoxymethoxy-4(S)-[N-(4-chlorophenylcarbonyl)amino]pentanoic acid

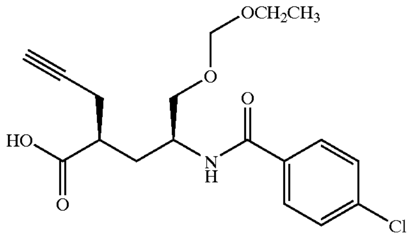

TLC: Rf 0.36 (Chloroform:Methanol=9:1);

NMR($CDCl_3$): δ7.71 (d, J=8.7 Hz, 2H), 7.38 (d, J=8.7 Hz, 2H), 6.81 (d, J=8.7 Hz, 1H), 4.73 (d, J=6.8 Hz, 1H), 4.69 (d, J=6.8 Hz, 1H), 4.50–4.35 (m, 1H), 3.80 (dd, J=10.2, 3.0 Hz, 1H), 3.70–3.55 (m, 3H), 2.78–2.45 (m, 3H), 2.25–2.10 (m, 1H), 2.10–1.95 (m, 2H), 1.20 (t, J=7.2 Hz, 3H).

Example 44(17)

2(R)-Methoxymethyl-5-ethoxymethoxy-4(S)-[N-(4-bromophenylcarbonyl)amino]pentanoic acid

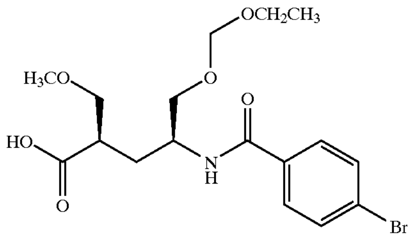

TLC: Rf 0.39 (Chloroform:Methanol=9:1);

NMR($CD_3OD$): δ7.73–7.69 (m, 2H), 7.65–7.59 (m, 2H), 4.67 (s, 2H), 4.37–4.28 (m, 1H), 3.63–3.53 (m, 6H), 3.32 (s, 3H), 2.75–2.64 (m, 1H), 1.96–1.89 (m, 2H), 1.15 (t, J=7.2 Hz, 3H).

Example 44(18)

2(R)-Methoxymethyl-5-ethoxymethoxy-4(S)-[N-(4-chlorophenylcarbonyl)amino]pentanoic acid

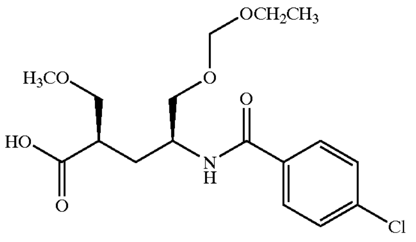

TLC: Rf 0.32 (Chloroform:Methanol=9:1);

NMR($CD_3OD$): δ7.78 (d, J=8.7 Hz, 2H), 7.45 (d, J=8.7 Hz, 2H), 4.66 (s, 2H), 4.37–4.27 (m, 1H), 3.63–3.54 (m, 6H), 3.32 (s, 3H), 2.74–2.62 (m, 1H), 1.97–1.88 (m, 2H), 1.15 (t, J=7.2 Hz, 3H).

Example 44(19)

2(R)-Benzyloxymethyl-5-(2-methoxyethoxy)methoxy-4(S)-[N-(4-cyanophenylcarbonyl)amino]pentanoic acid

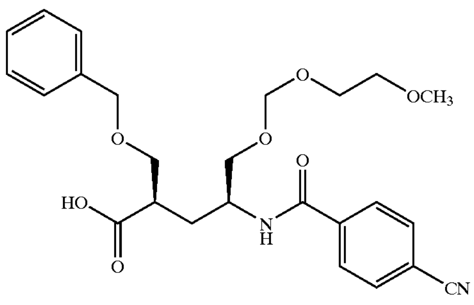

TLC: Rf 0.48 (Methylene chloride:Methanol=9:1);

NMR($CDCl_3$): δ7.87 (d, J=8.4 Hz, 2H), 7.67 (d, J=8.4 Hz, 2H), 7.31 (m, 5H), 7.16 (brd, J=9.0 Hz, 1H), 4.74 (d, J=7.2 Hz, 1H), 4.69 (d, J=7.2 Hz, 1H), 4.55 (s, 2H), 4.34 (m, 1H), 3.83 (dd, J=10.2, 3.6 Hz, 1H), 3.77–3.66 (m, 4H), 3.62 (dd, J=10.2, 4.2 Hz, 1H), 3.51 (t, J=4.5 Hz, 2H), 3.29 (s, 3H), 2.79 (m, 1H), 2.15 (ddd, J=14.1, 9.6, 7.5 Hz, 1H), 1.91 (ddd, J=14.1, 5.4, 5.4 Hz, 1 H).

Example 44(20)

2(R)-Benzyloxymethyl-5-ethoxymethoxy-4(S)-[N-(4-chlorophenylcarbonyl)amino]pentanoic acid

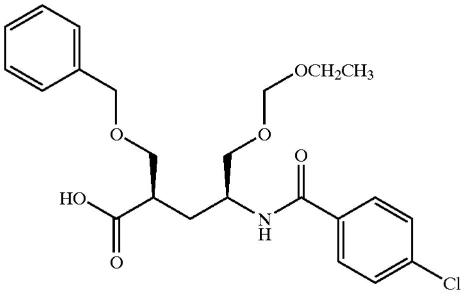

TLC: Rf 0.50 (Methylene chloride:Methanol=9:1);

NMR($CDCl_3$): δ7.69 (d, J=8.8 Hz, 2H), 7.35 (d, J=8.8 Hz, 2H), 7.31 (m, 5H), 6.81 (brd, J=8.8 Hz, 1H), 4.70 (d, J=7.5 Hz, 1H), 4.66 (d, J=7.5 Hz, 1H), 4.55 (s, 2H), 4.33 (m, 1H), 3.80–3.50 (m, 6H), 2.80 (m, 1H), 2.15 (ddd, J=14.2, 9.8, 7.6 Hz, 1H), 1.89 (ddd, J=14.2, 5.2, 5.2 Hz, 1H), 1.17 (t, J=7.4 Hz, 3H).

Example 44(21)

2(R)-Benzyloxymethyl-5-ethoxymethoxy-4(S)-[N-(4-bromophenylcarbonyl)amino]pentanoic acid

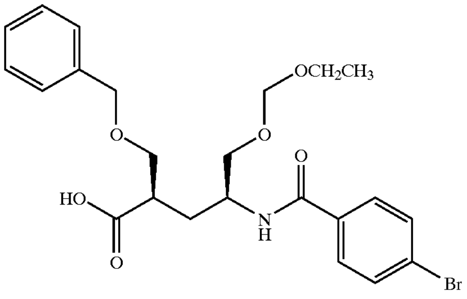

TLC: Rf 0.50 (Methylene chloride:Methanol=9:1);

NMR($CDCl_3$): δ7.62 (d, J=8.8 Hz, 2H), 7.51 (d, J=8.8 Hz, 2H), 7.31 (m, 5H), 6.81 (brd, J=8.8 Hz, 1H), 4.70 (d, J=7.0 Hz, 1H), 4.65 (d, J=7.0 Hz, 1H), 4.54 (s, 2H), 4.33 (m, 1H), 3.80–3.50 (m, 6H), 2.79 (m, 1H), 2.15 (ddd, J=14.2, 9.8, 7.6 Hz, 1H), 1.89 (ddd, J=14.2, 5.2, 5.2 Hz, 1H), 1.18 (t, J=7.4 Hz, 3H).

Example 44(22)

2(S)-Allyl-5-ethoxymethoxy-4(S)-[N-(4-bromophenylcarbonyl)amino]pentanoic acid

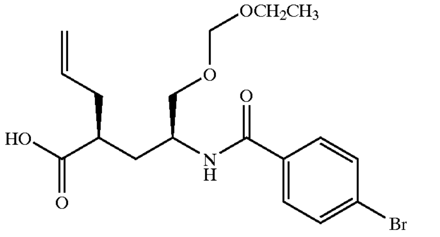

TLC: Rf 0.43 (Chloroform:Methanol=9:1);

NMR($CDCl_3$): δ7.63 (d, J=8.7 Hz, 2H), 7.53 (d, J=8.7 Hz, 2H), 6.72 (d, J=9.0 Hz, 1H), 5.83–5.65 (m, 1H), 5.18–5.02 (m, 2H), 4.71 (d, J=6.8 Hz, 1H), 4.67 (d, J=6.8 Hz, 1H), 4.45–4.30 (m, 1H), 3.76 (dd, J=10.4, 3.2 Hz, 1H), 3.70–3.50 (m, 3H), 2.62–2.50 (m, 1H), 2.50–2.25 (m, 2H), 2.18–2.00 (m, 1H), 1.81 (td, J=14.1, 5.1 Hz, 1H), 1.20 (t, J=7.1 Hz, 3H).

Example 44(23)

2(S)-Allyl-5-ethoxymethoxy-4(S)-[N-(4-chlorophenylcarbonyl)amino]pentanoic acid

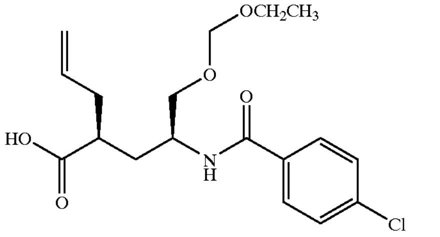

TLC: Rf 0.45 (Chloroform:Methanol=9:1);

NMR($CDCl_3$): δ7.70 (d, J=8.7 Hz, 2H), 7.38 (d, J=8.7 Hz, 2H), 6.73 (d, J=9.0 Hz, 1H), 5.82–5.65 (m, 1H), 5.18–5.02 (m, 2H), 4.71 (d, J=6.8 Hz, 1H), 4.67 (d, J=6.8 Hz, 1H), 4.45–4.30 (m, 1H), 3.76 (dd, J=10.5, 3.3 Hz, 1H), 3.70–3.50 (m, 3H), 2.62–2.50 (m, 1H), 2.50–2.25 (m, 2H), 2.18–2.00 (m, 1H), 1.81 (td, J=14.1, 5.3 Hz, 1H), 1.20 (t, J=6.9 Hz, 3H).

Example 44(24)

2(R)-(2-Methoxyethoxy)methyl-5-ethoxymethoxy-4(S)-[N-(4-bromophenylcarbonyl)amino]pentanoic acid

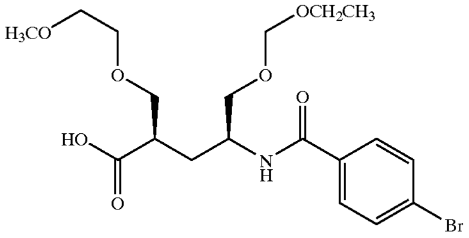

TLC: Rf 0.41 (Chloroform:Methanol=9:1);

NMR($CDCl_3$): δ7.65 (d, J=8.8 Hz, 2H), 7.54 (d, J=8.8 Hz, 2H), 6.85 (d, J=8.8 Hz, 1H), 4.70 (d, J=7.0 Hz, 1H), 4.66 (d, J.=7.0 Hz, 1H), 4.42–4.27 (m, 1H), 3.78–3.50 (m, 10H), 3.35 (s, 3H), 2.83–2.70 (m, 1H), 2.18 (ddd, J=14.0, 9.8, 7.0 Hz, 1H), 1.82 (ddd, J=14.0, 5.6, 4.4 Hz, 1H), 1.18 (t, J=7.4 Hz, 3H).

Example 44(25)

2(R)-(2-Methoxyethoxy)methyl-5-(2-methoxyethoxy)methoxy-4(S)-[N-(4-cyanophenylcarbonyl)amino]pentanoic acid

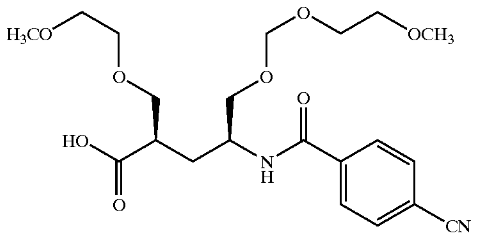

TLC: Rf 0.16 (Chloroform:Methanol=19:1);

NMR($CDCl_3$): δ7.91 (d, J=8.4 Hz, 2H), 7.71 (d, J=8.4 Hz, 2H), 7.20 (d, J=8.7 Hz, 1H), 4.75 (d, J=6.9 Hz, 1H), 4.70 (d, J=6.9 Hz, 1H), 4.42–4.31 (m, 1H), 3.84 (dd, J=10.5, 3.9 Hz, 1H), 3.78–3.60 (m, 7H), 3.57–3.50 (m, 4H), 3.36 (s, 3H), 3.32 (s, 3H), 2.82–2.72 (m, 1H), 2.18 (ddd, J=14.4, 10.2, 7.2 Hz, 1H), 1.85 (dt, J=14.4, 5.7 Hz, 1H).

Example 44(26)

2(R)-(2-Methoxyethoxy)methyl-5-ethoxymethoxy-4(S)[-N-(4-chlorophenylcarbonyl)amino]pentanoic acid

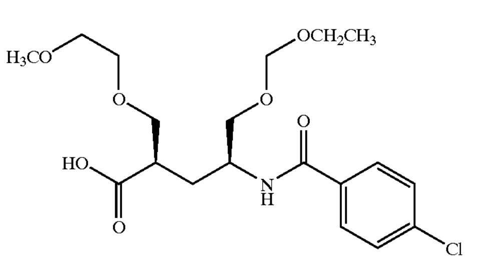

TLC: Rf 0.31 (Chloroform:Methanol=9:1);

NMR($CDCl_3$): δ7.72 (d, J=8.8 Hz, 2H), 7.39 (d, J=8.8 Hz, 2H), 6.84 (d, J=9.0 Hz, 1H), 4.70 (d, J=7.0 Hz, 1H), 4.66 (d, J=7.0 Hz, 1H), 4.43–4.27 (m, 1H), 3.78–3.50 (m, 10H), 3.35 (s, 3H), 2.82–2.69 (m, 1H), 2.19 (ddd, J=14.4, 10.6, 7.4 Hz, 1H), 1.82 (ddd, J=14.4, 5.6, 4.4 Hz, 1H), 1.19 (t, J=7.2 Hz, 3H).

Example 44(27)

2(S)-(2-Propynyl)-5-(2-methoxyethoxy)methoxy-4(S)-[N-(4-cyanophenylcarbonyl)amino]pentanoic acid

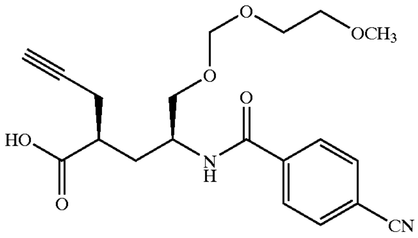

TLC: Rf 0.37(Chloroform:Methanol=9:1);

NMR($CDCl_3$): δ7.92 (d, J=8.7 Hz, 2H), 7.69 (d, J=8.7 Hz, 2H), 7.17 (d, J=9.0 Hz, 1H), 4.77 (d, J=7.1 Hz, 1H), 4.71 (d, J=7.1 Hz, 1H), 4.48–4.32 (m, 1H), 3.89 (dd, J=10.5, 3.6 Hz, 1H), 3.82–3.60 (m, 3H), 3.55 (t, J=4.5 Hz, 2H), 3.31 (s, 3H), 2.78–2.50(m, 3H), 2.25–2.10 (m, 1H), 2.10–1.95 (m, 2H).

Example 44(28)~44(29)

The following compounds were obtained by the same procedure as a series of reaction of Example 37→Example 39→Example 41 (using a corresponding compound instead of methoxymethyl chloride.)→Example 43 (using a corresponding compound instead of benzyl bromide.)→Example 5→Example 44, using a corresponding compound instead of the compound prepared in Reference Example 4.

Example 44(28)

2(S)-Methyl-5-ethoxymethoxy-4(S)-[N-methyl-N-(4-bromophenylcarbonyl)amino]pentanoic acid

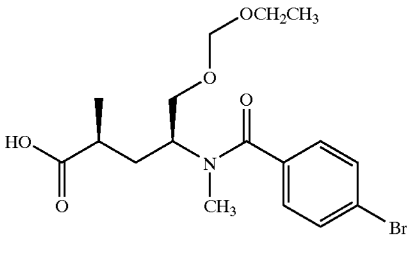

TLC: Rf 0.23 (Chloroform:Methanol=9:1);

NMR($d_6$-DMSO): δ12.15 (1H, brs), 7.63–7.56 (2H, m), 7.34–7.25 (2H, m), 4.82–4.72&3.79–3.69 (1H, m), 4.59&4.55 (2H, s), 3.61–3.37 (4H, m), 2.76&2.64 (3H, s), 2.08 (1H, sxt, J=6.9 Hz), 2.01–1.91&1.51–1.41&1.37–1.27 (2H, m), 1.14–1.04 (3H, m), 0.82 (3H, d, J=6.9 Hz).

Example 44(29)

2(S)-Methyl-5-ethoxymethoxy-4(S)-[N-methyl-N-(4-nitrophenylcarbonyl)amino]pentanoic acid

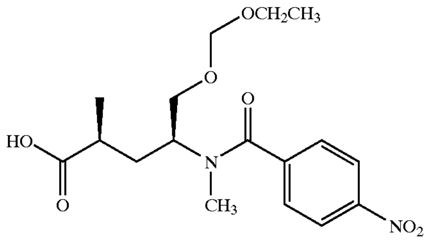

TLC: Rf 0.42 (Chloroform:Methanol=9:1);

NMR($CDCl_3$): δ8.27 and 8.25 (d and d, J=8.7 Hz and J=8.7 Hz, 2H), 7.68 and 7.58 (d and d, J=8.7 Hz and J=8.7 Hz, 2H), 5.10–4.98 and 3.92–3.80 (m and m, 1H), 4.76–4.63 (m, 2H), 3.72–3.42 (m, 4H), 2.96 and 2.80 (s and s, 3H), 2.62–2.50 and 2.27–2.21 (m and m, 1H), 2.12 and 1.59 (ddd and ddd, J=14.4, 10.5, 6.3 Hz and 14.4, 7.5, 4.2 Hz, 1H), 2.02 and 1.41 (dt and dt, J=14.4, 9.0 Hz and 14.4, 5.4 Hz, 1H), 1.32 and 1.08 (d and d, J=7.2 Hz and 6.9 Hz, 3H), 1.23 and 1.22 (t and t, J=7.2 and 7.2 Hz, 3H).

Example 45

4(S)-t-Butyldimethylsilyloxymethyl-4-(N-(4-(benzofuran-2-yl)phenylcarbonyl)amino)butyric acid methyl ester

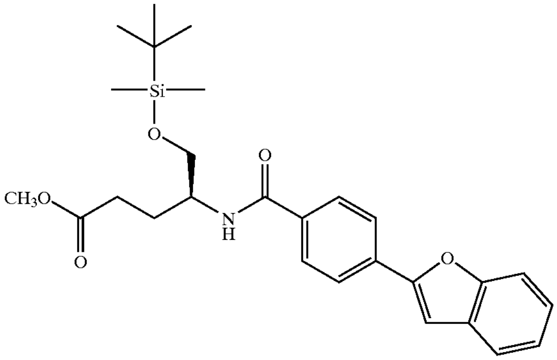

Imidazole (0.107 g) and t-butyldimethylsilyl chloride (0.241 g) were added to a solution of the compound prepared in Example 39 (0.294 g) in dimethylformamide (5 ml). The mixture was stirred at room temperature for 2 hours. The reaction mixture was diluted with ethyl acetate, washed with water and a saturated aqueous solution of sodium chloride, dried over anhydrous magnesium sulfate and concentrated. The residue was purified by column chromatography on silica gel (n-Hexane:Ethyl acetate=3:1) to give the title compound (0.361 g) having the following physical data.

TLC: Rf 0.83 (n-Hexane:Ethyl acetate=1:1);

NMR ($CDCl_3$): δ7.94 (2H, d, J=8.8 Hz), 7.84 (2H, d, J=8.8 Hz), 7.63–7.52 (2H, m), 7.37–7.20 (3H, m), 7.13 (1H, d, J=0.8 Hz), 6.62 (1H, d, J=8.8 Hz), 4.30–4.16 (1H, m), 3.74 (2H, d, J=3.6 Hz), 3.64 (3H, s), 2.59–2.38 (2H, m), 2.10–1.92 (2H, m), 0.92 (9H, s), 0.086 (3H, s), 0.066 (3H, s).

Example 46

2(S)-Benzyl-4(S)-t-butyldimethylsilyloxymethyl-4-(N-(4-(benzofuran-2-yl)phenylcarbonyl)amino) butyric acid methyl ester

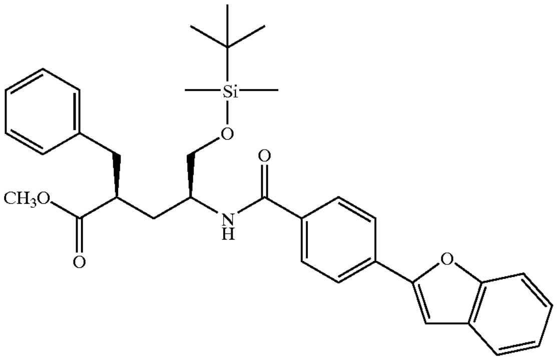

The title compound having the following physical data was obtained by the same procedure as a series of reaction of Example 42, using the compound prepared in Example 45 instead of the compound prepared in Example 41.

TLC: Rf 0.43 (n-Hexane:Ethyl acetate=7:3);

NMR ($CDCl_3$): δ7.93 (2H, d, J=8.4 Hz), 7.83 (2H, d, J=8.4 Hz), 7.63–7.50 (2H, m), 7.38–7.10 (8H, m), 6.35 (1H, d, J=8.8 Hz), 4.36–4.17 (1H, m),3.74–3.60 (2H, m), 3.43 (3H, s), 3.02–2.68 (3H, m), 2.20–2.00 (1H, m), 1.90–1.74 (1H, m), 0.88 (9H, s), 0.038 (3H, s), 0.026 (3H, s).

Example 47

2(S)-Benzyl-4(S)-t-butyldimethylsilyloxymethyl-4-(N-(4-(benzofuran-2-yl)phenylcarbonyl)amino) butyric acid

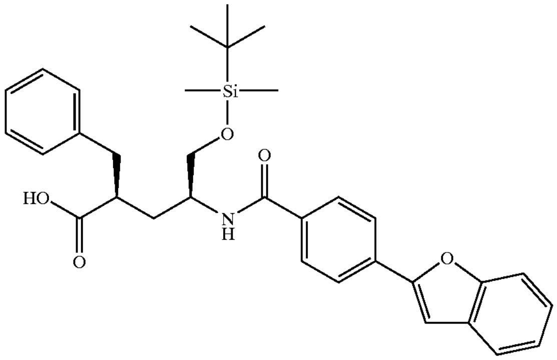

The title compound having the following physical data was obtained by the same procedure as a series of reaction of Example 2, using the compound prepared in Example 46 instead of the compound prepared in Example 1.

TLC: Rf 0.44 (Chloroform:Methanol=19:1);

NMR ($CD_3OD$): δ7.97 (2H, d, J=8.4 Hz), 7.90 (2H, d, J=8.4 Hz), 7.63–7.49 (2H, m), 7.37–7.10 (8H, m), 4.35–4.18 (1H, m), 3.74–3.60 (2H, m), 3.05–2.82 (2H, m), 2.80–2.64 (1H, m), 1.93 (2H, m), 0.87 (9H, s), 0.048 (6H, s).

Example 48

2(R)-Benzyl-4(S)-hydroxymethyl-4-(N-(4-(benzofuran-2-yl)phenylcarbonyl)amino)butyric acid

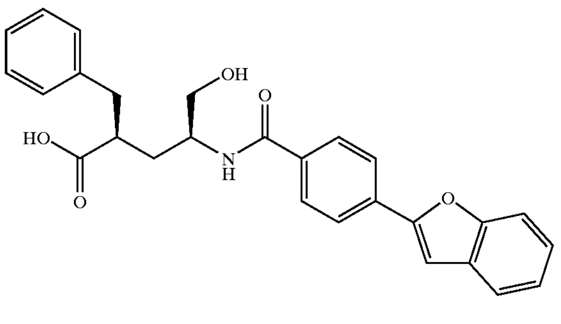

A solution of 1M tetrabutylammonium fluoride in tetrahydrofuran (0.4 ml) was added to a solution of the compound prepared in Example 47 (0.162 g) in tetrahydrofuran (5 ml) at room temperature. The mixture was stirred at room temperature for 2 hours. Water was added to the reaction mixture. The mixture was extracted with ethyl acetate. The extract was washed with a saturated aqueous solution of sodium chloride, dried over anhydrous magnesium sulfate and concentrated. The residue was purified by column chromatography on silica gel (n-Hexane:Ethyl acetate=9:1~1:9) to give the title compound (0.088 g) having the following physical data.

TLC: Rf 0.22 (Chloroform:Methanol=19:1);

NMR ($CD_3OD$): δ7.92 (4H, s), 7.60–7.42 (2H, m), 7.38–7.06 (8H, m), 4.40–4.20 (1H, m), 3.64 (2H, d, J=5.4 Hz), 3.02–2.82 (2H, m), 2.80–2.62 (1H, m), 2.10–1.75 (2H, m).

Example 48(1)

2(S)-Benzyl-4(S)-hydroxymethyl-4-(N-(4-(3-methoxy-1-propynyl)phenylcarbonyl)amino)butyric acid

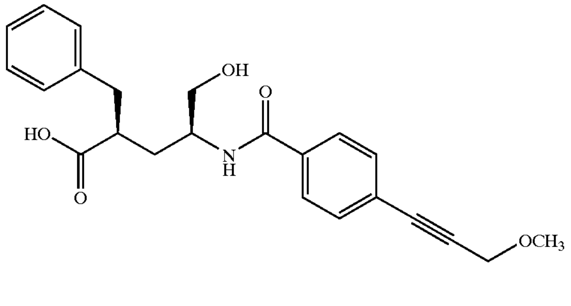

The title compound having the following physical data was obtained by the same procedure as a series of reaction of Example 37→Example 39→Example 45→Example 46→Example 47→Example 48, using a corresponding acyl halide instead of the compound prepared in Reference Example 4.

TLC: Rf 0.21 (Chloroform:Methanol=19:1).

Example 49

N-Hydroxy-4(S)-(morpholin-1-yl)carbonyl-4-(N-(4-(benzofuran-2-yl)phenylcarbonyl)amino)butyramide

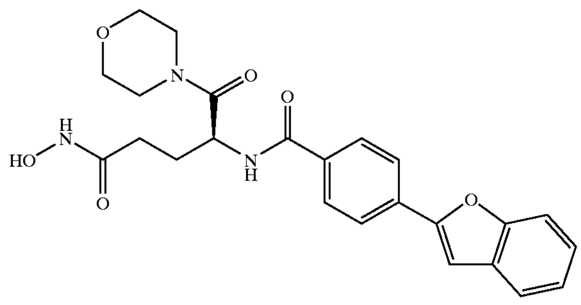

The title compound having the following physical data was obtained by the same procedure as a series of reaction of Example 3→Example 4, using the compound prepared in Example 38 instead of the compound prepared in Example 2.

TLC: Rf 0.39 (Chloroform:Methanol=9:1);

NMR ($d_6$-DMSO): δ10.42 (1H, s), 8.75 (1H, d, J=7.6 Hz), 8.04 (4H, s), 7.74–7.57 (3H, m), 7.42–7.25 (2H, m), 5.00–4.82 (1H, m), 3.71–3.40 (8H, m), 2.19–1.82 (4H, m).

Example 49(1)~49(8)

The following compounds were obtained by the same procedure as a series of reaction of Example 49, using the compound prepared in Example 40, Example 42, Example 44, Example 44(1)~44(3), Example 48 and Example 48(1), instead of the compound prepared in Example 38.

Example 49(1)

N-Hydroxy-4(S)-hydroxymethyl-4-(N-(4-(benzofuran-2-yl)phenylcarbonyl)amino)butyramide

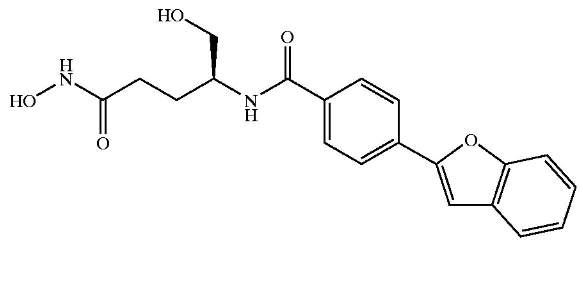

TLC: Rf 0.22 (Chloroform:Methanol=9:1);

NMR ($d_6$-DMSO): δ10.36 (1H, d, J=1.5 Hz), 8.67 (1H, d, J=1.5 Hz), 8.19 (1H, d, J=8.4 Hz), 8.00 (4H, s), 7.73–7.61 (2H, m), 7.57 (1H, d, J=0.8 Hz), 7.42–7.23 (2H, m), 4.73 (1H, t, J=5.8 Hz), 4.08–3.85 (1H, m), 3.58–3.38 (2H, m), 2.12–1.60 (4H, m).

Example 49(2)

N-Hydroxy-4(S)-methoxymethyloxymethyl-4-(N-(4-(benzofuran-2-yl)phenylcarbonyl)amino)butyramide

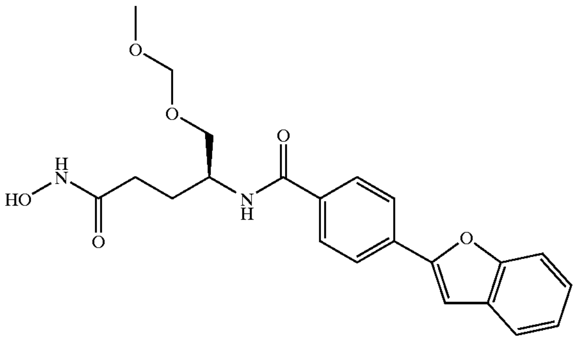

TLC: Rf 0.47 (Chloroform:Methanol=9:1);

NMR ($d_6$-DMSO): δ10.37 (1H, s), 8.34 (1H, d, J=8.4 Hz), 8.00 (4H, s), 7.73– 7.61 (2H, m), 7.56 (1H, s), 7.41–7.24 (2H, m), 4.58 (2H, s), 4.23–4.04 (1H, m), 3.62–3.44 (2H, m), 3.26 (3H, s), 2.12–1.62 (4H, m).

Example 49(3)

N-Hydroxy-2(S)-benzyl-4(S)-methoxymethyloxymethyl-4-(N-(4-(benzofuran-2-yl)phenylcarbonyl)amino)butyramide

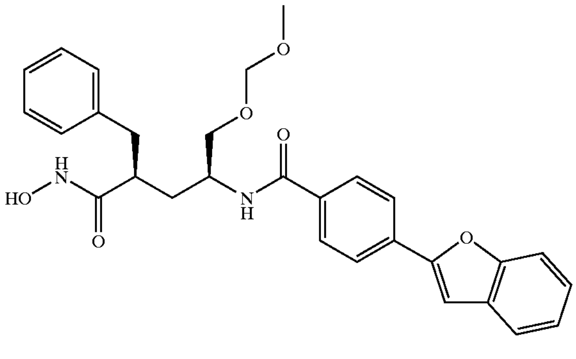

TLC: Rf 0.35 (Chloroform:Methanol=19:1);

NMR ($d_6$-DMSO): δ10.37 (1H, s), 8.69 (1H, s), 8.25 (1H, d, J=8.6 Hz), 8.01 (4H, s), 7.72–7.61 (2H, m), 7.57 (1H, s), 7.41–7.09 (7H, m), 4.55 (2H, s), 4.40–4.20 (1H, m), 3.53 (2H, d, J=5.6 Hz), 3.22 (3H, s), 2.79 (2H, d, J=7.4 Hz), 2.50–2.34 (1H, m), 1.90–1.60 (2H, m).

Example 49(4)

N-Hydroxy-2(S)-methyl-4(S)-methoxymethyloxymethyl-4-(N-(4-(benzofuran-2-yl)phenylcarbonyl)amino)butyramide

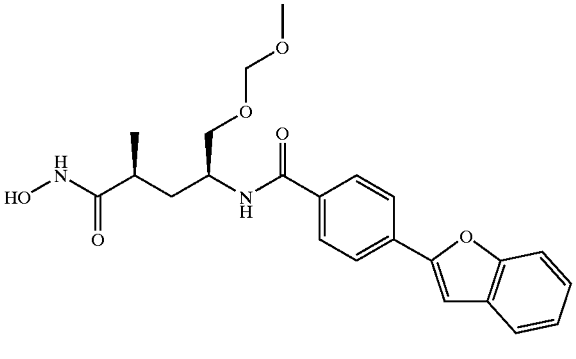

TLC: Rf 0.23 (Chloroform:Methanol=19 1);

NMR ($d_6$-DMSO): δ10.41 (1H, d, J=1.6 Hz), 8.68 (1H, d, J=1.6 Hz), 8.20 (1H, d, J=8.4 Hz), 8.00 (4H, s), 7.74–7.60 (2H, m), 7.56 (1H, d, J=0.8 Hz), 7.41–7.22 (2H, m), 4.58 (2H, s), 4.32–4.10 (1H, m), 3.62–3.41 (2H, m), 3.25 (3H, s), 2.30–2.14 (1H, m), 1.82–1.58 (2H, m), 1.05 (3H, d, J=6.6 Hz).

Example 49(5)

N-Hydroxy-2(S)-(3-phenyl-2-propenyl)-4(S)-methoxymethyloxymethyl-4-(N-(4-(benzofuran-2-yl)phenylcarbonyl)amino)butyramide

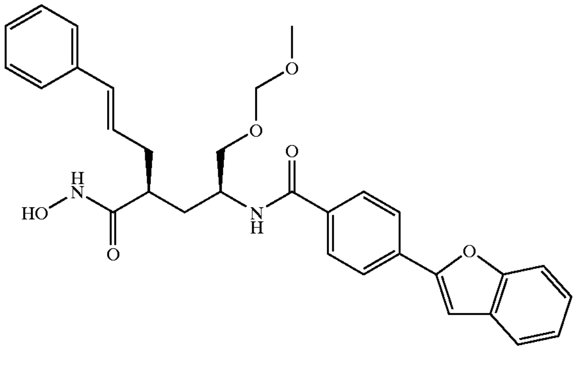

TLC: Rf 0.36 (Chloroform:Methanol=19:1);

NMR ($d_6$-DMSO): δ10.50 (1H, s), 8.78 (1H, s), 8.25 (1H, d, J=8.4 Hz), 8.00 (4H, s), 7.67 (2H, t, J=8.6 Hz), 7.56 (1H, s), 7.40–7.14 (7H, m), 6.41 (1H, d, J=16.0 Hz), 6.15 (1H, dt, J=16.0, 5.8 Hz), 4.57 (2H, s), 4.32–4.14 (1H, m), 3.62–3.45 (2H, m), 3.24 (3H, s), 2.46–2.22 (3H, m), 1.96–1.78 (2H, m).

Example 49(6)

N-Hydroxy-2(S)-(3-phenylpropyl)-4(S)-methoxymethyloxymethyl-4-(N-(4-(benzofuran-2-yl)phenylcarbonyl)amino)butyramide

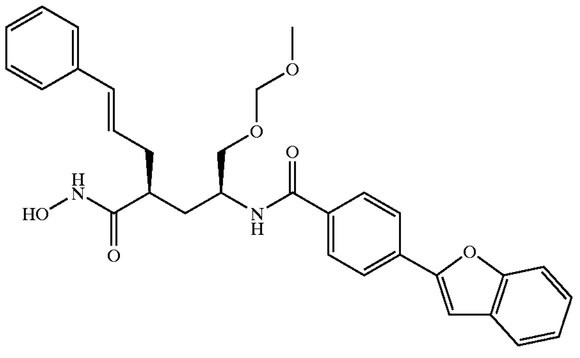

TLC: Rf 0.35 (Chloroform:Methanol=19:1);

NMR ($d_6$-DMSO): δ10.47 (1H, s), 8.82–8.66 (1H, brs), 8.20 (1H, d, J=8.4 Hz), 7.99 (4H, s), 7.72–7.61 (2H, m), 7.57 (1H, d, J=0.6 Hz), 7.41–7.10 (7H, m) 4.57 (2H, s), 4.23–4.02 (1H, m), 3.60–3.42 (2H, m), 3.24 (3H, s), 2.62–2.40 (2H, m), 2.22–2.06 (1H, m), 1.84–1.64 (2H, m), 1.60–1.38 (4H, m).

Example 49(7)

N-Hydroxy-2(R)-benzyl-4(S)-hydroxymethyl-4-(N-(4-(benzofuran-2-yl)phenylcarbonyl)amino) butyramide

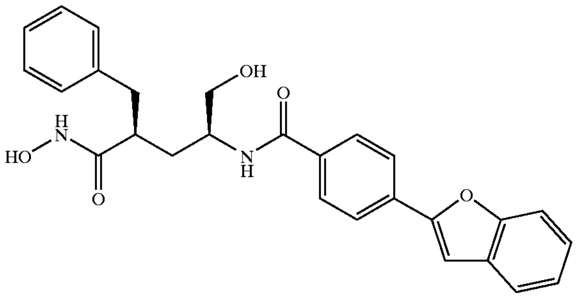

TLC: Rf 0.37 (Chloroform:Methanol=9:1);

NMR ($d_6$-DMSO): δ10.32 (1H, s), 8.68 (1H, s), 8.08 (1H, d, J=8.4 Hz), 8.02 (4H, s), 7.72–7.62 (2H, m), 7.59 (1H, s), 7.41–7.06 (7H, m), 4.82–4.66 (1H, m), 4.24–4.04 (1H, m), 3.60–3.36 (2H, m), 2.92–2.66 (2H, m), 2.50–2.30 (1H, m), 1.92–1.52 (2H, m).

Example 49(8)

N-Hydroxy-2(S)-benzyl-4(S)-hydroxymethyl-4-(N-(4-(3-methoxy-1-propynyl)phenylcarbonyl)amino) butyramide

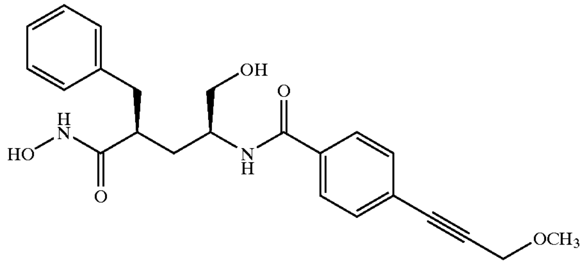

TLC: Rf 0.23 (Chloroform:Methanol=9:1);

NMR ($d_6$-DMSO): δ10.28 (1H, brs), 8.62 (1H, brs), 8.04(1H, d, J=8.4 Hz), 7.87 (2H, d, J=8.2 Hz), 7.53 (2H, d, J=8.2 Hz), 7.24–7.05 (5H, m), 4.69 (1H, t, J=5.7 Hz), 4.33 (2H, s), 4.18–4.02 (1H, m), 3.46–3.34 (2H, m), 3.31 (3H, s), 2.75 (2H, d, J=7.0 Hz), 2.42–2.26 (1H, m), 1.89–1.52 (2H, m).

Example 49(9)

N-Hydroxy-5-hydroxy-4(S)-[N-[4-(3-methoxy-1-propynyl)phenylcarbonyl]amino]pentanamide

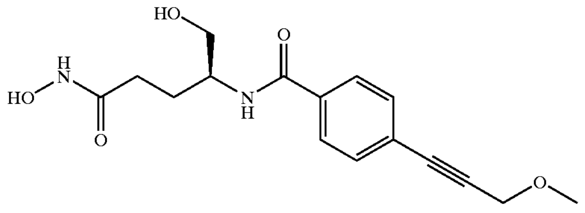

The title compound having the following physical data was obtained by the same procedure as a series of reaction of Example 37→Example 39→Example 40→Example 49, using a corresponding compound instead of the compound prepared in Reference Example 4.

TLC: Rf 0.36 (Chloroform:Methanol=4:1);

NMR ($d_6$-DMSO): δ10.35 (1H, s), 10.18 (1H, s), 8.18 (1H, d, J=8.4 Hz), 7.88 (2H, d, J=8.4 Hz), 7.55 (2H, d, J=8.4 Hz), 4.53 (2H, s), 4.02–3.84 (1H, m), 3.73–3.34 (2H, m), 3.35 (3H, s), 2.07–1.59 (4H, m).

Example 49(10)

N-Hydroxy-5-hydroxy-4(R)-[N-[4-(3-methoxy-1-propynyl)phenylcarbonyl]amino]pentanamide

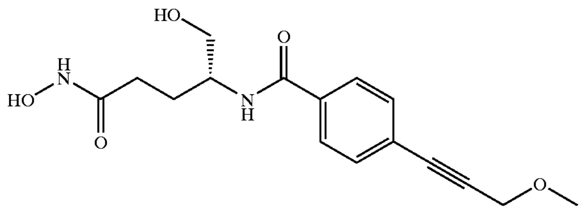

The title compound having the following physical data was obtained by the same procedure as a series of reaction of Example 37→Example 39→Example 40→Example 49, using 4(R)-carboxy-4-aminobutyric acid methyl ester instead of 4(S)-carboxy-4-aminobutyric acid methyl ester and a corresponding compound instead of the compound prepared in Reference Example 4.

TLC: Rf 0.28 (Chloroform:Methanol:Acetic acid:Water=85:15:1:1);

NMR ($CD_3OD$): δ7.83(2H, d, J=8.4 Hz), 7.51 (2H, d, J=8.4 Hz), 4.34(2H, s), 4.03–4.15(1H, m), 3.62(2H, d, J=5.6 Hz), 3.43(3H, s), 2.19(2H, t, J=7.4 Hz), 1.77–2.10(2H, m).

Example 49(11)~49(21)

The following compounds were obtained by the same procedure as a series of reaction of Example 37→Example 38 (using a corresponding amine compound.)→Example 49, using a corresponding compound instead of the compound prepared in Reference Example 4.

Example 49(11)

N-Hydroxy-4(S)-(4-hydroxybutylcarbamoyl)-4-[N-[4-(3-methoxy-1-propynyl)phenylcarbonyl]amino]butyramide

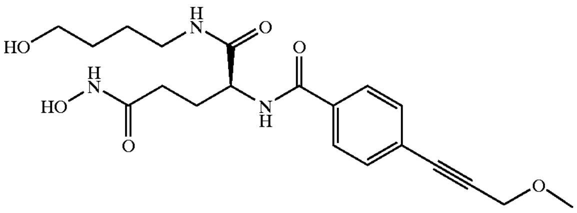

TLC: Rf 0.40 (Chloroform:Methanol=4:1);

NMR ($d_6$-DMSO): δ10.41 (1H, s), 8.61 (1H, d, J=7.8 Hz), 7.98–7.88 (3H, m), 7.55 (2H, d, J=8.4 Hz), 4.44–4.27 (3H, m), 3.38 (2H, t, J=6.2 Hz), 3.35 (3H, s), 3.13–3.00 (2H, m), 2.09–1.83 (4H, m), 1.48–1.34 (4H, m).

Example 49(12)

N-Hydroxy-4(S)-(3-phenylpropylcarbamoyl)-4-[N-[4-(3-methoxy-1-propynyl)phenylcarbonyl]amino]butyramide

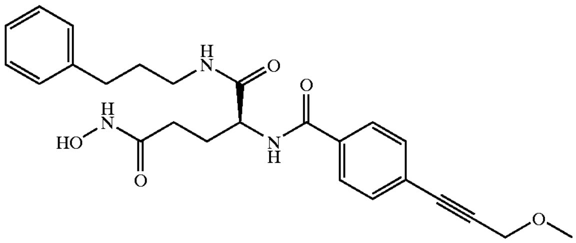

TLC: Rf 0.38 (Chloroform:Methanol=9:1);

NMR ($d_6$-DMSO): δ10.41 (1H, s), 8.72 (1H, s), 8.64 (1H, d, J=7.6 Hz), 8.04–7.94 (1H, m), 7.92 (2H, d, J=8.5 Hz), 7.55 (2H, d, J=8.5 Hz), 7.32–7.14 (5H, m), 4.43–4.35 (3H, m), 3.33 (3H, s), 3.16–3.02 (2H, m), 2.62–2.49 (2H, m), 2.14–1.84 (4H, m), 1.80–1.62 (2H, m).

Example 49(13)

N-Hydroxy-4(S)-propylcarbamoyl-4-[N-[4-(3-methoxy-1-propynyl)phenylcarbonyl]amino]butyramide

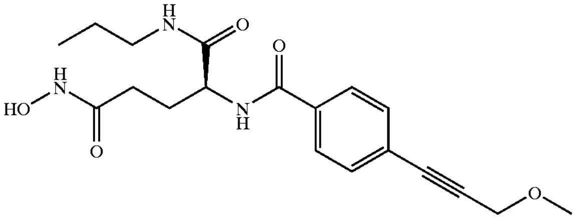

TLC: Rf 0.23 (Chloroform:Methanol=9:1);

NMR ($d_6$-DMSO): δ10.40 (1H, s), 8.71 (1H, s), 8.61 (1H, d, J=7.8 Hz), 7.96–7.88 (3H, m), 7.55 (2H, d, J=8.3 Hz), 4.43–4.26 (3H, m), 3.32 (3H, s), 3.09–2.95 (2H, m), 2.07–1.79 (4H, m), 1.41 (2H, sextet, J=7.3 Hz), 0.83 (3H, t, J=7.3 Hz).

Example 49(14)

N-Hydroxy-4(S)-(2-hydroxyethylcarbamoyl)-4-[N-[4-(3-methoxy-1-propynyl)phenylcarbonyl]amino]butyramide

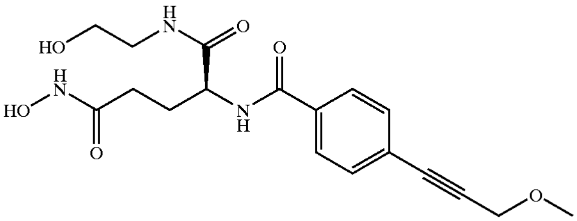

TLC: Rf 0.09 (Chloroform:Methanol=9:1);

NMR ($d_6$-DMSO): δ10.39 (1H, s), 8.71 (1H, s), 8.63 (1H, d, J=7.6 Hz), 7.97–7.87 (3H, m), 7.56 (2H, d, J=8.2 Hz), 4.66 (1H, t, J=5.4 Hz), 4.43–4.35 (3H, m), 3.40 (2H, m), 3.33 (3H, s), 3.19–3.08 (2H, m), 2.09–1.83 (4H, m).

Example 49(15)

N-Hydroxy-4(S)-(6-hydroxyhexylcarbamoyl)-4-[N-[4-(3-methoxy-1-propynyl)phenylcarbonyl]amino]butyramide

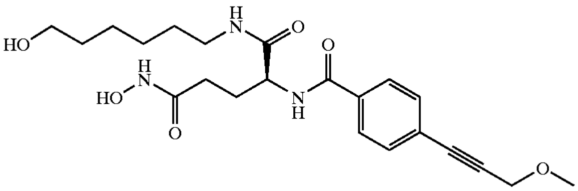

TLC: Rf 0.42 (Chloroform:Methanol=4:1);

NMR ($d_6$-DMSO): δ10.37 (1H, s), 8.68 (1H, s), 8.57 (1H, d, J=7.6 Hz), 7.93–7.83 (3H, m), 7.53 (2H, d, J=8.4 Hz), 4.37–4.25 (4H, m), 3.38–3.29 (5H, m), 3.09–2.93 (2H, m), 2.12–1.78 (4H, m), 1.43–1.15 (8H, m).

Example 49(16)

N-Hydroxy-4(S)-[2-(4-methoxyphenyl)ethylcarbamoyl]-4-[N-[4-(3-methoxy-1-propynyl)phenylcarbonyl]amino]butyramide

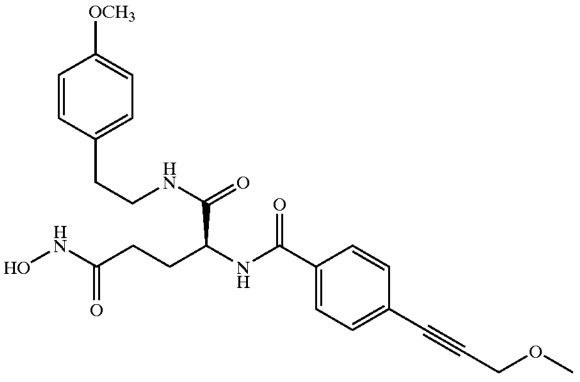

TLC: Rf 0.25 (Chloroform:Methanol=9:1);

NMR ($d_6$-DMSO): δ10.40 (1H, s), 8.72 (1H, s), 8.62 (1H, d, J=8.4 Hz), 8.00–7.86 (3H, m), 7.60–7.52 (2H, m), 7.10–7.08 (2H, d, J=8.4 Hz), 6.82–6.79 (2H, d, J=8.4 Hz), 4.40–4.25 (3H, m), 3.70–3.69 (3H, s), 3.35 (3H, s), 3.36–3.15 (2H, m), 2.63 (2H, t, J=7.3 Hz), 2.19–1.82 (4H, m).

Example 49(17)

N-Hydroxy-4(S)-(2-morpholinoethylcarbamoyl)-4-[N-[4-(3-methoxy-1-propynyl)phenylcarbonyl]amino]butyramide

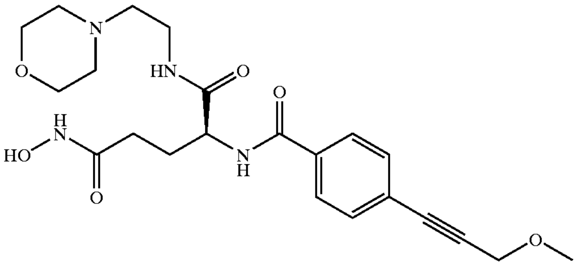

TLC: Rf 0.70 (Chloroform:Methanol=4:1);

NMR ($d_6$-DMSO): δ10.32 (1H, s), 8.60 (1H, d, J=7.6 Hz), 8.32 (1H, s), 7.92 (2H, d, J=8.4 Hz), 7.83 (1H, t, J=5.5 Hz), 7.56 (2H, d, J=8.4 Hz), 4.42–4.30 (3H, m), 3.55–3.48 (4H, m), 3.35 (3H, s), 3.23–3.20 (4H, m), 2.39–2.29 (4H, m), 2.21–1.83 (4H, m).

Example 49(18)

N-Hydroxy-4(S)-[2-(indol-3-yl)ethylcarbamoyl)-4-[N-[4-(3-methoxy-1-propynyl)phenylcarbonyl]amino]butyramide

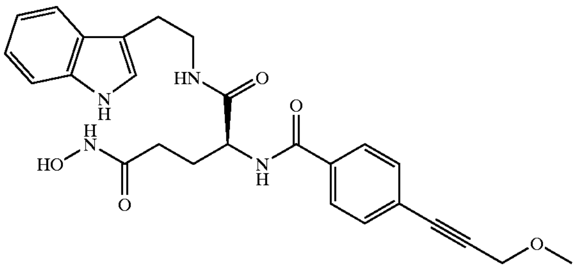

TLC: Rf 0.33 (Chloroform:Methanol=9:1);

NMR ($d_6$-DMSO): δ10.79 (1H, s), 10.41 (1H, s), 8.64 (1H, d, J=7.6 Hz), 8.12–8.04 (1H, m), 7.92 (2H, d, J=8.5 Hz), 7.61–7.52 (3H, m), 7.32 (1H, d, J=7.6 Hz), 7.17–6.92 (3H, m), 4.45–4.35 (3H, m), 3.42–3.33 (4H, m), 2.82 (2H, t, J=7.4 Hz), 2.17–1.84 (4H, m).

Example 49(19)

N-Hydroxy-4(S)-(4-phenylbutylcarbamoyl)-4-[N-[4-(3-methoxy-1-propynyl)phenylcarbonyl]amino]butyramide

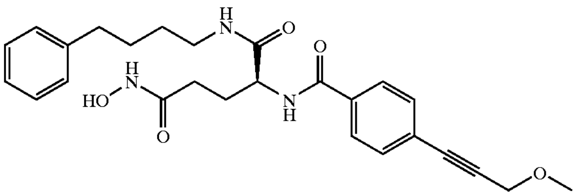

TLC: Rf 0.16 (Chloroform:Methanol=9:1);

NMR ($d_6$-DMSO): δ10.40 (1H, s), 8.70 (1H, brs), 8.62 (1H, d, J=7.8 Hz), 7.98–7.87 (3H, m), 7.55 (2H, d, J=8.5 Hz), 7.30–7.14 (5H, m), 4.40–4.34 (3H, m), 3.35 (3H, s), 3.09 (2H, q, J=6.0 Hz), 2.56 (2H, t, J=7.0 Hz), 2.12–1.83 (4H, m), 1.64–1.34 (4H, m).

Example 49(20)

N-Hydroxy-4(S)-(2-phenylethylcarbamoyl)-4-[N-[4-(3-methoxy-1-propynyl)phenylcarbonyl]amino]butyramide

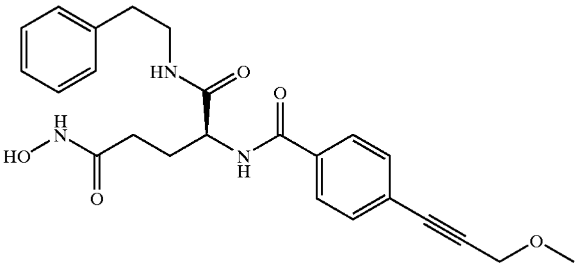

TLC: Rf 0.36 (Chloroform:Methanol=9:1);

NMR ($d_6$-DMSO): δ10.39 (1H, s), 8.72 (1H, s), 8.63 (1H, d, J=8.0 Hz), 8.01 (1H, t, J=5.7 Hz), 7.92 (2H, d, J=8.4 Hz), 7.57 (2H, d, J=8.4 Hz), 7.29–7.14 (5H, m), 4.39–4.28 (3H, m), 3.35–3.23 (5H, m ), 2.71 (2H, t, J=7.5 Hz), 2.09–1.82 (4H, m).

Example 49(21)

N-Hydroxy-4(S)-[3-(pyrazol-1-yl)propylcarbamoyl]-4-[N-[4-(3-methoxy-1-propynyl)phenylcarbonyl]amino]butyramide

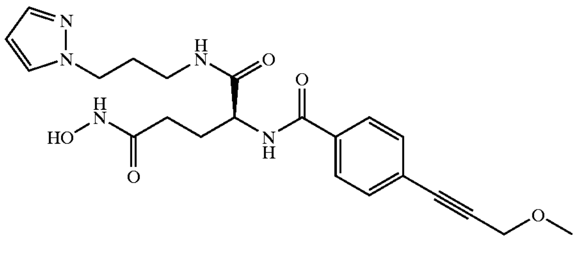

TLC: Rf 0.23 (Chloroform:Methanol:Acetic acid=9:1:0.5);

NMR ($d_6$-DMSO): δ10.43 (1H, s), 8.69 (1H, d, J=7.5 Hz), 8.06 (1H, t, J=5.6Hz), 7.93 (2H, d, J=8.4 Hz), 7.71 (1H, d, J=2.0 Hz), 7.56 (2H, d, J=8.4 Hz), 7.42 (1H, d, J=2.0 Hz), 6.21 (1H, t, J=2.0Hz), 4.37–4.27 (3H, m), 4.11 (2H, t, J=6.8 Hz), 3.35 (3H, s), 3.09–2.99 (2H, m), 2.12–1.86 (6H, m).

Example 49(22)

N-Hydroxy-4(R)-(3-phenylpropylcarbamoyl)-4-[N-[4-(3-methoxy-1-propynyl)phenylcarbonyl]amino]butyramide

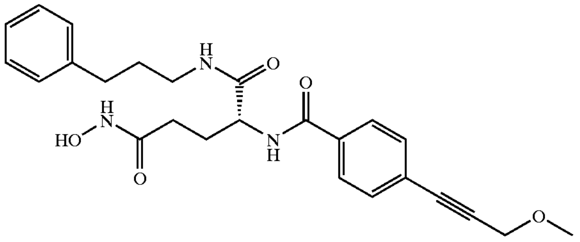

The title compound having the following physical data was obtained by the same procedure as a series of reaction of Example 37→Example 38 (using a corresponding amine compound.)→Example 49, using 4(R)-carboxy-4-aminobutyric acid methyl ester instead of 4(S)-carboxy-4-aminobutyric acid methyl ester and a corresponding compound instead of the compound prepared in Reference Example 4.

TLC: Rf 0.44 (Chloroform:Methanol=9:1);

NMR ($d_6$-DMSO): δ10.39(1H, brs), 8.70(1H, brs), 8.63 (1H, d, J=7.8 Hz), 7.98(1H, t, J=5.6 Hz), 7.90(2H, d, J=8.4 Hz), 7.54(2H, d, J=8.4 Hz), 7.10–7.28(5H, m), 4.42–4.35 (3H, m), 3.32(3H, s), 3.11–3.01(2H, m), 2.57–2.47(2H, m), 2.13–1.82(4H, m), 1.74–1.60(2H, m).

Example 49(23)

N-Hydroxy-2-(pyridin-3-yl)methyl-4-(2-phenylethylcarbamoyl)-4-[N-(4-phenoxyphenylcarbonyl)amino]butyramide

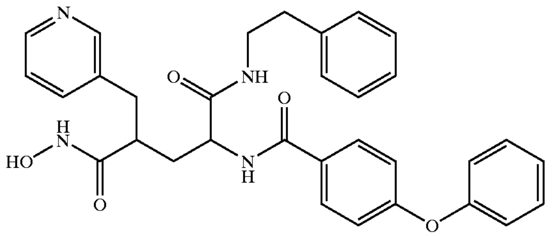

The title compound having the following physical data was obtained by the same procedure as a series of reaction of Example 43→Example 27→Example 37 (using a corresponding compound instead of the compound prepared in Reference Example 4.)→Example 14→Example 38 (using a corresponding amine compound.)→Example 49, using 4(S)-t-butoxycarbonyl-4-(N-benzyloxycarbonylamino)butyric acid methyl ester instead of 4(S)-carboxy-4-aminobutyric acid methyl ester and a corresponding compound instead of benzyl bromide.

TLC: Rf 0.30, 0.36 (Chloroform:Methanol:Acetic acid=9:1:0.5);

NMR ($d_6$-DMSO/MeOH): δ8.33–8.26 (2H, m), 7.89–7.82 (2H, m), 7.48 (1H, t, J=8.1 Hz), 7.39–7.31 (2H, m), 7.24–7.06 (5H, m), 7.02–6.90 (6H, m), 4.48 (1H of 2 isomers, dd, J=5.0 Hz, 10.1 Hz), 4.29 (1H of 2 isomers, dd, J=4.2 Hz, 10.5 Hz), 3.20–3.02 (2H, m), 2.95–2.84 (1H of 2 isomers, m), 2.79–2.57 (1H of 2 isomers+2H, m), 2.51–2.27 (2H, m), 2.04–1.92 (2H of 2 isomers, m), 1.88–1.77 (2H of 2 isomers, m).

Example 49(24)~49(35)

The following compounds were obtained by the same procedure as a series of reaction of Example 37→Example 39→Example 41 (using a corresponding compound instead of methoxymethyl chloride, if necessary.)→Example 42→Example 49, using a corresponding compound instead of the compound prepared in Reference Example 4.

Example 49(24)

N-Hydroxy-5-methoxymethoxy-4(S)-[N-[4-(3-methoxy-1-propynyl)phenylcarbonyl]amino]pentanamide

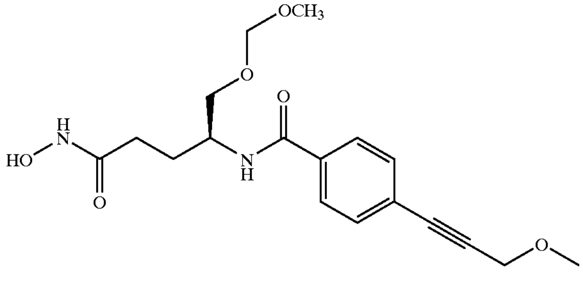

TLC: Rf 0.22 (Chloroform:Methanol=9:1);

NMR ($d_6$-DMSO): δ10.35 (1H, s), 8.32 (1H, d, J=8.6 Hz), 7.87 (2H, d, J=8.4 Hz), 7.55 (2H, d, J=8.4 Hz), 4.57 (2H, s), 4.36 (2H, s), 4.20–4.01 (1H, m), 3.55–3.44 (2H, m), 3.35 (3H, s), 3.24 (3H, s), 2.09–1.64 (4H, m).

Example 49(25)

N-Hydroxy-5-benzyloxymethoxy-4(S)-[N-[4-(3-methoxy-1-propynyl)phenylcarbonyl]amino] pentanamide

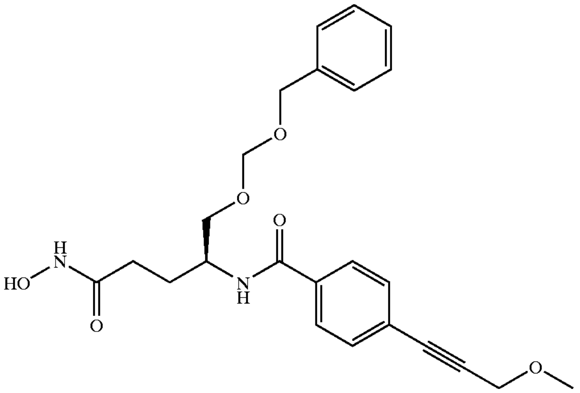

TLC: Rf 0.24 (Chloroform:Methanol=9:1);

NMR ($d_6$-DMSO): δ10.37 (1H, s), 8.36 (1H, d, J=8.8 Hz), 7.88 (2H, d, J=8.5 Hz), 7.55 (2H, d, J=8.5 Hz), 7.37–7.26 (5H, m), 4.72 (2H, s), 4.53 (2H, s), 4.35 (2H, s), 4.22–4.07 (1H, m), 3.63–3.55 (2H, m), 3.35 (3H, s), 2.09–1.68 (4H, m).

Example 49(26)

N-Hydroxy-5-(2-methoxyethoxy)methoxy-4-(S)-[N-[4-(3-phenoxy-1-propynyl)phenylcarbonyl]amino] pentanamide

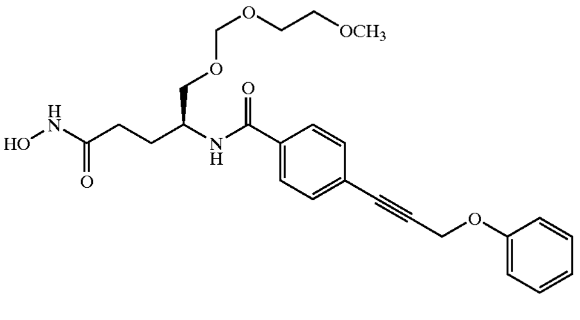

TLC: Rf 0.41 (Chloroform:Methanol:Acetic acid:Water=100:10:1:1);

NMR ($d_6$-DMSO): δ10.32(1H, s), 8.65(1H, s), 8.30(1H, d, J=8.6 Hz), 7.84(2H, d, J=8.4 Hz), 7.52(2H, d, J=8.4 Hz), 7.28–7.36(2H, m), 6.93–7.06(3H, m), 5.04(2H, s), 4.06(2H, s) 3.95–4.16(1H, m), 3.38–3.56(6H, m), 3.19(3H, s), 1.57–2.08(4H, m).

Example 49(27)

N-Hydroxy-5-methoxymethoxy-4(S)-[N-8 4-(3-phenoxy-1-propynyl)phenylcarbonyl]amino] pentanamide

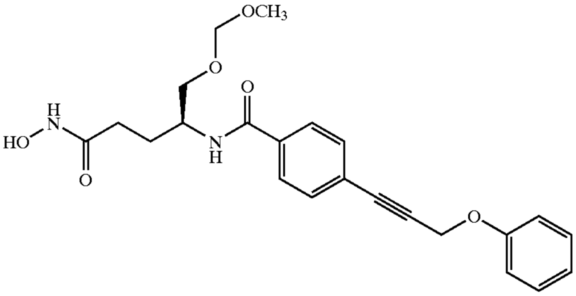

TLC: Rf 0.27 (Chloroform:Methanol:Acetic acid:Water=100:10:1:1);

NMR ($d_6$-DMSO): δ10.31(1H, s), 8.69(1H, brs), 8.29(1H, brs), 7.83(2H, d, J=8.7 Hz), 7.51(2H, d, J=8.4 Hz), 7.16(2H, t, J=8.0 Hz), 7.03(2H, d, J=8.7 Hz), 6.97(1H, t, J=7.5 Hz), 5.05(2H, s), 4.54(2H, s), 3.98–4.13(1H, m), 3.42–3.52(2H, m), 3.21(3H, s), 1.62–2.02(4H, m).

Example 49(28)

N-Hydroxy-5-benzyloxymethoxy-4(S)-[N-[4-(3-phenoxy-1-propynyl)phenylcarbonyl]amino] pentanamide

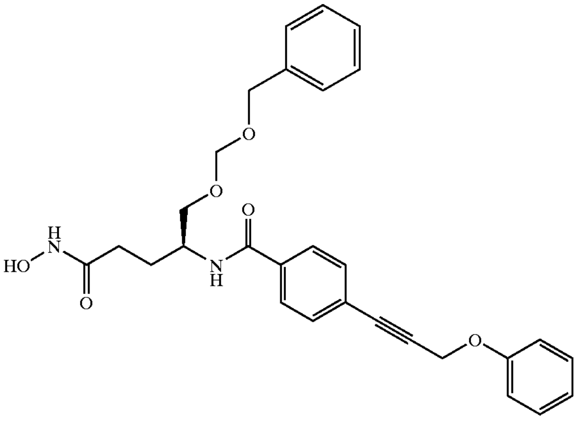

TLC: Rf 0.47 (Chloroform:Methanol=9:1);

NMR ($d_6$-DMSO): δ10.34(1H, s), 8.67(1H, s), 8.35(1H, d, J=8.0 Hz), 7.85(2H, d, J=8.4 Hz), 7.52(2H, d, J=8.4 Hz), 7.37–7.25(7H, m), 7.07–6.94(3H, m), 5.06(2H, s), 4.70(2H, s), 4.51(2H, s), 4.01–3.98(1H, m), 3.56(2H, d, J=6.0 Hz), 2.09–1.58(4H, m).

Example 49(29)

N-Hydroxy-5-methoxymethoxy-4(S)-[N-(4-phenoxyphenylcarbonyl)amino]pentanamide

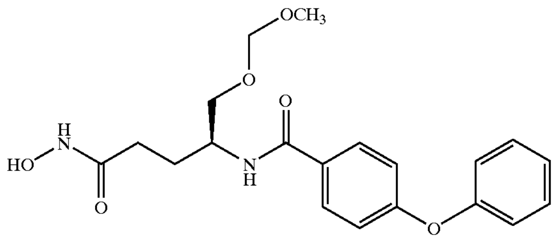

TLC: Rf 0.36 (Chloroform:Methanol:Acetic acid:Water=100:10:1:1);

NMR ($d_6$-DMSO): δ10.33(1H, s), 8.66(1H, s), 8.16(1H, d, J=8.4 Hz), 7.87(2H, d, J=8.8 Hz), 7.46–7.38(2H, m), 7.22–7.15(2H, m), 7.07–6.99(3H, m), 4.54(2H, s), 4.19–3.94(1H, m), 3.49–3.45(2H, m), 3.22(3H, s), 2.07–1.57(4H, m).

Example 49(30)

N-Hydroxy-5-methoxymethoxy-4(S)-[N-[4-(4-chlorophenyl)phenylcarbonyl]amino]pentanamide

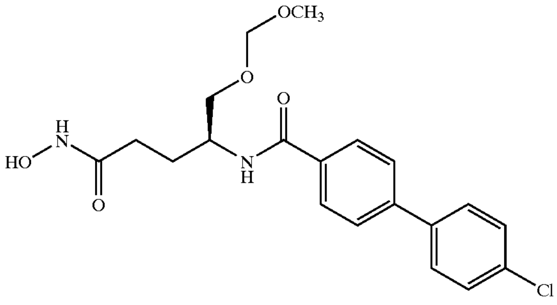

TLC: Rf 0.28 (Chloroform:Methanol=9:1);

NMR ($d_6$-DMSO): δ10.37 (1H, s), 8.31 (1H, d, J=8.2 Hz), 7.97 (2H, d, J=8.6 Hz), 7.81–7.75 (4H, m), 7.55 (2H, d, J=8.6 Hz), 4.58 (2H, s), 4.19–4.03 (1H, m), 3.56–3.49 (2H, m), 3.25 (3H, s), 2.09–1.77 (4H, m).

Example 49(31)

N-Hydroxy-5-methoxymethoxy-4(S)-[N-[4-[2-(4-methylphenyl)ethynyl]phenylcarbonyl]amino]pentanamide

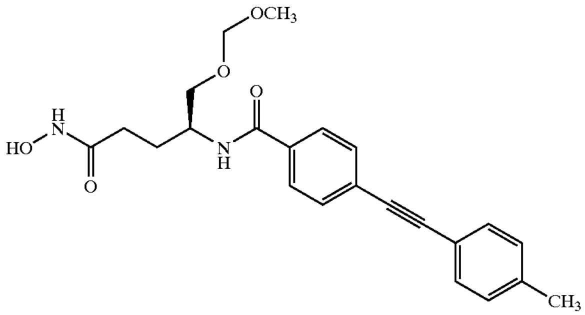

TLC: Rf 0.37 (Chloroform:Methanol:Acetic acid:Water=100:10:1:1);

NMR ($d_6$-DMSO): δ10.35(1H, brs.), 8.67(1H, brs.), 8.33 (1H, d, J=8.6 Hz), 7.89(2H, d, J=8.4 Hz), 7.62(2H, d, J=8.4 Hz), 7.47(2H, d, J=8.2 Hz), 7.25(2H, d, J=8.2 Hz), 4.56(2H, s), 4.19–3.98(1H, m), 3.56–3.42(2H, m), 3.23 (3H, s), 2.34(3H, s), 2.09–1.58(4H, m).

Example 49(32)

N-Hydroxy-5-methoxymethoxy-4(S)-[N-[4-[2E-(4-chlorophenyl)ethenyl]phenylcarbonyl]amino]pentanamide

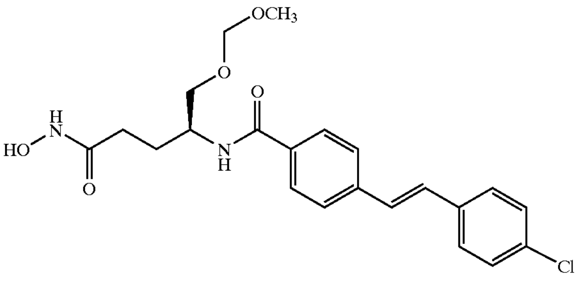

TLC: Rf 0.38 (Chloroform:Methanol=9:1);

NMR ($d_6$-DMSQ): δ10.35(1H, brs.), 8.67(1H, brs.), 8.23 (1H, d, J=8.6 Hz), 7.87(2H, d, J=8.2 Hz), 7.68(2H, d, J=8.4 Hz), 7.66(2H, d, J=8.4 Hz), 7.41 (2H, d, J=8.2 Hz), 7.40(1H, d, J=17.8 Hz), 7.31(1H, d, J=17.8 Hz), 4.56(2H, s), 4.19–3.98(1H, m), 3.58–3.41 (2H, m), 3.23 (3H, s), 2.11–1.56(4H, m).

Example 49(33)

N-Hydroxy-5-methoxymethoxy-4(S)-[N-[4-(1-heptynyl)phenylcarbonyl]amino]pentanamide

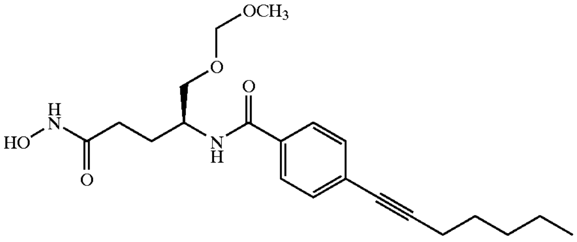

TLC: Rf 0.46 (Chloroform:Methanol=9:1);

NMR ($d_6$-DMSO): δ10.34(1H, s), 8.67(1H, s), 8.27(1H, d, J=8.4 Hz), 7.82(2H, d, J=8.2 Hz), 7.45(2H, d, J=8.2 Hz), 4.55(2H, s), 4.18–3.97(1H, m), 3.57–3.41(2H, m), 3.22(3H, s), 2.49–2.40(2H, m), 2.04–1.22(10H, m), 0.88(3H, t, J=6.8 Hz).

Example 49(34)

N-Hydroxy-5-ethoxymethoxy-4(S)-[N-(4-phenoxyphenylcarbonyl)amino]pentanamide

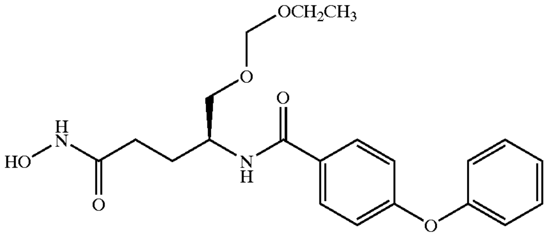

TLC: Rf 0.34 (Chloroform:Methanol=9:1);

NMR ($d_6$-DMSO): δ10.36 (s, 1H), 8.68 (s, 1H), 8.17 (d, J=8.4 Hz, 1H), 7.89 (d, J=8.9 Hz, 2H), 7.43 (dd, J=8.5, 7.5 Hz, 2H), 7.20 (t, J=7.5 Hz, 1H), 7.07 (dd, J=1.1, 8.5 Hz, 2H), 7.03 (d, J=8.9 Hz, 2H), 4.61 (s, 2H), 4.15–4.00 (m, 1H), 3.60–3.40 (m, 4H), 2.10–1.95 (m, 2H), 1.95–1.80 (m, 1H), 1.80–1.60 (m, 1H), 1.11 (t, J=7.1 Hz, 3H).

Example 49(35)

N-Hydroxy-5-ethoxymethoxy-4(S)-[N-(4-methylphenylcarbonyl)amino]pentanamide

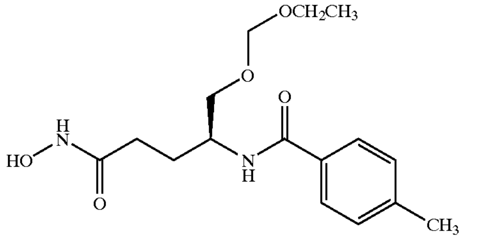

TLC: Rf 0.30 (Chloroform:Methanol=9:1);

NMR($d_6$-DMSO): δ10.32 (s, 1H), 8.65 (s, 1H), 8.10 (d, J=8.4 Hz, 1H), 7.73 (d, J=8.3 Hz, 2H), 7.22 (d, J=8.3 Hz, 2H), 4.57 (s, 2H), 4.10–3.98 (m, 1H), 3.52–3.40 (m, 4H), 2.32 (s, 3H), 2.01–1.94 (m, 2H), 1.91–1.78 (m, 1H), 1.73–1.61 (m, 1H), 1.05 (t, J=7.1 Hz, 3H).

Example 49(36)

N-Hydroxy-5-methoxymethoxy-4(R)-[N-[4-(3-methoxy-1-propynyl)phenylcarbonyl]amino]pentanamide

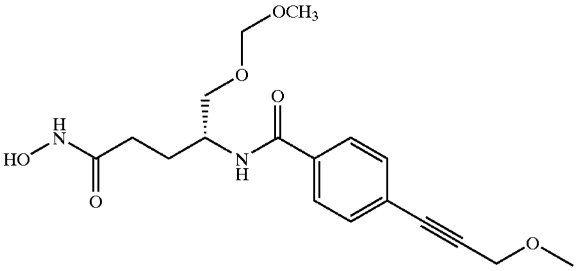

The compound having the following physical data was obtained by the same procedure as a series of reaction of Example 37→Example 39→Example 41→Example 42→Example 49, using 4(R)-carboxy-4-aminobutyric acid methyl ester instead of 4(S)-carboxy-4-aminobutyric acid methyl ester and a corresponding compound instead of the compound prepared in Reference Example 4.

TLC: Rf 0.25 (Chloroform:Methanol:Acetic acid:Water=100:10:1:1:1);

NMR ($CD_3OD$): δ8.32 (1H, d, J=8.8 Hz), 7.82 (2H, d, J=8.8 Hz), 7.52 (2H, d, J=8.8 Hz), 4.62 (2H, s), 4.34 (2H, s), 4.16–4.31 (1H, m), 3.62 (2H, d, J=5.6 Hz), 3.43 (3H, s), 3.33 (3H, s), 2.20 (2H, t, J=7.0 Hz), 1.17–2.11 (2H, m).

Example 49(37)~49(67)

The following compounds were obtained by the same procedure as a series of reaction of Example 37→Example 39→Example 41→Example 43 (using methyl idodide instead of benzyl bromide.)→Example 44→Example 49, using a corresponding compound instead of the compound prepared in Reference Example 4.

Example 49(37)

N-Hydroxy-2(S)-methyl-5-methoxymethoxy-4(S)-[N-[4-[2-(4-imidazolylphenyl)ethynyl]phenylcarbonyl]amino]pentanamide

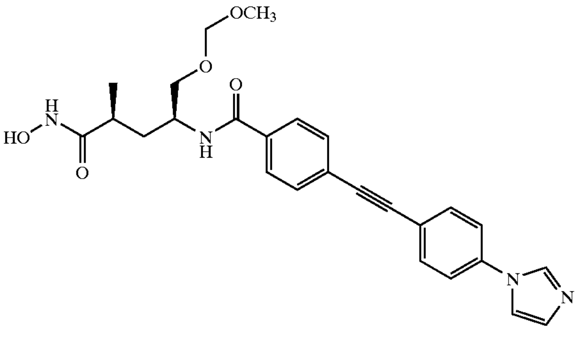

TLC: Rf 0.33 (Chloroform:Methanol=10:1);

NMR ($d_6$-DMSO): δ10.40 (1H, brs), 8.68 (1H, brs), 8.36 (1H, s), 8.24 (1H, d, J=9.0 Hz), 7.91 (2H, d, J=8.4 Hz), 7.84

(1H, brs), 7.77 (2H, d, J=9.0 Hz), 7.72 (2H, d, J=9.0 Hz), 7.66 (2H, d, J=8.4 Hz), 7.13 (1H, brs), 4.56 (2H, s), 4.22–4.11 (1H, m), 3.54–3.44 (2H, m), 3.23 (3H, s), 2.25–2.14 (1H, m), 1.76–1.61 (2H ,m), 1.03 (3H, d, J=6.6 Hz).

Example 49(38)

N-Hydroxy-2(S)-methyl-5-methoxymethoxy-4(S)-[N-[4-(4-phenyl-1,2,5,6-tetrahydropyridin-1-yl)phenylcarbonyl]amino]pentanamide

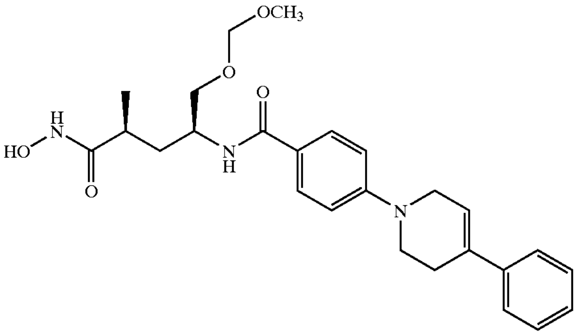

TLC: Rf 0.32 (Chloroform:Methanol=9:1);

NMR ($d_6$-DMSO): δ10.39 (1H, brs), 8.67 (1H, brs), 7.90–7.70 (3H, m), 7.49 (2H, d, J=7.5 Hz), 7.37 (2H, t, J=7.5 Hz), 7.27 (1H, t, J=7.5 Hz), 6.99 (2H, d, J=9.0 Hz), 6.35–6.25 (1H, brs), 4.56 (2H, s), 4.25–4.05 (1H, m), 4.00–3.90 (2H, m), 3.59 (2H, t, J=5.4 Hz), 3.55–3.40 (2H, m), 3.24 (3H, s), 2.70–2.55 (2H, m), 2.30–2.10 (1H, m), 1.80–1.60 (2H, m), 1.03 (3H, d, J=6.9 Hz).

Example 49(39)

N-Hydroxy-2(S)-methyl-5-methoxymethoxy-4(S)-[N-(4-phenoxyphenylcarbonyl)amino]pentanamide

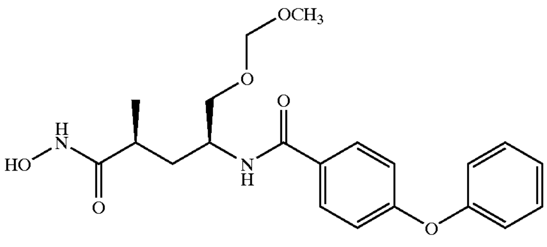

TLC: Rf 0.49 (Chloroform:Methanol:Acetic acid:Water=100:10:1:1);

NMR ($d_6$-DMSO): δ10.38(1H, d, J=1.5 Hz), 8.66(1H, d, J=1.5 Hz), 8.05(1H, d, J=8.4 Hz), 7.88(2H, d, J=8.7 Hz), 7.45–7.40(2H, m), 7.22–7.17(1H, m), 7.08–7.01(4H, m), 4.55(2H, s), 4.21–4.08(1H, m), 3.52–3.44(2H, m), 3.22(3H, s), 2.25–2.09(1H, m), 1.67(2H, t, J=7.2 Hz), 1.01 (3H, d, J=6.6 Hz).

Example 49(40)

N-Hydroxy-2(S)-methyl-5-methoxymethoxy-4(S)-[N-[4-[2-(4-chlorophenyl)ethenyl]phenylcarbonyl]amino]pentanamide

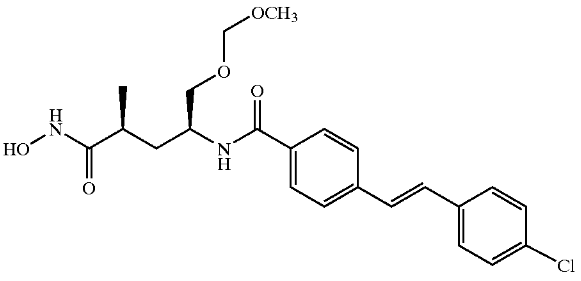

TLC: Rf 0.41 (Chloroform:Methanol:Acetic acid:Water=100:10:1:1);

NMR ($d_6$-DMSO): δ10.39(1H, s), 8.67(1H, s), 8.10(1H, d, J=8.6 Hz), 7.86(2H, d, J=8.4 Hz), 7.70–7.63(4H, m), 7.45(2H, d, J=8.6 Hz), 7.40(1H, d, J=16.6 Hz), 7.31(1H, d, J=16.6 Hz), 4.56(2H, s), 4.25–4.08 (1H, m), 3.57–3.41(2H, m), 3.23(3H, s), 2.25–2.15(1H, m), 1.68(2H, t, J=6.6 Hz), 1.02(3H, d, J=7.0 Hz).

Example 49(41)

N-Hydroxy-2(S)-methyl-5-methoxymethoxy-4(S)-[N-[4-(4-propylphenyl)phenylcarbonyl]amino]pentanamide

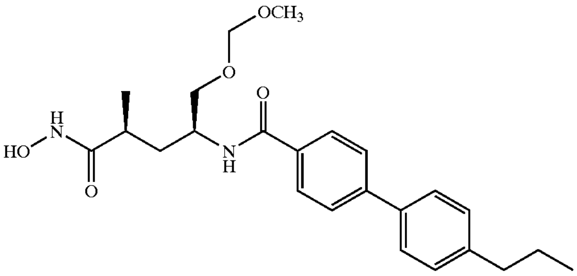

TLC: Rf 0.31 (Chloroform:Methanol=10:1);

NMR ($d_6$-DMSO): δ10.39 (1H, brs), 8.67 (1H, brs), 8.14 (1H, d, J=8.7 Hz), 7.93 (2H, d, J=8.4 Hz), 7.73 (2H, d, J=8.4 Hz), 7.63 (2H, d, J=8.1 Hz), 7.30 (2H, d, J=8.1 Hz), 4.56 (2H ,s), 4.24–4.12 (1H, m), 3.55–3.44 (2H, m), 3.23 (3H, s), 2.59 (2H, t, J=7.2 Hz), 2.26–2.35 (1H, m), 1.73–1.65 (2H, m), 1.61 (2H, m), 1.03 (3H, d, J=6.9 Hz), 0.91 (3H, t, J=7.2 Hz).

Example 49(42)

N-Hydroxy-2(S)-methyl-5-methoxymethoxy-4(S)-[N-[4-(benzothiophen-2-yl)phenylcarbonyl]amino]pentanamide

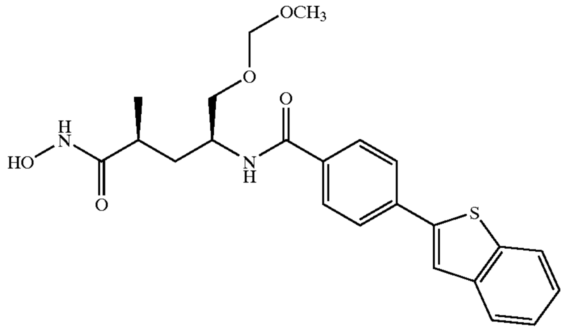

TLC: Rf 0.33 (Chloroform:Methanol=10:1);

NMR ($d_6$-DMSO): δ10.40 (1H, brs), 8.68 (1H, brs), 8.19 (1H, d, J=9.0 Hz), 8.01–7.94 (4H, m), 7.88–7.85 (3H, m), 7.44–7.35 (2H, m), 4.57 (2H, s), 4.24–4.12 (1H, m), 3.55–3.45 (2H, m), 3.24 (3H, s), 2.26–2.15 (1H, m), 1.77–1.62 (2H, m), 1.04 (3H, d, J=6.6 Hz).

Example 49(43)

N-Hydroxy-2(S)-methyl-5-methoxymethoxy-4(S)-[N-[4-(3-methoxyphenoxy)phenylcarbonyl]amino]pentanamide

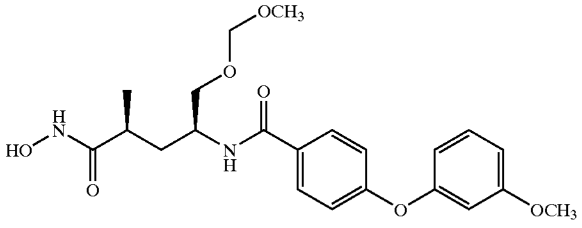

TLC: Rf 0.38 (Chloroform:Methanol:Acetic acid:Water=100:10:1:1);

NMR ($d_6$-DMSO): δ10.36 (s, 1H), 8.67 (s, 1H), 7.87 (d, J=8.8 Hz, 2H), 7.32 (m, 1H), 7.05 (d, J=8.8Hz, 2H), 6.77 (m, 1H), 6.63 (m, 1H), 6.60 (m, 1H), 4.55 (s, 2H), 4.15 (m, 1H), 3.74 (s, 3H), 3.22 (s, 3H), 2.18 (m, 1H), 1.66 (m, 2H), 1.02 (d, J=6.6 Hz, 3H).

Example 49(44)

N-Hydroxy-2(S)-methyl-5-methoxymethoxy-4(S)-[N-[4-(4-methoxyphenoxy)phenylcarbonyl]amino]pentanamide

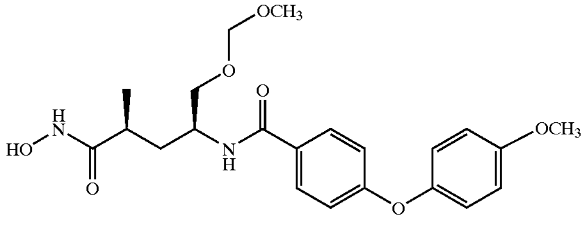

TLC: Rf 0.45 (Chloroform:Methanol=9:1);

NMR ($d_6$-DMSO): δ10.50–10.20 (br, 1H), 8.80–8.50 (br, 1H), 8.01 (d, J=8.4 Hz, 1H), 7.85 (d, J=8.7 Hz, 2H), 7.05 (d, J=9.2 Hz, 2H), 6.99 (d, J=9.2 Hz, 2H), 6.94 (d, J=8.7 Hz, 2H), 4.56 (s, 2H), 4.25–4.05 (m, 1H), 3.77 (s, 3H), 3.55–3.40 (m, 2H), 3.23 (s, 3H), 2.30–2.10 (m, 1H), 1.80–1.60 (m, 2H), 1.02 (d, J=6.9 Hz, 3H).

Example 49(45)

N-Hydroxy-2(S)-methyl-5-methoxymethoxy-4(S)-[N-(4-benzoylphenylcarbonyl)amino]pentanamide

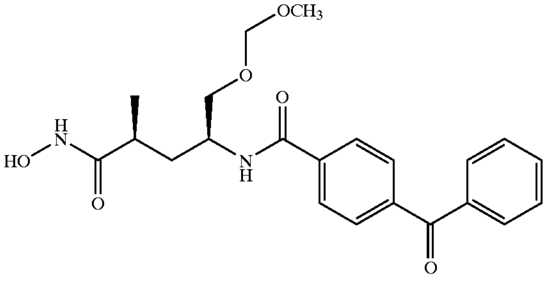

TLC: Rf 0.36 (Chloroform:Methanol=9:1);

NMR ($d_6$-DMSO): δ10.38 (1H, s), 8.66 (1H, s), 8.31 (1H, d, J=8.1 Hz), 7.98 (2H, d, J=8.7 Hz), 7.79–7.65 (5H, m), 7.55 (2H, t, J=7.5 Hz), 4.55 (2H, s), 4.24–4.12 (1H, m), 3.52–3.42 (2H, m), 3.21 (3H, s), 2.25–2.13 (1H, m), 1.71–1.63 (2H, m), 1.01 (3H, d, J=6.9 Hz).

Example 49(46)

N-Hydroxy-2(S)-methyl-5-methoxymethoxy-4(S)-[N-[4-(naphthalen-2-yl)phenylcarbonyl]amino] pentanamide

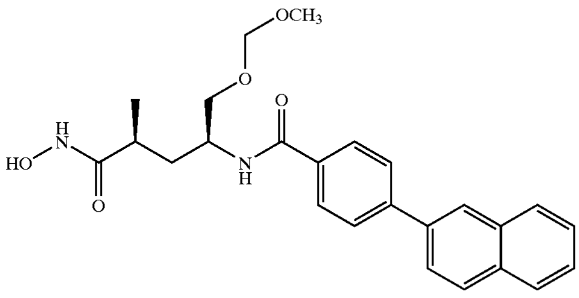

TLC: Rf 0.31 (Chloroform:Methanol:Acetic acid:Water=100:10:1:1);

NMR ($d_6$-DMSO): δ10.41 (br, 1H), 8.68 (br, 1H), 8.30 (s, 1H), 8.05–7.9 (m, 8H), 7.6–7.5 (m, 2H), 4.58 (s, 2H), 4.20 (m, 1H), 3.51 (m, 2H), 3.24 (s, 3H), 2.01 (m, 1H), 1.72 (m, 2H), 1.04 (d, J=6.6 Hz, 3H).

Example 49(47)

N-Hydroxy-2(S)-methyl-5-methoxymethoxy-4(S)-[N-[4-[(4-methoxybiphenyl-4'-yl)oxy] phenylcarbonyl]amino]pentanamide

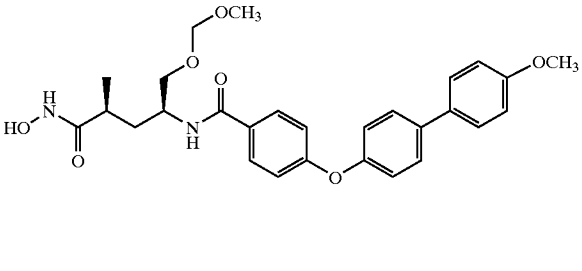

TLC: Rf 0.34 (Chloroform:Methanol=9:1);

NMR ($d_6$-DMSO): δ10.60–10.35 (br, 1H), 8.80–8.60 (br, 1H), 8.11 (d, J=8.4 Hz, 1H), 7.94 (d, J=8.4 Hz, 2H), 7.66 (d, J=8.8 Hz, 2H), 7.59 (d, J=8.8 Hz, 2H), 7.20–6.95 (m, 6H), 4.57 (s, 2H), 4.30–4.10 (m, 1H), 3.81 (s, 3H), 3.60–3.40 (m, 2H), 3.25 (s, 3H), 2.40–2.10 (m, 1H), 1.90–1.60 (m, 2H), 1.04 (d, J=6.6 Hz, 3H).

Example 49(48)

N-Hydroxy-2(S)-methyl-5-methoxymethoxy-4(S)-[N-[4-(4-ethoxyphenyl)phenylcarbonyl]amino] pentanamide

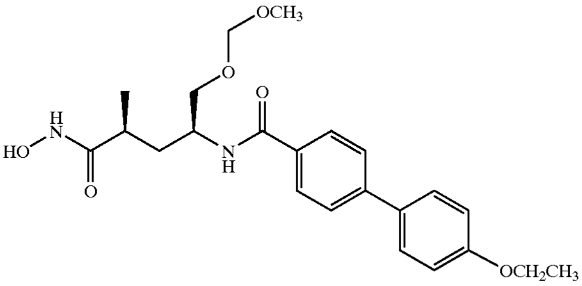

TLC: Rf 0.41 (Chloroform:Methanol=100:1);

NMR ($d_6$-DMSO): δ10.39 (1H, brs), 8.67 (1H, brs), 8.11 (1H, d, J=8.7 Hz), 7.91 (2H, d, J=8.1 Hz), 7.70 (2H, d, J=8.1 Hz), 7.66 (2H, d, J=8.7 Hz), 7.02 (2H, d, J=8.7 Hz), 4.56 (2H, s), 4.24–4.12 (1H, m), 4.07 (2H, q, J=6.9 Hz), 3.54–3.44 (2H, m), 3.23 (3H, s), 2.26–2.34 (1H, m), 1.73–1.65 (2H, m), 1.34 (3H, t, J=6.9 Hz), 1.03 (3H, d, J=6.9 Hz).

Example 49(49)

N-Hydroxy-2(S)-methyl-5-methoxymethoxy-4(S)-[N-[4-(4-phenoxyphenyl)phenylcarbonyl]amino] pentanamide

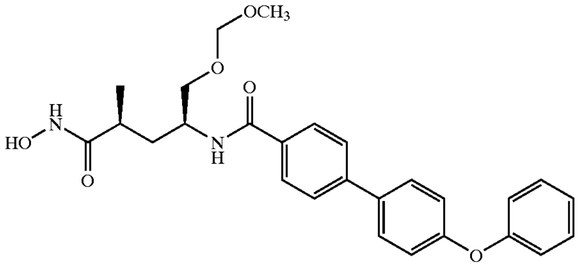

TLC: Rf 0.43 (Chloroform:Methanol=10:1);

NMR ($d_6$-DMSO): δ10.40 (1H, brs), 8.67 (1H, brs), 8.14 (1H, d, J=8.6 Hz), 7.94 (2H, d, J=8.4 Hz), 7.75 (2H, d, J=8.8 Hz), 7.74 (2H, d, J=8.4 Hz), 7.46–7.38 (2H, m), 7.21–7.05 (3H, m), 7.10 (2H, d, J=8.8 Hz), 4.57 (2H, s), 4.27–4.10 (1H, m), 3.58–3.42 (2H, m), 3.23 (3H, s), 2.29–2.12 (1H, m), 1.73–1.66 (2H, m), 1.03 (3H, d, J=6.6 Hz).

Example 49(50)

N-Hydroxy-2(S)-methyl-5-methoxymethoxy-4(S)-[N-[4-(3-cyanomethylphenyl)phenylcarbonyl]amino] pentanamide

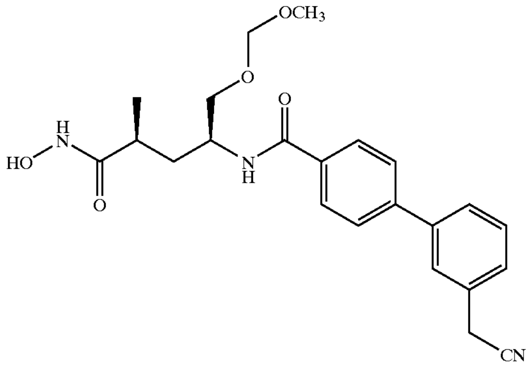

TLC: Rf 0.40 (Chloroform:Methanol=10:1);

NMR ($d_6$-DMSO): δ10.40 (1H, brs), 8.67 (1H, brs), 8.18 (1H, d, J=8.7 Hz), 7.96 (2H, d, J=8.4 Hz), 7.76 (2H d, J=8.4 Hz), 7.70 (1H, s), 7.69 (1H, d, J=7.8 Hz), 7.52 (1H, t, J=7.8 Hz), 7.39 (1H, d, J=7.8 Hz), 4.57 (2H, s), 4.24–4.13 (1H, m), 4.11 (2H, s), 3.52 (1H, dd, J=5.3, 9.9 Hz), 3.47 (1H, dd, J=6.0, 9.9 Hz), 3.23 (3H, s), 2.27–2.34 (1H, m), 1.77–1.62 (2H, m), 1.03 (3H, d, J=6.6 Hz).

Example 49(51)

N-Hydroxy-2(S)-methyl-5-methoxymethoxy-4(S)-[N-[4-(biphenyl-4-yl)phenylcarbonyl]amino] pentanamide

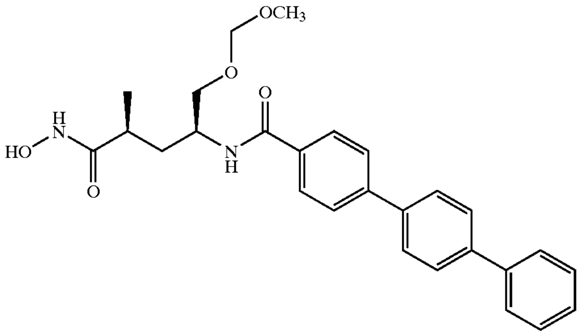

TLC: Rf 0.26 (Chloroform:Methanol:Acetic acid:Water=100:10:1:1);

NMR ($d_6$-DMSO): δ10.40 (br, 1H), 8.67 (br, 1H), 8.18 (d, J=8.8 Hz, 1H), 7.96 (d, J=8.5 Hz, 2H), 7.85–7.75 (m, 6H), 7.73 (m, 2H), 7.49 (m, 2H), 7.39 (m, 1H), 4.57 (s, 2H), 4.19 (m, 1H), 3.50 (m, 2H), 3.24 (s, 3H), 2.21 (m, 1H), 1.70 (m, 2H), 1.03 (d, J=6.6 Hz, 3H).

Example 49(52)

N-Hydroxy-2(S)-methyl-5-methoxymethoxy-4(S)-[N-[4-(3-hydroxyphenoxy)phenylcarbonyl]amino] pentanamide

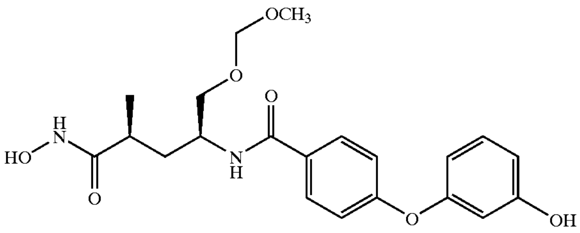

TLC: Rf 0.17 (Chloroform:Methanol:Acetic acid:Water=100:10:1:1);

NMR ($d_6$-DMSO): δ10.32 (br, 1H), 8.67 (br, 1H), 8.04 (d, J=8.8 Hz, 1H), 7.87 (d, J=8.8 Hz, 2H), 7.18 (t, J=8.2 Hz, 1H), 7.02 (d, J=8.8 Hz, 2H), 6.58 (m, 1H), 6.45 (m, 1H), 6.40 (m, 1H), 4.55 (s, 2H), 4.15 (m, 1H), 3.47 (m, 2H), 3.22 (s, 3H), 2.07 (m, 1H), 1.66 (m, 2H), 1.01 (d, J=6.9 Hz, 3H).

Example 49(53)

N-Hydroxy-2(S)-methyl-5-methoxymethoxy-4(S)-[N-[4-[2-(4-methylphenyl)ethynyl]phenylcarbonyl] amino]pentanamide

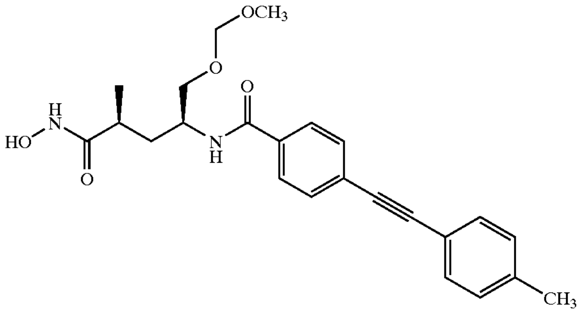

TLC: Rf 0.23 (Chloroform:Methanol=19:1);

NMR ($d_6$-DMSO): δ10.40 (1H, s), 8.21 (1H, d, J=8.4 Hz), 7.90 (2H, d, J=8.4 Hz), 7.61 (2H, d, J=8.4 Hz), 7.47 (2H, d, J=8.0 Hz), 7.25 (2H, d, J=8.0 Hz), 4.57 (2H, s), 4.30–4.10 (1H, m), 3.60–3.40 (2H, m), 3.24 (3H, s), 2.35 (3H, s), 2.28–2.10 (1H, m), 1.78–1.60 (2H, m), 1.04 (3H, d, J=7.0 Hz).

Example 49(54)

N-Hydroxy-2(S)-methyl-5-methoxymethoxy-4(S)-[N-[4-(4-hydroxyphenoxy)phenylcarbonyl]amino]pentanamide

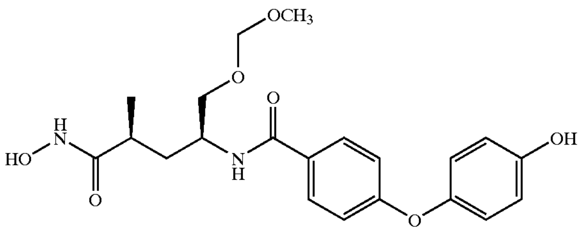

TLC: Rf 0.23 (Chloroform:Methanol=9:1);

NMR($d_6$-DMSO): δ10.38 (s, 1H), 9.41 (s, 1H), 8.67 (s, 1H), 7.98 (d, J=8.7 Hz, 1H), 7.84 (d, J=8.9 Hz, 2H), 6.95–6.85 (m, 4H), 6.81 (d, J=8.9 Hz, 2H), 4.56 (s, 2H), 4.25–4.10 (m, 1H), 3.55–3.40 (m, 2H), 3.24 (s, 3H), 2.25–2.10 (m, 1H), 1.70–1.60 (m, 2H), 1.03 (d, J=6.9 Hz, 3H).

Example 49(55)

N-Hydroxy-2(S)-methyl-5-methoxymethoxy-4(S)-[N-[4-(4-chlorophenyl)phenylcarbonyl]amino]pentanamide

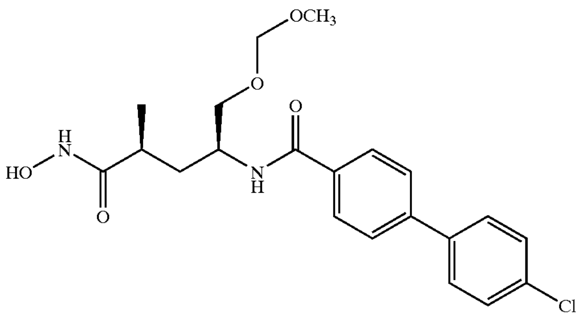

TLC: Rf 0.39 (Chloroform:Methanol=10:1);

NMR ($d_6$-DMSO): δ10.40 (1H, d, J=1.8 Hz), 8.67 (1H, d, J=1.8 Hz), 8.18 (1H, d, J=8.4 Hz), 7.95 (2H, d, J=8.4 Hz), 7.76 (2H, d, J=8.4 Hz), 7.76 (2H, d, J=8.7 Hz), 7.54 (2H, d, J=8.7 Hz), 4.56 (2H, s), 4.24–4.12 (1H, m), 3.55–3.44 (2H, m), 3.23 (3H, s), 2.26–2.14 (1H, m), 1.77–1.62 (2H, m), 1.03 (3H, d, J=6.9 Hz).

Example 49(56)

N-Hydroxy-2(S)-methyl-5-methoxymethoxy-4(S)-[N-[[5-(4-methoxyphenyl)-2-thienyl]carbonyl]amino]pentanamide

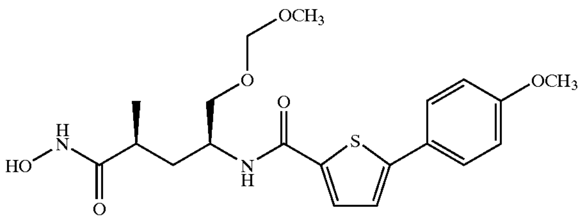

TLC: Rf 0.29 (Chloroform:Methanol=9:1);

NMR ($d_6$-DMSO): δ10.41 (s, 1H), 8.69 (s, 1H), 8.14 (d, J=8.7 Hz, 1H), 7.75 (d, J=3.9 Hz, 1H), 7.63 (d, J=8.7 Hz, 2H), 7.39 (d, J=3.9 Hz, 1H), 7.00 (d, J=8.7 Hz, 2H), 4.57 (s, 2H), 4.20–4.00 (m, 1H), 3.80 (s, 3H), 3.55–3.45 (m, 2H), 3.25 (s, 3H), 2.30–2.15 (m, 1H), 1.68 (t, J=7.2 Hz, 2H), 1.04 (d, J=6.9 Hz, 3H).

Example 49(57)

N-Hydroxy-2(S)-methyl-5-methoxymethoxy-4(S)-[N-[4-[(biphenyl-3-yl)oxy]phenylcarbonyl]amino]pentanamide

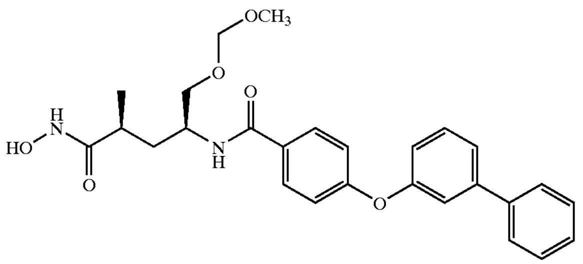

TLC: Rf 0.42 (Chloroform:Methanol:Acetic acid=100:10:1);

NMR ($d_6$-DMSO): δ10.38(1H, s), 8.66(1H, s), 8.06(1H, d, J=8.4 Hz), 7.90(2H, d, J=8.4 Hz), 7.68–7.63(2H, m), 7.52–7.33(6H, m), 7.12–7.00(3H, m), 4.55(2H, s), 4.24–4.05(1H, m), 3.54–3.40(2H, m), 3.32(3H, s), 2.15–2.25(1H, m), 1.67(2H, t, J=7.0 Hz), 1.01 (3H, d, J=7.0 Hz).

Example 49(58)

N-Hydroxy-2(S)-methyl-5-methoxymethoxy-4(S)-[N-[4-(1-heptynyl)phenylcarbonyl]amino]pentanamide

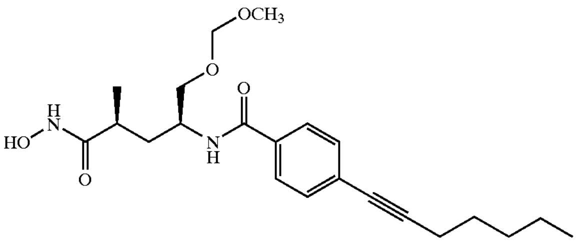

TLC: Rf 0.49 (Chloroform:Methanol=9:1);

NMR ($d_6$-DMSO): δ10.38 (1H, s), 8.66 (1H, s), 8.13 (1H, d, J=8.8 Hz), 7.82 (2H, d, J=8.4 Hz), 7.44 (2H, d, J=8.4 Hz), 4.56 (2H, s), 4.28–4.06 (1H, m), 3.60–3.40 (2H, m), 3.23 (3H, s), 2.43 (2H, t, J=6.8 Hz), 2.27–2.10 (1H, m), 1.74–1.46 (4H, m), 1.45–1.20 (4H, m), 1.03 (3H, t, J=6.6 Hz), 0.90 (3H, t, J=7.0 Hz).

Example 49(59)

N-Hydroxy-2(S)-methyl-5-methoxymethoxy-4(S)-[N-[4-(3-phenoxy-1-propynyl)phenylcarbonyl]amino]pentanamide

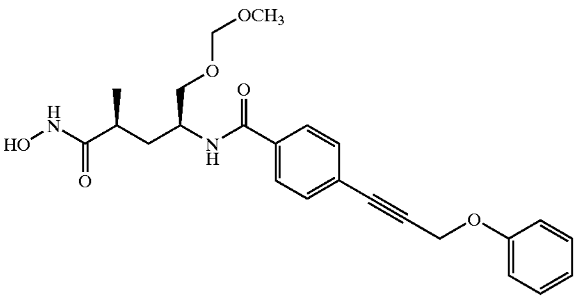

TLC: Rf 0.49 (Chloroform:Methanol=9:1);

NMR ($d_6$-DMSO): δ10.38 (1H, s), 8.66 (1H, s), 8.20 (1H, d, J=8.7 Hz), 7.85 (2H, d, J=8.4 Hz), 7.52 (2H, d, J=8.4 Hz), 7.37–7.29 (2H, m), 7.08–6.96 (3H, m), 5.06 (2H, s), 4.55 (2H, s), 4.22–4.10 (1H, m), 3.55–3.40 (2H, m), 3.22 (3H, s), 2.24–2.12 (1H, m), 1.67–1.58 (2H, m), 1.02 (3H, d, J=6.9 Hz).

Example 49(60)

N-Hydroxy-2(S)-methyl-5-methoxymethoxy-4(S)-[N-[4-(4-cyanophenyl)phenylcarbonyl]amino]pentanamide

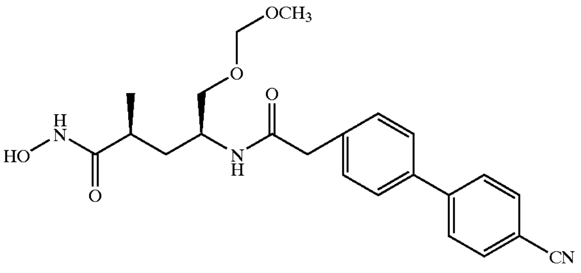

TLC: Rf 0.34 (Chloroform:Methanol=10:1);

NMR ($d_6$-DMSO): δ10.40 (1H, d, J=1.5 Hz), 8.67 (1H, d, J=1.5 Hz), 8.22 (1H, d, J=8.7 Hz), 7.98 (2H, d, J=8.4 Hz), 7.95 (4H, s), 7.85 (2H, d, J=8.4 Hz), 4.56 (2H, s), 4.24–4.32 (1H, m), 3.55–3.45 (2H, m), 3.23 (3H, s), 2.26–2.15 (1H, m), 1.77–1.62 (2H, m), 1.03 (3H, d, J=6.9 Hz).

Example 49(61)

N-Hydroxy-2(S)-methyl-5-methoxymethoxy-4(S)-[N-[4-(3-cyanophenyl)phenylcarbonyl]amino]pentanamide

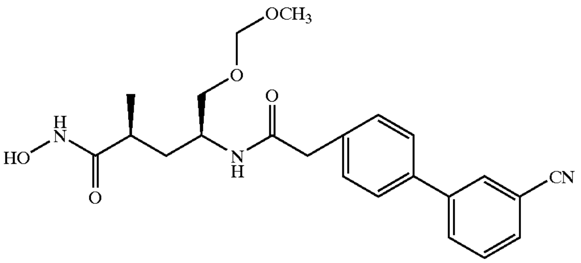

TLC: Rf 0.35 (Chloroform:Methanol=10:1);

NMR ($d_6$-DMSO): δ10.40 (1H, d, J=1.5 Hz), 8.67 (1H, d, J=1.5 Hz), 8.24 (1H, t, J=1.5 Hz), 8.21 (1H, d, J=8.7 Hz), 8.10–8.07 (1H, m), 7.97 (2H, d, J=8.4 Hz), 7.88–7.84 (1H, m), 7.85 (2H, d, J=8.4 Hz), 7.69 (1H, t, J=7.8 Hz), 4.57 (2H, s), 4.24–4.13 (1H, m), 3.55–3.45 (2H, m), 3.23 (3H, s), 2.26–2.15 (1H, m), 1.77–1.62 (2H, m), 1.03 (3H, d, J=6.9 Hz).

Example 49(62)

N-Hydroxy-2(S)-methyl-5-methoxymethoxy-4(S)-[N-(4-benzylphenylcarbonyl)amino]pentanamide

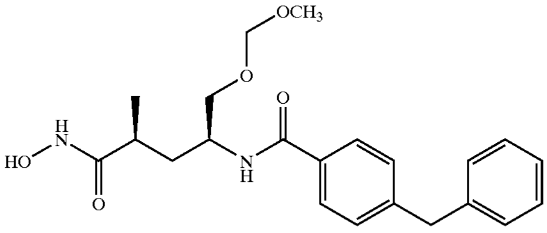

TLC: Rf 0.43 (Chloroform:Methanol=9:1);

NMR ($d_6$-DMSO): δ10.34 (1H, s), 8.64 (1H, s), 7.98 (1H, d, J=8.4 Hz), 7.74 (2H, d, J=8.1 Hz), 7.30–7.12 (7H, m), 4.52 (2H , s), 4.16–4.07 (1H, m), 3.96 (2H, s), 3.50–3.38 (2H, m), 3.19 (3H , s), 2.19–2.09 (1H, m), 1.64 (2H, t, J=7.4 Hz), 0.98 (3H, d, J=6.6 Hz).

Example 49(63)

N-Hydroxy-2(S)-methyl-5-methoxymethoxy-4(S)-[N-[4-[2E-(pyridin-4-yl)ethenyl]phenylcarbonyl]amino]pentanamide

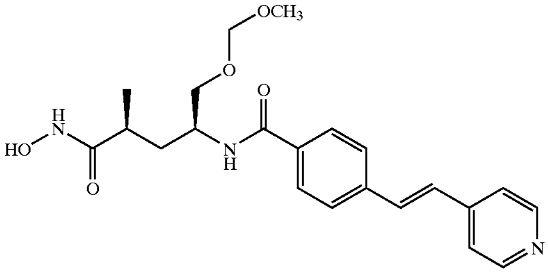

TLC: Rf 0.18 (Chloroform:Methanol:Acetic acid=100:10:1);

NMR ($d_6$-DMSO): δ10.42(1H, s), 8.67(1H, d, J=1.5 Hz), 8.56(2H, d, J=6.0 Hz), 8.16(1H, d, J=8.4 Hz), 7.89(2H, d, J=8.4 Hz), 7.73(2H, d, J=8.4 Hz), 7.59(1H, d, J=16.5 Hz), 7.57(2H, d, J=6.0 Hz), 7.36(1H, d, J=16.5 Hz), 4.56(2H, s), 4.23–4.08(1H, m), 3.54–3.44(2H, m), 3.22(3H, s), 2.28–2.15(1H, m), 1.72–1.66(2H, m), 1.02(3H, d, J=6.6 Hz).

Example 49(64)

N-Hydroxy-2(S)-methyl-5-methoxymethoxy-4(S)-[N-[4-(benzoxazol-2-yl)phenylcarbonyl]amino]pentanamide

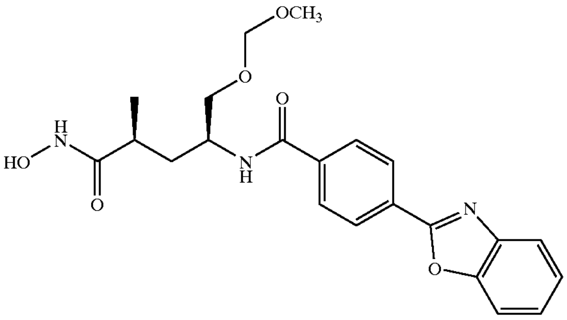

TLC: Rf 0.28 (Chloroform:Methanol=10:1);

NMR ($d_6$-DMSO): δ10.41 (1H, brs), 8.68 (1H, brs), 8.35 (1H, d, J=8.8 Hz), 8.28 (2H, d, J=8.4 Hz), 8.07 (2H, d, J=8.4 Hz), 7.86–7.80 (2H, m), 7.51–7.38 (2H, m), 4.57 (2H, s), 4.28–4.11 (1H, m), 3.59–3.42 (2H, m), 3.24 (3H, s), 2.30–2.13 (1H, m), 1.81–1.59 (2H, m), 1.04 (3H, d, J=6.6 Hz).

Example 49(65)

N-Hydroxy-2(S)-methyl-5-methoxymethoxy-4(S)-[N-[4-(3-ethoxyphenyl)phenylcarbonyl]amino]pentanamide

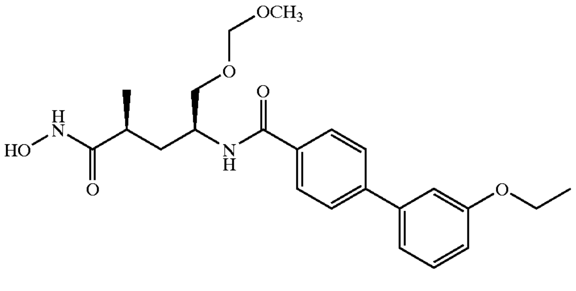

TLC: Rf 0.35 (Chloroform:Methanol=10:1);

NMR ($d_6$-DMSO): δ10.39 (brs, 1H), 8.67 (brs, 1H), 8.16 (d, J=8.4 Hz, 1H), 7.93 (d, J=8.12 Hz, 2H), 7.75 (d, J=8.1 Hz, 2H), 7.38 (t, J=8.1 Hz, 1H), 7.26 (br.d, J=8.1 Hz, 1H), 7.22 (brs, 1H), 6.96 (dd, J=8.1, 2.1 Hz, 1H), 4.57 (s, 2H), 4.24–4.13 (m, 1H), 4.10 (q, J=7.2 Hz, 2H), 3.55–3.45 (m, 2H), 3.23 (s, 3H), 2.26–2.1 4 (m, 1H), 1.77–1.62 (m, 2H), 1.35 (t, J=7.2 Hz, 3H), 1.03 (d, J=6.6 Hz, 3H).

Example 49(66)

N-Hydroxy-2(S)-methyl-5-methoxymethoxy-4(S)-[N-[4-(4-methylphenylcarbonylamino)phenylcarbonyl]amino]pentanamide

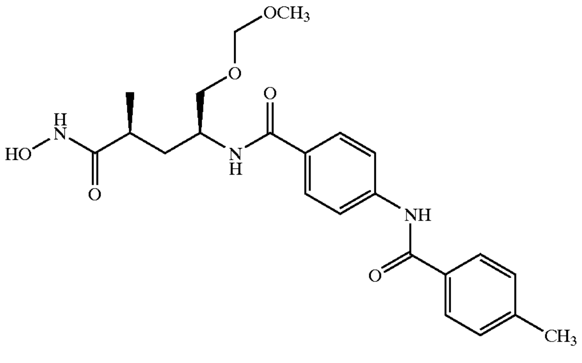

TLC: Rf 0.22 (Chloroform:Methanol=9:1);

NMR ($d_6$-DMSO): δ10.38 (brs, 1H), 8.05 (d, J=8.4 Hz, 1H), 7.96–7.84 (m, 6H), 7.34 (d, J=8.1 Hz, 2H), 4.57 (s, 2H), 4.25–4.10 (m, 1H), 3.60–3.40 (m, 2H), 3.25 (s, 3H), 2.40 (s, 3H), 2.30–2.15 (m, 1H), 1.85–1.60 (m, 2H), 1.04 (d, J=6.9 Hz, 3H).

Example 49(67)

N-Hydroxy-2(S)-methyl-5-methoxymethoxy-4(S)-[N-[[5-[2-(4-methylphenyl)ethynyl]-2-thienyl]carbonyl]amino]pentanamide

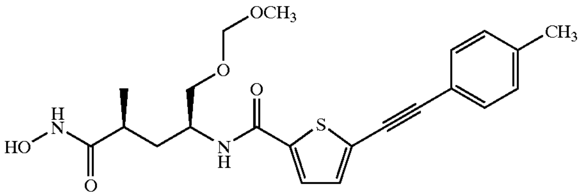

TLC: Rf 0.27 (Chloroform:Methanol=9:1);

NMR ($d_6$-DMSO): δ10.41 (s, 1H), 8.69 (s, 1H), 8.31 (d, J=8.7 Hz, 1H), 7.77 (d, J=4.1 Hz, 1H), 7.46 (d, J=7.8 Hz, 2H), 7.39 (d, J=4.1 Hz, 1H), 7.26 (d, J=7.8 Hz, 2H), 4.57 (s, 2H), 4.20–4.00 (m, 1H), 3.60–3.40 (m, 2H), 3.24 (s, 3H), 2.35 (s, 2H), 2.20 (m, 1H), 1.68 (t, J=7.2 Hz, 2H), 1.03 (d, J=6.9 Hz, 3H).

Example 49(68)~49(92)

The following compounds were obtained by the same procedure as a series of reaction of Example 49, using the compound prepared in Example 44(4)~44(6), 44(10) or the compound which was obtained by the same procedure as a series of reaction of Example 37→Example 39→Example 41 (using a corresponding compound instead of methoxymethyl chloride.)→Example 43 (using methyl iodide instead of benzyl bromide.)→Example 44, using a corresponding compound instead of the compound prepared in Reference Example 4.

Example 49(68)

N-Hydroxy-2(S)-methyl-5-(2-methoxyethoxy)methoxy-4(S)-[N-(4-phenoxyphenylcarbonyl)amino]pentanamide

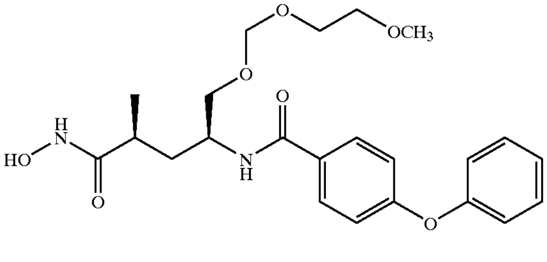

TLC: Rf 0.43 (Chloroform:Methanol=9:1);

NMR ($d_6$-DMSO): δ10.35 (1H, s), 8.64 (1H, s), 8.01 (1H, d, J=8.7 Hz), 7.85 (2H, d, J=8.7 Hz), 7.41 (2H, t, J=7.7 Hz), 7.17 (1H, t, J=7.7 Hz), 7.04 (2H, J=7.7 Hz), 7.00 (2H, d, J=8.7 Hz), 4.59 (2H, s), 4.18–4.06 (1H, m), 3.55–3.37 (6H, m), 3.19 (3H, s), 2.15 (1H, m), 1.68–1.60 (2H , m), 0.99 (3H, d, J=6.6 Hz).

Example 49(69)

N-Hydroxy-2(S)-methyl-5-t-butylcarbonyloxy-4(S)-[N-(4-phenoxyphenylcarbonyl)amino]pentanamide

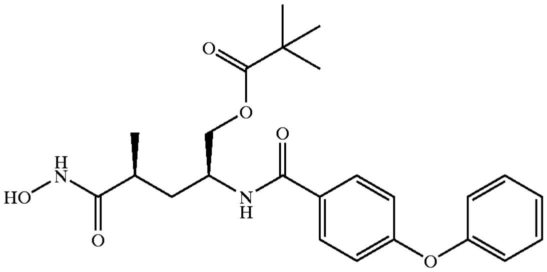

TLC: Rf 0.52 (Chloroform:Methanol=9:1);

NMR ($d_6$-DMSO): δ10.38 (1H, s), 8.07 (1H, d, J=9.0 Hz), 7.82 (2H, d, J=8.7 Hz), 7.41 (2H, t, J=7.7 Hz), 7.18 (1H, t, J=7.7 Hz), 7.07–6.99 (4H, m), 4.30– 4.18 (1H, m), 4.07–3.94 (2H, m), 2.20–2.11 (1H, m), 1.73–1.49 (2H, m), 1.06 (9H, s), 0.99(3H, d, J=6.6 Hz).

Example 49(70)

N-Hydroxy-2(S)-methyl-5-benzyloxymethoxy-4(S)-[N-(4-phenoxyphenylcarbonyl)amino]pentanamide

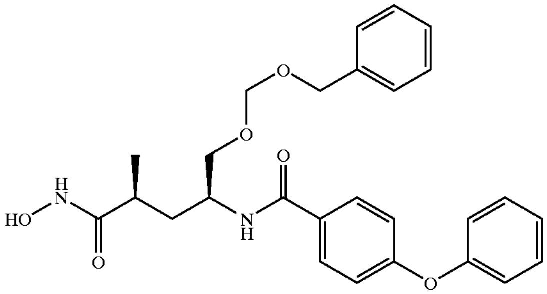

TLC: Rf 0.40 (Chloroform:Methanol:Acetic acid:Water=100:10:1:1);

NMR ($d_6$-DMSO): δ10.38 (s, 1H), 8.64 (s, 1H), 8.07 (d, J=8.5 Hz, 1H), 7.88 (d, J=8.8 Hz, 2H), 7.45–7.4 (m, 2H), 7.35–7.25 (m, 5H), 7.19 (t, J=7.4 Hz, 1H), 7.05 (d, J=8.8 Hz, 2H), 7.01 (d, J=8.5 Hz, 2H), 4.70 (s, 2H), 4.50 (s, 2H), 4.18 (m, 1H), 3.58 (d, J=11.3 Hz, 1H), 3.53 (d, J=11.3 Hz, 1H), 2.19 (m, 1H), 1.30 (m, 2H), 1.01 (d, J=6.9 Hz, 3H).

Example 49(71)

N-Hydroxy-2(S)-methyl-5-ethoxymethoxy-4(S)-[N-(trans-4-methylcyclohexylcarbonyl)amino]pentanamide

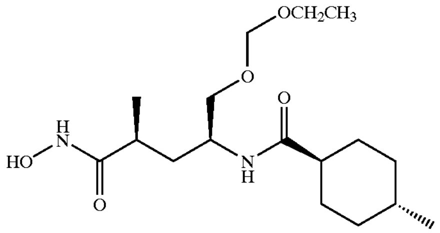

TLC: Rf 0.39 (Chloroform:Methanol=10:1);

NMR ($d_6$-DMSO): δ10.37 (brs, 1H), 8.66 (brs, 1H), 7.39 (d, J=8.4 Hz, 1H), 4.56 (s, 2H), 3.89–3.77 (m, 1H), 3.47 (q, J=7.2 Hz, 2H), 3.38–3.28 (m, 2H), 2.14–1.92 (m, 2H), 1.74–1.59 (m, 4H), 1.56–1.46 (m, 2H), 1.40–1.21 (m, 3H), 1.10 (t, J=7.2 Hz, 3H), 0.95 (d, J=6.9 Hz, 3H), 0.93–0.78 (m, 2H), 0.84 (d, J=6.6 Hz, 3H).

Example 49(72)

N-Hydroxy-2(S)-methyl-5-ethoxymethoxy-4(S)-[N-(4-methylphenylcarbonyl)amino]pentanamide

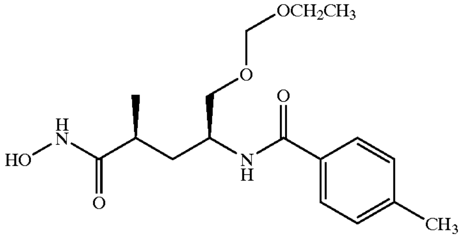

TLC: Rf 0.29 (Chloroform:Methanol=9:1);

NMR ($d_6$-DMSO): δ10.35 (s, 1H), 8.63 (brs, 1H), 7.95 (d, J=8.8 Hz, 1H), 7.72 (d, J=8.0 Hz, 2H), 7.22 (d, J=8.0 Hz, 2H), 4.58 (s, 2H), 4.18–4.04 (m, 1H), 3.53–3.39 (m, 4H), 2.32 (s, 3H), 2.15 (m, 1H), 1.64 (t, J=7.4Hz, 2H), 1.06 (t, J=7.1 Hz, 3H), 0.99 (d, J=7.0 Hz, 3H).

Example 49(73)

N-Hydroxy-2(S)-methyl-5-ethoxymethoxy-4(S)-[N-(4-chlorophenylcarbonyl)amino]pentanamide

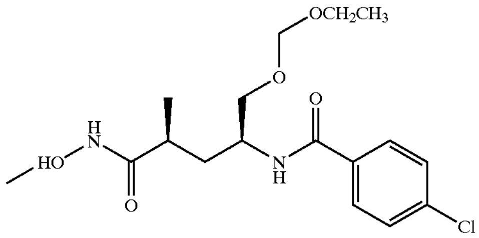

TLC: Rf 0.44 (Chloroform:Methanol=9:1);

NMR ($d_6$-DMSO): δ10.36 (s, 1H), 8.15 (d, J=8.4 Hz, 1H), 7.83 (d, J=8.8 Hz, 2H), 7.50 (d, J=8.8 Hz, 2H), 4.57 (s, 2H), 4.21–4.06 (m, 1H), 3.53–3.38 (m, 4H), 2.22–2.1 0 (m, 1H), 1.64 (t, J=7.0 Hz, 2H), 1.06 (t, J=6.9 Hz, 3H), 0.99 (d, J=6.6 Hz, 3H).

Example 49(74)

N-Hydroxy-2(S)-methyl-5-ethoxymethoxy-4(S)-[N-(adamanthylcarbonyl)amino]pentanamide

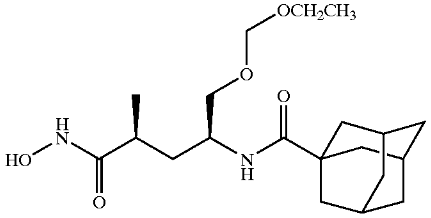

TLC: Rf 0.46 (Chloroform:Methanol=9:1);

NMR ($d_6$-DMSO): δ10.35 (s, 1H), 8.63 (s, 1H), 6.80 (d, J=9.0 Hz, 1H), 4.54 (s, 2H), 3.94–3.83 (m, 1H), 3.43 (q, J=7.2 Hz, 2H), 3.36–3.24 (m, 2H), 2.14–2.02 (m, 1H), 1.96–1.88 (m, 3H), 1.76–1.45 (m, 14H), 1.09 (t, J=7.2 Hz, 3H), 0.92 (d, J=6.6 Hz, 3H).

Example 49(75)

N-Hydroxy-2(S)-methyl-5-ethoxymethoxy-4(S)-[N-(2-furylcarbonyl)amino]pentanamide

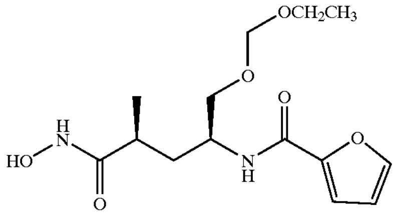

TLC: Rf 0.24 (Chloroform:Methanol=9:1);

NMR ($d_6$-DMSO): δ10.34 (s, 1H), 8.63 (s, 1H), 7.96 (d, J=8.4 Hz, 1H), 7.80–7.79 (m, 1H), 7.06 (d, J=3.4 Hz, 1H), 6.58 (dd, J=3.4 Hz, 1.7 Hz, 1H), 4.56 (s, 2H), 4.15–4.02 (m, 1H), 3.51–3.38 (m, 4H), 2.18–2.04 (m, 1H), 1.61 (t, J=6.2 Hz, 2H), 1.06 (t, J=7.1 Hz, 3H), 0.97 (d, J=6.8 Hz, 3H).

Example 49(76)

N-Hydroxy-2(S)-methyl-5-ethoxymethoxy-4(S)-[N-[(benzothiazol-6-yl)carbonyl]amino]pentanamide

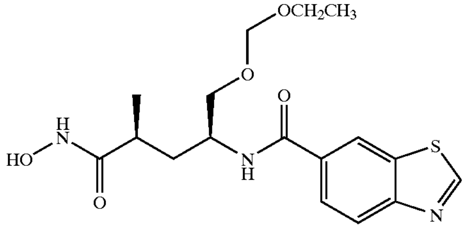

TLC: Rf 0.34 (Chloroform:Methanol=9:1);

NMR ($d_6$-DMSO): δ10.37 (s, 1H), 9.50 (s, 1H), 8.62 (d, J=1.5 Hz, 1H), 8.23 (d, J=8.4 Hz, 1H), 8.12 (d, J=8.7 Hz, 1H), 7.97 (dd, J=8.7 Hz, 1.9 Hz, 1H), 4.59 (s, 2H), 4.21–4.11 (m, 1H), 3.53–3.42 (m, 4H), 2.25–2.14 (m, 1H), 1.72–1.61 (m, 2H), 1.06 (t, J=7.2 Hz, 3H), 1.00 (d, J=6.6 Hz, 3H).

Example 49(77)

N-Hydroxy-2(S)-methyl-5-ethoxymethoxy-4(S)-[N-(4-fluorophenylcarbonyl)amino]pentanamide

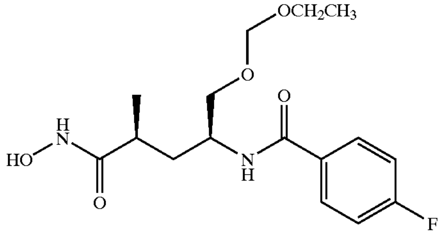

TLC: Rf 0.34 (Chloroform:Methanol=9:1);

NMR ($d_6$-DMSO): δ10.36 (s, 1H), 8.09 (d, J=8.7 Hz, 1H), 7.88 (dd, J=5.7 Hz, 9.0 Hz, 2H), 7.26 (t, J=9.0 Hz, 2H), 4.57 (s, 2H), 4.16–4.05 (m, 1H), 3.50–3.41 (m, 4H), 2.15 (m, 1H), 1.68–1.61 (m, 2H), 1.06 (t, J=7.0 Hz, 3H), 0.98 (d, J=6.8 Hz, 3H).

Example 49(78)

N-Hydroxy-2(S)-methyl-5-ethoxymethoxy-4(S)-[N-[(2-bromofuryl-5-yl)carbonyl]amino]pentanamide

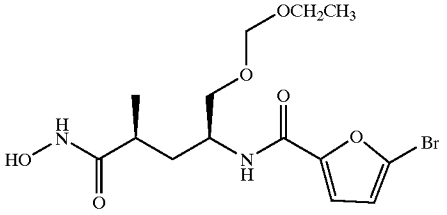

TLC: Rf 0.28 (Chloroform:Methanol=9:1);

NMR ($d_6$-DMSO): δ10.35 (s, 1H), 9.64 (s, 1H), 8.07 (d, J=8.7 Hz, 1H), 7.10 (d, J=3.6 Hz, 1H), 6.72 (d, J=3.6 Hz, 1H), 4.56 (s, 2H), 4.11–4.00 (m, 1H), 3.49–3.40 (m, 4H), 2.16–2.05 (m, 1H), 1.67–1.53 (m, 2H), 1.06 (t, J=7.2 Hz, 3H), 0.97 (d, J=6.3 Hz, 3H).

Example 49(79)

N-Hydroxy-2(S)-methyl-5-ethoxymethoxy-4(S)-[N-(4-nitrophenylcarbonyl)amino]pentanamide

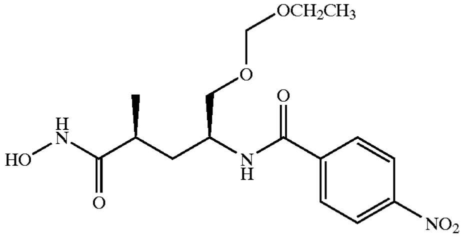

TLC: Rf 0.35 (Chloroform:Methanol=9:1);

NMR ($d_6$-DMSO): δ10.39 (brs, 1H), 8.66 (brs, 1H), 8.46 (brd, J=8.8 Hz, 1H), 8.30 (d, J=8.8 Hz, 1H), 8.06 (d, J=8.8 Hz, 2H), 4.59 (s, 2H), 4.15 (m, 1H), 3.50 (d, J=5.8 Hz, 1H), 3.47 (q, J=6.8 Hz, 2H), 2.17 (m, 1H), 1.67 (m, 2H), 1.07 (t, J=6.8 Hz, 3H), 1.02 (d, J=6.8 Hz, 3H).

Example 49(80)

N-Hydroxy-2(S)-methyl-5-ethoxymethoxy-4(S)-[N-(4-bromophenylcarbonyl)amino]pentanamide

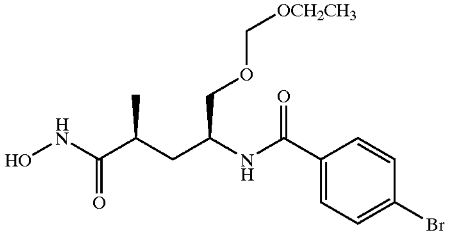

TLC: Rf 0.35(Methylene chloride:Methanol=9:1);

NMR ($d_6$-DMSO): δ10.37 (brs, 1H), 8.65 (brs, 1H), 8.17 (brd, J=8.4 Hz, 1H), 7.79 (d, J=8.8 Hz, 2H), 7.66 (d, J=8.8 Hz, 2H), 4.58 (s, 2H), 4.13 (m, 1H), 3.47 (d, J=7.0 Hz, 2H), 3.47 (q, J=7.0 Hz, 2H), 2.16 (m, 1H), 1.65 (m, 2H), 1.07 (t, J=7.0 Hz, 3H), 1.01 (d, J=6.6 Hz, 3H).

Example 49(81)

N-Hydroxy-2(S)-methyl-5-ethoxymethoxy-4(S)-[N-(4-cyanophenylcarbonyl)amino]pentanamide

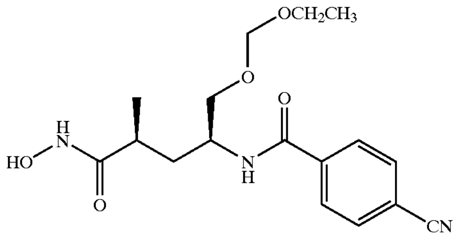

TLC: Rf 0.24 (Chloroform:Methanol=19:1);

NMR ($d_6$-DMSO): δ10.39 (s, 1H), 8.67 (s, 1H), 8.36 (d, J=8.7 Hz, 1H), 8.00 (d, J=8.4 Hz, 2H), 7.95 (d, J=8.4 Hz, 2H), 4.60 (s, 2H), 4.22–4.08(m, 1H), 3.58–3.40 (m, 4H), 2.23–2.12 (m, 1H), 1.78–1.58 (m, 2H), 1.09 (t, J=6.9 Hz, 3H), 1.03 (d, J=6.9 Hz, 3H).

Example 49(82)

N-Hydroxy-2(S)-methyl-5-ethoxymethoxy-4(S)-[N-[4-(4-pyridyloxy)phenylcarbonyl]amino] pentanamide

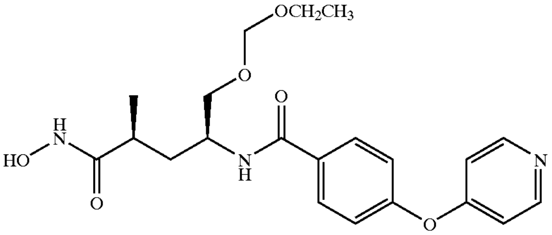

TLC: Rf 0.30 (Chloroform:Methanol=9:1);

NMR ($d_6$-DMSO): δ10.40 (s, 1H), 8.69 (s, 1H), 8.50 (dd, J=4.7, 1.5 Hz, 2H), 8.15 (d, J=8.4 Hz, 1H), 7.98 (d, J=8.7 Hz, 2H), 7.25 (d, J=8.7 Hz, 2H), 6.97 (dd, J=4.7, 1.5 Hz, 2H), 4.62 (s, 2H), 4.30–4.10 (m, 1H), 3.60–3.40 (m, 4H), 2.30–2.10 (m, 1H), 1.80–1.60 (m, 2H), 1.11 (t, J=7.1 Hz, 3H), 1.04 (d, J=6.9 Hz, 3H).

Example 49(83)

N-Hydroxy-2(S)-methyl-5-(2-methoxyethoxy) methoxy-4(S)-[N-(4-cyanophenylcarbonyl)amino] pentanamide

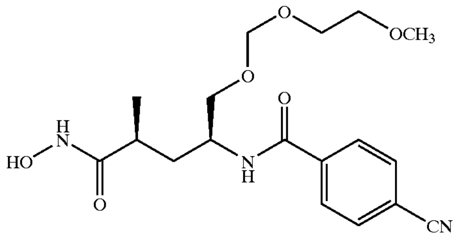

TLC: Rf 0.26 (Chloroform:Methanol=9:1);

NMR ($d_6$-DMSO): δ10.37 (s, 1H), 8.65 (s, 1H), 8.36 (d, J=8.7 Hz, 1H), 8.00–7.93 (m, 4H), 4.61 (s, 2H), 4.20–4.06 (m, 1H), 3.56–3.52 (m, 2H), 3.49 (d, J=6.0 Hz, 2H), 3.42–3.39 (m, 2H), 3.20 (s, 3H), 2.20–2.12 (m, 1H), 1.75–1.58 (m, 2H), 1.01 (t, J=6.9 Hz, 3H).

Example 49(84)

N-Hydroxy-2(S)-methyl-5-methoxymethoxy-4(S)-[N-(4-chlorophenylcarbonyl)amino]pentanamide

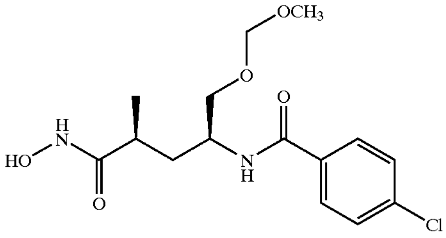

TLC: Rf 0.50(Methylene chloride:Methanol=9:1);

NMR ($d_6$-DMSO): δ10.36 (d, J=1.8 Hz, 1H), 8.64 (d, J=1.8 Hz, 1H), 8.17 (d, J=8.4 Hz, 1H), 7.85 (d, J=8.4 Hz, 2H), 7.51 (d, J=8.4 Hz, 2H), 4.53 (s, 2H), 4.11 (m, 1H), 3.46 (m, 2H), 3.20 (s, 3H), 2.16 (m, 1H), 1.65 (m, 2H), 1.00 (d, J=6.6 Hz, 3H).

Example 49(85)

N-Hydroxy-2(S)-methyl-5-benzyloxymethoxy-4(S)-[N-(4-chlorophenylcarbonyl)amino]pentanamide

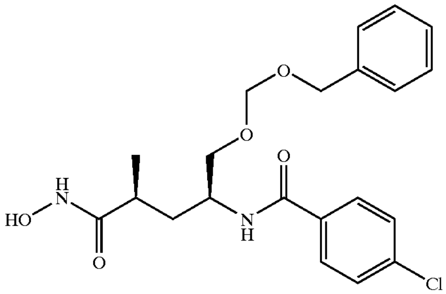

TLC: Rf 0.50(Methylene chloride:Methanol=9:1);

NMR ($d_6$-DMSO): δ10.36 (s, 1H), 8.64 (s, 1H), 8.19 (d, J=8.4 Hz, 1H), 7.86 (d, J=9.0 Hz, 2H), 7.51 (d, J=9.0 Hz, 2H), 7.28 (m, 5H), 4.69 (s, 2H), 4.49 (s, 2H), 4.15 (m, 1H), 3.54 (d, J=6.0 Hz, 2H), 2.17 (m, 1H), 1.68 (m, 2H), 1.00 (d, J=6.9 Hz, 3H).

Example 49(86)

N-Hydroxy-2(S)-methyl-5-(2-methoxyethoxy)methoxy-4(S)-[N-(4-chlorophenylcarbonyl)amino]pentanamide

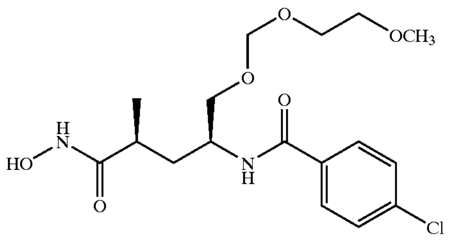

TLC: Rf 0.45(Methylene chloride:Methanol=9:1);

NMR ($d_6$-DMSO): δ10.36 (s, 1H), 8.64 (s, 1H), 8.16 (d, J=8.4 Hz, 1H), 7.85 (d, J=9.0 Hz, 2H), 7.51 (d, J=9.0 Hz, 2H), 4.60 (s, 2H), 4.13 (m, 1H), 3.55–3.38 (m, 6H), 3.19 (s, 3H), 2.14 (m, 1H), 1.65 (m, 2H), 1.00 (d, J=6.9 Hz, 3H).

Example 49(87)

N-Hydroxy-2(S)-methyl-5-ethoxymethoxy-4(S)-[N-(2-nitrophenylcarbonyl)amino]pentanamide

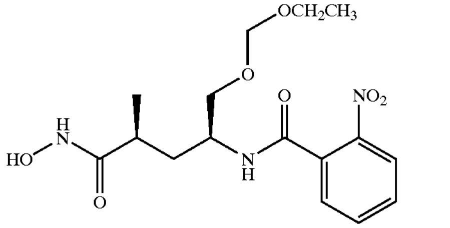

TLC: Rf 0.22 (Chloroform:Methanol=9:1);

NMR ($d_6$-DMSO): δ10.39 (d, J=1.2 Hz, 1H), 8.70 (d, J=1.2 Hz, 1H), 8.45 (d, J=8.4 Hz, 1H), 8.01 (dd, J=7.8 Hz, 1.2 Hz, 1H), 7.80–7.60 (m, 3H), 4.62 (s, 2H), 4.08–3.95 (m, 1H), 3.55–3.36 (m, 4H), 2.31–2.19 (m, 1H), 1.65 (t, J=7.2 Hz, 2H), 1.12 (t, J=7.2 Hz, 3H), 1.03 (d, J=7.2 Hz, 3H).

Example 49(88)

N-Hydroxy-2(S)-methyl-5-ethoxymethoxy-4(S)-[N-(3-nitrophenylcarbonyl)amino]pentanamide

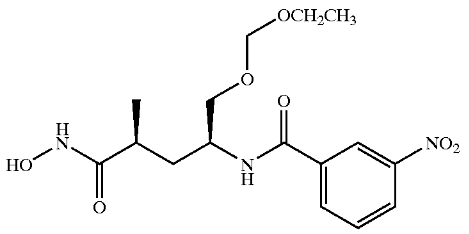

TLC: Rf 0.31 (Chloroform:Methanol=9:1);

NMR ($d_6$-DMSO): δ10.38 (s, 1H), 8.69–8.68 (m, 1H), 8.64 (brs, 1H), 8.52 (d, J=8.7 Hz, 1H), 8.39–8.35 (m, 1H), 8.30–8.27 (m, 1H), 7.77 (t, J=8.1 Hz, 1H), 4.60 (s, 2H), 4.24–4.11 (m, 1H), 3.52–3.44 (m, 4H), 2.22–2.11 (m, 1H), 1.78–1.60 (m, 2H), 1.08 (t, J=7.2 Hz, 3H), 1.02 (d, J=6.9 Hz, 3H).

Example 49(89)

N-Hydroxy-2(S)-methyl-5-ethoxymethoxy-4(S)-[N-(2-methoxy-4-nitrophenylcarbonyl)amino]pentanamide

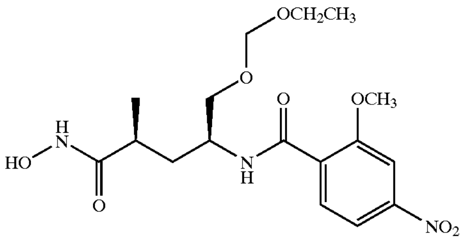

TLC: Rf 0.26 (Chloroform:Methanol=9:1);

NMR ($d_6$-DMSO): δ10.38 (s, 1H), 8.66 (brs, 1H), 8.09 (d, J=8.4 Hz, 1H), 7.87–7.77 (m, 3H), 4.61, (s, 2H), 4.14–4.02 (m, 1H), 3.95 (s, 3H), 3.53–3.43 (m, 4H), 2.25–2.13 (m, 1H), 1.75–1.55 (m, 2H), 1.09 (t, J=6.9 Hz, 3H), 1.02 (d, J=6.9 Hz, 3H).

Example 49(90)

N-Hydroxy-2(S)-methyl-5-ethoxymethoxy-4(S)-[N-(3-methoxy-4-nitrophenylcarbonyl)amino]pentanamide

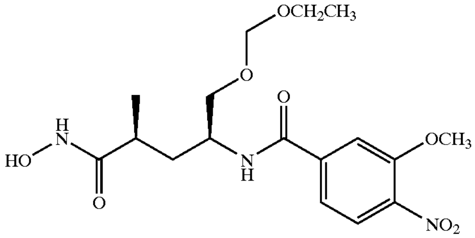

TLC: Rf 0.26 (Chloroform:Methanol=9:1);

NMR ($d_6$-DMSO): δ10.39 (s, 1H), 8.67 (s, 1H), 8.34 (d, J=8.4 Hz, 1H), 7.94 (d, J=8.7 Hz, 1H), 7.70 (d, J=1.2 Hz, 1H), 7.53 (dd, J=8.7 Hz, 1.2 Hz, 1H), 4.60 (s, 2H), 4.21–4.09 (m, 1H), 3.99 (s, 3H), 3.54–3.45 (m, 4H), 2.22–2.10 (m, 1H), 1.78–1.62 (m, 2H), 1.08 (t, J=6.9 Hz, 3H), 1.02 (d, J=6.9 Hz, 3H).

Example 49(91)

N-Hydroxy-2(S)-methyl-5-ethoxymethoxy-4(S)-[N-(3-hydroxy-4-nitrophenylcarbonyl)amino]pentanamide

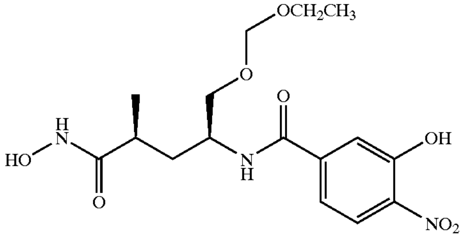

TLC: Rf 0.22 (Chloroform:Methanol=9:1);

NMR ($d_6$-DMSO): δ11.08 (s, 1H), 10.28 (s, 1H), 8.56 (s, 1H), 8.21 (d, J=8.7 Hz, 1H), 7.84 (d, J=8.4 Hz, 1H), 7.43 (d, J=1.8 Hz, 1H), 7.28 (dd, J=8.4 Hz, 1.8 Hz, 1H), 4.49 (s, 2H), 4.08–3.95 (m, 1H), 3.41–3.34 (m, 4H), 2.12–2.01 (m, 1H), 1.58–1.53 (m, 2H), 0.99 (t, J=6.9 Hz, 3H), 0.91 (d, J=6.9 Hz, 3H).

Example 49(92)

N-Hydroxy-2(S)-methyl-5-ethoxymethoxy-4(S)-[N-(4-dihydroxyboronylphenylcarbonyl)amino]pentanamide

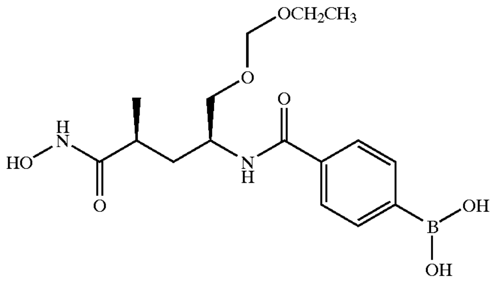

TLC: Rf 0.19 (Methylene chloride:Methanol:Acetic acid=18:1:1);

NMR ($d_6$-DMSO): δ10.37 (s, 1H), 8.65 (s, 1H), 8.16 (s, 2H), 8.05 (d, J=8.4 Hz, 1H), 7.83 (d, J=8.4 Hz, 2H), 7.77 (d, J=8.4 Hz, 2H), 4.58 (s, 2H), 4.14 (m, 1H), 3.47 (m, 4H), 2.16 (m, 1H), 1.66 (m, 2H), 1.07 (t, J=6.9 Hz, 3H), 1.01 (d, J=6.9 Hz, 3H).

Example 49(93)~49(111)

The following compounds were obtained by the same procedure as a series of reaction of Example 49, using the compound prepared in Example 44(7), 44(12), 44(13), 44(15), 44(16), 44(22), 44(23), 44(27) or the compound which was obtained by the same procedure as a series of reaction of Example 37→Example 39→Example 41 (using a corresponding compound instead of methoxymethyl chloride, if necessary.)→Example 43 (using a corresponding compound instead of benzyl bromide.)→Example 44, using a corresponding compound instead of the compound prepared in Reference Example 4.

Example 49(93)

N-Hydroxy-2(S)-isobutyl-5-methoxymethoxy-4(S)-[N-(4-phenoxyphenylcarbonyl)amino]pentanamide

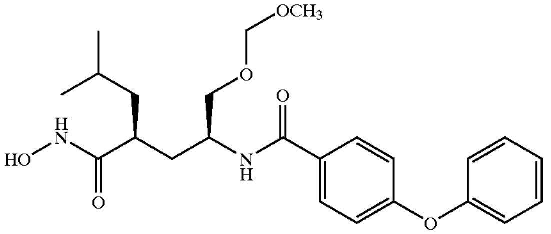

TLC: Rf 0.36 (Chloroform:Methanol=19:1);

NMR ($d_6$-DMSO): δ10.46 (1H, s), 8.72 (1H, s), 8.00 (1H, d, J=8.4 Hz), 7.88 (2H, d, J=8.8 Hz), 7.48–7.38 (2H, m), 7.23–7.16 (1H, m), 7.10–7.03 (2H, m), 7.01 (2H, d, J=8.8 Hz), 4.56 (2H, s), 4.22–4.01 (1H, m), 3.60–3.40 (2H, m), 3.24 (3H, s), 2.25–2.08 (1H, m), 1.78–1.60 (2H, m), 1.58–1.32 (2H, m), 1.28–1.07 (1H, m), 0.82 (3H, d, J=6.0 Hz), 0.80 (3H, d, J=6.0 Hz).

Example 49(94)

N-Hydroxy-2(S)-ethyl-5-methoxymethoxy-4(S)-[N-(4-phenoxyphenylcarbonyl)amino]pentanamide

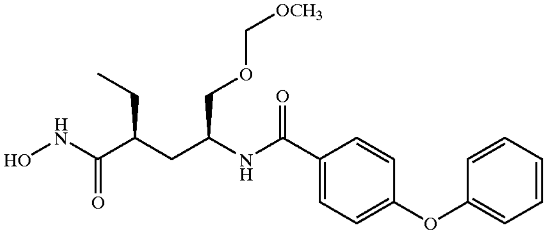

TLC: Rf 0.60 (Chloroform:Methanol:Acetic acid:Water=100:10:1:1);

NMR ($d_6$-DMSO): δ10.40(1H, s), 8.71(1H, s), 8.04(1H, d, J=8.1 Hz), 7.87(2H, d, J=9.0 Hz), 7.45–7.40(2H, m), 7.22–7.17(1H, m), 7.08–7.00(4H, m), 4.55(2H, s), 4.04–4.18(1H, m), 3.52–3.23(2H, m), 3.22(3H, s), 2.04–1.92(1H, m), 1.78–1.57(2H, m), 1.52–1.34(2H, m), 0.77(3H, t, J=7.2 Hz).

Example 49(95)

N-Hydroxy-2(S)-propyl-5-methoxymethoxy-4(S)-[N-(4-phenoxyphenylcarbonyl)amino]pentanamide

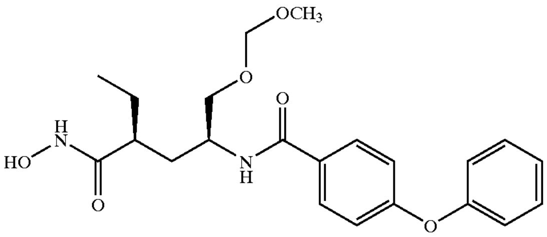

TLC: Rf 0.60 (Chloroform:Methanol:Acetic acid:Water=100:10:1:1);

NMR ($d_6$-DMSO): δ10.40(1H, s), 8.69(1H, s), 8.02(1H, d, J=8.4 Hz), 7.86(2H, d, J=8.8 Hz), 7.46–7.37(2H, m), 7.23–7.15(1H, m), 7.08–6.98(4H, m), 4.54(2H, s), 4.16–4.00(1H, m), 3.48–3.44(2H, m), 3.21(3H, s), 2.14–1.99(1H, m), 1.78–1.58(2H, m), 1.45–1.28(2H, m), 1.27–1.07(2H, m), 0.80(3H, t, J=7.2 Hz).

Example 49(96)

N-Hydroxy-2(R)-t-butoxycarbonylmethyl-5-methoxymethoxy-4(S)-[N-(4-phenoxyphenylcarbonyl)amino]pentanamide

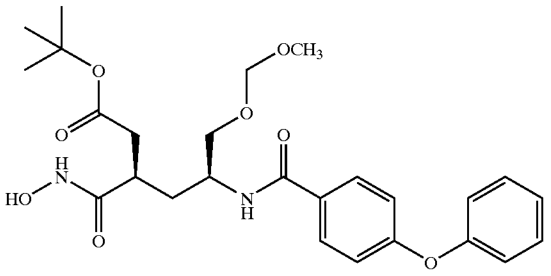

TLC: Rf 0.54 (Chloroform:Methanol=9:1);

NMR ($d_6$-DMSO): δ10.47 (1H, s), 8.75 (1H, s), 8.05 (1H, d, J=8.4 Hz), 7.88 (2H, d, J=8.7 Hz), 7.47–7.40 (2H, m), 7.23–7.17 (1H, m), 7.10–7.04 (2H, m), 7.03 (2H, d, J=8.7 Hz), 4.55 (2H, s), 4.20–4.03 (1H, m), 3.57–3.43 (2H, m), 3.23 (3H, s), 2.55–2.34 (3H, m), 1.74–1.66 (2H, m), 1.36 (9H, s).

Example 49(97)

N-Hydroxy-2(S)-allyl-5-methoxymethoxy-4(S)-[N-(4-phenoxyphenylcarbonyl)amino]pentanamide

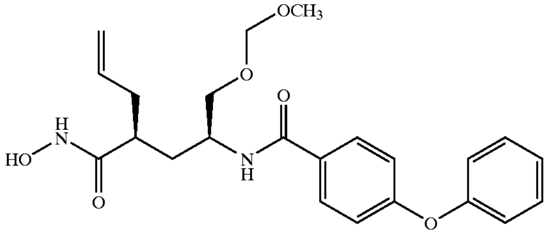

TLC: Rf 0.62 (Chloroform:Methanol:Acetic acid=100:5:1);

NMR ($d_6$-DMSO): δ10.43(1H, s), 8.66(1H, brs), 8.06(1H, d, J=8.4 Hz), 7.89–7.85(2H, m), 7.47–7.38(2H, m), 7.23–7.15(1H, m), 7.09–6.99(4H, m), 5.73–5.60(1H, m), 5.05–4.92(2H, m), 4.54(2H, s), 4.19–4.05(1H, m), 3.52(1H, dd, J=10.1 Hz, 5.2 Hz), 3.44(1H, dd, J=10.1 Hz, 5.2 Hz), 3.22(3H, s), 2.20–2.17(3H, m), 1.82–1.59(2H, m).

Example 49(98)

N-Hydroxy-2(S)-ethyl-5-ethoxymethoxy-4(S)-[N-(4-phenoxyphenylcarbonyl)amino]pentanamide

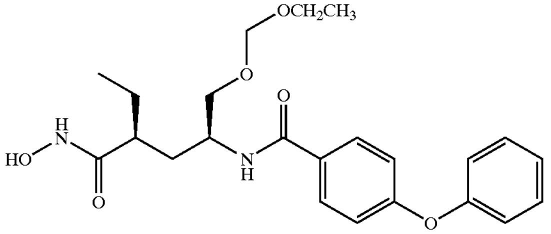

TLC: Rf 0.33 (Chloroform:Methanol:Acetic acid=100:5:1);

NMR ($d_6$-DMSO): δ10.40(1H, s), 8.70(1H, s), 8.02(1H, d, J=8.4 Hz), 7.86(2H, d, J=8.8 Hz), 7.46–7.38(2H, m), 7.23–7.15(1H, m), 7.08–6.99(4H, m), 4.59(2H, s), 4.19–4.01(1H, m), 3.52–3.42(2H, m), 3.47(2H, q, J=7.0 Hz), 2.05–1.92(1H, m), 1.79–1.32(4H, m), 1.07(3H, t, J=7.2 Hz), 0.76(3H, t, J=7.0 Hz).

Example 49(99)

N-Hydroxy-2(S)-ethyl-5-(2-methoxyethoxy)methoxy-4(S)-[N-(4-phenoxyphenylcarbonyl)amino]pentanamide

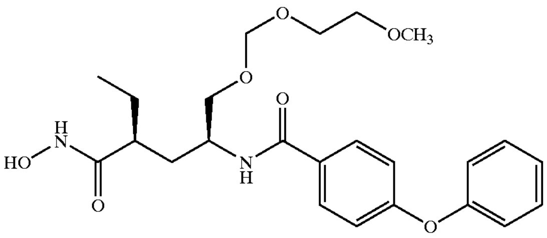

TLC: Rf 0.31 (Chloroform:Methanol=9:1);

NMR ($d_6$-DMSO): δ10.40 (1H, s), 8.71 (1H, s), 8.02 (1H, d, J=8.4 Hz), 7.88 (2H, d, J=8.8 Hz), 7.48–7.38 (2H, m), 7.23–7.15 (1H, m), 7.10–7.05 (2H, m), 7.02 (2H, d, J=8.8 Hz), 4.62 (2H, m), 4.22–4.00 (1H, m), 3.61–3.38 (6H, m), 3.22 (3H, s), 2.09–1.91 (1H, m), 1.82–1.60 (2H, m), 1.58–1.35 (2H, m), 0.78 (3H, t, J=7.0 Hz).

Example 49(100)

N-Hydroxy-2(S)-ethyl-5-t-butylcarbonyloxy-4(S)-[N-(4-phenoxyphenylcarbonyl)amino]pentanamide

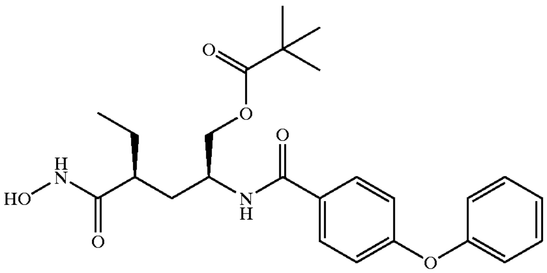

TLC: Rf 0.69 (Chloroform:Methanol=9:1);

NMR ($d_6$-DMSO): δ10.41 (1H, s), 8.71 (1H, s), 8.07 (1H, d, J=8.7 Hz), 7.81 (2H, d, J=8.6 Hz), 7.41 (2H, t, J=7.6 Hz), 7.17 (1H, t, J=7.6 Hz), 7.04 (2H, d, J=7.6 Hz), 7.00 (2H, d, J=8.6 Hz), 4.25–4.13 (1H, m), 4.08–3.94 (2H, m), 2.03–1.91 (1H, m), 1.63 (2H, t, J=6.9 Hz), 1.48–1.36 (2H, m), 1.06 (9H, s), 0.75 (3H, t, J=7.5 Hz).

Example 49(101)

N-Hydroxy-2(S)-allyl-5-ethoxymethoxy-4(S)-[N-(4-methylphenylcarbonyl)amino]pentanamide

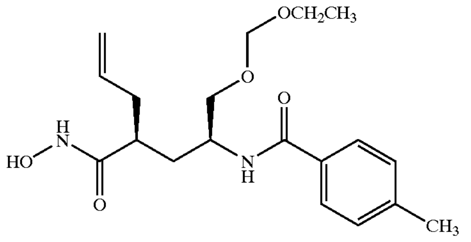

TLC: Rf 0.49 (Chloroform:Methanol=9:1);

NMR ($d_6$-DMSO): δ10.42 (s, 1H), 8.71 (s, 1H), 7.99 (d, J=8.8 Hz, 1H), 7.73 (d, J=8.0 Hz, 2H), 7.24 (d, J=8.0 Hz, 2H), 5.72–5.55 (m, 1H), 5.02–4.91 (m, 2H), 4.58 (s, 2H), 4.19–4.01 (m, 1H), 3.52–3.41 (m, 4H), 2.33 (s, 3H), 2.12 (m, 3H), 1.79–1.58 (m, 2H), 1.07 (t, J=7.0 Hz, 3H).

Example 49(102)

N-Hydroxy-2(S)-allyl-5-ethoxymethoxy-4(S)-[N-(4-nitrophenylcarbonyl)amino]pentanamide

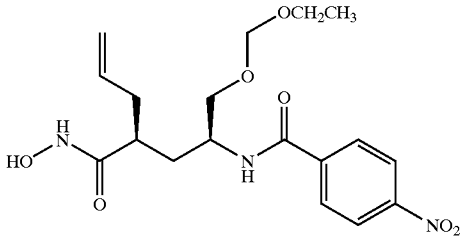

TLC: Rf 0.32 (Chloroform:Methanol=9:1);

NMR ($d_6$-DMSO): δ10.43 (d, J=1.5 Hz, 1H), 8.71 (d, J=1.5 Hz, 1H), 8.47 (d, J=8.4 Hz, 1H), 8.30–8.27 (m, 2H), 8.07–8.03 (m, 2H), 5.75–5.59 (m, 1H), 5.03–4.93 (m, 2H), 4.59 (s, 2H), 4.19–4.08 (m, 1H), 3.50 (d, J=5.1 Hz, 2H), 3.47 (q, J=7.2 Hz, 2H), 2.23–2.12 (m, 3H), 1.80–1.60 (m, 2H), 1.07 (t, J=7.2 Hz, 3H).

Example 49(103)

N-Hydroxy-2-methylidene-5-ethoxymethoxy-4(S)-[N-(4-nitrophenylcarbonyl)amino]pentanamide

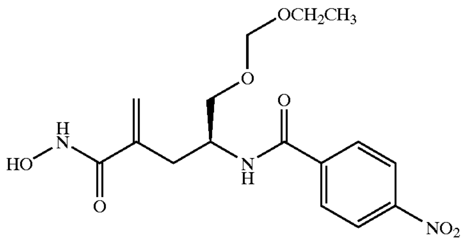

TLC: Rf 0.50 (Chloroform:Methanol=9:1);

NMR ($d_6$-DMSO): δ10.77 (s, 1H), 8.84 (s, 1H), 8.61 (d, J=8.4 Hz, 1H), 8.32–8.27 (m, 2H), 8.05–8.02 (m, 2H), 5.57 (s, 1H), 5.36 (s, 1H), 4.60 (s, 2H), 4.30–4.18 (m, 1H), 3.53–3.45 (m, 4H), 2.61 (dd, J=14.1 Hz, 4.5 Hz, 1H), 2.47–2.40 (m, 1H), 1.07 (t, J=6.9 Hz, 3H).

Example 49(104)

N-Hydroxy-2(S)-(2-propynyl)-5-ethoxymethoxy-4(S)-[N-(4-nitrophenylcarbonyl)amino]pentanamide

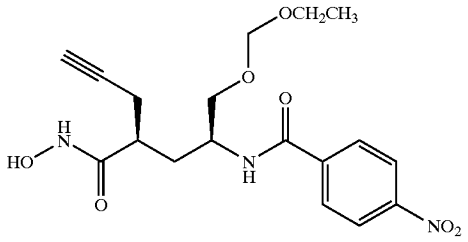

TLC: Rf 0.39 (Chloroform:Methanol=9:1);

NMR ($d_6$-DMSO): δ10.54 (s, 1H), 8.81 (s, 1H), 8.49 (d, J=8.4 Hz, 1H), 8.29 (d, J=8.7 Hz, 2H), 8.07 (d, J=8.7 Hz, 2H), 4.59 (s, 2H), 4.20–4.03 (m, 1H), 3.60–3.40 (m, 4H), 2.78 (s, 1H), 2.40–2.20 (m, 3H), 1.95–1.80 (m, 1H), 1.80–1.60 (m, 1H), 1.08 (t, J=7.1 Hz, 3H).

Example 49(105)

N-Hydroxy-2(S)-allyl-5-(2-methoxyethoxy)methoxy-4(S)-[N-(4-cyanophenylcarbonyl)amino]pentanamide

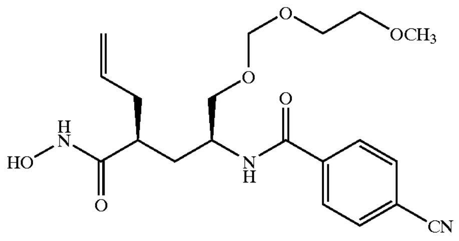

TLC: Rf 0.22 (Chloroform:Methanol=9:1);

NMR ($d_6$-DMSO): δ10.42 (s, 1H), 8.71 (s, 1H), 8.36 (d, J=8.7 Hz, 1H), 7.98 (d, J=8.4 Hz, 2H), 7.94 (d, J=8.4 Hz, 2H), 5.74–5.58 (m, 1H), 5.05–4.92 (m, 2H), 4.61 (s 2H), 4.0–4.04 (m, 1H), 3.58–3.43 (m, 4H), 3.44–3.37 (m, 2H), 3.19 (s, 3H), 2.22–2.10 (m, 3H), 1.81–1.58 (m, 2H).

Example 49(106)

N-Hydroxy-2(S)-(2-propynyl)-5-ethoxymethoxy-4(S)-[N-(4-bromophenylcarbonyl)amino]pentanamide

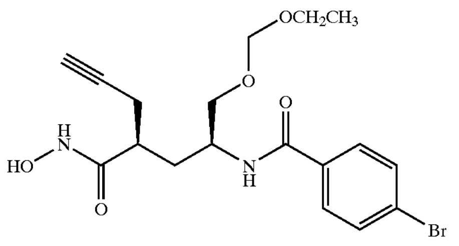

TLC: Rf 0.36 (Chloroform:Methanol=9:1);

NMR ($d_6$-DMSO): δ10.52 (s, 1H), 8.80 (s, 1H), 8.20 (d, J=8.7 Hz, 1H), 7.79 (d, J=8.4 Hz, 2H), 7.64 (d, J=8.4 Hz,

2H), 4.58 (s, 2H), 4.18–4.02 (m, 1H), 3.58–3.42 (m, 4H), 2.78–2.73 (brs, 1H), 2.38–2.20 (m, 3H), 1.95–1.75 (m, 1H), 1.75–1.60 (m, 1H), 1.08 (t, J=6.9 Hz, 3H).

Example 49(107)

N-Hydroxy-2(S)-(2-propynyl)-5-ethoxymethoxy-4(S)-[N-(4-chlorophenylcarbonyl)amino]pentanamide

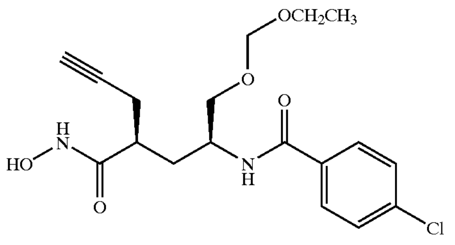

TLC: Rf 0.35 (Chloroform:Methanol=9:1);

NMR ($d_6$-DMSO): δ10.52 (s, 1H), 8.80 (s, 1H), 8.20 (d, J=8.7 Hz, 1H), 7.86 (d, J=8.6 Hz, 2H), 7.51 (d, J=8.6 Hz, 2H), 4.58 (s, 2H), 4.20–4.02 (m, 1H), 3.60–3.40 (m, 4H), 2.80–2.75 (brs, 1H), 2.40–2.20 (m, 3H), 1.95–1.78 (m, 1H), 1.78–1.60 (m, 1H), 1.08 (t, J=6.9 Hz, 3H).

Example 49(108)

N-Hydroxy-2(S)-allyl-5-ethoxymethoxy-4(S)-[N-(4-bromophenylcarbonyl)amino]pentanamide

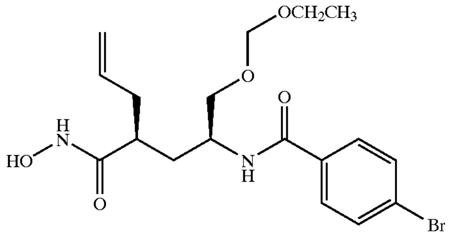

TLC: Rf 0.35 (Chloroform:Methanol=9:1);

NMR ($d_6$-DMSO): δ10.42 (s, 1H), 8.71 (s, 1H), 8.19 (d, J=8.7 Hz, 1H), 7.78 (d, J=8.6 Hz, 2H), 7.65 (d, J=8.6 Hz, 2H), 5.75–5.58 (m, 1H), 5.05–4.90 (m, 2H), 4.58 (s, 2H), 4.20–4.05 (m, 1H), 3.58–3.40 (m, 4H), 2.25–2.08 (m, 3H), 1.80–1.60 (m, 2H), 1.07 (t, J=7.1 Hz, 3H).

Example 49(109)

N-Hydroxy-2(S)-allyl-5-ethoxymethoxy-4(S)-[N-(4-chlorophenylcarbonyl)amino]pentanamide

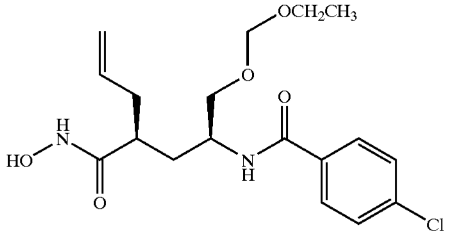

TLC: Rf 0.36 (Chloroform:Methanol=9:1);

NMR ($d_6$-DMSO): δ10.42 (s, 1H), 8.70 (s, 1H), 8.18 (d, J=8.7 Hz, 1H), 7.85 (d, J=8.6 Hz, 2H), 7.52 (d, J=8.6 Hz, 2H), 5.75–5.58 (m, 1H), 5.05–4.90 (m, 2H), 4.58 (s, 2H), 4.20–4.05 (m, 1H), 3.58–3.40 (m, 4H), 2.25–2.08 (m, 3H), 1.80–1.60 (m, 2H), 1.07 (t, J=7.1 Hz, 3H).

Example 49(110)

N-Hydroxy-2(R)-dimethylaminomethyl-5-ethoxymethoxy-4(S)-[N-(4-nitrophenylcarbonyl)amino]pentanamide

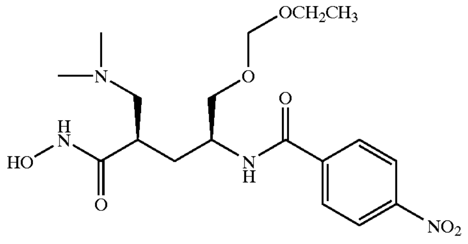

TLC: Rf 0.30 (Chloroform:Methanol:Acetic acid=10:2:1);

NMR ($d_6$-DMSO): δ10.44 (brs, 1H), 8.73 (brs, 1H), 8.48 (d, J=8.4 Hz, 1H), 8.29 (d, J=8.9 Hz, 2H), 8.05 (d, J=8.9 Hz, 2H), 4.59 (s, 2H), 4.20–4.05 (m, 1H), 3.60–3.40 (m, 4H), 2.55–2.38 (m, 1H), 2.38–2.20 (m, 1H), 2.20–2.00 (m, 7H), 1.85–1.70 (m, 1H), 1.70–1.58 (m, 1H), 1.08 (t, J=6.9 Hz, 3H).

Example 49(111)

N-Hydroxy-2(S)-(2-propynyl)-5-(2-methoxyethoxy)methoxy-4(S)-[N-(4-cyanophenylcarbonyl)amino]pentanamide

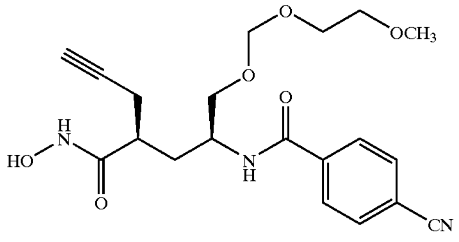

TLC: Rf 0.35 (Chloroform:Methanol=9:1);

NMR($d_6$-DMSO): δ10.53 (s, 1H), 8.81 (s, 1H), 8.41 (d, J=8.7 Hz, 1H), 7.99 (d, J=8.7 Hz, 2H), 7.94 (d, J=8.7 Hz, 2H), 4.61 (s, 2H), 4.20–4.05 (m, 1H), 3.60–3.45 (m, 4H), 3.45–3.35 (m, 2H), 3.20 (s, 3H), 2.79 (s, 1H), 2.35–2.00 (m, 3H), 1.92–1.75 (m, 1H), 1.75–1.60 (m, 1H).

Example 49(112)~49(116)

The following compounds were obtained by the same procedure as a series of reaction of Example 37→Example 39→Example 41 (using a corresponding compound instead of methoxymethyl chloride, if necessary.)→Example 43 (using a corresponding compound instead of benzyl bromide.)→Example 44→Example 49, using 4(R)-carboxy-4-aminobutyric acid methyl ester instead of 4(S)-carboxy-4-aminobutyric acid methyl ester and a corresponding compound instead of the compound prepared in Reference Example 4.

Example 49(112)

N-Hydroxy-2(R)-benzyl-5-methoxymethoxy-4(R)-[N-(4-phenoxyphenylcarbonyl)amino]pentanamide

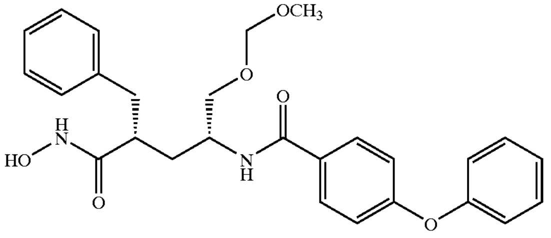

TLC: Rf 0.39 (Chloroform:Methanol:Acetic acid:Water=100:10:1:1);

NMR ($d_6$-DMSO): δ10.34(1H, s), 8.66(1H, s), 8.08(1H, d, J=8.8 Hz), 7.89(2H, d, J=8.4 Hz), 7.43(2H, t, J=8.0 Hz), 7.00–7.46(10H, m), 4.53(2H, s), 4.13–4.32(1H, m), 3.48 (2H, d, J=5.6 Hz), 3.19(3H, s), 2.76(2H, d, J=7.0 Hz), 2.29–2.44(1H, m), 1.58–1.84(2H, m).

Example 49(113)

N-Hydroxy-2(R)-benzyl-5-methoxymethoxy-4(R)-[N-[4-(3-phenoxy-1-propynyl)phenylcarbonyl]amino]pentanamide

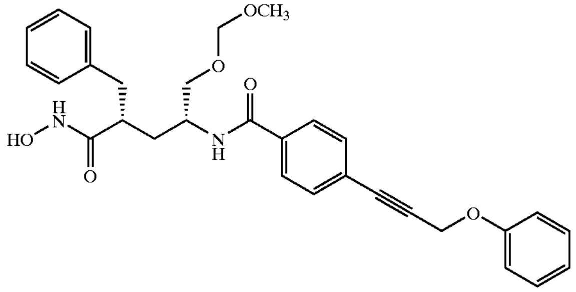

TLC: Rf 0.39 (Chloroform:Methanol:Acetic acid:Water=100:10:1:1);

NMR ($d_6$-DMSO): δ10.33(1H, s), 8.65(1H, s), 8.22(1H, d, J=8.7 Hz), 7.84(2H, d, J=8.4 Hz), 7.51(2H, d, J=8.4 Hz), 7.32(2H, t, J=7.8 Hz), 7.20(2H, t, J=6.9 Hz), 6.97–7.14(6H, m), 5.05(2H, s), 4.50(2H, s), 4.14–4.28(1H, m), 3.46(2H, d, J=5.7 Hz), 3.17(3H, s), 2.74(2H, d, J=7.2 Hz), 2.29–2.39 (1H, m), 1.60–1.79(2H, m).

Example 49(114)

N-Hydroxy-2(R)-methyl-5-ethoxymethoxy-4(R)-[N-[4-(4-cyanophenyl)phenylcarbonyl]amino] pentanamide

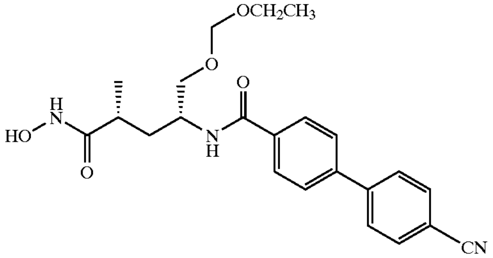

TLC: Rf 0.35 (Chloroform:Methanol=9:1);

NMR ($d_6$-DMSO): δ10.37 (s, 1H), 8.65 (s, 1H), 8.18 (d, J=8.4 Hz, 1H), 7.95 (d, J=8.6Hz, 2H), 7.83 (d, J=8.6 Hz, 2H), 4.59 (s, 2H), 4.16 (m, 1H), 3.60–3.40 (m, 4H), 2.17 (m, 1H), 1.67 (t, J=6.9 Hz, 2H), 1.07 (t, J=7.1 Hz, 3H), 1.01 (d, J=6.9 Hz, 3H).

Example 49(115)

N-Hydroxy-2(R)-allyl-5-ethoxymethoxy-4(R)-[N-(4-phenoxyphenylcarbonyl)amino]pentanamide

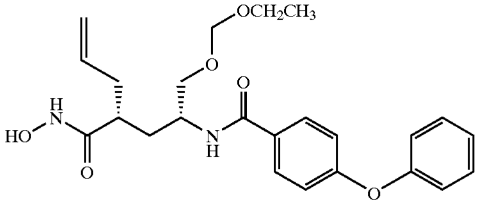

TLC: Rf 0.34 (Chloroform:Methanol=9:1);

NMR ($d_6$-DMSO): δ10.41 (s, 1H), 8.70 (s, 1H), 8.02 (d, J=8.4 Hz, 1H), 7.85 (d, J=9.0 Hz, 2H), 7.41 (t, J=7.9 Hz, 2H), 7.17 (t, J=7.9 Hz, 1H), 7.04 (d, J=7.9 Hz, 2H), 6.99 (d, J=9.0 Hz, 2H), 5.74–5.55 (m, 1H), 5.03–4.88 (m, 2H), 4.56 (s, 2H), 4.17–4.03 (m, 1H), 3.53–3.40 (m, 4H), 2.24–2.10 (m, 3H), 1.79–1.58 (m, 2H), 1.06 (t, J=7.0 Hz, 3H).

Example 49(116)

N-Hydroxy-2(R)-methyl-5-ethoxymethoxy-4(R)-[N-(4-phenoxyphenylcarbonyl)amino]pentanamide

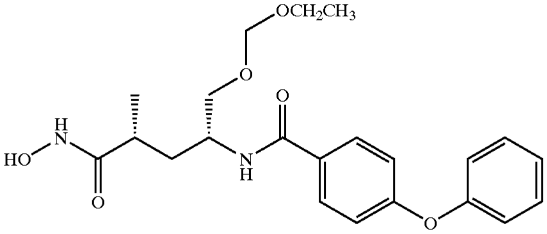

TLC: Rf 0.38 (Chloroform:Methanol=9:1);

NMR ($d_6$-DMSO): δ10.36 (s, 1H), 8.64 (s, 1H), 8.01 (d, J=8.7 Hz, 1H), 7.85 (d, J=8.7 Hz, 2H), 7.41 (t, J=7.6 Hz, 2H), 7.17 (t, J=7.6 Hz, 1H), 7.04 (d, J=7.6 Hz, 2H), 7.00 (d,

J=8.7 Hz, 2H), 4.57 (s,2H), 4.18–4.06 (m, 1H), 3.51–3.42 (m, 4H), 2.15 (m, 1H), 1.64 (t, J=7.1 Hz, 2H), 1.06 (t, J=7.2 Hz, 3H), 0.99 (d, J=7.1 Hz, 3H).

Example 49(117)~49(124)

The following compounds were obtained by the same procedure as a series of reaction of Example 37→Example 39→Example 41→Reference Example 43 (using a corresponding compound instead of benzyl bromide.)→Example 44→Example 49, using a corresponding compound instead of the compound prepared in Reference Example 4.

Example 49(117)

N-Hydroxy-2(S)-benzyl-5-methoxymethoxy-4(S)-[N-[4-[2E-(4-chlorophenyl)ethenyl]phenylcarbonyl]amino]pentanamide

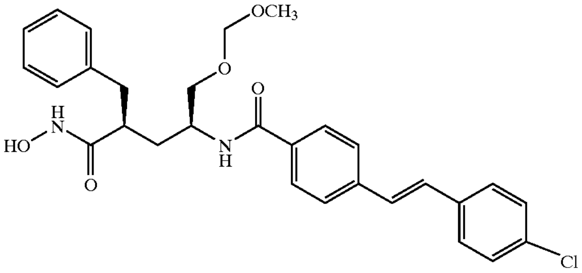

TLC: Rf 0.21 (Chloroform:Methanol=19:1);

NMR ($d_6$-DMSO): δ10.37 (1H, s), 8.15 (1H, d, J=8.4 Hz), 7.89 (2H, d, J=8.4 Hz), 7.68 (2H, d, J=8.4 Hz), 7.66 (2H, d, J=8.8 Hz), 7.45 (2H, d, J=8.8 Hz), 7.40–7.30 (2H, m), 7.29–7.08 (5H, m), 4.54 (2H, s), 4.38–4.18 (1H, m), 3.60–3.40 (2H, m), 3.21 (3H, s), 2.78 (2H, d, J=6.6 Hz), 2.55–2.30 (1H, m), 1.92–1.60 (2H, m).

Example 49(118)

N-Hydroxy-2(S)-(indol-3-yl)-5-methoxymethoxy-4(S)-[N-[4-(benzofuran-2-yl)phenylcarbonyl]amino]pentanamide

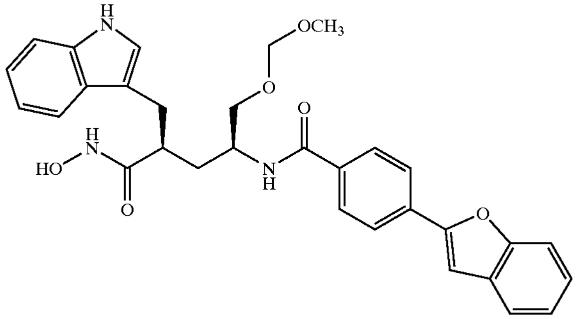

TLC: Rf 0.28 (Chloroform:Methanol=19:1);

NMR ($d_6$-DMSO): δ10.73 (1H, s), 10.37 (1H, s), 8.67 (1H, d, J=8.6 Hz), 8.01 (4H, s), 7.78–7.48 (4H, m), 7.44–7.20 (3H, m), 7.10–6.80 (3H, m), 4.53 (2H, s), 4.42–4.22 (1H, m), 3.62–3.40 (2H, m), 3.18 (3H, s), 3.00–2.78 (2H, m), 2.62–2.38 (1H, m), 2.00–1.65 (2H, m).

Example 49(119)

N-Hydroxy-2(S)-benzyl-5-methoxymethoxy-4(S)-[N-[4-[3-(4-chlorophenoxy-1-propynyl)phenylcarbonyl]amino]pentanamide

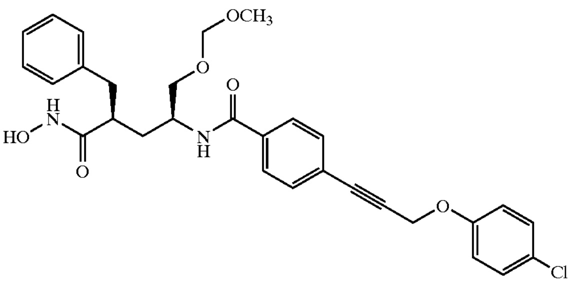

TLC: Rf 0.26 (Chloroform:Methanol=19:1);

NMR ($d_6$-DMSO): δ10.35 (1H, s), 8.67 (1H, s), 8.24 (1H, d, J=8.4 Hz), 7.87 (2H, d, J=8.4 Hz), 7.53 (2H, d, J=8.4 Hz), 7.38 (2H, d, J=9.2 Hz), 7.30–7.00 (7H, m), 5.08 (2H, s), 4.53 (2H, s), 4.25 (1H, m), 3.49 (2H, d, J=5.4 Hz), 3.20 (3H, s), 2.77 (2H, d, J=7.0 Hz), 2.38 (1H, m), 1.90–1.60 (2H, m).

Example 49(120)

N-Hydroxy-2(S)-benzyl-5-methoxymethoxy-4(S)-[N-(4-phenoxyphenylcarbonyl)amino]pentanamide

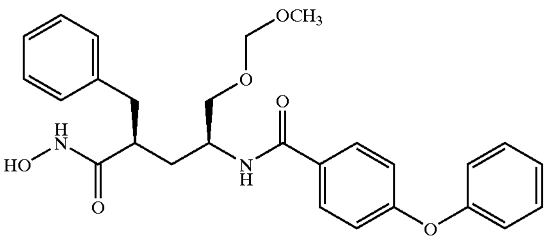

TLC: Rf 0.39 (Chloroform:Methanol=19:1);

NMR ($d_6$-DMSO): δ10.36 (1H, s), 8.09 (1H, d, J=8.6 Hz), 7.91 (2H, d, J=8.8 Hz), 7.50–7.38(2H, m), 7.30–7.08 (8H, m), 7.03 (2H, d, J=8.8 Hz), 4.54 (2H, s), 4.36–4.18 (1H, m), 3.58–3.40 (2H, m), 3.20 (3H, s), 2.84–2.65 (2H, m), 2.45–2.30 (1H, m), 1.88–1.58 (2H, m).

Example 49(121)

N-Hydroxy-2(S)-benzyl-5-methoxymethoxy-4(S)-[N-[4-(4-phenylpiperidin-1-yl)phenylcarbonyl]amino]pentanamide

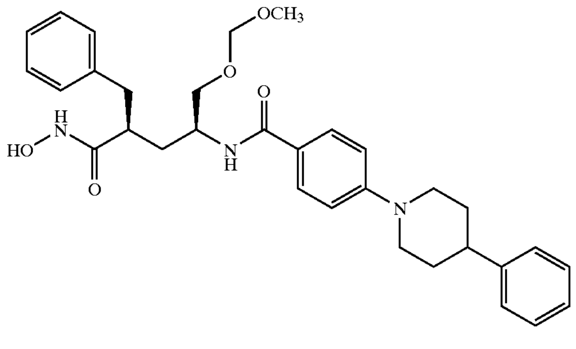

TLC: Rf 0.26 (Chloroform Methanol=19:1);

NMR ($d_6$-DMSO): δ10.33 (1H, s), 8.66 (1H, s), 7.82 (1H, d, J=8.8 Hz), 7.77 (2H, d, J=8.8 Hz), 7.38–7.06 (10H, m), 6.99 (2H, d, J=8.8 Hz), 4.54 (2H, s), 4.38–4.16 (1H, m), 4.04–3.90 (2H, m), 3.58–3.40 (2H, m), 3.21 (3H, s), 2.96–2.60 (5H, m), 2.44–2.28 (1H, m), 1.95–1.60 (6H, m).

Example 49(122)

N-Hydroxy-2(S)-benzyl-5-methoxymethoxy-4(S)-[N-[4-(6-imidazolyl-1-hexynyl)phenylcarbonyl]amino]pentanamide

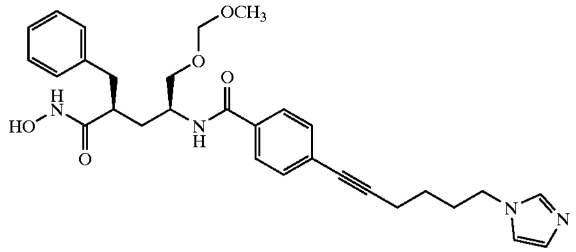

TLC: Rf 0.46 (Chloroform:Methanol=9:1);

NMR ($d_6$-DMSO): δ10.35 (1H, s), 8.67 (1H, s), 8.18 (1H, d, J=8.4 Hz), 7.83 (2H, d, J=8.4 Hz), 7.63 (1H, t, J=1.2 Hz), 7.44 (2H, d, J=8.4 Hz), 7.28–7.07 (6H, m), 6.89 (1H, t, J=1.2 Hz), 4.53 (2H, s), 4.36–4.17 (1H, m), 4.01 (2H, t, J=7.0 Hz), 3,60–3.40 (2H, m), 3.20 (3H, s), 2.84–2.70 (2H, m), 2.47 (2H, t, J=7.0 Hz), 2.46–2.30 (1H, m), 1.96–1.62 (4H, m), 1.58–1.40 (2H, m).

Example 49(123)

N-Hydroxy-2(S)-(naphthalene-1-yl)-5-methoxymethoxy-4(S)-[N-(4-phenoxyphenylcarbonyl)amino]pentanamide

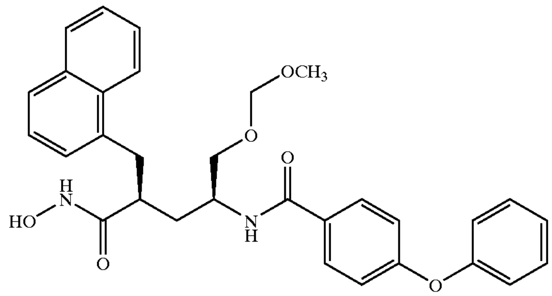

TLC: Rf 0.36 (Chloroform:Methanol=19:1);

NMR ($d_6$-DMSO): δ10.26 (1H, s), 8.63 (1H, s), 8.16 (1H, d, J=8.4 Hz), 8.04–7.82 (4H, m), 7.80–7.70 (1H, m), 7.52–7.16 (7H, m), 7.14–6.96 (4H, m), 4.52 (2H, s), 4.50–4.28 (1H, m), 3.61–3.40 (2H, m), 3.25–3.02 (5H, m), 2.69–2.52 (1H, m), 2.00–1.78 (2H, m).

Example 49(124)

N-Hydroxy-2(S)-[4-(benzofuran-2-yl)benzyl]-5-methoxymethoxy-4(S)-[N-(4-iodophenylcarbonyl)amino]pentanamide

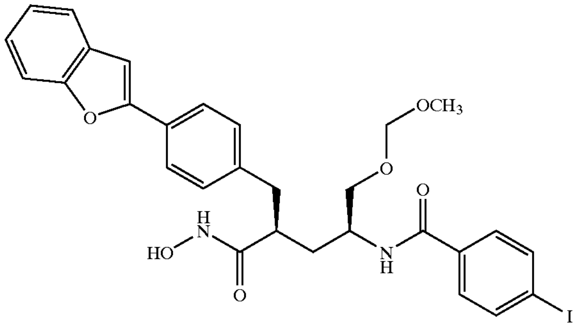

TLC: Rf 0.49 (Chloroform:Methanol=9:1);

NMR ($d_6$-DMSO): δ10.38 (1H,s), 8.70 (1H, s), 8.25 (1H, d, J=8.7 Hz), 7.85 (2H, d, J=8.4 Hz), 7.79 (2H, d, J=8.1 Hz), 7.70–7.56 (4H, m), 7.36 (1H, s), 7.34–7.20 (4H, m), 4.55 (2H, s), 4.35–4.20 (1H, m), 3.60–3.45 (2H, m), 3.21 (3H, s), 2.83 (2H, d, J=6.9 Hz), 2.45–2.30 (1H, m), 1.90–1.60 (2H, m).

Example 49(125)~49(233)

The following compounds were obtained by the same procedure as a series of reaction of Example 37→Example 39→Example 41 (using a corresponding compound instead of methoxymethyl chloride.)→Example 43 (using a corresponding compound instead of benzyl bromide.)→Example 44→Example 49, using a corresponding compound instead of the compound prepared in Reference Example 4.

Example 49(125)

N-Hydroxy-2(S)-benzyl-5-ethoxymethoxy-4(S)-[N-(trans-4-methylcyclohexylcarbonyl)amino] pentanamide

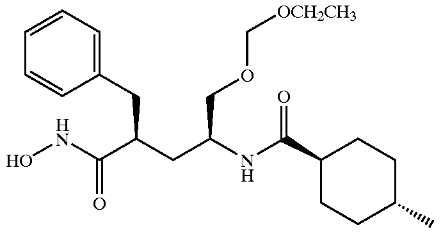

TLC: Rf 0.36 (Chloroform:Methanol=9:1);

NMR ($d_6$-DMSO): δ10.32 (s, 1H), 8.80–8.60 (brs, 1H), 7.43 (d, J=8.7 Hz, 1H), 7.28–7.19 (m, 2H), 7.19–7.07 (m, 3H), 4.54 (s, 2H), 4.05–3.85 (m, 1H), 3.60–3.20 (m, 4H), 2.80–2.60 (m, 2H), 2.38–2.20 (m, 1H), 2.10–1.90 (m, 1H), 1.80–1.60 (m, 5H), 1.60–1.45 (m, 1H), 1.45–1.20 (m, 3H), 1.11 (t, J=6.9 Hz, 3H), 1.00–0.80 (m, 5H).

Example 49(126)

N-Hydroxy-2(S)-(4-nitrobenzyl)-5-ethoxymethoxy-4(S)-[N-(trans-4-methylcyclohexylcarbonyl)amino] pentanamide

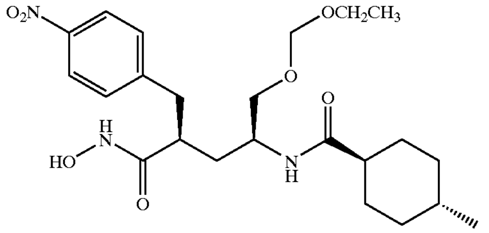

TLC: Rf 0.40 (Chloroform:Methanol=9:1);

NMR ($d_6$-DMSO): δ10.34 (s, 1H), 8.80–8.60 (brs, 1H), 8.12 (d, J=8.7 Hz, 2H), 7.48 (d, J=8.7 Hz, 1H), 7.37 (d, J=8.7 Hz, 2H), 4.57 (s, 2H), 4.10–3.90 (m, 1H), 3.55–3.25 (m, 4H), 3.00–2.70 (m, 2H), 2.40–2.25 (m, 1H), 2.10–1.95 (m, 1H), 1.85–1.60 (m, 5H), 1.60–1.20 (m, 4H), 1.11 (t, J=7.2 Hz, 3H), 1.00–0.80 (m, 5H).

Example 49(127)

N-Hydroxy-2(S)-(indol-3-yl)-5-ethoxymethoxy-4(S)-[N-(trans-4-methylcyclohexylcarbonyl)amino] pentanamide

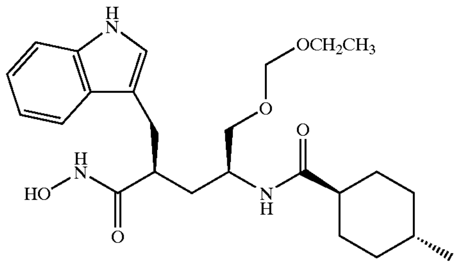

TLC: Rf 0.32 (Chloroform:Methanol=10:1);

NMR ($d_6$-DMSO): δ10.73 (brs, 1H), 10.32 (brs, 1H), 8.66 (d, J=1.5 Hz, 1H), 7.49 (d, J=7.8 Hz, 1H), 7.41 (d, J=8.7 Hz, 1H), 7.28 (d, J=8.1 Hz, 1H), 7.05–6.99 (m, 2H), 6.94–6.88 (m, 1H), 4.50 (d, J=6.9 Hz, 1H), 4.47 (d, J=6.9 Hz, 1H), 4.02–3.902 (m, 1H), 3.40 (q, J=7.2 Hz, 2H), 3.37–3.28 (m, 2H), 2.89–2.71 (m, 2H), 2.48–2.34 (m, 1H), 2.05–1.93 (m, 1H), 1.77–1.50 (m, 6H), 1.45–1.20 (m, 3H), 1.06 (t, J=7.2 Hz, 3H), 0.95–0.80 (m, 2H), 0.84 (d, J=6.6 Hz, 3H).

Example 49(128)

N-Hydroxy-2(S)-benzyl-5-ethoxymethoxy-4(S)-[N-[(pyridin-4-yl)carbonyl]amino]pentanamide

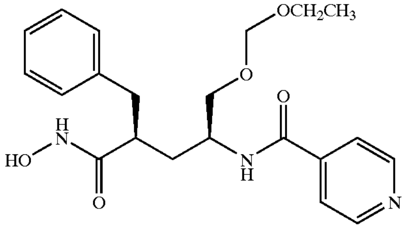

TLC: Rf 0.30 (Chloroform:Methanol=9:1);

NMR ($d_6$-DMSO): δ10.37 (s, 1H), 8.76–8.63 (m, 3H), 8.43 (d, J=8.6 Hz, 1H), 7.80–7.72 (m, 2H), 7.29–7.08 (m, 5H), 4.58 (s, 2H), 4.34–4.14 (m, 1H), 3.60–3.39 (m, 4H), 2.83–2.65 (m, 2H), 2.42–2.28 (m, 1H), 1.88–1.59 (m, 2H), 1.09 (t, J=7.0 Hz, 3H).

Example 49(129)

N-Hydroxy-2(S)-benzyl-5-ethoxymethoxy-4(S)-[N-(4-hydroxyphenylcarbonyl)amino]pentanamide

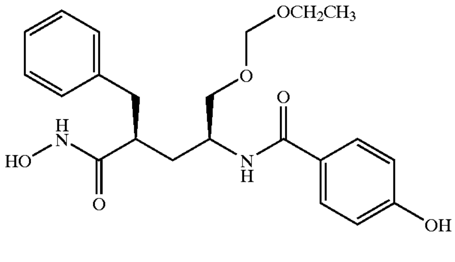

TLC: Rf 0.57 (Chloroform:Methanol=9:1);

NMR ($d_6$-DMSO): δ10.34 (s, 1H), 9.96–9.80 (br, 1H), 7.83 (d, J=8.4 Hz, 1H), 7.74 (d, J=9.0 Hz, 2H), 7.26–7.08 (m, 5H), 6.79 (d, J=9.0 Hz, 2H), 4.57 (s, 2H), 4.30–4.17 (m, 1H), 3.58–3.40 (m, 4H), 2.76 (d, J=6.6 Hz, 2H), 2.42–2.32 (m, 1H), 1.82–1.60 (m, 2H), 1.09 (t, J=7.2 Hz, 3H).

Example 49(130)

N-Hydroxy-2(S)-(2-nitrobenzyl)-5-ethoxymethoxy-4(S)-[N-(trans-4-methylcyclohexylcarbonyl)amino]pentanamide

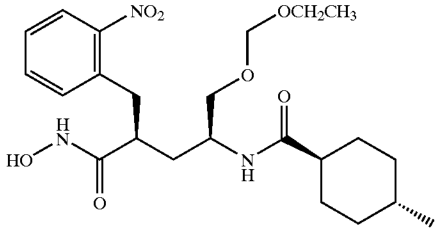

TLC: Rf 0.23 (Chloroform:Methanol=9:1);

NMR ($d_6$-DMSO): δ10.35 (s, 1H), 8.71 (s, 1H), 7.92 (dd, J=8.4, 1.2 Hz, 1H), 7.61 (td, J=7.4, 1.2 Hz, 1H), 7.50–7.40 (m, 2H), 7.36 (d, J=7.4 Hz, 1H), 4.55 (s, 2H), 3.90–3.75 (m, 1H), 3.55–3.25 (m, 4H, overlap with H2O in DMSO), 3.10–2.90 (m, 2H), 2.55–2.40 (m, 1 H, overlap with DMSO), 2.10–1.90 (m, 1H), 1.80– 1.55 (m, 6H), 1.50–1.20 (m, 3H), 1.10 (t, J=7.1 Hz, 3H),1.00–0.75 (m, 5H).

Example 49(131)

N-Hydroxy-2(S)-(3-nitrobenzyl)-5-ethoxymethoxy-4(S)-[N-(trans-4-methylcyclohexylcarbonyl)amino]pentanamide

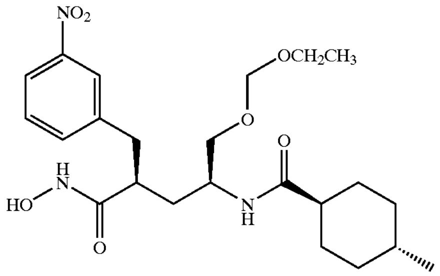

TLC: Rf 0.38 (Chloroform:Methanol=9:1);

NMR ($d_6$-DMSO): δ10.30 (s, 1H), 8.67 (s, 1H), 8.10–8.00 (m, 1H), 7.98 (s, 1H), 7.60–7.46 (m, 3H), 4.56 (s, 2H), 4.10–3.95 (m, 1H), 3.55–3.30 (m, 4H, overlap with H2O in DMSO), 2.94 (dd, J=13.0, 4.7 Hz, 1H), 2.80 (dd, J=13.0, 9.9 Hz, 1H),2.30–2.20 (m, 1H), 2.10–1.95 (m, 1H), 1.85–1.60 (m, 5H), 1.60–1.20 (m, 4H), 1.11 (t, J=7.1 Hz, 3H), 1.00–0.80 (m, 5H).

Example 49(132)

N-Hydroxy-2(S)-benzyl-5-ethoxymethoxy-4(S)-[N-[(1-methylpyrrol-2-yl)carbonyl]amino]pentanamide

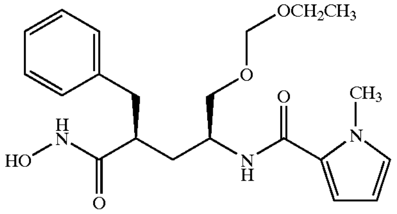

TLC: Rf 0.31 (Chloroform:Methanol=19:1);

NMR ($d_6$-DMSO): δ10.31 (s, 1H), 8.65 (d, J=1.2 Hz, 1H), 7.59 (d, J=8.8 Hz, 1H), 7.25–7.10 (m, 5H), 6.85–6.90 (m, 1H), 6.78–6.76 (m, 1H), 5.98 (t, J =3.2 Hz, 1H), 4.57 (s, 2H), 4.25–4.08 (m, 1H), 3.83 (s, 3H), 3.50–3.39 (m, 4H), 2.75 (d, J=7.0 Hz, 2H), 2.45–2.29 (m, 1H), 1.82–1.52 (m, 2H), 1.08 (t, J=7.0 Hz, 3H).

Example 49(133)

N-Hydroxy-2(S)-benzyl-5-ethoxymethoxy-4(S)-[N-(phenylcarbonyl)amino]pentanamide

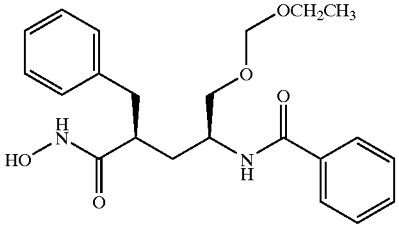

TLC: Rf 0.34 (Chloroform:Methanol=9:1);

NMR ($d_6$-DMSO): δ10.34 (s, 1H), 8.60 (d, J=1.6 Hz, 1H), 8.12 (d, J=8.8 Hz, 1H), 7.85 (dd, J=8.0 Hz, 1.8 Hz, 2H), 7.52–7.40 (m, 3H), 7.26–7.09 (m, 5H), 4.57 (s, 2H), 4.33–4.15 (m, 1H), 3.49 (d, J=5.4 Hz, 2H), 3.45 (q, J=7.0 Hz, 2H), 2.76 (d, J=7.0 Hz, 2H), 2.44–2.28 (m, 1H), 1.85–1.59 (m, 2H), 1.07 (t, J=7.0 Hz, 3H).

Example 49(134)

N-Hydroxy-2(S)-benzyl-5-ethoxymethoxy-4(S)-[N-(4-ethylphenylcarbonyl)amino]pentanamide

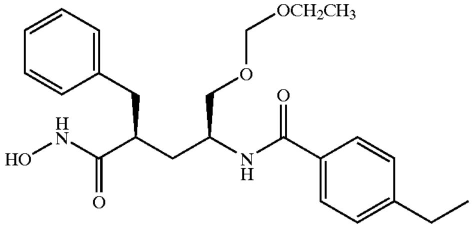

TLC: Rf 0.50 (Chloroform:Methanol=9:1);

NMR ($d_6$-DMSO): δ10.33 (d, J=1.2 Hz, 1H), 8.65 (s, 1H), 8.02 (d, J=8.4 Hz, 1H), 7.78 (d, J=8.2 Hz, 2H), 7.30–7.09 (m, 7H), 4.57 (s, 2H), 4.15–4.32 (m, 1H), 3.50–3.39 (m, 4H), 2.76 (d, J=7.4 Hz, 2H), 2.64 (q, J=7.4 Hz, 2H), 2.42–2.25 (m, 1H), 1.58–1.82 (m, 2H), 1.17 (t, J=7.6 Hz, 3H), 1.07 (t, J=7.4 Hz, 3H).

Example 49(135)

N-Hydroxy-2(S)-benzyl-5-ethoxymethoxy-4(S)-[N-(4-methylphenylcarbonyl)amino]pentanamide

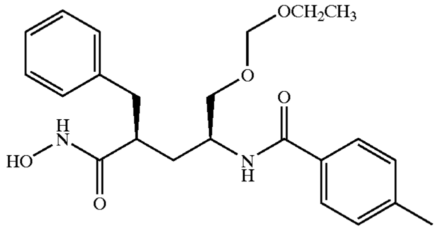

TLC: Rf 0.56 (Chloroform:Methanol=9:1);

NMR ($d_6$-DMSO): δ10.32 (s, 1H), 8.64 (s, 1H), 8.00 (d, J=8.7 Hz, 1H), 7.73 (d, J=8.1 Hz, 2H), 7.26–7.05 (m, 7H), 4.54 (s, 2H), 4.26–4.15 (m, 1H), 3.51–3.37 (m, 4H), 2.73 (d, J=7.2 Hz, 2H), 2.32 (s, 3H), 2.39–2.25 (m, 1H), 1.80–1.58 (m, 2H), 1.05 (t, J=7.1 Hz, 3H).

Example 49(136)

N-Hydroxy-2(S)-benzyl-5-ethoxymethoxy-4(S)-[N-(4-nitrophenylcarbonyl)amino]pentanamide

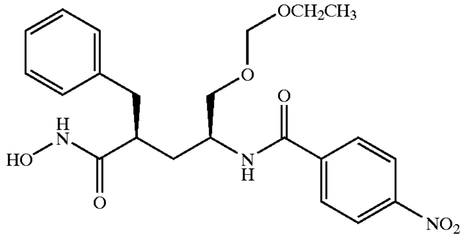

TLC: Rf 0.25 (Methylene chloride:Methanol=19:1);

NMR ($d_6$-DMSO): δ10.36 (d, J=1.5 Hz, 1H), 8.67 (d, J=1.5 Hz, 1H), 8.50 (d, J=8.4 Hz, 1H), 8.30 (d, J=9.0 Hz, 2H), 8.08 (d, J=9.0 Hz, 2H), 7.25–7.11 (m, 5H), 4.56 (s, 2H), 4.23(m, 1H), 3.50 (d, J=5.7 Hz, 2H), 3.43 (q, J=7.2 Hz, 2H), 2.75 (m, 2H), 2.36 (m, 1H), 1.72 (m, 2H), 1.07 (t, J=7.2 Hz, 3H).

Example 49(137)

N-Hydroxy-2(S)-benzyl-5-ethoxymethoxy-4(S)-[N-(2,2,3,3-tetramethylcyclopropylcarbonyl)amino]pentanamide

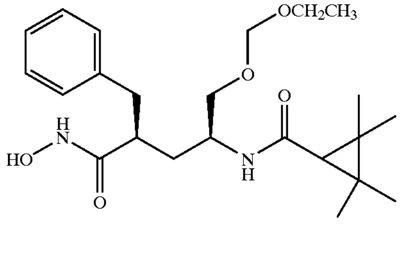

TLC: Rf 0.53 (Chloroform:Methanol=9:1);

NMR ($d_6$-DMSO): δ10.32 (d, J=1.2 Hz, 1H), 8.69 (d, J=1.2 Hz, 1H), 7.49 (d, J=8.4 Hz, 1H), 7.24–7.09 (m, 5H), 4.53 (s, 2H), 3.98–3.88 (m, 1H), 3.45 (q, J=7.2 Hz, 2H), 3.37–3.35 (m, 2H), 2.73–2.66 (m, 3H), 2.35–2.25 (m, 1H), 1.70–1.43 (m, 2H), 1.18–1.04 (m, 15H).

Example 49(138)

N-Hydroxy-2(S)-(3-methoxybenzyl)-5-ethoxymethoxy-4(S)-[N-(4-methylphenylcarbonyl)amino]pentanamide

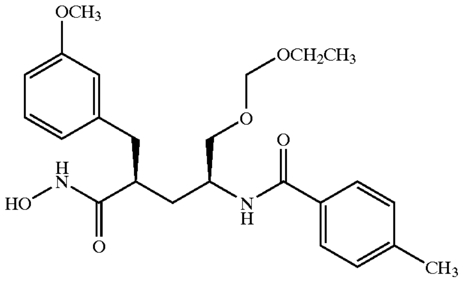

TLC: Rf 0.53 (Chloroform:Methanol=9:1);

NMR ($d_6$-DMSO): δ10.33 (d, J=1.8 Hz, 1H), 8.67 (d, J=1.8 Hz, 1H), 8.06 (d, J=9.0 Hz, 1H), 7.76 (d, J=8.4 Hz, 2H), 7.24 (d, J=8.4 Hz, 2H), 7.13–7.08 (m, 1H), 6.71–6.66 (m, 3H), 4.56 (s, 2H), 4.17–4.30 (m, 1H), 3.65 (s, 3H), 3.53–3.41 (m, 4H), 2.72 (d, J=7.2 Hz, 2H), 2.40–2.30 (m, 1H), 2.34 (s, 3H), 1.81–1.59 (m, 2H), 1.07 (t, J=7.2 Hz, 3H).

Example 49(139)

N-Hydroxy-2(S)-benzyl-5-ethoxymethoxy-4(S)-[N-(1-cyclohexenylcarbonyl)amino]pentanamide

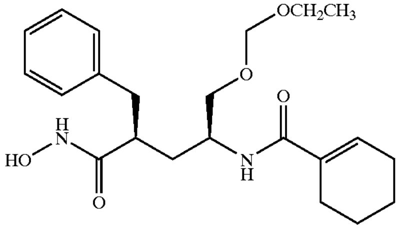

TLC: Rf 0.25 (Methylene chloride:Methanol=19:1);

NMR ($d_6$-DMSO): δ10.31 (brs, 1H), 8.65 (brs, 1H), 7.28–7.08 (m, 6H), 6.49 (brs, 1H), 4.53 (s, 2H), 4.05 (m, 1H), 3.43 (q, J=7.2 Hz, 2H), 3.47–3.35 (m, 2H), 2.69 (m, 2H), 2.28 (m, 1H), 2.20–2.04 (m, 4H), 1.74–1.46 (m, 6H), 1.09 (t, J=7.2 Hz, 3H).

Example 49(140)

N-Hydroxy-2(S)-benzyl-5-ethoxymethoxy-4(S)-[N [(1-cyclohexen-4-yl)carbonyl]amino]pentanamide

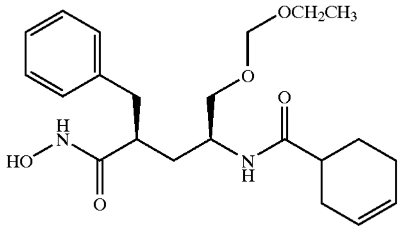

TLC: Rf 0.25 (Methylene chloride:Methanol=19:1);

NMR ($d_6$-DMSO): δ10.31 (brs, 1H), 8.67 (brs, 1H), 7.54 (d, J=8.4 Hz, 1H), 7.24–7.08 (m, 5H), 5.64 (m, 2H), 4.53 (s, 2H), 3.95 (m, 1H), 3.43 (q, J=7.2 Hz, 2H), 3.47–3.28 (m, 2H), 2.75–2.63 (m, 2H), 2.33–1.44 (m, 10H), 1.09 (t, J=7.2 Hz, 3H).

Example 49(141)

N-Hydroxy-2(S)-benzyl-5-ethoxymethoxy-4(S)-[N-(4-dimethylaminophenylcarbonyl)amino] pentanamide

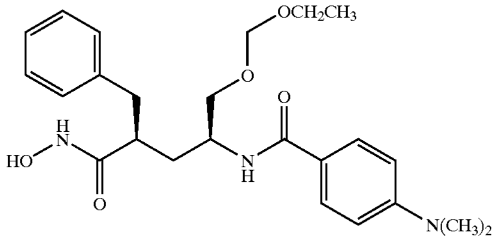

TLC: Rf 0.63 (Chloroform:Methanol=9:1);

NMR($d_6$-DMSO): δ10.33 (s, 1H), 8.65 (s, 1H), 7.78–7.69 (m, 3H), 7.25–7.08 (m, 5H), 6.69 (d, J=9.0 Hz, 2H), 4.58 (s, 2H), 4.29–4.18 (m, 1H), 3.56–3.41 (m, 4H), 2.97 (s, 6H), 2.77 (d, J=7.2 Hz, 2H), 2.42–2.32 (m, 1H), 1.82–1.62 (m, 2H), 1.10 (t, J=6.9 Hz, 3H).

Example 49(142)

N-Hydroxy-2(S)-benzyl-5-ethoxymethoxy-4(S)-[N-(4-carbamoylphenylcarbonyl)amino]pentanamide

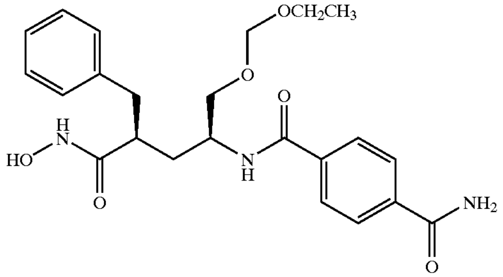

TLC: Rf 0.37 (Chloroform:Methanol=9:1);

NMR ($d_6$-DMSO): δ10.37 (s, 1H), 8.68 (s, 1H), 8.24 (d, J=8.7 Hz, 1H), 8.08 (s, 1H), 7.98–7.87 (m, 4H), 7.48 (s, 1H), 7.28–7.10 (m, 5H), 4.58 (s, 2H), 4.32–4.19 (m, 1H), 3.58–3.40 (m, 4H), 2.77 (d, J=6.9 Hz, 2H), 2.42–2.32 (m, 1H), 1.83–1.61 (m, 2H), 1.09 (t, J=7.2 Hz, 3H).

Example 49(143)

N-Hydroxy-2(S)-benzyl-5-ethoxymethoxy-4(S)-[N-(4-methoxycarbonylphenylcarbonyl)amino] pentanamide

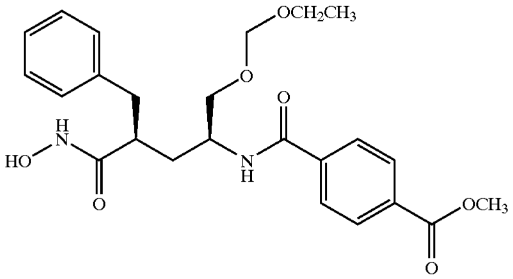

TLC: Rf 0.31 (Chloroform:Methanol=19:1);

NMR ($d_6$-DMSO): δ10.38 (s, 1H), 8.69 (s, 1H), 8.35 (d, J=8.4 Hz, 1H), 8.04 (d, J=8.8 Hz, 2H), 7.98 (d, J=8.8 Hz, 2H), 7.28–7.06 (m, 5H), 4.58 (s, 2H), 4.35–4.18 (m, 1H), 3.89 (s, 3H), 3.60–3.39 (m, 4H), 2.77 (d, J=7.0 Hz, 2H), 2.42–2.28 (m, 1H), 1.88–1.59 (m, 2H), 1.09 (t, J=7.0 Hz, 3H).

Example 49(144)

N-Hydroxy-2(S)-benzyl-5-ethoxymethoxy-4(S)-[N-(cyclopentylcarbonyl)amino]pentanamide

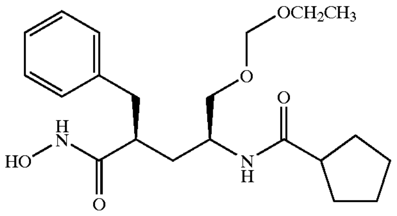

TLC: Rf 0.51 (Methylene chloride:Methanol=9:1);

NMR ($d_6$-DMSO): δ10.32 (brs, 1H), 8.68 (brs, 1H), 7.49 (d, J=8.7 Hz, 1H), 7.25–7.08 (m, 5H), 4.53 (s, 2H), 3.92 (m, 1H), 3.43 (q, J=7.2 Hz, 2H), 3.40–3.35 (m, 2H), 2.72 (dd, J=13.5, 8.7 Hz, 1H), 2.65 (dd, J=13.5, 5.6 Hz, 1H), 2.49 (m, 1H), 2.29 (m, 1H), 1.80–1.40 (m, 10H), 1.09 (t, J=7.2 Hz, 3H).

Example 49(145)

N-Hydroxy-2(S)-(naphthalene-2-yl)-5-ethoxymethoxy-4(S)-[N-(trans-4-methylcyclohexylcarbonyl)amino]pentanamide

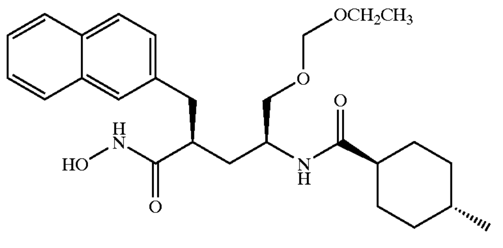

TLC: Rf 0.31 (Chloroform:Methanol=19:1);

NMR ($d_6$-DMSO): δ10.33 (s, 1H), 7.90–7.73 (m, 3H), 7.60 (s, 1H), 7.54–7.37 (m, 3H), 7.34–7.22 (m, 1H), 4.60–4.46 (m, 2H), 4.12–3.90 (m, 1H), 3.52–3.22 (m, 4H), 2.87 (d, J=6.6 Hz, 2H), 2.45–2.28 (m, 1H), 2.17–1.94 (m, 1H), 1.88–1.18 (m, 10H), 1.09 (t, J=7.0 Hz, 3H), 1.00–0.72 (m, 4H).

Example 49(146)

N-Hydroxy-2(S)-benzyl-5-ethoxymethoxy-4(S)-[N-(4-trifluoromethylphenylcarbonyl)amino] pentanamide

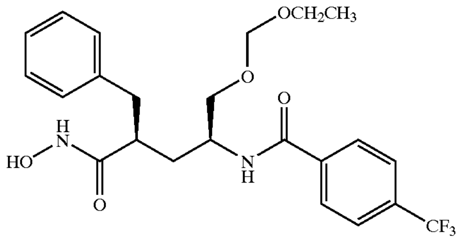

TLC: Rf 0.58 (Chloroform:Methanol=9:1);

NMR ($d_6$-DMSO): δ10.34 (s, 1H), 8.67 (d, J=2.1 Hz, 1H), 8.38 (d, J=8.7 Hz, 1H), 8.04 (d, J=8.4 Hz, 2H), 7.83(d, J=8.4 Hz, 2H), 7.25–7.10 (m, 5H), 4.56(s, 2H), 4.30–4.18 (m, 1H), 3.50–3.36 (m , 4H), 2.76–2.74 (m, 2H), 2.41–2.30 (m, 1H), 1.81–1.62 (m, 2H), 1.07 (t, J=7.2 Hz, 3H).

Example 49(147)

N-Hydroxy-2(S)-benzyl-5-ethoxymethoxy-4(S)-[N-(4-iodophenylcarbonyl)amino]pentanamide

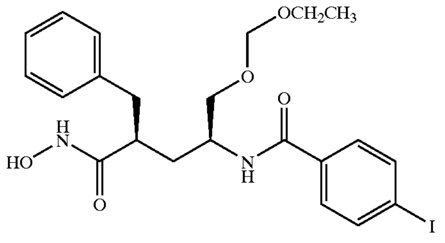

TLC: Rf 0.45 (Chloroform:Methanol=9:1);

NMR ($d_6$-DMSO): δ10.33 (s, 1H), 8.65 (brs, 1H), 8.19 (d, J=8.4 Hz, 1H), 7.83 (d, J=8.4 Hz, 2H), 7.63 (d, J=8.4 Hz, 2H), 7.24–7.09 (m, 5H), 4.55 (s, 2H), 4.28–4.15 (m, 1H), 3.48–3.39 (m, 4H), 2.74 (d, J=7.2 Hz, 2H), 2.38–2.29 (m, 1H), 1.79–1.59 (m, 2H), 1.06 (t, J=7.2 Hz, 3H).

Example 49(148)

N-Hydroxy-2(S)-benzyl-5-ethoxymethoxy-4(S)-[N-[4-(2-iodoethynyl)phenylcarbonyl]amino] pentanamide

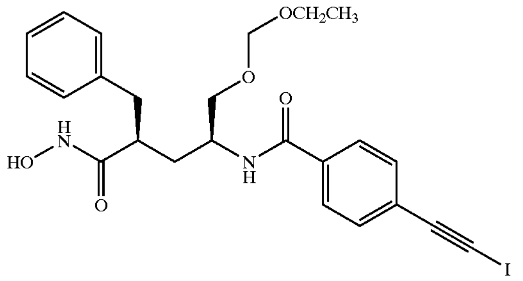

TLC: Rf 0.37 (Chloroform:Methanol=9:1);

NMR ($d_6$-DMSO): δ10.35 (s, 1H), 8.66 (d, J=1.5 Hz, 1H), 8.28 (d, J=8.4 Hz, 1H), 7.90 (d, J=8.4 Hz, 2H), 7.71 (d, J=8.4 Hz, 2H), 7.24–7.10 (m, 5H), 4.56 (s, 2H), 4.29–4.18 (m, 1H), 3.50–3.35 (m, 4H), 2.75 (d, J=6.9 Hz, 2H), 2.40–2.31 (m, 1H), 1.81–1.61 (m, 2H), 1.07 (t, J=6.9 Hz, 3H).

Example 49(149)

N-Hydroxy-2(S)-benzyl-5-ethoxymethoxy-4(S)-[N-(cycloheptylcarbonyl)amino]pentanamide

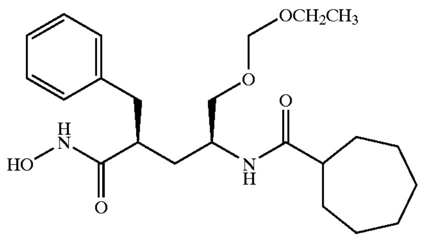

TLC: Rf 0.26 (Methylene chloride:Methanol=19:1);

NMR ($d_6$-DMSO): δ10.32 (brs, 1H), 8.68 (brs, 1H), 7.41 (d, J=8.7 Hz, 1H), 7.25–7.08 (m, 5H), 4.53 (s, 2H), 3.90 (m, 1H), 3.43 (q, J=7.2 Hz, 2H), 3.40–3.30 (m, 2H), 2.68 (m, 2H), 2.33–2.20 (m, 2H), 1.80–1.30 (m, 14H), 1.09 (t, J=7.2 Hz, 3H).

Example 49(150)

N-Hydroxy-2(S)-benzyl-5-ethoxymethoxy-4(S)-[N-(2-thienylcarbonyl)amino]pentanamide

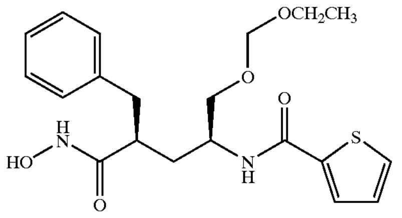

TLC: Rf 0.48 (Chloroform:Methanol=9:1);

NMR ($d_6$-DMSO): δ10.35 (s, 1H), 8.17 (d, J=9.0 Hz, 1H), 7.79–7.76 (m, 1H), 7.72–7.69 (m, 1H), 7.23–7.06 (m, 6H), 4.54 (s, 2H), 4.19–4.08 (m, 1H), 3.50–3.38 (m, 4H), 2.76–2.67 (m, 2H), 2.40–2.30 (m, 1H), 1.79–1.57 (m, 2H), 1.05 (t, J=7.2 Hz, 3H).

Example 49(151)

N-Hydroxy-2(R)-(3,4,4-trimethyl-2,5-dioxoimidazolizin-1-yl)methyl-5-ethoxymethoxy-4(S)-[N-(4-methylphenylcarbonyl)amino]pentanamide

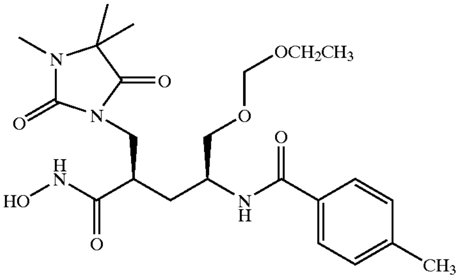

TLC: Rf 0.41 (Chloroform:Methanol=9:1);

NMR ($d_6$-DMSO): δ10.63 (s, 1H), 8.78 (s, 1H), 7.99 (d, J=7.8 Hz, 1H), 7.73 (d, J=8.1 Hz, 2H), 7.24 (d, J=8.1 Hz, 2H), 4.57 (s, 2H), 4.10–3.95 (m, 1H), 3.60–3.30 (m, 6H, overlap with H2O in DMSO), 2.78 (s, 3H), 2.70–2.50 (m, 1H), 2.35 (s, 3H), 1.72 (t, J=6.9 Hz, 2H), 1.30 (s, 3H), 1.28 (s, 3H), 1.08 (t, J=6.9 Hz, 3H).

Example 49(152)

N-Hydroxy-2(S)-benzyl-5-ethoxymethoxy-4(S)-[N-[(2-bromo-5-thienyl)carbonyl]amino]pentanamide

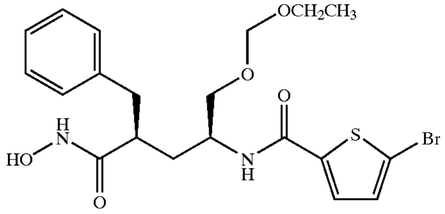

TLC: Rf 0.38 (Chloroform:Methanol=9:1);

NMR ($d_6$-DMSO): δ10.35 (s, 1H), 8.27 (d, J=8.7 Hz, 1H), 7.60 (d, J=3.9 Hz, 1H), 7.27–7.17 (m, 3H), 7.17–7.06 (m, 3H), 4.53 (s, 2H), 4.14–4.03 (m, 1H), 3.49–3.36 (m, 4H), 2.78–2.63 (m, 2H), 2.38–2.27 (m, 1H), 1.77–1.56 (m, 2H), 1.05 (t, J=6.9 Hz, 3H).

Example 49(153)

N-Hydroxy-2(S)-benzyl-5-ethoxymethoxy-4(S)-[N-(4-bromophenylcarbonyl)amino]pentanamide

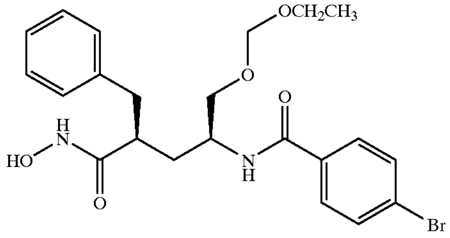

TLC: Rf 0.46 (Chloroform:Methanol=9:1);

NMR ($d_6$-DMSO): δ10.32 (s, 1H), 8.19 (d, J=8.4 Hz, 1H), 7.78 (d, J=8.5 Hz, 2H), 7.64 (d, J=8.5 Hz, 2H), 7.23–7.06 (m, 5H), 4.54 (s, 2H), 4.24–4.13 (m, 1H), 3.50–3.36 (m, 4H), 2.76–2.69 (m, 2H), 2.38–2.27 (m, 1H), 1.79–1.58 (m, 2H), 1.05 (t, J=7.0 Hz, 3H).

Example 49(154)

N-Hydroxy-2(S)-benzyl-5-ethoxymethoxy-4(S)-[N-(4-hydroxymethylphenylcarbonyl)amino]pentanamide

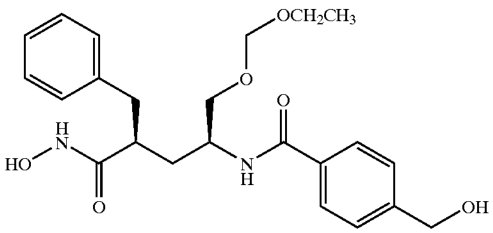

TLC: Rf 0.25 (Chloroform:Methanol=9:1);

NMR ($d_6$-DMSO): δ10.32 (s, 1H), 8.65 (s, 1H), 8.04 (d, J=8.4 Hz, 1H), 7.79 (d, J=7.8 Hz, 2H), 7.35 (d, J=7.8 Hz, 2H), 7.23–7.06 (m, 5H), 5.26 (t, J=5.7 Hz, 1H), 4.55 (s, 2H), 4.52(d, J=5.7 Hz, 2H), 4.27–4.15 (m, 1H), 3.55–3.37 (m, 4H), 2.76–2.70 (m, 2H), 2.34 (m, 1H), 1.81–1.59 (m, 2H), 1.06 (t, J=7.2 Hz, 3H).

Example 49(155)

N-Hydroxy-2(S)-(benzothiophen-3-yl)-5-ethoxymethoxy-4(S)-[N-(trans-4-methylcyclohexylcarbonyl)amino]pentanamide

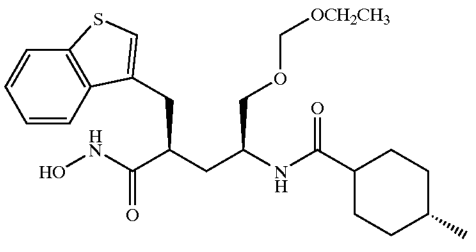

TLC: Rf 0.37 (Chloroform:Methanol=19:1);

NMR ($d_6$-DMSO): δ10.39 (s, 1H), 8.72 (s, 1H), 7.95–7.90 (m, 1H), 7.83–7.76 (m, 1H), 7.48 (d, J=8.7 Hz, 1H), 7.40–7.30 (m, 2H), 7.29 (s, 1H), 4.56–4.48 (m, 2H), 4.12–3.97 (m, 1H), 3.47–3.28 (m, 4H), 3.01 (dd, J=14.4, 9.3 Hz, 1H), 2.93 (dd, J=14.4, 5.1 Hz, 1H), 2.56–2.41 (m, 1H), 2.09–1.96 (m, 1H), 1.82–1.53 (m, 6H), 1.48–1.20 (m, 3H), 1.09 (t, J=6.9 Hz, 3H), 0.98–0.78 (m, 5H).

Example 49(156)

N-Hydroxy-2(S)-benzyl-5-ethoxymethoxy-4(S)-[N-(4-cyanophenylcarbonyl)amino]pentanamide

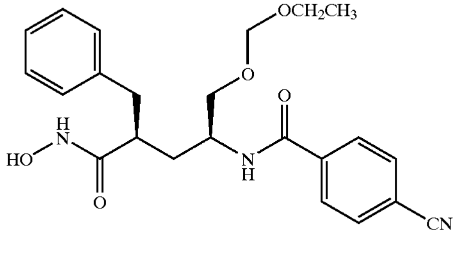

TLC: Rf 0.32 (Chloroform:Methanol=19:1);

NMR ($d_6$-DMSO): δ10.38 (s, 1H), 8.69 (s,1H), 8.42 (d, J=8.7 Hz, 1H), 8.02 (d, J=8.4 Hz, 2H), 7.94 (d, J=8.4 Hz, 2H), 7.30–7.09 (m, 5H), 4.58 (s, 2H), 4.31–3.97 (m, 1H), 3.57–3.39 (m, 4H), 2.83–2.68 (m, 2H), 2.42–2.30 (m, 1H), 1.83–1.61 (m, 2H), 1.09 (t, J=7.2 Hz, 3H).

Example 49 (157)

N-Hydroxy-2(S)-benzyl-5-ethoxymethoxy-4(S)-[N-[(1-acetylpiperidin-4-yl)carbonyl]amino] pentanamide

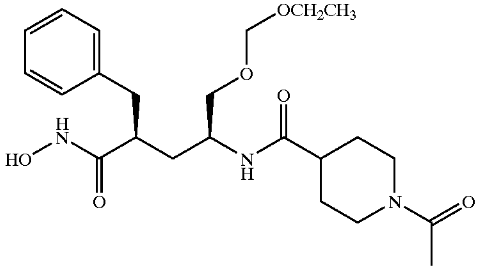

TLC: Rf 0.64 (Chloroform:Methanol=5:1);

NMR ($d_6$-DMSO): δ10.32 (brs, 1H), 7.58 (brd, J=9.0 Hz, 1H), 7.25–7.08 (m, 5H), 4.53 (s, 2H), 4.32 (brd, J=9.6 Hz, 1H), 3.93 (m, 1H), 3.79 (brd, J=12.6 Hz, 1H), 3.43 (q, J=6.9 Hz, 2H), 3.35 (m, 2H), 2.98 (brt, J=12.0 Hz, 1H), 2.68 (m, 2H), 2.49 (m, 1H), 2.40–2.20 (m, 2H), 1.98 (s, 3H), 1.75–1.30 (m, 6H), 1.09 (t, J=6.9 Hz, 3H).

Example 49(158)

N-Hydroxy-2(S)-benzyl-5-ethoxymethoxy-4(S)-[N-[(1-methylpiperidin-4-yl)carbonyl]amino] pentanamide

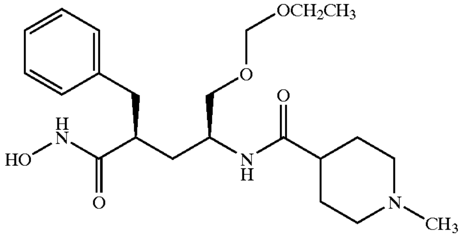

TLC: Rf 0.39 (Chloroform:Methanol:Acetic acid=7:2:1);

NMR ($d_6$-DMSO): δ10.30 (brs, 1H), 8.67 (brs, 1H), 7.48 (brd, J=9.0 Hz, 1H), 7.24–7.07 (m, 5H), 4.52 (s, 2H), 3.93 (m, 1H), 3.42 (q, J=7.2 Hz, 2H), 3.34 (m, 2H), 2.70 (m, 4H), 2.26 (m, 1H), 2.00 (m, 1H), 2.1 0 (s, 3 H), 1.81–1.45 (m, 8H), 1.08 (t, J=7.2 Hz, 3H).

Example 49(159)

N-Hydroxy-2(S)-benzyl-5-ethoxymethoxy-4(S)-[N-(4-formylphenylcarbonyl)amino]pentanamide

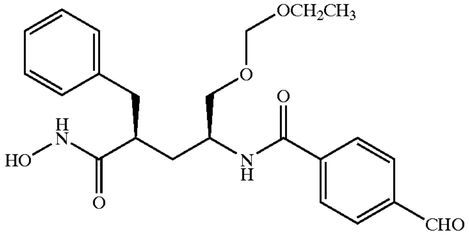

TLC: Rf 0.36 (Chloroform:Methanol=9:1);

NMR ($d_6$-DMSO): δ10.38 (s, 1H), 10.09 (s, 1H), 8.69 (s, 1H), 8.38 (d, J=8.4 Hz, 1H), 8.05 (d, J=8.4 Hz, 2H), 7.99 (d, J=8.4 Hz, 2H), 7.30–7.20 (m, 2H), 7.20–7.10 (m, 3H), 4.58 (s, 2H), 4.32–4.20 (m, 1H), 3.60–3.40 (m, 4H), 2.83–2.70 (m, 2H), 2.45–2.32 (m, 1H), 1.85–1.62 (m, 2H), 1.09 (t, J=6.9 Hz, 3H).

Example 49(160)

N-Hydroxy-2(S)-(3-methoxybenzyl)-5-ethoxymethoxy-4(S)-[N-(4-nitrophenylcarbonyl)amino]pentanamide

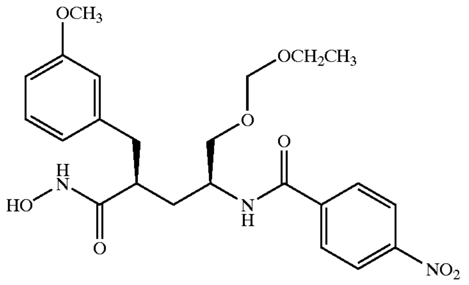

TLC: Rf 0.40 (Chloroform:Methanol=9:1);

NMR ($d_6$-DMSO): δ10.38 (d, J=1.8 Hz, 1H), 8.70 (d, J=1.8 Hz, 1H), 8.51 (d, J=8.4 Hz, 1H), 8.31 (d, J=8.9 Hz, 2H), 8.09 (d, J=8.9 Hz, 2H), 7.18–7.10 (m, 1H), 6.75–6.65 (m, 3H), 4.58 (s, 2H), 4.30–4.20 (m, 1H), 3.69 (s, 3H), 3.60–3.40 (m, 4H), 2.80–2.65 (m, 2H), 2.45–2.30 (m, 1H), 1.85–1.60 (m, 2H), 1.09 (t, J=7.1 Hz, 3H).

Example 49(161)

N-Hydroxy-2(S)-(3-methoxybenzyl)-5-ethoxymethoxy-4(S)-[N-(4-chlorophenylcarbonyl)amino]pentanamide

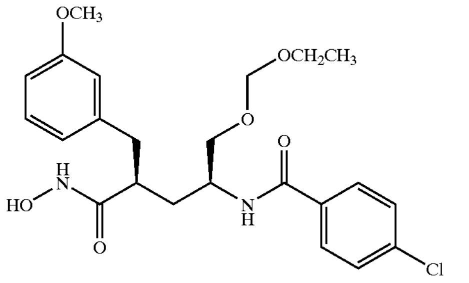

TLC: Rf 0.47 (Chloroform:Methanol=9:1);

NMR ($d_6$-DMSO): δ10.36 (s, 1H), 8.23 (d, J=8.4 Hz, 1H), 7.89 (d, J=8.6 Hz, 2H), 7.53 (d, J=8.6 Hz, 2H), 7.17–7.08 (m, 1H), 6.80–6.65 (m, 3H), 4.58 (s, 2H), 4.30–4.18 (m, 1H), 3.68 (s, 3H), 3.60–3.35 (m, 4H, overlap with H2O in DMSO), 2.80–2.65 (m, 2H), 2.42–2.30 (m, 1H), 1.85–1.60 (m, 2H), 1.09 (t, J=6.9 Hz, 3H).

Example 49(162)

N-Hydroxy-2(S)-(4-methoxybenzyl)-5-ethoxymethoxy-4(S)-[N-(4-methylphenylcarbonyl)amino]pentanamide

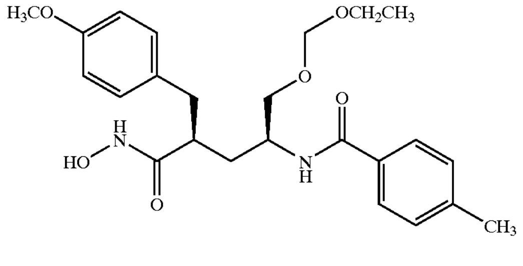

TLC: Rf 0.49 (Chloroform:Methanol=9:1);

NMR ($d_6$-DMSO): δ10.30 (s, 1H), 8.64 (s, 1H), 8.02 (d, J=8.8 Hz, 1H), 7.75 (d, J=8.4 Hz, 2H), 7.24 (d, J=8.4 Hz, 2H), 7.02 (d, J=8.4 Hz, 2H), 6.76 (d, J=8.4 Hz, 2H), 4.56 (s, 2H), 4.12–4.30 (m, 1H), 3.68 (s, 3H), 3.49–3.38 (m, 4H), 2.68 (d, J=7.4 Hz, 2H), 2.39–2.22 (m, 1H), 2.34 (s, 3H), 1.82–1.58 (m, 2H), 1.07 (t, J=7.2 Hz, 3H).

Example 49(163)

N-Hydroxy-2(S)-(2-methoxybenzyl)-5-ethoxymethoxy-4(S)-[N-(4-methylphenylcarbonyl)amino]pentanamide

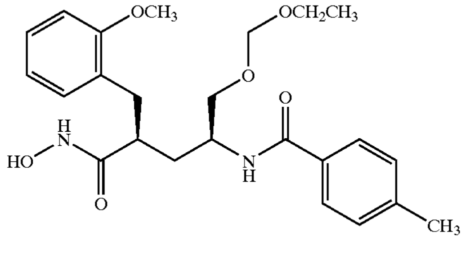

TLC: Rf 0.51 (Chloroform:Methanol=9:1);

NMR ($d_6$-DMSO): δ10.30 (s, 1H), 8.63 (d, J=1.5 Hz, 1H), 7.93 (d, J=8.4 Hz, 1H), 7.74 (d, J=8.4 Hz, 2H), 7.23 (d, J=8.4 Hz, 2H), 7.16–6.76 (m, 4H), 4.55 (s, 2H), 4.19–4.08 (m, 1H), 3.62 (s, 3H), 3.48–3.38 (m, 4H), 2.71–2.62 (m, 2H), 2.51–2.40 (m, 1H), 2.33 (s, 3H), 1.75–1.70 (m, 2H), 1.06 (t, J=7.2 Hz, 3H).

Example 49(164)

N-Hydroxy-2(S)-(naphthalene-1-yl)methyl-5-ethoxymethoxy-4(S)-[N-(4-methylphenylcarbonyl)amino]pentanamide

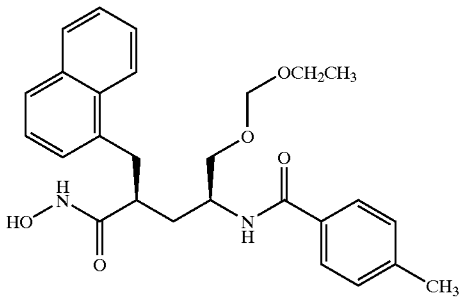

TLC: Rf 0.44 (Chloroform:Methanol=9:1);

NMR ($d_6$-DMSO): δ10.24 (s, 1H), 8.61 (s, 1H), 8.11 (d, J=8.4 Hz, 1H), 7.98 (d, J=8.4 Hz, 1H), 7.86–7.79 (m, 4H), 7.74–7.71 (d, J=8.4 Hz, 1H), 7.44–7.23 (m, 5H), 4.54 (s, 2H), 4.30–4.20 (m, 1H), 3.50–3.47 (m, 2H), 3.95 (q, J=7.2 Hz, 2H), 3.29–3.10 (m, 2H), 2.62–2.51 (m, 1H), 1.95–1.75 (m, 2H), 1.04 (t, J=7.2 Hz, 3H).

Example 49(165)

N-Hydroxy-2(S)-(3-methoxybenzyl)-5-ethoxymethoxy-4(S)-[N-(trans-4-methylcyclohexylcarbonyl)amino]pentanamide

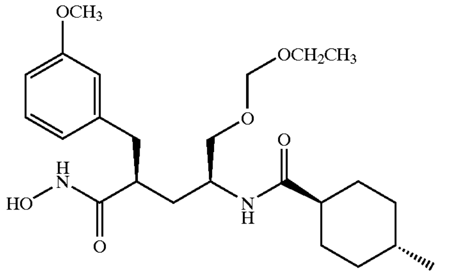

TLC: Rf 0.56 (Chloroform:Methanol=9:1);

NMR ($d_6$-DMSO): δ10.31 (s, 1H), 9.00–8.30 (brs, 1H), 7.44 (d, J=8.7 Hz, 1H), 7.13 (t, J=8.0 Hz, 1H), 6.80–6.65 (m, 3H), 4.55 (d, J=6.6 Hz, 1H), 4.51 (d, J=6.6 Hz, 1H), 4.00–3.85 (m, 1H), 3.70 (s, 3H), 3.44 (q, J=7.1 Hz, 2H), 3.50–3.20 (m, 2H), 2.75–2.50 (m, 2H), 2.30–2.20 (m, 1H), 2.10–1.90 (m, 1H), 1.8–1.20 (m, 9H), 1.09 (t, J=7.1 Hz, 3H), 0.84 (d, J=6.6 Hz, 3H), 1.00–0.80 (m, 2H).

Example 49(166)

N-Hydroxy-2(S)-benzyl-5-ethoxymethoxy-4(S)-[N-(4-methoxycyclohexylcarbonyl)amino]pentanamide

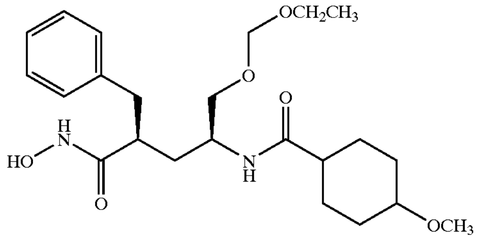

TLC: Rf 0.40 (Methylene chloride:Methanol=9:1);

NMR ($d_6$-DMSO): δ10.30 (brs, 1H), 8.67 (brs, 1H), 7.48 (brd, J=8.4 Hz, 0.4H), 7.41 (brd, J=8.4 Hz, 0.6H), 7.24–7.08 (m, 5H), 4.53 (s, 2H), 3.93 (m, 1H), 3.43 (q, J=7.2 Hz, 2H), 3.34 (m, 3H), 3.21 (s, 1.2H), 3.18 (s, 1.8H), 2.67 (m, 2H), 2.30–1.30 (m, 12H), 1.09 (t, J=7.2 Hz, 3H).

Example 49(167)

N-Hydroxy-2(S)-(benzothiophen-3-yl)methyl-5-ethoxymethoxy-4(S)-[N-(4-bromophenylcarbonyl)amino]pentanamide

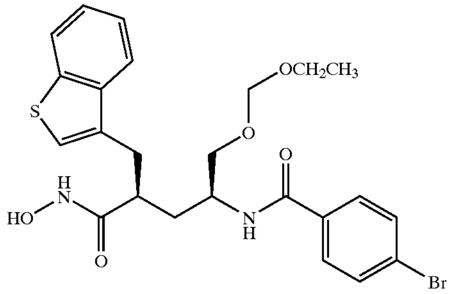

TLC: Rf 0.43 (Chloroform:Methanol=9:1);

NMR ($d_6$-DMSO): δ10.38 (d, J=1.2 Hz, 1H), 8.68 (d, J=1.2 Hz, 1H), 8.27 (d, J=8.4 Hz, 1H), 7.91 (d, J=7.5 Hz, 1H), 7.83–7.76 (m, 3H), 7.69–7.66 (m, 2H), 7.34–7.22 (m, 3H), 4.55 (s, 2H), 4.38–4.25 (m, 1H), 3.49 (d, J=5.1 Hz, 2H), 3.42 (q, J=7.2 Hz, 2H), 3.02–2.98 (m, 2H), 2.56–2.48 (m, 1H), 1.91–1.70 (m, 2H), 1.04 (t, J=7.2 Hz, 3H).

Example 49(168)

N-Hydroxy-2(S)-(benzothiophen-3-yl)-5-ethoxymethoxy-4(S)-[N-(4-chlorophenylcarbonyl)amino]pentanamide

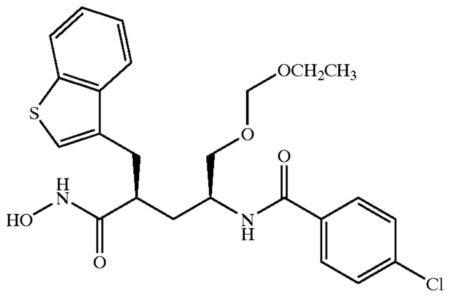

TLC: Rf 0.44 (Chloroform:Methanol=9:1);

NMR ($d_6$-DMSO): δ10.38 (d, J=1.5 Hz, 1H), 8.68 (d, J=1.5 Hz, 1H), 8.27 (d, J=8.4 Hz, 1H), 7.93–7.87 (m, 3H), 7.78 (d,J=7.5 Hz, 1H), 7.55–7.52 (m, 2H), 7.34–7.22 (m, 3H), 4.55 (s, 2H), 4.38–4.24 (m, 1H), 3.49 (d, J=5.4 Hz, 2H), 3.41 (q, J=7.2 Hz, 2H), 3.04–2.92 (m, 2H), 2.58–2.42 (m, 1H), 1.90–1.70 (m, 2H), 1.05 (t, J=7.2 Hz, 3H).

Example 49(169)

N-Hydroxy-2(S)-benzyl-5-ethoxymethoxy-4(S)-[N-[(2-chloropyridin-5-yl)carbonyl]amino]pentanamide

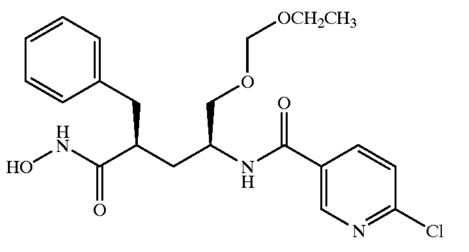

TLC: Rf 0.36 (Chloroform:Methanol=9:1);

NMR ($d_6$-DMSO): δ10.35 (s, 1H), 8.81 (d, J=2.4 Hz, 1H), 8.65 (s, 1H), 8.43 (d, J=9.0 Hz, 1H), 8.21 (dd, J=2.4 Hz, 8.5 Hz, 1H), 7.61 (d, J=8.5 Hz, 1H), 7.24–7.07 (m, 5H), 4.54 (s, 2H), 4.24–4.14 (m, 1H), 3.50–3.37 (m, 4H), 2.79–2.66 (m, 2H), 2.39–2.28 (m, 1H), 1.79–1.60 (m, 2H), 1.05 (t, J=7.1 Hz, 3H).

Example 49(170)

N-Hydroxy-2(S)-(3,5-dimethoxybenzyl)-5-ethoxymethoxy-4(S)-[N-(4-methylphenylcarbonyl)amino]pentanamide

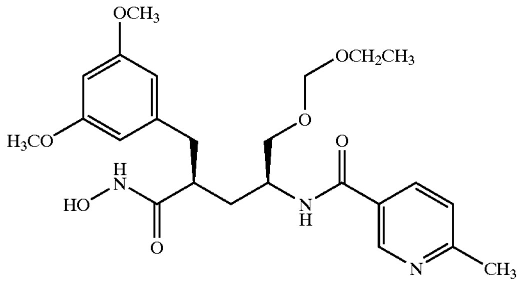

TLC: Rf 0.33 (Chloroform:Methanol=9:1);

NMR ($d_6$-DMSO): δ10.33 (brs, 1H), 8.67 (brs, 1H), 8.02 (brd, J=8.7 Hz, 1H), 7.76 (d, J=8.1 Hz, 2H), 7.25 (d, J=8.1 Hz, 2H), 6.26 (s, 3H), 4.57 (s, 2H), 4.24 (m, 1H), 3.63 (s, 6H), 3.49 (m, 2H), 3.45 (q, J=7.2 Hz, 2H), 2.68 (brd, J=7.2 Hz, 2H), 2.34 (s, 3H), 2.34 (m, 1H), 1.80–1.59 (m, 2H), 1.07 (t, J=7.2 Hz, 3H).

Example 49(171)

N-Hydroxy-2(S)-benzyl-5-ethoxymethoxy-4(S)-[N-(4-methylcyclohexylcarbonyl)amino]pentanamide

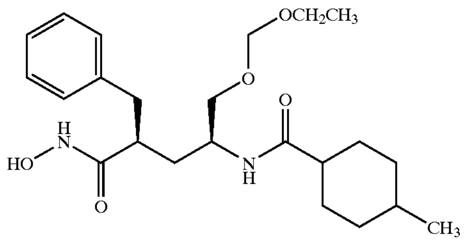

TLC: Rf 0.38 (Chloroform:Methanol=9:1);

NMR ($d_6$-DMSO): δ10.29 (d, J=1.5 Hz, 1H), 8.65 (d, J=1.5 Hz, 1H), 7.42 (brd, J=8.4 Hz, 0.16H), 7.34 (brd, J=8.4 Hz, 0.84H), 7.23–7.08 (m, 5H) 4.52 (s, 2H), 3.95 (m, 1H), 3.43 (q, J=7.2 Hz, 2H), 3.35 (m, 2H), 2.68 (m, 2H), 2.30–2.10 (m 2H), 1.80–1.30 (m, 11H), 1.08 (t, J=7.2 Hz, 3H), 0.88 (d, J=6.6 Hz, 2.5H), 0.83 (d, J=6.6 Hz, 0.5H).

Example 49(172)

N-Hydroxy-2(S)-(3-methoxybenzyl)-5-ethoxymethoxy-4(S)-[N-(4-cyanophenylcarbonyl)amino]pentanamide

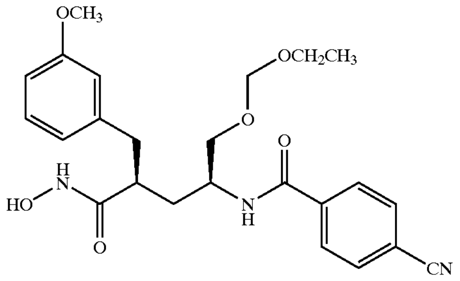

TLC: Rf 0.32 (Chloroform:Methanol=19:1);

NMR ($d_6$-DMSO): δ10.37 (s, 1H), 8.68 (s, 1H), 8.42 (d, J=8.4 Hz, 1H), 8.02 (d, J=8.4 Hz, 2H), 7.95 (d, J=8.4 Hz, 2H), 7.20–7.08 (m, 1H), 6.76–6.65 (m, 3H), 4.58 (s, 2H), 4.33–4.15 (m, 1H), 3.68 (s, 3H), 3.55–3.39 (m, 4H), 2.80–2.56 (m, 2H), 2.43–2.28 (m, 1H), 1.88–1.58 (m, 2H), 1.09 (t, J=7.2 Hz, 3H).

Example 49(173)

N-Hydroxy-2(R)-(3,4,4-trimethyl-2,5-dioxoimidazolidin-1-yl)methyl-5-ethoxymethoxy-4(S)-[N-(trans-4-ethylcyanohexylcarbonyl)amino]pentanamide

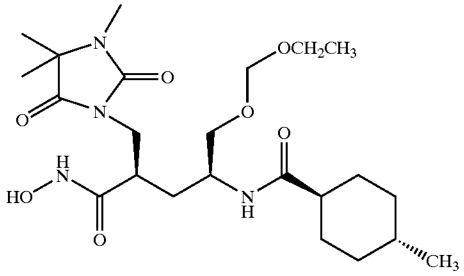

TLC: Rf 0.47 (Chloroform:Methanol=19:1);

NMR ($d_6$-DMSO): δ10.59 (s, 1H), 8.78 (s, 1H), 7.43 (d, J=8.4 Hz, 1H), 4.52 (d, J=6.9 Hz, 1H), 4.50 (d, J=6.9 Hz, 1H), 3.77–3.65 (m, 1H), 3.48–3.33 (m, 4H), 2.76 (s, 3H), 2.52–2.41 (m, 1H), 2.03–1.92 (m, 1H), 1.45–1.71 (m, 6H), 1.37–1.20 (m, 1H), 1.27 (s, 3H), 1.26 (s, 3H), 1.08 (t, J=7.2 Hz, 3H), 0.89–0.78 (m, 2H), 0.83 (d, J=6.3 Hz, 3H).

Example 49(174)

N-Hydroxy-2(R)-(benzofuran-2-yl)methyl-5-ethoxymethoxy-4(S)-[N-(trans-4-methylcyclohexylcarbonyl)amino]pentanamide

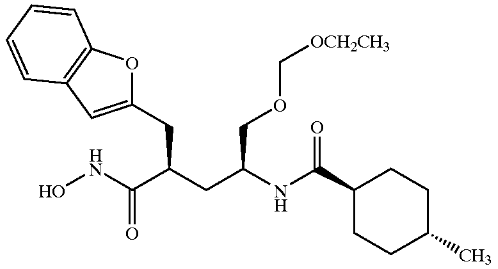

TLC: Rf 0.42 (Chloroform:Methanol=19:1);

NMR ($d_6$-DMSO): δ10.52 (s, 1H), 8.78 (s, 1H), 7.52–7.42 (m, 3H), 7.23–7.13 (m, 2H), 6.53 (s, 1H), 4.54 (d, J=6.6 Hz, 1H), 4.51 (d, J=6.6 Hz, 1H), 3.95–3.82 (m, 1H), 3.46–3.33 (m, 4H), 2.97–2.81 (m, 2H), 2.55–2.42 (m, 1H), 2.04–1.95 (m, 1H), 1.74–1.56 (m, 7H), 1.39–1.26 (m, 4H), 1.07 (t, J=7.2 Hz, 3H), 0.84 (d, J=6.6 Hz, 3H).

Example 49(175)

N-Hydroxy-2(S)-(benzothiophen-3-yl)methyl-5-ethoxymethoxy-4(S)-[N-(4-nitrophenylcarbonyl)amino]pentanamide

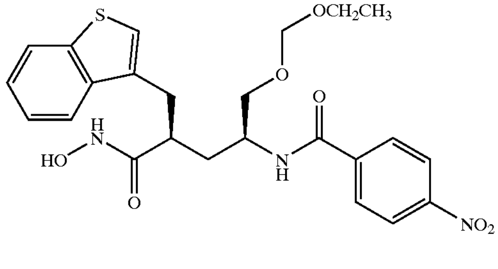

TLC: Rf 0.36 (Chloroform:Methanol=19:1);

NMR ($d_6$-DMSO): δ10.42 (s, 1H), 8.70 (brs, 1H), 8.55 (d, J=8.4 Hz, 1H), 8.32–8.29 (m, 2H), 8.11–8.08 (m, 2H), 7.93–7.90 (m, 1H), 7.81–7.78 (m, 1H), 7.34–7.25 (m, 3H), 4.55 (s, 2H), 4.38–4.25 (m, 1H), 3.51 (d, J=5.7 Hz, 2H), 3.41 (q, J=7.2 Hz, 2H), 3.05–2.94 (m, 2H), 2.57–2.53 (m, 1H), 1.91–1.72 (m, 2H), 1.04 (t, J=7.2 Hz, 3H).

Example 49(176)

N-Hydroxy-2(S)-benzyl-5-ethoxymethoxy-4(S)-[N-(4-cyanophenylcarbonyl)amino]pentanamide

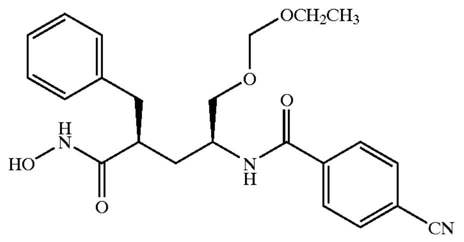

TLC: Rf 0.47 (Chloroform:Methanol=9:1);

NMR ($d_6$-DMSO): δ10.34 (s, 1H), 8.66 (s, 1H), 8.22 (d, J=8.4 Hz, 1H), 7.85 (d, J=8.4 Hz, 2H), 7.55 (d, J=8.4 Hz, 2H), 7.24–7.09 (m, 5H), 4.56 (s, 2H), 4.35 (s, 1H), 4.28–4.16 (m, 1H), 3.48 (d, J=6.0 Hz, 2H), 3.43 (q, J=6.9 Hz, 2H), 2.75 (d, J=7.2 Hz, 2H), 2.40–2.29 (m, 1H), 1.81–1.61 (m, 2H), 1.07 (t, J=6.9 Hz, 3H).

Example 49(177)

N-Hydroxy-2(S)-benzyl-5-ethoxymethoxy-4(S)-[N-(4-methylidencyclohexylcarbonyl)amino] pentanamide

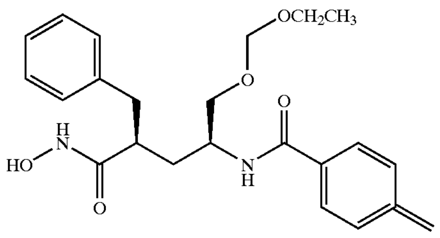

TLC: Rf 0.40 (Methylene chloride:Methanol=9:1);

NMR ($d_6$-DMSO): δ10.31 (s, 1H), 8.67 (s, 1H), 7.50 (brd, J=8.7 Hz, 1H), 7.25–7.08 (m, 5H), 4.61 (s, 2H), 4.53 (s, 2H), 3.93 (m, 1H), 3.43 (q, J=6.9 Hz, 2H), 3.35 (m, 2H), 2.68 (m, 2H), 2.25 (m, 4H), 2.05–1.30 (m, 8H), 1.09 (t, J=6.9 Hz, 3H).

Example 49(178)

N-Hydroxy-2(S)-benzyl-5-ethoxymethoxy-4(S)-[N-[(1-formylpiperidin-4-yl)carbonyl]amino] pentanamide

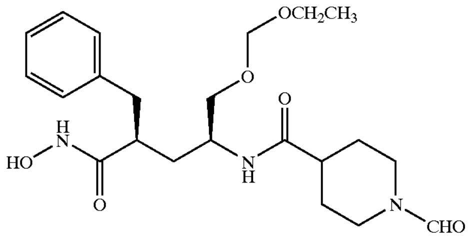

TLC: Rf 0.38 (Methylene chloride:Methanol=9:1);

NMR ($d_6$-DMSO): δ10.32 (s, 1H), 8.68 (s, 1H), 7.96 (s, 1H), 7.58 (brd, J=8.7 Hz, 1H), 7.25–7.08 (m, 5H), 4.53 (s, 2H), 4.13 (brd, J=12.3 Hz, 1H), 3.93 (m, 1H), 3.67 (brd, J=10.5 Hz, 1H), 3.43 (q, J=6.9 Hz, 2H), 3.35 (m, 2H), 3.00 (brt, J=12.3 Hz, 1H), 2.75–2.20 (m, 5H), 1.80–1.30 (m, 6H), 1.09 (t, J=6.9 Hz, 3H).

Example 49(179)

N-Hydroxy-2(S)-benzyl-5-ethoxymethoxy-4(S)-[N-[(1-methyl-1-cyclohexen-4-yl)carbonyl]amino] pentanamide

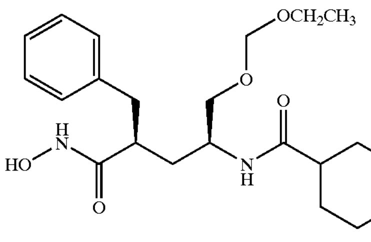

TLC: Rf 0.30 (Chloroform:Methanol=10:1);

NMR ($d_6$-DMSO): δ10.33 (brs, 1H), 7.53 (d, J=8.4 Hz, 1H), 7.30–7.05 (m, 5H), 5.35 (brs, 1H), 4.54 (s, 2H), 4.00–3.85 (m, 1H), 3.60–3.20 (m, 4H), 2.80–2.60 (m, 2H), 2.40–1.40 (m, 10H), 1.60 (s, 3H), 1.10 (t, J=7.2 Hz, 3H).

Example 49(180)

N-Hydroxy-2(S)-benzyl-5-ethoxymethoxy-4(S)-[N-[(4-methyl-1-cyclohexenyl)carbonyl]amino] pentanamide

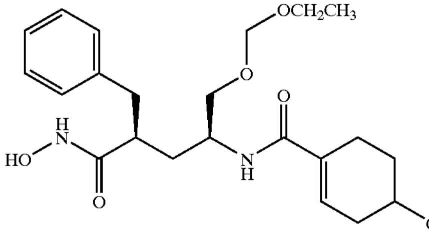

TLC: Rf 0.35 (Chloroform:Methanol=10:1);

NMR ($d_6$-DMSO): δ10.32 (s, 1H), 8.65 (s, 1H), 7.35–7.00 (m, 6H), 6.46 (brs, 1H), 4.54 (s, 2H), 4.20–3.90 (m, 1H), 3.50–3.20 (m, 4H), 2.80–2.60 (m, 2H), 2.40–2.20 (m, 4H), 1.80–1.50 (m, 5H), 1.20–1.00 (m, 1H), 1.09 (t, J=7.1 Hz, 3H), 0.93 (d, J=6.3 Hz, 3H).

Example 49(181)

N-Hydroxy-2(S)-benzyl-5-ethoxymethoxy-4(S)-[N-(4-fluorophenylcarbonyl)amino]pentanamide

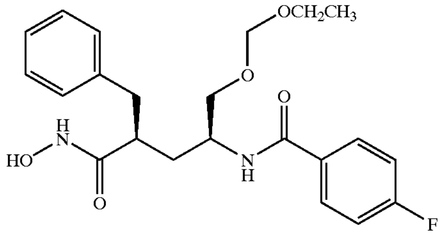

TLC: Rf 0.45 (Chloroform:Methanol=9:1);

NMR ($d_6$-DMSO): δ10.36 (s, 1H), 8.60–8.55 (br, 1H), 8.16 (d, J=8.7 Hz, 1H), 7.94 (dd, J=9.0, 5.4 Hz, 2H), 7.35–7.20 (m, 4H), 7.20–7.08 (m, 3H), 4.58 (s, 2H), 4.30–4.18 (m, 1H), 3.60–3.40 (m, 4H), 2.82–2.70 (m, 2H), 2.42–2.30 (m, 1H), 1.82–1.60(m, 2H), 1.09 (t, J=6.9 Hz, 3H).

Example 49(182)

N-Hydroxy-2(S)-benzyl-5-ethoxymethoxy-4(S)-[N-(4-chlorophenylcarbonyl)amino]pentanamide

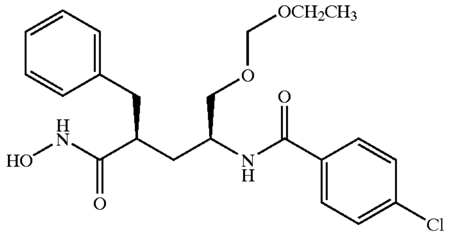

TLC: Rf 0.38 (Chloroform:Methanol=9:1);

NMR ($d_6$-DMSO): δ10.36 (s, 1H), 8.80–8.55 (br, 1H), 8.22 (d, J=8.4 Hz, 1H), 7.89 (d, J=8.7 Hz, 2H), 7.53 (d, J=8.7 Hz, 2H), 7.30–7.10 (m, 5H), 4.57 (s, 2H), 4.30–4.15 (m, 1H), 3.60–3.40 (m, 4H), 2.82–2.70 (m, 2H), 2.42–2.30 (m, 1H), 1.82–1.60 (m, 2H), 1.09 (t, J=7.1 Hz, 3H).

Example 49(183)

N-Hydroxy-2(S)-benzyl-5-ethoxymethoxy-4(S)-[N-(4-hydroxycyclohexylcarbonyl)amino]pentanamide

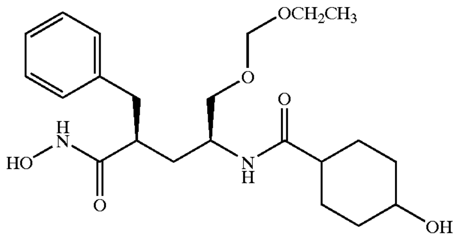

TLC: Rf 0.38 (Chloroform:Methanol:Acetic acid=9:1:0.5);

NMR ($d_6$-DMSO): δ10.29 (s, 1H), 7.44 (d, J=8.8 Hz, 0.4H), 7.35 (d, J=8.8 Hz, 0.6H), 7.26–7.03 (m, 5H), 4.51 (s, 2H), 4.02–3.82 (m, 1H), 3.76–3.67 (m, 1H), 3.41 (q, J=7.1 Hz, 2H), 3.39–3.26 (m, 2H), 2.72–2.62 (m, 2H), 2.33–2.19 (m, 1H), 2.15–1.90 (m, 1H), 1.87–1.24 (m, 10H), 1.07 (t, J=7.1 Hz, 3H).

Example 49(184)

N-Hydroxy-2(S)-(benzofuran-3-yl)methyl-5-ethoxymethoxy-4(S)-[N-(trans-4-methylcyclohexylcarbonyl)amino]pentanamide

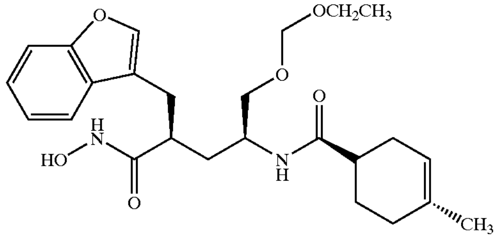

TLC: Rf 0.33 (Chloroform:Methanol=19:1);

NMR ($d_6$-DMSO): δ10.41 (s, 1H), 8.74 (s, 1H), 7.76–7.56 (m, 2H), 7.55–7.38 (m, 2H), 7.37–7.15 (m, 2H), 4.58–4.46 (m, 2H), 4.13–3.90 (m, 1H), 3.58–3.30 (m, 4H), 2.92–2.62 (m, 2H), 2.50–2.34 (m, 1H), 2.12–1.92 (m, 1H), 1.82–1.50 (m, 6H), 1.48–1.18 (m, 3H), 1.09 (t, J=7.0 Hz, 3H), 1.00–0.70 (m, 5H).

Example 49(185)

N-Hydroxy-2(S)-(3-methoxybenzyl)-5-ethoxymethoxy-4(S)-[N-(4-trifluoromethylphenylcarbonyl)amino]pentanamide

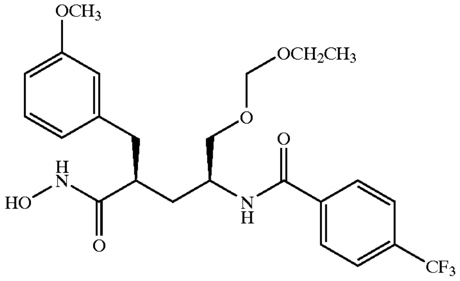

TLC: Rf 0.41 (Chloroform:Methanol=9:1);

NMR ($d_6$-DMSO): δ10.34 (s, 1H), 8.67 (s, 1H), 8.39 (d, J=8.7 Hz, 1H), 8.05 (d, J=8.0 Hz, 2H), 7.83 (d, J=8.0 Hz, 2H), 7.12 (t, J=8.4 Hz, 1H), 6.72–6.68 (m, 3H), 4.57 (s, 2H), 4.32–4.15 (m, 1H), 3.66 (s, 3H), 3.51–3.39 (m, 4H), 2.73 (d, J=7.0 Hz, 2H), 2.41–2.27 (m, 1H), 1.82–1.59 (m, 2H), 1.07 (t, J=7.0 Hz, 3H).

Example 49(186)

N-Hydroxy-2(S)-(1-methylindol-3-yl)methyl-5-(2-methoxyethoxy)methoxy-4(S)-[N-(trans-4-methylcyclohexylcarbonyl)amino]pentanamide

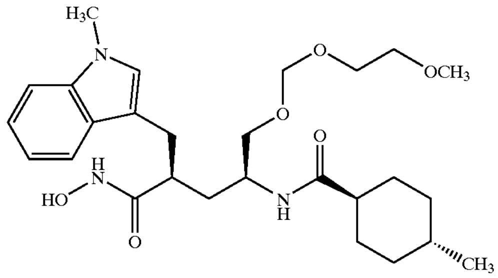

TLC: Rf 0.33 (Chloroform:Methanol=19:1);

NMR ($d_6$-DMSO): δ10.30 (s, 1H), 8.64 (s, 1H), 7.52 (d, J=7.8 Hz, 1H), 7.42 (d, J=8.4 Hz, 1H), 7.32 (d, J=7.8 Hz, 1H), 7.11 (t, J=7.8 Hz, 1H), 6.98 (s, 1H), 6.96 (t, J=7.8 Hz, 1H), 4.58–4.48 (m, 2H), 4.03–3.92 (m, 1H), 3.70 (s, 3H), 3.51–3.25 (m, 6H), 3.23 (s, 3H), 2.89–2.70 (m, 2H), 2.43–2.34 (m, 1H), 2.08–1.95 (m, 1H), 1.80–1.48 (m, 6H), 1.47–1.20 (m, 3H), 0.96–0.78 (m, 5H).

Example 49(187)

N-Hydroxy-2(S)-benzyl-5-ethoxymethoxy-4(S)-[N-[(1,3-dithian-2-yl)carbonyl]amino]pentanamide

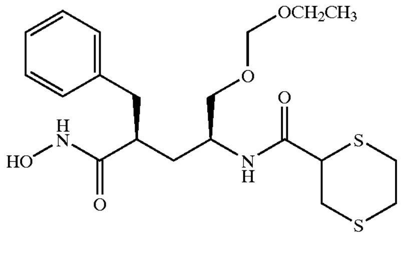

TLC: Rf 0.39 (Chloroform:Methanol=9:1);

NMR ($d_6$-DMSO): δ10.33 (s, 1H), 8.71 (brs, 1H), 7.81 (d, J=8.1 Hz, 1H), 7.25–7.08 (m, 5H), 4.51 (s, 2H), 4.41 (s, 1H), 3.47–3.17 (m, 6H), 2.78–2.56 (m, 4H), 2.38–2.27 (m, 1H), 1.98–1.82 (m, 2H), 1.67–1.49 (m, 2H), 1.08 (t, J=7.0 Hz, 3H).

Example 49(188)

N-Hydroxy-2(S)-(3-methoxybenzyl)-5-ethoxymethoxy-4(S)-[N-(4-bromophenylcarbonyl)amino]pentanamide

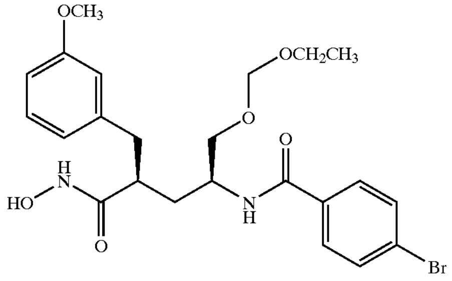

TLC: Rf 0.47 (Chloroform:Methanol=9:1);

NMR ($d_6$-DMSO): δ10.34 (s, 1H), 8.68 (brs, 1H), 8.22 (d, J=8.7 Hz, 1H), 7.81–7.68 (m, 2H), 7.68–7.64 (m, 2H), 7.12 (t, J=8.1 Hz, 1H), 6.71–6.66 (m, 3H), 4.56 (s, 2H), 4.16–4.27 (m, 1H), 3.66 (s, 3H), 3.48 (d, J=5.7 Hz, 2H), 3.43 (q, J=6.9 Hz, 2H), 2.71 (d, J=6.0 Hz, 2H), 2.39–2.28 (m, 1H), 1.79–1.59 (m, 2H), 1.07 (t, J=6.9 Hz, 3H).

Example 49(189)

N-Hydroxy-2(S)-(3-methoxybenzyl)-5-ethoxymethoxy-4(S)-[N-[(2-bromothiophen-5-yl)carbonyl]amino]pentanamide

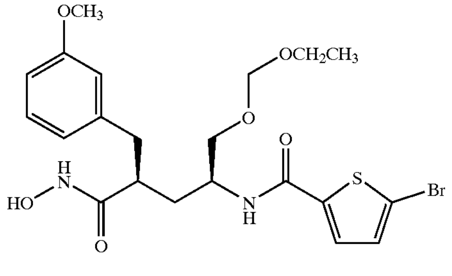

TLC: Rf 0.46 (Chloroform:Methanol=9:1);

NMR ($d_6$-DMSO): δ10.35 (s, 1H), 8.68 (s, 1H), 8.28 (d, J=8.7 Hz, 1H), 7.62 (d, J=4.2 Hz, 1H), 7.26 (d, J=4.2 Hz, 1H), 7.12 (t, J=7.8 Hz, 1H), 6.72–6.66 (m, 3H), 4.55 (s, 2H), 4.18–4.05 (m, 1H), 3.68 (s, 3H), 3.49–3.38 (m, 4H), 2.75–2.62 (m, 2H), 2.38–2.26 (m, 1H), 1.78–1.58 (m, 2H), 1.07 (t, J=7.2 Hz, 1H).

Example 49(190)

N-Hydroxy-2(S)-(2-methoxybenzyl)-5-ethoxymethoxy-4(S)-[N-(trans-4-methylcyclohexylcarbonyl)amino]pentanamide

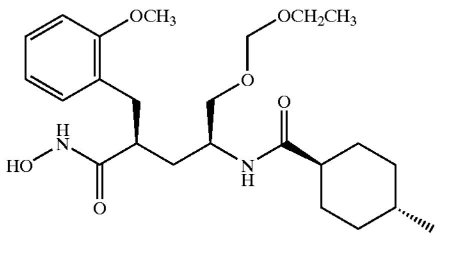

TLC: Rf 0.30 (Chloroform:Methanol=19:1);

NMR ($d_6$-DMSO): δ10.31 (s, 1H), 8.67 (s, 1H), 7.36 (d, J=8.0 Hz, 1H), 7.21–7.09 (m, 1H), 7.08–7.00 (m, 1H), 6.89 (d, J=7.4 Hz, 1H), 6.81 (t, J=7.4 Hz, 1H), 4.56–4.48 (m, 2H), 3.90–3.75 (m, 1H), 3.74 (s, 3H), 3.43 (q, J=7.0 Hz, 2H), 3.40–3.24 (m, 2H), 2.80–2.56 (m, 2H), 2.44–2.28 (m, 1H), 2.09–1.89 (m, 1H), 1.78–1.48 (m, 6H), 1.44–1.17 (m, 3H), 1.10 (t, J=7.0 Hz, 3H), 1.00–0.70 (m, 5H).

Example 49(191)

N-Hydroxy-2(S)-benzyl-5-ethoxymethoxy-4(S)-[N-[(2-methylpyridin-5-yl)carbonyl]amino]pentanamide

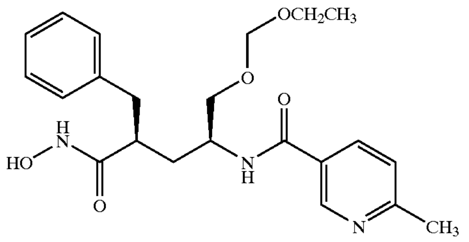

TLC: Rf 0.22 (Chloroform:Methanol=9:1);

NMR ($d_6$-DMSO): δ10.33 (s, 1H), 8.86 (d, J=2.0 Hz, 1H), 8.64 (s, 1H), 8.24 (d, J=8.8 Hz, 1H), 8.06 (dd, J=8.0 Hz, 2.0 Hz, 1H), 7.31 (d, J=8.0 Hz, 1H), 7.26–7.06 (m, 5H), 4.55 (s, 2H), 4.30–4.12 (m, 1H), 3.50–3.43 (m, 2H), 3.42 (q, J=7.0 Hz, 2H), 2.78–2.66 (m, 2H), 2.49 (s, 3H), 2.44–2.27 (m, 1H), 1.83–1.56 (m, 2H), 1.05 (t, J=7.0 Hz, 3H).

Example 49(192)

N-Hydroxy-2(S)-(benzofuran-3-yl)methyl-5-ethoxymethoxy-4(S)-[N-(4-nitrophenylcarbonyl)amino]pentanamide

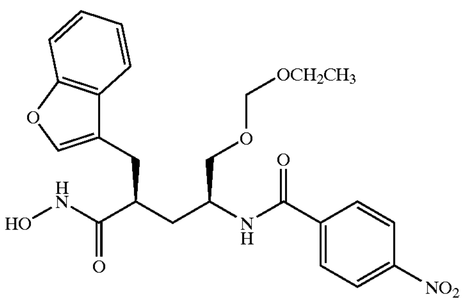

TLC: Rf 0.45 (Chloroform:Methanol=9:1);

NMR ($d_6$-DMSO): δ10.43 (s, 1H), 8.71 (brs, 1H), 8.54 (d, J=8.4 Hz, 1H), 8.31 (d, J=8.8 Hz, 2H), 8.09 (d, J=8.8 Hz, 2H), 7.63–7.60 (m, 1H), 7.49 (d, J=7.6 Hz, 1H), 7.29–7.13 (m, 2H), 4.55 (s, 2H), 4.38–4.21 (m, 1H), 3.51 (d, J=5.6 Hz, 2H), 3.42 (q, J=7.0 Hz, 2H), 2.84 (d, J=7.4 Hz, 2H), 2.40–2.20 (m, 1H), 1.91–1.63 (m, 2H), 1.05 (t, J=7.0 Hz, 3H).

Example 49(193)

N-Hydroxy-2(S)-benzyl-5-ethoxymethoxy-4(S)-[N-(trans-4-hydroxycyclohexylcarbonyl)amino]pentanamide

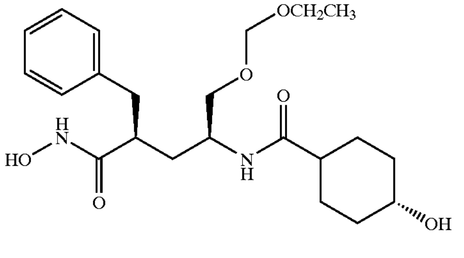

TLC: Rf 0.41 (Chloroform:Methanol:Acetic acid=9:1:0.5);

NMR ($d_6$-DMSO): δ10.29 (s, 1H), 8.62 (brs, 1H), 7.42 (d, J=8.7 Hz, 1H), 7.24–7.05 (m, 5H), 4.51 (s, 2H), 3.96–3.85 (m, 1H), 3.51–3.25 (m, 5H), 2.73–2.50 (m, 2H), 2.30–2.19 (m, 1H), 2.03–1.91 (m, 1H), 1.85–1.56 (m, 5H), 1.53–1.24 (m, 3H), 1.13–1.03 (m, 5H).

Example 49(194)

N-Hydroxy-2(S)-(3-chlorobenzyl)-5-ethoxymethoxy-4(S)-[N-(4-methylphenylcarbonyl)amino]pentanamide

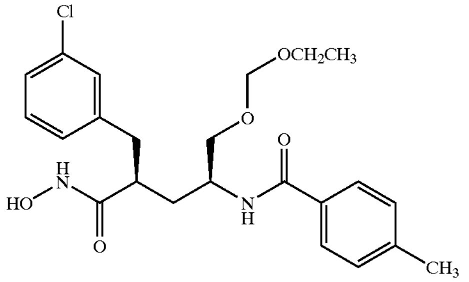

TLC: Rf 0.50 (Methylene chloride:Methanol=9:1);

NMR ($d_6$-DMSO): δ10.34 (s, 1H), 8.06 (brd, J=8.8 Hz, 1H), 7.77 (d, J=8.4 Hz, 2H), 7.27–7.03 (m, 6H), 4.57 (s, 2H), 4.23 (m, 1H), 3.50 (m, 2H), 3.44 (q, J=7.0 Hz, 2H), 2.90 (m, 2H), 2.34 (s, 3H), 2.34 (m, 1H), 1.80–1.60 (m, 2H), 1.08 (t, J=7.0 Hz, 3H).

Example 49(195)

N-Hydroxy-2(S)-benzyl-5-ethoxymethoxy-4(S)-[N-[(2-hydroxypyridin-5-yl)carbonyl]amino]pentanamide

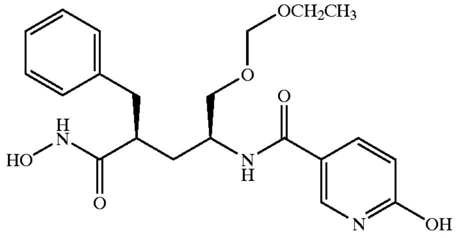

TLC: Rf 0.42 (Chloroform:Methanol:Acetic acid=9:1:0.5);

NMR ($d_6$-DMSO): δ11.93 (brs, 1H), 10.32 (s, 1H), 7.98 (d, J=2.4 Hz, 1H), 7.90 (d, J=8.4 Hz, 1H), 7.84 (dd, J=2.4 Hz, 8.4 Hz, 1H), 7.24–7.06 (m, 5H), 6.31 (d, J=9.6 Hz, 1H), 4.53 (s, 2H), 4.18–4.02 (m, 1H), 3.45–3.33 (m, 4H), 2.75–2.64 (m, 2H), 2.36–2.25 (m, 1H), 1.73–1.53 (m, 2H), 1.06 (t, J=7.0 Hz, 3H).

Example 49(196)

N-Hydroxy-2(R)-(3,4,4-trimethyl-2,5-dioxoimidazolidin-1-yl)methyl-5-ethoxymethoxy-4(S)-[N-(4-bromophenylcarbonyl)amino]pentanamide

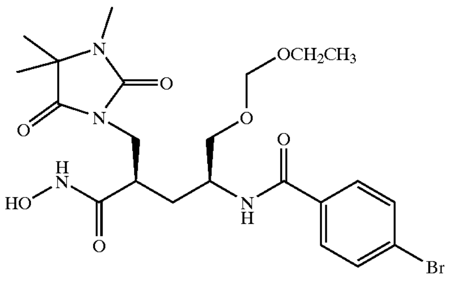

TLC: Rf 0.53 (Chloroform:Methanol=9:1);

NMR ($d_6$-DMSO): δ10.60 (s, 1H), 8.75 (brs, 1H), 8.19 (d, J=7.8 Hz, 1H), 7.77–7.74 (m, 2H), 7.66–7.62 (m, 2H), 4.54 (s, 2H), 4.06–3.96 (m, 1H), 3.50–3.37 (m, 6H), 2.75 (s, 3H), 2.64–2.51 (m, 1H), 1.69 (t, J=7.2 Hz, 2H), 1.27 (s, 3H), 1.26 (s, 3H), 1.05 (t, J=6.9 Hz, 3H).

Example 49(197)

N-Hydroxy-2(S)-(3-methoxybenzyl)-5-ethoxymethoxy-4(S)-[N-(4-dimethoxymethylphenylcarbonyl)amino]pentanamide

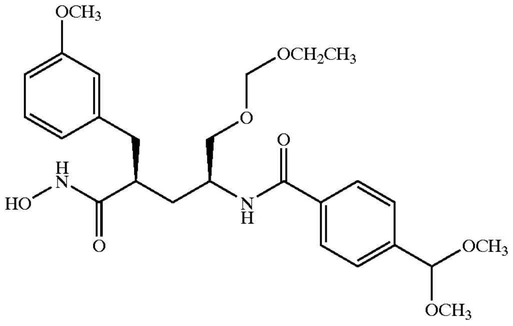

TLC: Rf 0.50 (Chloroform:Methanol=9:1);

NMR ($d_6$-DMSO): δ10.36 (s, 1H), 8.68 (s, 1H), 8.16 (d, J=8.4 Hz, 1H), 7.89 (d, J=8.2 Hz, 2H), 7.46 (d, J=8.2 Hz, 2H), 7.13 (t, J=8.0 Hz, 1H), 6.80–6.65 (m, 3H), 5.44 (s, 1H), 4.58 (s, 2H), 4.35–4.20 (m, 1H), 3.66 (s, 3H), 3.60–3.35 (m, 4H), 3.25 (s, 6H), 2.74 (d, J=6.9 Hz, 2H), 2.45–2.30 (m, 1H), 1.85–1.60 (m, 2H), 1.09 (t, J=6.9 Hz, 3H).

Example 49(198)

N-Hydroxy-2(S)-(3-trifluoromethyloxybenzyl)-5-ethoxymethoxy-4(S)-[N-(4-chlorophenylcarbonyl) amino]pentanamide

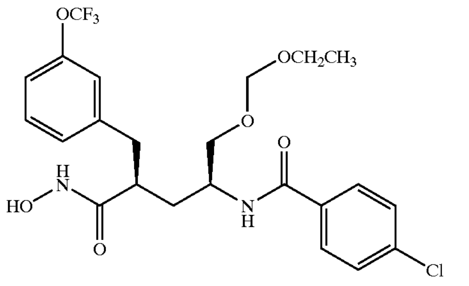

TLC: Rf 0.38 (Chloroform:Methanol=9:1);

NMR ($d_6$-DMSO): δ10.38 (s, 1H), 8.70 (s, 1H), 8.24 (d, J=8.7 Hz, 1H), 7.89 (d, J=8.7 Hz, 2H), 7.53 (d, J=8.7 Hz, 2H), 7.36 (t, J=7.8 Hz, 1H), 7.20–7.06 (m, 3H), 4.58 (s, 2H), 4.32–4.18 (m, 1H), 3.60–3.40 (m, 4H), 2.90–2.75 (m, 2H), 2.42–2.30 (m, 1H), 1.85–1.60 (m, 2H), 1.09 (t, J=7.1 Hz, 3H).

Example 49(199)

N-Hydroxy-2(S)-(3-methoxybenzyl)-5-ethoxymethoxy-4(S)-[N-[2-nitrothiophen-5-yl) carbonyl]amino]pentanamide

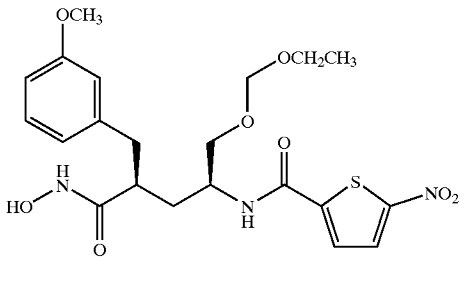

TLC: Rf 0.46 (Chloroform:Methanol=9:1);

NMR ($d_6$-DMSO): δ10.38 (s, 1H), 8.73–8.69 (m, 2H), 8.13 (d, J=4.5 Hz, 1H), 7.83 (d, J=4.5 Hz, 1H), 7.16–7.11 (m, 1H), 6.73–6.67 (m, 3H), 4.56 (s, 2H), 4.18–4.09 (m, 1H), 3.69 (s, 3H), 3.49 (d, J=8.1 Hz, 2H), 3.43 (q, J=7.2 Hz, 2H), 2.79–2.63 (m, 2H), 2.29–2.40 (m, 1H), 1.80–1.59 (m, 2H), 1.07 (t, J=7.2 Hz, 3H).

Example 49(200)

N-Hydroxy-2(R)-(benzotriazol-1-yl)methyl-5-ethoxymethoxy-4(S)-[N-(4-nitrophenylcarbonyl) amino]pentanamide

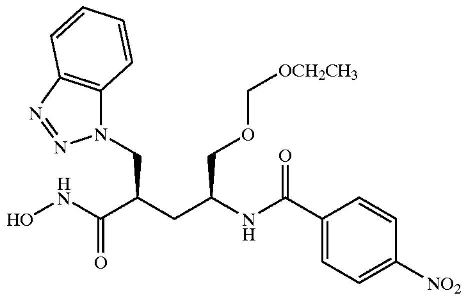

TLC: Rf 0.29 (Chloroform:Methanol=9:1);

NMR ($d_6$-DMSO): δ10.52 (s, 1H), 8.62 (d, J=8.4 Hz, 1H), 8.32 (d, J=9.0 Hz, 2H), 8.08 (d, J=9.0 Hz, 2H), 8.00 (d, J=8.1 Hz, 1H), 7.80 (d, J=8.1 Hz, 1H), 7.51 (t, J=8.1 Hz, 1H), 7.34 (t, J=8.1 Hz, 1H), 4.88 (dd, J=14.1 Hz, 9.0 Hz, 1H), 4.75 (dd, J=14.1 Hz, 5.7 Hz, 1H), 4.54 (s, 2H), 4.35–4.24 (m, 1H), 3.51 (d, J=5.1 Hz, 2H), 3.41 (q, J=7.2 Hz, 2H), 2.95–2.86 (m, 1H), 1.86–1.81 (m, 2H), 1.05 (t, J=7.2 Hz, 3H).

Example 49(201)

N-Hydroxy-2(R)-(3,4,4-trimethyl-2,5-dioxoimidazolidin-1-yl)methyl-5-ethoxymethoxy-4 (S)-[N-(4-nitrophenylcarbonyl)amino]pentanamide

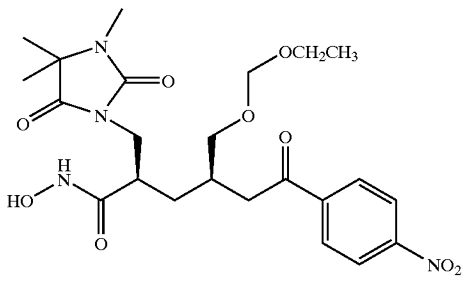

TLC: Rf 0.40 (Chloroform:Methanol=9:1);

NMR ($d_6$-DMSO): δ10.63 (s, 1H), 8.76 (s, 1H), 8.47 (d, J=8.1 Hz, 1H), 8.28 (d, J=8.9 Hz, 2H), 8.03 (d, J=8.9 Hz, 2H), 4.56 (s, 2H), 4.10–3.98 (m, 1H), 3.60–3.32 (m, 6H), 2.76 (s, 3H), 2.65–2.50 (m, 1H), 1.80–1.65 (m, 2H), 1.28 (s, 3H), 1.27 (s, 3H), 1.06 (t, J=7.2 Hz, 3H).

Example 49(202)

N-Hydroxy-2(R)-(3,4,4-trimethyl-2,5-dioxoimidazolidin-1-yl)methyl-5-ethoxymethoxy-4(S)-[N-(4-chlorophenylcarbonyl)amino]pentanamide

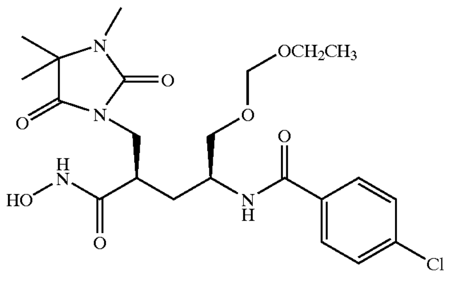

TLC: Rf 0.40 (Chloroform:Methanol=9:1);

NMR ($d_6$-DMSO): δ10.61 (s, 1H), 8.75 (s, 1H), 8.18 (d, J=8.1 Hz, 1H), 7.82 (d, J=8.6 Hz, 2H), 7.50 (d, J=8.6 Hz, 2H), 4.55 (s, 2H), 4.10–3.95 (m, 1H), 3.60–3.35 (m, 6H), 2.76 (s, 3H), 2.65–2.45 (m, 1H), 1.80–1.62 (m, 2H), 1.28 (s, 3H), 1.26 (s, 3H), 1.06 (t, J=6.9 Hz, 3H).

Example 49(203)

N-Hydroxy-2(S)-(3-phenylpropyl)-5-methoxymethoxy-4(S)-[N-(4-phenoxyphenylcarbonyl)amino]pentanamide

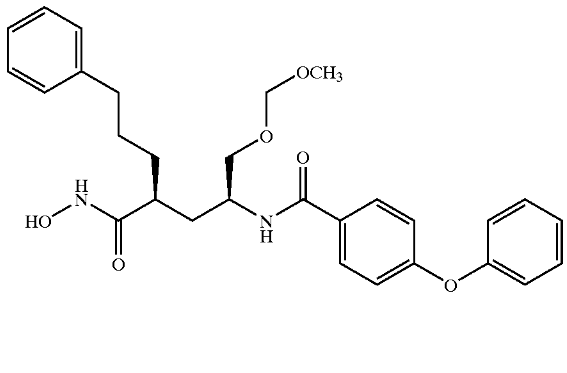

TLC: Rf 0.57 (Chloroform:Methanol=10:1);

NMR ($d_6$-DMSO): δ10.44 (1H, brs), 8.72 (1H, brs), 8.04 (1H, d, J=8.1 Hz), 7.87 (2H, d, J=8.8 Hz), 7.45–7.40 (2H, m), 7.27–7.12 (6H, m), 7.08–7.04 (2H, m), 7.01 (2H, d, J=8.8 Hz), 4.54 (2H, s), 4.14–4.03 (1H, m), 3.53–3.42 (2H, m), 3.21 (3H, s), 2.60–2.40 (2H, m), 2.16–2.06 (1H, m), 1.78–1.60 (2H, m), 1.52–1.38 (4H, m).

Example 49(204)

N-Hydroxy-2(S)-(3-phenylpropyl)-5-methoxymethoxy-4(S)-[N-[4-[2E-(4-chlorophenyl)ethenyl]phenylcarbonyl]amino]pentanamide

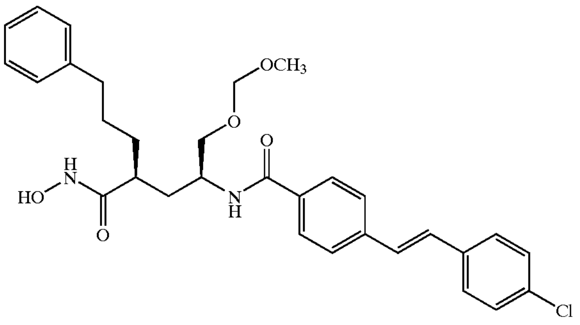

TLC: Rf 0.58 (Chloroform:Methanol=10:1);

NMR ($d_6$-DMSO): δ10.46 (1H, brs), 8.74 (1H, brs), 8.10 (1H, d, J=8.7 Hz), 7.86 (2H, d, J=8.3 Hz), 7.67 (2H, d, J=8.3 Hz), 7.65 (2H, d, J=8.8 Hz), 7.44 (2H, d, J=8.8 Hz), 7.38 (1H, d, J=16.5 Hz), 7.32 (1H, d, J=16.5 Hz), 7.27–7.22 (2H, m), 7.16–7.12 (3H, m), 4.55 (2H, s), 4.16–4.05 (1H, m), 3.55–3.46 (2H, m), 3.22 (3H, s), 2.59–2.42 (2H, m), 2.17–2.07 (1H, m), 1.79–1.62 (2H, m), 1.53–1.41 (4H, m).

Example 49(205)

N-Hydroxy-2(S)-(3-phenylpropyl)-5-methoxymethoxy-4(S)-[N-[4-(4-phenyl-1,2,5,6-tetrahydropyridin-1-yl)phenylcarbonyl]amino]pentanamide

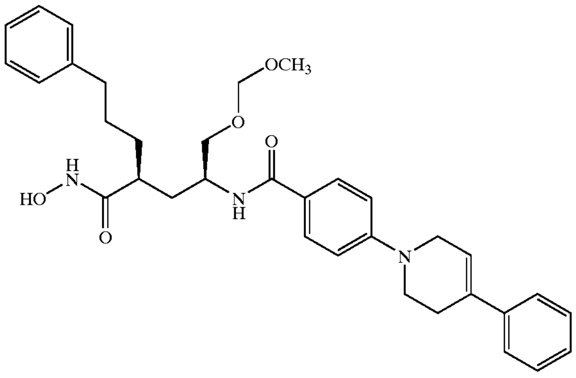

TLC: Rf 0.31 (Chloroform:Methanol=20:1);

NMR ($d_6$-DMSO): δ10.45 (1H, brs), 8.73 (1H, brs), 7.80 (1H, d, J=8.3 Hz), 7.77 (2H, d, J=9.0 Hz), 7.48 (2H, d, J=7.2 Hz), 7.36 (2H, t, J=7.2 Hz), 7.28–7.22 (3H, m), 7.16–7.12 (3H, m), 6.98 (2H, d, J=9.0 Hz), 6.29 (1H, brs), 4.54 (2H, s), 4.13–4.02 (1H, m), 3.94 (2H, s), 3.58 (2H, t, J=5.7 Hz), 3.53–3.42 (2H, m), 3.21 (3H, s), 2.66–2.58 (2H, m), 2.58–2.43 (2H, m), 2.18–2.07 (1H, m), 1.78–1.60 (2H, m), 1.52–1.40 (4H, m).

Example 49(206)

N-Hydroxy-2(S)-(3-phenyl-2-propenyl)-5-ethoxymethoxy-4(S)-[N-(trans-4-methylcyclohexylcarbonyl)amino]pentanamide

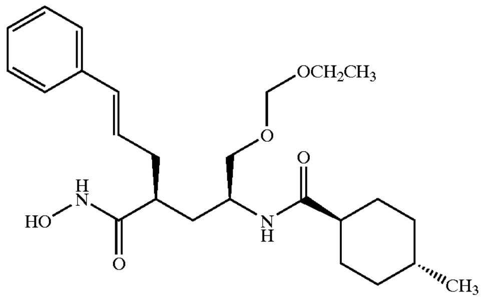

TLC: Rf 0.41 (Chloroform:Methanol=9:1);

NMR ($d_6$-DMSO): δ10.43 (s, 1H), 8.73 (brs, 1H), 7.43 (d, J=8.4 Hz, 1H), 7.33–7.24 (m, 4H), 7.20–7.14 (m, 1H), 6.33 (d, J=15.9 Hz, 1H), 6.08 (dt, J=15.9, 6.9 Hz, 1H), 4.53 (s, 2H), 3.90–3.78 (m, 1H), 3.44 (q, J=7.1 Hz, 2H), 3.40–3.31 (m, 2H), 2.31–2.22 (m, 2H), 2.19–2.08 (m, 1H), 2.03–1.92 (m, 1H), 1.74–1.58 (m, 5H), 1.56–1.43 (m, 1H), 1.40–1.18 (m, 3H), 1.06 (t, J=7.1 Hz, 3H), 0.91–0.81 (m, 5H).

Example 49(207)

N-Hydroxy-2(S)-(3-phenylpropyl)-5-ethoxymethoxy-4(S)-[N-(trans-4-methylcyclohexylcarbonyl)amino]pentanamide

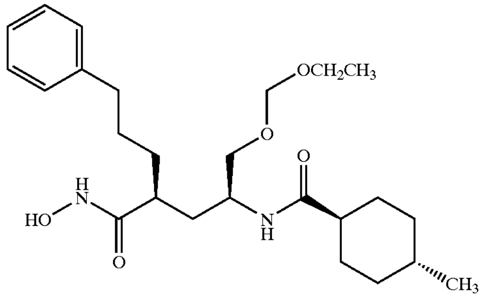

TLC: Rf 0.51 (Chloroform:Methanol=9:1);

NMR ($d_6$-DMSO): δ10.40 (s, 1H), 8.65 (brs, 1H), 7.38 (d, J=8.4 Hz, 1H), 7.26–7.20 (m, 2H), 7.16–7.08 (m, 3H), 4.53 (s, 2H), 3.83–3.72 (m, 1H), 3.49–3.27 (m, 4H), 2.58–2.38 (m, 2H), 2.04–1.89 (m, 2H), 1.77–1.52 (m, 5H), 1.50–1.21 (m, 8H), 1.07 (t, J=6.9 Hz, 3H), 0.91–0.77 (m, 5H).

Example 49(208)

N-Hydroxy-2(S)-(2-phenylethyl)-5-(2-methoxyethoxy)methoxy-4(S)-[N-(trans-4-methylcyclohexylcarbonyl)amino]pentanamide

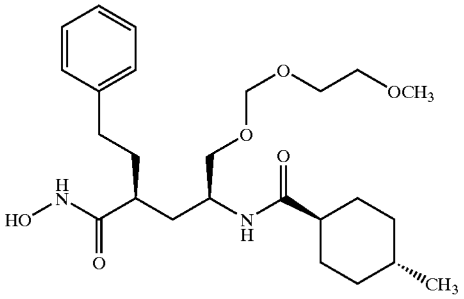

TLC: Rf 0.34 (Chloroform:Methanol=10:1);

NMR ($d_6$-DMSO): δ10.45 (s, 1H), 9.20–8.40 (brs, 1H), 7.39 (d, J=8.4 Hz, 1H), 7.28–7.23 (m, 2H), 7.20–7.10 (m, 3H), 4.57 (s, 2H). 3.90–3.80 (m, 1H), 3.60–3.20 (m, 6H), 3.22 (s, 3H), 2.60–2.30 (m, 2H), 2.10–2.00 (m ,1H), 2.05–1.90 (m, 1H), 1.80–1.40 (m, 9H), 1.40–1.20 (m, 2H), 0.95–0.75 (m, 2H), 0.84 (d, J=6.6 Hz, 3H).

Example 49(209)

N-Hydroxy-2(S)-(4-phenylbutyl)-5-(2-methoxyethoxy)methoxy-4(S)-[N-(trans-4-methylcyclohexylcarbonyl)amino]pentanamide

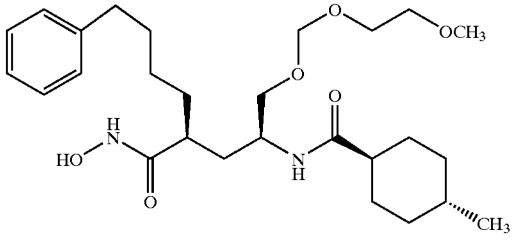

TLC: Rf 0.36 (Chloroform:Methanol=9:1);

NMR ($d_6$-DMSO): δ10.38 (s, 1H), 7.39 (d, J=8.4 Hz, 1H), 7.30–7.20 (m, 2H), 7.20–7.10 (m, 3H), 4.57 (s, 2H), 3.90–3.75 (m, $_1$H), 3.65–3.15 (m, 6H), 3.22 (s, 3H), 2.60–2.40 (m, 2H), 2.05–1.90 (m, 2H), 1.85–1.05 (m, 15H), 0.95–0.75 (m, 2H), 0.84 (d, J=6.3 Hz, 3H).

Example 49(210)

N-Hydroxy-2(S)-(3-phenylpropyl)-5-ethoxymethoxy-4(S)-[N-(4-bromophenylcarbonyl)amino]pentanamide

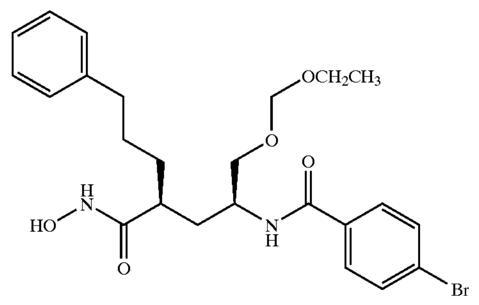

TLC: Rf 0.33 (Chloroform:Methanol=19:1);

NMR ($d_6$-DMSO): δ10.44 (s, 1H), 8.72 (s, 1H), 8.16 (d, J=8.2 Hz, 1H), 7.79 (d, J=8.4 Hz, 2H), 7.65 (d, J=8.4 Hz, 2H), 7.32–7.08 (m, 5H), 4.59 (s, 2H), 4.20–3.98 (m, 1H), 3.63–3.40 (m, 4H), 2.68–2.38 (m, 2H), 2.20–2.01 (m, 1H), 1.82–1.61 (m, 2H), 1.60–1.30 (m, 4H), 1.08 (t, J=7.0 Hz, 3H).

Example 49(211)

N-Hydroxy-2(S)-(3-phenylpropyl)-5-ethoxymethoxy-4(S)-[N-(4-nitrophenylcarbonyl)amino]pentanamide

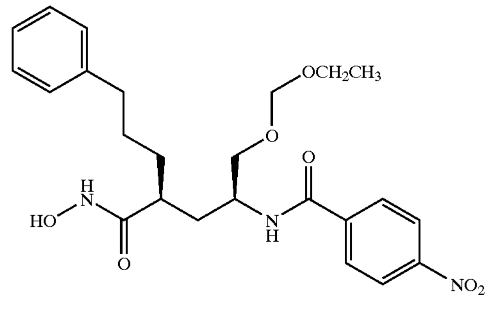

TLC: Rf 0.29 (Chloroform:Methanol=19:1);

NMR ($d_6$-DMSO): δ10.45 (s, 1H), 8.72 (s, 1H), 8.45 (d, J=8.4 Hz, 1H), 8.29 (d, J=9.0 Hz, 2H), 8.06 (d, J=9.0 Hz, 2H), 7.29–7.20 (m, 2H), 7.19–7.09 (m, 3H), 4.59 (s, 2H), 4.17–4.01 (m, 1H), 3.56–3.40 (m, 4H), 2.61–2.40 (m, 2H), 2.16–2.03 (m, 1H), 1.80–1.60 (m, 2H), 1.58–1.32 (m, 4H), 1.07 (t, J=7.2 Hz, 3H).

Example 49(212)

N-Hydroxy-2(R)-(2-phenoxyethyl)-5-ethoxymethoxy-4(S)-[N-(4-nitrophenylcarbonyl)amino]pentanamide

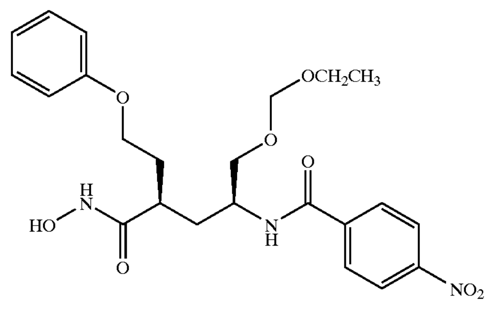

TLC: Rf 0.35 (Chloroform:Methanol=9:1);

NMR ($d_6$-DMSO): δ10.51 (s, 1H), 8.76 (s, 1H), 8.47 (d, J=8.4 Hz, 1H), 8.29 (d, J=8.9 Hz, 2H), 8.07 (d, J=8.9 Hz, 2H), 7.30–7.20 (m, 2H), 6.95–6.80 (m, 3H), 4.59 (s, 2H), 4.25–4.12 (m, 1H), 3.95–3.78 (m, 2H), 3.60–3.40 (m, 4H), 2.40–2.25 (m, 1H), 2.00–1.65 (m, 4H), 1.07 (t, J=7.1 Hz, 3H).

Example 49(213)

N-Hydroxy-2(R)-(2-pyridyl)methyl-5-methoxymethoxy-4(S)-[N-(4-phenoxyphenylcarbonyl)amino]pentanamide

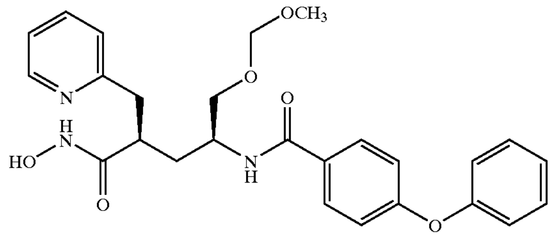

TLC: Rf 0.20 (Chloroform:Methanol=19:1);

NMR ($d_6$-DMSO): δ10.44 (1H, s), 8.69 (1H, s), 8.48–8.40 (1H, m), 8.06 (1H, d, J=8.4 Hz), 7.88 (2H, d, J=8.8 Hz), 7.65 (1H, td, J=7.8, 1.8 Hz), 7.50–7.38 (2H, m), 7.24–7.12 (3H, m), 7.11–7.04 (2H, m), 7.02 (2H, d, J=8.8 Hz), 4.52 (2H, s), 4.23–4.02 (1H, m), 3.49 (2H, d, J=5.6 Hz), 3.19 (3H, s), 2.96 (1H, dd, J=13.8, 8.4 Hz), 2.85 (1H, dd, J=13.8, 6.6 Hz), 2.75–2.60 (1H, m), 1.77 (2H, t, J=7.0 Hz).

Example 49(214)

N-Hydroxy-2(R)-(2-pyridyl)methyl-5-methoxymethoxy-4(S)-[N-[4-(benzofuran-2-yl)phenylcarbonyl]amino]pentanamide

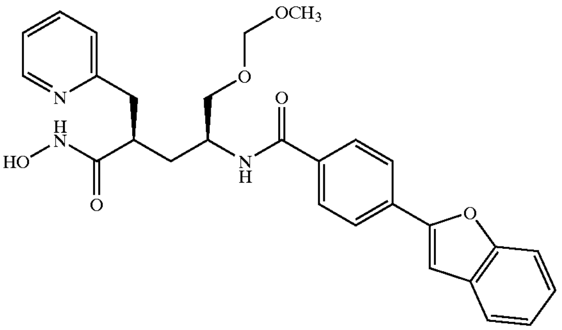

TLC: Rf 0.45 (Chloroform:Methanol=9:1);

NMR ($d_6$-DMSO): δ10.70–10.40 (1H, brs), 9.00–8.60 (1H, brs), 8.50–8.25 (2H, m), 7.99 (4H, s), 7.80–7.44 (4H, m), 7.41–7.06 (4H, m), 4.52 (2H, s), 4.31–4.10 (1H, m), 3.64–3.46 (2H, m), 3.19 (3H, s), 3.06–2.82 (2H, m), 2.80–2.63 (1H, m), 2.00–1.70 (2H, m).

Example 49(215)

N-Hydroxy-2(S)-(3-pyridyl)methyl-5-methoxymethoxy-4(S)-[N-(4-phenoxyphenylcarbonyl)amino]pentanamide

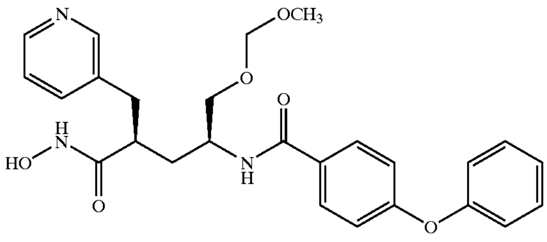

TLC: Rf 0.43 (Chloroform:Methanol=9:1);

NMR ($d_6$-DMSO): δ10.36 (1H, s), 8.69 (1H, s), 8.40–8.32 (2H, m), 8.12 (1H, d, J=9.4 Hz), 7.91 (2H, d, J=8.8 Hz), 7.54–7.38 (3H, m), 7.29–7.17 (2H, m), 7.12–7.06 (2H, m), 7.03 (2H, d, J=8.8 Hz), 4.56 (2H, s), 4.40–4.20 (1H, m), 3.60–3.42 (2H, m), 3.22 (3H, s), 2.87 (1H, dd, J=13.6, 4.8 Hz), 2.75 (1H, dd, J=13.6, 9.6 Hz), 2.43–2.28 (1H, m), 1.90–1.59 (2H, m).

Example 49(216)

N-Hydroxy-2(S)-(3-pyridyl)methyl-5-methoxymethoxy-4(S)-[N-[4-[2-(4-methylphenyl)ethynyl]phenylcarbonyl]amino]pentanamide

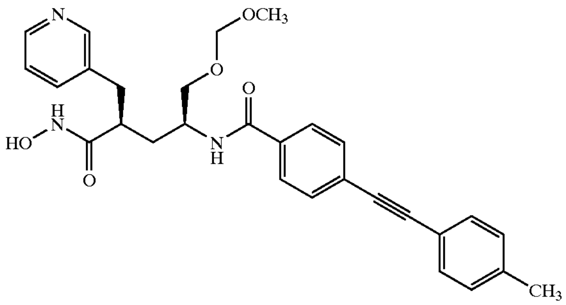

TLC: Rf 0.40 (Chloroform:Methanol=9:1);

NMR ($d_6$-DMSO): δ10.37 (1H, s), 8.70 (1H, s), 8.40–8.33 (2H, m), 8.29 (1H, d, J=8.0 Hz), 7.92 (2H, d, J=8.4 Hz), 7.63 (2H, d, J=8.4 Hz), 7.57–7.42 (3H, m), 7.31–7.20 (3H, m), 4.56 (2H, s), 4.40–4.20 (1H, m), 3.62–3.44 (2H, m), 3.22 (3H, s), 2.87 (1H, dd, J=13.6, 4.8 Hz), 2.76 (1H, dd, J=13.6, 9.2 Hz), 2.42–2.26 (4H, m), 1.91–1.59 (2H, m).

Example 49(217)

N-Hydroxy-2(S)-(3-pyridyl)methyl-5-methoxymethoxy-4(S)-[N-[4-(1-heptynyl)phenylcarbonyl]amino]pentanamide

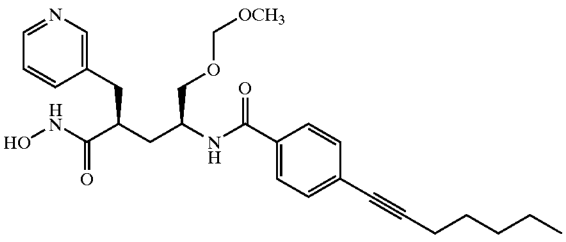

TLC: Rf 0.34 (Chloroform:Methanol:Acetic acid:Water=100:10:1:1);

NMR ($d_6$-DMSO): δ10.35(1H, brs), 8.69(1H, brs), 8.37–8.33(2H, m), 8.23(1H, d, J=8.4 Hz), 7.83(2H, d, J=8.0 Hz), 7.51–7.43(3H, m), 7.25(1H, dd, J=7.8 Hz, 4.8 Hz), 4.54(2H, s), 4.38–4.15(1H, m), 3.50(2H, d, J=5.4 Hz), 3.20(3H, s), 2.92–2.68(2H, m), 2.49–2.39(1H, m), 1.91–1.20(10H, m), 0.88(3H, t, J=7.0 Hz).

Example 49(218)

N-Hydroxy-2(S)-(3-pyridyl)methyl-5-methoxymethoxy-4(S)-[N-[4-[2E-(4-chlorophenyl) ethenyl]phenylcarbonyl]amino]pentanamide

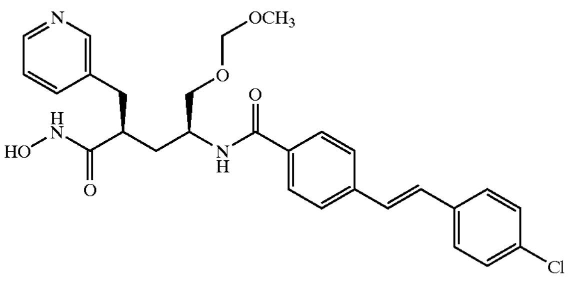

TLC: Rf 0.26 (Chloroform:Methanol:Acetic acid:Water=100:10:1:1);

NMR ($d_6$-DMSO): δ10.40(1H, brs), 8.72(1H, brs), 8.35 (2H, s), 8.21(1H, d, J=8.7 Hz), 7.89(2H, d, J=8.4 Hz), 7.68(2H, d, 8.4 Hz), 7.65(2H, d, J=8.7 Hz), 7.51 (1H, d, J=7.2 Hz), 7.44(2H, d, J=8.7 Hz), 7.39(1H, d, J=16.8 Hz), 7.32(1H, d, J=16.8 Hz), 7.27–7.23(1H, m), 4.55(2H, s), 4.39–4.21(1H, m), 3.61–3.42(2H, m), 3.21(3H, s), 2.91–2.69(2H, m), 2.45–2.31(1H, m), 1.91–1.60(2H, m).

Example 49(219)

N-Hydroxy-2(S)-(3-pyridyl)methyl-5-methoxymethoxy-4(S)-[N-(trans-4-methylcyclohexylcarbonyl)amino]pentanamide

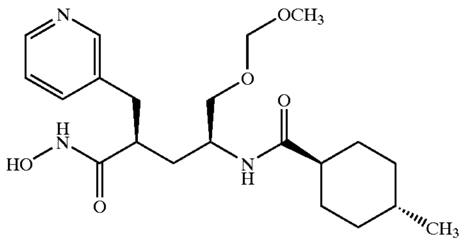

TLC: Rf 0.34 (Chloroform:Methanol=9:1);

NMR ($d_6$-DMSO): δ10.34 (1H, brs), 8.72 (1H, brs), 8.36 (1H, dd, J=4.8, 1.5 Hz), 8.32–8.30 (1H, m), 7.52–7.45 (2H, m), 7.29–7.22 (1H, m), 4.51 (2H, s), 4.05–3.93 (1H, m), 3.44–3.35 (2H, m), 3.22 (3H, s), 2.77 (1H, dd, J=13.2, 4.8 Hz), 2.69 (1H, dd, J=13.2, 9.6 Hz), 2.35–2.22 (1H, m), 2.10–1.97 (1H, m), 1.82–1.61 (5H, m), 1.60–1.44 (1H, m), 1.43–1.20 (3H, m), 0.97–0.79 (5H, m).

Example 49(220)

N-Hydroxy-2(S)-(4-pyridyl)methyl-5-methoxymethoxy-4(S)-[N-(4-phenoxyphenylcarbonyl)amino]pentanamide

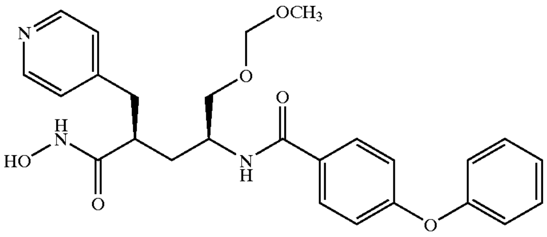

TLC: Rf 0.27 (Chloroform:Methanol=9:1);

NMR ($d_6$-DMSO): δ10.44–10.30 (1H, brs), 8.75–8.62 (1H, brs), 8.40 (2H, d, J=6.0 Hz), 8.13 (1H, d, J=8.4 Hz), 7.91 (2H, d, J=8.7 Hz), 7.48–7.38 (2H, m), 7.22–7.18 (1H, m), 7.13 (2H, d, J=6.0 Hz), 7.06 (2H, d, J=7.8 Hz), 7.02 (2H, d, J=8.7 Hz), 4.55 (2H, s), 4.34–4.21 (1H, m), 3.58–3.42 (2H, m), 3.22 (3H, s), 2.91–2.71 (2H, m), 2.46–2.32 (1H, m), 1.85–1.61 (2H, m).

Example 49(221)

N-Hydroxy-2(R)-(2-pyridyl)methyl-5-(2-methoxyethoxy)methoxy-4(S)-[N-(4-phenoxyphenylcarbonyl)amino]pentanamide

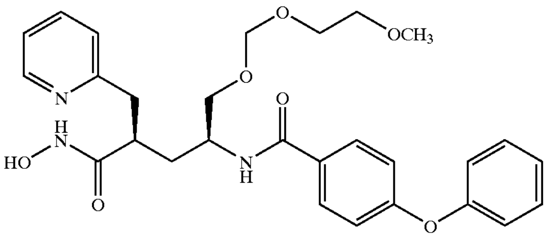

TLC: Rf 0.38 (Chloroform:Methanol:Acetic acid:Water=100:10:1:1);

NMR ($d_6$-DMSO): δ10.43(1H, s), 8.69(1H, s), 8.45(1H, d, J=4.5 Hz), 8.60(1H, d, J=8.4 Hz), 7.87(2H, d, J=8.4 Hz), 7.65(1H, t, J=7.5 Hz), 7.42(2H, t, J=8.1 Hz), 7.21–7.15(3H, m), 7.08–7.00(4H, m), 4.58(2H, s), 4.06–4.22(1H, m), 3.43–3.60(4H, m), 3.42–3.38(2H, m), 3.20(3H, s), 2.98–2.81(2H, m), 2.61–2.78(1H, m), 1.75(2H, t, J=7.2 Hz).

Example 49(222)

N-Hydroxy-2(S)-(3-pyridyl)methyl-5-ethoxymethoxy-4(S)-[N-(2-methylphenylcarbonyl)amino]pentanamide

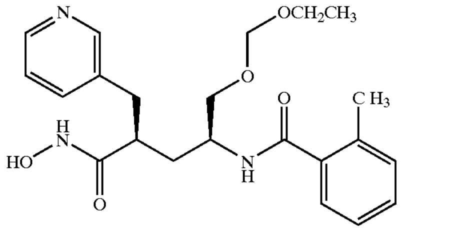

TLC: Rf 0.38 (Chloroform:Methanol=9:1);

NMR ($d_6$-DMSO+$CD_3OD$ (5 drops)): δ8.36–8.32 (m, 2H), 7.50 (d, J=7.5 Hz, 1H), 7.34 (d, J=7.5 Hz, 1H), 7.31–7.14 (m, 4H), 4.59 (2H, s), 4.26–4.16 (m, 1H), 3.52–3.43 (m, 4H), 2.87–2.69 (m, 2H), 2.43–2.34 (m, 1H), 2.31 (s, 3H), 1.77–1.57 (m, 2H), 1.09 (t, J=6.9 Hz, 3H).

Example 49(223)

N-Hydroxy-2(S)-(3-pyridyl)methyl-5-ethoxymethoxy-4(S)-[N-(3-methylphenylcarbonyl)amino]pentanamide

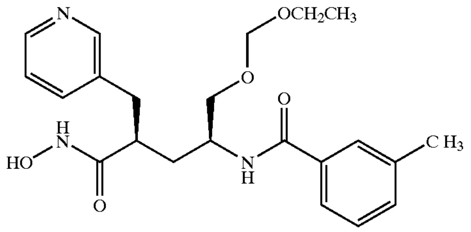

TLC: Rf 0.38 (Chloroform:Methanol=9:1);

NMR ($CD_3OD$): δ8.44–8.37 (m, 2H), 7.75–7.66 (m, 3H), 7.42–7.34 (m, 3H), 4.73 (s, 2H), 4.52–4.41 (m, 1H), 3.71–3.57 (m, 4H), 3.13–2.88 (m, 2H), 2.55–2.42 (m, 4H), 2.06–1.90 (m, 2H), 1.21 (t, J=7.2 Hz, 3H).

Example 49(224)

N-Hydroxy-2(S)-(3-pyridyl)methyl-5-ethoxymethoxy-4(S)-[N-(4-methylphenylcarbonyl)amino]pentanamide

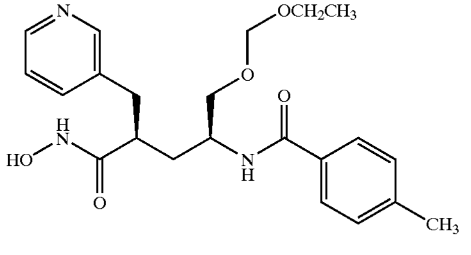

TLC: Rf 0.38 (Chloroform:Methanol=9:1);

NMR ($CD_3OD$+$d_6$-DMSO (5 drops)): δ8.46–8.42 (m, 2H), 7.84 (d, J=8.4 Hz, 2H), 7.72 (d, J=7.8 Hz, 1H), 7.42–7.33 (m, 3H), 4.75 (s, 2H), 4.53–4.44 (m, 1H), 3.71–3.59 (m, 4H), 3.13–2.88 (m, 2H), 2.57–2.45 (m, 4H), 2.09–1.88 (m, 2H), 1.23 (t, J=7.2 Hz, 3H).

Example 49(225)

N-Hydroxy-2(S)-(3-pyridyl)methyl-5-ethoxymethoxy-4(S)-[N-(4-methoxyphenylcarbonyl)amino]pentanamide

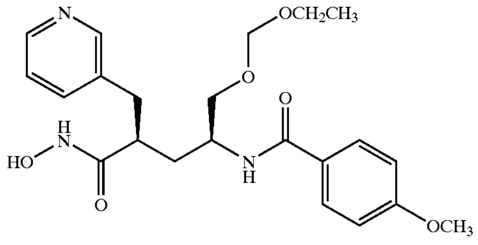

TLC: Rf 0.30 (Chloroform:Methanol=9:1)

NMR ($d_6$-DMSO): δ10.35 (s, 1H), 8.68 (s, 1H), 8.40–8.30 (m, 2H), 8.00 (d, J=8.8 Hz, 1H), 7.86 (d, J=8.8 Hz, 2H), 7.53–7.44 (m, 1H), 7.28–7.20 (m, 1H), 6.99 (d, J=8.8 Hz, 2H), 4.59 (s, 2H), 4.38–4.17 (m, 1H), 3.81 (s, 3H), 3.60–3.40 (m, 4H), 2.86 (dd, J=13.2, 5.2 Hz, 1H), 2.74 (dd, J=13.2, 9.2 Hz, 1H), 2.44–2.28 (m, 1H), 1.90–1.58 (m, 2H), 1.09 (t, J=6.8 Hz, 3H).

Example 49(226)

N-Hydroxy-2(S)-(3-pyridyl)methyl-5-ethoxymethoxy-4(S)-(N-cyclohexylcarbonylamino)pentanamide

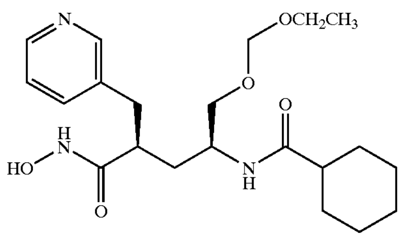

TLC: Rf 0.21 (Chloroform:Methanol=10:1);

NMR ($d_6$-DMSO): δ10.33 (brs, 1H), 8.70 (brs, 1H), 8.36 (dd, J=1.8, 4.5 Hz, 1H), 8.30 (d, J=1.8 Hz, 1H), 7.48–7.45 (m, 2H), 7.26 (dd, J=4.5, 7.6 Hz, 1H), 4.55 (s, 2H), 4.40–3.51 (m, 1H), 3.45 (q, J=7.2 Hz, 2H), 3.83–3.32 (m, 2H), 2.80–2.63 (m, 2H), 2.32–2.21 (m, 1H), 2.14–2.03 (m, 1H), 1.78–1.45 (m, 7H), 1.40–1.06 (m, 5H), 1.10 (t, J=6.9 Hz, 3H).

Example 49(227)

N-Hydroxy-2(S)-(3-pyridyl)methyl-5-ethoxymethoxy-4(S)-[N-(4-nitrophenylcarbonyl)amino]pentanamide

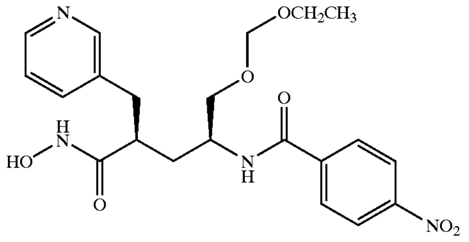

TLC: Rf 0.22 (Chloroform:Methanol=9:1);

NMR ($d_6$-DMSO): δ10.36 (s, 1H), 8.69 (s, 1H), 8.53 (d, J=8.7 Hz, 1H), 8.37–8.29 (m, 3H), 8.10–8.06 (m, 2H), 7.52–7.48 (m, 1H), 7.28–7.23 (m, 1H), 4.58 (s, 2H), 4.21–4.32, (m, 1H), 3.52 (d, J=5.7 Hz, 2H), 3.45 (q, J=7.2 Hz, 2H), 2.86–2.69 (m, 2H), 2.42–2.23 (m, 1H), 1.85–1.62 (m 2H), 1.08 (t, J=7.2 Hz, 3H).

Example 49(228)

N-Hydroxy-2(S)-(3-pyridyl)methyl-5-ethoxymethoxy-4(S)-[N-(4-bromophenylcarbonyl)amino]pentanamide

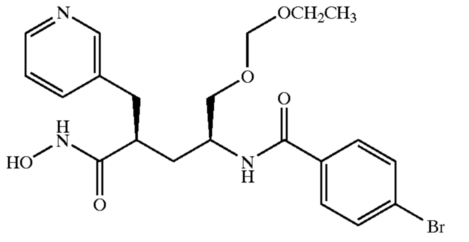

TLC: Rf 0.32 (Chloroform:Methanol:Acetic acid=90:10:1);

NMR ($d_6$-DMSO): δ10.34 (s, 1H), 8.68 (s, 1H), 8.37–8.24 (m, 3H), 7.80 (d, J=8.7 Hz, 2H), 7.67 (d, J=8.7 Hz, 2H), 7.49 (dt, J=8.1 Hz, 1.8 Hz, 1H), 4.57 (s, 2H), 4.31–4.18 (m, 1H), 3.50 (d, J=6.0 Hz, 2H), 3.45 (q, J=7.2 Hz, 2H), 2.87–2.68 (m, 2H), 2.40–2.24(m, 1H), 1.82–1.59 (m, 2H), 1.07 (t, J=7.2 Hz, 3H).

Example 49(229)

N-Hydroxy-2(S)-(3-quinolyl)methyl-5-ethoxymethoxy-4(S)-[N-(trans-4-methylcyclohexylcarbonyl)amino]pentanamide

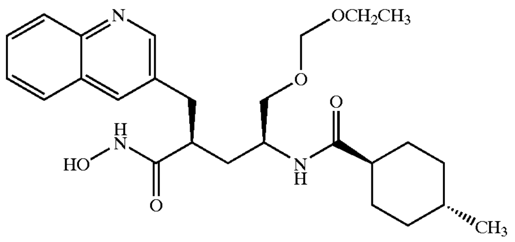

TLC: Rf 0.37 (Chloroform:Methanol=9:1);

NMR ($d_6$-DMSO): δ10.31 (s, 1H), 8.67–8.65 (m, 2H), 7.98–7.83 (m, 3H), 7.73–7.49 (m, 3H), 4.55 (s, 2H), 4.13–3.97 (m, 1H), 3.43 (q, J=7.0 Hz, 2H), 3.42–3.36 (m, 2H), 3.06–2.80 (m, 2H), 2.48–2.30 (m, 1H), 2.15–1.98 (m, 1H), 1.81–1.26 (m 9H), 1.08 (t, J=7.0 Hz, 3H), 0.99–0.79 (m, 2H), 0.85(d, J=7.0 Hz, 3H).

Example 49(230)

N-Hydroxy-2(S)-phenylthio-5-methoxymethoxy-4(S)-[N-(4-phenoxyphenylcarbonyl)amino]pentanamide

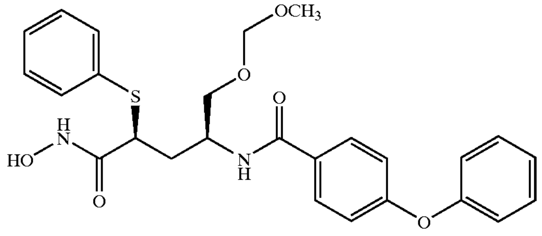

TLC: Rf 0.27 (Chloroform:Methanol:Acetic acid=100:5:1);

NMR ($d_6$-DMSO): δ10.69(1H, s), 8.97(1H, s), 8.17(1H, d, J=8.0 Hz), 7.86(2H, d, J=8.8 Hz), 7.47–7.39(4H, m), 7.34–7.16(4H, m), 7.08–6.99(4H, m), 4.53(2H, s), 4.38–4.25(1H, m), 3.62–3.35(3H, m), 3.19(3H, s), 2.02(2H, t, J=6.8 Hz).

Example 49(231)

N-Hydroxy-2(S)-phenylthio-5-ethoxymethoxy-4(S)-[N-(trans-4-methylcyclohexylcarbonyl)amino]pentanamide

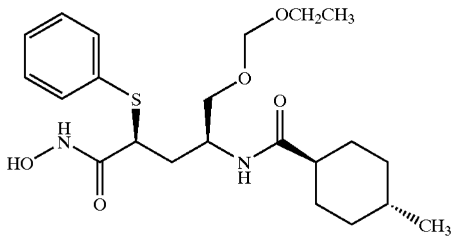

TLC: Rf 0.37 (Chloroform:Methanol=9:1);

NMR ($d_6$-DMSO): δ10.67 (s, 1H), 8.94 (brs, 1H), 7.52 (d, J=8.1 Hz, 1H), 7.38–7.22 (m, 5H), 4.52 (s, 2H), 4.04–3.93 (m, 1H), 3.52–3.24 (m, 5H), 2.01–1.78 (m, 3H), 1.69–1.55 (m, 4H), 1.36–1.19 (m, 3H), 1.07 (t, J=7.0 Hz, 3H), 0.91–0.75 (m, 5H).

Example 49(232)

N-Hydroxy-2(S)-methylthio-5-ethoxymethoxy-4(S)-[N-(trans-4-methylcyclohexylcarbonyl)amino] pentanamide

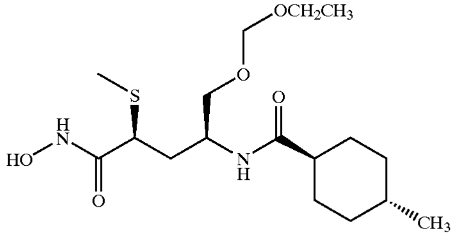

TLC: Rf 0.38 (Chloroform:Methanol=9:1);

NMR ($d_6$-DMSO): δ10.56 (s, 1H), 8.88 (s, 1H), 7.48 (d, J=8.4 Hz, 1H), 4.55 (s, 2H), 4.04–3.90 (m, 1H), 3.46 (q, J=7.1 Hz, 2H), 3.39–3.25 (m, 2H), 2.96–2.87 (m, 1H), 2.04–1.91 (m, 4H), 1.90–1.77 (m, 1H), 1.76–1.55 (m, 5H), 1.40–1.18 (m, 3H), 1.08 (t, J=7.1 Hz, 3H), 0.92–0.74 (m, 5H).

Example 49(233)

N-Hydroxy-2(S)-(4-pyridyl)thio-5-ethoxymethoxy-4(S)-[N-(trans-4-methylcyclohexylcarbonyl)amino] pentanamide

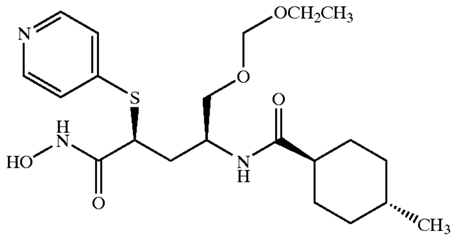

TLC: Rf 0.29 (Chloroform:Methanol=9:1);

NMR ($d_6$-DMSO): δ10.87 (s, 1H), 9.08 (s, 1H), 8.35 (d, J=6.0 Hz, 2H), 7.58 (d, J=8.1 Hz, 1H), 7.27 (d, J=6.0 Hz, 2H), 4.56 (s, 2H), 3.99–3.88 (m, 1H), 3.78 (t, J=7.4 Hz, 1H), 3.45 (q, J=7.2 Hz, 2H), 3.42–3.31 (m, 2H), 2.02–1.87 (m, 3H), 1.71–1.56 (m, 4H), 1.35–1.17 (m, 3H), 1.07 (t, J=7.2 Hz, 3H), 0.91–0.76 (m, 5H).

Example 49(234)~49(253)

The following compounds were obtained by the same procedure as a series of reaction of Example 49, using the compound prepared in Example 44(8), 44(9), 44(11), 44(14), 44(17)~44(21), 44(24)~44(26), or the compound which was obtained by the same procedure as a series of Example 37→Example 39→Example 41→Example 43 (using a corresponding compound instead of benzyl bromide.)→Example 44, using a corresponding compound instead of the compound prepared in Reference Example 4.

Example 49(234)

N-Hydroxy-2(S)-hydroxy-5-methoxymethoxy-4(S)-[N-(4-phenoxyphenylcarbonyl)amino]pentanamide

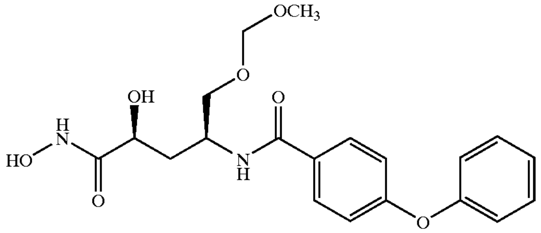

TLC: Rf 0.57 (Chloroform:Methanol:Acetic acid=85:15:1);

NMR ($d_6$-DMSO): δ10.44(1H, s), 8.69(1H, brs), 8.19(1H, d, J=8.4 Hz), 8.89(2H, d, J=8.8 Hz), 7.48–7.38(2H, m), 7.22–7.16(1H, m), 7.09–7.01(4H, m), 5.36(1H, brs), 4.55 (2H, s), 4.41–4.24(1H, m), 3.87(1H, dd, J=9.8 Hz, 2.6 Hz), 3.56–3.42(2H, m), 3.22(3H, s), 1.96–1.66(2H, m).

Example 49(235)

N-Hydroxy-2(R)-hydroxymethyl-5-ethoxymethoxy-4(S)-[N-(4-chlorophenylcarbonyl)amino] pentanamide

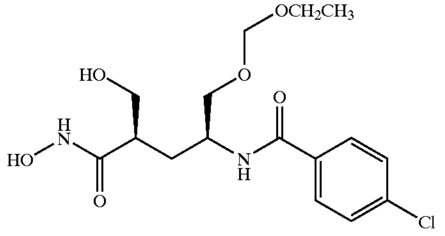

TLC: Rf 0.23 (Chloroform:Methanol:Acetic acid=90:10:1);

NMR ($d_6$-DMSO): δ10.55–10.10 (brs, 1H), 8.90–8.50 (brs, 1H), 8.21 (d, J=8.4 Hz, 1H), 7.86 (d, J=8.7 Hz, 2H), 7.52 (d, J=8.7 Hz, 2H), 4.59 (s, 2H), 4.20–4.00 (m, 1H), 3.60–3.38 (m, 6H), 2.30–2.18 (m, 1H), 1.85–1.70 (m, 1H), 1.70–1.55 (m, 1H), 1.09 (t, J=7.1 Hz, 3H).

Example 49(236)

N-Hydroxy-2(R)-methoxymethyl-5-ethoxymethoxy-4(S)-[N-(4-nitrophenylcarbonyl)amino]pentanamide

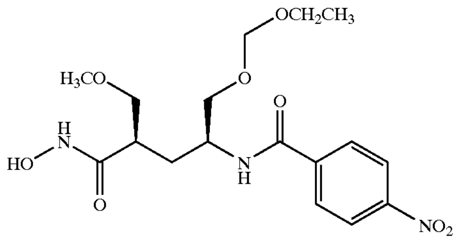

TLC: Rf 0.22 (Chloroform:Methanol=19:1);

NMR ($d_6$-DMSQ): 10.46 (s, 1H), 8.75 (s, 1H), 8.48 (d, J=8.4 Hz, 1H), 8.29 (d, J=8.8 Hz, 2H), 8.06 (d, J=8.8 Hz,

2H), 4.59 (s, 2H), 4.22–4.00 (m, 1H), 3.58–3.25 (m, 6H), 3.18 (s, 3H), 2.43–2.31 (m, 1H), 1.83–1.54 (m, 2H), 1.08 (t, J=7.0 Hz, 3H).

Example 49(237)

N-Hydroxy-2(R)-benzyloxymethyl-5-ethoxymethoxy-4(S)-[N-(4-nitrophenylcarbonyl)amino]pentanamide

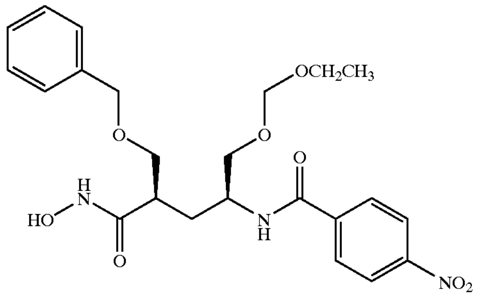

TLC: Rf 0.35 (Chloroform:Methanol=19:1);

NMR ($d_6$-DMSO): δ10.52 (s, 1H), 8.79 (s, 1H), 8.50 (d, J=8.7 Hz, 1H), 8.30 (d, J=8.7 Hz, 2H), 8.07 (d, J=8.7 Hz, 2H), 7.40–7.22 (m, 5H), 4.60 (s, 2H), 4.47 (d, J=12.0 Hz, 1H), 4.41 (d, J=12.0 Hz, 1H), 4.20–4.07 (m, 1H), 3.61–3.42 (m, 6H), 2.53–2.40 (m, 1H), 1.89–1.78 (m, 1H), 1.77–1.62 (m, 1H), 1.08 (t, J=7.2 Hz, 3H).

Example 49(238)

N-Hydroxy-2(R)-(2-methoxyethoxy)methyl-5-ethoxymethoxy-4(S)-[N-(4-nitrophenylcarbonyl)amino]pentanamide

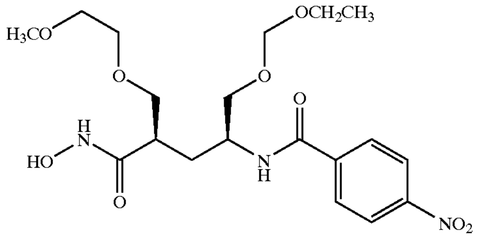

TLC: Rf 0.24 (Chloroform:Methanol=19:1);

NMR ($d_6$-DMSO): δ10.47 (s, 1H), 8.77 (s, 1H), 8.49 (d, J=8.1 Hz, 1H), 8.30 (d, J=8.7 Hz, 2H), 8.08 (d, J=8.7 Hz, 2H), 4.61 (s, 2H), 4.20–4.07 (m, 1H), 3.58–3.38 (m, 10H), 3.23 (s, 3H), 2.47–2.36 (m, 1H), 1.83–1.58 (m, 2H), 1.10 (t, J=7.2 Hz, 3H).

Example 49(239)

N-Hydroxy-2(R)-methoxymethyl-5-(2-methoxyethoxy)methoxy-4(S)-[N-(4-cyanophenylcarbonyl)amino]pentanamide

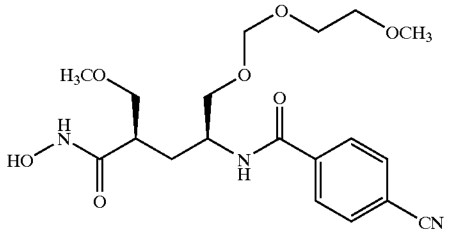

TLC: Rf 0.26 (Chloroform:Methanol=19:1);

NMR ($d_6$-DMSO): δ10.45 (s, 1H), 8.74 (s, 1H), 8.40 (d, J=8.4 Hz, 1H), 7.98 (d, J=8.8 Hz, 2H), 7.93 (d, J=8.8 Hz, 2H), 4.61 (s, 2H), 4.20–4.00 (m, 1H), 3.60–3.24 (m, 8H), 3.20 (s, 3H), 3.17 (s, 3H), 2.43–2.29 (m, 1H), 1.82–1.50 (m, 2H).

Example 49(240)

N-Hydroxy-2(R)-methoxymethyl-5-ethoxymethoxy-4(S)-[N-(trans-4-methylcyclohexylcarbonyl)amino]pentanamide

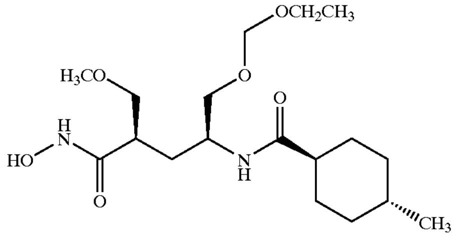

TLC: Rf 0.27 (Chloroform:Methanol=19:1);

NMR ($d_6$-DMSO): δ10.41 (s, 1H), 8.75 (s, 1H), 7.43 (d, J=8.7 Hz, 1H), 4.56 (s, 2H), 3.86–3.72 (m, 1H), 3.47 (q, J=7.2 Hz, 2H),3.41 –3.20 (m, 4H), 3.15 (s, 3H), 2.36–2.24 (m, 1H),2.05–1.93 (m, 1H), 1.77–1.56 (m, 5H), 1.49–1.18 (m, 4H), 1.10 (t, J=7.2 Hz, 3H), 0.95–0.77 (m, 5H).

Example 49(241)

N-Hydroxy-2(R)-methoxymethyl-5-ethoxymethoxy-4(S)-[N-(4-bromophenylcarbonyl)amino]pentanamide

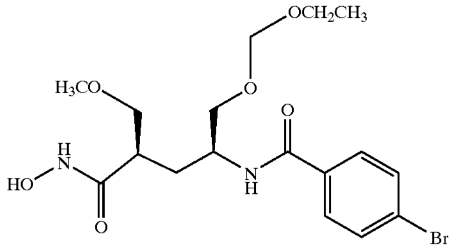

TLC: Rf 0.31 (Chloroform:Methanol=9:1);

NMR ($d_6$-DMSO): δ10.43 (s, 1H), 8.74 (brs, 1H), 8.21 (d, J=8.4 Hz, 1H), 7.78 (d, J=8.7 Hz, 2H), 7.66 (d, J=8.7 Hz, 2H), 4.58 (s, 2H), 4.13–4.01 (m, 1H), 3.50–3.31 (m, 6H), 3.16 (s, 3H), 2.42–2.12 (m, 1H), 1.79–1.53 (m, 2H), 1.07 (t, J=7.2 Hz, 3H).

Example 49(242)

N-Hydroxy-2(R)-methoxymethyl-5-ethoxymethoxy-4(S)-[N-(4-chlorophenylcarbonyl)amino] pentanamide

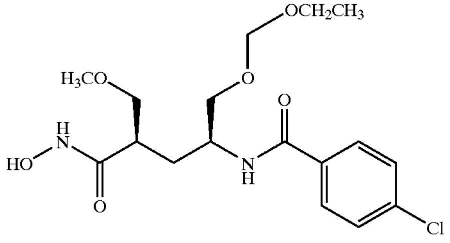

TLC: Rf 0.31 (Chloroform:Methanol=9:1);

NMR ($d_6$-DMSO): δ10.44 (s, 1H), 8.74 (s, 1H), 8.21 (d, J=8.4 Hz, 1H), 7.76 (d, J=8.7 Hz, 2H), 7.52 (d, J=8.7 Hz, 2H), 4.58 (s, 2H), 4.16–4.02 (m, 1H), 3.50–3.33 (m, 6H), 3.16 (s, 3H), 2.42–2.32 (m, 1H), 1.79–1.55 (m, 2H), 1.07 (t, J=7.2 Hz, 3H).

Example 49(243)

N-Hydroxy-2(R)-benzyloxymethyl-5-(2-methoxyethoxy)methoxy-4(S)-[N-(4-cyanophenylcarbonyl)amino]pentanamide

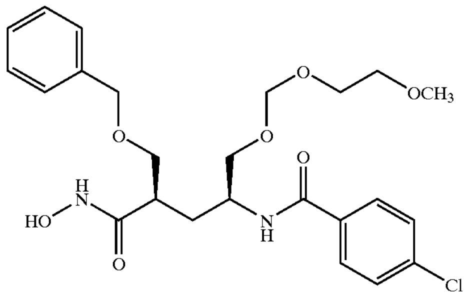

TLC: Rf 0.30 (Methylene chloride:Methanol=19:1);

NMR ($d_6$-DMSO): δ10.49 (d, J=1.5 Hz, 1H), 8.77 (d, J=1.5 Hz, 1H), 8.41 (d, J=8.4 Hz, 1H), 7.98 (d, J=8.7 Hz, 2H), 7.94 (d, J=8.7 Hz, 2H), 7.29 (m, 5H), 4.60 (s, 2H), 4.45 (d, J=12.0 Hz, 1H), 4.39 (d, J=12.0 Hz, 1H), 4.10 (m, 1H), 3.60–3.36 (m, 8H), 3.18 (s, 3H), 2.45 (m, 1H), 1.78 (m, 1H), 1.63 (m, 1H).

Example 49(244)

N-Hydroxy-2(R)-benzyloxymethyl-5-ethoxymethoxy-4(S)-[N-(4-chlorophenylcarbonyl) amino]pentanamide

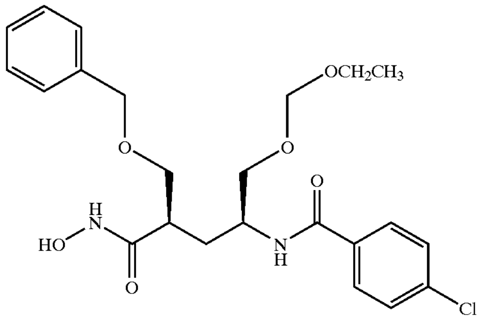

TLC: Rf 0.32 (Methylene chloride:Methanol=19:1);

NMR ($d_6$-DMSO): δ10.48 (s, 1H), 8.76 (s, 1H), 8.22 (d, J=8.4 Hz, 1H), 7.85 (d, J=8.7 Hz, 2H), 7.52 (d, J=8.7 Hz, 2H), 7.29 (m, 5H), 4.57 (s, 2H), 4.44 (d, J=12.0 Hz, 1H), 4.39 (d, J=12.0 Hz,1H), 4.08 (m,1H), 3.55–3.40 (m, 6H), 2.45 (m, 1H), 1.78 (m, 1H), 1.62 (m, 1H), 1.05 (t, J=7.2 Hz, 3H).

Example 49(245)

N-Hydroxy-2(R)-benzyloxymethyl-5-ethoxymethoxy-4(S)-[N-(4-bromophenylcarbonyl) amino]pentanamide

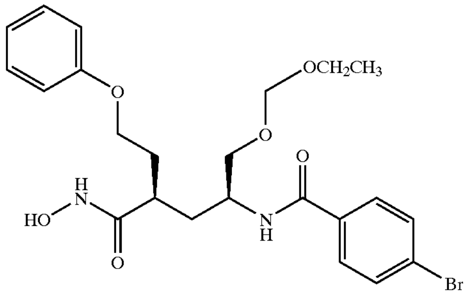

TLC: Rf 0.32 (Methylene chloride:Methanol=19:1);

NMR ($d_6$-DMSO): δ10.49 (d, J=1.8 Hz, 1H), 8.77 (d, J=1.8 Hz, 1H), 8.22 (d, J=8.4 Hz, 1H), 7.78 (d, J=8.7 Hz, 2H), 7.66 (d, J=8.7 Hz, 2H), 7.29 (m, 5H), 4.57 (s, 2H), 4.44 (d, J=12.0 Hz, 1H), 4.39 (d, J=12.0 Hz, 1H), 4.08 (m, 1H), 3.55–3.40 (m, 6H), 2.45 (m, 1H), 1.78 (m, 1H), 1.62 (m, 1H), 1.05 (t, J=7.2 Hz, 3H).

Example 49(246)

N-Hydroxy-2(R)-[2-(3-methoxyphenoxy)ethyl]-5-ethoxymethoxy-4(S)-[N-(4-nitrophenylcarbonyl)amino]pentanamide

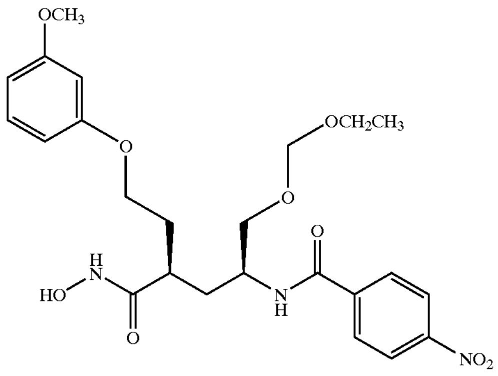

TLC: Rf 0.40 (Chloroform:Methanol=9:1);

NMR ($d_6$-DMSO): δ10.50 (s, 1H), 8.76 (s, 1H), 8.48 (d, J=8.4 Hz, 1H), 8.30 (d, J=8.6 Hz, 2H), 8.06 (d, J=8.6 Hz, 2H), 7.13 (t, J=8.3 Hz, 1H), 6.52–6.35 (m, 3H), 4.59 (s, 2H), 4.25–4.12 (m, 1H), 3.95–3.75 (m, 2H), 3.68 (s, 3H), 3.60–3.40 (m, 4H), 2.40–2.25 (m, 1H), 2.00–1.65 (m, 4H), 1.07 (t, J=7.1 Hz, 3H).

Example 49(247)

N-Hydroxy-2(R)-methoxymethyl-5-ethoxymethoxy-4(S)-[N-[(2-nitrothiophen-5-yl)carbonyl]amino]pentanamide

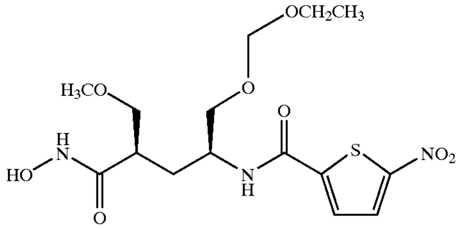

TLC: Rf 0.37 (Chloroform:Methanol=9:1);

NMR ($d_6$-DMSO): δ10.46 (s, 1H), 8.75 (brs, 1H), 8.71 (d, J=8.4 Hz, 1H), 8.13 (d, J=4.2 Hz, 1H), 7.82 (d, J=4.2 Hz, 1H), 4.58 (s, 2H), 3.97–4.09 (m, 1H), 3.50–3.38 (m, 6H), 3.17 (s, 3H), 2.41–2.32 (m, 1H), 1.79–1.55 (m, 2H), 1.07 (t, J=7.2 Hz, 3H).

Example 49(248)

N-Hydroxy-2(R)-methoxymethyl-5-ethoxymethoxy-4(S)-[N-[(2-bromothiophen5-yl)carbonyl]amino]pentanamide

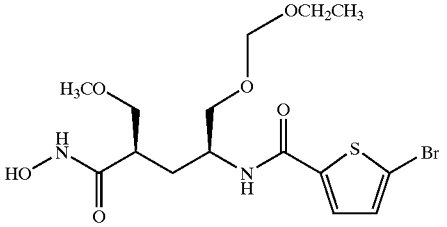

TLC: Rf 0.34 (Chloroform:Methanol=9:1);

NMR ($d_6$-DMSO): δ10.44 (s, 1H), 8.75 (s, 1H), 8.27 (d, J=8.1 Hz, 1H), 7.61 (d, J=4.2 Hz, 1H), 7.27 (d, J=4.2 Hz, 1H), 4.57 (s, 2H), 4.05–3.91 (m, 1H), 3.50–3.37 (m, 6H), 3.16 (s, 3H), 2.41–2.31 (m, 1H), 1.78–1.51 (m, 2H), 1.07 (t, J=7.2 Hz, 3H).

Example 49(249)

N-Hydroxy-2(R)-(2-methoxyethoxy)methyl-5-ethoxymethoxy-4(S)-[N-(4-bromophenylcarbonyl)amino]pentanamide

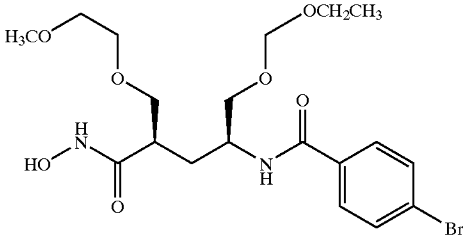

TLC: Rf 0.31 (Chloroform:Methanol=9:1);

NMR ($d_6$-DMSO): δ10.43 (s, 1H), 8.74 (s, 1H), 8.20 (d, J=8.6 Hz, 1H), 7.78 (d, J=8.6 Hz, 2H), 7.65 (d, J=8.6 Hz, 2H), 4.58 (s, 2H), 4.18–4.01 (m, 1H), 3.50–3.36 (m, 10H), 3.20 (s, 3H), 2.44–2.39 (m, 1H), 1.81–1.52 (m, 2H), 1.07 (t, J=7.0 Hz, 3H).

Example 49(250)

N-Hydroxy-2(R)-(2-methoxyethoxy)methyl-5-(2-methoxyethoxy)methoxy-4(S)-[N-(4-cyanophenylcarbonyl)amino]pentanamide

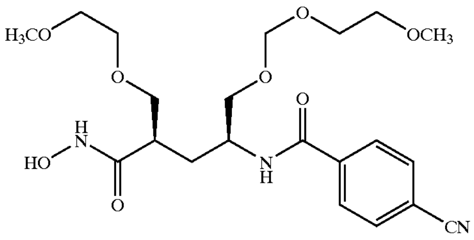

TLC: Rf 0.24 (Chloroform:Methanol=1:1);

NMR ($d_6$-DMSO): δ10.45 (brs, 1H), 8.78 (brs, 1H), 8.43 (d, J=8.1 Hz, 1H), 7.99 (d, J=8.4 Hz, 2H), 7.94 (d, J=8.4 Hz, 2H), 4.61 (s, 2H), 4.16–4.02 (m, 1H), 3.57–3.35 (m, 12H), 3.21 (s, 3H), 3.20 (s, 3H), 2.42–2.32 (m, 1H), 1.80–1.56 (m, 2H).

Example 49(251)

N-Hydroxy-2(R)-(2-methoxyethoxy)methyl-5-ethoxymethoxy-4(S)-[N-(4-chlorophenylcarbonyl)amino]pentanamide

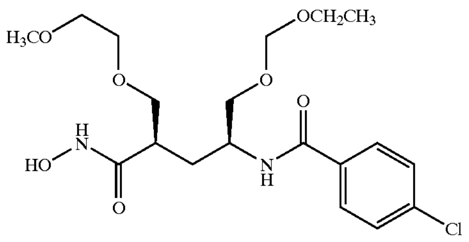

TLC: Rf 0.34 (Chloroform:Methanol=9:1);

NMR ($d_6$-DMSO): δ10.43 (s, 1H), 8.74 (brs, 1H), 8.20 (d, J=8.4 Hz, 1H), 7.87–7.83 (m, 2H), 7.54–7.49 (m, 2H) 4.58 (s, 2H), 4.18–4.10 (m, 1H), 3.52–3.36 (m, 10H), 3.20 (s, 3H), 2.42–2.29 (m, 1H), 1.81–1.53 (m, 2H), 1.07 (t, J=7.0 Hz, 3H).

Example 49(252)

N-Hydroxy-2(R)-benzyloxymethyl-5-ethoxymethoxy-4(S)-[N-(trans-4-methylcyclohexylcarbonyl)amino]pentanamide

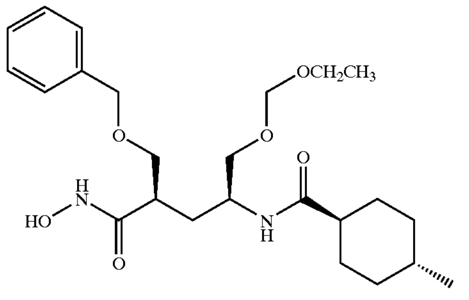

TLC: Rf 0.34 (Chloroform:Methanol=19:1);

NMR ($d_6$-DMSO): δ10.46 (s, 1H), 8.78 (s, 1H), 7.44 (d, J=8.4 Hz, 1H), 7.38–7.21 (m, 5H), 4.59–4.52 (m, 2H), 4.43 (d, J=12.0 Hz, 1H), 4.37 (d, J=12.0 Hz, 1H), 3.85–3.72 (m, 1H), 3.54–3.28 (m, 6H), 2.43–2.30 (m, 1H),2.06–1.92 (m, 1H), 1.76–1.59 (m, 5H), 1.52–1.20 (m, 4H), 1.09 (t, J=6.9 Hz, 3H), 0.93–0.75 (m, 5H).

Example 49(253)

N-Hydroxy-2(R)-(3-thienyl)methoxymethyl-5-ethoxymethoxy-4(S)-[N-(4-nitrophenylcarbonyl)amino]pentanamide

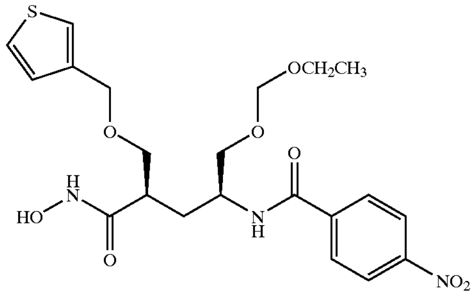

TLC: Rf 0.34 (Chloroform:Methanol=19:1);

NMR ($d_6$-DMSO): δ10.49 (s, 1H), 8.76 (s, 1H), 8.49 (d, J=8.4 Hz, 1H), 8.30 (d, J=8.8 Hz, 2H), 8.06 (d, J=8.8 Hz, 2H), 7.49 (dd, J=5.2, 2.8 Hz, 1H), 7.40–7.36 (m, 1H), 7.03 (dd, J=5.2, 1.6 Hz, 1H), 4.59 (s, 2H), 4.50–4.36 (m, 2H), 4.21–4.00 (m, 1H), 3.60–3.36 (m, 6H), 2.52–2.38 (m, 1H), 1.88–1.56 (m, 2H), 1.07 (t, J=7.0 Hz, 3H).

Example 49(254)~49(263)

The following compounds were obtained by the same procedure as a series of reaction of Example 37→Example 39→Example 45→Example 46 (using a corresponding compound instead of benzyl bromide.)→Example 47→Example 48→Example 49, using a corresponding compound instead of the compound prepared in Reference Example 4.

Example 49(254)

N-Hydroxy-2(R)-(2-pyridinyl)methyl-5-hydroxy-4(S)-[N-(4-phenoxyphenylcarbonyl)amino]pentanamide

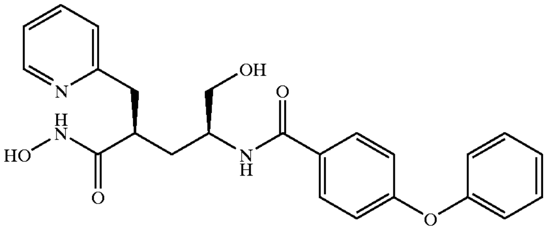

TLC: Rf 0.17 (Chloroform:Methanol:Acetic acid:Water=100:10:1:1);

NMR ($d_6$-DMSO): δ10.35(1H, brs), 8.63(1H, brs), 8.42–8.40(1H, m), 7.91–7.86(3H, m), 7.64(1H, dt, J=7.8 Hz, 1.8 Hz), 7.45–7.39(2H, m), 7.25–7.14(3H, m), 7.07–7.00 (4H, m), 4.67(1H, brs), 4.15–3.94(1H, m), 3.50–3.34(2H, m), 2.97–2.81(2H, m), 2.71–2.62(1H, m), 1.82–1.65(2H, m).

Example 49(255)

N-Hydroxy-2(S)-methyl-5-hydroxy-4(S)-[N-(4-phenoxyphenylcarbonyl)amino]pentanamide

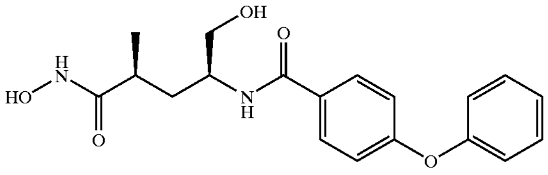

TLC: Rf 0.14 (Chloroform:Methanol=9:1);

NMR ($d_6$-DMSO): δ10.33 (1H, s), 8.62 (1H, s), 7.89–7.83 (3H, m), 7.41 (2H, t, J=7.6 Hz), 7.17 (1H, t, J=7.6Hz), 7.04 (2H, d, J=7.6Hz), 7.00 (2H, d, J=8.7 Hz), 4.68 (1H, t, J=5.7 Hz), 4.02–3.91 (1H, m), 3.45–3.28 (2H, m), 2.21–2.08 (1H, m), 1.72–1.55 (2H, m), 0.98 (3H, d, J=6.6 Hz).

Example 49(256)

N-Hydroxy-2(S)-methyl-5-hydroxy-4(S)-[N-(4-bromophenylcarbonyl)amino]pentanamide

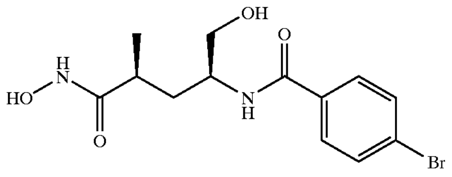

TLC: Rf 0.25 (Chloroform:Methanol=9:1);

NMR ($d_6$-DMSO): δ10.37 (s, 1H), 8.64 (s, 1H), 8.02 (d, J=8.6 Hz, 1H), 7.81 (d, J=8.4 Hz, 2H), 7.65 (d, J=8.4 Hz, 2H), 4.80–4.64 (m, 1H), 4.10–3.88 (m, 1H), 3.60–3.10 (m, 2H), 2.26–2.06 (m, 1H), 1.80–1.56 (m, 2H), 1.02 (d, J=6.8 Hz, 3H).

Example 49(257)

N-Hydroxy-2(S)-(3-methoxybenzyl)-5-hydroxy-4(S)-[N-(4-bromophenylcarbonyl)amino]pentanamide

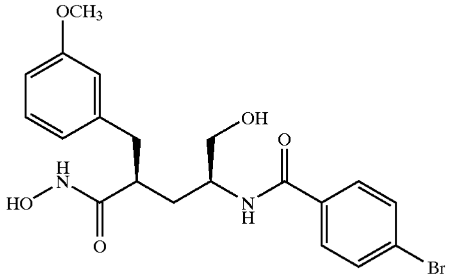

TLC: Rf 0.45 (Methylene chloride:Methanol=9:1);

NMR ($d_6$-DMSO): δ10.28 (s, 1H), 8.63 (s, 1H), 8.04 (brd, J=8.4 Hz, 1H), 7.82 (d, J=8.4 Hz, 2H), 7.66 (d, J=8.4 Hz, 2H), 7.11 (t, J=8.0 Hz, 1H), 6.67 (m, 3H), 4.69 (brt, J=5.8 Hz, 1H), 4.09 (m, 1H), 3.65 (s, 3H), 3.44 (m, 2H), 2.75 (brd, J=7.2 Hz, 2H), 2.33 (m, 1H), 1.85–1.50 (m, 2H).

Example 49(258)

N-Hydroxy-2(S)-(3-methoxybenzyl)-5-hydroxy-4(S)-[N-(4-nitrophenylcarbonyl)amino]pentanamide

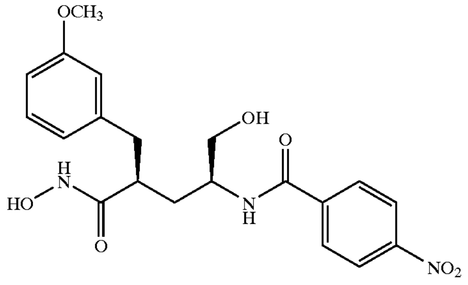

TLC: Rf 0.52 (Methylene chloride:Methanol=9:1);

NMR ($d_6$-DMSO): δ10.31 (s, 1H), 8.64 (s, 1H), 8.34 (brd, J=8.4 Hz, 1H), 8.30 (d, J=9.2 Hz, 2H), 8.09 (d, J=9.2 Hz, 2H), 7.11 (t, J=8.8 Hz, 1H), 6.70 (m, 3H), 4.73 (brt, J=5.8 Hz, 1H), 4.10 (m, 1H), 3.67 (s, 3H), 3.43 (m, 2H), 2.73 (brd, J=7.0 Hz, 2H), 2.35 (m, 1H), 1.85–1.55 (m, 2H).

Example 49(259)

N-Hydroxy-2(S)-(3-methoxybenzyl)-5-hydroxy-4(S)-[N-(4-chlorophenylcarbonyl)amino]pentanamide

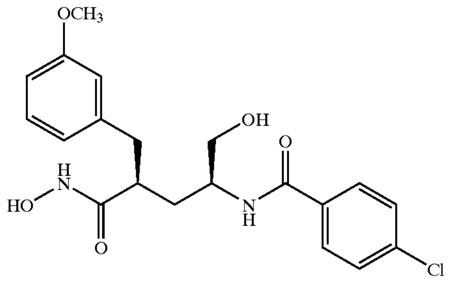

TLC: Rf 0.52 (Methylene chloride:Methanol=9:1);

NMR ($d_6$-DMSO): δ10.28 (s, 1H), 8.63 (s, 1H), 8.06 (brd, J=8.4 Hz, 1H), 7.89 (d, J=8.7 Hz, 2H), 7.52 (d, J=8.7 Hz, 2H), 7.11 (t, J=8.4 Hz, 1H), 6.67 (m, 3H), 4.70 (brt, J=5.7 Hz, 1H), 4.10 (m, 1H), 3.65 (s, 3H), 3.41 (m, 2H), 2.72 (brd, J=7.2 Hz, 2H), 2.33 (m, 1H), 1.82–1.55 (m, 2H).

Example 49(260)

N-Hydroxy-2(S)-(3-methoxybenzyl)-5-hydroxy-4(S)-[N-[(2-bromothiophen-5-yl)carbonyl]amino]pentanamide

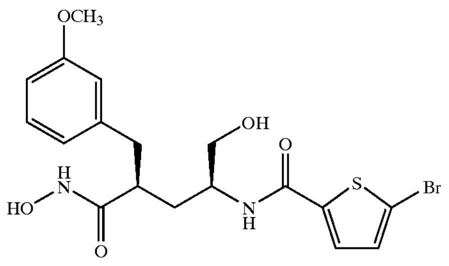

TLC: Rf 0.52 (Methylene chloride:Methanol=9:1);

NMR ($d_6$-DMSO): δ10.30 (s, 1H), 8.64 (s, 1H), 8.13 (brd, J=8.8 Hz, 1H), 7.63 (d, J=4.0 Hz, 1H), 7.27 (d, J=4.0 Hz, 1H), 7.12 (t, J=8.4 Hz, 1H), 6.69 (m, 3H), 4.72 (brs, 1H), 4.00 (m, 1H), 3.68 (s, 3H), 3.39 (m, 2H), 2.71 (brd, J=7.2 Hz, 2H), 2.32 (m, 1H), 1.83–1.49 (m, 2H).

Example 49(261)

N-Hydroxy-2(S)-(3-methoxybenzyl)-5-hydroxy-4 (S)-[N-[(2-nitrothiophen-5-yl)carbonyl]amino] pentanamide

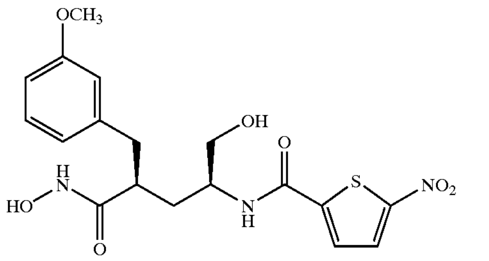

TLC: Rf 0.47 (Methylene chloride:Methanol=9:1);

NMR ($d_6$-DMSO): δ10.32 (s, 1H), 8.65 (s, 1H), 8.57 (brd, J=9.0 Hz, 1H), 8.14 (d, J=4.5 Hz, 1H), 7.84 (d, J=4.5 Hz, 1H), 7.12 (t, J=8.4 Hz, 1H), 6.69 (m, 3H), 4.78 (brs, 1H), 4.01 (m, 1H), 3.69 (s, 3H), 3.42 (m, 2H), 2.71 (m, 2H), 2.33 (m, 1H), 1.81–1.54 (m, 2H).

Example 49(262)

N-Hydroxy-2(S)-(3-methoxybenzyl)-5-hydroxy-4 (S)-[N-(4-cyanophenylcarbonyl)amino]pentanamide

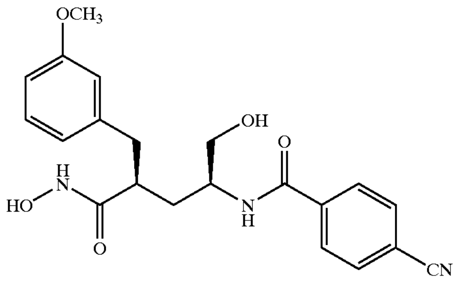

TLC: Rf 0.39 (Chloroform:Methanol=9:1);

NMR ($d_6$-DMSO): δ10.31 (s, 1H), 8.64 (s, 1H), 8.23 (d, J=8.8 Hz, 1H), 8.03 (d, J=8.4 Hz, 2H), 7.93 (d, J=8.4 Hz, 2H), 7.18–7.06 (m, 1H), 6.75–6.64 (m, 3H), 4.71 (t, J=5.8 Hz, 1H), 4.21–4.00 (m, 1H), 3.67 (s, 3H), 3.57–3.37 (m, 2H), 2.74 (d, J=7.0 Hz, 2H), 2.42–2.25 (m, 1H), 1.90–1.52 (m, 2H).

Example 49(263)

N-Hydroxy-2(R)-benzyloxymethyl-5-hydroxy-4(S)-[N-(4-nitrophenylcarbonyl)amino]pentanamide

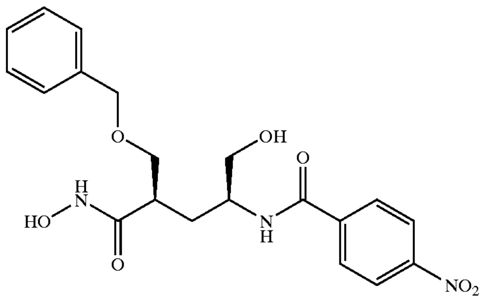

TLC: Rf 0.62 (Methylene chloride:Methanol=9:1);

NMR ($d_6$-DMSO): δ10.47 (s, 1H), 8.74 (s, 1H), 8.33 (d, J=8.8 Hz, 1H), 8.29 (d, J=8.6 Hz, 2H), 8.06 (d, J=8.6 Hz, 2H), 7.29 (m, 5H), 4.72 (t, J=5.6 Hz, 1H), 4.45 (d, J=12.4 Hz, 1H), 4.38 (d, J=12.0 Hz, 1H), 3.95 (m, 1H), 3.60–3.35 (m, 4H), 2.45 (m, 1H), 1.78 (m, 1H), 1.62 (m, 1H).

Example 49(264)~49(269)

The following compounds were obtained by the same procedure as a series of reaction of Example 37→Example 39→Example 41 (using a corresponding compound instead of methoxymethyl chloride, if necessary.)→Example 43 (using a corresponding compound instead of benzyl bromide.)→Example 5→Example 44→Example 49, using a corresponding compound.

Example 49(264)

N-Hydroxy-5-methoxymethoxy-4(S)-[N-methyl-N-[4-(4-chlorophenyl)phenylcarbonyl]amino] pentanamide

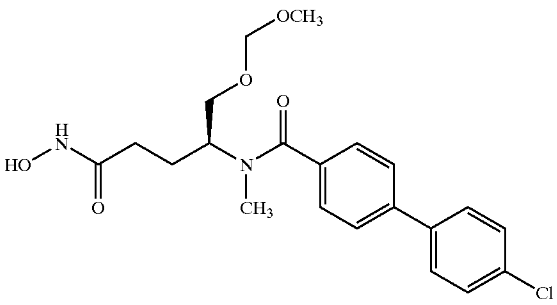

TLC: Rf 0.22 (Chloroform:Methanol=9:1);

NMR ($d_6$-DMSO): δ10.36 (1H, s), 7.75–7.65 (4H, m), 7.54–7.37 (4H, m), 4.66–3.68 (3H, m), 3.64–3.35 (2H, m), 3.25, 3.21 (3H, s), 2.81, 2.74 (3H, s), 2.07–1.55 (4H, m).

Example 49(265)

N-Hydroxy-2(S)-(3-pyridyl)methyl-5-methoxymethoxy-4(S)-[N-methyl-N-[4-(4-chlorophenyl)phenylcarbonyl]amino]pentanamide

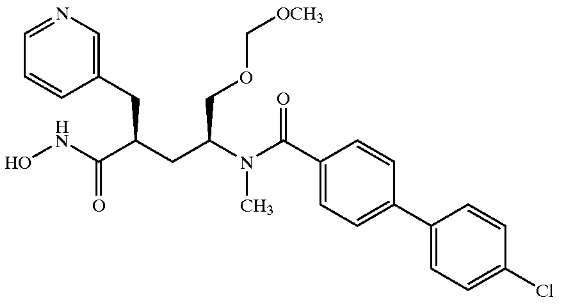

TLC: Rf 0.42 (Chloroform:Methanol:Acetic acid=9:1:0.5);

NMR ($d_6$-DMSO): δ10.43 (1H, s), 8.72 (1H, s), 8.45–8.29 (2H, m), 7.78–7.60 (5H, m), 7.58–7.40 (4H, m), 7.33–7.22 (1H, m), 4.97–4.84 (0.6H, m), 4.56–4.44 (2H, m), 3.94–3.84 (0.4H, m), 3.64–3.30 (2H, m), 3.25, 3.20 (3H, s), 2.82, 2.73 (3H, s), 2.85–2.21 (3H, m), 1.88–1.49 (2H, m).

Example 49(266)

N-Hydroxy-2(S)-methyl-5-ethoxymethoxy-4(S)-[N-methyl-N-(4-bromophenylcarbonyl)amino] pentanamide

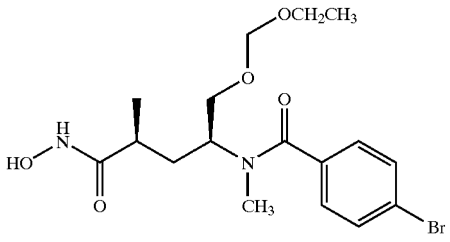

TLC: Rf 0.36 (Chloroform:Methanol=9:1);

NMR ($d_6$-DMSO): δ10.47&10.45 (s, 1H), 8.72&8.69 (s, 1H), 7.63& 7.60 (d, J=8.4 Hz, 2H), 7.32&7.30 (d, J=8.4 Hz, 2H), 4.79–4.67&3.77–3.64 (m, 1H), 4.61& 4.56 (s, 2H), 3.60–3.36 (m, 4H), 2.78&2.65 (s, 3H), 2.18–2.06&2.03–1.92 (m, 1H), 1.85–1.67 (m, 1H), 1.54–1.43&1.38–1.27 (m, 1H), 1.10 (q, J=6.6 Hz, 3H), 1.03&0.73 (d, J=6.9 Hz, 3H).

Example 49(267)

N-Hydroxy-2(S)-(3-methoxybenzyl)-5-ethoxymethoxy-4(S)-[N-methyl-N-(4-bromophenylcarbonyl)amino]pentanamide

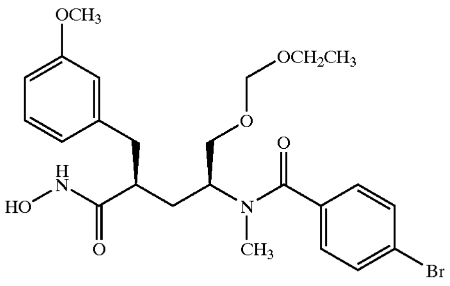

TLC: Rf 0.47 (Chloroform:Methanol=9:1);

NMR ($d_6$-DMSO): δ10.44&10.42 (s, 1H), 8.71 (s, 1H), 7.66&7.53 (d, J=8.1 Hz, 2H), 7.36&7.29 (d, J=8.1 Hz, 2H), 7.14 (t, J=8.0 Hz, 1H), 6.80–6.58 (m, 3H), 4.89–4.79&3.75–3.63 (m, 1H), 4.60&4.52 (s, 2H), 3.71 &3.67 (s, 3H), 3.58–3.36 (m, 4H), 2.78&2.68 (s, 3H), 2.77–2.56 (m, 2H), 2.33–2.15 (m, 1H), 1.85–1.72 (m, 1H), 1.66–1.57&1.54–1.43 (m, 1H), 1.15–1.04 (m, 3H).

Example 49(268)

N-Hydroxy-2(S)-methyl-5-ethoxymethoxy-4(S)-[N-methyl-N-(4-nitrophenylcarbonyl)amino] pentanamide

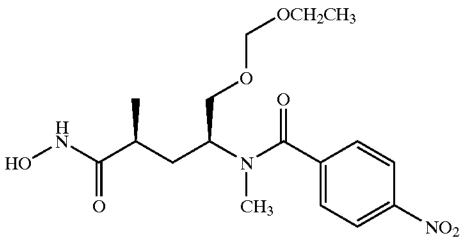

TLC: Rf 0.27 (Chloroform:Methanol=19:1);

NMR ($d_6$-DMSO): δ10.51 and 10.45 (s, 1H), 8.76 and 8.70 (s, 1H), 8.29 and 8.26 (d, J=8.8 Hz, 2H), 7.64 and 7.60 (d, J=8.8 Hz, 2H), 4.86–4.51 (m, 3H), 3.70–3.36 (m, 4H), 2.84 and 2.65 (s, 3H), 2.22–1.65 (m, 2H), 1.60–1.20 (m, 1H), 1.15 and 1.12 (t, J=7.0 Hz, 3H), 1.07 and 0.79 (d, J=7.0 Hz, 3H).

Example 49(269)

N-Hydroxy-2(S)-methyl-5-benzyloxymethoxy-4(S)-[N-methyl-N-(4-nitrophenylcarbonyl)amino] pentanamide

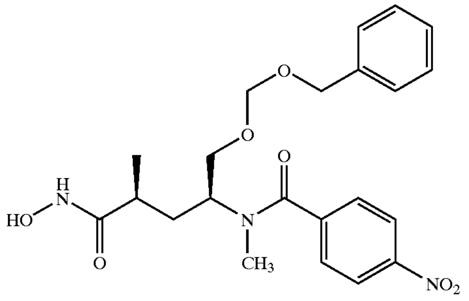

TLC: Rf 0.43 (Chloroform:Methanol=9:1);

NMR ($d_6$-DMSO): δ10.50&10.43 (s, 1H), 8.75&8.69 (d, J=1.5 Hz, 1H), 8.27&8.25 (d, J=8.9 Hz, 2H), 7.63&7.60 (d, J=8.9 Hz, 2H), 7.37–7.26 (m, 5H), 4.83–4.67 (m, 2.5H), 4.58–4.46 (m, 2H), 3.69–3.56&3.48–3.37 (m, 2.5H), 2.83&2.63 (s, 3H), 2.20–2.10& 2.06–1.95 (m, 1H), 1.90–1.72 (m, 1H), 1.55–1.44 &1.39–1.29 (m, 1H), 1.05&0.76 (d, J=6.8 Hz, 3H).

Example 49(270)~49(277)

The following compounds were obtained by the same procedure as a series of reaction of Example 37→Example 39→Example 45→Example 46 (using a corresponding compound instead of benzyl, bromide.)→Example 5→Example 47→Example48→Example 49, using a corresponding compound instead of the compound prepared in Reference Example 4.

Example 49(270)

N-Hydroxy-2(S)-(3-methoxybenzyl)-5-hydroxy-4(S)-[N-methyl-N-(4-chlorophenylcarbonyl)amino] pentanamide

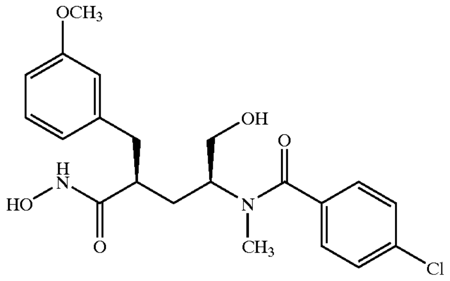

TLC: Rf 0.51 (Methylene chloride:Methanol=9:1);

NMR ($d_6$-DMSO): δ10.40 (s, 0.45H), 10.38 (s, 0.55H), 8.67 (s, 1H), 7.53–7.35 (m, 3.45H), 7.24–7.10 (m, 1.55H), 6.73–6.56 (m, 3H), 4.94 (brt, J=5.2 Hz, 0.45H), 4.79 (brt, J=5.2 Hz, 0.55H), 4.72 (m, 0.55H), 3.70 (s, 1.65H), 3.67 (s, 1.35H), 3.70–3.30 (m, 2.45H), 2.78 (s, 1.35H), 2.66 (s, 1.65H), 2.80–2.10 (m, 4H), 1.80–1.35 (m, 2H).

Example 49(271)

N-Hydroxy-2(S)-(3-methoxybenzyl)-5-hydroxy-4(S)-[N-methyl-N-(4-nitrophenylcarbonyl)amino] pentanamide

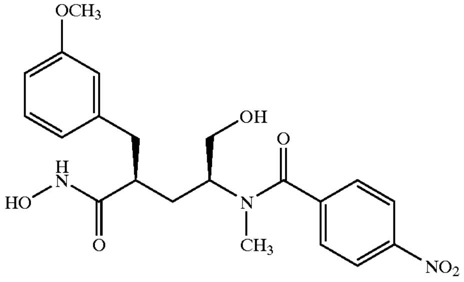

TLC: Rf 0.56 (Methylene chloride:Methanol=9:1);

NMR ($d_6$-DMSO): δ10.39 (s, 0.5H), 10.37 (s, 0.5H), 8.69 (s, 0.5H), 8.64 (s, 0.5H), 8.28 (d, J=8.8 Hz, 1H), 8.17 (d, J=8.8 Hz, 1H), 7.68 (d, J=8.8 Hz, 1H), 7.59 (d, J=8.8 Hz, 1H), 7.11 (m, 1H), 6.72 (m, 2H), 6.57 (m, 1H), 4.95 (brt, J=5.2 Hz, 0.5H), 4.82 (brt, J=5.2 Hz, 0.5H), 4.69 (m, 0.5H), 3.68 (s, 3H), 3.60–3.30 (m, 2.5H), 3.55–3.25 (m, 2H), 2.80 (s, 1.5H), 2.63 (s, 1.5H), 2.80–2.10 (m, 4H), 1.80–1.35 (m, 2H).

Example 49(272)

N-Hydroxy-2(S)-(3-methoxybenzyl)-5-hydroxy-4(S)-[N-methyl-N-(4-bromophenylcarbonyl)amino] pentanamide

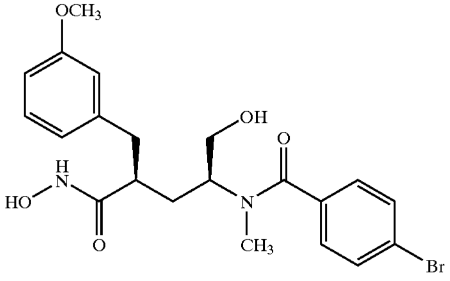

TLC: Rf 0.45 (Methylene chloride:Methanol=9:1);

NMR ($d_6$-DMSO): δ10.41 (s, 0.45H), 10.38 (s, 0.55H), 8.67 (s, 1H), 7.64 (d, J=8.4 Hz, 1.1H), 7.53 (d, J=8.4 Hz, 0.9H), 7.39 (d, J=8.4 Hz, 1.1H), 7.35 (d, J=8.4 Hz, 0.9H), 7.13 (t, J=7.8 Hz, 1H), 6.70 (m, 2.1H), 6.57 (m, 0.9H), 4.94 (brt, J=5.1 Hz, 0.45H), 4.79 (brt, J=5.7 Hz, 0.55H), 4.70 (m, 0.55H), 3.70 (s, 1.65H), 3.67 (s, 1.35H), 3.70–3.60 (m, 0.45H), 3.55–3.25 (m, 2H), 2.78 (s, 1.35H), 2.66 (s, 1.65H), 2.80–2.10 (m, 4H), 1.80–1.35 (m, 2H).

Example 49(273)

N-Hydroxy-2(S)-methyl-5-hydroxy-4(S)-[N-methyl-N-(4-nitrophenylcarbonyl)amino]pentanamide

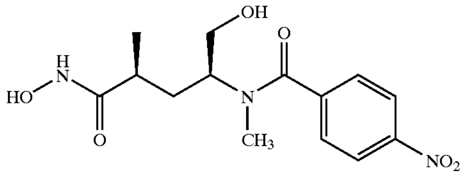

TLC: Rf 0.16 (Chloroform:Methanol=9:1);

NMR ($d_6$-DMSO): δ10.49&10.42 (s, 1H), 8.72&8.67 (d, J=1.5 Hz, 1H), 8.27&8.25 (d, J=8.8 Hz, 2H), 7.65&7.62 (d, J=8.8 Hz, 2H), 5.01 &4.83(t, J=5.4 Hz, 1H), 4.65–4.54&3.51–3.40 (m, 1H), 3.53–3.27 (m, 2H), 2.81 &2.62 (s, 3H), 2.17–2.09&2.03–1.91 (m, 1H), 1.80–1.63 (m, 1H), 1.52–1.42&1.33–1.22 (m, 1H), 1.05&0.72 (d, J=6.9 Hz, 3H).

Example 49(274)

N-Hydroxy-2(S)-benzyl-5-hydroxy-4(S)-[N-methyl-N-(4-nitrophenylcarbonyl)amino]pentanamide

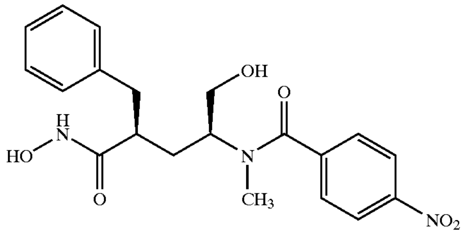

TLC: Rf 0.25 (Chloroform:Methanol:Water=9:1:0.1);

NMR ($d_6$-DMSO): δ10.40 and 10.37 (s, 1H), 8.70 and 8.65 (brs, 1H), 8.29 and 8.19 (d, J=8.7 Hz, 2H), 7.69 and 7.60 (d, J=8.7 Hz, 2H), 7.30–7.01 (m, 5H), 4.91 and 4.84 (t, J=5.4 Hz, 1H), 4.75–4.64 and 3.54–3.44 (m, 1H), 3.49–3.25 (m, 2H), 2.81 and 2.65 (s, 3H), 2.84–2.51 (m, 2H), 2.35–2.12 (m, 1H), 1.84–1.56 and 1.47–1.36 (m, 2H).

Example 49(275)

N-Hydroxy-2(S)-methyl-5-hydroxy-4(S)-[N-methyl-N-(4-bromophenylcarbonyl)amino]pentanamide

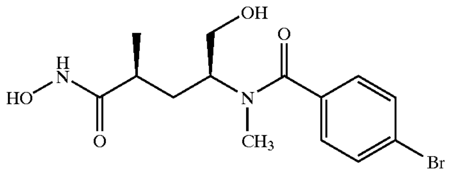

TLC: Rf 0.17 (Chloroform:Methanol:Water=9:1:0.1);

NMR ($d_6$-DMSO): δ10.43 (s, 1H), 8.66 (s, 1H), 7.62 and 7.59 (d, J=8.1 Hz, 2H), 7.35 (d, J=8.1 Hz, 2H), 4.98–4.92 and 4.81–4.73 (m, 1H), 4.63–4.52 and 3.64–3.52 (m, 1H), 3.52–3.39 (m, 2H), 2.77 and 2.64 (s, 3H), 2.15–2.05 and 2.00–1.89 (m, 1H), 1.77–1.58 and 1.53–1.43 and 1.32–1.21 (m, 2H), 1.04 and 0.68 (d, J=6.7 Hz, 3H).

Example 49(276)

N-Hydroxy-2(S)-benzyl-5-hydroxy-4(S)-[N-methyl-N-(4-bromophenylcarbonyl)amino]pentanamide

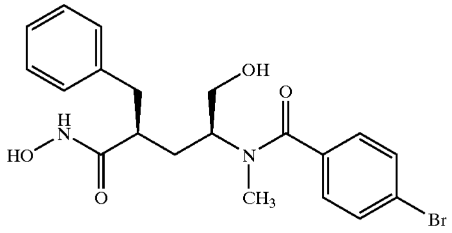

TLC: Rf 0.25 (Chloroform:Methanol:Water=9:1:0.1);

NMR ($d_6$-DMSO): δ10.40 and 10.37 (s, 1H), 8.66 (s, 1H), 7.64 and 7.54 (d, J=8.6 Hz, 2H), 7.39 and 7.36 (d, J=8.6 Hz, 2H), 7.28–6.97 (m, 5H), 4.95 and 4.79 (t, J=5.4 Hz, 1H), 4.75–4.65 and 3.69–3.60 (m, 1H), 3.52–3.26 (m, 2H, 2.78 and 2.66 (s, 3H), 2.82–2.55 (m, 2H), 2.31–2.12 (m, 1H), 1.80–1.56 and 1.67–1.35 (m, 2H).

Example 49(277)

N-Hydroxy-2(S)-methyl-5-hydroxy-4(S)-[N-methyl-N-(4-chlorophenylcarbonyl)amino]pentanamide

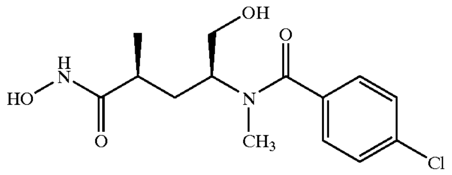

TLC: Rf 0.17 (Chloroform:Methanol:Water=9:1:0.1);

NMR ($d_6$-DMSO): δ10.45 and 10.43 (s, 1H), 8.69 and 8.66 (s, 1H), 7.53–7.38 (m, 4H), 4.96 and 4.77 (t, J=5.3 Hz, 1H), 4.63–4.52 and 3.65–3.51 (m, 1H), 3.51–3.40 (m, 2H), 2.78 and 2.64 (s, 3H), 2.15–2.05 and 1.98–1.88 (m, 1H), 1.77–1.54 (m, 1H), 1.54–1.43 and 1.32–1.21 (m, 1H), 1.03 and 0.67 (d, J=6.8 Hz, 3H).

Example 50

2(S)-Benzyloxy-3(S)-hydroxy-4-(N-(4-(3-methoxy-1-propynyl)phenylcarbonyl)amino)butyric acid ethyl ester

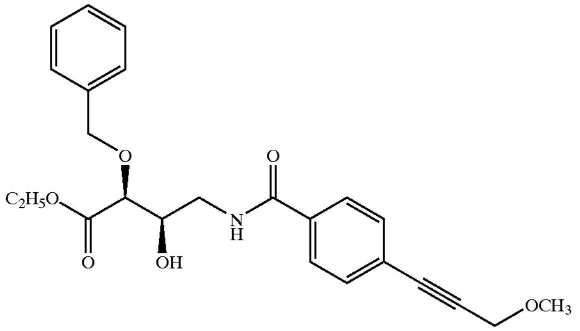

The title compound having the following physical data was obtained by the same procedure as a series of reaction of Example 1, using 2(S)-benzyloxy-3(S)-hydroxy-4-aminobutyric acid ethyl ester (prepared by the same procedure as described in Bioorg. Med. Chem. Lett., 2, 515 (1992).) instead of 4-aminobutyric acid ethyl ester and a corresponding acyl halide instead of the compound prepared in Reference Example 4.

TLC: Rf 0.20 (n-Hexane:Ethyl acetate=3:2).

Example 51

2(S)-Benzyloxy-3(S)-hydroxy-4-(N-(4-(3-methoxy-1-propynyl)phenylcarbonyl)amino)butyric acid

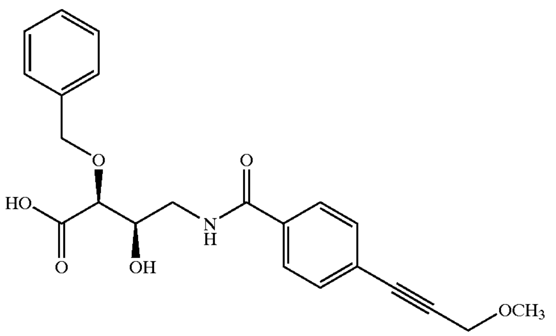

The title compound having the following physical data was obtained by the same procedure as a series of reaction of Example 2, using the compound prepared in Example 50 instead of the compound prepared in Example 1.

TLC: Rf 0.22 (Chloroform:Methanol=9:1).

Example 52

2(S)-Benzyloxy-3(S)-t-butylcarbonyloxy-4-(N-(4-(3-methoxy-1-propynyl)phenylcarbonyl)amino)butyric acid ethyl ester

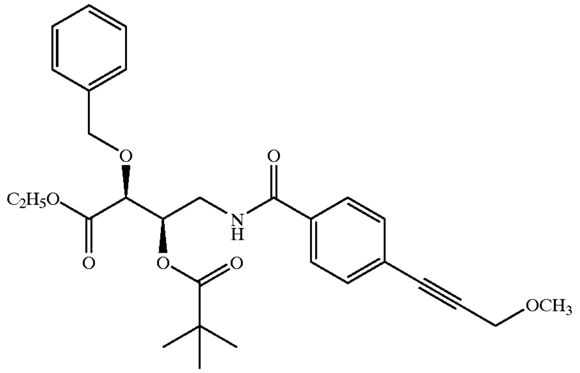

The title compound having the following physical data was obtained by the same procedure as a series of reaction of Example 1 (using pivaloyl chloride instead of the compound prepared in Reference Example 4.), using the compound prepared in Example 50 instead of 4-aminobutyric acid ethyl ester.

TLC: Rf 0.44 (n-Hexane:Ethyl acetate=7:3);

NMR ($CDCl_3$): δ7.49 (2H, d, J=8.8 Hz), 7.43–7.30 (7H, m), 6.80–6.68 (1H, m), 5.36 (1H, td, J=5.6, 3.8 Hz), 4.87 (1H, d, J=11.4 Hz), 4.43 (1H, d, J=11.4 Hz), 4.34 (2H, s), 4.25 (1H, d, J=3.8 Hz), 4.22 (2H, q, J=7.0 Hz), 3.90 (1H, dt, J=14.2, 5.6 Hz), 3.66 (1H, dt, J=14.2, 5.6 Hz), 3.46 (3H, s), 1.29 (3H, t, J=7.0 Hz), 1.14 (9H, s).

Example 53

2-Benzyloxy-4-(N-(4-(3-methoxy-1-propynyl)phenylcarbonyl)amino)-2-butenoic acid

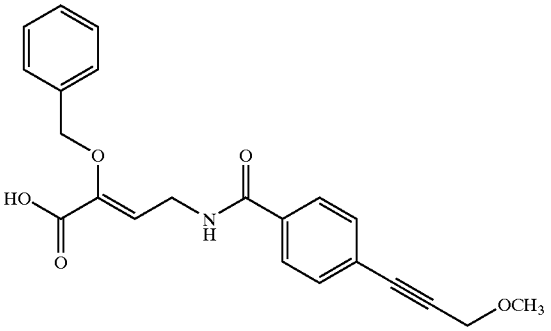

The title compound having the following physical data was obtained by the same procedure as a series of reaction of Example 2, using the compound prepared in Example 52 instead of the compound prepared in Example 1.

TLC: Rf 0.36 (Chloroform:Methanol=9:1).

Example 54

N-Hydroxy-2(S)-benzyloxy-3(S)-hydroxy-4-(N-(4-(3-methoxy-1-propynyl)phenylcarbonyl)amino)butyramide

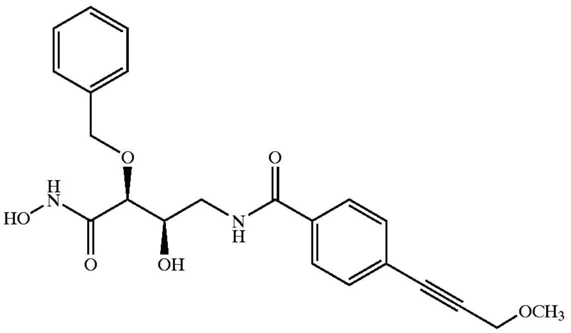

The title compound having the following physical data was obtained by the same procedure as a series of reaction of Example 3→Example 4, using the compound prepared in Example 51 instead of the compound prepared in Example 2.

TLC: Rf 0.25 (Chloroform:Methanol=9:1);

NMR ($CD_3OD$): δ7.74 (2H, d, J=8.4 Hz), 7.49 (2H, d, J=8.4 Hz), 7.45–7.20 (5H), m), 4.73 (1H, d, J=11.4 Hz), 4.49 (1H, d, J=11.4 Hz), 4.34 (2H, s), 4.14–3.95 (1H, m), 3.91 (1H, d, J=3.4 Hz), 3.60 (1H, dd, J=3.6, 5.4 Hz), 3.44 (3H, s), 3.42 (1H), dd, J=13.6, 7.2 Hz).

Example 54(1)

N-Hydroxy-2-benzyloxy-4-(N-(4-(3-methoxy-1-propynyl)phenylcarbonyl)amino)-2-butenamide

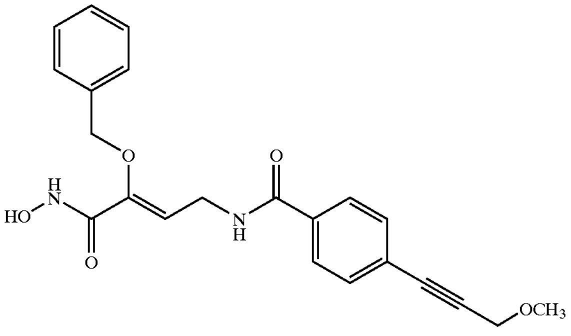

The title compound having the following physical data was obtained by the same procedure as a series of reaction of Example 54, using the compound prepared in Example 53 instead of the compound prepared in Example 51.

TLC: Rf 0.37 (Chloroform:Methanol=9:1);

NMR ($CD_3OD$): δ8.52–8.40 (1H, m), 7.74 (2H, d, J=8.4 Hz), 7.49 (2H, d, J=8.4 Hz), 7.45–7.20 (5H, m), 5.89 (1H, t, J=6.6 Hz), 4.88 (2H, s), 4.33 (2H), s), 4.02–3.90 (2H, m), 3.43 (3H, s).

Example 55 cis-1-Carboxymethyl-2-(N-(4-(3-methoxy-1-propynyl)phenylcarbonyl)amino)cyclopentane

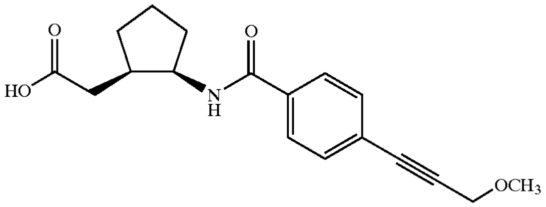

The title compound having the following physical data was obtained by the same procedure as a series of reaction of Example 1, using cis-1-carboxymethyl-2-aminocyclopentane (it was described in J. Chem. Soc., PerkinTrans. 1, 11, 2553 (1982).) instead of 4-aminobutyric acid ethyl ester, and a corresponding acyl halide instead of the compound prepared in Reference Example 4.

TLC: Rf 0.80 (Chloroform:Methanol:Acetic acid=18:2:1).

Example 55(1)~55(4)

The following compounds were obtained by the same procedure as a series of reaction of Example 55, using trans-1-carboxymethyl-2-aminocyclopentane, cis-3-aminocyclopentanoic acid, trans-3-aminocyclopentanoic acid (it was described in Chem. Ber., 101, 1525 (1968).) and 2-aminomethylcyclopentanoic acid instead of cis-1-carboxymethyl-2-aminocyclopentan.

Example 55(1)

trans-1-Carboxymethyl-2-(N-(4-(3-methoxy-1-propynyl)phenylcarbonyl)amino)cyclopentane

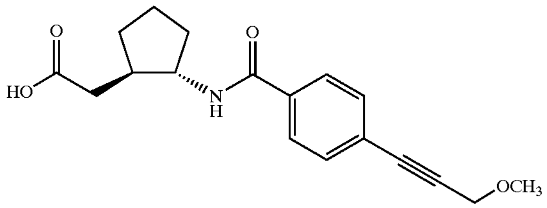

TLC: Rf 0.36 (Chloroform:Methanol=10:1);

NMR ($CDCl_3$): δ7.72 (2H, d, J=8.4 Hz), 7.49 (2H, d, J=8.4 Hz), 6.49 (1H, d, J=7.4 Hz), 4.34 (2H, s), 4.04 (1H, m), 3.46 (3H, s), 2.56 (2H, m), 2.25 (2H, m), 1.99 (1H, m), 1.75 (2H, m), 1.50 (2H, m).

Example 55(2)

trans-3-(N-(4-(3-Methoxy-1-propynyl)phenylcarbonyl)amino)cyclopentanoic acid

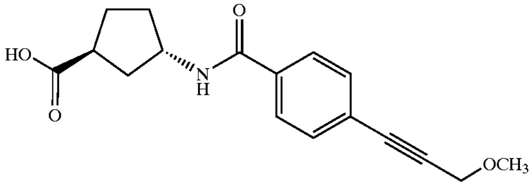

TLC: Rf 0.21 (Chloroform:Methanol=9:1);

NMR ($d_6$-DMSO): δ12.09 (1H, s), 8.40 (1H, d, J=6.8 Hz), 7.85 (2H, d, J=8.4 Hz), 7.53 (2H, d, J=8.4 Hz), 4.42–4.22 (3H, m), 3.34 (3H, s), 3.30–2.82 (1H, m), 2.20–1.48 (6H, m).

Example 55(3)

cis-3-(N-(4-(3-Methoxy-1-propynyl)phenylcarbonyl)amino)cyclopentanoic acid

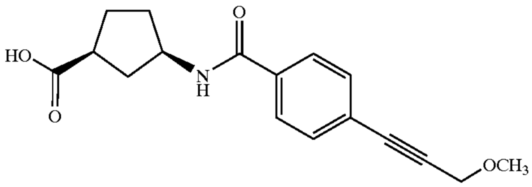

TLC: Rf 0.32 (Chloroform:Methanol=9:1);

NMR ($d_6$-DMSO): δ12.11 (1H, s), 8.45 (1H, d, J=7.4 Hz), 7.85 (2H, d, J=8.8 Hz), 7.52 (2H, d, J=8.8 Hz), 4.34 (2H, s), 4.33–4.18 (1H, m), 3.34 (3H, s), 2.84–2.66 (1H, m), 2.18 (1H, m), 2.00–1.50 (5H, m).

Example 55(4)

trans-2-(N-(4-(3-Methoxy-1-propynyl)phenylcarbonyl)aminomethyl)cyclopentanoic acid

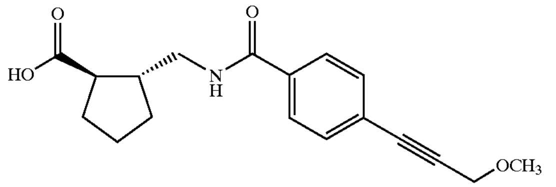

TLC: Rf 0.26 (Chloroform:Methanol=19:1);

NMR ($CDCl_3$): δ7.72 (2H, d, J=8.2 Hz), 7.46 (2H, d, J=8.2 Hz), 7.08–6.98 (1H, m), 4.33 (2H, s), 3.69 (1H, dt, J=13.8, 5.4 Hz), 3.45 (3H, s), 3.34 (1H, ddd, J=13.8, 8.8, 5.4 Hz), 2.62–2.30 (2H, m), 2.06–1.84 (3H, m), 1.80–1.62 (2H, m), 1.52–1.32 (1H, m).

Example 56 cis-1-(N-Hydroxyaminocarbonylmethyl)-2-(N-(4-(3-methoxy-1-propynyl)phenylcarbonyl)amino)cyclopentane

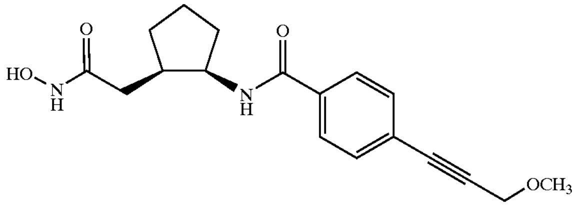

The title compound having the following physical data was obtained by the same procedure as a series of reaction of Example 3→Example 4, using the compound prepared in Example 55 instead of the compound prepared in Example 2.

TLC: Rf 0.33 (Chloroform:Methanol=10:1);

NMR ($d_6$-DMSO): δ10.40 (1H, s), 8.37 (1H, d, J=7.8 Hz), 7.86 (2H, d, J=8.4Hz), 7.54 (2H, d, J=8.4Hz), 4.38 (1H, m), 4.35 (2H, s), 3.35 (3H, s), 2.35 (1H, m), 2.09 (1H, dd, J=14.6, 4.6 Hz), 1.91 (1H, m), 1.83 (1H, m), 1.80–1.50 (4H, m), 1.44 (1H, m).

Example 56(1)~56(4)

The following compounds were obtained by the same procedure as a series of reaction of Example 56, using the compound prepared in Example 55(1)~(4) instead of the compound prepared in Example 55.

Example 56(1)

trans-1-(N-Hydroxyaminocarbonylmethyl)-2-(N-(4-(3-methoxy-1-propynyl)phenylcarbonyl)amino)cyclopentane

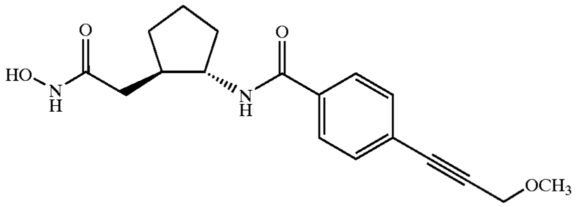

TLC: Rf 0.43 (Chloroform:Methanol=10:1);

NMR ($d_6$-DMSO): δ10.37 (1H, s), 8.41 (1H, d, J=8.0 Hz), 7.87 (2H, d, J=8.4 Hz), 7.53 (2H, d, J=8.4 Hz), 4.35 (2H, s), 3.90 (1H, m), 3.35 (3H, s), 2.19 (2H, m), 1.87 (3H, m), 1.58 (3H, m,), 1.24 (1H, m).

Example 56(2)

trans-1-(N-Hydroxyaminocarbonyl)-3-(N-(4-(3-methoxy-1-propynyl)phenylcarbonyl)amino)cyclopentane

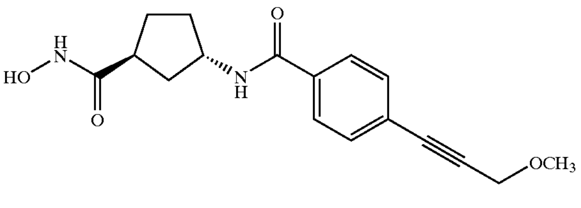

TLC: Rf 0.26 (Chloroform:Methanol=9:1);

NMR ($d_6$-DMSO): δ10.42 (1H, s), 8.80–8.60 (1H, br), 8.37 (1H, d, J=7.0 Hz), 7.85 (2H, d, J=8.4 Hz), 7.53 (2H, d, J=8.4 Hz), 4.44–4.24 (3H, m), 3.35 (3H, s), 2.78–2.68 (1H, m), 2.10–1.50 (6H, m).

Example 56(3)

cis-1-(N-Hydroxyaminocarbonyl)-3-(N-(4-(3-methoxy-1-propynyl)phenylcarbonyl)amino)cyclopentane

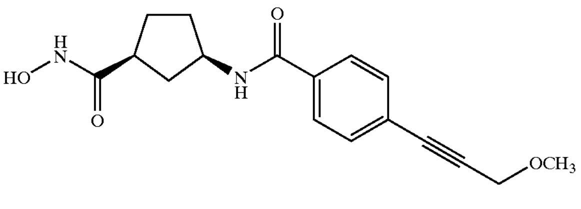

TLC: Rf 0.38 (Chloroform:Methanol=9:1);

NMR ($d_6$-DMSO): δ10.62 (1H, s), 8.94–8.76 (1H, br), 8.82 (1H, d, J=7.8 Hz), 7.87 (2H, d, J=8.4 Hz), 7.53 (2H, d, J=8.4 Hz), 4.34 (2H, s), 4.42–4.22 (1H, m), 3.35 (3H, s), 2.70–2.55 (1H, m), 2.14–1.95 (1H, m), 1.92–1.62 (5H, m).

Example 56(4)

trans-1-(N-Hydroxyaminocarbonyl)-2-(N-(4-(3-methoxy-1-propynyl)phenylcarbonyl)aminomethyl) cyclopentane

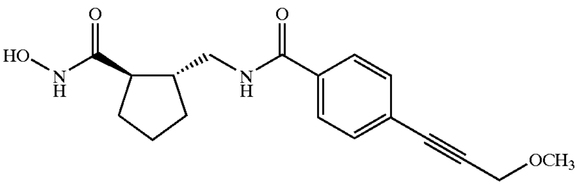

TLC: Rf 0.31 (Chloroform:Methanol=9:1);

NMR ($d_6$-DMSO): δ10.39 (1H, s), 8.50 (1H, t, J=5.6 Hz), 7.83 (2H, d, J=8.2 Hz), 7.52 (2H, d, J=8.2 Hz), 4.34 (2H, s), 3.35 (3H, s), 3.32–3.14 (2H, m), 2.40–2.22 (1H, m), 2.20–2.04 (1H, m), 1.90–1.50 (5H, m), 1.48–1.24 (1H, m).

Example 57

2(R)-Allyl-5-ethoxymethoxy-4(S)-[N-(4-phenoxyphenylcarbonyl)amino]pentanoic acid

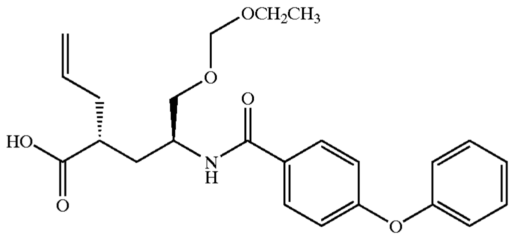

2(S-2-Propenyl-4(S)-ethoxymethoxymethyl-4-(N-(4-phenoxyphenylcarbonyl)aminobutyl acid methyl easter was obtained by the same procedure as a series of reaction of Example 37→Example 39→Example 41 (using ethoxymethyl chloride instead of methoxymethyl chloride.) →Example 43 (using allyl bromide instead of benzyl bromide.), using a corresponding compound instead of the compound prepared in Reference Example 4. A solution of the above obtained compound (1.06 g) in tetrahydrofuran (4 ml) was added dropwise to a solution of lithium diisopropylamide (3.6 ml) in tetrahydrofuran (20 ml) at −20° C. The mixture was stirred at −15° C. for 30 minutes. A saturated solution of ammonium chloride and water were added thereto. The mixture was extracted with ethyl acetate. The extract was washed with an aqueous saturated solution of sodium chloride, dried over anhydrous sodium sulfate and concentrated. The residue was purified by column chromatography on silica gel (Toluene:Ethyl acetate=87:13). The title compound (193 mg) having the following physical data was obtained by the same procedure as a series of reaction of Example 2, using such a purified, compound (200 mg).

TLC: Rf 019 (Chloroform:Methanol=9:1).

Example 58

N-Hydroxy-2(R)-allyl-5-ethoxymethoxy-4(S)-[N-(4-phenoxyphenylcarbonyl)amino]pentanamide

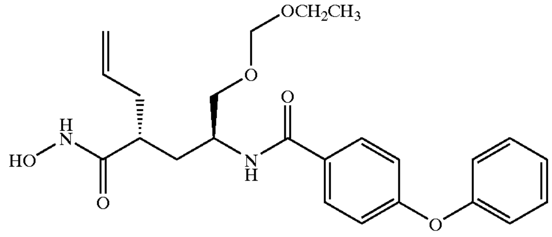

The title compound having the following physical data was obtained by the same procedure as a series of reaction of Example 3→Example 4, using the compound prepared in Example 57.

TLC: Rf 0.23 (Chloroform:Methanol=10:1);

NMR ($d_6$-DMSO): δ10.37 (s, 1H), 8.74 (brs, 1H), 8.13 (d, J=8.1 Hz, 1H), 7.90–7.85 (m, 2H), 7.45–7.39 (m, 2H), 7.19 (t, J=7.2 Hz, 1H), 7.07–6.99 (m, 4H), 5.69–5.60 (m, 1H), 5.02–4.93 (m, 2H), 4.56 (s, 2H), 3.99–3.89 (m, 1H), 3.80–3.39 (m, 4H), 2.26–2.01 (m, 3H), 1.85–1.79 (m, 1H), 1.61–1.54 (m, 1H), 1.07 (t, J=7.2 Hz, 3H).

Example 58(1)~58(3)

The following compounds were obtained by the same procedure as a series of reaction of Example 57→Example 58, using a corresponding compound.

Example 58(1)

N-Hydroxy-2(R)-benzyl-5-methoxymethoxy-4(S)-[N-[4-(benzofuran-2-yl)phenylcarbonyl]amino] pentanamide

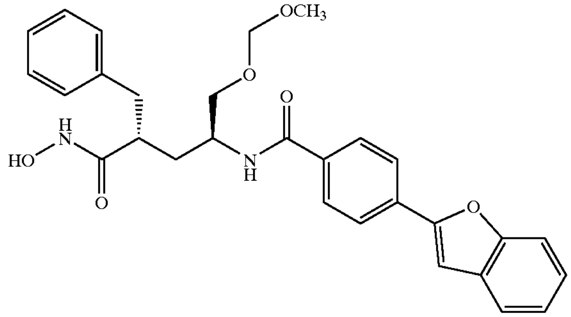

TLC: Rf 0.35 (Chloroform:Methanol=19:1);

NMR ($d_6$-DMSO): δ10.37 (1H, s), 8.72 (1H, s), 8.28 (1H, d, J=7.2 Hz), 8.02 (2H, d, J=8.8 Hz), 7.97 (2H, d, J=8.8 Hz), 7.74–7.62 (2H, m), 7.57 (1H, d, J=0.6 Hz), 7.41–7.10 (7H, m), 4.56 (2H, s), 4.18–3.98 (1H, m), 3.57–3.39 (2H, m), 3.23 (3H, s), 2.85 (1H, dd, J=13.6,8.4 Hz), 2.64 (1H, dd, J=13.6, 6.0 Hz), 2.54–2.40 (1H, m), 2.03–1.80 (1H, m), 1.72–1.52 (1H, m).

Example 58(2)

N-Hydroxy-2(R)-methyl-5-ethoxymethoxy-4(S)-[N-(4-phenoxyphenylcarbonyl)amino]pentanamide

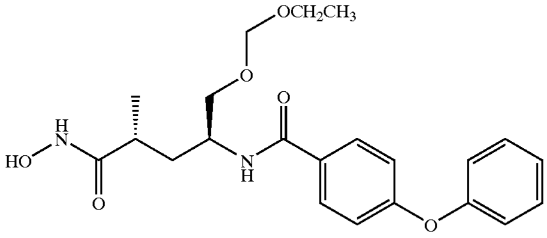

TLC: Rf 0.29 (Chloroform:Methanol:Acetic acid=100:10:1);

NMR ($d_6$-DMSO): δ10.35 (s, $_1$H), 8.70 (s, $_1$H), 8.13 (d, J=8.1 Hz, $_1$H), 7.88 (d, J=8.4 Hz, 2H), 7.45–7.39 (m, 2H), 7.19 (t, J=7.2 Hz, 1H), 7.07–7.01 (m, 4H), 4.57 (s, 2H), 4.01–3.88 (m, 1H), 3.47 (q, J=7.2 Hz, 2H), 3.44–3.38 (m, 2H), 2.30–2.18 (m, 1H), 1.91–1.82 (m, 1H), 1.55–1.46 (m, 1H), 1.07 (t, J=7.2 Hz, 3H), 0.99 (d, J=6.9 Hz, 3H).

Example 58(3)

N-Hydroxy-2(R)-methyl-5-ethoxymethoxy-4(S)-[N-[4-(4-cyanophenyl)phenylcarbonyl]amino]pentanamide

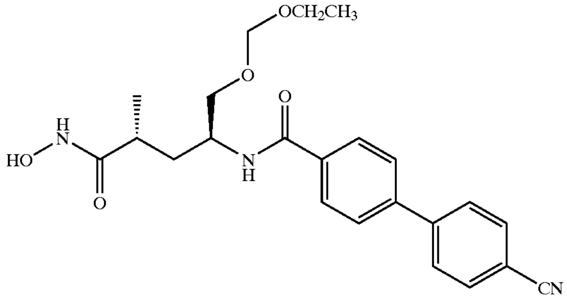

TLC: Rf 0.49 (Chloroform:Methanol=9:1);

NMR ($d_6$-DMSO): δ10.36 (s, 1H), 8.69 (s, 1H), 8.28 (d, J=8.2 Hz, 1H), 8.00–7.94 (m, 6H), 7.84 (d, J=8.4 Hz, 2H), 4.57 (s, 2H), 4.06–3.88 (m, 1H), 3.52–3.42 (m, 4H), 2.34–2.18 (m, 1H), 1.95–1.81 (m, 1H), 1.60–1.45 (m, 1H), 1.07 (t, J=7.2 Hz, 3H), 1.00 (d, J=6.6 Hz).

Example 59(1)~59(2)

The following compounds were obtained by the same procedure as a series of reaction of Example 57→Example 2→Example 3→Example 4, using 4(R)-carboxy-4-aminobutyric acid methyl ester instead of 4(S)-carboxy-4-aminobutyric acid methyl ester and the compound which was obtained by the same procedure as series of reaction of Example 37→Example 39→Example 41 (using a corresponding compound instead of methoxymethyl chloride, if necessary.)→Example 43 (using a corresponding compound instead of benzyl bromide.), using a corresponding compound instead of the compound prepared in Reference Example 4.

Example 59(1)

N-Hydroxy-2(S)-benzyl-5-methoxymethoxy-4(R)-[N-(4-phenoxyphenylcarbonyl)amino]pentanamide

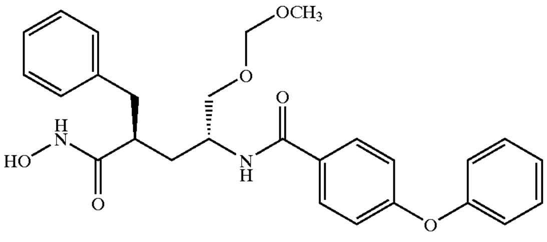

TLC: Rf 0.41 (Chloroform:Methanol:Acetic acid:Water 100:10:1:1);

NMR ($d_6$-DMSO): δ10.33(1H, s), 8.69(1H, s), 8.12(1H, d, J=8.0 Hz), 7.85(2H, d, J=8.8 Hz), 7.37–7.46(2H, m), 6.99–7.27(10H, m), 4.52(2H, s), 3.90–4.13(1H, m), 3.38–3.44(2H, m), 3.20(3H, s), 2.81 (1H, dd, J=13.2 Hz, 6.2 Hz), 2.59(1H, dd, J=13.2 Hz, 6.2 Hz), 2.38–2.52(1H, m), 1.79–1.93(1H, m), 1.50–1.63(1H, m).

Example 59(2)

N-Hydroxy-2(S)-benzyl-5-methoxymethoxy-4(R)-[N-[4-(3-phenoxy-1-propynyl)phenylcarbonyl]amino]pentanamide

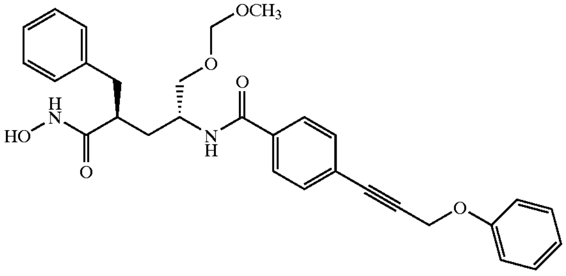

TLC: Rf 0.41 (Chloroform:Methanol:Acetic acid:Water=100:10:1:1);

NMR ($d_6$-DMSO): δ10.31 (1H, s), 8.68(1H, s), 8.24(1H, d, J=8.1 Hz), 7.81(2H, d, J=7.8 Hz), 7.51(2H, d, J=7.8 Hz), 7.32(2H, t, J=7.8 Hz), 6.95–7.24(8H, m), 5.05(2H, s), 4.50 (2H, s), 3.90–4.07(1H, m), 3.37–3.42(2H, m), 3.18(3H, s), 2.79(1H, dd, J=13.5 Hz, 6.2 Hz), 2.58(1H, dd, J=13.5 Hz, 6.2Hz), 2.43–2.52(1H, m), 1.82–1.89(1H, m), 1.54–1.62 (1H, m).

Example 60(1)~60(5)

The compounds having the following physical data were obtained by the same procedure as a series of reaction of Example 37→Example 39→Example 41 (using a corresponding compound instead of methoxymethyl chloride.)→Example 43 (using a corresponding compound instead of benzyl bromide.)→Example 2→Example 3→Example 4→Example 27, using a corresponding compound instead of the compound prepared in Reference Example 4.

Example 60(1)

N-Hydroxy-2(S)-(3-aminobenzyl)-5-ethoxymethoxy-4(S)-[N-(trans-4-methylcyclohexylcarbonyl)amino]pentanamide

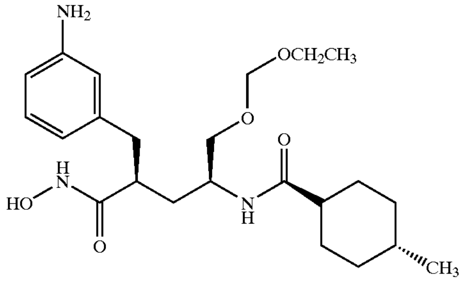

TLC: Rf 0.27 (Chloroform:Methanol=9:1);

NMR ($d_6$-DMSO): δ10.45–10.10 (brs, 1H), 8.80–8.45 (brs, 1H), 7.40 (d, J=8.1 Hz, 1H), 6.86 (t, J=7.7 Hz, 1H), 6.35 (d, J=7.7 Hz, 1H), 6.32 (s, 1H), 6.32 (d, J=7.7 Hz, 1H), 4.85 (s, 2H), 4.54 (s, 2H), 3.95–3.80 (m, 1H), 3.55–3.20 (m, 4H, overlap with H2O in DMSO), 2.59 (dd, J=13.2, 8.4 Hz, 1H), 2.45 (dd, J=13.2, 5.7 Hz, 1H), 2.32–2.20 (m, 1H), 2.08–1.92 (m, 1H), 1.80–1.57 (m, 5H), 1.57–1.44 (m, 1H), 1.44–1.20 (m, 3H), 1.11 (t, J=7.1 Hz, 3H), 0.96–0.76 (m, 5H).

Example 60(2)

N-Hydroxy-2(S)-benzyl-5-ethoxymethoxy-4(S)-[N-(4-carboxyphenylcarbonyl)amino]pentanamide

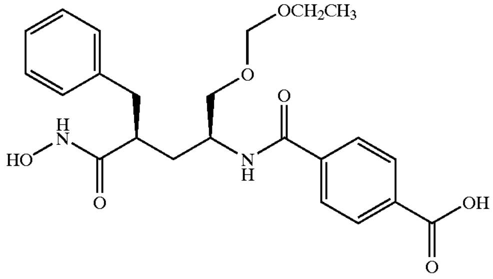

TLC: Rf 0.22 (Chloroform:Methanol:Acetic acid=90:10:1);

NMR ($d_6$-DMSO): δ13.50–12.70 (br, 1H), 10.37 (s, 1H), 8.82–8.58 (br, 1H), 8.31 (d, J=8.7Hz, 1H), 8.01 (d, J=8.7Hz, 2H), 7.95 (d, J=8.7Hz, 2H), 7.27–7.08 (m, 5H), 4.58 (s, 2H), 4.34–4.19 (m, 1H), 3.60–3.40 (m, 4H), 2.77 (d, J=7.2, 2H), 2.42–2.32 (m, 1H), 1.85–1.62 (m, 2H), 1.09 (t, J=6.9 Hz, 3H).

Example 60(3)

N-Hydroxy-2(S)-benzyl-5-ethoxymethoxy-4(S)-[N-(4-aminophenylcarbonyl)amino]pentanamide

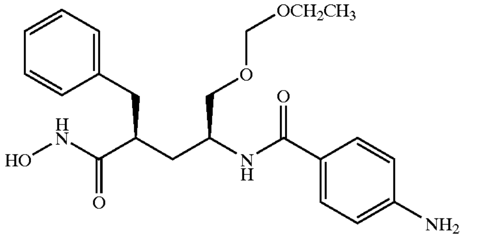

TLC: Rf 0.36 (Methylene chloride:Methanol=19:1);

NMR ($d_6$-DMSO): δ10.34 (brs, 1H), 8.65 (brs, 1H), 7.61 (brd, J=9.0 Hz, 1H), 7.58 (d, J=8.4 Hz, 2H), 7.22–7.08 (m, 5H), 6.52 (d, J=8.4 Hz, 2H), 5.57 (brs, 2H), 4.55 (s, 2H), 4.20 (m, 1H), 3.50–3.40 (m, 4H), 2.74 (d, J=7.2 Hz, 2H), 2.35 (m, 1H), 1.80–1.59 (m, 2H), 1.07 (t, J=7.2 Hz, 3H).

Example 60(4)

N-Hydroxy-2(S)-benzyl-5-ethoxymethoxy-4(S)-[N-(4-piperidylcarbonyl)amino]pentanamide

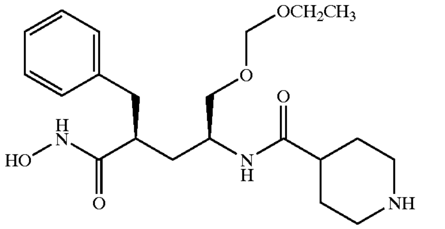

TLC: Rf 0.50 (Chloroform:Methanol:Acetic acid 7:2:1);

NMR ($d_6$-DMSO): δ10.30 (brs, 1H), 7.47 (brd, J=9.0 Hz, 1H), 7.25–7.08 (m, 5H), 4.53 (s, 2H), 3.93 (m, 1H), 3.43 (q, J=6.9Hz, 2H), 3.35 (m, 2H), 2.94 (brd, J=12.0 Hz, 2H), 2.68 (m, 2H), 2.49 (m, 2H), 2.35–2.10 (m, 2H), 1.70–1.40 (m, 6H), 1.09 (t, J=6.9 Hz, 3H).

Example 60(5)

N-Hydroxy-2(S)-(3-hydroxybenzyl)-5-ethoxymethoxy-4(S)-[N-(4-methylphenylcarbonyl)amino]pentanamide

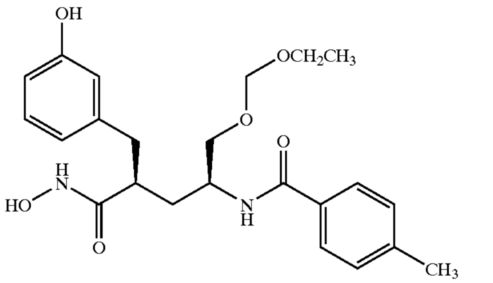

TLC: Rf 0.45 (Methylene chloride:Methanol=9:1);

NMR ($d_6$-DMSO): δ10.33 (s, 1H), 9.16 (s, 1H), 8.64 (s, 1H), 7.99 (brd, J=8.4 Hz, 1H), 7.75 (d, J=8.4 Hz, 2H), 7.23

(d, J=8.4 Hz, 2H), 6.97 (t, J=7.2 Hz, 1H), 6.51 (m, 3H), 4.55 (s, 2H), 4.17 (m, 1H), 3.50 (m, 2H), 3.44 (q, J=7.2 Hz, 2H), 2.62 (m, 2H), 2.33 (s, 3H), 2.33 (m, 1H), 1.80–1.60 (m, 2H), 1.06 (t, J=7.2 Hz, 3H).

Example 61(1)~61(13)

The title compounds having the following physical data were obtained by the same procedure as a series of reaction of Example 43→Example 2→Example 3→Example 4, using the compound prepared in Example 1 or the compound which was obtained by the same procedure as a series of reaction of Example 1 with using a corresponding compound, and benzyl bromide or a corresponding compound.

Example 61(1)

N-Hydroxy-2-benzyl-4-[N-[4-(benzofuran-2-yl) phenylcarbonyl]amino]butyramide

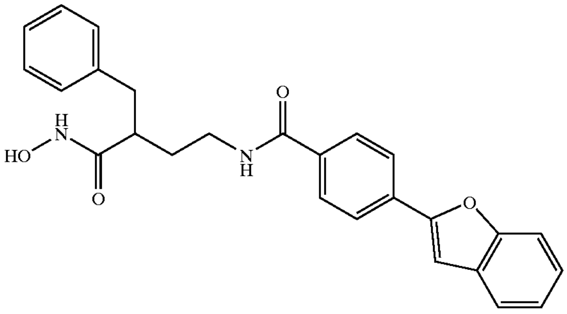

TLC: Rf 0.39 (Chloroform:Methanol=10:1);

NMR ($d_6$-DMSO): δ10.43 (1H, s), 8.52 (1H, t, J=5.6 Hz), 8.00 (2H, d, J=8.8 Hz), 7.94 (2H, d, J=8.8 Hz), 7.71–7.63 (2H, m), 7.57 (1H, s), 7.39–7.16 (7H, m), 3.30–3.15 (2H, m), 2.83 (1H, dd, J=8.6, 13.6 Hz), 2.66 (1H, dd, J=6.2, 13.6 Hz), 2.44–2.31 (1H, m), 1.88–1.53 (2H, m).

Example 61(2)

N-Hydroxy-2-(3-phenylpropyl)-4-[N-[4-(benzofuran-2-yl)phenylcarbonyl]amino]butyramide

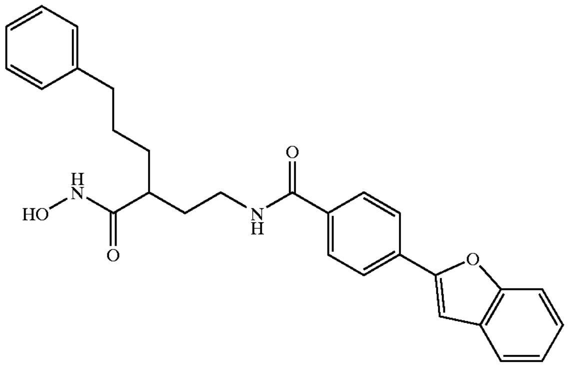

TLC: Rf 0.41 (Chloroform:Methanol=10:1);

NMR ($d_6$-DMSO): δ10.48 (1H, s), 8.50 (1H, t, J=5.6 Hz), 8.01 (2H, d, J=8.8 Hz), 7.95 (2H, d, J=8.8 Hz), 7.71–7.63 (2H, m), 7.57 (1H, s), 7.39–7.11 (7H, m), 3.25–3.15 (2H, m), 2.59–2.47 (2H, m), 2.18–2.02 (1H, m), 1.82–1.36 (6H, m).

Example 61(3)

N-Hydroxy-2-(2-phenylethyl)-4-[N-[4-(benzofuran-2-yl)phenylcarbonyl]amino]butyramide

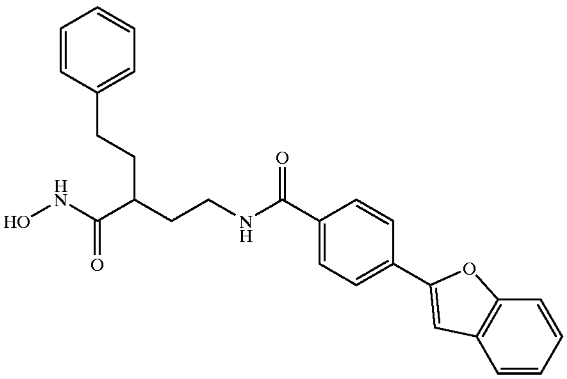

TLC: Rf 0.47 (Chloroform:Methanol=10:1);

NMR ($CD_3OD$): δ7.98 (2H, d, J=8.4 Hz), 7.89 (2H, d, J=8.4 Hz), 7.64–7.60 (1H, m), 7.56–7.52 (1H, m), 7.36–7.09 (7H, m), 7.32 (1H, brs), 3.51–3.24 (2H, m), 2.68–2.50 (2H, m), 2.28–2.14 (1H, m), 2.04–1.69 (4H, m).

Example 61(4)

N-Hydroxy-2-benzyl-4-[N-[4-[2E-(4-chlorophenyl) ethenyl]phenylcarbonyl]amino]butyramide

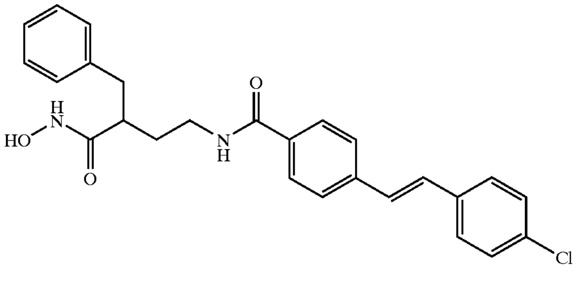

TLC: Rf 0.46 (Chloroform:Methanol=10:1);

NMR ($d_6$-DMSO): δ10.41 (1H, brs), 8.76 (1H, brs), 8.41 (1H, t, J=5.4 Hz), 7.83 (2H, d, J=8.4 Hz), 7.66 (2H, d, J=8.4 Hz), 7.65 (2H, d, J=8.8 Hz), 7.44 (2H, d, J=8.8 Hz), 7.35–7.12 (7H, m), 3.28–3.15 (2H, m), 2.83 (1H, dd, J=8.4, 13.2 Hz), 2.65 (1H, dd. J=5.8, 13.2 Hz), 2.46–2.30 (1H, m), 1.86–1.51 (2H, m).

Example 61(5)

N-Hydroxy-2-benzyl-4-[N-(4-phenoxyphenylcarbonyl)amino]butyramide

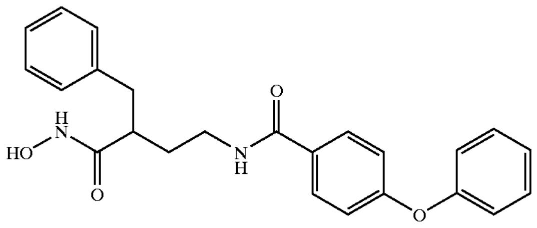

TLC: Rf 0.45 (Chloroform:Methanol=10:1);

NMR ($d_6$-DMSO): δ10.40 (1H, s), 8.75 (1H, brs), 8.35 (1H, t, J=5.6 Hz), 7.84 (2H, d, J=8.8 Hz), 7.47–7.38 (2H, m), 7.30–6.99 (10H, m), 3.26–3.14 (2H, m), 2.82 (1H, dd, J=8.4, 13.6 Hz), 2.64 (1H, dd, J=6.2, 13.6 Hz), 2.43–2.28 (1H, m), 1.84–1.49 (2H, m).

Example 61(6)

N-Hydroxy-2-(naphthalene-1-yl)methyl-4-[N-(4-phenoxyphenylcarbonyl)amino]butyramide

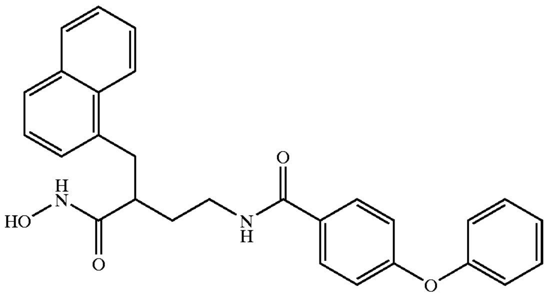

TLC: Rf 0.45 (Chloroform:Methanol=10:1);

NMR ($d_6$-DMSO): δ10.39 (1H, brs), 8.74 (1H, brs), 8.33 (1H, t, J=5.4 Hz), 8.08–8.03 (1H, m), 7.92–7.75 (2H, m), 7.81 (2H, d, J=8.8 Hz), 7.54–7.40 (9H, m), 7.00 (2H, d, J=8.8 Hz), 3.33–3.07 (4H, m), 2.63–2.45 (1H, m), 1.96–1.56 (2H, m).

Example 61(7)

N-Hydroxy-2-isopropyl-4-[N-(4-phenoxyphenylcarbonyl)amino]butyramide

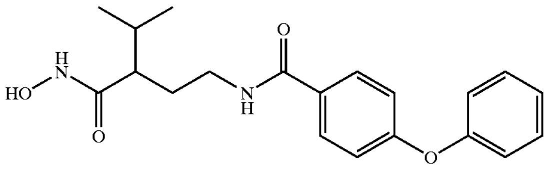

TLC: Rf 0.35 (Chloroform:Methanol=10:1);

NMR ($d_6$-DMSO): δ10.39 (1H, brs), 8.34 (1H, t, J=5.6 Hz), 7.90 (2H, d, J=8.8 Hz), 7.43 (2H, t, J=7.4 Hz), 7.19 (1H, t, J=7.4 Hz), 7.09–7.04 (2H, m), 7.01 (2H, d, J=8.8 Hz), 3.22–3.06 (2H, m), 1.78–1.61 (4H, m), 0.87 (3H, d, J=6.8 Hz), 0.83 (3H, d, J=6.0 Hz).

Example 61(8)

N-Hydroxy-2-(quinoline-4-yl)methyl-4-[N-(4-phenoxyphenylcarbonyl)amino]butyramide

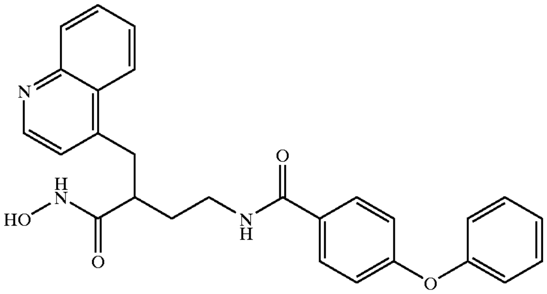

TLC: Rf 0.38 (Chloroform:Methanol=10:1);

NMR ($d_6$-DMSO): δ10.41 (1H, brs), 8.76 (1H, brs), 8.76 (1H, d, J=4.4 Hz), 8.37 (1H, t, J=5.6 Hz), 8.15 (1H, br.d, 7.6 Hz), 8.00 (1H, d, J=7.4 Hz), 7.83 (2H, d, J=8.8 Hz), 7.77–7.69 (1H, m), 7.62–7.54 (1H, m), 7.47–7.38 (2H, m), 7.30 (1H, d, J=4.4 Hz), 7.23–7.16 (1H, m), 7.08–7.05 (2H, m), 7.01 (2H, d, J=8.8 Hz), 3.33–3.14 (4H, m), 2.64–2.50 (1H, m), 1.98–1.58 (2H, m).

Example 61(9)

N-Hydroxy-2-(2-pyridyl)methyl-4-[N-(4-phenoxyphenylcarbonyl)amino]butyramide

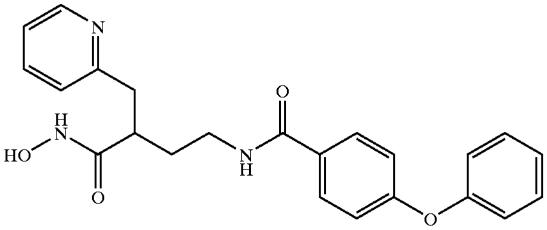

TLC: Rf 0.34 (Chloroform:Methanol=10:1);

NMR ($d_6$-DMSO): δ10.47 (1H, brs), 8.76 (1H, s), 8.47–8.43 (1H, m), 8.34 (1H, t, J=5.6 Hz), 7.83 (2H, d, J=8.8 Hz), 7.66 (1H, dt, J=1.8, 7.6 Hz), 7.46–7.39 (2H, m), 7.23–7.15 (3H, m), 7.09–7.03 (2H, m), 7.01 (2H, d, J=8.8 Hz), 3.25–3.12 (2H, m), 2.97 (1H, dd, J=7.6, 13.6 Hz), 2.78 (1H, dd, J=6.6, 13.6 Hz), 2.76–2.56 (1H, m), 1.85–1.46 (2H, m).

Example 61(10)

N-Hydroxy-2-(3-pyridyl)methyl-4-[N-(4-phenoxyphenylcarbonyl)amino]butyramide

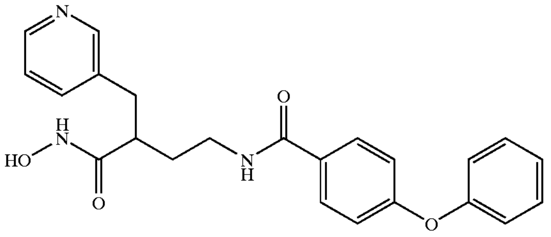

TLC: Rf 0.20 (Chloroform:Methanol=10:1);

NMR ($d_6$-DMSO): δ10.41 (1H, brs), 8.76 (1H, s), 8.40–8.37 (3H, m), 7.85 (2H, d, J=8.8 Hz), 7.56 (1H, dt, J=7.6, 2.2 Hz), 7.47–7.38 (2H, m), 7.30–7.16 (2H, m), 7.10–7.04 (2H, m), 7.02 (2H, d, J=8.8 Hz), 3.30–3.13 (2H, m), 2.87–2.66 (2H, m), 2.44–2.30 (1H, m), 1.86–1.52 (2H, m).

Example 61(11)

N-Hydroxy-2-(naphthalene-2-yl)methyl-4-[N-(4-phenoxyphenylcarbonyl)-amino]butyramide

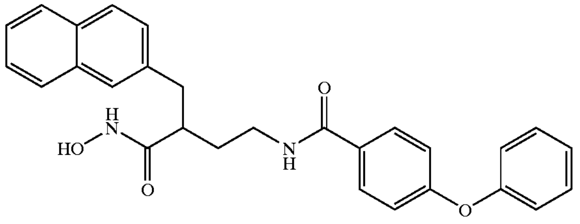

TLC: Rf 0.45 (Chloroform:Methanol=10:1);

NMR ($d_6$-DMSO): δ10.40 (1H, d, J=1.4 Hz), 8.74 (1H, d, J=1.4 Hz), 8.36 (1H, t, J=5.6 Hz), 7.84 (2H, d, J=8.8 Hz), 7.83–7.79 (3H, m), 7.65 (1H, brs), 7.50–7.33 (5H, m), 7.19 (1H, tt, J=1.8, 7.4 Hz), 7.09–7.04 (2H, m), 7.01 (2H, d, J=8.8 Hz), 3.30–3.12 (2H, m), 2.98 (1H, dd, J=8.8,13.6 Hz), 2.83 (1H, dd, J=6.0, 13.6 Hz), 2.50–2.40 (1H, m), 1.90–1.54 (2H, m).

Example 61(12)

N-Hydroxy-2-(4-pyridyl)methyl-4-[N-(4-phenoxyphenylcarbonyl)amino]butyramide

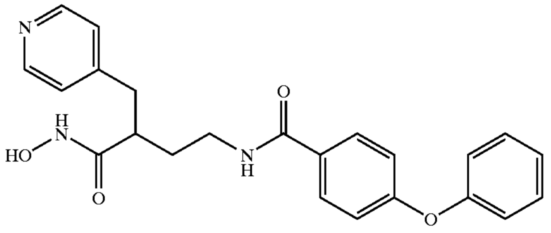

TLC: Rf 0.17 (Chloroform:Methanol=10:1);

NMR ($d_6$-DMSO): δ10.44 (1H, brs), 8.78 (1H, brs), 8.42 (2H, d, J=5.8 Hz), 8.38 (1H, t, J=5.6 Hz), 7.85 (2H, d, J=8.8 Hz), 7.47–7.38 (2H, m), 7.23–7.15 (3H, m), 7.10–7.05 (2H, m), 7.02 (2H, d, J=8.8 Hz), 3.30–3.13 (2H, m), 2.87–2.66 (2H, m), 2.48–2.33 (1H, m), 1.85–1.52 (2H, m).

Example 61(13)

N-Hydroxy-2-(3-methoxybenzyl)-4-[N-(4-phenoxyphenylcarbonyl)amino]butyramide

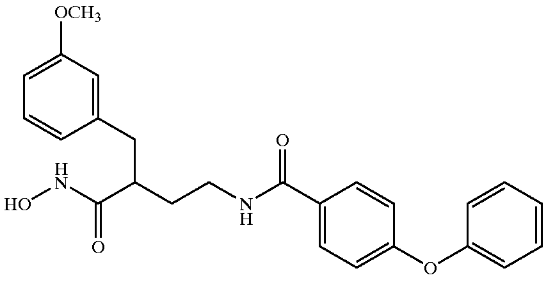

TLC: Rf 0.41 (Chloroform:Methanol=10:1);

NMR ($d_6$-DMSO): δ10.40 (1H, s), 8.76 (1H, brs), 8.35 (1H, t, J=5.6 Hz), 7.84 (2H, d, J=8.8 Hz), 7.47–7.39 (2H, m), 7.24–7.04 (4H, m), 7.01 (2H, d, J=8.8 Hz, 6.75–6.70 (3H, m), 3.70 (3H, s), 3.30–3.10 (2H, m), 2.79 (1H dd, J=8.8, 13.4 Hz), 2.61 (1H, dd, J=6.2, 13.4 Hz), 2.43–2.29 (1H, m), 1.83–1.48 (2H, m).

Example 62

N-Hydroxy-2-isobutyl-4-[N-(4-phenoxyphenylcarbonyl)amino]butyramide

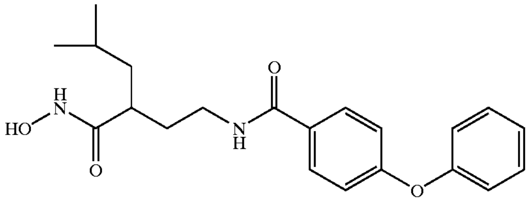

The title compound having the following physical data was obtained by the same procedure as a series of Example 43→Example 27→Example 2→Example 3→Example 4, using the compound which was obtained by the same procedure as a series of reaction of Example 1 with using a corresponding compound, and 3-bromo-2-methylpropen.

TLC: Rf 0.33 (Chloroform:Methanol=10:1);

NMR ($d_6$-DMSO): δ10.47 (1H, s), 9.10–8.41 (1H, brs), 8.33 (1H, t, J=5.2 Hz), 7.85 (2H, d, J=8.8 Hz), 7.23 (2H, t, J=7.4 Hz), 7.19 (1H, t, J=7.4 Hz), 7.09–1.04 (2H, m), 7.01 (2H, d, J=8.8 Hz), 3.21–3.11 (2H, m), 2.22–2.04 (1H, m), 1.76–1.34 (4H, m), 1.16–1.02 (1H, m), 0.84 (3H, d, J=5.4 Hz), 0.81 (3H, d, J=5.8 Hz).

Example 63

5-Methoxy-4(S)-[N-[4-(4-chlorophenyl)phenylcarbonyl]amino]pentanoic acid

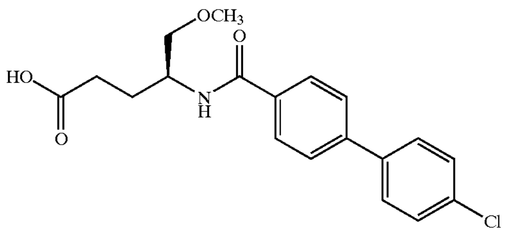

5-Hydroxy-4(S)-[N-(4'-chlorobiphenyl-4-yl)carbonyl]aminopentanoic acid methyl ester was obtained by the same procedure as a series of reaction of Example 37→Example 38, using a corresponding compound. A solution of silica gel (500 mg) and diazomethane in ether (4 ml) was added to a solution of the above obtained compound (1.7 g) in tetrahydrofuran (5 ml). The mixture was stirred at room temperature for 10 minutes and concentrated. A solution of diazomethane in ether (4 ml) was added to a solution of the residue in tetrahydrofuran (5 ml). The mixture was stirred for 10 minutes. Such a procedure was repeated ten times. The residue was purified by column chromatography on silica gel (Hexane:Ethyl acetate=9:1→3:1) to give the methyl ester of the title compound (1.42 g). The title compound (1.2 g) having the following physical data was obtained by the same procedure as a series of reaction of Example 2, using the obtained methyl ester (1.4 g).

TLC: Rf 0.50 (Methylene chloride:Methanol=9:1).

Example 64

N-Hydroxy-5-methoxy-4(S)-[N-[4-(4-chlorophenyl)phenylcarbonyl]amino]pentanamide

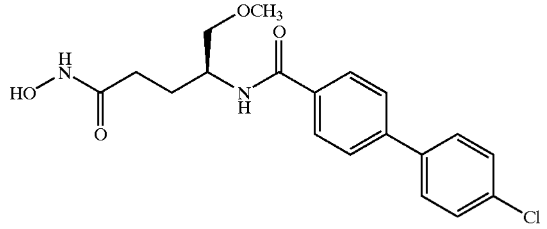

The title compound having the following physical data was obtained by the same procedure as a series of reaction of Example 3→Example 4, using the compound prepared in Example 63.

TLC: Rf 0.38 (Chloroform:Methanol=10:1);

NMR ($d_6$-DMSO): δ10.35 (1H, brs), 8.27 (1H, d, J=8.4 Hz), 7.95 (2H, d, J=8.4 Hz), 7.77 (2H, d, J=8.4 Hz), 7.76 (2H, d, J=8.8 Hz), 7.54 (2H, d, J=8.8 Hz), 4.20–4.03 (1H, m), 3.42 (1H, dd, J=6.2, 9.6 Hz), 3.33 (1H, dd, J=6.2, 9.6 Hz), 3.26 (3H, s), 2.08–1.95 (2H, m), 1.94–1.58 (2H, m).

Reference Example 7

2(S)-Methyl-5-hydroxy-4(S)-(N-benzyloxycarbonyl)aminopentanoic acid t-butyl ester

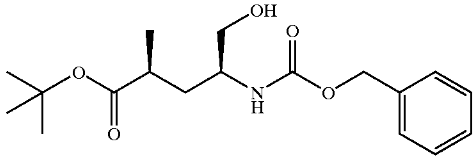

The title compound having the following physical data was obtained by the same procedure as a series of reaction of Example 39→Example 45→Example 46 (using methyl iodide instead of benzyl bromide.)→Example 48, using 4(S)-carboxy-4-(N-benzyloxycarbonylamino)butyric acid t-butyl ester.

TLC: Rf 0.36 (Hexane:Ethyl acetate=3:1).

Example 65

2(S)-Methyl-5-succinimide-4(S)-[N-(4-chlorophenylcarbonyl)amino]pentanoic acid

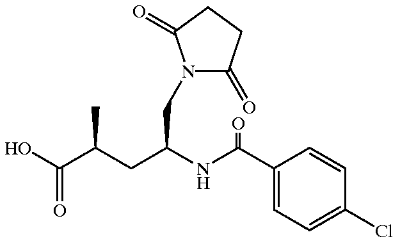

The compound prepared in Reference Example 7 (1.42 g), succinimide(521 mg) and triphenylphosphine (1.38 g) were dissolved into anhydrous tetrahydrofuran (20 ml). The mixture was cooled to 0° C. A solution of azodicaroboxylic acid diethyl (2.3 ml; 40%) in toluene was added dropwise to the mixture. The mixture was stirred at 0° C. for 2 hours and concentrated. The reside was purified by column chromatography on silica gel (Hexane:Acetone=9:1, Hexane:Ethyl acetate=3:1→2:1) twice to give the mixture (2.09 g) of title compound and triphenylphosphinoxide. To a solution of this mixture in methanol (20 ml), 10% Palladium-Carbon (400 mg) was added. The mixture was stirred under an atmosphere of hydrogen at room temperature for 1 hour and filtered by Celite (Trade Mark). The filtrate was concentrated. The residue was dissolved into dichloromethane (20 ml) and cooled to 0° C. Triethylamine (2 ml) and p-chlorobenzoyl chloride (1.10 g) were added to this solution. The mixture was stirred at 0° C. or for 2 hours. The reaction mixture was diluted with ethyl acetate, washed with 1N hydrochloric acid, water, an aqueous saturated solution of sodium carbonate, water and an aqueous saturated solution of sodium chloride successively, dried over anhydrous sodium sulfate and concentrated. The residue was purified by column chromatography on silica gel (Hexane:Ethyl acetate=3:1→ 2:1→3:2) to give t-butyl ester (1.29 g) of the title compound. The title compound (845 mg) having the following physical data was obtained by the same procedure as a series of reaction of Example 29, using the obtained t-butyl ester (1.07 g).

TLC: Rf 0.40 (Methylene chloride:Methanol=9:1);

NMR ($CDCl_3$): δ7.64 (d, J=9.0 Hz, 2H), 7.35 (d, J=9.0 Hz, 2H), 6.55 (d, J=8.7 Hz, 1H), 4.51 (m, 1H), 3.69 (dd, J=13.8, 9.3 Hz, 1H), 3.62 (dd, J=13.8, 4.2 Hz, 1H), 2.75–2.51 (m, 5H), 1.97 (ddd, J=14.4,10.8,7.2 Hz, 1H), 1.65 (ddd, J=14.4, 6.3, 4.2 Hz, 1H), 1.26 (d, J=7.2 Hz, 3H).

Example 66

N-Hydroxy-2(S)-methyl-5-succinimide-4(S)-[N-(4-chlorophenylcarbonyl)amino]pentanamide

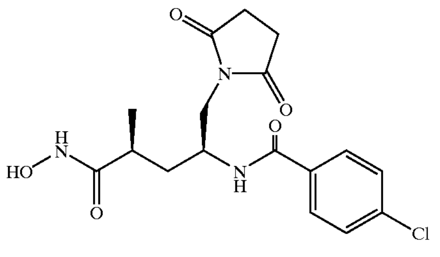

The title compound having the following physical data was obtained by the same procedure as a series of reaction of Example 3→Example 4, using the compound prepared in Example 65.

TLC: Rf 0.42 (Methylene chloride:Methanol=9:1);

NMR ($d_6$-DMSO): δ10.35 (d, J=1.5 Hz, 1H), 8.65 (d, J=1.5 Hz, 1H), 8.12 (d, J=9.0 Hz, 1H), 7.75 (d, J=8.4 Hz, 2H), 7.51 (d, J=8.4 Hz, 2H), 4.22 (m, 1H), 3.49 (m, 2H), 2.53 (m, 4H), 2.17 (m, 1H), 1.70 (ddd, J=13.8, 10.5, 5.4 Hz, 1H), 1.50 (ddd, J=13.8, 9.0, 4.5 Hz, 1H), 0.96 (d, J=6.9 Hz, 3H).

Example 66(1)

N-Hydroxy-2(S)-methyl-5-succinimidoxy-4(S)-[N-methyl-N-(4-nitrophenylcarbonyl)amino] pentanamide

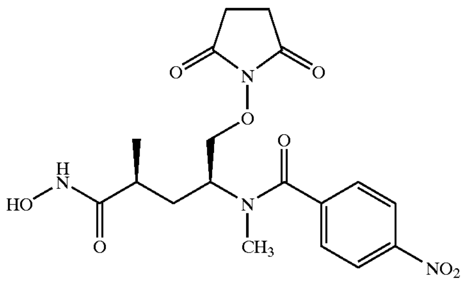

The title compound having the following physical data was obtained by the same procedure as a series of reaction of Example 65 (using N-hydroxysuccinimide instead of succinimide, and p-nitrobenzoyl chloride instead of p-chlorobenzoyl chloride. Then, the obtained t-butyl ester was used in the next reaction.)→Example 5→Example 29→Example 66, using the compound prepared in Reference Example 7.

TLC: Rf 0.45 (Methylene chloride:Methanol=9:1);

NMR ($d_6$-DMSO): δ10.50 (s, 0.7H), 10.45 (s, 0.3H), 8.28 (d, J=9.0 Hz, 1.4H), 8.24 (d, J=9.0 Hz, 0.6H), 7.69 (d, J=9.0 Hz, 1.4H), 7.61 (d, J=9.0 Hz, 0.6H), 4.86 (m, 0.7H), 4.20–4.00 (m, 2H), 3.72 (m, 0.3H), 2.89 (s, 0.9H), 2.71 (s, 2.1H), 2.60 (m, 4H), 2.20–1.70 (m, 2H), 1.60–1.30 (m, 1H), 1.05 (d, J=6.9 Hz, 2.1H), 0.74 (d, J=6.9 Hz, 0.9H).

Reference Example 8

5-Ethoxymethoxy-4(S)-[N-(4-phenoxyphenylcarbonyl)amino]pentanol

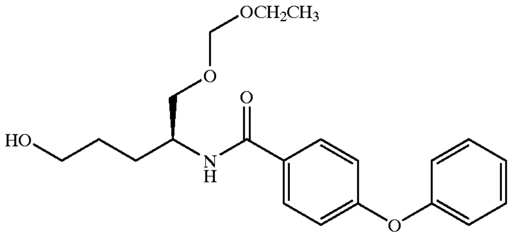

5-Ethoxymethoxy-4(S)-(N-(4-phenoxyphenylcarbonyl) aminopentanoic acid was obtained by the same procedure as a series of reaction of Example 37→Example 39→Example 41→Example 42, using a corresponding compound instead of the compound of a series of Reference Example 4. A solution of the above obtained compound (3.62 g) in tetrahydrofuran (100 ml) was cooled to 0° C. Triethylamine (1.69 ml) and ethylchloro formate (1.2 ml) were added dropwise thereto. The mixture was stirred at 0° C. for 1.5 hours. Sodium hydrogen borone (0.5 equivalent) was added to the reaction mixture. The mixture was stirred for 30 minutes. Acetic acid (5 ml) was added dropwise thereto. The mixture was stirred for 30 minutes and concentrated. To the residue, ethyl acetate and water were added. The organic layer was collected, washed with water and an aqueous saturated solution of sodium chloride, dried over anhydrous sodium sulfate and concentrated. The residue was purified by column chromatography on silica gel (Ethyl acetate:Hexane=2:1 (containing 1% triethylamine.)→4:1) to give the title compound (1.84 g) having the following physical data.

TLC: Rf 0.52 (Ethyl acetate:Hexane=4:1).

Reference Example 9

1-Bromo-5-ethoxymethoxy-4(S)-[N-(4-phenoxyphenylcarbonyl)amino]pentane

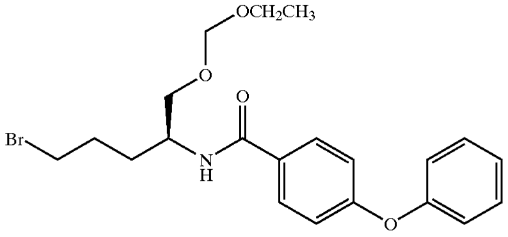

Triphenylphosphine (409 mg) and sodium hydrogen carbonate (328 mg) were added to a solution of the compound prepared in Reference Example 8 (490 mg) in methylene chloride (10 ml). The mixture was cooled to 0° C. A solution of tetrabromo methane (647 mg) in methylene chloride (5 ml) was added dropwise thereto. The mixture was stirred at 0° C. for 15 minutes. The reaction mixture was poured into water bath and extracted with ethyl acetate. The extract was washed with water and an aqueous saturated solution of sodium chloride, dried over anhydrous sodium sulfate and concentrated. The reside was purified by column chromatography on silica gel (Hexane:Ethyl acetate=3:1) to give the title compound (293 g) having the following physical data.

TLC: Rf 0.41 (Hexane:Ethyl acetate=2:1).

Example 67

1-Acetylthio-5-ethoxymethoxy-4(S)-[N-(4-phenoxyphenylcarbonyl)amino]pentane

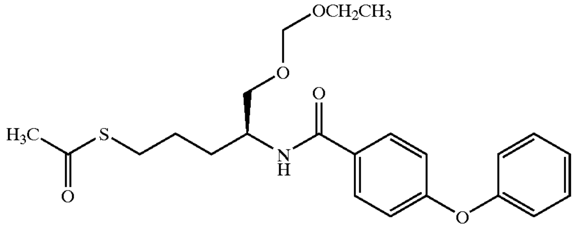

Potassium thioacetate (113 mg) was added to a solution of the compound prepared in Reference Example 9 (290 mg) in acetone (8 ml). The mixture was refluxed for 2 hours. After cooling, the reaction mixture was poured into water and extracted with ethyl acetate. The extract was washed with water and an aqueous saturated solution of sodium chloride, dried over anhydrous sodium sulfate and concentrated. The residue was purified by column chromatography on silica gel (Hexane:Ethyl acetate=3:1) to give the title compound (268 mg) having the following physical data.

TLC: Rf 0.28 (Hexane:Ethyl acetate=2:1).

NMR ($CDCl_3$): δ7.77 (d, J=8.7 Hz, 2H), 7.38 (t, J=7.5 Hz, 2H), 7.17 (t, J=7.5 Hz, 1H), 7.05 (d, J=7.5 Hz) and 7.01 (d, J=8.7 Hz) total 4H, 6.54 (d, J=8,7 Hz, 1H), 4.72 (d, J=6.9 Hz, 1H), 4.68 (d, J=6.9 Hz, 1H), 4.35–4.25 (m, 1H), 3.74 (dd, J=10, 3 Hz, 1H), 3.63–3.58 (m, 3H), 2.92 (t, J=6.9 Hz, 2H), 2.32(s, 3H), 1.80–1.65 (m, 4H), 1.21 (t, J=7.2 Hz, 3H).

Example 68

5-Ethoxymethoxy-4(S)-[N-(4-phenoxyphenylcarbonyl)amino]pentanthiol

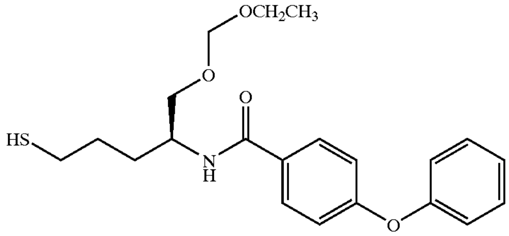

Potassium carbonate (146 mg) was added to a solution of the compound prepared in Example 67 (230 mg) in methanol (5 ml) at room temperature. The mixture was stirred for 2 hour and poured into ice/1N hydrochloric acid and extracted with ethyl acetate. The extract was washed with water and an aqueous saturated solution of sodium chloride, dried over anhydrous sodium sulfate and concentrated. The residue was purified by column chromatography on silica gel (Hexane:Ethyl acetate=3:1) to give the title compound (170 mg) having the following physical data.

TLC: Rf 0.27 (Hexane:Ethyl acetate=2:1),

NMR ($CDCl_3$): δ7.77 (d, J=9 Hz, 2H), 7.40–7.34 (m, 2H), 7.17 (t, J=7.5 Hz, 1H), 7.08–6.96 (m, 4H), 6.54 (d, J=9 Hz, 1H), 4.73 (d, J=6.9 Hz, 1H), 4.69 (d, J=6.9 Hz, 1H), 4.34–4.24 (m, 1H), 3.77 (dd, J=10.2, 3 Hz, 1H), 3.66–3.56 (m, 3H), 2.63–2.53 (m, 2H), 1.83–1.65 (m, 4H), 1.37 (t, J=7.5 Hz, 1H), 1.22 (t, J=7.2 Hz, 3H).

Example 69

5-Ethoxymethoxy-4(S)-[N-(4-phenoxyphenylcarbonyl)amino]pentanoic acid methyl ester

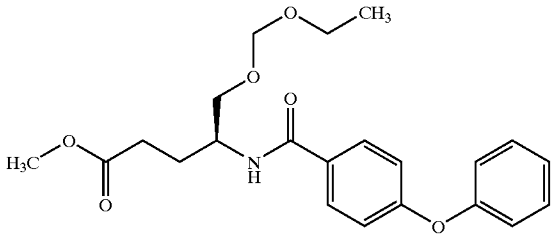

5(S)-Ethoxymethoxy-4(S )-(benzyloxycarbonyl)aminopentanoic acid methyl ester was obtained by the same procedure as a series of reaction of Example 39→Example 41 (using ethoxymethylchloride instead of methoxymethylchloride.), using 4(S)-carboxy-4-(N-benzyloxycarbonylamino)butyric acid methyl ester. To a solution of the obtained compound (10 g) in methanol (150 ml), 10% Palladium-Carbon (1 g) was added. The mixture was refluxed under an atmosphere of hydrogen for 2 hours. The reaction mixture was cooled and filtered by Celite. The filtrate was concentrated. To a solution of the residue in dimethylformamide (DMF) (150 ml), 1-hydroxybenzotriazol.mono hydrate (4.8 g) and 4-phenoxybenzoic acid (6 g) were added. The mixture was cooled with ice. To the mixture, 1-ethyl-3-(3-dimethylaminopropyl)carbodiimide.hydrochloride (6.5 g) was added. Triethylamine (4.7 ml) was added dropwise thereto. The mixture was stirred at room temperature overnight. Water was added thereto. The reaction mixture was extracted with ethyl acetate. The extract was washed with 1N hydrochloric acid, an aqueous saturated solution of sodium carbonate and an aqueous saturated solution of sodium chloride, dried over anhydrous sodium sulfate and concentrated. The residue was washed with n-hexane to give the title compound (8.1 g) having the following physical data.

TLC: Rf 0.22 (n-Hexane:Ethyl acetate 1:1).

Example 70

2(S)-Methyl-5-ethoxymethoxy-4(S)-[N-(4-phenoxyphenylcarbonyl)amino]pentanoic acid

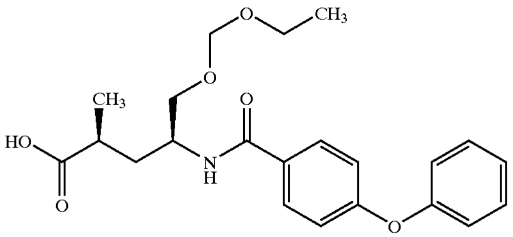

The title compound having the following physical data was obtained by the same procedure as a series of reaction of Example 43 (using methyl iodide instead of benzyl bromide.)→Example 2, using the compound prepared in Example, 69.

TLC: Rf 0.45 (Chloroform:Methanol:Acetic acid:Water=100:10:1:1),

NMR (DMSO-$d_6$): δ7.75(2H, d, J=8.8 Hz), 7.37(2H, m), 7.17(1H, t, J=7.4 Hz), 7.03(2H, m), 6.97(2H, d, J=8.8Hz), 6.58(1H, d, J=9.1 Hz), 4.71 (1H, d, J=4.68(1H, d, J=6.9 Hz), 4.43(1H, m), 3.74(1H, dd, J=3.0, 10.2 Hz), 3.65–3.55(3H, m), 2.56(1H, m), 2.16(1H, m), 1.68(1H, m), 1.27(3H, d, J=6.9 Hz), 1.18(3H, t, J=7.1 Hz).

Example 70(1)~70(2)

The following compounds were obtained by the same procedure as a series of reaction of Example 69→Example 70, using a corresponding compound.

Example 70(1)

2(S)-Allyl-5-ethoxymethoxy-4(S)-[N-(4-phenoxyphenylcarbonyl)amino]pentanoic acid

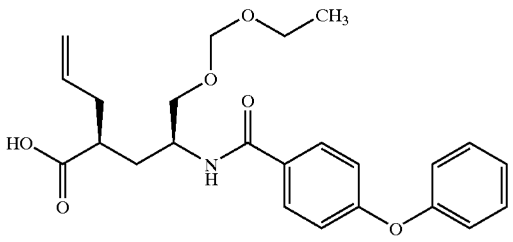

TLC: Rf 0.49 (Chloroform:Methanol:Acetic acid=100:10:1).

Example 70(2)

2(S)-Methyl-5-ethoxymethoxy-4(S)-[N-[4-(4-cyanophenyl)phenylcarbonyl]amino]pentanoic acid

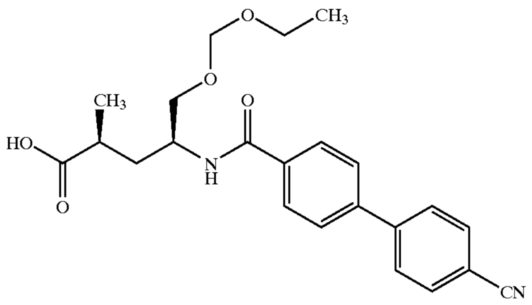

NMR (DMSO-$d_6$): δ12.7(1H, s), 8.29–8.25(2H, m), 7.97–7.92(6H, m), 7.83(2H, d, J=8.4 Hz), 4.59(2H, s), 4.28–4.16(1H, m), 3.53–3.42(4H, m), 2.39–2.30(1H, m), 1.95–1.84(1H, m), 1.64–1.54(1H, m), 1.12–1.04(6H, m).

Example 71

N-Hydroxy-2(S)-methyl-5-ethoxymethoxy-4(S)-[N-(4-phenoxyphenylcarbonyl)-amino]pentanamide

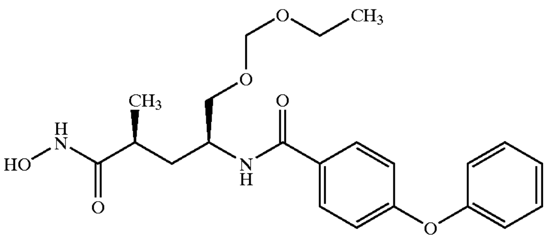

The title compound having the following physical data was obtained by the same procedure as a series of reaction of Example 3→Example 4, using the compound prepared in Example 70.

TLC: Rf 0.40 (Chloroform:Methanol:Acetic acid:Water=100:10:1:1);

NMR (DMSO-$d_6$): δ10.37(1H, brs), 8.66(1H, brs), 8.03 (1H, d, J=8.8 Hz), 7.87(2H, d, J=8.8 Hz), 7.43(2H, dd, J=7.4, 8.5 Hz), 7.20(1H, t, J=7.4 Hz), 7.06 (2H, d, J=8.5 Hz), 7.02(2H, d, J=8.8 Hz), 4.59(2H, s), 4.14(1H, m), 3.50–3.45 (4H, m), 2.17(1H, m), 1.66(2H, m), 1.09(3H, t, J=7.1 Hz), 1.01 (3H, d, J=6.9 Hz).

Example 71(1)~71(2)

The following compounds were obtained by the same procedure as a series of reaction of Example 71, using the compound prepared in Example 70(1) or 70(2).

Example 71(1)

N-Hydroxy-2(S)-allyl-5-ethoxymethoxy-4(S)-[N-(4-phenoxyphenylcarbonyl)amino]pentanamide

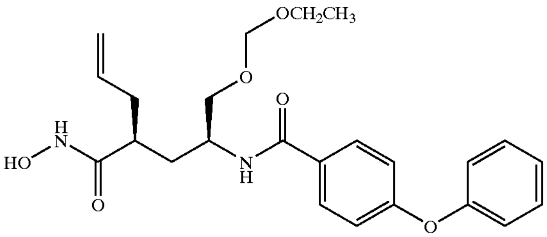

TLC: Rf 0.26 (Chloroform:Methanol:Acetic acid=100:10:1);

NMR ($d_6$-DMSO): δ10.42(1H, s), 8.70(1H, s), 8.03(1H, d, J=8.8 Hz), 7.89–7.85(2H, m), 7.47–7.37(2H, m), 7.23–7.15(1H, m), 7.09–6.99(4H, m), 5.77–5.55(1H, m), 5.03–4.92(2H, m), 4.58(2H, s), 4.19–4.05 (1H, m), 3.53–3.42(2H, m), 3.47(2H, q, J=7.0 Hz), 2.19–2.17(3H, m), 1.38–1.82(2H, m), 1.08(3H, t, J=7.0 Hz).

Example 71(2)

N-Hydroxy-2(S)-methyl-5-ethoxymethoxy-4(S)-[N-[4-(4-cyanophenyl)phenylcarbonyl]amino] pentanamide

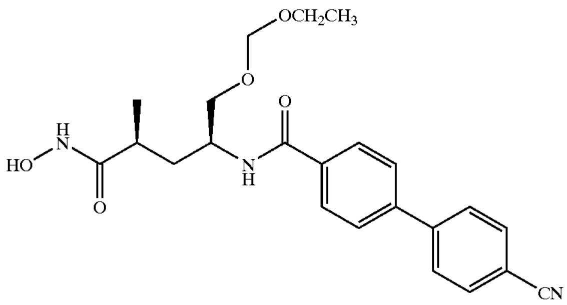

TLC: Rf 0.48 (Chloroform:Methanol=9:1);

NMR ($d_6$-DMSO): δ10.37 (1H, s), 8.18 (1H, d, J=8.4 Hz), 7.99–7.91 (6H, m), 7.83 (2H, d, J=8.2 Hz), 4.58 (2H, s), 4.24–4.07 (1H, m), 3.54–3.41 (4H, m), 2.26–2.10 (1H, m), 1.74–1.62 (2H, m), 1.12–0.97 (6H, m).

Formulation Example

Formulation Example 1

The following components were admixed in conventional method and punched out to obtain 100 tablets each containing 50 mg of active ingredient.

| | |
|---|---|
| N-Hydroxy-2(S)-methyl-5-ethoxymethoxy-4(S)-[N-(4-phenoxyphenylcarbonyl)amino]pentanamide | 5.0 g |
| Carboxymethyl Cellulose calcium (disintegrating agent) | 0.2 g |
| Magnesium stearate (lubricating agent) | 0.1 g |
| Microcrystalline cellulose | 4.7 g |

Formulation Example 2

The following components were admixed in conventional method. The solution was sterilized in conventional manner, placed 5 ml portions into ampoules and freeze-dried to obtain 100 ampoules each containing 20 mg of the active ingredient.

| | |
|---|---|
| N-Hydroxy-2(S)-methyl-5-ethoxymethoxy-4(S)-[N-(4-phenoxyphenylcarbonyl)amino]pentanamide | 2.0 g |
| Mannitol | 20 g |
| distilled water | 500 ml |

What is claimed is:

1. An aminobutyric acid derivative of the formula (I):

(I)

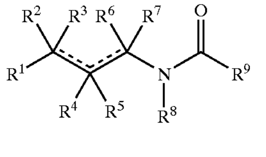

wherein $R^1$ is —$COOR^{10}$, —$CONHOR^{10}$, —$CONHNHR^{10}$, —$(CH_2)SR^{50}$ or —Y—$P(OR^{51})_2$;

$R^{10}$ is (i) hydrogen, (ii) C1–8 alkyl, (iii) phenyl, (iv) C1–8 alkyl substituted by phenyl or C1–8 alkoxy, or (v) oxycarbonyl substituted by phenyl, benzyl or C1–8 alkyl;

n is 0–3;

$R^{50}$ is (i) hydrogen, (ii) C1–8 alkyl, (iii) —$COR^{52}$, in which $R^{52}$ is C1–8 alkyl or phenyl; or (iv) —$SR^{53}$, in which $R^{53}$ is hydrogen, C1–8 alkyl or phenyl;

$R^{51}$ is hydrogen, C1–8 alkyl or phenyl;

Y is a single bond, —$CH_2$— or —O—;

$R^2$, $R^3$, $R^4$, $R^5$, $R^6$ and $R^7$ each, independently, is (1) hydrogen,
(2) C1–8 alkyl,
(3) C2–8 alkenyl
(4) —$OR^{11}$,
(5) —$SR^{11}$,
(6) —$NR^{12}R^{13}$,
(8) Cycl,
(9) C1–8 alkyl substituted by —$OR^{11}$, —$SR^{11}$, —$NR^{12}R^{13}$, —$COR^{14}$, guanidino or Cycl, or
(10) C2–8 alkenyl substituted by —$OR^{11}$, —$SR^{11}$, —$NR^{12}R^{13}$, $COR^{14}$, guanidino or Cycl, or $R^3$ and $R^4$, taken together is C1–8 alkylene, $R^5$ and $R^6$, taken together is C1–8 alkylene, $R^3$ and $R^6$, taken together is C1–8 alkylene, $R^2$ and $R^3$, taken together is C2–8 alkylene, $R^4$ and $R^5$, taken together is C2–8 alkylene, or $R^6$ and $R^7$, taken together is C2–8 alkylene, or $R^2$ is 2-propynyl, and $R^3$, $R^4$, $R^5$, $R^6$ and $R^7$ each, independently, is (1) hydrogen,
(2) C1–8 alkyl,
(3) C2–8 alkenyl,
(4) —$OR^{11}$,
(5) —$SR^{11}$,
(6) —$NR^{12}R^{13}$,
(8) Cycl,
(9) C1–8 alkyl substituted by —$OR^{11}$, —$SR^{11}$, —$N^{12}R^{13}$, —$COR^{14}$, guanidino or Cycl, or
(10) C2–8 alkenyl substituted by —$OR^{11}$, —$SR^{11}$, —$NR^{12}R^{13}$, —$COR^{14}$, guanidino or Cycl, or $R^3$ and $R^4$, taken together is C1–8 alkylene, $R^5$ and $R^6$, taken together is C1–8 alkylene, $R^3$ and $R^6$, taken together is C1–8 alkylene, $R^4$ and $R^5$, taken together is C2–8 alkylene, or $R^6$ and $R^7$, taken together is C2–8 alkylene;

in which Cycl is carbocyclic ring or heterocyclic ring and these carbocyclic ring and heterocyclic ring may be substituted by one or more of (i) C1–8 alkyl, (ii) C1–8 alkoxy, (iii) nitro, (iv) guanidino, (v) amidino, (vi) halogen atom, (vii) nitrile (viii) hydroxy, (ix) benzyloxy, (x) —$NR^{101}R^{102}$, in which $R^{101}$ and $R^{102}$ each, independently, is hydrogen or C1–8 alkyl, (xi) —$COOR^{103}$, in which $R^{103}$ is hydrogen or C1–8 alkyl, (xii) trifluoromethyl, (xiii) trifluoromethyloxy, (xiv) phenyl, (xv) phenyl substituted by C1–8 alkyl or C1–8 alkoxy, (xvi) phenyloxy, (xvii) phenylsulfonyl, (xviii) C1–8 alkyl substituted by phenyl or nitrile, (xix) heterocyclic ring, (xx) keto, and (xxi) C1–8 alkoxy substituted by —$CONR^{104}R^{105}$, in which $R^{104}$ and $R^{105}$ each, independently, is hydrogen, C1–8 alkyl or phenyl;

$R^{11}$ is (i) hydrogen, (ii) C1–8 alkyl, (iii) Cycl, or (iv) —$COR^{18}$, or C1–8 alkyl substituted by —$OR^{15}$, —$SR^{15}$, —$NR^{16}R^{17}$, —$COR^{18}$, guanidino or Cycl;

$R^{15}$ is hydrogen, C1–8 alkyl, Cyc1 or C1–8 alkyl substituted by Cyc1 or C1–8 alkoxy;

$R^{16}$ is hydrogen or C1–8 alkyl;

$R^{17}$ is hydrogen, C1–8 alkyl or —$COR^{19}$, in which $R^{19}$ is C1–8 alkyl, Cyc1 or C1–8 alkyl substituted by Cyc1;

$R^{18}$ is hydroxy, C1–8 alkyl, C1–8 alkoxy or —$NR^{20}R^{21}$, in which $R^{20}$ and $R^{21}$, each independently, is hydrogen, C1–8 alkyl, Cyc1 or C1–8 alkyl substituted by Cyc1;

$R^{12}$ is hydrogen, C1–8 alkyl, Cyc1 or C1–8 alkyl, substituted by Cyc1;

$R^{13}$ is hydrogen, C1–8 alkyl, Cyc1, C1–8 alkyl substituted by Cyc1, or —$COR^{22}$, in which $R^{22}$ is C1–8 alkyl, Cyc1 or C1–8 alkyl substituted by Cyc1;

$R^{14}$ is hydroxy, C1–8 alkyl, C1–8 alkoxy, $Cyc_1$, C1–8 alkyl substituted by Cyc1, or —$NR^{23}R^{24}$, in which $R^{23}$ and $R^{24}$, each independently, is (i) hydrogen, (ii) C1–8 alkyl, (iii) Cyc1 or (iv) C1–8 alkyl substituted by Cyc1 or hydroxy;

(1) $R^8$ is 1) hydrogen,
2) C1–8 alkyl,
3) C1–8 alkoxycarbonyl,
4) C1–8 alkyl substituted by —$OR^{26}$, —$SR^{26}$, —$NR^{27}R^{28}$ or —$COR^{29}$, or
5) C1–8 alkoxycarbonyl substituted by Cyc2, and $R^9$ is

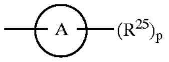
; or (2) $R^8$ is

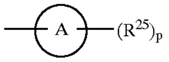
or

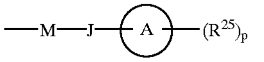
, and $R^9$ is

1) C1–8 alkyl,
2) C1–8 alkoxy,
3) C1–8 alkoxy substituted by Cyc2,
4) C1–8 alkyl substituted by —$OR^{26}$, —$SR^{26}$, —$NR^{27}R^{28}$, —$COR^{29}$ or Cyc2 or
5)

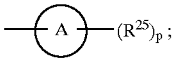
;

in which Cyc2 is carbocyclic ring or heterocyclic ring and these carbocyclic ring and heterocyclic ring may be substituted by one or more of (i) C1–8 alkyl, (ii) C1–8 alkoxy, (iii) nitro, (iv) guanidino, (v) amidino, (vi) halogen atom, (vii) nitrile (viii) hydroxy, (ix) benzyloxy, (x) —$NR^{201}R^{202}$, in which $R^{201}$ and $R^{202}$ each, independently, is hydrogen or C1–8 alkyl, (xi) —$COOR^{203}$, in which $R^{203}$ is hydrogen or C1–8 alkyl, (xii) trifluoromethyl, (xiii) trifluoromethyloxy, (xiv) phenyl, (xv) phenyl substituted by C1–8 alkyl or C1–8 alkoxy, (xvi) phenyloxy, (xvii) phenylsulfonyl, (xviii) C1–8 alkyl substituted by phenyl or nitrile, (xix) heterocyclic ring, (xx) keto, and (xxi) C1–8 alkoxy substituted by —$CONR^{204}R^{205}$, in which $R^{204}$ and $R^{205}$ each, independently, is hydrogen, C1–8 alkyl or phenyl;

$R^{26}$ is hydrogen, C1–8 alkyl, Cyc2 or C1–8 alkyl substituted by Cyc2;

$R^{27}$ is hydrogen, C1–8 alkyl, Cyc2 or C1–8 alkyl substituted by Cyc2;

$R^{28}$ is hydrogen, C1–8 alkyl, Cyc2, C1–8 alkyl substituted by Cyc2, or —$COR^{30}$, in which $R^{30}$ is C1–8 alkyl, Cyc2 or C1–8 alkyl substituted by Cyc2;

$R^{29}$ is hydroxy, C1–8 alkyl, Cyc2, C1–8 alkyl substituted by Cyc2, or —$NR^{31}R^{32}$, in which $R^{31}$ and $R^{32}$, each independently, is hydrogen, C1–8 alkyl, Cyc2 or C1–8 alkyl substituted by Cyc2;

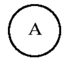

is carbocyclic ring or heterocyclic ring;

$R^{25}$ is —E—G;

E is 1) a single bond,
2) —$CONR^{33}$—,
3) —$NR^{33}CO$—,
4) —CO—O—,
5) —O—CO—,
6) —$NR^{33}$—CO—$NR^{34}$—,
7) —CO—$CH_2$—,
8) —CO—,
9) —O—CO—$NR^{33}$—,
10) —$NR^{33}$—CO—O—,
11) —O—CO—O—,
12) —CS—$NR^{33}$—,
13) —$NR^{33}$—CS—,
14) —CS—C—,
15) —O—CS—,
16) —$NR^{33}$—CS—$R^{34}$—,
17) —CS—$CH_2$—,
18) —CS—,
19) —O—CS—$NR^{33}$—,
20) $NR^{33}$ —CS—O—,
21) —O—CS—O—,
22) —$CH_2$—$CH_2$—,
23) —HC═CH—,
24) —C≡C—,
25) —$SO_2$—$NR^{33}$—,
26) —$NR^{33}$—$SO_2$—,
27) —$SO_2$—$CH_2$— or
28) —$CH_2$—$SO_2$—;

$R^{33}$ and $R^{34}$, each independently, is hydrogen, C1–8 alkyl, Cyc3 or C1–8 alkyl substituted by Cyc3;

Cyc 3 is carbocyclic ring or heterocyclic ring and these carbocyclic ring and heterocyclic ring may be substituted by one or more of (i) C1–8 alkyl, (ii) C1–8 alkoxy, (iii) nitro, (iv) guanidino, (v) amidino, (vi) halogen atom, (vii) nitrile, (viii) hydroxy, (ix) benzyloxy, (x) —$NR^{301}R^{302}$, in which $R^{301}$ and $R^{302}$ each, independently, is hydrogen or C1–8 alkyl, (xi) —$COOR^{303}$, in which $R^{303}$ is hydrogen or C1–8 alkyl, (xii) trifluoromethyl, (xiii) trifluoromethyloxy, (xiv) phenyl, (xv) phenyl substituted by C1–8 alkyl or C1–8 alkoxy, (xvi) phenyloxy, (xvii) phenylsulfonyl, (xviii) C1–8 alkyl substituted by phenyl or nitrile, (xix) heterocyclic ring, (xx) keto, and (xxi) C1–8 alkoxy substituted by —$CONR^{304}R^{305}$, in which $R^{304}$ and $R^{305}$ each, independently, is hydrogen, C1–8 alkyl or phenyl;

G is 1) hydrogen,
2) C1–8 alkyl,
3) Cyc4,
4) —$OR^{35}$,
5) —$SR^{35}$,
6) halogen atom,
7) nitro,
8) nitrile,
9) —$NR^{36}R^{37}$,
10) —$COR^{38}$,
11) C1–8 alkyl substituted by Cyc4, —$OR^{35}$, —$SR^{35}$, halogen atom, —$NR^{36}R^{37}$ or —$COR^{38}$;

in which Cyc4 is carbocyclic ring or heterocyclic ring and these carbocyclic ring and heterocyclic ring may be substituted by one or more of (i) C1–8 alkyl, (ii) C1–8 alkoxy, (iii) nitro, (iv) guanidino, (v) amidino, (vi) halogen atom, (vii) nitrile (viii) hydroxy, (ix) benzyloxy, (x) —$NR^{401}R^{402}$, in which $R^{401}$ and $R^{402}$ each, independently, is hydrogen or C1–8 alkyl, (xi) —$COOR^{403}$, in which $R^{403}$ is hydrogen or C1–8 alkyl, (xii) trifluoromethyl, (xiii) trifluoromethyloxy, (xiv) phenyl, (xv) phenyl substituted by C1–8 alkyl or C1–8 alkoxy, (xvi) phenyloxy, (xvii) phenylsulfonyl, (xviii) C1–8 alkyl substituted by phenyl or nitrile, (xix) heterocyclic ring, (xx) keto, and (xxi) C1–8 alkoxy substituted by —$CONR^{404}R^{405}$, in which $R^{404}$ and $R^{405}$ each, independently, is hydrogen, C1–8 alkyl or phenyl;

$R^{35}$ is hydrogen, C1–8 alkyl, C1–8 alkoxy, Cyc4 or C1–8 alkyl substituted by Cyc4;

$R^{36}$ is hydrogen, C1–8 alkyl, Cyc4 or C1–8 alkyl substituted by Cyc4;

$R^{37}$ is hydrogen, C1–8 alkyl, Cyc4, C1–8 alkyl substituted by Cyc4, or —$COR^{39}$, in which $R^{39}$ is C1–8 alkyl, Cyc4 or C1–8 alkyl substituted by Cyc4;

$R^{38}$ is hydroxy, C1–8 alkyl, Cyc4, C1–8 alkyl substituted by Cyc4, or —$NR^{40}OR^{41}$, in which $R^{40}$ and $R^{41}$, each independently, is hydrogen, C1–8 alkyl, Cyc4 or C1–8 alkyl substituted by Cyc4; or —E—G taken together, is C1–4 alkylidene;

p is 1–5;

M is C1–8 alkylene;

J is a single bond, an oxygen atom, a sulfur atom or —$NR^{42}$—, in which $R^{42}$ is hydrogen or C1–8 alkyl;

$=\!=\!=$ may be double bond, by releasing the hydrogens, when two of $R^2$, $R^3$, $R^4$, $R^5$, $R^6$ and $R^7$ that do not bond to the same carbon atom and bond to neighboring carbon atoms, are hydrogens, with the proviso that (1) $=\!=\!=$ is not double bond when $R^3$ and $R^4$ taken together is C1–8 alkylene, $R^5$ and $R^6$, taken together is C1–8 alkylene, $R^3$ and $R^6$, taken together is C1–8 alkylene;

(2) when one of $R^6$ and $R^7$ is hydrogen and the other is hydrogen or C1–8 alkyl, each $R^2$, $R^3$, $R^4$, $R^5$ and $R^6$ is hydrogen, ring A in $R^9$ is phenyl and E is a single bond, then G is 2) C1–8 alkyl,
3) Cyc4,
4) —$OR^{35}$,
5) —$SR^{35}$,
6) halogen atoms,
7) nitro,
8) nitrile,
9) —$NR^{36}R^{37}$,
10) —$COR^{38}$,
11) C1–8 alkyl substituted by Cyc4, —$OR^{35}$, —$SR^{35}$, halogen atoms, —$NR^{36}R^{37}$ or —$COR^{38}$, and (3) when one of $R^2$ and $R^3$ is hydrogen or C1–8 alkyl and the other is $NR^{12}R^{13}$ in which $R^{12}$ is hydrogen and $R^3$ is $COR^{22}$, then $R^{22}$ is C1–8 alkyl or C1–8 alkyl substituted by Cyc1;

or non-toxic salts thereof.

2. A compound according to claim 1, wherein $R^2$, $R_3$, $R^4$, $R^5$, $R^6$ and $R^7$ each, independently, is (1) hydrogen,
(2) C1–8 alkyl,
(3) C2–8 alkenyl,
(4) —$OR^{11}$,
(5) —$SR^{11}$,
(6) —$NR^{12}R^{13}$,
(7) —$COR^{14}$,
(8) Cyc1,
(9) C1–8 alkyl substituted by —$OR^{11}$, —$SR^{11}$, —$NR^{12}R^{13}$, —$COR^{14}$, guanidino or Cyc1, or
(10) C2–8 alkenyl substituted by —$OR^{11}$, —$SR^{11}$, —$NR^{12}R^{13}$, —$COR^{14}$, guanidino or Cyc1, or $R^3$ and $R^4$, taken together is C1–8 alkylene, $R^5$ and $R^6$, taken together is C1–8 alkylene, $R^3$ and $R^6$, taken together is C1–8 alkylene, $R^2$ and $R^3$, taken together is C2–8 alkylene, $R^4$ and $R^5$, taken together is C2–8 alkylene, or $R^6$ and $R^7$, taken together is C2–8 alkylene.

3. A compound according to claim 1, wherein $R^2$ is 2-propynyl, and $R^3$, $R^4$, $R^5$, $R^6$ and $R^7$ each, independently, is (1) hydrogen,
(2) C1–8 alkyl,
(3) C2–8 alkenyl,
(4) —$OR^{11}$,
(5) —$SR^{11}$,
(6) —$NR^{12}R^{13}$,
(7) —$COR^{14}$,
(8) Cyc1,
(9) C1–8 alkyl substituted by —$OR^{11}$, —$SR^{11}$, —$NR^{12}R^{13}$, —$COR^{14}$, guanidino or Cyc1, or
(10) C2–8 alkenyl substituted by —$OR^{11}$, —$SR^{11}$, —$NR^{12}R^{13}$, —$COR^{14}$, guanidino or Cyc1, or $R^3$ and $R^4$, taken together is C1–8 alkylene, $R^5$ and $R^6$, taken together is C1–8 alkylene, $R^3$ and $R^6$, taken together is C1–8 alkylene, $R^4$ and $R^5$, taken together is C2–8 alkylene, or $R^6$ and $R^7$, taken together is C2–8 alkylene.

4. A compound according to claim 1, wherein $R^1$ is —$COOR^{10}$.

5. A compound according to claim 1, wherein $R^1$ is —$CONHOR^{10}$.

6. A compound according to claim 1, wherein $R^1$ is —$CONHNHR^{10}$.

7. A compound according to claim 1, wherein $R^1$ is —$(CH_2)_nSR^{50}$.

8. A compound according to claim 1, wherein $R^1$ is —Y—$P(OR^{51})_2$.

9. A compound according to claim 2, which is selected from (1) 1-Acetylthio-5-ethoxymethoxy-4-[N-(4-phenoxyphenylcarbonyl)amino]pentane, (2) 5-Ethoxymethoxy-4-[N-(4-phenoxyphenylcarbonyl)amino]pentanthiol, and non-toxic salts thereof.

10. A compound according to claim 3, which is selected from

(64) 2(S)-(2-Propynyl)-5-ethoxymethoxy-4(S)-[N-(4-nitrophenylcarbonyl)amino]pentanoic acid,
(67) 2(S)-(2-Propynyl)-5-ethoxymethoxy-4(S)-[N-(4-bromophenylcarbonyl)amino]pentanoic acid,
(68) 2(S)-(2-Propynyl)-5-ethoxymethoxy-4(S)-[N-(4-chlorophenylcarbonyl)amino]pentanoic acid,
(79) 2(S)-(2-Propynyl)-5-(2-methoxyethoxy)methoxy-4(S)-[N-(4-cyanophenylcarbonyl)amino]pentanoic acid, and non-toxic salts thereof.

11. A compound according to claim 3, which is selected from (170) N-Hydroxy-2(S)-(2-propynyl)-5-ethoxymethoxy-4(S)-[N-(4-nitrophenylcarbonyl)amino]pentanamide,
(172) N-Hydroxy-2(S)-(2-propynyl)-5-ethoxymethoxy-4(S)-[N-(4-bromophenylcarbonyl)amino]pentanamide,
(173) N-Hydroxy-2(S)-(2-propynyl)-5-ethoxymethoxy-4(S)-[N-(4-chlorophenylcarbonyl)amino]pentanamide,
(177) N-Hydroxy-2(S)-(2-propynyl)-5-(2-methoxyethoxy)methoxy-4(S)-[N-(4-cyanophenylcarbonyl)amino]pentanamide, and non-toxic salts thereof.

12. A compound which is selected from

(26) N-Hydroxy-5-[N-[4-(benzofuran-2-yl)phenylcarbonyl]amino]pentanamide,
(27) N-Hydroxy-6-[N-[4-(benzofuran-2-yl)phenylcarbonyl]amino]hexanamide, and non-toxic salts thereof.

13. A matrix metalloproteinase inhibitor containing a compound according to claim 1 as an active ingredient and non-toxic salts thereof.

14. A matrix metalloproteinase inhibitor containing a compound according to claim 12 as an active ingredient and non-toxic salts thereof.

15. A compound according to claim 2, which is selected from (1) N-Hydroxy-4-(N-(4-(benzofuran-2-yl)phenylcarbonyl)amino)butyramide,
(2) N-Hydroxy-4-(N-(4-methylphenylcarbonyl)amino)butyramide,
(3) N-Hydroxy-4-(N-(4-butyloxyphenylcarbonyl)amino)butyramide,
(4) N-Hydroxy-4-(N-(3-butyloxyphenylcarbonyl)amino)butyramide,
(5) N-Hydroxy-4-[N-[4-((4-methylphenyl)ethynyl)furan-2-ylcarbonyl]amino]butyramide,
(6) N-Hydroxy-4-(N-(4-(pyrrol-1-yl)phenylcarbonyl)amino)butyramide,
(7) N-Hydroxy-4-(N-(trans-4-methylcyclohexylcarbonyl)amino)butyramide,
(8) N-Hydroxy-4-(N-(4-(3-methoxy-1-propynyl)phenylcarbonyl)amino)butyramide,
(9) N-Hydroxy-4-(N-(4-butylphenylcarbonyl)amino)butyramide,
(10) N-Hydroxy-4-(N-(benzofura-2-ylcarbonyl)amino)butyramide,
(11) N-Hydroxy-4-[N-[4-(2-(4-chlorophenyl)ethenyl)phenylcarbonyl]amino]butyramide,
(12) N-Hydroxy-4-[N-[4-((4-(imidazol-1-yl)phenyl)ethynyl)phenylcarbonyl]amino]butyramide,
(13) N-Hydroxy-4-(N-(trans-4-propylcyclohexylcarbonyl)amino)butyramide,
(14) N-Hydroxy-4-[N-[4-((4-methylphenyl)ethynyl)phenylcarbonyl]amino]butyramide,
(15) N-Hydroxy-4-[N-[4-((4-bromophenyl)aminosulfonyl)phenylcarbonyl]amino]butyramide,
(16) N-Hydroxy-4-[N-(4-cyclohexylphenylcarbonyl)amino]butyramide,
(17) N-Hydroxy-4-[N-[4-(4-propylphenyl)phenylcarbonyl]amino]butyramide,
(18) N-Hydroxy-4-[N-[4-(4-hydroxyphenyl)phenylcarbonyl]amino]butyramide,
(19) N-Hydroxy-4-[N-[4-(4-chlorophenyl)furan-2-ylcarbonyl]amino]butyramide,
(20) N-Hydroxy-4-[N-[4-(4-heptylphenyl)phenylcarbonyl]amino]butyramide,
(21) N-Hydroxy-4-[N-[4-(4-methoxyphenyl)phenylcarbonyl]amino]butyramide,
(22) N-Hydroxy-4-[N-[4-(4-chlorophenyl)phenylcarbonyl]amino]butyramide,
(23) N-Hydroxy-4-[N-(5-benzyloxyindol-2-ylcarbonyl)amino]butyramide,
(24) N-Hydroxy-4-[N-[5-(2-(4-chlorophenyl)ethenyl)furan-2-ylcarbonyl]amino]butyramide,
(25) N-Hydroxy-4-[N-(4-phenoxyphenylcarbonyl)amino]butyramide,
(26) N-Hydroxy-4-[N-[[(4'-carbamoylmethoxy)biphenyl-4-yl]carbonyl]amino]butyramide,
(27) N-Hydroxy-4-[N-[4-(4-phenylpiperidin-1-y)phenylcarbonyl]amino]butyramide,
(28) N-Hydroxy-4-[N-[4-[3-(4-chlorophenoxy)-1-propynyl]phenylcarbonyl]amino]butyramide,
(29) N-Hydroxy-4-[N-[4-(3-phenoxy-1-propynyl)phenylcarbonyl]amino]butyramide,
(30) N-Hydroxy-4-[N-[4-(4-methoxyphenoxy)phenylcarbonyl]amino]butyramide,
(31) N-Hydroxy-4-[N-[4-(4-hydroxyphenoxy)phenylcarbonyl]amino]butyramide,
(32) N-Hydroxy-4-[N-[4-(4-phenoxypiperazin-1-yl)phenylcarbonyl]amino]butyramide,
(33) N-Hydroxy-4-[N-[4-(4-phenyl-1,2,5,6-tetrahydropyridin-1-yl)phenylcarbonyl]amino]butyramide,
(34) N-Hydroxy-4-(N-(4-(1-heptynyl)phenylcarbonyl)amino)butyramide,
(35) N-Hydroxy-4-(N-(4-benzyloxyphenylcarbonyl)amino)butyramide,
(36) N-Hydroxy-4-(N-methyl-N-(4-(benzofuran-2-yl)phenylcarbonyl)amino)butyramide,
(37) N-Hydroxy-4-(N-(4-(benzofuran-2-yl)phenylcarbonyl)amino)-2(S)-hydroxybutyramide,
(38) N-Hydroxy-4-(N-(4-(benzofuran-2-yl)phenylcarbonyl)amino)-2(R)-hydroxybutyramide,
(39) N-Hydroxy-4-(N-(4-(benzofuran-2-yl)phenylcarbonyl)amino)-2(S)-benzyloxymethoxybutyramide,
(40) N-Hydroxy-4-(N-(4-(benzofuran-2-yl)phenylcarbonyl)amino)-2-(R)-benzyloxymethoxybutyramide,
(41) N-Hydroxy-4-(N-(4-(2-(4-chlorophenyl)ethenyl)phenylcarbonyl)amino)-2(S)-benzyloxymethoxybutyramide,
(42) N-Hydroxy-4-(N-(4-chlorophenylcarbonyl)amino)-2-benzyloxymethoxybutyramide,
(43) N-Hydroxy-4-(N-(4-chlorophenylcarbonyl)amino)-2-((N-benzyl-N-methylamino)carbonylmethoxy)butyramide,

(44) N-Hydroxy-4-(N-(4-chlorophenylcarbonyl)amino)-2-((N-phenyl-N-methylamino)carbonylmethoxy)butyramide,
(45) N-Hydroxy-4-(N-(4-chlorophenylcarbonyl)amino)-2-((N-phenylethyl-N-methylamino)carbonylmethoxy)butyramide
(46) N-Hydroxy-3(S)-hydroxy-4-(N-(4-(benzofuran-2-yl)phenylcarbonyl)amino)butyramide,
(47) N-Hydroxy-3-(R)-hydroxy-4-(N-(4-(benzofuran-2-yl)phenylcarbonyl)amino)butyramide,
(48) N-Hydroxy-3(S)-methoxymethyloxy-4-(N-(4-(benzofuran-2-yl)phenylcarbonyl)amino(butyramide,
(49) N-Hydroxy-4-(N-(4-(benzofuran-2-yl)phenylcarbonyl)amino)-2-butenamide,
(50) N-Hydroxy-3(R)-methoxymethyloxy-4-(N-(4-(benzofuran-2-yl)phenylcarbonyl)amino)butyramide,
(51) N-Hydroxy-4-(N-(4-(benzofuran-2-yl)phenylcarbonyl)amino)-3-butenamide,
(52) N-Hydroxy-4-[N-(4-(benzofuran-2-yl)phenylcarbonyl]amino]-3(S)-benzyloxymethoxybutyramide,
(53) N-Hydroxy-2-benzyloxymethyl-4-(N-(4-methylphenylcarbonyl)amino)butyramide,
(54) N-Hydroxy-2(RS)-hydroxymethyl-4-(N-(4-methylphenylcarbonyl)amino)butyramide,
(55) N-Hydroxy-2(R)-hydroxymethyl-4-(N-(4-methylphenylcarbonyl)amino)butyramide,
(56) N-Hydroxy-2(S)-hydroxymethyl-4-(N-(4-methylphenylcarbonyl)amino)butyramide,
(65) N-Hydroxy-4(S)-hydroxymethyl-4-(N-(4-(benzofuran-2-yl)phenylcarbonyl)amino)butyramide,
(66) N-Hydroxy-4(S)-methoxymethyloxymethyl-4-(N-4-(benzofuran-2-yl)phenylcarbonyl)amino)butyramide,
(67) N-Hydroxy-2(S)-benzyl-4(S)-methoxymethyloxymethyl-4-(N-(4-(benzofuran-2-yl)phenylcarbonyl)amino)butyramide,
(68) N-Hydroxy-2(S)-methyl-4(S)-methoxymethyloxymethyl-4-(N-(4-(benzofuran-2-yl)phenylcarbonyl)amino)butyramide,
(69) N-Hydroxy-2(S)-(3-phenyl-2-propenyl)-4(S)-methoxymethyloxymethyl-4-(N-(4-(benzofuran-2-yl)phenylcarbonyl)amino)butyramide,
(70) N-Hydroxy-2(S)-(3-phenylpropyl)-4(S)-methoxymethyloxymethyl-4-(N-4-(benzofuran-2-yl)phenylcarbonyl)amino)butyramide,
(71) N-Hydroxy-2(R)-benzyl-4(S)-hydroxymethyl-4-(N-(4-(benzofuran-2-yl)phenylcarbonyl)amino)butyramide,
(72) N-Hydroxy-2(S)-benzyl-4(S)-hydroxymethyl-4-(N-(4-(3-methoxy-1-propynyl)phenylcarbonyl)amino)butyramide,
(73) N-Hydroxy-5-hydroxy-4(S)-[N-[4-(3-methoxy-1-propynyl)phenylcarbonyl]amino]pentanamide,
(74) N-Hydroxy-5-hydroxy-4(R)-(N-(4-(3-methoxy-1-propynyl)phenylcarbonyl)amino)pentanamide,
(88) N-Hydroxy-5-methoxymethoxy-4(S)-[N-[4-(3-methoxy-1-propynyl)phenylcarbonyl]amino]pentanamide,
(89) N-Hydroxy-5-benzyloxymethoxy-4(S)-[N-[4-(3-methoxy-1-propynyl)phenylcarbonyl]amino]pentanamide,
(90) N-Hydroxy-5-(2-methoxyethoxy)methoxy-4(S)-[N-[4-(3-phenoxy-1-propynyl)phenylcarbonyl]amino]pentanamide,
(91) N-Hydroxy-5-methoxymethoxy-4(S)-[N-[4-(3-phenoxy-1-propynyl)phenylcarbonyl]amino]pentanamide,
(92) N-Hydroxy-5-benzyloxymethoxy-4(S)-[N-[4-(3-phenoxy-1-propynyl)phenylcarbonyl]amino]pentanamide,
(93) N-Hydroxy-5-methoxymethoxy-4(S)-[N-[4-phenoxyphenylcarbonyl]amino]pentanamide,
(94) N-Hydroxy-5-methoxymethoxy-4(S)-[N-[4-(4-chlorophenyl)phenylcarbonyl]amino]pentanamide,
(95) N-Hydroxy-5-methoxymethoxy-4(S)-[N-[4-[2-(4-methylphenyl)ethynyl]phenylcarbonyl]amino]pentanamide,
(96) N-Hydroxy-5-methoxymethoxy-4(S)-[N-[4-[2E-(4-chlorophenyl)ethenyl]phenylcarbonyl]amino]pentanamide,
(97) N-Hydroxy-5-methoxymethoxy-4(S)-[N-[4-(1-heptynyl)phenylcarbonyl]amino]pentanamide,
(98) N-Hydroxy-5-ethoxymethoxy-4(S)-[N-(4-phenoxyphenylcarbonyl)amino]pentanamide,
(99) N-Hydroxy-5-ethoxymethoxy-4(S)-[N-(4-methylphenylcarbonyl)amino]pentanamide,
(100) N-Hydroxy-5-methoxymethoxy-4(R)-[N-[4-(3-methoxy-1-propynyl)phenylcarbonyl]amino]pentanamide,
(101) N-Hydroxy-2(S)-methyl-5-methoxymethoxy-4(S)-[N-[4-[2-(4-imidazolylphenyl)ethynyl]phenylcarbonyl]amino]pentanamide,
(102) N-Hydroxy-2(S)-methyl-5-methoxymethoxy-4(S)-[N-[4-(4-phenyl-1,2,5,6-tetrahydropyridin-1-yl)phenylcarbonyl]amino]pentanamide,
(103) N-Hydroxy-2(S)-methyl-5-methoxymethoxy-4(S)-[N-(4-phenoxyphenylcarbonyl)amino]pentanamide,
(104) N-Hydroxy-2(S)-methyl-5-methoxymethoxy-4(S)-[N-[4-[2-(4-chlorophenyl)ethenyl]phenylcarbonyl]amino]pentanamide,
(105) N-Hydroxy-2(S)-methyl-5-methoxymethoxy-4(S)-[N-[4-(4-propylphenyl)phenylcarbonyl]amino]pentanamide,
(106) N-Hydroxy-2(S)-methyl-5-methoxymethoxy-4(S)-[N-[4-(benzothiophen-2-yl)phenylcarbonyl]amino]pentanamide,
(107) N-Hydroxy-2(S)-methyl-5-methoxymethoxy-4(S)-[N-[4-(3-methoxyphenoxy)phenylcarbonyl]amino]pentanamide,
(108) N-Hydroxy-2(S)-methyl-5-methoxymethoxy-4(S)-[N-[4-(4-methoxyphenoxy)phenylcarbonyl]amino]pentanamide,
(109) N-Hydroxy-2(S)-methyl-5-methoxymethoxy-4(S)-[N-(4-benzoylphenylcarbonyl)amino]pentanamide,
(110) N-Hydroxy-2(S)-methyl-5-methoxymethoxy-4(S)-[N-[4-(naphthalen-2-yl)phenylcarbonyl]amino]pentanamide,
(111) N-Hydroxy-2(S)-methyl-5-methoxymethoxy-4(S)-[N-[4-[4-methoxybiphenyl-4'-yl)oxy]phenylcarbonyl]amino]pentanamide,
(112) N-Hydroxy-2(S)-methyl-5-methoxymethoxy-4(S)-[N-[4-(4-ethoxyphenyl)phenylcarbonyl]amino]pentanamide,
(113) N-Hydroxy-2(S)-methyl-5-methoxymethoxy-4(S)-[N-[4-(4-phenoxyphenyl)phenylcarbonyl]amino]pentanamide,
(114) N-Hydroxy-2(S)-methyl-5-methoxymethoxy-4(S)-[N-[4-(3-cyanomethylphenyl)phenylcarbonyl]amino]pentanamide,
(115) N-Hydroxy-2(S)-methyl-5-methoxymethoxy-4(S)-[N-[4-(biphenl-4-yl)phenylcarbonyl]amino]pentanamide,
(116) N-Hydroxy-2(S)-methyl-5-methoxymethoxy-4(S)-[N-[4-(3-hydroxyphenoxy)phenylcarbonyl]amino]pentanamide,
(117) N-Hydroxy-2(S)-methyl-5-methoxymethoxy-4(S)-[N-[4-[2-(4-methylphenyl)ethynyl]phenylcarbonyl]amino]pentanamide, (118) N-Hydroxy-2(S)-methyl-5-methoxymethoxy-4(S)-[N-[4-(4-hydroxyphenoxy)phenylcarbonyl]amino]pentanamide,
(119) N-Hydroxy-2(S)-Methyl-5-methoxymethoxy-4(S)-[N-[4-(4-chlorophenyl)phenylcarbonyl]amino]pentanamide,
(120) N-Hydroxy-2(S)-methyl-5-methoxymethoxy-4(S)-[N-[[5-(4-methoxyphenyl)-2-thienyl]carbonyl]amino]pentanamide,
(121) N-Hydroxy-2(S)-methyl-5-methoxymethoxy-4(S)-[N-[4-[(biphenyl-3-yl)oxy]phenylcarbonyl]amino]pentanamide,
(122) N-Hydroxy-2(S)-methyl-5-methoxymethoxy-4(S)-[N-[4-(1-heptynyl)phenylcarbonyl]amino]pentanamide,
(123) N-Hydroxy-2(S)-methyl-5-methoxymethoxy-4(S)-[N-[4-(3-phenoxy-1-propynyl)phenylcarbonyl]amino]pentanamide,
(124) N-Hydroxy-2(S)-methyl-5-methoxymethoxy-4(S)-[N-[4-(4-cyanophenyl)phenylcarbonyl]amino]pentanamide,
(125) N-Hydroxy-2(S)-methyl-5-methoxymethoxy-4(S)-[N-[4-(3-cyanophenyl)phenylcarbonyl]amino]pentanamide,
(126) N-Hydroxy-2(S)-methyl-5-methoxymethoxy-4(S)-[N-(4-benzylphenylcarbonyl)amino]pentanamide,
(127) N-Hydroxy-2(S)-methyl-5-methoxymethoxy-4(S)-[N-[4-[2E-(pyridin-4-yl)ethenyl]phenylcarbonyl]amino]pentanamide,
(128) N-Hydroxy-2(S)-methyl-5-methoxymethoxy-4(S)-[N-[4-(benzoxazol-2-yl)phenylcarbonyl]amino]pentanamide,
(129) N-Hydroxy-2(S)-methyl-5-methoxymethoxy-4(S)-[N-[4-(3-ethoxyphenyl)phenylcarbonyl]amino]pentanamide,
(130) N-Hydroxy-2(S)-methyl-5-methoxymethoxy-4(S)-[N-[4-(4-methylphenylcarbonylamino)phenylcarbonyl]amino]pentanamide,
(131) N-Hydroxy-2(S)-methyl-5-methoxymethoxy-4(S)-[N-[[5-(2-(4-methylphenyl)ethynyl]-2-thienyl]carbonyl]amino]pentanamide,
(132) N-Hydroxy-2(S)-methyl-5-(2-methoxymethoxy)methoxy-4(S)-[N-(4-phenoxyphenylcarbonyl)amino]pentanamide,
(133) N-Hydroxy-2(S)-methyl-5-t-butylcarbonyloxy-4(S)-[N-(4-phenoxyphenylcarbonyl)amino]pentanamide,
(134) N-Hydroxy-2(S)-methyl-5-benzyloxymethoxy-4(S)-[N-(4-phenoxyphenylcarbonyl)amino]pentanamide,
(135) N-Hydroxy-2(S)-methyl-5-ethoxymethoxy-4(S)-[N-(trans-4-methylcyclohexylcarbonyl)amino]pentanamide,
(136) N-Hydroxy-2(S)-methyl-5-ethoxymethoxy-4(S)-[N-(4-methylphenylcarbonyl)amino]pentanamide,
(137) N-Hydroxy-2(S)-methyl-5-ethoxymethoxy-4(S)-[N-(4-chlorophenylcarbonyl)amino]pentanamide,
(138) N-Hydroxy-2(S)-methyl-5-ethoxymethoxy-4(S)-[N-(adamantylcarbonyl)amino]pentanamide,
(139) N-Hydroxy-2(S)-methyl-5-ethoxymethoxy-4(S)-[N-(2-furylcarbonyl)amino]pentanamide,
(140) N-Hydroxy-2(S)-methyl-5-ethoxymethoxy-4(S)-[N-[(benzothiazol-6-yl)carbonyl]amino]pentanamide,
(141) N-Hydroxy-2(S)-methyl-5-ethoxymethoxy-4(S)-[N-(4-fluorophenylcarbonyl)amino]pentanamide,
(142) N-Hydroxy-2(S)-methyl-5-ethoxymethoxy-4(S)-[N-[(2-bromofuryl-5-yl)carbonyl]amino]pentanamide,
(143) N-Hydroxy-2(S)-methyl-5-ethoxymethoxy-4(S)-[N-(4-nitrophenylcarbonyl)amino]pentanamide,
(144) N-Hydroxy-2(S)-methyl-5-ethoxymethoxy-4(S)-[N-(4-bromophenylcarbonyl)amino]pentanamide,
(145) N-Hydroxy-2(S)-methyl-5-ethoxymethoxy-4(S)-[N-(4-cyanophenylcarbonyl)amino]pentanamide,
(146) N-Hydroxy-2(S)-methyl-5-ethoxymethoxy-4(S)-[N-(4-(4-pyridyloxy)phenylcarbonyl)amino]pentanamide,
(147) N-Hydroxy-2(S)-methyl-5-(2-methoxyethoxy)methoxy-4(S)-[N-(4-cyanophenylcarbonyl)amino]pentanamide,
(148) N-Hydroxy-2(S)-methyl-5-methoxymethoxy-4-(S)-[N-(4-chlorophenylcarbonyl)amino]pentanamide,
(149) N-Hydroxy-2(S)-methyl-5-benzyloxymethoxy-4(S)-[N-(4-chlorophenylcarbonyl)amino]pentanamide,
(150) N-Hydroxy-2(S)-methyl-5-(2-methoxyethoxy)methoxy-4(S)-[N-(4-chlorophenylcarbonyl)amino]pentanamide,
(151) N-Hydroxy-2(S)-methyl-5-ethoxymethoxy-4(S)-[N-(2-nitrophenylcarbonyl)amino]pentanamide,
(152) N-Hydroxy-2(S)-methyl-5-ethoxymethoxy-4(S)-[N-(3-nitrophenylcarbonyl)amino]pentanamide,
(153) N-Hydroxy-2(S)-methyl-5-ethoxymethoxy-4(S)-[N-(2-methoxy-4-nitrophenylcarbonyl)amino]pentanamide,
(154) N-Hydroxy-2(S)-methyl-5-ethoxymethoxy-4(S)-[N-(3-methoxy-4-nitrophenylcarbonyl)amino]pentanamide,
(155) N-Hydroxy-2(S)-methyl-5-ethoxymethoxy-4(S)-[N-(3-hydroxy-4-nitrophenylcarbonyl)amino]pentanamide,
(156) N-Hydroxy-2(S)-methyl-5-ethoxymethoxy-4(S)-[N-(4-dihydroboronylphenylcarbonyl)amino]pentanamide,
(157) N-Hydroxy-2(S)-isobutyl-5-methoxymethoxy-4(S)-[N-(4-phenoxyphenylcarbonyl)amino]pentanamide,
(158) N-Hydroxy-2(S)-ethyl-5-methoxymethoxy-4(S)-[N-(4-phenoxyphenylcarbonyl)amino]pentanamide,
(159) N-Hydroxy-2(S)-propyl-5-methoxymethoxy-4(S)-[N-(4-phenoxyphenylcarbonyl)amino]pentanamide,
(160) N-Hydroxy-2(R)-t-butoxycarbonylmethyl-5-methoxymethoxy-4(S)-[N-(4-phenoxyphenylcarbonyl)amino]pentanamide,
(161) N-Hydroxy-2(S)-allyl-5-methoxymethoxy-4(S)-[N-(4-phenoxyphenylcarbonyl)amino]pentanamide,
(162) N-Hydroxy-2(S)-ethyl-5-ethoxymethoxy-4(S)-[N-(4-phenoxyphenylcarbonyl)amino]pentanamide,
(163) N-Hydroxy-2(S)-ethyl-5-(2-methoxyethoxy)methoxy-4(S)-[N-(4-phenoxyphenylcarbonyl)amino]pentanamide,
(164) N-Hydroxy-2(S)-ethyl-5-t-butylcarbonyloxy-4(S)-[N-(4-phenoxyphenylcarbonyl)amino]pentanamide,
(165) N-Hydroxy-2(S)-allyl-5-ethoxymethoxy-4(S)-[N-(4-methylphenylcarbonyl)amino]pentanamide,
(166) N-Hydroxy-2(S)-allyl-5-ethoxymethoxy-4(S)-[N-(4-nitrophenylcarbonyl)amino]pentanamide,
(167) N-Hydroxy-2-methylidene-5-ethoxymethoxy-4(S)-[N-(4-nitrophenylcarbonyl)amino]pentanamide,
(168) N-Hydroxy-2(S)-allyl-5-(2-methoxyethoxy)methoxy-4(S)-[N-(4-cyanophenylcarbonyl)amino]pentanamide,
(169) N-Hydroxy-2(S)-allyl-5-ethoxymethoxy-4(S)-[N-(4-bromophenylcarbonyl)amino]pentanamide,
(170) N-Hydroxy-2(S)-allyl-5-ethoxymethoxy-4(S)-[N-(4-chlorophenylcarbonyl)amino]pentanamide,
(171) N-Hydroxy-2(R)-dimethylaminomethyl-5-ethoxymethoxy-4(S)-[N-(4-nitrophenylcarbonyl)amino]pentanamide,
(172) N-Hydroxy-2(R)-benzyl-5-methoxymethoxy-4(R)-[N-(4-phenoxyphenylcarbonyl)amino]pentanamide,
(173) N-Hydroxy-2(R)-benzyl-5-methoxymethoxy-4(R)-[N-[4-(3-phenoxy-1-propynyl)phenylcarbonyl]amino]pentanamide,
(174) N-Hydroxy-2(R)-methyl-5-ethoxymethoxy-4(R)-[N-[4-(4-cyanophenyl)phenylcarbonyl]amino]pentanamide,
(175) N-Hydroxy-2(R)-allyl-5-ethoxymethoxy-4(R)-[N-(4-phenoxyphenylcarbonyl)amino]pentanamide, (176) N-Hydroxy-2(R)-methyl-5-ethoxymethoxy-4(R)-[N-(4-phenoxyphenylcarbonyl)amino]pentanamide, (177) N-Hydroxy-2(S)-benzyl-5-methoxymethoxy-4(S)-[N-[4-[2E-(4-chlorophenyl)ethenyl]phenylcarbonyl]amino]pentanamide, (178) N-Hydroxy-2(S)-(indol-3-yl)-5-methoxymethoxy-4(S)-[N-[4-(benzofuran-2-yl)phenylcarbonyl]amino]pentanamide, (179) N-Hydroxy-2(S)-benzyl-5-methoxymethoxy-4(S)-[N-[4-[3-(4-chlorophenoxy-1-propynyl]phenylcarbonyl]amino]pentanamide, (180) N-Hydroxy-2(S)-benzyl-5-methoxymethoxy-4(S)-[N-(4-phenoxyphenylcarbonyl)amino]pentanamide, (181) N-Hydroxy-2(S)-benzyl-5-methoxymethoxy-4(S)-[N-[4-(4-phenylpiperidin-1-yl)phenylcarbonyl]amino]pentanamide, (182) N-Hydroxy-2(S)-benzyl-5-methoxymethoxy-4(S)-[N-[4-(6-imidazolyl-1-hexynyl)phenylcarbonyl]amino]pentanamide, (183) N-Hydroxy-2(S)-(naphthalen-1-yl)-5-methoxymethoxy-4(S)-[N-(4-phenoxyphenylcarbonyl)amino]pentanamide, (184) N-Hydroxy-2(S)-[4-(benzofuran-2-yl)benzyl]-5-methoxymethoxy-4(S)-[N-(4-iodophenylcarbonyl)amino]pentanamide, (185) N-Hydroxy-2(S)-benzyl-5-ethoxymethoxy-4(S)-[N-(trans-4-methylcyclohexylcarbonyl)amino]pentanamide, (186) N-Hydroxy-2(S)-(4-nitrobenzyl)-5-ethoxymethoxy-4(S)-[N-(trans-4-methylcyclohexylcarbonyl)amino]pentanamide, (187) N-Hydroxy-2(S)-(indol-3-yl)-5-ethoxymethoxy-4(S)-[N-(trans-4-methylcyclohexylcarbonyl)amino]pentanamide, (188) N-Hydroxy-2(S)-benzyl-5-ethoxymethoxy-4(S)-[N-[(pyridin4-yl)carbonyl]amino]pentanamide, (189) N-Hydroxy-2(S)-benzyl-5-ethoxymethoxy-4(S)-[N-(4-hydroxyphenylcarbonyl)amino]pentanamide, (190) N-Hydroxy-2(S)-(2-nitrobenzyl)-5-ethoxymethoxy-4(S)-[N-(trans-4-methylcyclohexylcarbonyl)amino]pentanamide, (191) N-Hydroxy-2(S)-(3-nitrobenzyl)-5-ethoxymethoxy-4(S)-[N-(trans-4-methylcyclohexylcarbonyl)amino]pentanamide, (192) N-Hydroxy-2(S)-benzyl-5-ethoxymethoxy-4(S)-[N-[(1-methylpyrrol-2-yl)carbonyl]amino]pentanamide, (193) N-Hydroxy-2(S)-benzyl-5-ethoxymethoxy-4(S)-[N-(phenylcarbonyl)amino]pentanamide, (194) N-Hydroxy-2(S)-benzyl-5-ethoxymethoxy-4(S)-[N-(4-ethylphenylcarbonyl)amino]pentanamide, (195) N-Hydroxy-2(S)-benzyl-5-ethoxymethoxy-4(S)-[N-(4-methylphenylcarbonyl)amino]pentanamide, (196) N-Hydroxy-2(S)-benzyl-5-ethoxymethoxy-4(S)-[N-(4-nitrophenylcarbonyl)amino]pentanamide, (197) N-Hydroxy-2(S)-benzyl-5-ethoxymethoxy-4(S)-[N-(2,2,3,3-tetramethylcyclopropylcarbonyl)amino]pentanamide, (198) N-Hydroxy-2(S)-(3-methoxybenzyl)-5-ethoxymethoxy-4(S)-[N-(4-methylphenylcarbonyl)amino]pentanamide, (199) N-Hydroxy-2(S)-benzyl-5-ethoxymethoxy-4(S)-[N-(1-cyclohexenylcarbonyl)amino]pentanamide, (200) N-Hydroxy-2(S)-benzyl-5-ethoxymethoxy-4(S)-[N-[(1-cyclohexen-4-yl)carbonyl]amino]pentanamide, (201) N-Hydroxy-2(S)-benzyl-5-ethoxymethoxy-4(S)-[N-(4-dimethylaminophenylcarbonyl)amino]pentanamide, (202) N-Hydroxy-2(S)-benzyl-5-ethoxymethoxy-4(S)-[N-(4-carbamoylphenylcarbonyl)amino]pentanamide, (203) N-Hydroxy-2(S)-benzyl-5-ethoxymethoxy-4(S)-[N-(4-methoxycarbonylphenylcarbonyl)amino]pentanamide, (204) N-Hydroxy-2(S)-benzyl-5-ethoxymethoxy-4(S)-[N-(cyclopentylcarbonyl)amino]pentanamide, (205) N-Hydroxy-2(S)-(naphthalen-2-yl)-5-ethoxymethoxy-4(S)-[N-(trans-4-methylcyclohexylcarbonyl)amino]pentanamide, (206) N-Hydroxy)-2(S)-benzyl-5-ethoxymethoxy-4(S)-[N-(4-trifiuoromethylphenylcarbonyl)amino]pentanamide, (207) N-Hydroxy-2(S)-benzyl-5-ethoxymethoxy-4(S)-[N-(4-iodophenylcarbonyl)amino]pentanamide, (208) N-Hydroxy-2(S)-benzyl-5-ethoxymethoxy-4(S)-[N-[4-(2-iodoethynyl)phenylcarbonyl]amino]pentanamide, (209) N-Hydroxy-2(S)-benzyl-5-ethoxymethoxy-4(S)-[N-(cycloheptylcarbonyl)amino]pentanamide, (210) N-Hydroxy-2(S)-benzyl-5-ethoxymethoxy-4(S)-[N-(2-thienylcarbonyl)amino]pentanamide, (211) N-Hydroxy-2(R)-(3,4,4-trimethyl-2,5-dioxoimidazolidin-1-yl)methyl-5-ethoxymethoxy-4(S)-[N-(4-methylphenylcarbonyl)amino]pentanamide, (212) N-Hydroxy-2(S)-benzyl-5-ethoxymethoxy-4(S)-[N-[(2-bromo-5-thienyl)carbonyl]amino]pentanamide, (213) N-Hydroxy-2(S)-benzyl-5-ethoxymethoxy-4(S)-[N-(4-bromophenylcarbonyl)amino]pentanamide, (214) N-Hydroxy-2(S)-benzyl-5-ethoxymethoxy-4(S)-[N-(4-hydroxymethylphenylcarbonyl)amino]pentanamide, (215) N-Hydroxy-2(S)-(benzothiophen-3-yl)-5-ethoxymethoxy-4(S)-[N-(trans-4-methylcyclohexylcarbonyl)amino]pentanamide, (216) N-Hydroxy-2(S)-benzyl-5-ethoxymethoxy-4(S)-[N-(4-cyanophenylcarbonyl)amino]pentanamide, (217) N-Hydroxy-2(S)-benzyl-5-ethoxymethoxy-4(S)-[N-[(1-acetylpiperidin-4-yl)carbonyl]amino]pentanamide, (218) N-Hydroxy-2(S)-benzyl-5-ethoxymethoxy-4(S)-[N-[(1-methylpiperidin-4-yl)carbonyl]amino]pentanamide, (219) N-Hydroxy-2(S)-benzyl-5-ethoxymethoxy-4(S)-[N-(4-formylphenylcarbonyl)amino]pentanamide, (220) N-Hydroxy-2(S)-(3-methoxybenzyl)-5-ethoxymethoxy-4(S)-[N-(4-nitrophenylcarbonyl)amino]pentanamide, (221) N-Hydroxy-2(S)-(3-methoxybenzyl)-5-ethoxymethoxy-4(S)-[N-(4-chlorophenylcarbonyl)amino]pentanamide, (222) N-Hydroxy-2(S)-(4-methoxybenzyl)-5-ethoxymethoxy-4(S)-[N-(4-methylphenylcarbonyl)amino]pentanamide, (223) N-Hydroxy-2(S)-(2-methoxybenzyl)-5-ethoxymethoxy-4(S)-[N-(4-methylphenylcarbonyl)amino]pentanamide, (224) N-Hydroxy-2(S)-(naphthalen-1-yl)methyl-5-ethoxymethoxy-4(S)-[N-(4-methylphenylcarbonyl)amino]pentanamide, (225) N-Hydroxy-2(S)-(3-methoxybenzyl)-5-ethoxymethoxy-4(S)-[N-(trans-4-methylcyclohexylcarbonyl)amino]pentanamide, (226) N-Hydroxy-2(S)-benzyl-5-ethoxymethoxy-4(S)-[N-(4-methoxycyclohexylcarbonyl)amino]pentanamide, (227) N-Hydroxy-2(S)-(benzothiophen-3-yl)methyl-5-ethoxymethoxy-4(S)-[N-(4-bromophenylcarbonyl)amino]pentanamide, (228) N-Hydroxy-2(S)-(benzothiophen-3-yl)methyl-5-ethoxymethoxy-4(S)-[N-(4-chlorophenylcarbonyl)amino]pentanamide, (229) N-Hydroxy-2(S)-benzyl-5-ethoxymethoxy-4(S)-[N-[(2-chloropyridin-5-yl)carbonyl]amino]pentanamide, (230) N-Hydroxy-2(S)-(3,5-dimethoxybenzyl)-5-ethoxymethoxy-4(S)-[N-(4-methylphenylcarbonyl)amino]pentanamide, (231) N-Hydroxy-2(S)-benzyl-5-ethoxylmethoxy-4(S)-[N-(4-methylcyclohexylcarbonyl)amino]pentanamide, (232) N-Hydroxy-2(S)-(3-methoxybenzyl)-5-ethoxymethoxy-4(S)-[N-(4-cyanophenylcarbonyl)amino]pentanamide, (233) N-Hydroxy-2(R)-(3,4,4-trimethyl-2,5-dioxoimidazolidin-1-yl)methyl-5-ethoxymethoxy-4(S)-[N-(trans-4-methylcyclohexylcarbonyl)amino]pentanamide, (234) N-Hydroxy-2(R)-(benzofuran-2-yl)methyl-5-ethoxymethoxy-4(S)-[N-(trans-4-methylcyclohexylcarbonyl)amino]pentanamide, (235) N-Hydroxy-2(S)-(benzothiophen-3-yl)methyl-5-ethoxymethoxy-4(S)-[N-(4-nitrophenylcarbonyl)amino]pentanamide, (236) N-Hydroxy-2(S)-benzyl-5-ethoxymethoxy-4(S)-[N-(4-cyanophenylcarbonyl)amino]pentanamide, (237) N-Hydroxy-2(S)-benzyl-5-ethoxymethoxy-4(S)-[N-(4-methylidenecyclohexylcarbonyl)amino]pentanamide, (238) N-Hydroxy-2(S)-benzyl-5-ethoxymethoxy-4(S)-[N-[(1-formylpiperidin-4-yl)carbonyl]amino]pentanamide, (239) N-Hydroxy-2(S)-benzyl-5-ethoxymethoxy-4(S)-[N-[(1-methyl-1-cyclohexen-4-yl)carbonyl]amino]pentanamide, (240) N-Hydroxy-2(S)-benzyl-5-ethoxymethoxy-4(S)-[N-[(4-methyl-1-cyclohexenyl)carbonyl]amino]pentanamide, (241) N-Hydroxy-2(S)-benzyl-5-ethoxymethoxy-4(S)-[N-(4-fluorophenylcarbonyl)amino]pentanamide, (242) N-Hydroxy-2(S)-benzyl-5-ethoxymethoxy-4(S)-[N-(4-chlorophenylcarbonyl)amino]pentanamide, (243) N-Hydroxy-2(S)-benzyl-5-ethoxymethoxy-4(S)-[N-(4-hydroxycyclohexylcarbonyl)amino]pentanamide, (244) N-Hydroxy-2(S)-(benzofuran-3-yl)methyl-5-ethoxymethoxy-4(S)-[N-(trans-4-methylcyclohexylcarbonyl)amino]pentanamide, (245) N-Hydroxy-2(S)-(3-methoxybenzyl)-5-ethoxymethoxy-4(S)-[N-(4-trifluoromethylphenylcarbonyl)amino]pentanamide, (246) N-Hydroxy-2(S)-(1-methylindol-3-yl)methyl-5-(2-methoxyethoxy)methoxy-4(S)-[N-(trans-4-methylcyclohexylcarbonyl)amino]pentanamide, (247) N-Hydroxy-2(S)-benzyl-5-ethoxymethoxy-4(S)-[N-[(1,3-dithian-2-yl)carbonyl]amino]pentanamide, (248) N-Hydroxy-2(S)-(3-methoxybenzyl)-5-ethoxymethoxy-4(S)-[N-(4-bromophenylcarbonyl)amino]pentanamide, (249) N-Hydroxy-2(S)-(3-methoxybenzyl)-5-ethoxymethoxy-4(S)-[N-[(2-bromothiophen-5-yl)carbonyl]amino]pentanamide, (250) N-Hydroxy-2(S)-(2-methoxybenzyl)-5-ethoxymethoxy-4(S)-[N-(trans-4-methylcyclohexylcarbonyl)amino]pentanamide, (251) N-Hydroxy-2(S)-benzyl-5-ethoxymethoxy-4(S)-[N-[(2-methylpyridin-5-yl)carbonyl]amino]pentanamide, (252) N-Hydroxy-2(S)-(benzofuran-3-yl)methyl-5-ethoxymethoxy-4(S)-[N-(4-nitrophenylcarbonyl)amino]pentanamide, (253) N-Hydroxy-2(S)-benzyl-5-ethoxymethoxy-4(S)-[N-(trans-4-hydroxycyclohexylcarbonyl)amino]pentanamide, (254) N-Hydroxy-2(S)-(3-chlorobenzyl)-5-ethoxymethoxy-4(S)-[N-(4-methylphenylcarbonyl)amino]pentanamide, (255) N-Hydroxy-2(S)-benzyl-5-ethoxymethoxy-4(S)-[N-[(2-hydroxypyridin-5-yl)carbonyl]amino]pentanamide, (256) N-Hydroxy-2(R)-(3,4,4-trimethyl-2,5-dioxoimidazolidin-1-yl)methyl-5-ethoxymethoxy-4(S)-[N-(4-bromophenylcarbonyl)amino]pentanamide, (257) N-Hydroxy-2(S)-(3-methoxybenzyl)-5-ethoxymethoxy-4(S)-[N-(4-dimethoxymethylphenylcarbonyl)amino]pentanamide, (258) N-Hydroxy-2(S)-(3-trifluoromethyloxybenzyl)-5-ethoxymethoxy-4(S)-[N-(4-chlorophenylcarbonyl)amino]pentanamide, (259) N-Hydroxy-2(S)-(3-methoxybenzyl)-5-ethoxymethoxy-4(S)-[N-(2-nitrothiphen-5-yl)carbonyl)amino]pentanamide, (260) N-Hydroxy-2(R)-(benzotriazol-1-yl)methyl-5-ethoxymethoxy-4(S)-[N-(4-nitrophenylcarbonyl)amino]pentanamide, (261) N-Hydroxy-2(R)-(3,4,4-trimethyl-2,5-dioxoimidazolidin-1-yl)methyl-5-ethoxymethoxy-4(S)-[N-(4-nitrophenylcarbonyl)amino]pentanamide, (262) N-Hydroxy-2(R)-(3,4,4-trimethyl-2,5-dioxoimidazolidin-1-yl)methyl-5-ethoxymethoxy-4(S)-[N-(4-chlorophenylcarbonyl)amino]pentanamide, (263) N-Hydroxy-2(S)-(3-phenylpropyl)-5-methoxymethoxy-4(S)-[N-(4-phenoxyphenylcarbonyl)amino]pentanamide, (264) N-Hydroxy-2(S)-(3-phenylpropyl)-5-methoxymethoxy-4(S)-[N-[4-[2E-(4-chlorophenyl)ethenyl]phenylcarbonyl]amino]pentanamide, (265) N-Hydroxy-2(S)-(3-phenylpropyl)-5-methoxymethoxy-4(S)-[N-[4-(4-phenyl-1,2,5,6-tetrahydropyridin-1-yl)phenylcarbonyl]amino])pentanamide, (266) N-Hydroxy-2(S)-(3-phenyl-2-propenyl)-5-ethoxymethoxy-4(S)-[N-(trans-4-methylcyclohexylcarbonyl)amino]pentanamide, (267) N-Hydroxy-2(S)-(3-phenylpropyl)-5-ethoxymethoxy-4(S)-[N-(trans-4-methylcyclohexylcarbonyl)amino]pentanamide, (268) N-Hydroxy-2(S)-(2-phenylethyl)-5-(2-methoxyethoxy)methoxy-4(S)-[N-(trans-4-methylcyclohexylcarbonyl)amino]pentanamide, (269) N-Hydroxy-2(S)-(4-phenylbutyl)-5-(2-methoxyethoxy)methoxy-4(S)-[N-(trans-4-methylcyclohexylcarbonyl)amino]pentanamide, (270) N-Hydroxy-2(S)-(3-phenylpropyl)-5-ethoxymethoxy-4(S)-[N-(4-bromophenylcarbonyl)amino]pentanamide, (271) N-Hydroxy-2(S)-(3-phenylpropyl)-5-ethoxymethoxy-4(S)-[N-(4-nitrophenylcarbonyl)amino]pentanamide, (272) N-Hydroxy-2(R)-(2-phenoxyethyl)-5-ethoxymethoxy-4(S)-[N-(4-nitrophenylcarbonyl)amino]pentanamide, (273) N-Hydroxy-2(R)-(2-pyridyl)methyl-5-methoxymethoxy-4(S)-[N-(4-phenoxyphenylcarbonyl)amino]pentanamide, (274) N-Hydroxy-2(R)-(2-pyridyl)methyl-5-methoxymethoxy-4(S)-[N-[4-(benzofuran-2-yl)phenylcarbonyl]amino]pentanamide, (275) N-Hydroxy-2(S)-(3-pyridyl)methyl-5-methoxymethoxy-4(S)-[N-(4-phenoxyphenylcarbonyl)amino]pentanamide, (276) N-Hydroxy-2(S)-(3-pyridyl)methyl-5-methoxymethoxy-4(S)-[N-[4-[2-(4-methylphenyl)ethynyl]phenylcarbonyl]amino]pentanamide, (277) N-Hydroxy-2(S)-(3-pyridyl)methyl-5-methoxymethoxy-4(S)-[N-[4-(1-heptynyl)phenylcarbonyl]amino]pentanamide, (278) N-Hydroxy-2(S)-(3-pyridyl)methyl-5-methoxymethoxy-4(S)-[N-[4-[2E-(4-chlorophenyl)ethenyl]phenylcarbonyl]amino]pentanamide, (279) N-Hydroxy-2(S)-(3-pyridyl)methyl-5-methoxymethoxy-4(S)-[N-(trans-4-methylcyclohexylcarbonyl)amino]pentanamide, (280) N-Hydroxy-2(S)-(4-pyridyl)methyl-5-methoxymethoxy-4(S)-[N-(4-phenoxyphenylcarbonyl)amino]pentanamide, (281) N-Hydroxy-2(R)-(2-pyridyl)methyl-5-(2-methoxyethoxy)methoxy-4(S)-[N-(4-phenoxyphenylcarbonyl)amino]pentanamide, (282) N-Hydroxy-2(S)-(3-pyridyl)methyl-5-ethoxymethoxy-4(S)-[N-(2-methylphenylcarbonyl)amino]pentanamide, (283) N-Hydroxy-2(S)-(3-pyridyl)methyl-5-ethoxymethoxy-4(S)-[N-(3-methylphenylcarbonyl)amino]pentanamide, (284) N-Hydroxy-2(S)-(3-pyridyl)methyl-5-ethoxymethoxy-4(S)-[N-(4-methylphenylcarbonyl)amino]pentanamide, (285) N-Hydroxy-2(S)-(3-pyridyl)methyl-5-ethoxymethoxy-4(S)-[N-(4-methoxyphenylcarbonyl)amino]pentanamide, (286) N-Hydroxy-2(S)-(3-pyridyl)methyl-5-ethoxymethoxy-4(S)-[N-cyclohexylcarbonyl)amino]pentanamide, (287) N-Hydroxy-2(S)-(3-pyridyl)methyl-5-ethoxymethoxy-4(S)-[N-(4-nitrophenylcarbonyl)amino]pentanamide, (288) N-Hydroxy-2(S)-(3-pyridyl)methyl-5-ethoxymethoxy-4(S)-[N-(4-bromophenylcarbonyl)amino]pentanamide, (289) N-Hydroxy-2(S)-(3-quinolyl)methyl-5-ethoxymethoxy-4(S)-[N-(trans-4-methylcyclohexylcarbonyl)amino]pentanamide, (290) N-Hydroxy-2(S)-phenylthio-5-methoxymethoxy-4(S)-[N-(4-phenoxyphenylcarbonyl)amino]pentanamide, (291) N-Hydroxy-2(S)-phenylthio-5-ethoxymethoxy-4(S)-[N-(trans-4-methylcyclohexylcarbonyl)amino]pentanamide, (292) N-Hydroxy-2(S)-methylthio-5-ethoxymethoxy-4(S)-[N-(trans-4-methylcyclohexylcarbonyl)amino]pentanamide, (293) N-Hydroxy-2(S)-(4-pyridyl)thio-5-ethoxymethoxy-4(S)-[N-(trans-4-methylcyclohexylcarbonyl)amino]pentanamide, (294) N-Hydroxy-2(S)-hydroxy-5-methoxymethoxy-4(S)-[N-(4-phenoxyphenylcarbonyl)amino]pentanamide, (295) N-Hydroxy-2(R)-hydroxymethyl-5-ethoxymethoxy-4(S)-[N-(4-chlorophenylcarbonyl)amino]pentanamide, (296) N-Hydroxy-2(R)-methoxymethyl-5-ethoxymethoxy-4(S)-[N-(4-nitrophenylcarbonyl)amino]pentanamide, (297) N-Hydroxy-2(R)-benzyloxymethyl-5-ethoxymethoxy-4(S)-[N-(4-nitrophenylcarbonyl)amino]pentanamide, (298) N-Hydroxy-2(R)-(2-methoxyethoxy)methyl-5-ethoxymethoxy-4(S)-[N-(4-nitrophenylcarbonyl)amino]pentanamide, (299) N-Hydroxy-2(R)-methoxymethyl-5-(2-methoxyethoxy)methoxy-4(S)-[N-(4-cyanophenylcarbonyl)amino]pentanamide, (300) N-Hydroxy-2(R)-methoxymethyl-5-ethoxymethoxy-4(S)-[N-(trans-4-methylcyclohexylcarbonyl)amino]pentanamide, (301) N-Hydroxy-2(R)-methoxymethyl-5-ethoxymethoxy-4(S)-[N-(4-bromophenylcarbonyl)amino]pentanamide, (302) N-Hydroxy-2(R)-methoxymethyl-5-ethoxymethoxy-4(S)-[N-(4-chlorophenylcarbonyl)amino]pentanamide, (303) N-Hydroxy-2(R)-benzyloxymethyl-5-(2-methoxyethoxy)methoxy-4(S)-[N-(4-cyanophenylcarbonyl)amino]pentanamide, (304) N-Hydroxy-2(R)-benzyloxymethyl-5-ethoxymethoxy-4(S)-[N-(4-chlorophenylcarbonyl)amino]pentanamide, (305) N-Hydroxy-2(R)-benzyloxymethyl-5-ethoxymethoxy-4(S)-[N-(4-bromophenylcarbonyl)amino]pentanamide, (306) N-Hydroxy-2(R)-[2-(3-methoxyphenoxy)ethyl]-5-ethoxymethoxy-4(S)-[N-(4-nitrophenylcarbonyl)amino]pentanamide, (307) N-Hydroxy-2(R)-methoxymethyl-5-ethoxymethoxy-4(S)-[N-[(2-nitrothiphen-5-yl)carbonyl]amino]pentanamide, (308) N-Hydroxy-2(R)-methoxymethyl-5-ethoxymethoxy-4(S)-[N-[(2-bromothiophen-5-yl)carbonyl]amino]pentanamide, (309) N-Hydroxy-2(R)-(2-methoxyethoxy)methyl-5-ethoxymethoxy-4(S)-[N-(4-bromophenylcarbonyl)amino]pentanamide, (310) N-Hydroxy-2(R)-(2-methoxyethoxy)methyl-5-(2-methoxyethoxy)methoxy-4(S)-[N-(4-cyanophenylcarbonyl)amino]pentanamide, (311) N-Hydroxy-2(R)-(2-methoxyethoxy)methyl-5-ethoxymethoxy-4(S)-[N-(4-chlorophenylcarbonyl)amino]pentanamide, (312) N-Hydroxy-2(R)-benzyloxymethyl-5-ethoxymethoxy-4(S)-[N-(trans-4-methylcyclohexylcarbonyl)amino]pentanamide, (313) N-Hydroxy-2(R)-(3-thienyl)methoxymethyl-5-ethoxymethoxy-4(S)-[N-(4-nitrophenylcarbonyl)amino]pentanamide, (314) N-Hydroxy-2(R)-(2-pyridinyl)methyl-5-hydroxy-4(S)-[N-(4-phenoxyphenylcarbonyl)amino]pentanamide, (315) N-Hydroxy-2(S)-methyl-5-hydroxy-4(S)-[N-(4-phenoxyphenylcarbonyl)amino]pentanamide, (316) N-Hydroxy-2(S)-methyl-5-hydroxy-4(S)-[N-(4-bromophenylcarbonyl)amino]pentanamide, (317) N-Hydroxy-2(S)-(3-methoxybenzyl)-5-hydroxy-4(S)-[N-(4-bromophenylcarbonyl)amino]pentanamide, (318) N-Hydroxy-2(S)-(3-methoxybenzyl)-5-hydroxy-4(S)-[N-(4-nitrophenylcarbonyl)amino]pentanamide, (319) N-Hydroxy-2(S)-(3-methoxybenzyl)-5-hydroxy-4(S)-[N-(4-chlorophenylcarbonyl)amino]pentanamide, (320) N-Hydroxy-2(S)-(3-methoxybenzyl)-5-hydroxy-4(S)-[N-[(2-bromothiophen-5-yl)carbonyl]amino]pentanamide, (321) N-Hydroxy-2(S)-(3-methoxybenzyl)-5-hydroxy-4(S)-[N-[(2-nitrothiphen-5-yl)carbonyl]amino]pentanamide, (322) N-Hydroxy-2(S)-(3-methoxybenzyl)-5-hydroxy-4(S)-[N-(4-cyanophenylcarbonyl)amino]pentanamide, (323) N-Hydroxy-2(R)-benzyloxymethyl-5-hydroxy-4(S)-[N-(4-nitrophenylcarbonyl)amino]pentanamide, (324) N-Hydroxy-5-methoxymethoxy-4(S)-[N-methyl-N-[4-(4-chlorophenyl)phenylcarbonyl]amino]pentanamide, (325) N-Hydroxy-2(S)-(3-pyridyl)methyl-5-methoxymethoxy-4(S)-[N-methyl-N-[4-(4-chlorophenyl)phenylcarbonyl]amino]pentanamide, (326) N-Hydroxy-2(S)-methyl-5-ethoxymethoxy-4(S)-[N-methyl-N-(4-bromophenylcarbonyl)amino]pentanamide, (327) N-Hydroxy-2(S)-(3-methoxybenzyl)-5-ethoxymethoxy-4(S)-[N-methyl-N-(4-bromophenylcarbonyl)amino]pentanamide, (328) N-Hydroxy-2(S)-methyl-5-ethoxymethoxy-4(S)-[N-methyl-N-(4-nitrophenylcarbonyl)amino]pentanamide, (329) N-Hydroxy-2(S)-methyl-5-benzyloxymethoxy-4(S)-[N-methyl-N-(4-nitrophenylcarbonyl)amino]pentanamide, (330) N-Hydroxy-2(S)-(3-methoxybenzyl)-5-hydroxy-4(S)-[N-methyl-N-(4-chlorophenylcarbonyl)amino]pentanamide, (331) N-Hydroxy-2(S)-(3-methoxybenzyl)-5-hydroxy-4(S)-[N-methyl-N-(4-nitrophenylcarbonyl)amino]pentanamide, (332) N-Hydroxy-2(S)-(3-methoxybenzyl)-5-hydroxy-4(S)-[N-methyl-N-(4-bromophenylcarbonyl)amino]pentanamide,
(333) N-Hydroxy-2(S)-methyl-5-hydroxy-4(S)-[N-methyl-N-(4-nitrophenylcarbonyl)amino]pentanamide,
(334) N-Hydroxy-2(S)-benzyl-5-hydroxy-4(S)-[N-methyl-N-(4-nitrophenylcarbonyl)amino]pentanamide,
(335) N-Hydroxy-2(S)-methyl-5-hydroxy-4(S)-[N-methyl-N-(4-bromophenylcarbonyl)amino]pentanamide,
(336) N-Hydroxy-2(S)-benzyl-5-hydroxy-4(S)-[N-methyl-N-(4-bromophenylcarbonyl)amino]pentanamide,
(337) N-Hydroxy-2(S)-methyl-5-hydroxy-4(S)-[N-methyl-N-(4-chlorophenylcarbonyl)amino]pentanamide,
(338) N-Hydroxy-2(S)-benzyloxy-3(S)-hydroxy-4-(N-(4-(3-methoxy-1-propynyl)phenylcarbonyl)amino)butyramide,
(339) N-Hydroxy-2-benzyloxy-4-(N-(4-(3-methoxy-1-propynyl)phenylcarbonyl)amino)-2-butenamide,
(340) cis-1-(N-hydroxyaminocarbonylmethyl)-2-(N-(4-(3-methoxy-1-propynyl)phenylcarbonyl)amino)cyclopentane,
(341) trans-1-(N-hydroxyaminocarbonylmethyl)-2-(N-(4-(3-methoxy 1-propynyl)phenylcarbonyl)amino)cyclopentane,
(342) trans-1-(N-hydroxyaminocarbonyl)-3-(N-(4-(3-methoxy-1-propynyl)phenylcarbonyl)amino)cyclopentane,
(343) cis-1-(N-hydroxyaminocarbonyl)-3-(N-(4-(3-methoxy-1-propynyl)phenylcarbonyl)amino)cyclopentane,
(344) trans-1-(N-hydroxyaminocarbonyl)-2-(N-(4-(3-methoxy-1-propynyl)phenylcarbonyl)aminomethyl)cyclopentane,
(345) N-Hydroxy-2(R)-allyl-5-ethoxymethoxy-4(S)-[N-(4-phenoxyphenylcarbonyl)amino]pentanamide,
(346) N-Hydroxy-2(R)-benzyl-5-methoxymethoxy-4(S)-[N-[4-(benzofuran-2-yl)phenylcarbonyl]amino]pentanamide,
(347) N-Hydroxy-2(R)-methyl-5-ethoxymethoxy-4(S)-[N-(4-phenoxyphenylcarbonyl)amino]pentanamide,
(348) N-Hydroxy-2(R)-methyl-5-ethoxymethoxy-4(S)-[N-[4-(4-cyanophenyl)phenylcarbonyl]amino]pentanamide,
(349) N-Hydroxy-2(S)-benzyl-5-methoxymethoxy-4(R)-[N-(4-phenoxyphenylcarbonyl)amino]pentanamide,
(350) N-Hydroxy-2(S)-benzyl-5-methoxymethoxy-4(R)-[N-[4-(3-phenoxy-1-propynyl)phenylcarbonyl]amino]pentanamide,
(351) N-Hydroxy-2(S)-(3-aminobenzyl)-5-ethoxymethoxy-4(S)-[N-(trans-4-methylcyclohexylcarbonyl)amino]pentanamide,
(352) N-Hydroxy-2(S)-benzyl-5-ethoxymethoxy-4(S)-[N-(4-carboxyphenylcarbonyl)amino]pentanamide,
(353) N-Hydroxy-2(S)-benzyl-5-ethoxymethoxy-4(S)-[N-(4-aminophenylcarbonyl)amino]pentanamide,
(354) N-Hydroxy-2(S)-benzyl-5-ethoxymethoxy-4(S)-[N-(4-piperidylcarbonyl)amino]pentanamide,
(355) N-Hydroxy-2(S)-(3-hydroxybenzyl)-5-ethoxymethoxy-4(S)-[N-(4-methylphenylcarbonyl)amino]pentanamide,
(356) N-Hydroxy-2-benzyl-4-[N-[4-(benzofuran-2-yl)phenylcarbonyl]amino]butyramide,
(357) N-Hydroxy-2-(3-phenylpropyl)-4-[N-[4-(benzofuran-2-yl)phenylcarbonyl]amino]butyramide,
(358) N-Hydroxy-2-(2-phenylethyl)-4-[N-[4-(benzofuran-2-yl)phenylcarbonyl]amino]butyramide,
(359) N-Hydroxy-2-benzyl-4-[N-[4-[2E-(4-chlorophenyl)ethenyl]phenylcarbonyl]amino]butyramide,
(360) N-Hydroxy-2-benzyl-4-[N-(4-phenoxyphenylcarbonyl)amino]butyramide,
(361) N-Hydroxy-2-(naphthalen-1-yl)methyl-4-[N-(4-phenoxyphenylcarbonyl)amino]butyramide,
(362) N-Hydroxy-2-isopropyl-4-[N-(4-phenoxyphenylcarbonyl)amino]butyramide,
(363) N-Hydroxy-2-(quinolin-4-yl)methyl-4-[N-(4-phenoxyphenylcarbonyl)amino]butyramide,
(364) N-Hydroxy-2-(2-pyridyl)methyl-4-[N-(4-phenoxyphenylcarbonyl)amino]butyramide,
(365) N-Hydroxy-2-(3-pyridyl)methyl-4-[N-(4-phenoxyphenylcarbonyl)amino]butyramide,
(366) N-Hydroxy-2-(naphthalen-2-yl)methyl-4-[N-(4-phenoxyphenylcarbonyl)amino]butyramide,
(367) N-Hydroxy-2-(4-pyridyl)methyl-4-[N-(4-phenoxyphenylcarbonyl)amino]butyramide,
(368) N-Hydroxy-2-(3-methoxybenzyl)-4-[N-(4-phenoxyphenylcarbonyl)amino]butyramide,
(369) N-Hydroxy-2-isobutyl-4-[N-(4-phenoxyphenylcarbonyl)amino]butyramide,
(370) N-Hydroxy-5-methoxy-4(S)-[N-[4-(4-chlorophenyl)phenylcarbonyl]amino]pentanamide,
(371) N-Hydroxy-2(S)-methyl-5-succinimide-4(S)-[N-(4-chlorophenylcarbonyl)amino]pentanamide,
(372) N-Hydroxy-2(S)-methyl-5-succinimideoxy-4(S)-[N-methyl-N-(4-nitrophenylcarbonyl)amino]pentanamide,
(373) N-Hydroxy-2(S)-methyl-5-ethoxymethoxy-4(S)-[N-(4-phenoxyphenylcarbonyl)amino]pentanamide,
(374) N-Hydroxy-2(S)-allyl-5-ethoxymethoxy-4(S)-[N-(4-phenoxyphenylcarbonyl)amino]pentanamide,
(375) N-Hydroxy-2(S)-methyl-5-ethoxymethoxy-4(S)-[N-[4-(4-cyanophenyl)phenylcarbonyl]amino]pentanamide, and non-toxic salts thereof.

16. A method for treating a condition or disease selected from the group consisting of rheumatoid diseases, arthrosteitis, unusual bone resorption, osteoporosis, periodontitis, interstitial nephritis, arteriosclerosis, pulmonary emphysema, cirrhosis, cornea injury, metastasis of, invasion of or growth of tumor cells, autoimmune disease, disease caused by vascular emigration or infiltration of leukocytes, arterialization, multiple sclerosis, aorta aneurysm and endometriosis, said method comprising administering an effective amount of a compound according to claim 1 and non-toxic salts thereof to a patient.

17. A method for treating a condition or disease selected from the group consisting of rheumatoid diseases, arthrosteitis, unusual bone resorption, osteoporosis, periodontitis, interstitial nephritis, arteriosclerosis, pulmonary emphysema, cirrhosis, cornea injury, metastasis of, invasion of or growth of tumor cells, autoimmune disease, disease caused by vascular emigration or infiltration of leukocytes, arterialization, multiple sclerosis, aorta aneurysm and endometriosis, said method comprising administering an effective amount of a compound according to claim 12 and non-toxic salts thereof to a patient.

18. The method for treating a condition or disease of claim 16, wherein the autoimmune disease is selected from the group consisting of Chron's disease Sjogren's syndrome.

19. The method for treating a condition or disease of claim 17, wherein the autoimmune disease is selected from the group consisting of Chron's disease and Sjogren's syndrome.

20. A compound according to claim 2, which is selected from (1) 4-(N-(4-(Benzofuran-2-yl)phenylcarbonyl)amino)butyric acid, (2) 4-(N-(4-Methylphenylcarbonyl)amino)butyric acid,
(3) 4-(N-(4-Butyloxyphenylcarbonyl)amino)butyric acid,
(4) 4-(N-(3-Butyloxyphenylcarbonyl)amino)butyric acid,
(5) 4-[N-[4-(2-(4-Methylphenyl)ethynyl)furan-2-ylcarbonyl]amino]butyric acid,
(6) 4-(N-(4-(Pyrrol-1-yl)phenylcarbonyl)amino)butyric acid,
(7) 4-(N-(trans-4-Methylcyclohexylcarbonyl)amino)butyric acid,
(8) 4-(N-(4-(3-Methoxy-1-propynyl)phenylcarbonyl)amino)butyric acid,
(9) 4-(N-(4-Butylphenylcarbonyl)amino)butyric acid,
(10) 4-(N-(Benzofuran-2-ylcarbonyl)amino)butyric acid,
(11) 4-[N-[4-(2-(4-Chlorophenyl)ethenyl)phenylcarbonyl]amino]butyric acid,
(12) 4-[N-[4-(2-(4-(Imidazol-1-yl)phenyl)ethynyl)phenylcarbonyl]amino]butyric acid,
(13) 4-(N-(trans-4-Propylcyclohexylcarbonyl)amino)butyric acid,
(14) 4-[N-[4-(2-(4-Methylphenyl)ethynyl)phenylcarbonyl]amino]butyric acid,
(15) 4-[N-[4-((4-Bromophenyl)aminosulfonyl)phenylcarbonyl]amino]butyric acid,
(16) 4-[N-(4-Cyclohexylphenylcarbonyl)amino]butyric acid,
(17) 4-[N-[4-(4-Propylphenyl)phenylcarbonyl]amino]butyric acid,
(18) 4-[N-[4-(4-Hydroxyphenyl)phenylcarbonyl]amino]butyric acid,
(19) 4-[N-[4-(4-Chlorophenyl)furan-2-ylcarbonyl]amino]butyric acid,
(20) 4-[N-[4-(4-Heptylphenyl)phenylcarbonyl]amino]butyric acid,
(21) 4-[N-[4-(4-Methoxyphenyl)phenylcarbonyl]amino]butyric acid,
(22) 4-[N-[4-(4-Chlorophenyl)phenylcarbonyl]amino]butyric acid,
(23) 4-[N-(5-Benzyloxyindol-2-ylcarbonyl)amino]butyric acid,
(24) 4-[N-[5-(2-(4-Chlorophenyl)ethenyl)furan-2-ylcarbonyl]amino]butyric acid,
(25) 4-[N-(4-Phenoxyphenylcarbonyl)amino]butyric acid,
(26) 4-(N-methyl-N-(4(benzofuran-2-yl)phenlcarbonyl)amino)butyric acid,
(27) 4-(N-(4-(Benzofuran-2-yl)phenylcarbonyl)amino)-2(S)-hydroxybutyric acid,
(28) 4-(N-(4-(Benzofuran-2-yl)phenylcarbonyl)amino)-2(R)-hydroxybutyric acid,
(29) 4-(N-(4-(Benzofuran-2-yl)phenylcarbonyl)amino)-2(S)-benzyloxymethoxybutyric acid,
(30) 4-(N-(4-(Benzofuran-2-yl)phenylcarbonyl)amino)-2(R)-benzyloxymethoxybutyric acid,
(31) 4-(N-(4-(2-(4-Chlorophenyl)ethenyl)phenylcarbonyl)amino)-2(S)-benzyloxymethoxybutyric acid,
(32) 4-(N-(4-Chlorophenylcarbonyl)amino)-2-benzyloxymethoxybutyric acid,
(33) 4-(N-(4-Chlorophenylcarbonyl)amino)-2-((N-benzyl-N-methylamino)carbonylmethoxy)butyric acid,
(34) 4-(N-(4-Chlorophenylcarbonyl)amino)-2-((N-phenyl-N-methylamino)carbonylmethoxy)butyric acid,
(35) 4-(N-(4-Chlorophenylcarbonyl)amino)-2-((N-phenylethyl-N-methylamino)carbonylmethoxy)butyric acid,
(36) 3(S)-Hydroxy-4-(N-(4-(benzofuran-2-yl)phenylcarbonyl)amino)butyric acid,
(37) 3(R)-Hydroxy-4-(N-(4-(benzofuran-2-yl)phenylcarbonyl)amino)butyric acid,
(38) 3(S)-Methoxymethyloxy-4-(N-(4-(benzofuran-2-yl)phenylcarbonyl)amino)butyric acid,
(39) 4-(N-(4-(Benzofuran-2-yl)phenylcarbonyl)amino)-2-butenoic acid,
(40) 3(R)-Methoxymethyloxy-4-(N-(4-(benzofuran-2-yl)phenylcarbonyl)amino)butyric acid,
(41) 4-(N-(4-(Benzofuran-2-yl)phenylcarbonyl)amino)-3-butenoic acid,
(42) 2-Benzyloxymethyl-4-(N-(4-methylphenylcarbonyl)amino)butyric acid,
(49) 4(S)-(Morpholin-1-yl)carbonyl-4-(N-(4-(benzofuran-2-yl)phenylcarbonyl)amino)butyric acid,
(50) 4(S)-Hydroxymethyl-4-(N-(4-(benzofuran-2-yl)phenylcarbonyl)amino)butyric acid,
(51) 4(S)-Methyloxymethoxymethyl-4-(N-(4-(benzofuran-2-yl)phenylcarbonyl)amino)butyric acid,
(52) 2(S)-Benzyl-4(S)-methoxymethyloxymethyl-4-(N-(4-(benzofuran-2-yl)phenylcarbonyl)amino)butyric acid,
(53) 2(S)-Methyl-4(S)-methoxymethyloxymethyl-4-(N-(4-(benzofuran-2-yl)phenylcarbonyl)amino)butyric acid,
(54) 2(S)-(3-Phenyl-2-propenyl)-4(S)-methoxymethyloxymethyl-4-(N-(4-(benzofuran-2-yl)phenylcarbonyl)amino)butyric acid,
(55) 2(S)-(3-Phenylpropyl)-4(S)-methoxymethyloxymethyl-4-(N-(4-(benzofuran-2-yl)phenylcarbonyl)amino)butyric acid,
(56) 2(S)-Methyl-5-ethoxymethoxy-4(S)-[N-(4-chlorophenylcarbonyl)amino]pentanoic acid,
(57) 2(S)-Methyl-5-ethoxymethoxy-4(S)-[N-(4-nitrophenylcarbonyl)amino]pentanoic acid,
(58) 2(S)-Methyl-5-ethoxymethoxy-4(S)-[N-(4-bromophenylcarbonyl)amino]pentanoic acid,
(59) 2(S)-Allyl-5-ethoxymethoxy-4(S)-[N-(4-nitrophenylcarbonyl)amino]pentanoic acid,
(60) 2(R)-Methoxymethyl-5-ethoxymethoxy-4(S)-[N-(4-nitrophenylcarbonyl)amino]pentanoic acid,
(61) 2(R)-Benzyloxymethyl-5-ethoxymethoxy-4(S)-[N-(4-nitrophenylcarbonyl)amino]pentanoic acid,
(62) 2(S)-Methyl-5-(2-methoxyethoxy)methoxy-4(S)-[N-(4-cyanophenylcarbonyl)amino]pentanoic acid,
(63) 2(R)-(2-Methoxyethoxy)methyl-5-ethoxymethoxy-4(S)-[N-(4-nitrophenylcarbonyl)amino]pentanoic acid
(64) 2(S)-Allyl-5-(2-methoxyethoxy)methoxy-4(S)-[N-(4-cyanophenylcarbonyl)amino]pentanoic acid,
(65) 2(S)-Methoxymethyl-5-(2-methoxyethoxy)methoxy-4(S)-[N-(4-cyanophenylcarbonyl)amino]pentanoic acid
(66) 2(R)-Methoxymethyl-5-ethoxymethoxy-4(S)-[N-(4-bromophenylcarbonyl)amino]pentanoic acid,
(67) 2(R)-Methoxymethyl-5-ethoxymethoxy-4(S)-[N-(4-chlorophenylcarbonyl)amino]pentanoic acid,
(68) 2(R)-Benzyloxymethyl-5-(2-methoxyethoxy)methoxy-4(S)-[N-4-cyanophenylcarbonyl)amino]pentanoic acid,
(69) 2(R)-Benzyloxymethyl-5-ethoxymethoxy-4(S)-[N-(4-chlorophenylcarbonyl)amino]pentanoic acid,
(70) 2(R)-Benzyloxymethyl-5-ethoxymethoxy-4(S)-[N-(4-bromophenylcarbonyl)amino]pentanoic acid,
(71) 2(S)-Allyl-5-ethoxymethoxy-4(S)-[N-(4-bromophenylcarbonyl)amino]pentanoic acid,
(72) 2(S)-Allyl-5-ethoxymethoxy-4(S)-[N-(4-chlorophenylcarbonyl)amino]pentanoic acid,
(73) 2(R)-(2-Methoxyethoxy)methyl-5-ethoxymethoxy-4(S)-[N-(4-bromophenylcarbonyl)amino]pentanoic acid,
(74) 2(R)-(2-Methoxyethoxy)methyl-5-(2-methoxyethoxy)methoxy-4(S)-[N-(4-cyanophenylcarbonyl)amino]pentanoic acid,
(75) 2(R)-(2-Methoxyethoxy)methyl-5-ethoxymethoxy-4(S)-[N-(4-chlorophenylcarbonyl)amino]pentanoic acid,

(76) 2(S)-Methyl-5-ethoxymethoxy-4(S)-[N-methyl-N-(4-bromophenylcarbonyl)amino]pentanoic acid,

(77) 2(S)-Methyl-57ethoxymethoxy-4(S)-[N-methyl-N-(4-nitrophenylcarbonyl)amino]pentanoic acid,

(78) 2(S)-Benzyl-4(S)-t-butyldimethylsilyloxymethyl-4-(N-(4-(benzofuran-2-yl)phenylcarbonyl)amino)butyric acid,

(79) 2(R)-Benzyl-4(S)-hydroxymethyl-4-(N-(4-benzofuran-2-yl)phenylcarbonyl)amino)butyric acid,

(80) 2(S)-Benzyl-4(S)-hydroxymethyl-4-(N-(4-(3-methoxy-1-propynyl)phenylcarbonyl)amino)butyric acid,

(81) 2(S)-Benzyloxy-3(S)-Hydroxy-4-(N-(4-(3-methoxy-1-propynyl)phenylcarbonyl)amino)butyric acid,

(82) 2-Benzyloxy-4-(N-(4-(3-methoxy-1-propynyl)phenylcarbonyl)amino)-2-butenoic acid,

(83) cis-1-Carboxymethyl-2-(N-(4-(3-methoxy-1-propynyl)phenylcarbonyl)amino)cyclopentane,

(84) trans-1-Carboxymethyl-2-(N-(4-(3-methoxy-1-propynyl)phenylcarbonyl)amino)cyclopentane,

(85) trans-3-(N-(4-(3-Methoxy-1-propynyl)phenylcarbonyl)amino)cyclopentanoic acid,

(86) cis-3-(N-(4-(3-Methoxy-1-propynyl)phenylcarbonyl)amino)cyclopentanoic acid,

(87) trans-2-(N-(4-(3-Methoxy-1-propynyl)phenylcarbonyl)aminomethyl)cyclopentanoic acid,

(88) 2(R)-Allyl-5-ethoxymethoxy-4(S)-[N-(4-phenoxyphenylcarbonyl)amino]pentanoic acid,

(89) 5-Methoxy-4(S)-[N-[4-(4-chlorophenyl)phenylcarbonyl]amino]pentanoic acid,

(90) 2(S)-Methyl-5-succinimide-4(S)-[N-(4-chlorophenylcarbonyl)amino]pentanoic acid,

(91) 2(S)-Methyl-5-ethoxymethoxy-4(S)-[N-(4-phenoxyphenylcarbonyl)amino]pentanoic acid,

(92) 2(S)-Allyl-5-ethoxymethoxy-4(S)-[N-(4-phenoxyphenylcarbonyl)amino]pentanoic acid,

(93) 2(S)-Methyl-5-ethoxymethoxy-4(S)-[N-[N-(4-cyanophenyl)phenylcarbonyl]amino]pentanoic acid, and methyl ester, ethyl ester, t-butyl ester and non-toxic salts thereof.

* * * * *

UNITED STATES PATENT AND TRADEMARK OFFICE

CERTIFICATE OF CORRECTION

PATENT NO. : 6,420,427 B1
DATED : July 16, 2002
INVENTOR(S) : Takahashi et al.

It is certified that error appears in the above-identified patent and that said Letters Patent is hereby corrected as shown below:

Title page,
Item [22], please change the "PCT Filed" date to read -- October 7, 1998 --

Signed and Sealed this

Seventeenth Day of December, 2002

JAMES E. ROGAN
*Director of the United States Patent and Trademark Office*